(12) United States Patent
Hutchinson et al.

(10) Patent No.: US 7,538,105 B2
(45) Date of Patent: May 26, 2009

(54) ANTI-INFECTIVE AGENTS

(75) Inventors: Douglas K. Hutchinson, Antioch, IL (US); John R. Bellettini, Antioch, IL (US); David A. Betebenner, Libertyville, IL (US); Richard D. Bishop, Third Lake, IL (US); Thomas B. Borchardt, Kenosha, WI (US); Todd D. Bosse, Chicago, IL (US); Russell D. Cink, Grayslake, IL (US); Charles A. Flentge, Salem, WI (US); Bradley D. Gates, Mount Prospect, IL (US); Brian E. Green, Wonder Lake, IL (US); Mira M. Hinman, Libertyville, IL (US); Peggy P. Huang, Lake Bluff, IL (US); Larry L. Klein, Lake Forest, IL (US); Allan C. Krueger, Gurnee, IL (US); Daniel P. Larson, Oak Creek, WI (US); M. Robert Leanna, Grayslake, IL (US); Dachun Liu, Waukegan, IL (US); Darold L. Madigan, Elk Grove Village, IL (US); Keith F. McDaniel, Wauconda, IL (US); John T. Randolph, Libertyville, IL (US); Todd W. Rockway, Grayslake, IL (US); Teresa A. Rosenberg, Gurnee, IL (US); Kent D. Stewart, Gurnee, IL (US); Vincent S. Stoll, Libertyville, IL (US); Rolf Wagner, Gurnee, IL (US); Ming C. Yeung, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/098,024

(22) Filed: Apr. 4, 2008

(65) Prior Publication Data

US 2008/0193413 A1    Aug. 14, 2008

(51) Int. Cl.
*C07D 513/04* (2006.01)
*A61K 31/542* (2006.01)
(52) U.S. Cl. ...................... 514/222.8; 544/10
(58) Field of Classification Search ............. 544/10; 514/222.8
See application file for complete search history.

(56) References Cited

U.S. PATENT DOCUMENTS

2005/0107364 A1   5/2005   Hutchinson et al. ....... 514/223.2
2006/0287300 A1   12/2006  Klein et al. ............... 514/223.2

FOREIGN PATENT DOCUMENTS

WO    WO 02/098424 A1    12/2002
WO    WO 2005/019191 A2   3/2005
WO    WO 2006/093801 A1   9/2006

OTHER PUBLICATIONS

U.S. Appl. No. 10/647,490, filed Aug. 25, 2003, abandoned.

*Primary Examiner*—Kahsay T Habte
(74) *Attorney, Agent, or Firm*—Lydia N. Nenow; Michael J. Ward

(57) ABSTRACT

Compounds having the formula

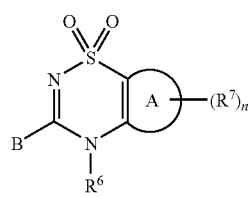

(I)

are hepatitis C(HCV) polymerase inhibitors. Also disclosed are a composition and method for inhibiting hepatitis C(HCV) polymerase, processes for making the compounds, and synthetic intermediates employed in the processes.

19 Claims, No Drawings

US 7,538,105 B2

ANTI-INFECTIVE AGENTS

This application claims priority to U.S. patent application Ser. No. 60/497,607, filed Aug. 25, 2003 and is incorporated herein by reference.

TECHNICAL FIELD

The present invention relates to novel anti-infective agents. Specifically, the present invention relates to compounds, a composition, a method for inhibiting hepatitis C virus (HCV) polymerase, a method for inhibiting HCV viral replication, and a method for treating or preventing HCV infection, and processes for making the compounds, and synthetic intermediates employed in the processes.

BACKGROUND OF THE INVENTION

Infection with hepatitis C virus (HCV) is a major cause of human liver disease throughout the world. More than 85% of all infected individuals become chronically infected. Chronic HCV infection accounts for 30% of all cirrhosis, end-stage liver disease, and liver cancer in the United States. The CDC estimates that the number of deaths due to HCV will increase to 38,000/year by the year 2010.

While initial therapy consisted of interferon alone, the combination of interferon alpha-2b with ribavirin for either 24 or 48 weeks is currently the most efficacious approved therapy for the treatment of chronic HCV infection. However, there are many adverse side effects associated with this therapy (flu-like symptoms, leukopenia, thrombocytopenia, and depression from interferon, as well as anemia induced by ribavirin). Furthermore, this therapy is less effective against infections caused by HCV genotype 1 which constitutes about 75% of all HCV infections.

Based on the foregoing, there exists a significant need to identify compounds with the ability to inhibit HCV. The present invention provides novel anti-infective agents which are HCV polymerase inhibitors.

SUMMARY OF THE INVENTION

In its principle embodiment, the present invention provides a compound of formula (I)

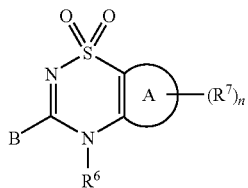

(I)

or a pharmaceutically acceptable salt form, stereoisomer or tautomer, or combination thereof, wherein:

B is

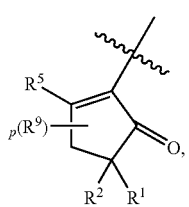

(a)

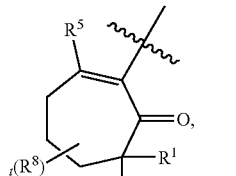

(b)

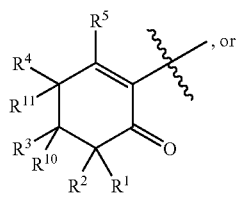

(c)

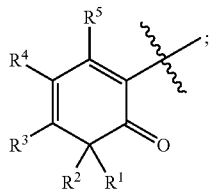

(d)

A is a monocyclic or bicyclic ring selected from the group consisting of aryl, cycloalkyl, cycloalkenyl, heteroaryl and heterocycle;

$R^1$ is hydrogen, alkyl, alkenyl, alkynyl, —C(O)OR$_a$, —C(O)NR$_a$R$_b$ or R$_{1p}$;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, N(R$_e$)SO$_2$N(R$_e$)C(O)OR$_a$, —C(O)R$_a$, —C(O)OR$_a$, —C(O)NR$_a$R$_b$, —N=CR$_j$R$_k$, —C(R$_e$)=CR$_j$R$_k$, and R$_{1q}$;

$R^2$ is hydrogen, alkyl, alkenyl or alkynyl;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, and R$_{2q}$;

alternatively, $R^1$ and $R^2$, together with the carbon atom to which they are attached, form a monocyclic ring selected from the group consisting of cycloalkyl and cycloalkenyl;

wherein each of the cycloalkyl and cycloalkenyl is unsubstituted or substituted with 1, 2 or 3 substituents selected from the group consisting of halo, —OH, —O(alkyl), —NH$_2$, —N(H)(alkyl), —N(alkyl)$_2$, alkyl and haloalkyl;

$R^3$ is hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_a$)C(O)R$_a$, —N(R$_e$)C(O)NR$_a$R$_b$, —N(R$_e$)C(O)OR$_a$, —N(R$_a$)SO$_2$R$_a$, —N(R$_e$)

$-SO_2NR_aR_b$, $-N(R_e)SO_2N(R_e)C(O)OR_a$, $-C(O)R_a$, $-C(O)OR_a$, $-C(O)NR_aR_b$, alkyl, alkenyl, alkynyl, or $R_{3p}$;

wherein each of the alkyl, alkenyl and alkynyl is independently substituted with 0, 1, 2 or 3 substituents independently selected from the group consisting of cyano, formyl, oxo, halo, nitro, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{3q}$;

$R^4$ is hydrogen, cyano, formyl, halo, oxo, nitro, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, alkyl, alkenyl, alkynyl, or $R_{4p}$;

wherein each of the alkyl, alkenyl and alkynyl is independently substituted with 0, 1, 2 or 3 substituents independently selected from the group consisting of cyano, formyl, oxo, halo, nitro, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2Ra$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{4q}$;

alternatively, $R^3$ and $R^4$, together with the carbon atoms to which they are attached, form a ring selected from the group consisting of aryl, heteroaryl, cycloalkyl, cycloalkenyl and heterocycle, wherein each of the of aryl, heteroaryl, cycloalkyl, cycloalkenyl and heterocycle is independently substituted with $(R^8)_m$;

$R^5$ is $-OR_d$, $-SR_d$, $-NR_dR_e$, $-N(H)C(O)R_d$, $-N(H)C(O)OR_d$, $-N(H)SO_2R_d$, or $-N(H)SO_2NR_dR_e$;

$R^6$ is hydrogen, alkyl, alkenyl, alkynyl or -alkyl$R_{106}$;

$R^7$ at each occurrence is independently selected from the group consisting of cyano, formyl, nitro, oxo, halo, alkyl, alkenyl, alkynyl, $-OR_a$, $-OC(O)R_a$, $-OC(O)OR_a$, $-OC(O)NR_aR_b$, $-OP(=O)(R_e)(OR_e)$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(=NH)R_e$, $-N(R_e)C(=Nalkyl)R_e$, $-N(R_e)C(O)R_a$, $-N(R_e)C(O)NR_aR_b$, $-N(R_e)C(=S)NR_aR_b$, $-N(R_e)C(=S)N(R_e)C(O)R_a$, $-N(R_e)C(O)OR_a$, $-N(R_e)SOR_a$, $-N(R_e)SO_2R_a$, $-N(R_e)SO_2NR_aR_b$, $-N(R_e)SO_2N(R_e)C(O)OR_a$, $-N(R_e)SO_2N(R_e)C(O)OR_a$, $-C(O)R_a$, $-C(O)OR_a$, $-C(O)NR_aR_b$, and $R_{7p}$;

wherein each of the alkyl, alkenyl and alkynyl is independently substituted with 0, 1, 2 or 3 substituents selected from the group consisting of cyano, formyl, oxo, nitro, halo, $-N_3$, $-OR_a$, $-OC(O)R_a$, $-OC(O)OR_a$, $-OC(O)NR_aR_b$, $-OSO_2R_a$, $-_{OSO2}NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SOR_a$, $-N(R_e)SO_2R_a$, $-N(R_e)SO_2NR_aR_b$, $-N(R_e)SO_2N(R_e)C(O)R_a$, $-N(R_e)SO_2N(R_e)C(O)OR_a$, $-C(O)R_a$, $-C(O)OR_a$, $-C(O)NR_aR_b$, and $R_{7q}$;

$R^8$ at each occurrence is independently selected from the group consisting of cyano, formyl, nitro, oxo, halo, alkyl, alkenyl, alkynyl, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{8p}$;

wherein each of the alkyl, alkenyl and alkynyl is independently substituted with 0, 1, 2 or 3 substituents selected from the group consisting of cyano, formyl, nitro, oxo, halo, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{8q}$;

$R^9$ at each occurrence is independently selected from the group consisting of alkyl, alkenyl, alkynyl, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{9p}$;

wherein each of the alkyl, alkenyl and alkynyl is independently substituted with 0, 1, 2 or 3 substituents selected from the group consisting of cyano, formyl, nitro, oxo, halo, $-OR_a$, $-OC(O)R_a$, $-OC(O)OR_a$, $-OC(O)NR_aR_b$, $-OSO_2R_a$, $-OSO_2NR_aR_b$, $-SR_a$, $-S(O)R_a$, $-SO_2R_a$, $-SO_2OR_a$, $-SO_2NR_aR_b$, $-NR_aR_b$, $-N(R_e)C(O)R_a$, $-N(R_e)C(O)NR_aR_b$, $-N(R_e)C(O)OR_a$, $-N(R_e)SO_2R_a$, $-N(R_e)SO_2NR_aR_b$, $-N(R_e)SO_2N(R_e)C(O)OR_a$, $-C(O)R_a$, $-C(O)OR_a$, $-C(O)NR_aR_b$, and $R_{9q}$;

$R^{10}$ is hydrogen or alkyl;

$R^{11}$ is hydrogen or alkyl;

$R_a$ at each occurrence is independently selected from the group consisting of hydrogen, alkyl, alkenyl, alkynyl, and $R_p$;

wherein each of the alkyl, alkenyl and alkynyl is independently substituted with 0, 1, 2 or 3 substituents independently selected from the group consisting of cyano, formyl, oxo, halo, nitro, $-OR_c$, $-OC(O)R_c$, $-OC(O)OR_c$, $-OC(O)NR_cR_d$, $-OSO_2R_c$, $-OSO_2NR_cR_d$, $-SR_c$, $-S(O)R_c$, $-SO_2R_c$, $-SO_2OR_c$, $-SO_2NR_cR_d$, $-NR_cR_d$, $-N(R_e)C(O)R_c$, $-N(R_e)C(O)NR_cR_d$, $-N(R_e)C(O)OR_c$, $-N(R_e)SO_2R_c$, $-N(R_e)SO_2NR_cR_d$, $-N(R_e)SO_2N(R_e)C(O)OR_c$, $-C(O)R_c$, $-C(O)OR_c$, $-C(O)NR_cR_d$, $-C(O)N(R_e)NR_cR_d$, and $R_q$;

$R_b$ at each occurrence is independently selected from the group consisting of hydrogen, alkyl, alkenyl, alkynyl, $R_{106}$, haloalkyl, hydroxyalkyl, alkoxyalkyl, and -alkyl$R_{106}$;

alternatively, $R_a$ and $R_b$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, $-OR_c$, $-OC(O)R_c$, $-OC(O)OR_c$, $-OC(O)NR_cR_d$, $-OSO_2R_c$, $-OSO_2NR_cR_d$, $-SR_c$, $-S(O)R_c$, $-SO_2R_c$, $-SO_2OR_b$, $-SO_2NR_cR_d$, $-NR_cR_d$, $-N(R_e)C(O)R_c$, $-N(R_e)C(O)NR_cR_d$, $-N(R_e)C(O)OR_c$, $-N(R_e)SO_2R_c$, $-N(R_e)SO_2NR_cR_d$, $-N(R_e)SO_2N(R_e)C(O)OR_c$, $-C(O)R_c$, $-C(O)OR_c$, and $-C(O)NR_cR_d$; and wherein each of the alkyl, alkenyl and alkynyl is independently substituted with 0, 1 or 2 substituents selected from the group consisting of cyano, halo, nitro, oxo, $-OR_c$, $-OC(O)R_c$, $-OC(O)OR_c$, $-OC(O)NR_cR_d$, $-OSO_2R_c$, $-OSO_2NR_cR_d$, $-SR_c$, $-S(O)R_c$, $-SO_2R_c$, $-SO_2OR_c$, $-SO_2NR_cR_d$, $-NR_cR_d$, $-N(R_e)C(O)R_c$, $-N(R_e)C(O)NR_cR_d$, $-N(R_e)C(O)OR_c$, $-N(R_e)SO_2R_c$, $-N(R_e)SO_2N(R_e)C(O)OR_c$, $-C(O)R_c$, $-C(O)OR_c$, $-C(O)NR_cR_d$, and $R_q$;

$R_c$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, formyl, oxo, halo, nitro, —$OR_f$, —$OC(O)R_f$, —$OC(O)OR_f$, —$OC(O)NR_f R_g$, —$OSO_2R_f$, —$OSO_2NR_f R_g$, —$SR_f$, —$S(O)R_f$, —$SO_2R_f$, —$SO_2OR_f$, —$SO_2NR_f R_g$, —$NR_f R_g$, —$N(R_e)C(O)R_f$, —$N(R_e)C(O)NR_f R_g$, —$N(R_e)C(O)OR_f$, —$N(R_e)SO_2R_f$, —$N(R_e)SO_2NR_f R_g$, —$N(R_e)SO_2N(R_e)C(O)OR_f$, —$C(O)R_f$, —$C(O)OR_f$, —$C(O)NR_f R_g$, and $R_{103}$;

$R_d$ at each occurrence is independently selected from the group consisting of hydrogen, alkyl, alkenyl, alkynyl, $R_{106}$, haloalkyl, alkoxyalkyl, hydroxyalkyl, and -alkyl$R_{106}$;

alternatively, $R_c$ and $R_d$, together with the nitrogen atom to which they are attached, form a ring selected from the group consisting of heterocycle and heteroaryl;

wherein each of the heteroaryl and heterocycle is independently substituted with 0, 1, 2 or 3 substituents independently selected from the group consisting of alkyl, alkenyl, alkynyl, cyano, formyl, halo, nitro, oxo, —$OR_f$, —$OC(O)R_f$, —$OC(O)OR_f$, —$OC(O)NR_f R_g$, —$OSO_2R_f$, —$OSO_2NR_f R_g$, —$SR_f$, —$S(O)R_f$, —$SO_2R_f$, —$SO_2OR_f$, —$SO_2NR_f R_g$, —$NR_f R_g$, —$N(R_e)C(O)R_f$, —$N(R_e)C(O)NR_f R_g$, —$N(R_e)C(O)OR_f$, —$N(R_e)SO_2R_f$, —$N(R_e)SO_2NR_f R_g$, —$N(R_e)SO_2N(R_e)C(O)OR_f$, —$C(O)R_f$, —$C(O)OR_f$, and —$C(O)NR_f R_g$; and wherein each of the alkyl, alkenyl and alkynyl is independently substituted with 0, 1, 2 or 3 substituents independently selected from the group consisting of cyano, halo, nitro, oxo, —$OR_f$, —$OC(O)R_f$, —$OC(O)OR_f$, —$OC(O)NR_f R_g$, —$OSO_2R_f$, —$OSO_2NR_f R_g$, —$SR_f$, —$S(O)R_f$, —$SO_2R_f$, —$SO_2OR_f$, —$SO_2NR_f R_g$, —$NR_f R_g$, —$N(R_e)C(O)R_f$, —$N(R_e)C(O)NR_f R_g$, —$N(R_e)C(O)OR_f$, —$N(R_e)SO_2R_f$, —$N(R_e)SO_2NR_f R_g$, —$N(R_e)SO_2N(R_e)C(O)OR_f$, —$C(O)R_f$, —$C(O)OR_f$, —$C(O)NR_f R_g$, and $R_{103}$;

$R_e$ at each occurrence is independently selected from the group consisting of hydrogen, alkyl, alkenyl, alkynyl, $R_{106}$, haloalkyl, and -alkyl$R_{106}$;

$R_f$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O($R_{106}$), —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl), —C(O)N(alkyl)$_2$, and $R_{103}$;

$R_g$ at each occurrence is independently selected from the group consisting of hydrogen, alkyl, alkenyl, alkynyl, $R_{106}$, haloalkyl and -alkyl$R_{106}$;

alternatively, $R_f$ and $R_g$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OH, —O(alkyl), —O(cyanoalkyl), —O(haloalkyl), —$OR_{106}$, —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl), —C(O)N(alkyl)$_2$, and $R_{103}$;

$R_j$ at each occurrence is independently selected from the group consisting of hydrogen, alkyl, alkenyl, alkynyl, $R_{103}$, haloalkyl and -alkyl$R_{103}$;

$R_k$ at each occurrence is independently selected from the group consisting of hydrogen, alkyl, alkenyl and alkynyl;

alternatively, $R_j$ and $R_k$, together with the carbon atom to which they are attached, form a ring selected from the group consisting of cycloalkyl, cycloalkenyl, heterocycle, aryl and heteroaryl; wherein each ring is independently substituted with 0, 1, 2, 3, 4 or 5 substituents independently selected from the group consisting of alkyl, alkenyl, alkynyl, nitro, cyano, formyl, halo, oxo, —OH, —O(alkyl), —O(cyanoalkyl), —O(haloalkyl), —$OR_{106}$, —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —$OR_{106}$, —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl), —C(O)N(alkyl)$_2$, and $R_{103}$;

m is 0, 1, 2, 3 or 4;

n is 0, 1, 2, 3 or 4;

p is 0, 1 or 2;

t is 0, 1, 2, 3 or 4.

$R_p$, $R_q$, $R_{1p}$, $R_{1q}$, $R_{2q}$, $R_{3p}$, $R_{3q}$, $R_{4p}$, $R_{4q}$, $R_{7p}$, $R_{7q}$, $R_{8p}$, $R_{8q}$, $R_{9p}$, and $R_{9q}$, at each occurrence, are independently selected from the group consisting of cycloalkyl, cycloalkenyl, aryl, heteroaryl, and heterocycle; wherein each of the $R_p$, $R_q$, $R_{1p}$, $R_{1q}$, $R_{2q}$, $R_{3p}$, $R_{3q}$, $R_{4p}$, $R_{4q}$, $R_{7p}$, $R_{7q}$, $R_{8p}$, $R_{8q}$, $R_{9p}$, and $R_{9q}$, at each occurrence, is independently substituted with 0, 1, 2, 3, 4 or 5 substituents selected from the group consisting of alkyl, alkenyl, alkynyl, cyano, formyl, halo, nitro, oxo, —$OR_{101}$, —$OC(O)R_{101}$, —$OC(O)OR_{101}$, —$OC(O)NR_{101}R_{102}$, —$OSO_2R_{101}$, —$OSO_2NR_{101}R_{102}$, —$SR_{101}$, —$S(O)R_{101}$, —$SO_2R_{101}$, —$SO_2OR_{101}$, —$SO_2NR_{101}R_{102}$, —$NR_{101}R_{102}$, —$N(R_{102})C(O)R_{101}$, —$N(R_{102})C(O)OR_{101}$, —$N(R_{102})C(O)NR_{101}R_{102}$, —$N(R_{102})SO_2R_{101}$, —$N(R_{102})SO_2NR_{101}R_{102}$, —$N(R_{102})SO_2N(R_{102})C(O)OR_{101}$, —$C(O)R_{101}$, —$C(O)OR_{101}$, and —$C(O)NR_{101}R_{102}$; and wherein each of the alkyl, alkenyl and alkynyl is independently substituted with 0, 1, 2 or 3 substituents independently selected from the group consisting of cyano, formyl, halo, nitro, oxo, —$OR_{101}$, —$OC(O)R_{101}$, —$OC(O)OR_{101}$, —$OC(O)NR_{101}R_{102}$, —$OSO_2R_{101}$, —$OSO_2NR_{101}R_{102}$, —$SR_{101}$, —$S(O)R_{101}$, —$SO_2R_{101}$, —$SO_2OR_{101}$, —$SO_2NR_{101}R_{102}$, —$NR_{101}R_{102}$, —$N(R_{102})C(O)R_{101}$, —$N(R_{102})C(O)OR_{101}$, —$N(R_{102})C(O)NR_{101}R_{102}$, —$N(R_{102})SO_2R_{101}$, —$N(R_{102})SO_2NR_{101}R_{102}$, —$N(R_{102})SO_2N(R_{102})C(O)OR_{101}$, —$C(O)R_{101}$, —$C(O)OR_{101}$, and —$C(O)NR_{101}R_{102}$;

$R_{101}$ at each occurrence is independently selected from the group consisting of hydrogen, alkyl, alkenyl, alkynyl, $R_{103}$, -alkyl$R_{103}$, -alkenyl$R_{103}$, -alkynyl$R_{103}$, haloalkyl, cyanoalkyl, -alkylC(O)$R_{104}$, -alkylC(O)$OR_{104}$, -alkylC(O)$NR_{104}R_{105}$, -alkyl-$OR_{104}$, -alkyl-OC(O)$R_{104}$, -alkyl-OC(O)$OR_{104}$, -alkyl$SR_{104}$, -alkylS(O)$R_{104}$, -alkyl$SO_2R_{104}$, -alkyl$SO_2OR_{104}$, -alkyl$SO_2NR_{104}R_{105}$, -alkyl$NR_{104}R_{105}$, -alkylN($R_{105}$)C(O)$R_{104}$, -alkylN($R_{105}$)C(O)$OR_{104}$, -alkylN($R_{105}$)C(O)$NR_{104}R_{105}$, -alkylN($R_{105}$)$SO_2R_{104}$, and -alkylN($R_{105}$)$SO_2NR_{104}R_{105}$;

$R_{103}$ at each occurrence is independently selected from the group consisting of cycloalkyl, cycloalkenyl, aryl, heteroaryl and heterocycle; wherein each $R_{103}$ is independently substituted with 0, 1, 2, 3, 4 or 5 substituents independently selected from the group consisting of alkyl, alkenyl, alkynyl, halo, nitro, cyano, oxo, formyl, haloalkyl, $-OR_{104}$, $-OC(O)R_{104}$, $-OC(O)OR_{104}$, $-OC(O)NR_{104}R_{105}$, $-OSO_2NR_{104}R_{105}$, $-SO_2R_{105}$, $-S(O)R_{104}$, $-NR_{104}R_{105}$, $-N(R_{105})C(O)NR_{104}R_{105}$, $-N(R_{105})COR_{104}$, $-N(R_{105})SO_2R_{104}$, $-N(R_{105})SO_2NR_{104}R_{105}$, $-C(O)R_{104}$, $-C(O)OR_{104}$, $-C(O)NR_{104}R_{105}$, -alkylOR$_{104}$, -alkylOC(O)R$_{104}$, -alkylOC(O)OR$_{104}$, -alkylOC(O)NR$_{104}$R$_{105}$, -alkylOSO$_2$NR$_{104}$R$_{105}$, -alkylSO$_2$R$_{104}$, -alkylS(O)R$_{104}$, -alkylNR$_{104}$R$_{105}$, -alkylN(R$_{105}$)COR$_{104}$, -alkylN(R$_{105}$)SO$_2$R$_{104}$, -alkylN(R$_{104}$)C(O)NR$_{104}$R$_{105}$, -alkylN(R$_{105}$)SO$_2$NR$_{104}$R$_{105}$, -alkylC(O)R$_{104}$, -alkylC(O)OR$_{104}$, and -alkylC(O)NR$_{104}$R$_{105}$;

$R_{102}$, $R_{104}$, and $R_{105}$, at each occurrence, are independently selected from the group consisting of hydrogen, alkyl, alkenyl, alkynyl, hydroxyalkyl, alkoxyalkyl, haloalkyl and benzyl;

alternatively, $R_{101}$ and $R_{102}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

alternatively, $R_{104}$ and $R_{105}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl; and $R_{106}$ at each occurrence is independently selected from the group consisting of aryl and heteroaryl, wherein each $R_{106}$ is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl.

In another embodiment, the present invention provides a pharmaceutical composition comprising a compound or combination of compounds of formula (I) or a pharmaceutically acceptable salt form, stereoisomer, or tautomer, or combination thereof, in combination with a pharmaceutically acceptable carrier. The invention is also directed to a prodrug of a compound of the present invention, or pharmaceutically acceptable salt, tautomer or stereoisomer thereof.

In yet another embodiment, the present invention provides a method of inhibiting the replication of an RNA-containing virus comprising contacting said virus with a therapeutically effective amount of a compound or combination of compounds of the present invention or a pharmaceutically acceptable salt thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention or a pharmaceutically acceptable salt form, stereoisomer, or tautomer, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, stereoisomer or tautomer, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

As used in the present specification the following terms have the meanings indicated:

As used herein, the singular forms "a", "an", and "the" include plural reference unless the context clearly dictates otherwise.

The term "alkenyl," as used herein, refers to a straight or branched chain group of 2, 3, 4, 5, 6, 7, or 8 carbon atoms containing at least one carbon-carbon double bond. Examples of alkenyl groups include allyl, propenyl, 3-methylbut-2-enyl, 4-ethylpenta-2,4-dienyl, and the like.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, refers to an alkoxy group, as defined herein, appended to the parent molecular moiety through an alkyl group, as defined herein.

The term "alkyl," as used herein, refers to a group derived from a straight or branched chain saturated hydrocarbon containing 1, 2, 3, 4, 5, 6, 7, 8, 9, or 10 carbon atoms. Examples of alkyl groups include propyl, butyl, methyl, ethyl, 2-methylbutyl, 3-methylbutyl, 3,3-dimethylbutyl, 5,5-dimethylhexyl, 3-methylpentyl, and the like.

The term "alkynyl," as used herein, refers to a straight or branched chain hydrocarbon of 2, 3, 4, 5, or 6 carbon atoms containing at least one carbon-carbon triple bond. Examples of alkynyl groups include ethynyl, 2-methyl-3-butynyl, 3-pentynyl, and the like.

The term "aryl," as used herein, refers to a phenyl group, or a bicyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Examples of aryl groups include anthracenyl, azulenyl, fluorenyl, indanyl, indenyl, naphthyl (naphthalenyl), phenyl, tetrahydronaphthyl, and the like. The aryl groups of the present invention can be substituted or unsubstituted, and can be connected to the parent molecular moiety through any substitutable carbon atom of the group.

The term "cyano," as used herein, refers to —CN.

The term "cyanoalkyl" as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl," as used herein, refers to a non-aromatic, partially unsaturated, monocyclic or bicyclic ring system, having 3, 4, 5, 6, 7, 8, 9, 10, 11, 12, 13, or 14 carbon atoms and zero heteroatom. The three-, four- or five-membered ring have one double bond. The six-membered ring has one or two double bonds. The seven and eight-membered rings have one, two, or three double bonds. The bicyclic fused ring systems have a monocyclic cycloalkenyl group fused to a monocyclic cycloalkyl group, as defined herein, or a second monocyclic cycloalkenyl group, as defined herein. The monocyclic Examples of cycloalkenyl groups include cyclohexenyl, octahydronaphthalenyl, norbornylenyl, and the like. The cycloalkenyl groups of the present invention can be unsubstituted or substituted, and are attached to the parent molecular moiety through any substitutable carbon atom of the group.

The term "cycloalkyl," as used herein, refers to a saturated monocyclic, or bicyclic fused ring system having 3, 4, 5, 6, 7, 8, 9, 10, 11, 12, 13, or 14 carbon atoms and zero heteroatom. The bicyclic fused ring systems have a monocyclic cycloalkyl group fused to a second mocyclic cycloalkyl group, as defined herein. The cycloalkyl groups of the present invention can be unsubstituted or substituted, and are attached to the parent molecular moiety through any substitutable carbon atom of the group. Examples of cycloalkyl groups include cyclopropyl, cyclobutyl, cyclopentyl, cyclohexyl, cycloheptyl, bicyclo[3.1.1]heptyl, 6,6-dimethylbcyclo[3.1.1]heptyl, adamantyl, and the like The term "formyl," as used herein, refers to —CHO.

The terms "halo," and "halogen," as used herein, refer to F, Cl, Br, and I.

The term "haloalkyl," as used herein, refers to an alkyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The term "heteroaryl" also includes bicyclic fused ring systems where a heteroaryl ring is fused to a phenyl group, a monocyclic cycloalkyl group, as defined herein, a heterocycle group, as defined herein, or an additional heteroaryl group. Examples of heteroaryl groups include benzimidazolyl, benzothienyl, benzoxadiazolyl, furanyl, imidazolyl, indazolyl, indolyl, isoindolyl, isoxazolyl, isoquinolinyl, isothiazolyl, oxadiazolyl, oxadiazolyl, oxazolyl, thiazolyl, thienopyridinyl, thienyl, triazolyl, thiadiazolyl, pyridinyl, pyridazinyl, pyrimidinyl, pyrazinyl, pyrazolyl, pyrrolyl, quinolinyl, triazinyl, and the like. The heteroaryl groups of the present invention can be unsubstituted or substituted and are connected to the parent molecular moiety through any substitutable carbon or nitrogen atom of the groups. In addition, The nitrogen heteroatoms can be optionally quaternized or oxidized to the N-oxide. Also, the nitrogen containing rings can be optionally N-protected.

The term "heterocycle," as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic fused ring systems where a heterocycle ring is fused to a phenyl group, a monocyclic cycloalkenyl group, as defined herein, a monocyclic cycloalkyl group, as defined herein, or an additional monocyclic heterocycle group. The heterocycle groups of the invention can be unsubstituted or substituted and are connected to the parent molecular moiety through any substitutable carbon or nitrogen atom in the group. Examples of heterocycle groups include azetidinyl, 4,5-dihydro-1,3-oxazol-2-yl, dihydroindolyl, dihydropyridinyl, 1,3-dioxanyl, 1,4-dioxanyl, 1,3-dioxolanyl, 1,1-dioxidoisothiazolidin-2-yl, isoindolinyl, morpholinyl, piperazinyl, pyrrolidinyl, tetrahydropyridinyl, piperidinyl, thiomorpholinyl, tetrahydropyranyl, and the like. In addition, The nitrogen heteroatoms can be optionally quaternized or oxidized to the N-oxide. Also, the nitrogen containing heterocyclic rings can be optionally N-protected.

The term "hydroxy" as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and 2-ethyl-4-hydroxyheptyl.

It is understood that each of the following terms as defined hereinabove: alkenyl, alkyl, alkynyl, aryl, cycloalkyl, cycloalkenyl, heteroaryl, heterocycle, may be unsubstituted or substituted.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 3rd edition, John Wiley & Sons, New York (1999). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfanyl, triphenylmethylsulfanyl, and the like; sulfinyl groups such as p-methylphenylsulfinyl, t-butylsulfinyl, and the like; carbamate forming groups such as benzyloxycarbonyl, p-chlorobenzyloxycarbonyl, p-methoxybenzyoxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "nitro," as used herein, refers to —NO$_2$.

The term "oxo," as used herein, refers to =O.

In a first embodiment the present invention provides a compound of formula (I)

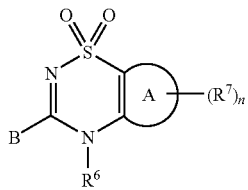

(I)

or a pharmaceutically acceptable form, stereoisomer, or tautomer, or combination thereof, wherein:

B is

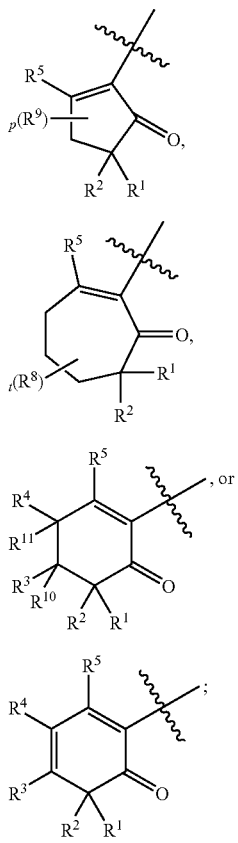

(a)

(b)

(c) , or (d) ;

A is a monocyclic or bicyclic ring selected from the group consisting of aryl, cycloalkyl, cycloalkenyl, heteroaryl and heterocycle;

$R^1$ is hydrogen, alkyl, alkenyl, alkynyl, —C(O)OR$_a$, —C(O)NR$_a$R$_b$ or R$_{1p}$;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, —C(R$_e$)=CR$_j$R$_k$, and R$_{1q}$;

$R^2$ is hydrogen, alkyl, alkenyl or alkynyl;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, and R$_{2q}$;

alternatively, $R^1$ and $R^2$, together with the carbon atom to which they are attached, form a monocyclic ring selected from the group consisting of cycloalkyl and cycloalkenyl;

wherein each of the cycloalkyl and cycloalkenyl is unsubstituted or substituted with 1, 2 or 3 substituents selected from the group consisting of halo, —OH, —O(alkyl), —NH$_2$, —N(H)(alkyl), —N(alkyl)$_2$, alkyl and haloalkyl;

$R^3$ is hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, or R$_{3p}$;

wherein each of the alkyl, alkenyl and alkynyl is independently substituted with 0, 1, 2 or 3 substituents independently selected from the group consisting of cyano, formyl, oxo, halo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{3q}$;

$R^4$ is hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, or R$_{4p}$;

wherein each of the alkyl, alkenyl and alkynyl is independently substituted with 0, 1, 2 or 3 substituents independently selected from the group consisting of cyano, formyl, oxo, halo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$Ra, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{4q}$;

alternatively, $R^3$ and $R^4$, together with the carbon atoms to which they are attached, form a ring selected from the group consisting of aryl, heteroaryl, cycloalkyl, cycloalkenyl and heterocycle, wherein each of the of aryl, heteroaryl, cycloalkyl, cycloalkenyl and heterocycle is independently substituted with (R$^8$)$_m$;

$R^5$ is —OR$_d$, —SR$_d$, —NR$_d$R$_e$, —N(H)C(O)R$_d$, —N(H)C(O)OR$_d$, —N(H)SO$_2$R$_d$, or —N(H)SO$_2$NR$_d$R$_e$;

$R^6$ is hydrogen, alkyl, alkenyl, alkynyl or -alkylR$_{106}$;

$R^7$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OP(=O)(R$_e$)(OR$_e$), —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(=NH)R$_e$, —N(R$_e$)C(=Nalkyl)R$_e$, —N(R$_e$)C(O)R$_a$, —N(R$_e$)C(O)NR$_a$R$_b$, —N(R$_e$)C(=S)NR$_a$R$_b$, —N(R$_e$)C(=S)N(R$_e$)C(O)R$_a$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7p}$;

wherein each of the alkyl, alkenyl and alkynyl is independently substituted with 0, 1, 2 or 3 substituents selected from the group consisting of cyano, formyl, oxo, nitro, halo, —N$_3$, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7q}$;

R$^8$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8p}$;

wherein each of the alkyl, alkenyl and alkynyl is independently substituted with 0, 1, 2 or 3 substituents selected from the group consisting of cyano, formyl, nitro, oxo, halo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8q}$;

R$^9$ at each occurrence is independently selected from the group consisting of alkyl, alkenyl, alkynyl, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{9p}$;

wherein each of the alkyl, alkenyl and alkynyl is independently substituted with 0, 1, 2 or 3 substituents selected from the group consisting of cyano, formyl, nitro, oxo, halo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{9q}$;

R$^{10}$ is hydrogen or alkyl;

R$_{11}$ is hydrogen or alkyl;

R$_a$ at each occurrence is independently selected from the group consisting of hydrogen, alkyl, alkenyl, alkynyl, and R$_p$;

wherein each of the alkyl, alkenyl and alkynyl is independently substituted with 0, 1, 2 or 3 substituents selected from the group consisting of cyano, formyl, oxo, halo, nitro, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, —C(O)N(R$_e$)NR$_c$R$_d$, and R$_q$;

R$_b$ at each occurrence is independently selected from the group consisting of hydrogen, alkyl, alkenyl, alkynyl, R$_{106}$, haloalkyl, hydroxyalkyl, alkoxyalkyl, and -alkylR$_{106}$;

alternatively, R$_a$ and R$_b$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$; —C(O)OR$_c$, and —C(O)NR$_c$R$_d$; and wherein each of the alkyl, alkenyl and alkynyl is independently substituted with 0, 1 or 2 substituents selected from the group consisting of cyano, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, and R$_q$;

R$_c$ at each occurrence is independently selected from the group consisting of hydrogen, alkyl, alkenyl, alkynyl, and R$_{103}$;

wherein each of the alkyl, alkenyl and alkynyl is independently substituted with 0, 1, 2 or 3 substituents independently selected from the group consisting of cyano, formyl, oxo, halo, nitro, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$;

R$_d$ at each occurrence is independently selected from the group consisting of hydrogen, alkyl, alkenyl, alkynyl, R$_{106}$, haloalkyl, alkoxyalkyl, hydroxyalkyl, and -alkylR$_{106}$;

alternatively, R$_c$ and R$_d$, together with the nitrogen atom to which they are attached, form a ring selected from the group consisting of heterocycle and heteroaryl;

wherein each of the heteroaryl and heterocycle is independently substituted with 0, 1, 2 or 3 substituents independently selected from the group consisting of alkyl, alkenyl, alkynyl, cyano, formyl, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, and —C(O)NR$_f$R$_g$; and wherein each of the alkyl, alkenyl and alkynyl is independently substituted with 0, 1, 2 or 3 substituents independently selected from the group consisting of cyano, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$;

R$_e$ at each occurrence is independently selected from the group consisting of hydrogen, alkyl, alkenyl, alkynyl, R$_{106}$, haloalkyl, and -alkylR$_{106}$;

R$_f$ at each occurrence is independently selected from the group consisting of hydrogen, alkyl, alkenyl, alkynyl, and R$_{103}$;

wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O(R$_{106}$), —NH$_2$, —N(H)(alkyl), —N(alkyl)$_2$, —N(H)

($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

$R_g$ at each occurrence is independently selected from the group consisting of hydrogen, alkyl, alkenyl, alkynyl, $R_{106}$, haloalkyl and -alkyl$R_{106}$;

alternatively, $R_f$ and $R_g$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OH, —O(alkyl), —O(cyanoalkyl), —O(haloalkyl), —O$R_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O$R_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

$R_j$ at each occurrence is independently selected from the group consisting of hydrogen, alkyl, alkenyl, alkynyl, $R_{103}$, haloalkyl and -alkyl$R_{103}$;

$R_k$ at each occurrence is independently selected from the group consisting of hydrogen, alkyl, alkenyl and alkynyl;

alternatively, $R_j$ and $R_k$, together with the carbon atom to which they are attached, form a ring selected from the group consisting of cycloalkyl, cycloalkenyl, heterocycle, aryl and heteroaryl; wherein each ring is independently substituted with 0, 1, 2, 3, 4 or 5 substituents independently selected from the group consisting of alkyl, alkenyl, alkynyl, nitro, cyano, formyl, halo, oxo, —OH, —O(alkyl), —O(cyanoalkyl), —O(haloalkyl), —O$R_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O$R_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

m is 0, 1, 2, 3 or 4;
n is 0, 1, 2, 3 or 4;
p is 0, 1 or 2;
t is 0, 1, 2, 3 or 4.

$R_p$, $R_q$, $R_{1p}$, $R_{1q}$, $R_{2q}$, $R_{3p}$, $R_{3q}$, $R_{4p}$, $R_{4q}$, $R_{7p}$, $R_{7q}$, $R_{8p}$, $R_{8q}$, $R_{9p}$, and $R_{9q}$, at each occurrence, are independently selected from the group consisting of cycloalkyl, cycloalkenyl, aryl, heteroaryl, and heterocycle; wherein each of the $R_p$, $R_q$, $R_{1p}$, $R_{1q}$, $R_{2q}$, $R_{3p}$, $R_{3q}$, $R_{4p}$, $R_{4q}$, $R_{7p}$, $R_{7q}$, $R_{8p}$, $R_{8q}$, $R_{9p}$, and $R_{9q}$, at each occurrence, is independently substituted with 0, 1, 2, 3, 4 or 5 substituents independently selected from the group consisting of alkyl, alkenyl, alkynyl, cyano, formyl, halo, nitro, oxo, —O$R_{101}$, —OC(O)$R_{101}$, —OC(O)O$R_{101}$, —OC(O)N$R_{101}R_{102}$, —OSO$_2R_{101}$, —OSO$_2$N$R_{101}R_{102}$, —S$R_{101}$, —S(O)$R_{101}$, —SO$_2R_{101}$, —SO$_2$O$R_{101}$, —SO$_2$N$R_{101}R_{102}$, —N$R_{101}R_{102}$, —N($R_{102}$)C(O)$R_{101}$, —N($R_{102}$)C(O)O$R_{101}$, —N($R_{102}$)C(O)N$R_{101}R_{102}$, —N($R_{102}$)SO$_2R_{101}$, —N($R_{102}$)SO$_2$N$R_{101}R_{102}$, —N($R_{102}$)SO$_2$N($R_{102}$)C(O)O$R_{101}$, —C(O)$R_{101}$, —C(O)O$R_{101}$, and —C(O)N$R_{101}R_{102}$; and wherein each of the alkyl, alkenyl and alkynyl is independently substituted with 0, 1, 2 or 3 substituents independently selected from the group consisting of cyano, formyl, halo, nitro, oxo, —O$R_{101}$, —OC(O)$R_{101}$, —OC(O)O$R_{101}$, —OC(O)N$R_{101}R_{102}$, —OSO$_2R_{101}$, —OSO$_2$N$R_{101}R_{102}$, —S$R_{101}$, —S(O)$R_{101}$, —SO$_2R_{101}$, —SO$_2$O$R_{101}$, —SO$_2$N$R_{101}R_{102}$, —N$R_{101}R_{102}$, —N($R_{102}$)C(O)$R_{101}$, —N($R_{102}$)C(O)O$R_{101}$, —N($R_{102}$)C(O)N$R_{101}R_{102}$, —N($R_{102}$)SO$_2R_{101}$, —N($R_{102}$)SO$_2$N($R_{102}$)C(O)O$R_{101}$, —C(O)$R_{101}$, —C(O)O$R_{101}$, and —C(O)N$R_{101}R_{102}$;

$R_{101}$ at each occurrence is independently selected from the group consisting of hydrogen, alkyl, alkenyl, alkynyl, $R_{103}$, -alkyl$R_{103}$, -alkenyl$R_{103}$, -alkynyl$R_{103}$, haloalkyl, cyanoalkyl, -alkylC(O)$R_{104}$, -alkylC(O)O$R_{104}$, -alkylC(O)N$R_{104}R_{105}$, -alkyl-O$R_{104}$, -alkyl-OC(O)$R_{104}$, -alkyl-OC(O)O$R_{104}$, -alkylS$R_{104}$, -alkylS(O)$R_{104}$, -alkylSO$_2R_{104}$, -alkylSO$_2$O$R_{104}$, -alkylSO$_2$N$R_{104}R_{105}$, -alkylN$R_{104}R_{105}$, -alkylN($R_{105}$)C(O)$R_{104}$, -alkylN($R_{105}$)C(O)O$R_{104}$, -alkylN($R_{105}$)C(O)N$R_{104}R_{105}$, -alkylN($R_{105}$)SO$_2R_{104}$, and -alkylN($R_{105}$)SO$_2$N$R_{104}R_{105}$;

$R_{103}$ at each occurrence is independently selected from the group consisting of cycloalkyl, cycloalkenyl, aryl, heteroaryl and heterocycle; wherein each $R_{103}$ is independently substituted with 0, 1, 2, 3, 4 or 5 substituents independently selected from the group consisting of alkyl, alkenyl, alkynyl, halo, nitro, cyano, oxo, formyl, haloalkyl, —O$R_{104}$, —OC(O)$R_{104}$, —OC(O)O$R_{104}$, —OC(O)N$R_{104}R_{105}$, —OSO$_2$N$R_{104}R_{105}$, —SO$_2R_{105}$, —S(O)$R_{104}$, —N$R_{104}R_{105}$, —N($R_{105}$)C(O)N$R_{104}R_{105}$, —N($R_{105}$)CO$R_{104}$, —N($R_{105}$)SO$_2R_{104}$, —N($R_{105}$)SO$_2$N$R_{104}R_{105}$, —C(O)$R_{104}$, —C(O)O$R_{104}$, —C(O)N$R_{104}R_{105}$, -alkylO$R_{104}$, -alkylOC(O)$R_{104}$, -alkylOC(O)O$R_{104}$, -alkylOC(O)N$R_{104}R_{105}$, -alkylOSO$_2$N$R_{104}R_{105}$, -alkylSO$_2R_{104}$, -alkylS(O)$R_{104}$, -alkylN$R_{104}R_{105}$, -alkylN($R_{105}$)CO$R_{104}$, -alkylN($R_{105}$)SO$_2R_{104}$, -alkylN($R_{104}$)C(O)N$R_{104}R_{105}$, -alkylN($R_{105}$)SO$_2$N$R_{104}R_{105}$, -alkylC(O)$R_{104}$, -alkylC(O)O$R_{104}$, and -alkylC(O)N$R_{104}R_{105}$;

$R_{102}$, $R_{104}$, and $R_{105}$, at each occurrence, are independently selected from the group consisting of hydrogen, alkyl, alkenyl, alkynyl, hydroxyalkyl, alkoxyalkyl, haloalkyl and benzyl;

alternatively, $R_{101}$ and $R_{102}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

alternatively, $R_{104}$ and $R_{105}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)

Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl; and R$_{106}$ at each occurrence is independently selected from the group consisting of aryl and heteroaryl, wherein each R$_{106}$ is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl.

For example, the first embodiment of the present invention provides a compound of formula (I) wherein R$^5$ is —OR$_d$ wherein R$_d$ is hydrogen.

For example, the first embodiment of the present invention provides a compound of formula (I) wherein R$^6$ is hydrogen or alkyl.

For example, the first embodiment of the present invention provides a compound of formula (I) wherein R$^1$ is —C(O)OR$_a$, —C(O)NR$_a$R$_b$, R$_{1p}$, alkyl or alkenyl; and R$^2$ is alkyl.

For example, the first embodiment of the present invention provides a compound of formula (I) wherein R$^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and R$^2$ is alkyl.

For example, the first embodiment of the present invention provides a compound of formula (I) wherein R$^1$ is
  alkyl, wherein the alkyl is unsubstituted or substituted with 1 or 2 substituents selected from the group consisting of
    halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;
  alkenyl, wherein the alkenyl is unsubstituted or substituted with one substituent selected from the group consisting of
    —C(O)OR$_a$, wherein R$_a$ is alkyl, and
    R$_{1q}$, wherein R$_{1q}$ is aryl,
  —C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$ and wherein R$_{101}$ is alkyl,
  —C(O)NR$_a$R$_b$, wherein R$_a$ is alkyl, or alkyl substituted with one substituent selected from the group consisting of —OC(O)R$_c$, and —OR$_c$ wherein R$_c$ is hydrogen or alkyl, and R$_b$ is alkyl, alternatively, R$_a$ and R$_b$, together with the nitrogen atom to which they are attached, form a heterocyclic ring substituted with one alkyl substitutent wherein the alkyl substituent is substituted with one substituent selected from the group consisting of —OR$_c$, and —OC(O)R$_c$, and wherein R$_c$ is hydrogen or alkyl, or
  R$_{1p}$; wherein R$_{1p}$ is heterocycle; and
R$^2$ is alkyl.

For example, the first embodiment of the present invention provides a compound of formula (I) wherein R$^1$ is
  propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
    halo,
    —OR$_a$, wherein R$_a$ is hydrogen,
    —OC(O)R$_a$, wherein R$_a$ is methyl, ethyl, or isopropyl,
    —OC(O)NR$_a$R$_b$, wherein R$_a$ is methyl, ethyl or isopropyl and R$_b$ is hydrogen,
    —C(O)OR$_a$, wherein R$_a$ is methyl, ethyl, or isopropyl,
    —C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
    —R$_{1q}$; wherein R$_{1q}$ is phenyl, cyclopropyl, cyclobutyl, cyclopentyl or cyclohexyl;
  allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
    —C(O)OR$_a$, wherein R$_a$ is methyl, ethyl or isopropyl, and
    —R$_{1q}$, wherein R$_{1q}$ is aryl,
  —C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
  —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl substitutent wherein the methyl is substituted with one substituent selected from the group consisting of —OR$_c$, and —OC(O)R$_c$, and wherein R$_c$ is hydrogen or methyl, or
  R$_{1p}$; wherein R$_{1p}$ is 4,5-dihydro-1,3-oxazol-2-yl; and
R$^2$ is propyl, butyl, methyl, ethyl, 2-methylbutyl, 3-methylbutyl, 3,3-dimethylbutyl, 5,5-dimethylhexyl, or 3-methylpentyl.

For example, the first embodiment of the present invention provides a compound of formula (I) wherein R$^3$ and R$^4$, together with the carbon atoms to which they are attached, form a ring selected from the group consisting of cycloalkyl, cycloalkenyl, aryl, heterocycle or heteroaryl, wherein each of the ring is substituted with (R$^8$)$_m$.

For example, the first embodiment of the present invention provides a compound of formula (I) wherein R$^3$ and R$^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl.

For example, the first embodiment of the present invention provides a compound of formula (I) wherein R$^3$ and R$^4$ are independently selected from the group consisting of hydrogen and alkyl.

For example, the first embodiment of the present invention provides a compound of formula (I) wherein A is a monocyclic ring selected from the group consisting of cycloalkyl, cycloalkenyl, heterocycle, aryl and heteroaryl.

For example, the first embodiment of the present invention provides a compound of formula (I) wherein A is phenyl, thienyl, furanyl, pyrrolyl, thiazolyl, oxazolyl, imidazolyl, pyrazolyl, pyridyl, pyrimidinyl, pyridazinyl or pyrazinyl.

For example, the first embodiment of the present invention provides a compound of formula (I) wherein A is a bicyclic ring selected from the group consisting of aryl and heteroaryl.

For example, the first embodiment of the present invention provides a compound of formula (I) wherein A is benzimidazolyl, benzthiazolyl or benzoxazolyl.

For example, the first embodiment of the present invention provides a compound of formula (I) wherein $R^5$ is —$OR_d$ wherein $R_d$ is hydrogen, and $R^6$ is hydrogen or alkyl.

For example, the first embodiment of the present invention provides a compound of formula (I) wherein B is

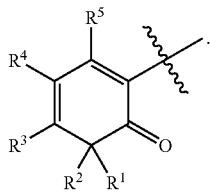

For example, the first embodiment of the present invention provides a compound of formula (I) wherein B is

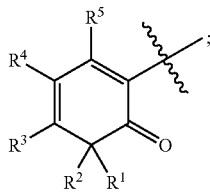

$R^5$ is —$OR_d$ wherein $R_d$ is hydrogen, and $R^6$ is hydrogen or alkyl.

For example, the first embodiment of the present invention provides a compound of formula (I) $R^5$ is —$OR_d$ wherein $R_d$ is hydrogen, $R^6$ is hydrogen or alkyl and $R^3$ and $R^4$, together with the carbon atoms to which they are attached, form a ring selected from the group consisting of cycloalkyl, cycloalkenyl, heterocycle, aryl and heteroaryl.

For example, the first embodiment of the present invention provides a compound of formula (I) wherein B is

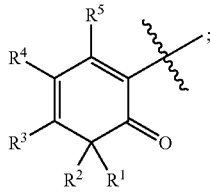

$R^5$ is —$OR_d$ wherein $R_d$ is hydrogen, $R^6$ is hydrogen or alkyl and $R^3$ and $R^4$, together with the carbon atoms to which they are attached, form a ring selected from the group consisting of cycloalkyl, cycloalkenyl, heterocycle, aryl and heteroaryl.

For example, the first embodiment of the present invention provides a compound of formula (I) $R^5$ is —$OR_d$ wherein $R_d$ is hydrogen, $R^6$ is hydrogen or alkyl, and $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl.

For example, the first embodiment of the present invention provides a compound of formula (I) wherein B is

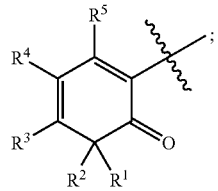

$R^5$ is —$OR_d$ herein $R_d$ is hydrogen, $R^6$ is hydrogen or alkyl, and $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl.

For example, the first embodiment of the present invention provides a compound of formula (I) wherein $R^5$ is —$OR_d$ wherein $R_d$ is hydrogen, $R^6$ is hydrogen or alkyl, and A is a monocyclic ring selected from the group consisting of aryl, cycloalkyl, cycloalkenyl, heterocycle or heteroaryl.

For example, the first embodiment of the present invention provides a compound of formula (I) wherein B is

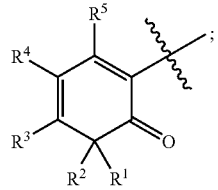

$R^5$ is —$OR_d$ wherein $R_d$ is hydrogen, $R^6$ is hydrogen or alkyl, and A is a monocyclic ring selected from the group consisting of aryl, cycloalkyl, cycloalkenyl, heterocycle or heteroaryl.

For example, the first embodiment of the present invention provides a compound of formula (I) wherein B is

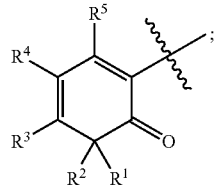

$R^5$ is —$OR_d$ wherein $R_d$ is hydrogen, $R^6$ is hydrogen or alkyl and A is a bicyclic heteroaryl ring.

For example, the first embodiment of the present invention provides a compound of formula (I) wherein $R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl and A is a monocyclic ring selected from the group consisting of aryl, cycloalkyl, cycloalkenyl, heterocycle or heteroaryl.

For example, the first embodiment of the present invention provides a compound of formula (I) wherein B is

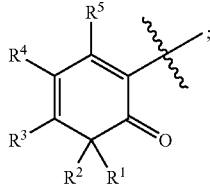

$R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl and A is a monocyclic ring selected from the group consisting of aryl, cycloalkyl, cycloalkenyl, heterocycle or heteroaryl.

For example, the first embodiment of the present invention provides a compound of formula (I) wherein B is

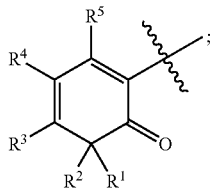

$R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl and A is a monocyclic ring selected from the group consisting of phenyl, thienyl, furanyl, pyrrolyl, thiazolyl, oxazolyl, imidazolyl, pyrazolyl, pyridyl, pyrimidinyl, pyridazinyl and pyrazinyl.

For example, the first embodiment of the present invention provides a compound of formula (I) wherein B is

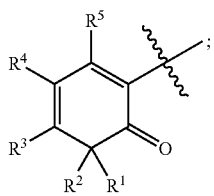

$R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl; A is a monocyclic ring selected from the group consisting of phenyl, thienyl, furanyl, pyrrolyl, thiazolyl, oxazolyl, imidazolyl, pyrazolyl, pyridyl, pyrimidinyl, pyridazinyl and pyrazinyl; $R^1$ is —$C(O)OR_a$, —$C(O)NR_aR_b$, $R_{1p}$, alkyl or alkenyl; and $R^2$ is alkyl.

For example, the first embodiment of the present invention provides a compound of formula (I) wherein B is

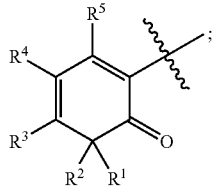

$R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl; A is a monocyclic ring selected from the group consisting of phenyl, thienyl, furanyl, pyrrolyl, thiazolyl, oxazolyl, imidazolyl, pyrazolyl, pyridyl, pyrimidinyl, pyridazinyl and pyrazinyl; $R^1$ is —$C(O)OR_a$, —$C(O)NR_aR_b$, $R_{1p}$, alkyl or alkenyl, wherein the alkyl and alkenyl are independently substituted with 0, 1 or 2 substituents selected from the group consisting of halo, —$OR_a$, —$OC(O)R_a$, —$OC(O)NR_aR_b$, —$C(O)OR_a$, —$C=CR_jR_k$, and —$R_{1q}$; and $R^2$ is alkyl.

For example, the first embodiment of the present invention provides a compound of formula (I) wherein B is

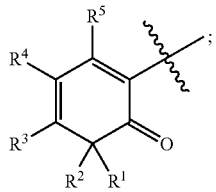

$R^5$ is —$OR_d$ wherein $R_d$ is hydrogen, $R^6$ is hydrogen or alkyl, $R^3$ and $R^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl; A is a monocyclic ring selected from the group consisting of phenyl, thienyl, furanyl, pyrrolyl, thiazolyl, oxazolyl, imidazolyl, pyrazolyl, pyridyl, pyrimidinyl, pyridazinyl and pyrazinyl; $R^1$ is alkyl, wherein the alkyl is unsubstituted or substituted with 1 or 2 substituents selected from the group consisting of halo,
- —$OR_a$, wherein $R_a$ is hydrogen,
- —$OC(O)R_a$, wherein $R_a$ is alkyl,
- —$OC(O)NR_aR_b$, wherein $R_a$ is alkyl, $R_b$ is hydrogen,
- —$C(O)OR_a$, wherein $R_a$ is alkyl,
- —$C=CR_jR_k$, wherein $R_j$ and $R_k$ together with the carbon atom to which they are attached form a cycloalkyl ring; and
- —$R_{1q}$; wherein $R_{1q}$ is aryl or cycloalkyl;

alkenyl, wherein the alkenyl is unsubstituted or substituted with one substituent selected from the group consisting of
- —$C(O)OR_a$, wherein $R_a$ is alkyl, and
- —$R_{1q}$, wherein $R_{1q}$ is aryl, —C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$ and wherein R$^{101}$ is alkyl, —C(O)NR$_a$R$_b$, wherein R$_a$ is alkyl, or alkyl substituted with one substituent selected from the group consisting of —OC(O)R$_c$, and —OR$_c$ wherein R$_c$ is hydrogen or alkyl, and R$_b$ is alkyl, alternatively, R$_a$ and R$_b$, together with the nitrogen atom to which they are attached, form a heterocyclic ring substituted with one alkyl substitutent wherein the alkyl substituent is substituted with one substituent selected from the group consisting of —OR$_c$, and —OC(O)R$_c$, and wherein R$_c$ is hydrogen or alkyl, or R$_{1p}$; wherein R$_{1p}$ is heterocycle; and
R$^2$ is alkyl.

For example, the first embodiment of the present invention provides a compound of formula (I) wherein B is

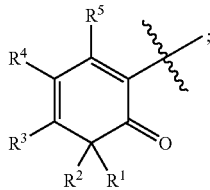

R$^5$ is —OR$_d$ wherein R$_d$ is hydrogen, R$^6$ is hydrogen or alkyl, R$^3$ and R$^4$, together with the carbon atoms to which they are attached, form a ring selected from the group consisting of cyclopentyl, cyclohexyl, cycloheptyl, cyclopentenyl, cyclohexenyl, cycloheptenyl, phenyl, thienyl, furanyl, pyrrolyl, thiazolyl, oxazolyl, imidazolyl, pyrazolyl, pyridyl, pyrimidinyl, pyridazinyl and pyrazinyl; A is a monocyclic ring selected from the group consisting of phenyl, thienyl, furanyl, pyrrolyl, thiazolyl, oxazolyl, imidazolyl, pyrazolyl, pyridyl, pyrimidinyl, pyridazinyl and pyrazinyl; R$^1$ is propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of halo,
—OR$_a$, wherein R$_a$ is hydrogen,
—OC(O)R$_a$, wherein R$_a$ is methyl, ethyl, or isopropyl,
—OC(O)NR$_a$R$_b$, wherein R$_a$ is methyl, ethyl or isopropyl and R$_b$ is hydrogen,
—C(O)OR$_a$, wherein R$_a$ is methyl, ethyl, or isopropyl,
—C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
—R$_{1q}$; wherein R$_{1q}$ is phenyl, cyclopropyl, cyclobutyl, cyclopentyl or cyclohexyl;

allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—C(O)OR$_a$, wherein R$_a$ is methyl, ethyl or isopropyl, and
R$_{1q}$, wherein R$_{1q}$ is aryl,
—C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl, —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$ wherein R$_c$ is hydrogen or methyl, and R$_b$ is methyl, alternatively, R$_a$ and R$_b$, together with the nitrogen atom to which they are attached, form a pyrrolidine ring substituted with one methyl substitutent wherein the methyl is substituted with one substituent selected from the group consisting of —OR$_c$, and —OC(O)R$_c$, and wherein R$_c$ is hydrogen or methyl, or R$_{1p}$; wherein R$_{1p}$ is 4,5-dihydro-1,3-oxazol-2-yl; and R$^2$ is propyl, butyl, methyl, ethyl, 2-methylbutyl, 3-methylbutyl, 3,3-dimethylbutyl, 5,5-dimethylhexyl, or 3-methylpentyl.

Accordingly, a second embodiment of this invention is directed to a compound of formula (II)

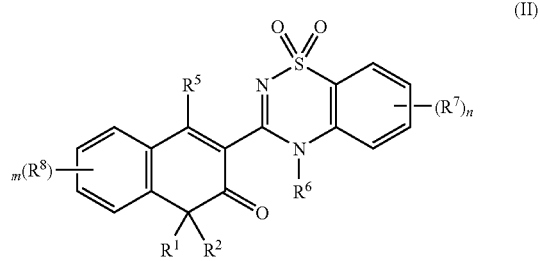

(II)

or a pharmaceutically acceptable form, stereoisomer, or tautomer, or combination thereof, wherein:

R$^1$ is hydrogen, alkyl, alkenyl, alkynyl, —C(O)OR$_a$, —C(O)NR$_a$R$_b$ or R$_{1p}$;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, —C(R$_e$)=CR$_j$R$_k$, and R$_{1q}$;

R$^2$ is hydrogen, alkyl, alkenyl or alkynyl;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$R$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, and R$_{2q}$;

alternatively, R$^1$ and R$^2$, together with the carbon atom to which they are attached, form a monocyclic ring selected from the group consisting of cycloalkyl and cycloalkenyl;

wherein each of the cycloalkyl and cycloalkenyl is unsubstituted or substituted with 1, 2 or 3 substituents selected from the group consisting of halo, —OH, —O(alkyl), —NH$_2$, —N(H)(alkyl), —N(alkyl)$_2$, alkyl and haloalkyl;

$R^5$ is —$OR_d$, —$SR_d$, —$NR_dR_e$, —N(H)C(O)$R_d$, —N(H)C(O)O$R_d$, —N(H)SO$_2R_d$, or —N(H)SO$_2NR_dR_e$;

$R^6$ is hydrogen, alkyl, alkenyl, alkynyl or -alkyl$R_{106}$;

$R^7$ at each occurrence is independently selected from the group consisting of cyano, formyl, nitro, oxo, halo, alkyl, alkenyl, alkynyl, —$OR_a$, —OC(O)$R_a$, —OC(O)O$R_a$, —OC(O)N$R_aR_b$, —OP(=O)($R_e$)(O$R_e$), —OSO$_2R_a$, —OSO$_2$N$R_aR_b$, —S$R_a$, —S(O)$R_a$, —SO$_2R_a$, —SO$_2$O$R_a$, —SO$_2$N$R_aR_b$, —N$R_aR_b$, —N($R_e$)C(=NH)$R_e$, —N($R_e$)C(=Nalkyl)$R_e$, —N($R_e$)C(O)$R_a$, —N($R_e$)C(O)N$R_aR_b$, —N($R_e$)C(=S)N$R_aR_b$, —N($R_e$)C(=S)N($R_e$)C(O)$R_a$, —N($R_e$)C(O)O$R_a$, —N($R_e$)SO$R_a$, —N($R_e$)SO$_2R_a$, —N($R_e$)SO$_2$N$R_aR_b$, —N($R_e$)SO$_2$N($R_e$)C(O)$R_a$, —N($R_e$)SO$_2$N($R_e$)C(O)O$R_a$, —C(O)$R_a$, —C(O)O$R_a$, —C(O)N$R_aR_b$, and $R_{7p}$;

wherein each of the alkyl, alkenyl and alkynyl is independently substituted with 0, 1, 2 or 3 substituents selected from the group consisting of cyano, formyl, oxo, nitro, halo, —N$_3$, —O$R_a$, —OC(O)$R_a$, —OC(O)O$R_a$, —OC(O)N$R_aR_b$, —OSO$_2R_a$, —OSO$_2$N$R_aR_b$, —S$R_a$, —S(O)$R_a$, —SO$_2R_a$, —SO$_2$O$R_a$, —SO$_2$N$R_aR_b$, —N$R_aR_b$, —N($R_e$)C(O)$R_a$, —N($R_e$)C(O)N$R_aR_b$, —N($R_e$)C(O)O$R_a$, —N($R_e$)SO$R_a$, N($R_e$)SO$_2R_a$, —N($R_e$)SO$_2$N$R_aR_b$, —N($R_e$)SO$_2$N($R_e$)C(O)$R_a$, —N($R_e$)SO$_2$N($R_e$)C(O)O$R_a$, —C(O)$R_a$, —C(O)O$R_a$, —C(O)N$R_aR_b$, and $R_{7q}$;

$R^8$ at each occurrence is independently selected from the group consisting of cyano, formyl, nitro, oxo, halo, alkyl, alkenyl, alkynyl, —O$R_a$, —OC(O)$R_a$, —OC(O)O$R_a$, —OC(O)N$R_aR_b$, —OSO$_2R_a$, —OSO$_2$N$R_aR_b$, —S$R_a$, —S(O)$R_a$, —SO$_2R_a$, —SO$_2$O$R_a$, —SO$_2$N$R_aR_b$, —N$R_aR_b$, —N($R_e$)C(O)$R_a$, —N($R_e$)C(O)N$R_aR_b$, —N($R_e$)C(O)O$R_a$, —N($R_e$)SO$_2R_a$, —N($R_e$)SO$_2$N$R_aR_b$, —N($R_e$)SO$_2$N($R_e$)C(O)O$R_a$, —C(O)$R_a$, —C(O)O$R_a$, —C(O)N$R_aR_b$, and $R_{8p}$;

wherein each of the alkyl, alkenyl and alkynyl is independently substituted with 0, 1, 2 or 3 substituents selected from the group consisting of cyano, formyl, nitro, oxo, halo, —O$R_a$, —OC(O)$R_a$, —OC(O)O$R_a$, —OC(O)N$R_aR_b$, —OSO$_2R_a$, —OSO$_2$N$R_aR_b$, —S$R_a$, —S(O)$R_a$, —SO$_2R_a$, —SO$_2$O$R_a$, —SO$_2$N$R_aR_b$, —N$R_aR_b$, —N($R_e$)C(O)$R_a$, —N($R_e$)C(O)N$R_aR_b$, —N($R_e$)C(O)O$R_a$, —N($R_e$)SO$_2R_a$, —N($R_e$)SO$_2$N$R_aR_b$, —N($R_e$)SO$_2$N($R_e$)C(O)O$R_a$, —C(O)$R_a$, —C(O)O$R_a$, —C(O)N$R_aR_b$, and $R_{8q}$;

$R_a$ at each occurrence is independently selected from the group consisting of hydrogen, alkyl, alkenyl, alkynyl, and $R_p$;

wherein each of the alkyl, alkenyl and alkynyl is independently substituted with 0, 1, 2 or 3 substituents independently selected from the group consisting of cyano, formyl, oxo, halo, nitro, —O$R_c$, —OC(O)$R_c$, —OC(O)O$R_c$, —OC(O)N$R_cR_d$, —OSO$_2R_c$, —OSO$_2$N$R_cR_d$, —S$R_c$, —S(O)$R_c$, —SO$_2R_c$, —SO$_2$O$R_c$, —SO$_2$N$R_cR_d$, —N$R_cR_d$, —N($R_e$)C(O)$R_c$, —N($R_e$)C(O)N$R_cR_d$, —N($R_e$)C(O)O$R_c$, —N($R_e$)SO$_2R_c$, —N($R_e$)SO$_2$N$R_cR_d$, —N($R_e$)SO$_2$N($R_e$)C(O)O$R_c$, —C(O)$R_c$, —C(O)O$R_c$, —C(O)N$R_cR_d$, —C(O)N($R_e$)N$R_cR_d$, and $R_q$;

$R_b$ at each occurrence is independently selected from the group consisting of hydrogen, alkyl, alkenyl, alkynyl, $R_{106}$, haloalkyl, hydroxyalkyl, alkoxyalkyl, and -alkyl$R_{106}$;

alternatively, $R_a$ and $R_b$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —O$R_c$, —OC(O)$R_c$, —OC(O)O$R_c$, —OC(O)N$R_cR_d$, —OSO$_2R_c$, —OSO$_2$N$R_cR_d$, —S$R_c$, —S(O)$R_c$, —SO$_2R_c$, —SO$_2$O$R_c$, —SO$_2$N$R_cR_d$, —N$R_cR_d$, —N($R_e$)C(O)$R_c$, —N($R_e$)C(O)N$R_cR_d$, —N($R_e$)C(O)O$R_c$, —N($R_e$)SO$_2R_c$, —N($R_e$)SO$_2$N$R_cR_d$, —N($R_e$)SO$_2$N($R_e$)C(O)O$R_c$, —C(O)$R_c$, —C(O)O$R_c$, and —C(O)N$R_cR_d$; and wherein each of the alkyl, alkenyl and alkynyl is independently substituted with 0, 1 or 2 substituents selected from the group consisting of cyano, halo, nitro, oxo, —O$R_c$, —OC(O)$R_c$, —OC(O)O$R_c$, —OC(O)N$R_cR_d$, —OSO$_2R_c$, —OSO$_2$N$R_cR_d$, —S$R_c$, —S(O)$R_c$, —SO$_2R_c$, —SO$_2$O$R_c$, —SO$_2$N$R_cR_d$, —N$R_cR_d$, —N($R_e$)C(O)$R_c$, —N($R_e$)C(O)N$R_cR_d$, —N($R_e$)C(O)O$R_c$, —N($R_e$)SO$_2R_c$, —N($R_e$)SO$_2$N($R_e$)C(O)O$R_c$, —C(O)$R_c$, —C(O)O$R_c$, —C(O)N$R_cR_d$, and $R_q$;

$R_c$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, formyl, oxo, halo, nitro, —O$R_f$, —OC(O)$R_f$, —OC(O)O$R_f$, —OC(O)N$R_fR_g$, —OSO$_2R_f$, —OSO$_2$N$R_fR_g$, —S$R_f$, —S(O)$R_f$, —SO$_2R_f$, —SO$_2$O$R_f$, —SO$_2$N$R_fR_g$, —N$R_fR_g$, —N($R_e$)C(O)$R_f$, —N($R_e$)C(O)N$R_fR_g$, —N($R_e$)C(O)O$R_f$, —N($R_e$)SO$_2R_f$, —N($R_e$)SO$_2$N$R_fR_g$, —N($R_e$)SO$_2$N($R_e$)C(O)O$R_f$, —C(O)$R_f$, —C(O)O$R_f$, —C(O)N$R_fR_g$, and $R_{103}$;

$R_d$ at each occurrence is independently selected from the group consisting of hydrogen, alkyl, alkenyl, alkynyl, $R_{106}$, haloalkyl, alkoxyalkyl, hydroxyalkyl, and -alkyl$R_{106}$;

alternatively, $R_c$ and $R_d$, together with the nitrogen atom to which they are attached, form a ring selected from the group consisting of heterocycle and heteroaryl;

wherein each of the heteroaryl and heterocycle is independently substituted with 0, 1, 2 or 3 substituents independently selected from the group consisting of alkyl, alkenyl, alkynyl, cyano, formyl, halo, nitro, oxo, —O$R_f$, —OC(O)$R_f$, —OC(O)O$R_f$, —OC(O)N$R_fR_g$, —OSO$_2R_f$, —OSO$_2$N$R_fR_g$, —S$R_f$, —S(O)$R_f$, —SO$_2R_f$, —SO$_2$O$R_f$, —SO$_2$N$R_fR_g$, —N$R_fR_g$, —N($R_e$)C(O)$R_f$, —N($R_e$)C(O)N$R_fR_g$, —N($R_e$)C(O)O$R_f$, —N($R_e$)SO$_2R_f$, —N($R_e$)SO$_2$N$R_fR_g$, —N($R_e$)SO$_2$N($R_e$)C(O)O$R_f$, —C(O)$R_f$, —C(O)O$R_f$, and —C(O)N$R_fR_g$; and wherein each of the alkyl, alkenyl and alkynyl is independently substituted with 0, 1, 2 or 3 substituents independently selected from the group consisting of cyano, halo, nitro, oxo, —O$R_f$, —OC(O)$R_f$, —OC(O)O$R_f$, —OC(O)N$R_fR_g$, —OSO$_2R_f$, —OSO$_2$N$R_fR_g$, —S$R_f$, —S(O)$R_f$, —SO$_2R_f$, —SO$_2$O$R_f$, —SO$_2$N$R_fR_g$, —N$R_fR_g$, —N($R_e$)C(O)$R_f$, —N($R_e$)C(O)N$R_fR_g$, —N($R_e$)C(O)O$R_f$, —N($R_e$)SO$_2R_f$, —N($R_e$)SO$_2$N$R_fR_g$, —N($R_e$)SO$_2$N($R_e$)C(O)O$R_f$, —C(O)$R_f$, —C(O)O$R_f$, —C(O)N$R_fR_g$, and $R_{103}$;

$R_e$ at each occurrence is independently selected from the group consisting of hydrogen, alkyl, alkenyl, alkynyl, $R_{106}$, haloalkyl, and -alkyl$R_{106}$;

$R_f$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O($R_{106}$), —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

$R_g$ at each occurrence is independently selected from the group consisting of hydrogen, alkyl, alkenyl, alkynyl, $R_{106}$, haloalkyl and -alkyl$R_{106}$;

alternatively, $R_f$ and $R_g$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

R$_j$ at each occurrence is independently selected from the group consisting of hydrogen, alkyl, alkenyl, alkynyl, R$_{103}$, haloalkyl and -alkylR$_{103}$;

R$_k$ at each occurrence is independently selected from the group consisting of hydrogen, alkyl, alkenyl and alkynyl;

alternatively, R$_j$ and R$_k$, together with the carbon atom to which they are attached, form a ring selected from the group consisting of cycloalkyl, cycloalkenyl, heterocycle, aryl and heteroaryl; wherein each ring is independently substituted with 0, 1, 2, 3, 4 or 5 substituents independently selected from the group consisting of alkyl, alkenyl, alkynyl, nitro, cyano, formyl, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

m is 0, 1, 2, 3 or 4;

n is 0, 1, 2, 3 or 4;

R$_p$, R$_q$, R$_{1p}$, R$_{1q}$, R$_{2q}$, R$_{7p}$, R$_{7q}$, R$_{8p}$, and R$_{8q}$, at each occurrence, are independently selected from the group consisting of cycloalkyl, cycloalkenyl, aryl, heteroaryl, and heterocycle; wherein each of the R$_p$, R$_q$, R$_{1p}$, R$_{1q}$, R$_{2q}$, R$_{7p}$, R$_{7q}$, R$_{8p}$, and R$_{8q}$, at each occurrence, is independently substituted with 0, 1, 2, 3, 4 or 5 substituents selected from the group consisting of alkyl, alkenyl, alkynyl, cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, —SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{101}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$; and wherein each of the alkyl, alkenyl and alkynyl is independently substituted with 0, 1, 2 or 3 substituents independently selected from the group consisting of cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, —SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{10l}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$;

R$_{101}$ at each occurrence is independently selected from the group consisting of hydrogen, alkyl, alkenyl, alkynyl, R$_{103}$, -alkylR$_{103}$, -alkenylR$_{103}$, -alkynylR$_{103}$, haloalkyl, cyanoalkyl, -alkylC(O)R$_{104}$, -alkylC(O)OR$_{104}$, -alkylC(O)NR$_{104}$R$_{105}$, -alkyl-OR$_{104}$, -alkyl-OC(O)R$_{104}$, -alkyl-OC(O)OR$_{104}$, -alkylSR$_{104}$, -alkylS(O)R$_{104}$, -alkylSO$_2$R$_{104}$, -alkylSO$_2$OR$_{104}$, -alkylSO$_2$NR$_{104}$R$_{105}$, -alkylNR$_{104}$R$_{105}$, -alkylN(R$_{105}$)C(O)R$_{104}$, -alkylN(R$_{105}$)C(O)OR$_{104}$, -alkylN(R$_{105}$)C(O)NR$_{104}$R$_{105}$, -alkylN(R$_{105}$)SO$_2$R$_{104}$, and -alkylN(R$_{105}$)SO$_2$NR$_{104}$R$_{105}$;

R$_{103}$ at each occurrence is independently selected from the group consisting of cycloalkyl, cycloalkenyl, aryl, heteroaryl and heterocycle; wherein each R$_{103}$ is independently substituted with 0, 1, 2, 3, 4 or 5 substituents independently selected from the group consisting of alkyl, alkenyl, alkynyl, halo, nitro, cyano, oxo, formyl, haloalkyl, —OR$_{104}$, —OC(O)R$_{104}$, —OC(O)OR$_{104}$, —OC(O)NR$_{104}$R$_{105}$, —OSO$_2$NR$_{104}$R$_{105}$, —SO$_2$R$_{105}$, —S(O)R$_{104}$, —NR$_{104}$R$_{105}$, —N(R$_{105}$)C(O)NR$_{104}$R$_{105}$, —N(R$_{105}$)COR$_{104}$, —N(R$_{105}$)SO$_2$R$_{104}$, —N(R$_{105}$)SO$_2$NR$_{104}$R$_{105}$, —C(O)R$_{104}$, —C(O)OR$_{104}$, —C(O)NR$_{104}$R$_{105}$, -alkylOR$_{104}$, -alkylOC(O)R$_{104}$, -alkylOC(O)OR$_{104}$, -alkylOC(O)NR$_{104}$R$_{105}$, -alkylOSO$_2$NR$_{104}$R$_{105}$, -alkylSO$_2$R$_{104}$, -alkylS(O)R$_{104}$, -alkylNR$_{104}$R$_{105}$, -alkylN(R$_{105}$)COR$_{104}$, -alkylN(R$_{105}$)SO$_2$R$_{104}$, -alkylN(R$_{104}$)C(O)NR$_{104}$R$_{105}$, -alkylN(R$_{105}$)SO$_2$NR$_{104}$R$_{105}$, -alkylC(O)R$_{104}$, -alkylC(O)OR$_{104}$, and -alkylC(O)NR$_{104}$R$_{105}$;

R$_{102}$, R$_{104}$, and R$_{105}$, at each occurrence, are independently selected from the group consisting of hydrogen, alkyl, alkenyl, alkynyl, hydroxyalkyl, alkoxyalkyl, haloalkyl and benzyl;

alternatively, R$_{101}$ and R$_{102}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

alternatively, R$_{104}$ and R$_{105}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl; and R$_{106}$ at each occurrence is independently selected from the group consisting of aryl and heteroaryl, wherein each R$_{106}$ is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN (H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl.

For example, the second embodiment of the present invention provides a compound of formula (II) wherein $R^5$ is —OR$_d$ wherein R$_d$ is hydrogen.

For example, the second embodiment of the present invention provides a compound of formula (II) wherein $R^6$ is hydrogen or alkyl.

For example, the second embodiment of the present invention provides a compound of formula (II) wherein $R^1$ is —C(O)OR$_a$, —C(O)NR$_a$R$_b$, R$_{1p}$, alkyl or alkenyl; and $R^2$ is alkyl.

For example, the second embodiment of the present invention provides a compound of formula (II) wherein $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and $R^2$ is alkyl.

For example, the second embodiment of the present invention provides a compound of formula (II) wherein $R^1$ is
  alkyl, wherein the alkyl is unsubstituted or substituted with 1 or 2 substituents selected from the group consisting of halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;
  alkenyl, wherein the alkenyl is unsubstituted or substituted with one substituent selected from the group consisting of
    —C(O)OR$_a$, wherein R$_a$ is alkyl, and
    R$_{1q}$, wherein R$_{1q}$ is aryl,
  —C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$ and wherein R$_{101}$ is alkyl,
  —C(O)NR$_a$R$_a$, wherein R$_a$ is alkyl, or alkyl substituted with one substituent selected from the group consisting of —OC(O)R$_c$, and —OR$_c$ wherein R$_c$ is hydrogen or alkyl, and R$_b$ is alkyl, alternatively, R$_a$ and R$_b$, together with the nitrogen atom to which they are attached, form a heterocyclic ring substituted with one alkyl substitutent wherein the alkyl substituent is substituted with one substituent selected from the group consisting of —OR$_c$, and —OC(O)R$_c$, and wherein R$_c$ is hydrogen or alkyl, or
  R$_{1p}$; wherein R$_{1p}$ is heterocycle; and
  $R^2$ is alkyl.

For example, the second embodiment of the present invention provides a compound of formula (II) wherein $R^1$ is
  propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
    halo,
    —OR$_a$, wherein R$_a$ is hydrogen,
    —OC(O)R$_a$, wherein R$_a$ is methyl, ethyl, or isopropyl,
    —OC(O)NR$_a$R$_b$, wherein R$_a$ is methyl, ethyl or isopropyl and R$_b$ is hydrogen,
    —C(O)OR$_a$, wherein R$_a$ is methyl, ethyl, or isopropyl,
    —C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
    —R$_{1q}$; wherein R$_{1q}$ is phenyl, cyclopropyl, cyclobutyl, cyclopentyl or cyclohexyl;
  allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
    —C(O)OR$_a$, wherein R$_a$ is methyl, ethyl or isopropyl, and
    —R$_{1q}$, wherein R$_{1q}$ is aryl,
  —C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
  —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substituent selected from the group consisting of —OR$_c$, and —OC(O)R$_c$, and wherein R$_c$ is hydrogen or methyl, or
  R$_{1p}$; wherein R$_{1p}$ is 4,5-dihydro-1,3-oxazol-2-yl; and
  $R^2$ is propyl, butyl, methyl, ethyl, 2-methylbutyl, 3-methylbutyl, 3,3-dimethylbutyl, 5,5-dimethylhexyl, or 3-methylpentyl.

For example, the second embodiment of the present invention provides a compound of formula (II) wherein $R^5$ is —OR$_d$ wherein R$_d$ is hydrogen, and $R^6$ is hydrogen or alkyl.

For example, the second embodiment of the present invention provides a compound of formula (II) wherein $R^5$ is —OR$_d$ wherein R$_d$ is hydrogen, $R^6$ is hydrogen or alkyl, $R^1$ is —C(O)OR$_a$, —C(O)NR$_a$R$_b$, R$_{1p}$, alkyl or alkenyl; and $R^2$ is alkyl.

For example, the second embodiment of the present invention provides a compound of formula (II) wherein $R^5$ is —OR$_d$ wherein R$_d$ is hydrogen, $R^6$ is hydrogen or alkyl, $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and $R^2$ is alkyl.

For example, the second embodiment of the present invention provides a compound of formula (II) wherein $R^5$ is —OR$_d$ wherein R$_d$ is hydrogen, $R^6$ is hydrogen or alkyl, $R^1$ is
  alkyl, wherein the alkyl is unsubstituted or substituted with 1 or 2 substituents selected from the group consisting of halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;

alkenyl, wherein the alkenyl is unsubstituted or substituted with one substituent selected from the group consisting of
— $C(O)OR_a$, wherein $R_a$ is alkyl, and
— $R_{1q}$, wherein $R_{1q}$ is aryl,
— $C(O)OR_a$, wherein $R_a$ is alkyl, or alkyl substituted with one $R_{1q}$, wherein $R_{1q}$ is a heterocyclic ring, unsubstituted or substituted with one — $C(O)OR_{101}$ and wherein $R_{101}$ is alkyl,
— $C(O)NR_aR_b$, wherein $R_a$ is alkyl, or alkyl substituted with one substituent selected from the group consisting of — $OC(O)R_c$, and — $OR_c$ wherein $R_c$ is hydrogen or alkyl, and $R_b$ is alkyl, alternatively, $R_a$ and $R_b$, together with the nitrogen atom to which they are attached, form a heterocyclic ring substituted with one alkyl substitutent wherein the alkyl substituent is substituted with one substituent selected from the group consisting of — $OR_c$, and — $OC(O)R_c$, and wherein $R_c$ is hydrogen or alkyl, or
$R_{1p}$; wherein $R_{1p}$ is heterocycle; and
$R^2$ is alkyl.

For example, the second embodiment of the present invention provides a compound of formula (II) wherein $R^5$ is — $OR_d$ wherein $R_d$ is hydrogen, $R^6$ is hydrogen or methyl, $R^1$ is
propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
halo,
— $OR_a$, wherein $R_a$ is hydrogen,
— $OC(O)R_a$, wherein $R_a$ is methyl, ethyl, or isopropyl,
— $OC(O)NR_aR_b$, wherein $R_a$ is methyl, ethyl or isopropyl and $R_b$ is hydrogen,
— $C(O)OR_a$, wherein $R_a$ is methyl, ethyl, or isopropyl,
— $C=CR_jR_k$, wherein $R_j$ and $R_k$ together with the carbon atom to which they are attached form a ring selected from the group consisting of cyclopropyl, cyclobutyl, cyclopentyl and cyclohexyl,
— $R_{1q}$; wherein $R_{1q}$ is phenyl, cyclopropyl, cyclobutyl, cyclopentyl or cyclohexyl;
allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
— $C(O)OR_a$, wherein $R_a$ is methyl, ethyl or isopropyl, and
— $R_{1q}$, wherein $R_{1q}$ is aryl,
— $C(O)OR_a$, wherein $R_a$ is methyl, ethyl or isopropyl, wherein each of the methyl, ethyl or isopropyl is unsubstituted or substituted with one $R_{1q}$, wherein $R_{1q}$ is a pyrrolidine ring, unsubstituted or substituted with one — $C(O)OR_{101}$, wherein $R_{101}$ is methyl, ethyl or isopropyl,
— $C(O)NR_aR_b$, wherein $R_a$ is methyl or ethyl, wherein each of the methyl or ethyl is unsubstituted or substituted with one substituent selected from the group consisting of — $OC(O)R_c$, and — $OR_c$ wherein $R_c$ is hydrogen or methyl, and $R_b$ is methyl, alternatively, $R_a$ and $R_b$, together with the nitrogen atom to which they are attached, form a pyrrolidine ring substituted with one methyl wherein the methyl is substituted with one substituent selected from the group consisting of — $OR_c$, and — $OC(O)R_c$, and wherein $R_c$ is hydrogen or methyl, or
$R_{1p}$; wherein $R_{1p}$ is 4,5-dihydro-1,3-oxazol-2-yl; and
$R^2$ is propyl, butyl, methyl, ethyl, 2-methylbutyl, 3-methylbutyl, 3,3-dimethylbutyl, 5,5-dimethylhexyl, or 3-methylpentyl.

For example, the second embodiment of the present invention provides a compound of formula (II) wherein $R^5$ is — $OR_d$ wherein $R_d$ is hydrogen, $R^6$ is hydrogen or alkyl, $R^1$ is — $C(O)OR_a$, — $C(O)NR_aR_b$, $R_{1p}$, alkyl or alkenyl, $R^2$ is alkyl, $R^7$ is formyl, — $OR_a$, — $OP(=O)(R_e)(OR_e)$, — $NR_aR_b$, — $N(R_e)C(=NH)R_e$, — $N(R_e)C(O)R_a$, — $N(R_e)C(O)NR_aR_b$, — $N(R_e)C(=S)NR_aR_b$, — $N(R_e)C(=S)N(R_e)C(O)R_a$, — $N(R_e)C(O)OR_a$, — $N(R_e)SOR_a$, — $N(R_e)SO_2R_a$, — $N(R_e)SO_2NR_aR_b$, — $N(R_e)SO_2N(R_e)C(O)R_a$, — $N(R_e)SO_2N(R_e)C(O)OR_a$, or alkyl substituted with one substituent selected from the group consisting of $N_3$, — $OR_a$, — $NR_aR_b$, — $N(R_e)SOR_a$, — $N(R_e)SO_2R_a$, — $N(R_e)SO_2NR_aR_b$, — $N(R_e)SO_2N(R_e)C(O)OR_a$, — $C(O)NR_aR_a$ and $R_{7q}$, and n is 0 or 1.

For example, the second embodiment of the present invention provides a compound of formula (II) wherein $R^5$ is — $OR_d$ wherein $R_d$ is hydrogen; $R^6$ is hydrogen or alkyl; $R^1$ is
alkyl, wherein the alkyl is unsubstituted or substituted with 1 or 2 substituents selected from the group consisting of
halo,
— $OR_a$, wherein $R_a$ is hydrogen,
— $OC(O)R_a$, wherein $R_a$ is alkyl,
— $OC(O)NR_aR_b$, wherein $R_a$ is alkyl, $R_b$ is hydrogen,
— $C(O)OR_a$, wherein $R_a$ is alkyl,
— $C=CR_jR_k$, wherein $R_j$ and $R_k$, together with the carbon atom to which they are attached form a cycloalkyl ring; and
— $R_{1q}$; wherein $R_{1q}$ is aryl or cycloalkyl;
alkenyl, wherein the alkenyl is unsubstituted or substituted with one substituent selected from the group consisting of
— $C(O)OR_a$, wherein $R_a$ is alkyl, and
— $R_{1q}$, wherein $R_{1q}$ is aryl,
— $C(O)OR_a$, wherein $R_a$ is alkyl, or alkyl substituted with one $R_{1q}$, wherein $R_{1q}$ is a heterocyclic ring, unsubstituted or substituted with one — $C(O)OR_{101}$ and wherein $R_{101}$ is alkyl,
— $C(O)NR_aR_b$, wherein $R_a$ is alkyl, or alkyl substituted with one substituent selected from the group consisting of — $OC(O)R_c$, and — $OR_c$ wherein $R_c$ is hydrogen or alkyl, and $R_b$ is alkyl, alternatively, $R_a$ and $R_b$, together with the nitrogen atom to which they are attached, form a heterocyclic ring substituted with one alkyl substitutent wherein the alkyl substituent is substituted with one substituent selected from the group consisting of — $OR_c$, and — $OC(O)R_c$, and wherein $R_c$ is hydrogen or alkyl, or
$R_{1p}$; wherein $R_{1p}$ is heterocycle;
$R^2$ is alkyl;
$R^7$ is
formyl,
— $OR_a$, wherein $R_a$ is hydrogen, or alkyl substituted with one substituent selected from the group consisting of cyano and — $C(O)NR_cR_d$, wherein $R_c$ is hydrogen, and $R_d$ is hydrogen,
— $OP(=O)(R_e)(OR_e)$, wherein $R_e$ at each occurrence is independently selected from the group consisting of hydrogen and alkyl, —NR$_a$R$_b$, wherein R$_a$ is hydrogen or alkyl substituted with one cyano, and R$_b$ is hydrogen, —N(R$_e$)C(=NH)R$_e$, wherein R$_e$ at each occurrence is independently selected from the group consisting of hydrogen and alkyl, —N(R$_e$)C(O)R$_a$, wherein R$_a$ is alkyl, or alkyl substituted with 1, 2 or 3 halo, and R$_e$ is hydrogen or alkyl, —N(R$_e$)C(O)NR$_a$R$_b$, wherein R$_a$ is hydrogen, R$_b$ is hydrogen, and R$_e$ is hydrogen or alkyl, —N(R$_e$)C(=S)NR$_a$R$_b$, wherein R$_a$ is hydrogen, R$_b$ is hydrogen, and R$_e$ is hydrogen or alkyl, —N(R$_e$)C(=S)N(R$_e$)C(O)R$_a$, wherein R$_e$ at each occurrence is independently selected from the group consisting of hydrogen and alkyl, and R$_a$ is R$_p$ wherein R$_p$ is aryl, —N(R$_e$)C(O)OR$_a$, wherein R$_a$ is alkyl and R$_e$ is hydrogen or alkyl, —N(R$_e$)SOR$_a$, wherein R$_a$ is alkyl, and R$_e$ is hydrogen or alkyl, —N(R$_e$)SO$_2$R$_a$, wherein R$_e$ is hydrogen or alkyl, R$_a$ is alkyl, alkenyl, R$_p$, wherein R$_p$ is selected from the group consisting of heteroaryl and aryl, or alkyl substituted with 1, 2 or 3 substituents independently selected from the group consisting of
halo,
—C(O)OR$_c$, wherein R$_c$ is hydrogen or alkyl,
—OR$_c$, wherein R$_c$ is hydrogen, and
—C(O)NR$_c$R$_d$, wherein R$_c$ is hydrogen, and R$_d$ is hydrogen, —N(R$_e$)SO$_2$NR$_a$R$_b$, wherein R$_e$ is hydrogen or alkyl, R$_b$ is hydrogen, and R$_a$ is hydrogen, alkyl, or alkyl substituted with one substituent selected from the group consisting of:
—OR$_c$, wherein R$_c$ is hydrogen,
—NR$_c$R$_d$, wherein R$_c$ and R$_d$ are hydrogen, and
—OC(O)NR$_c$R$_d$, wherein R$_c$ and R$_d$ together with the nitrogen atom to which they are attached, form a heterocycle ring; alternatively, R$_a$ and R$_b$, together with the nitrogen atom to which they are attached, form a heterocycle ring;

—N(R$_e$)SO$_2$N(R$_e$)C(O)R$_e$, wherein R$_e$ at each occurrence is independently selected from the group consisting of hydrogen and alkyl, and R$_a$ is alkyl, —N(R$_e$)SO$_2$N(R$_e$)C(O)OR$_a$, wherein R$_e$ at each occurrence is independently selected from the group consisting of hydrogen and alkyl, and R$_a$ is alkyl substituted with one R$_q$ wherein R$_q$ is aryl, or alkyl substituted with one substituent selected from the group consisting of
N$_3$,
—OR$_a$, wherein R$_a$ is hydrogen or alkyl substituted with one —OR$_c$ wherein R$_c$ is alkyl,
—NR$_a$R$_b$, wherein R$_a$ is hydrogen and R$_b$ is hydrogen,
—N(R$_e$)SOR$_a$, wherein R$_a$ is alkyl and R$_e$ is hydrogen or alkyl,
—N(R$_e$)SO$_2$R$_a$, wherein R$_e$ is hydrogen or alkyl, and R$_a$ is alkyl, or alkyl substituted with one substituent selected from the group consisting of halo and R$_q$; wherein R$_q$ is heterocycle;
—N(R$_e$)SO$_2$NR$_a$R$_b$, wherein R$_a$, R$_b$ are hydrogen, and R$_e$ is hydrogen or alkyl,
—N(R$_e$)SO$_2$N(R$_e$)C(O)OR$_a$, wherein R$_e$ at each occurrence is independently selected from the group consisting of hydrogen and alkyl, R$_a$ is alkyl substituted with R$_q$, wherein R$_q$ is aryl,
—C(O)NR$_a$R$_b$ wherein R$_a$ is hydrogen and R$_b$ is hydrogen, and
R$_{7q}$, wherein R$_{7q}$ is heterocycle; and n is 0 or 1.

For example, the second embodiment of the present invention provides a compound of formula (II) wherein R$^5$ is —OR$_d$ wherein R$_d$ is hydrogen; R$^6$ is hydrogen or alkyl; R$^1$ is propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubutituted or substituted with 1 or 2 substituents selected from the group consisting of
halo,
—OR$_a$, wherein R$_a$ is hydrogen,
—OC(O)R$_a$, wherein R$_a$ is methyl, ethyl, or isopropyl,
—OC(O)NR$_a$R$_b$, wherein R$_a$ is methyl, ethyl or isopropyl and R$_b$ is hydrogen,
—C(O)OR$_a$, wherein R$_a$ is methyl, ethyl, or isopropyl,
—C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
—R$_{1q}$; wherein R$_{1q}$ is phenyl, cyclopropyl, cyclobutyl, cyclopentyl or cyclohexyl;

allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—C(O)OR$_a$, wherein R$_a$ is methyl, ethyl or isopropyl, and R$_{1q}$, wherein R$_{1q}$ is aryl,
—C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
—C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substitutent selected from the group consisting of —OR$_c$, and —OC(O)R$_c$, and wherein R$_c$ is hydrogen or methyl,
or
R$_{1p}$; wherein R$_{1p}$ is 4,5-dihydro-1,3-oxazol-2-yl;

R$^2$ is propyl, butyl, methyl, ethyl, 2-methylbutyl, 3-methylbutyl, 3,3-dimethylbutyl, 5,5-dimethylhexyl, or 3-methylpentyl;

R$^7$ is formyl,
—OR$_a$, wherein R$_a$ is hydrogen, or methyl substituted with one substituent selected from the group consisting of cyano and —C(O)NR$_c$R$_d$, wherein R$_c$ is hydrogen, and R$_d$ is hydrogen,
—OP(=O)(R$_e$)(OR$_e$), wherein R$_e$ at each occurrence is independently selected from the group consisting of hydrogen, methyl and ethyl.
—NR$_a$R$_b$, wherein R$_a$ is hydrogen, or methyl substituted with one cyano, and R$_b$ is hydrogen, —N($R_e$)C(=NH)$R_e$, wherein $R_e$ at each occurrence is independently selected from the group consisting of hydrogen and methyl, —N($R_e$)C(O)$R_a$, wherein $R_a$ is methyl or ethyl wherein each of the methyl or ethyl is unsubstituted or substituted with 1, 2 or 3 halo, and $R_e$ is hydrogen or methyl, —N($R_e$)C(O)N$R_aR_b$, wherein $R_a$ is hydrogen, $R_b$ is hydrogen, and $R_e$ is hydrogen or methyl, —N($R_e$)C(=S)N$R_aR_b$, wherein $R_a$ is hydrogen, $R_b$ is hydrogen, and $R_e$ is hydrogen or methyl, —N($R_e$)C(=S)N($R_e$)C(O)$R_a$, $R_e$ at each occurrence is independently selected from the group consisting of hydrogen and methyl, and $R_a$ is $R_p$, wherein $R_p$ is phenyl, —N($R_e$)C(O)O$R_a$, wherein $R_a$ is tert-butyl and $R_e$ is hydrogen or methyl, —N($R_e$)SO$R_a$, wherein $R_a$ is methyl, and $R_e$ is hydrogen or methyl, —N($R_e$)SO$_2R_a$, wherein $R_e$ is hydrogen or methyl, $R_a$ is methyl, ethyl, propyl, isopropyl, butyl, ethylenyl or $R_p$, wherein $R_p$ is selected from the group consisting of imidazolyl, thienyl, benzimidazolyl, phenyl, and naphthyl, wherein each of the methyl, ethyl, propyl, isopropyl and butyl is independently unsubstituted or substituted with 1, 2 or 3 substituents independently selected from the group consisting of halo, —C(O)O$R_c$, wherein $R_c$ is hydrogen, methyl or tert-butyl, —O$R_c$, wherein $R_c$ is hydrogen, and —C(O)N$R_cR_d$, wherein $R_c$ is hydrogen, and $R_d$ is hydrogen, —N($R_e$)SO$_2$N$R_aR_b$, wherein $R_e$ is hydrogen or methyl, $R_b$ is hydrogen, and $R_a$ is hydrogen, methyl, or ethyl, wherein each of the methyl or ethyl is independently unsubstituted or substituted with one substituent selected from the group consisting of:

—O$R_c$, wherein $R_c$ is hydrogen,

—N$R_cR_d$, wherein $R_c$ and $R_d$ are hydrogen, and

—OC(O)N$R_cR_d$, wherein $R_c$ and $R_d$ together with the nitrogen atom to which they are attached, form a heterocycle ring wherein the heterocycle is azetidine; alternatively, $R_a$ and $R_b$, together with the nitrogen atom to which they are attached, form a heterocycle ring wherein the heterocycle is pyrrolidine or azetidine;

—N($R_e$)SO$_2$N($R_e$)C(O)$R_a$, wherein $R_e$ at each occurrence is independently selected from the group consisting of hydrogen and methyl, and $R_a$ is methyl, ethyl, propyl or butyl;

—N($R_e$)SO$_2$N($R_e$)C(O)O$R_a$, wherein $R_e$ at each occurrence is independently selected from the group consisting of hydrogen and methyl, and $R_a$ is methyl substituted with one $R_q$ wherein $R_q$ is phenyl;

methyl substituted with one substituent selected from the group consisting of $N_3$, —O$R_a$, wherein $R_a$ is hydrogen, or methyl substituted with one —O$R_c$ wherein $R_c$ is methyl;

—N$R_aR_b$, wherein $R_a$ is hydrogen and $R_b$ is hydrogen;

—N($R_e$)SO$R_a$, wherein $R_a$ is methyl, and $R_e$ is hydrogen or methyl;

—N($R_e$)SO$_2R_a$, wherein $R_e$ is hydrogen or methyl, and $R_a$ is methyl or ethyl; wherein each of the methyl or ethyl is independently unsubstituted or substituted with one substituent selected from the group consisting of halo and $R_q$; wherein $R_q$ is morpholinyl;

—N($R_e$)SO$_2$N$R_aR_b$, wherein $R_a$ and $R_b$ are hydrogen, and $R_e$ is hydrogen or methyl;

—N($R_e$)SO$_2$N($R_e$)C(O)O$R_a$, wherein $R_e$ at each occurrence is independently selected from the group consisting of hydrogen and methyl, $R_a$ is methyl substituted with $R_q$, wherein $R_q$ is phenyl;

—C(O)N$R_aR_b$ wherein $R_a$ is hydrogen and $R_b$ is hydrogen, and $R_{7q}$, wherein $R_{7q}$ is 1,1-dioxidoisothiazolidin-2-yl;

or ethyl substituted with —C(O)N$R_aR_b$, wherein $R_a$ and $R_b$ are hydrogen; and n is 0 or 1.

For example, the second embodiment of the present invention provides a compound of formula (II) wherein $R^5$ is —O$R_d$ wherein $R_d$ is hydrogen, $R^6$ is hydrogen or alkyl, $R^1$ is —C(O)O$R_a$, —C(O)N$R_aR_b$, $R_{1p}$, alkyl or alkenyl, $R^2$ is alkyl, $R^7$ is formyl, —O$R_a$, —OP(=O)($R_e$)(O$R_e$), —N$R_aR_b$, —N($R_e$)c(=NH)$R_e$, —N($R_e$)C(O)$R_a$, —N($R_e$)C(O)N$R_aR_b$, —N($R_e$)C(=S)N$R_aR_b$, —N($R_e$)C(=S)N($R_e$)C(O)$R_a$, —N($R_e$)C(O)O$R_a$, —N($R_e$)SO$R_a$, —N($R_e$)SO$_2R_a$, —N($R_e$)SO$_2$N$R_aR_b$, —N($R_e$)SO$_2$N($R_e$)C(O)$R_a$, —N($R_e$)SO$_2$N($R_e$)C(O)O$R_a$, or alkyl substituted with one substituent selected from the group consisting of $N_3$, —O$R_a$, —N$R_aR_b$, —N($R_e$)SO$R_a$, —N($R_e$)SO$_2R_a$, —N($R_e$)SO$_2$N$R_aR_b$, —N($R_e$)SO$_2$N($R_e$)C(O)O$R_a$, —C(O)N$R_aR_b$ and $R_{7q}$, $R^8$ is halo or —O$R_a$, m is 0 or 1; and n is 0 or 1.

For example, the second embodiment of the present invention provides a compound of formula (II) wherein $R^5$ is —O$R_d$ wherein $R_d$ is hydrogen; $R^6$ is hydrogen or alkyl; $R^1$ is alkyl, wherein the alkyl is unsubstituted or substituted with 1 or 2 substituents selected from the group consisting of halo, —O$R_a$, wherein $R_a$ is hydrogen, —OC(O)$R_a$, wherein $R_a$ is alkyl, —OC(O)N$R_aR_b$, wherein $R_a$ is alkyl, $R_b$ is hydrogen, —C(O)O$R_a$, wherein $R_a$ is alkyl, —C=C$R_jR_k$, wherein $R_j$ and $R_k$ together with the carbon atom to which they are attached form a cycloalkyl ring; and —$R_{1q}$; wherein $R_{1q}$ is aryl or cycloalkyl;

alkenyl, wherein the alkenyl is unsubstituted or substituted with one substituent selected from the group consisting of —C(O)O$R_a$, wherein $R_a$ is alkyl, and —$R_{1q}$, wherein $R_{1q}$ is aryl, —C(O)O$R_a$, wherein $R_a$ is alkyl, or alkyl substituted with one $R_{1q}$, wherein $R_{1q}$ is a heterocyclic ring, unsubstituted or substituted with one —C(O)O$R_{101}$ and wherein $R_{101}$ is alkyl, —C(O)N$R_aR_b$, wherein $R_a$ is alkyl, or alkyl substituted with one substituent selected from the group consisting of —OC(O)$R_c$, and —O$R_c$ wherein $R_c$ is hydrogen or alkyl, and $R_b$ is alkyl, alternatively, $R_a$ and $R_b$, together with the nitrogen atom to which they are attached, form a heterocyclic ring substituted with one alkyl substitutent wherein the alkyl substituent is substituted with one substituent selected from the group consisting of —O$R_c$, and —OC(O)$R_c$, and wherein $R_c$ is hydrogen or alkyl, or $R_{1p}$; wherein $R_{1p}$ is heterocycle;

$R^2$ is alkyl;

$R^7$ is formyl,

—OR$_a$, wherein R$_a$ is hydrogen, or alkyl substituted with one substituent selected from the group consisting of cyano and —C(O)NR$_c$R$_d$, wherein R$_c$ is hydrogen, and R$_d$ is hydrogen, —OP(=O)(R$_e$)(OR$_e$), wherein R$_e$ at each occurrence is independently selected from the group consisting of hydrogen and alkyl, —NR$_a$R$_b$, wherein R$_a$ is hydrogen or alkyl substituted with one cyano, and R$_b$ is hydrogen, —N(R$_e$)C(=NH)R$_e$, wherein R$_e$ at each occurrence is independently selected from the group consisting of hydrogen and alkyl, —N(R$_e$)C(O)R$_a$, wherein R$_a$ is alkyl, or alkyl substituted with 1, 2 or 3 halo, and R$_e$ is hydrogen or alkyl, —N(R$_e$)C(O)NR$_a$R$_b$, wherein R$_a$ is hydrogen, R$_b$ is hydrogen, and R$_e$ is hydrogen or alkyl, —N(R$_e$)C(=S)NR$_a$R$_b$, wherein R$_a$ is hydrogen, R$_b$ is hydrogen, and R$_e$ is hydrogen or alkyl, —N(R$_e$)C(=S)N(R$_e$)C(O)R$_a$, wherein R$_e$ at each occurrence is independently selected from the group consisting of hydrogen and alkyl, and R$_a$ is R$_p$ wherein R$_p$ is aryl, —N(R$_e$)C(O)OR$_a$, wherein R$_a$ is alkyl and R$_e$ is hydrogen or alkyl, —N(R$_e$)SOR$_a$, wherein R$_a$ is alkyl, and R$_e$ is hydrogen or alkyl, —N(R$_e$)SO$_2$R$_a$, wherein R$_e$ is hydrogen or alkyl, R$_a$ is alkyl, alkenyl, R$_p$, wherein R$_p$ is selected from the group consisting of heteroaryl and aryl, or alkyl substituted with 1, 2 or 3 substituents independently selected from the group consisting of halo, —C(O)OR$_c$, wherein R$_c$ is hydrogen or alkyl, —OR$_c$, wherein R$_c$ is hydrogen, and —C(O)NR$_c$R$_d$, wherein R$_c$ is hydrogen, and R$_d$ is hydrogen, —N(R$_e$)SO$_2$NR$_a$R$_b$, wherein R$_e$ is hydrogen or alkyl, R$_b$ is hydrogen, and R$_a$ is hydrogen, alkyl, or alkyl substituted with one substituent selected from the group consisting of:

—OR$_c$, wherein R$_c$ is hydrogen,

—NR$_c$R$_d$, wherein R$_c$ and R$_d$ are hydrogen, and

—OC(O)NR$_c$R$_d$, wherein R$_c$ and R$_d$ together with the nitrogen atom to which they are attached, form a heterocycle ring; alternatively, R$_a$ and R$_b$, together with the nitrogen atom to which they are attached, form a heterocycle ring;

—N(R$_e$)SO$_2$N(R$_e$)C(O)R$_a$, wherein R$_e$ at each occurrence is independently selected from the group consisting of hydrogen and alkyl, and R$_a$ is alkyl, —N(R$_e$)SO$_2$N(R$_e$)C(O)OR$_a$, wherein R$_e$ at each occurrence is independently selected from the group consisting of hydrogen and alkyl, and R$_a$ is alkyl substituted with one R$_q$ wherein R$_q$ is aryl, or alkyl substituted with one substituent selected from the group consisting of

N$_3$,

—OR$_a$, wherein R$_a$ is hydrogen or alkyl substituted with one —OR$_c$ wherein R$_c$ is alkyl, —NR$_a$R$_b$, wherein R$_a$ is hydrogen and R$_b$ is hydrogen, —N(R$_e$)SOR$_a$, wherein R$_a$ is alkyl and R$_e$ is hydrogen or alkyl, —N(R$_e$)SO$_2$R$_a$, wherein R$_e$ is hydrogen or alkyl, and R$_a$ is alkyl, or alkyl substituted with one substituent selected from the group consisting of halo and R$_q$; wherein R$_q$ is heterocycle;

—N(R$_e$)SO$_2$NR$_a$R$_b$, wherein R$_a$, R$_b$ are hydrogen, and R$_e$ is hydrogen or alkyl, —N(R$_e$)SO$_2$N(R$_e$)C(O)OR$_a$, wherein R$_e$ at each occurrence is independently selected from the group consisting of hydrogen and alkyl, R$_a$ is alkyl substituted with R$_q$, wherein R$_q$ is aryl, —C(O)NR$_a$R$_b$ wherein R$_a$ is hydrogen and R$_b$ is hydrogen, and R$_{7q}$, wherein R$_{7q}$ is heterocycle;

R$^8$ is halo or —OR$_a$, wherein R$_a$ is hydrogen or alkyl;

m is 0 or 1; and n is 0 or 1.

For example, the second embodiment of the present invention provides a compound of formula (II) wherein R$^5$ is —OR$_d$ wherein R$_d$ is hydrogen; R$^6$ is hydrogen or alkyl;

R$^1$ is propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of halo, —OR$_a$, wherein R$_a$ is hydrogen, —OC(O)R$_a$, wherein R$_a$ is methyl, ethyl, or isopropyl, —OC(O)NR$_a$R$_b$, wherein R$_a$ is methyl, ethyl or isopropyl and R$_b$ is hydrogen, —C(O)OR$_a$, wherein R$_a$ is methyl, ethyl, or isopropyl, —C=CR$_j$R$_k$, wherein R$_j$ and R$_k$ together with the carbon atom to which they are attached form a ring selected from the group consisting of cyclopropyl, cyclobutyl, cyclopentyl and cyclohexyl, —R$_{1q}$; wherein R$_{1q}$ is phenyl, cyclopropyl, cyclobutyl, cyclopentyl or cyclohexyl;

allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of —C(O)OR$_a$, wherein R$_a$ is methyl, ethyl or isopropyl, and —R$_{1q}$, wherein R$_{1q}$ is aryl, —C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl, —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substitutent selected from the group consisting of —OR$_c$, and —OC(O)R$_c$, and wherein R$_c$ is hydrogen or methyl, or R$_{1p}$; wherein R$_{1p}$ is 4,5-dihydro-1,3-oxazol-2-yl; R$^2$ is propyl, butyl, methyl, ethyl, 2-methylbutyl, 3-methylbutyl, 3,3-dimethylbutyl, 5,5-dimethylhexyl, or 3-methylpentyl;

R⁷ is
  formyl,
  —OR$_a$, wherein R$_a$ is hydrogen, or methyl substituted with one substituent selected from the group consisting of cyano and —C(O)NR$_c$R$_d$, wherein R$_c$ is hydrogen, and R$_d$ is hydrogen,
  —OP(=O)(R$_e$)(OR$_e$), wherein R$_e$ at each occurrence is independently selected from the group consisting of hydrogen, methyl and ethyl.
  —NR$_a$R$_b$, wherein R$_a$ is hydrogen, or methyl substituted with one cyano, and R$_b$ is hydrogen,
  —N(R$_e$)C(=NH)R$_e$, wherein R$_e$ at each occurrence is independently selected from the group consisting of hydrogen and methyl,
  —N(R$_e$)C(O)R$_a$, wherein R$_a$ is methyl or ethyl wherein each of the methyl or ethyl is unsubstituted or substituted with 1, 2 or 3 halo, and R$_e$ is hydrogen or methyl,
  —N(R$_e$)C(O)NR$_a$R$_b$, wherein R$_a$ is hydrogen, R$_b$ is hydrogen, and R$_e$ is hydrogen or methyl,
  —N(R$_e$)C(=S)NR$_a$R$_b$, wherein R$_a$ is hydrogen, R$_b$ is hydrogen, and R$_e$ is hydrogen or methyl,
  —N(R$_e$)C(=S)N(R$_e$)C(O)R$_a$, R$_e$ at each occurrence is independently selected from the group consisting of hydrogen and methyl, and R$_a$ is R$_p$, wherein R$_p$ is phenyl,
  —N(R$_e$)C(O)OR$_a$, wherein R$_a$ is tert-butyl and R$_e$ is hydrogen or methyl,
  —N(R$_e$)SOR$_a$, wherein R$_a$ is methyl, and R$_e$ is hydrogen or methyl,
  —N(R$_e$)SO$_2$R$_a$, wherein R$_e$ is hydrogen or methyl, R$_a$ is methyl, ethyl, propyl, isopropyl, butyl, ethylenyl or R$_p$, wherein R$_p$ is selected from the group consisting of imidazolyl, thienyl, benzimidazolyl, phenyl, and naphthyl, wherein each of the methyl, ethyl, propyl, isopropyl and butyl is independently unsubstituted or substituted with 1, 2 or 3 substituents independently selected from the group consisting of
    halo,
    —C(O)OR$_c$, wherein R$_c$ is hydrogen, methyl or tert-butyl,
    —OR$_c$, wherein R$_c$ is hydrogen, and
    —C(O)NR$_c$R$_d$, wherein R$_c$ is hydrogen, and R$_d$ is hydrogen,
  —N(R$_e$)SO$_2$NR$_a$R$_b$, wherein R$_e$ is hydrogen or methyl, R$_b$ is hydrogen, and R$_a$ is hydrogen, methyl, or ethyl, wherein each of the methyl or ethyl is independently unsubstituted or substituted with one substituent selected from the group consisting of:
    —OR$_c$, wherein R$_c$ is hydrogen,
    —NR$_c$R$_d$, wherein R$_c$ and R$_d$ are hydrogen, and
    —OC(O)NR$_c$R$_d$, wherein R$_c$ and R$_d$ together with the nitrogen atom to which they are attached, form a heterocycle ring wherein the heterocycle is azetidine; alternatively, R$_a$ and R$_b$, together with the nitrogen atom to which they are attached, form a heterocycle ring wherein the heterocycle is pyrrolidine or azetidine;
  —N(R$_e$)SO$_2$N(R$_e$)C(O)R$_a$, wherein R$_e$ at each occurrence is independently selected from the group consisting of hydrogen and methyl, and R$_a$ is methyl, ethyl, propyl or butyl;
  —N(R$_e$)SO$_2$N(R$_e$)C(O)OR$_a$, wherein R$_e$ at each occurrence is independently selected from the group consisting of hydrogen and methyl, and R$_a$ is methyl substituted with one R$_q$ wherein R$_q$ is phenyl;
  methyl substituted with one substituent selected from the group consisting of
    N$_3$,
    —OR$_a$, wherein R$_a$ is hydrogen, or methyl substituted with one —OR$_c$ wherein R$_c$ is methyl;
    —NR$_a$R$_b$, wherein R$_a$ is hydrogen and R$_b$ is hydrogen;
    —N(R$_e$)SOR$_a$, wherein R$_a$ is methyl, and R$_e$ is hydrogen or methyl;
    —N(R$_e$)SO$_2$R$_a$, wherein R$_e$ is hydrogen or methyl, and R$_a$ is methyl or ethyl; wherein each of the methyl or ethyl is independently unsubstituted or substituted with one substituent selected from the group consisting of halo and R$_q$; wherein R$_q$ is morpholinyl;
    —N(R$_e$)SO$_2$NR$_a$R$_b$, wherein R$_a$ and R$_b$ are hydrogen, and R$_e$ is hydrogen or methyl;
    —N(R$_e$)SO$_2$N(R$_e$)C(O)OR$_a$, wherein R$_e$ at each occurrence is independently selected from the group consisting of hydrogen and methyl, R$_a$ is methyl substituted with R$_q$, wherein R$_q$ is phenyl;
    —C(O)NR$_a$R$_b$ wherein R$_a$ is hydrogen and R$_b$ is hydrogen, and
    R$_{7q}$, wherein R$_{7q}$ is 1,1-dioxidoisothiazolidin-2-yl;
  or
  ethyl substituted with —C(O)NR$_a$R$_b$, wherein R$_a$ and R$_b$ are hydrogen;
R⁸ is halo or OR$_a$, wherein R$_a$ is hydrogen or methyl;
m is 0 or 1; and
n is 0 or 1.

Exemplary compounds of the second embodiment include, but not limited to, the following:

3-(1,1-dioxido-4H-1,2,4-benzothiadiazin-3-yl)-4-hydroxy-1,1-dipropyl-2(1H)-naphthalenone;
4-hydroxy-3-(7-hydroxy-1,1-dioxido-4H-1,2,4-benzothiadiazin-3-yl)-1,1-dipropyl-2(1H)-naphthalenone;
2-{[3-(1-hydroxy-3-oxo-4,4-dipropyl-3,4-dihydro-2-naphthalenyl)-1,1-dioxido-4H-1,2,4-benzothiadiazin-7-yl]oxy}acetamide;
1,1-dibutyl-3-(1,1-dioxido-4H-1,2,4-benzothiadiazin-3-yl)-4-hydroxy-2(1H)-naphthalenone;
2-{[3-(4,4-dibutyl-1-hydroxy-3-oxo-3,4-dihydro-2-naphthalenyl)-1,1-dioxido-4H-1,2,4-benzothiadiazin-7-yl]oxy}acetamide;
3-(1,1-dioxido-4H-1,2,4-benzothiadiazin-3-yl)-4-hydroxy-1,1-diisopentyl-2(1H)-naphthalenone;
4-hydroxy-3-(7-hydroxy-1,1-dioxido-4H-1,2,4-benzothiadiazin-3-yl)-1,1-diisopentyl-2(1H)-naphthalenone;
2-{[3-(1-hydroxy-4,4-diisopentyl-3-oxo-3,4-dihydro-2-naphthalenyl)-1,1-dioxido-4H-1,2,4-benzothiadiazin-7-yl]oxy}acetamide;
3-(1,1-dioxido-4H-1,2,4-benzothiadiazin-3-yl)-4-hydroxy-1,1-dimethyl-2(1H)-naphthalenone;
N-[3-(4,4-dibutyl-1-hydroxy-3-oxo-3,4-dihydro-2-naphthalenyl)-1,1-dioxido-4H-1,2,4-benzothiadiazin-7-yl]methanesulfonamide;
N-{3-[1-hydroxy-4,4-bis(3-methylbutyl)-3-oxo-3,4-dihydronaphthalen-2-yl]-1,1-dioxido-4H-1,2,4-benzothiadiazin-7-yl}methanesulfonamide;
3-(1,1-dioxido-4H-1,2,4-benzothiadiazin-3-yl)-6-fluoro-4-hydroxy-1,1-dipropylnaphthalen-2(1H)-one;
6-fluoro-4-hydroxy-3-(7-hydroxy-1,1-dioxido-4H-1,2,4-benzothiadiazin-3-yl)-1,1-dipropylnaphthalen-2(1H)-one;
2-{[3-(7-fluoro-1-hydroxy-3-oxo-4,4-dipropyl-3,4-dihydronaphthalen-2-yl)-1,1-dioxido-4H-1,2,4-benzothiadiazin-7-yl]oxy}acetamide;
N-[3-(7-fluoro-1-hydroxy-3-oxo-4,4-dipropyl-3,4-dihydronaphthalen-2-yl)-1,1-dioxido-4H-1,2,4-benzothiadiazin-7-yl]sulfamide;

1,1-dibutyl-3-(1,1-dioxido-4H-1,2,4-benzothiadiazin-3-yl)-6-fluoro-4-hydroxynaphthalen-2(1H)-one;

N-[3-(4,4-dibutyl-7-fluoro-1-hydroxy-3-oxo-3,4-dihydronaphthalen-2-yl)-1,1-dioxido-4H-1,2,4-benzothiadiazin-7-yl]methanesulfonamide;

3-[3-(4,4-dibutyl-7-fluoro-1-hydroxy-3-oxo-3,4-dihydronaphthalen-2-yl)-1,1-dioxido-4H-1,2,4-benzothiadiazin-7-yl]propanamide;

3-(4,4-dibutyl-7-fluoro-1-hydroxy-3-oxo-3,4-dihydronaphthalen-2-yl)-4H-1,2,4-benzothiadiazine-7-carbaldehyde 1,1-dioxide;

N-{3-[(4R)-7-fluoro-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-7-fluoro-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4R)-4-(3,3-dimethylbutyl)-7-fluoro-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4S)-4-(3,3-dimethylbutyl)-7-fluoro-1-hydroxy-4-methyl-3-oxo-3,4-dihydronaphthalen-2-yl]-1,1-dioxido-4H-1,2,4-benzothiadiazin-7-yl}methanesulfonamide;

2-{[3-(1-hydroxy-4-methyl-3-oxo-4-propyl-3,4-dihydronaphthalen-2-yl)-1,1-dioxido-4H-1,2,4-benzothiadiazin-7-yl]oxy}acetamide;

2-{[3-(4-butyl-1-hydroxy-4-methyl-3-oxo-3,4-dihydronaphthalen-2-yl)-1,1-dioxido-4H-1,2,4-benzothiadiazin-7-yl]oxy}acetamide;

2-({3-[1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide;

3-(1,1-dioxido-4H-1,2,4-benzothiadiazin-3-yl)-4-hydroxy-1-methyl-1-propylnaphthalen-2(1H)-one;

1-butyl-3-(1,1-dioxido-4H-1,2,4-benzothiadiazin-3-yl)-4-hydroxy-1-methylnaphthalen-2(1H)-one;

3-(1,1-dioxido-4H-1,2,4-benzothiadiazin-3-yl)-4-hydroxy-1-methyl-1-(3-methylbutyl)naphthalen-2(1H)-one;

N-[3-(1-hydroxy-4-methyl-3-oxo-4-propyl-3,4-dihydronaphthalen-2-yl)-1,1-dioxido-4H-1,2,4-benzothiadiazin-7-yl]methanesulfonamide;

N-[3-(4-butyl-1-hydroxy-4-methyl-3-oxo-3,4-dihydronaphthalen-2-yl)-1,1-dioxido-4H-1,2,4-benzothiadiazin-7-yl]methanesulfonamide;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

1-(5,5-dimethylhexyl)-3-(1,1-dioxido-4H-1,2,4-benzothiadiazin-3-yl)-4-hydroxy-1-methylnaphthalen-2(1H)-one;

1-(3-cyclohexylpropyl)-3-(1,1-dioxido-4H-1,2,4-benzothiadiazin-3-yl)-4-hydroxy-1-methylnaphthalen-2(1H)-one;

N-{3-[4-(5,5-dimethylhexyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(3-cyclohexylpropyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(cyclohexylmethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide;

N-(3-{1-hydroxy-4-methyl-4-[(3S)-3-methylpentyl]-3-oxo-3,4-dihydronaphthalen-2-yl}-1,1-dioxido-4H-1,2,4-benzothiadiazin-7-yl)methanesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}acetamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethanimidamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-N-methylmethanesulfonamide;

N-{3-[(4S)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-ethyl-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4S)-4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4R)-4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}sulfamide;

tert-butyl 3-[4-(cyclobutylmethyl)-1-hydroxy-4-methyl-3-oxo-3,4-dihydronaphthalen-2-yl]-1,1-dioxido-4H-1,2,4-benzothiadiazin-7-ylcarbamate;

3-(7-amino-1,1-dioxido-4H-1,2,4-benzothiadiazin-3-yl)-1-(cyclobutylmethyl)-4-hydroxy-1-methylnaphthalen-2(1H)-one;

N-{3-[4-(cyclobutylmethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(cyclobutylmethyl)-1-hydroxy-4-methyl-3-oxo-3,4-dihydronaphthalen-2-yl]-1,1-dioxido-4H-1,2,4-benzothiadiazin-7-yl}-2,2,2-trifluoroacetamide;

3-(1-hydroxy-3-oxo-4,4-dipropyl-3,4-dihydronaphthalen-2-yl)-1,1-dioxido-4H-1,2,4-benzothiadiazin-7-yl methyl methylphosphonate;

3-(1-hydroxy-3-oxo-4,4-dipropyl-3,4-dihydronaphthalen-2-yl)-1,1-dioxido-4H-1,2,4-benzothiadiazin-7-yl hydrogen methylphosphonate;

ethyl 3-(1-hydroxy-3-oxo-4,4-dipropyl-3,4-dihydronaphthalen-2-yl)-1,1-dioxido-4H-1,2,4-benzothiadiazin-7-yl methylphosphonate;

tert-butyl 3-(4,4-dibutyl-1-hydroxy-3-oxo-3,4-dihydronaphthalen-2-yl)-1,1-dioxido-4H-1,2,4-benzothiadiazin-7-ylcarbamate;

3-(7-amino-1,1-dioxido-4H-1,2,4-benzothiadiazin-3-yl)-1,1-dibutyl-4-hydroxynaphthalen-2(1H)-one;

tert-butyl 3-(1-hydroxy-3-oxo-4,4-dipropyl-3,4-dihydronaphthalen-2-yl)-1,1-dioxido-4H-1,2,4-benzothiadiazin-7-ylcarbamate;

3-(7-amino-1,1-dioxido-4H-1,2,4-benzothiadiazin-3-yl)-4-hydroxy-1,1-dipropylnaphthalen-2(1H)-one;

2,2,2-trifluoro-N-[3-(1-hydroxy-3-oxo-4,4-dipropyl-3,4-dihydronaphthalen-2-yl)-1,1-dioxido-4H-1,2,4-benzothiadiazin-7-yl]acetamide;

N-[3-(1-hydroxy-3-oxo-4,4-dipropyl-3,4-dihydronaphthalen-2-yl)-1,1-dioxido-4H-1,2,4-benzothiadiazin-7-yl]butane-1-sulfonamide;

N-[3-(1-hydroxy-3-oxo-4,4-dipropyl-3,4-dihydronaphthalen-2-yl)-1,1-dioxido-4H-1,2,4-benzothiadiazin-7-yl]methanesulfonamide;

N-[3-(1-hydroxy-3-oxo-4,4-dipropyl-3,4-dihydronaphthalen-2-yl)-1,1-dioxido-4H-1,2,4-benzothiadiazin-7-yl]-1-methyl-1H-imidazole-4-sulfonamide;

N-[3-(1-hydroxy-3-oxo-4,4-dipropyl-3,4-dihydronaphthalen-2-yl)-1,1-dioxido-4H-1,2,4-benzothiadiazin-7-yl]-2-methoxybenzenesulfonamide;

N-[3-(1-hydroxy-3-oxo-4,4-dipropyl-3,4-dihydronaphthalen-2-yl)-1,1-dioxido-4H-1,2,4-benzothiadiazin-7-yl]thiophene-2-sulfonamide;

{[3-(4,4-dibutyl-1-hydroxy-3-oxo-3,4-dihydronaphthalen-2-yl)-1,1-dioxido-4H-1,2,4-benzothiadiazin-7-yl]oxy}acetonitrile;

{[3-(1-hydroxy-3-oxo-4,4-dipropyl-3,4-dihydronaphthalen-2-yl)-1,1-dioxido-4H-1,2,4-benzothiadiazin-7-yl]amino}acetonitrile;

1-chloro-N-[3-(1-hydroxy-3-oxo-4,4-dipropyl-3,4-dihydronaphthalen-2-yl)-1,1-dioxido-4H-1,2,4-benzothiadiazin-7-yl]methanesulfonamide;

2-chloro-N-[3-(1-hydroxy-3-oxo-4,4-dipropyl-3,4-dihydronaphthalen-2-yl)-1,1-dioxido-4H-1,2,4-benzothiadiazin-7-yl]benzenesulfonamide;

2,2,2-trifluoro-N-[3-(1-hydroxy-3-oxo-4,4-dipropyl-3,4-dihydronaphthalen-2-yl)-1,1-dioxido-4H-1,2,4-benzothiadiazin-7-yl]ethanesulfonamide;

methyl({[3-(1-hydroxy-3-oxo-4,4-dipropyl-3,4-dihydronaphthalen-2-yl)-1,1-dioxido-4H-1,2,4-benzothiadiazin-7-yl]amino}sulfonyl)acetate;

4-{[3-chloro-5-(trifluoromethyl)pyridin-2-yl]oxy}-N-[3-(1-hydroxy-3-oxo-4,4-dipropyl-3,4-dihydronaphthalen-2-yl)-1,1-dioxido-4H-1,2,4-benzothiadiazin-7-yl]benzenesulfonamide;

benzyl {[3-(1-hydroxy-3-oxo-4,4-dipropyl-3,4-dihydronaphthalen-2-yl)-1,1-dioxido-4H-1,2,4-benzothiadiazin-7-yl]amino}sulfonylcarbamate;

N-[3-(1-hydroxy-3-oxo-4,4-dipropyl-3,4-dihydronaphthalen-2-yl)-1,1-dioxido-4H-1,2,4-benzothiadiazin-7-yl]sulfamide;

benzyl({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonylcarbamate;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

benzyl[{3-[1-hydroxy-4-methyl-4-(3-methylbutyl)-3-oxo-3,4-dihydronaphthalen-2-yl]-1,1-dioxido-4H-1,2,4-benzothiadiazin-7-yl}(methyl)amino]sulfonyl(methyl)carbamate;

N-(2-hydroxyethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

2-{[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]amino}ethyl 3-hydroxyazetidine-1-carboxylate;

3-hydroxy-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}azetidine-1-sulfonamide;

3-amino-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}pyrrolidine-1-sulfonamide;

N-(2-aminoethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

benzyl({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl(methyl)carbamate;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-N'-methylsulfamide;

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetamide;

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]pentanamide;

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]butanamide;

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]propanamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethylenesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}naphthalene-2-sulfonamide;

N-{6-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]-2-naphthyl}acetamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}naphthalene-1-sulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-1H-benzimidazole-2-sulfonamide;

2-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]-1H-benzimidazole-6-carboxylic acid;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-6-nitro-1H-benzimidazole-2-sulfonamide;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}propane-2-sulfonamide;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-4-nitrobenzenesulfonamide;

N-{4-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]phenyl}acetamide;

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-1,2-dimethyl-1H-imidazole-4-sulfonamide;

methyl[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetate;

2-hydroxy-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide;

4-amino-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}benzenesulfonamide;

2-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetamide;

N-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)carbonothioyl]benzamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}thiourea;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}urea;

[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetic acid;

1-chloro-N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-[3-(4-allyl-1-hydroxy-4-methyl-3-oxo-3,4-dihydronaphthalen-2-yl)-1,1-dioxido-4H-1,2,4-benzothiadiazin-7-yl]methanesulfonamide;

N-(3-{1-hydroxy-4-methyl-3-oxo-4-[3-phenylprop-2-enyl]-3,4-dihydronaphthalen-2-yl}-1,1-dioxido-4H-1,2,4-benzothiadiazin-7-yl)methanesulfonamide;

ethyl 4-(4-hydroxy-1-methyl-3-{7-[(methylsulfonyl)amino]-1,1-dioxido-4H-1,2,4-benzothiadiazin-3-yl}-2-oxo-1,2-dihydronaphthalen-1-yl)but-2-enoate;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

N-{3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

ethyl 4-(4-hydroxy-1-methyl-3-{7-[(methylsulfonyl)amino]-1,1-dioxido-4H-1,2,4-benzothiadiazin-3-yl}-2-oxo-1,2-dihydronaphthalen-1-yl)butanoate;

N-{3-[1-hydroxy-4-methyl-3-oxo-4-(3-phenylpropyl)-3,4-dihydronaphthalen-2-yl]-1,1-dioxido-4H-1,2,4-benzothiadiazin-7-yl}methanesulfonamide;

tert-butyl 3-(4-allyl-1-hydroxy-4-methyl-3-oxo-3,4-dihydronaphthalen-2-yl)-1,1-dioxido-4H-1,2,4-benzothiadiazin-7-ylcarbamate;

tert-butyl 3-{1-hydroxy-4-methyl-3-oxo-4-[3-phenylprop-2-enyl]-3,4-dihydronaphthalen-2-yl}-1,1-dioxido-4H-1,2,4-benzothiadiazin-7-ylcarbamate;

tert-butyl 3-[1-hydroxy-4-methyl-3-oxo-4-(3-phenylpropyl)-3,4-dihydronaphthalen-2-yl]-1,1-dioxido-4H-1,2,4-benzothiadiazin-7-ylcarbamate;

ethyl 4-(3-({7-[(tert-butoxycarbonyl)amino]-1,1-dioxido-4H-1,2,4-benzothiadiazin-3-yl}-4-hydroxy-1-methyl-2-oxo-1,2-dihydronaphthalen-1-yl)but-2-enoate;

3-(7-amino-1,1-dioxido-4H-1,2,4-benzothiadiazin-3-yl)-4-hydroxy-1-methyl-1-(3-phenylpropyl)naphthalen-2(1H)-one;

2-({3-[1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide;

benzyl({3-[1-hydroxy-4-methyl-3-oxo-4-(3-phenylpropyl)-3,4-dihydronaphthalen-2-yl]-1,1-dioxido-4H-1,2,4-benzothiadiazin-7-yl}amino)sulfonylcarbamate;

N-{3-[1-hydroxy-4-methyl-3-oxo-4-(3-phenylpropyl)-3,4-dihydronaphthalen-2-yl]-1,1-dioxido-4H-1,2,4-benzothiadiazin-7-yl}sulfamide;

ethyl 4-(3-{7-[(tert-butoxycarbonyl)amino]-1,1-dioxido-4H-1,2,4-benzothiadiazin-3-yl}-4-hydroxy-1-methyl-2-oxo-1,2-dihydronaphthalen-1-yl)butanoate;

N-{3-[1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide;

N-{3-[(4R)-1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide;

N-{3-[(4S)-1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide;

N-(3-{4-[4-ethylpenta-2,4-dienyl]-1-hydroxy-4-methyl-3-oxo-3,4-dihydronaphthalen-2-yl}-1,1-dioxido-4H-1,2,4-benzothiadiazin-7-yl)methanesulfonamide;

N-{3-[4-(2-cyclobutylideneethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclobutylethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclopentylideneethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclopentylethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclohexylideneethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclohexylethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[1-hydroxy-4-(3-hydroxypropyl)-4-methyl-3-oxo-3,4-dihydronaphthalen-2-yl]-1,1-dioxido-4H-1,2,4-benzothiadiazin-7-yl}methanesulfonamide;

N-{3-[4-(2,3-dihydroxypropyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[1-hydroxy-4-(3-hydroxy-3-methylbutyl)-4-methyl-3-oxo-3,4-dihydronaphthalen-2-yl]-1,1-dioxido-4H-1,2,4-benzothiadiazin-7-yl}methanesulfonamide;

N-{3-[4-(3-chloro-3-methylbutyl)-1-hydroxy-4-methyl-3-oxo-3,4-dihydronaphthalen-2-yl]-1,1-dioxido-4H-1,2,4-benzothiadiazin-7-yl}methanesulfonamide;

2-({3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide;

2-({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide;

N-{3-[1-hydroxy-7-methoxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[1,7-dihydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

tert-butyl 3-[4-(2-cyclopropylethyl)-1-hydroxy-4-methyl-3-oxo-3,4-dihydronaphthalen-2-yl]-1,1-dioxido-4H-1,2,4-benzothiadiazin-7-ylcarbamate;

3-(7-amino-1,1-dioxido-4H-1,2,4-benzothiadiazin-3-yl)-1-(2-cyclopropylethyl)-4-hydroxy-1-methylnaphthalen-2(1H)-one;

N-{3-[4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[4-(2-cyclopropylethyl)-1-hydroxy-4-methyl-3-oxo-3,4-dihydronaphthalen-2-yl]-1,1-dioxido-4H-1,2,4-benzothiadiazin-7-yl}-2,2,2-trifluoroacetamide;

tert-butyl[({3-[4-(2-cyclopropylethyl)-1-hydroxy-4-methyl-3-oxo-3,4-dihydronaphthalen-2-yl]-1,1-dioxido-4H-1,2,4-benzothiadiazin-7-yl}amino)sulfonyl]acetate;

N-{3-[(4R)-4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4S)-4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide;

tert-butyl 3-[4-(cyclopropylmethyl)-1-hydroxy-4-methyl-3-oxo-3,4-dihydronaphthalen-2-yl]-1,1-dioxido-4H-1,2,4-benzothiadiazin-7-ylcarbamate;

3-(7-amino-1,1-dioxido-4H-1,2,4-benzothiadiazin-3-yl)-1-(cyclopropylmethyl)-4-hydroxy-1-methylnaphthalen-2(1H)-one;

N-{3-[4-(cyclopropylmethyl)-1-hydroxy-4-methyl-3-oxo-3,4-dihydronaphthalen-2-yl]-1,1-dioxido-4H-1,2,4-benzothiadiazin-7-yl}methanesulfonamide;

methyl 1-butyl-4-hydroxy-3-{7-[(methylsulfonyl)amino]-1,1-dioxido-4H-1,2,4-benzothiadiazin-3-yl}-2-oxo-1,2-dihydronaphthalene-1-carboxylate;

isopropyl 4-hydroxy-1-methyl-3-{7-[(methylsulfonyl)amino]-1,1-dioxido-4H-1,2,4-benzothiadiazin-3-yl}-2-oxo-1,2-dihydronaphthalene-1-carboxylate;

4-hydroxy-N,N-dimethyl-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxamide;

N-{3-[(4R)-1-hydroxy-4-{[(2S)-2-(methoxymethyl)pyrrolidin-1-yl]carbonyl}-4-(3-methylbutyl)-3-oxo-3,4-dihydronaphthalen-2-yl]-1,1-dioxido-4H-1,2,4-benzothiadiazin-7-yl}methanesulfonamide;

{(2R)-1-[((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)carbonyl]pyrrolidin-2-yl}methyl acetate;

N-{3-[(4S)-1-hydroxy-4-{[(2R)-2-(hydroxymethyl)pyrrolidin-1-yl]carbonyl}-4-(3-methylbutyl)-3-oxo-3,4-dihydronaphthalen-2-yl]-1,1-dioxido-4H-1,2,4-benzothiadiazin-7-yl}methanesulfonamide;

(2R)-pyrrolidin-2-ylmethyl (1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate;

methyl (2R)-2-({[((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)carbonyl]oxy}methyl)pyrrolidine-1-carboxylate;

N-{3-[4-(4,5-dihydro-1,3-oxazol-2-yl)-1-hydroxy-4-(3-methylbutyl)-3-oxo-3,4-dihydronaphthalen-2-yl]-1,1-dioxido-4H-1,2,4-benzothiadiazin-7-yl}methanesulfonamide;

2-{methyl[(1-(3-methylbutyl)-3-{7-[(methylsulfonyl)amino]-1,1-dioxido-4H-1,2,4-benzothiadiazin-3-yl}-2,4-dioxo-1,2,3,4-tetrahydronaphthalen-1-yl)carbonyl]amino}ethyl acetate;

N-(2-hydroxyethyl)-N-methyl-1-(3-methylbutyl)-3-{7-[(methylsulfonyl)amino]-1,1-dioxido-4H-1,2,4-benzothiadiazin-3-yl}-2,4-dioxo-1,2,3,4-tetrahydronaphthalene-1-carboxamide;

methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate;

(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl acetate;

(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl isopropylcarbamate;

N-{3-[1-hydroxy-4-(3-methylbutyl)-3-oxo-4-vinyl-3,4-dihydronaphthalen-2-yl]-1,1-dioxido-4H-1,2,4-benzothiadiazin-7-yl}methanesulfonamide;

N-[3-(1-hydroxy-4,4-dimethyl-3-oxo-3,4-dihydronaphthalen-2-yl)-1,1-dioxido-4H-1,2,4-benzothiadiazin-7-yl]methanesulfonamide; and

[3-(1-hydroxy-3-oxo-4,4-dipropyl-3,4-dihydronaphthalen-2-yl)-1,1-dioxido-4H-1,2,4-benzothiadiazin-7-yl][methyl(oxido)-$\lambda^4$-sulfanylidyne]ammonium;

or its pharmaceutically acceptable form, stereoisomer, or tautomer, or combination thereof.

In a third embodiment the present invention is directed to a compound of formula (III)

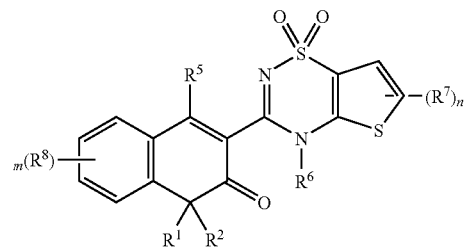

(III)

or a pharmaceutically acceptable form, stereoisomer, or tautomer, or combination thereof, wherein:

$R^1$ is hydrogen, alkyl, alkenyl, alkynyl, —C(O)OR$_a$, —C(O)NR$_a$R$_b$ or R$_{1p}$;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, —C(R$_e$)=CR$_j$R$_k$, and R$_{1q}$;

$R^2$ is hydrogen, alkyl, alkenyl or alkynyl;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$Ra, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, and R$_{2q}$;

alternatively, $R^1$ and $R^2$, together with the carbon atom to which they are attached, form a monocyclic ring selected from the group consisting of cycloalkyl and cycloalkenyl;

wherein each of the cycloalkyl and cycloalkenyl is unsubstituted or substituted with 1, 2 or 3 substituents selected from the group consisting of halo, —OH, —O(alkyl), —NH$_2$, —N(H)(alkyl), —N(alkyl)$_2$, alkyl and haloalkyl;

$R^5$ is —OR$_d$, —SR$_d$, —NR$_d$R$_e$, —N(H)C(O)R$_d$, —N(H)C(O)OR$_d$, —N(H)SO$_2$R$_d$, or —N(H)SO$_2$NR$_d$R$_e$;

$R^6$ is hydrogen, alkyl, alkenyl, alkynyl or -alkylR$_{106}$;

$R^7$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OP(=O)(R$_e$)(OR$_e$), —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(=NH)R$_e$, —N(R$_e$)C(=Nalkyl)R$_e$, —N(R$_e$)C(O)R$_a$, —N(R$_e$)C(O)NR$_a$R$_b$, —N(R$_e$)C(=S)NR$_a$R$_b$, —N(R$_e$)C(=S)N(R$_e$)C(O)R$_a$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7p}$;

wherein each of the alkyl, alkenyl and alkynyl is independently substituted with 0, 1, 2 or 3 substituents selected from the group consisting of cyano, formyl, oxo, nitro, halo, —N$_3$, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7q}$;

$R^8$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8p}$;

wherein each of the alkyl, alkenyl and alkynyl is independently substituted with 0, 1, 2 or 3 substituents selected from the group consisting of cyano, formyl, nitro, oxo, halo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8q}$;

R$_a$ at each occurrence is independently selected from the group consisting of hydrogen, alkyl, alkenyl, alkynyl, and R$_p$;

wherein each of the alkyl, alkenyl and alkynyl is independently substituted with 0, 1, 2 or 3 substituents independently selected from the group consisting of cyano, formyl, oxo, halo, nitro, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, —C(O)N(R$_e$)NR$_c$R$_d$, and R$_q$;

R$_b$ at each occurrence is independently selected from the group consisting of hydrogen, alkyl, alkenyl, alkynyl, R$_{106}$, haloalkyl, hydroxyalkyl, alkoxyalkyl, and -alkylR$_{106}$;

alternatively, R$_a$ and R$_b$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, and —C(O)NR$_c$R$_d$; and wherein each of the alkyl, alkenyl and alkynyl is independently substituted with 0, 1 or 2 substituents selected from the group consisting of cyano, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, and R$_q$;

R$_c$ at each occurrence is independently selected from the group consisting of hydrogen, alkyl, alkenyl, alkynyl, and R$_{103}$;

wherein each of the alkyl, alkenyl and alkynyl is independently substituted with 0, 1, 2 or 3 substituents independently selected from the group consisting of cyano, formyl, oxo, halo, nitro, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$;

R$_d$ at each occurrence is independently selected from the group consisting of hydrogen, alkyl, alkenyl, alkynyl, R$_{106}$, haloalkyl, alkoxyalkyl, hydroxyalkyl, and -alkylR$_{106}$;

alternatively, R$_c$ and R$_d$, together with the nitrogen atom to which they are attached, form a ring selected from the group consisting of heterocycle and heteroaryl;

wherein each of the heteroaryl and heterocycle is independently substituted with 0, 1, 2 or 3 substituents independently selected from the group consisting of alkyl, alkenyl, alkynyl, cyano, formyl, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, and —C(O)NR$_f$R$_g$; and wherein each of the alkyl, alkenyl and alkynyl is independently substituted with 0, 1, 2 or 3 substituents independently selected from the group consisting of cyano, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$;

R$_e$ at each occurrence is independently selected from the group consisting of hydrogen, alkyl, alkenyl, alkynyl, R$_{106}$, haloalkyl, and -alkylR$_{106}$;

R$_f$ at each occurrence is independently selected from the group consisting of hydrogen, alkyl, alkenyl, alkynyl, and R$_{103}$;

wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O(R$_{106}$), —NH$_2$, —N(H)(alkyl), —N(alkyl)$_2$, —N(H)

$(R_{106})$, —N(alkyl)$(R_{106})$, —C(O)OH, —C(O)Oalkyl, —C(O)NH$_2$, —C(O)N(H)(alkyl), —C(O)N(alkyl)$_2$, and $R_{103}$;

$R_g$ at each occurrence is independently selected from the group consisting of hydrogen, alkyl, alkenyl, alkynyl, $R_{106}$, haloalkyl and -alkyl$R_{106}$;

alternatively, $R_f$ and $R_g$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OH, —O(alkyl), —O(cyanoalkyl), —O(haloalkyl), —OR$_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

$R_j$ at each occurrence is independently selected from the group consisting of hydrogen, alkyl, alkenyl, alkynyl, $R_{103}$, haloalkyl and -alkyl$R_{103}$;

$R_k$ at each occurrence is independently selected from the group consisting of hydrogen, alkyl, alkenyl and alkynyl;

alternatively, $R_j$ and $R_k$, together with the carbon atom to which they are attached, form a ring selected from the group consisting of cycloalkyl, cycloalkenyl, heterocycle, aryl and heteroaryl; wherein each ring is independently substituted with 0, 1, 2, 3, 4 or 5 substituents independently selected from the group consisting of alkyl, alkenyl, alkynyl, nitro, cyano, formyl, halo, oxo, —OH, —O(alkyl), —O(cyanoalkyl), —O(haloalkyl), —OR$_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)($R_{106}$), —N(alkyl)($R_{106}$), —C(O)OH, —C(O)Oalkyl, —C(O)NH$_2$, —C(O)N(H)(alkyl), —C(O)N(alkyl)$_2$, and $R_{103}$;

m is 0, 1, 2, 3 or 4;

n is 0, 1, 2, 3 or 4;

$R_p$, $R_q$, $R_{1p}$, $R_{1q}$, $R_{2q}$, $R_{7p}$, $R_{7q}$, $R_{8p}$, and $R_{8q}$, at each occurrence, are independently selected from the group consisting of cycloalkyl, cycloalkenyl, aryl, heteroaryl, and heterocycle; wherein each of the $R_p$, $R_q$, $R_{1p}$, $R_{1q}$, $R_{2q}$, $R_{7p}$, $R_{7q}$, $R_{8p}$, and $R_{8q}$, at each occurrence, is independently substituted with 0, 1, 2, 3, 4 or 5 substituents independently selected from the group consisting of alkyl, alkenyl, alkynyl, cyano, formyl, halo, nitro, oxo, —OR$_{101}$, —OC(O)$R_{101}$, —OC(O)O$R_{101}$, —OC(O)N$R_{101}R_{102}$, —OSO$_2R_{101}$, —OSO$_2$N$R_{101}R_{102}$, —S$R_{101}$, —S(O)$R_{101}$, —SO$_2R_{101}$, —SO$_2$O$R_{101}$, —SO$_2$N$R_{101}R_{102}$, —N$R_{101}R_{102}$, —N($R_{102}$)C(O)$R_{101}$, —N($R_{102}$)C(O)O$R_{101}$, —N($R_{102}$)C(O)N$R_{101}R_{102}$, —N($R_{102}$)SO$_2R_{101}$, —N($R_{102}$)SO$_2$N$R_{101}R_{102}$, —N($R_{102}$)SO$_2$N($R_{102}$)C(O)O$R_{101}$, —C(O)$R_{101}$, —C(O)O$R_{101}$, and —C(O)N$R_{101}R_{102}$; and wherein each of the alkyl, alkenyl and alkynyl is independently substituted with 0, 1, 2 or 3 substituents independently selected from the group consisting of cyano, formyl, halo, nitro, oxo, —OR$_{101}$, —OC(O)$R_{101}$, —OC(O)O$R_{101}$, —OC(O)N$R_{101}R_{102}$, —OSO$_2R_{101}$, —OSO$_2$N$R_{101}R_{102}$, —S$R_{101}$, —S(O)$R_{101}$, —SO$_2R_{101}$, —SO$_2$O$R_{101}$, —SO$_2$N$R_{101}R_{102}$, —N$R_{101}R_{102}$, —N($R_{102}$)C(O)$R_{101}$, —N($R_{102}$)C(O)O$R_{101}$, —N($R_{102}$)C(O)N$R_{101}R_{102}$, —N($R_{102}$)SO$_2R_{101}$, —N($R_{102}$)SO$_2$N($R_{102}$)C(O)O$R_{101}$, —C(O)$R_{101}$, —C(O)O$R_{101}$, and —C(O)N$R_{101}R_{102}$;

$R_{101}$ at each occurrence is independently selected from the group consisting of hydrogen, alkyl, alkenyl, alkynyl, $R_{103}$, -alkyl$R_{103}$, -alkenyl$R_{103}$, -alkynyl$R_{103}$, haloalkyl, cyanoalkyl, -alkylC(O)$R_{104}$, -alkylC(O)O$R_{104}$, -alkylC(O)N$R_{104}R_{105}$, -alkyl-O$R_{104}$, -alkyl-OC(O)$R_{104}$, -alkyl-OC(O)O$R_{104}$, -alkylS$R_{104}$, -alkylS(O)$R_{104}$, -alkylSO$_2R_{104}$, -alkylSO$_2$O$R_{104}$, -alkylSO$_2$N$R_{104}R_{105}$, -alkylN$R_{104}R_{105}$, -alkylN($R_{105}$)C(O)$R_{104}$, -alkylN($R_{105}$)C(O)O$R_{104}$, -alkylN($R_{105}$)C(O)N$R_{104}R_{105}$, -alkylN($R_{105}$)SO$_2R_{104}$, and -alkylN($R_{105}$)SO$_2$N$R_{104}R_{105}$;

$R_{103}$ at each occurrence is independently selected from the group consisting of cycloalkyl, cycloalkenyl, aryl, heteroaryl and heterocycle; wherein each $R_{103}$ is independently substituted with 0, 1, 2, 3, 4 or 5 substituents independently selected from the group consisting of alkyl, alkenyl, alkynyl, halo, nitro, cyano, oxo, formyl, haloalkyl, —OR$_{104}$, —OC(O)$R_{104}$, —OC(O)O$R_{104}$, —OC(O)N$R_{104}R_{105}$, —OSO$_2$N$R_{104}R_{105}$, —SO$_2R_{105}$, —S(O)$R_{104}$, —N$R_{104}R_{105}$, —N($R_{105}$)C(O)N$R_{104}R_{105}$, —N($R_{105}$)COR$_{104}$, —N($R_{105}$)SO$_2R_{104}$, —N($R_{105}$)SO$_2$N$R_{104}R_{105}$, —C(O)$R_{104}$, —C(O)OR$_{104}$, —C(O)NR$_{104}R_{105}$, -alkylOR$_{104}$, -alkylOC(O)$R_{104}$, -alkylOC(O)OR$_{104}$, -alkylOC(O)NR$_{104}R_{105}$, -alkylOSO$_2$NR$_{104}R_{105}$, -alkylSO$_2R_{104}$, -alkylS(O)$R_{104}$, -alkylNR$_{104}R_{105}$, -alkylN($R_{105}$)COR$_{104}$, -alkylN($R_{105}$)SO$_2R_{104}$, -alkylN($R_{104}$)C(O)NR$_{104}R_{105}$, -alkylN($R_{105}$)SO$_2$NR$_{104}R_{105}$, -alkylC(O)R$_{104}$, -alkylC(O)OR$_{104}$, and -alkylC(O)NR$_{104}R_{105}$;

$R_{102}$, $R_{104}$, and $R_{105}$, at each occurrence, are independently selected from the group consisting of hydrogen, alkyl, alkenyl, alkynyl, hydroxyalkyl, alkoxyalkyl, haloalkyl and benzyl;

alternatively, $R_{101}$ and $R_{102}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

alternatively, $R_{104}$ and $R_{105}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl; and $R_{106}$ at each occurrence is independently selected from the group consisting of aryl and heteroaryl, wherein each $R_{106}$ is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl.

For example, the third embodiment of the present invention provides a compound of formula (III) wherein $R^5$ is —OR$_d$ wherein $R_d$ is hydrogen.

For example, the third embodiment of the present invention provides a compound of formula (III) wherein $R^6$ is hydrogen or alkyl.

For example, the third embodiment of the present invention provides a compound of formula (III) wherein $R^1$ is —C(O)OR$_a$, —C(O)NR$_a$R$_b$, R$_{1p}$, alkyl or alkenyl; and $R^2$ is alkyl.

For example, the third embodiment of the present invention provides a compound of formula (III) wherein $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and $R^2$ is alkyl.

For example, the third embodiment of the present invention provides a compound of formula (III) wherein $R^1$ is
  alkyl, wherein the alkyl is unsubstituted or substituted with 1 or 2 substituents selected from the group consisting of
    halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;
  alkenyl, wherein the alkenyl is unsubstituted or substituted with one substituent selected from the group consisting of
    —C(O)OR$_a$, wherein R$_a$ is alkyl, and
    —R$_{1q}$, wherein R$_{1q}$ is aryl,
  —C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$ and wherein R$_{101}$ is alkyl,
  —C(O)NR$_a$R$_b$, wherein R$_a$ is alkyl, or alkyl substituted with one substituent selected from the group consisting of —OC(O)R$_c$, and —OR$_c$ wherein R$_c$ is hydrogen or alkyl, and R$_b$ is alkyl, alternatively, R$_a$ and R$_b$, together with the nitrogen atom to which they are attached, form a heterocyclic ring substituted with one alkyl substitutent wherein the alkyl substituent is substituted with one substituent selected from the group consisting of —OR$_c$, and —OC(O)R$_c$, and wherein R$_c$ is hydrogen or alkyl, or
  R$_{1p}$; wherein R$_{1p}$ is heterocycle; and
  $R^2$ is alkyl.

For example, the third embodiment of the present invention provides a compound of formula (III) wherein $R^1$ is
  propyl, butyl, methyl, ethyl, 2-methylbutyl, 3-methylbutyl, 3,3-dimethylbutyl, 5,5-dimethylhexyl, 3-methylpentyl,
  wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
    halo,
    —OR$_a$, wherein R$_a$ is hydrogen,
    —OC(O)R$_a$, wherein R$_a$ is methyl, ethyl, or isopropyl,
    —OC(O)NR$_a$R$_b$, wherein R$_a$ is methyl, ethyl or isopropyl and R$_b$ is hydrogen,
    —C(O)OR$_a$, wherein R$_a$ is methyl, ethyl, or isopropyl,
    —C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
    —R$_{1q}$; wherein R$_{1q}$ is phenyl, cyclopropyl, cyclobutyl, cyclopentyl or cyclohexyl;
  allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
    —C(O)OR$_a$, wherein R$_a$ is methyl, ethyl or isopropyl, and
    —R$_{1q}$, wherein R$_{1q}$ is aryl,
  —C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
  —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substitutent selected from the group consisting of —OR$_c$, and —OC(O)R$_c$, and wherein R$_c$ is hydrogen or methyl, or
  R$_{1p}$; wherein R$_{1p}$ is 4,5-dihydro-1,3-oxazol-2-yl; and
  $R^2$ is propyl, butyl, methyl, ethyl, 2-methylbutyl, 3-methylbutyl, 3,3-dimethylbutyl, 5,5-dimethylhexyl, or 3-methylpentyl.

For example, the third embodiment of the present invention provides a compound of formula (III) wherein $R^5$ is —OR$_d$ wherein $R_d$ is hydrogen, and $R^6$ is hydrogen or alkyl.

For example, the third embodiment of the present invention provides a compound of formula (III) wherein $R^5$ is —OR$_d$ wherein $R_d$ is hydrogen, $R^6$ is hydrogen or alkyl, $R^1$ is —C(O)OR$_a$, —C(O)NR$_a$R$_b$, R$_{1p}$, alkyl or alkenyl; and $R^2$ is alkyl.

For example, the third embodiment of the present invention provides a compound of formula (III) wherein $R^5$ is —OR$_d$ wherein $R_d$ is hydrogen, $R^6$ is hydrogen or alkyl, $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and $R^2$ is alkyl.

For example, the third embodiment of the present invention provides a compound of formula (III) wherein $R^5$ is —OR$_d$ wherein $R_d$ is hydrogen, $R^6$ is hydrogen or alkyl, $R^1$ is
  alkyl, wherein the alkyl is unsubstituted or substituted with 1 or 2 substituents selected from the group consisting of
    halo,
    —OR$_a$, wherein R$_a$ is hydrogen, —OC(O)R$_a$, wherein R$_a$ is alkyl,
—OC(O)NR$_a$R$_b$, wherein R$_a$ is alkyl, R$_b$ is hydrogen,
—C(O)OR$_a$, wherein R$_a$ is alkyl,
—C=CR$_j$R$_k$, wherein R$_j$ and R$_k$ together with the carbon atom to which they are attached form a cycloalkyl ring; and
—R$_{1q}$; wherein R$_{1q}$ is aryl or cycloalkyl;

alkenyl, wherein the alkenyl is unsubstituted or substituted with one substituent selected from the group consisting of
—C(O)OR$_a$, wherein R$_a$ is alkyl, and
—R$_{1q}$, wherein R$_{1q}$ is aryl,
—C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$ and wherein R$_{101}$ is alkyl,
—C(O)NR$_a$R$_b$, wherein R$_a$ is alkyl, or alkyl substituted with one substituent selected from the group consisting of —OC(O)R$_c$, and —OR$_c$ wherein R$_c$ is hydrogen or alkyl, and R$_b$ is alkyl, alternatively, R$_a$ and R$_b$, together with the nitrogen atom to which they are attached, form a heterocyclic ring substituted with one alkyl substituent wherein the alkyl substituent is substituted with one substituent selected from the group consisting of —OR$_c$, and —OC(O)R$_c$, and wherein R$_c$ is hydrogen or alkyl, or
R$_{1p}$; wherein R$_{1p}$ is heterocycle; and
R$_2$ is alkyl.

For example, the third embodiment of the present invention provides a compound of formula (III) wherein R$^5$ is —OR$_d$ wherein R$_d$ is hydrogen, R$^6$ is hydrogen or methyl, R$^1$ is
propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
halo,
—OR$_a$, wherein R$_a$ is hydrogen,
—OC(O)R$_a$, wherein R$_a$ is methyl, ethyl, or isopropyl,
—OC(O)NR$_a$R$_b$, wherein R$_a$ is methyl, ethyl or isopropyl and R$_b$ is hydrogen,
—C(O)OR$_a$, wherein R$_a$ is methyl, ethyl, or isopropyl,
—C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
—R$_{1q}$; wherein R$_{1q}$ is phenyl, cyclopropyl, cyclobutyl, cyclopentyl or cyclohexyl;
allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—C(O)OR$_a$, wherein R$_a$ is methyl, ethyl or isopropyl, and
—R$_{1q}$, wherein R$_{1q}$ is aryl,
—C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
—C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substituent selected from the group consisting of —OR$_c$, and —OC(O)R$_c$, and wherein R$_c$ is hydrogen or methyl, or
R$_{1p}$; wherein R$_{1p}$ is 4,5-dihydro-1,3-oxazol-2-yl; and
R$^2$ is propyl, butyl, methyl, ethyl, 2-methylbutyl, 3-methylbutyl, 3,3-dimethylbutyl, 5,5-dimethylhexyl, or 3-methylpentyl.

For example, the third embodiment of the present invention provides a compound of formula (III) wherein R$^5$ is —OR$_d$ wherein R$_d$ is hydrogen, R$^6$ is hydrogen or alkyl, R$^1$ is —C(O)OR$_a$, —C(O)NR$_a$R$_b$, R$_{1p}$, alkyl or alkenyl, R$^2$ is alkyl, R$^7$ is formyl, —OR$_a$, —OP(=O)(R$_e$)(OR$_e$), —NR$_a$R$_b$, —N(R$_e$)C(=NH)R$_e$, —N(R$_e$)C(O)R$_a$, —N(R$_e$)C(O)NR$_a$R$_b$, —N(R$_e$)C(=S)NR$_a$R$_b$, —N(R$_e$)C(=S)N(R$_e$)C(O)R$_a$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, or alkyl substituted with one substituent selected from the group consisting of N$_3$, —OR$_a$, —NR$_a$R$_b$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)NR$_a$R$_b$ and R$_{7q}$, and n is 0 or 1.

For example, the third embodiment of the present invention provides a compound of formula (III) wherein R$^5$ is —OR$_d$ wherein R$_d$ is hydrogen; R$^6$ is hydrogen or alkyl; R$^1$ is
alkyl, wherein the alkyl is unsubstituted or substituted with 1 or 2 substituents selected from the group consisting of
halo,
—OR$_a$, wherein R$_a$ is hydrogen,
—OC(O)R$_a$, wherein R$_a$ is alkyl,
—OC(O)NR$_a$R$_b$, wherein R$_a$ is alkyl, R$_b$ is hydrogen,
—C(O)OR$_a$, wherein R$_a$ is alkyl,
—C=CR$_j$R$_k$, wherein R$_j$ and R$_k$ together with the carbon atom to which they are attached form a cycloalkyl ring; and
—R$_{1q}$; wherein R$_{1q}$ is aryl or cycloalkyl;
alkenyl, wherein the alkenyl is unsubstituted or substituted with one substituent selected from the group consisting of
—C(O)OR$_a$, wherein R$_a$ is alkyl, and
—R$_{1q}$, wherein R$_{1q}$ is aryl,
—C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$, wherein R$_{101}$ is alkyl,
—C(O)NR$_a$R$_b$, wherein R$_a$ is alkyl, or alkyl substituted with one substituent selected from the group consisting of —OC(O)R$_c$, and —OR$_c$, wherein R$_c$ is hydrogen or alkyl, and R$_b$ is alkyl, alternatively, R$_a$ and R$_b$, together with the nitrogen atom to which they are attached, form a heterocyclic ring substituted with one alkyl substituent wherein the alkyl is substituted with one substituent selected from the group consisting of —OR$_c$, and —OC(O)R$_c$, and wherein R$_c$ is hydrogen or alkyl, or
R$_{1p}$; wherein R$_{1p}$ is heterocycle;
R$^2$ is alkyl;
R$^7$ is
formyl,
—OR$_a$, wherein R$_a$ is hydrogen, or alkyl substituted with one substituent selected from the group consisting of cyano and —C(O)NR$_c$R$_d$, wherein R$_c$ is hydrogen, and R$_d$ is hydrogen,
—OP(=O)(R$_e$)(OR$_e$), wherein R$_e$ at each occurrence is independently selected from the group consisting of hydrogen and alkyl, —$NR_aR_b$, wherein $R_a$ is hydrogen or alkyl substituted with one cyano, and $R_b$ is hydrogen, —$N(R_e)C(=NH)R_e$, wherein $R_e$ at each occurrence is independently selected from the group consisting of hydrogen and alkyl, —$N(R_e)C(O)R_a$, wherein $R_a$ is alkyl, or alkyl substituted with 1, 2 or 3 halo, and $R_e$ is hydrogen or alkyl, —$N(R_e)C(O)NR_aR_b$, wherein $R_a$ is hydrogen, $R_b$ is hydrogen, and $R_e$ is hydrogen or alkyl, —$N(R_e)C(=S)NR_aR_b$, wherein $R_a$ is hydrogen, $R_b$ is hydrogen, and $R_e$ is hydrogen or alkyl, —$N(R_e)C(=S)N(R_e)C(O)R_a$, wherein $R_e$ at each occurrence is independently selected from the group consisting of hydrogen and alkyl, and $R_a$ is $R_p$ wherein $R_p$ is aryl, —$N(R_e)C(O)OR_a$, wherein $R_a$ is alkyl and $R_e$ is hydrogen or alkyl, —$N(R_e)SOR_a$, wherein $R_a$ is alkyl, and $R_e$ is hydrogen or alkyl, —$N(R_e)SO_2R_a$, wherein $R_e$ is hydrogen or alkyl, $R_a$ is alkyl, alkenyl, $R_p$, wherein $R_p$ is selected from the group consisting of heteroaryl and aryl, or alkyl substituted with 1, 2 or 3 substituents independently selected from the group consisting of
  halo,
  —$C(O)OR_c$, wherein $R_c$ is hydrogen or alkyl,
  —$OR_c$, wherein $R_c$ is hydrogen, and
  —$C(O)NR_cR_d$, wherein $R_c$ is hydrogen, and $R_d$ is hydrogen, —$N(R_e)SO_2NR_aR_b$, wherein $R_e$ is hydrogen or alkyl, $R_b$ is hydrogen, and $R_a$ is hydrogen, alkyl, or alkyl substituted with one substituent selected from the group consisting of:
  —$OR_c$, wherein $R_c$ is hydrogen,
  —$NR_cR_d$, wherein $R_c$ and $R_d$ are hydrogen, and
  —$OC(O)NR_cR_d$, wherein $R_c$ and $R_d$ together with the nitrogen atom to which they are attached, form a heterocycle ring; alternatively, $R_a$ and $R_b$, together with the nitrogen atom to which they are attached, form a heterocycle ring;

—$N(R_e)SO_2N(R_e)C(O)R_a$, wherein $R_e$ at each occurrence is independently selected from the group consisting of hydrogen and alkyl, and $R_a$ is alkyl, —$N(R_e)SO_2N(R_e)C(O)OR_a$, wherein $R_e$ at each occurrence is independently selected from the group consisting of hydrogen and alkyl, and $R_a$ is alkyl substituted with one $R_q$ wherein $R_q$ is aryl, or alkyl substituted with one substituent selected from the group consisting of
  $N_3$,
  —$OR_a$, wherein $R_a$ is hydrogen or alkyl substituted with one —$OR_c$ wherein $R_c$ is alkyl,
  —$NR_aR_b$, wherein $R_a$ is hydrogen and $R_b$ is hydrogen,
  —$N(R_e)SOR_a$, wherein $R_a$ is alkyl and $R_e$ is hydrogen or alkyl,
  —$N(R_e)SO_2R_a$, wherein $R_e$ is hydrogen or alkyl, and $R_a$ is alkyl, or alkyl substituted with one substituent selected from the group consisting of halo and $R_q$; wherein $R_q$ is heterocycle;
  —$N(R_e)SO_2NR_aR_b$, wherein $R_a$, $R_b$ are hydrogen, and $R_e$ is hydrogen or alkyl,
  —$N(R_e)SO_2N(R_e)C(O)R_a$, wherein $R_e$ at each occurrence is independently selected from the group consisting of hydrogen and alkyl, $R_a$ is alkyl substituted with $R_q$, wherein $R_q$ is aryl,
  —$C(O)NR_aR_b$ wherein $R_a$ is hydrogen and $R_b$ is hydrogen, and
  $R_{7q}$, wherein $R_{7q}$ is heterocycle; and n is 0 or 1.

For example, the third embodiment of the present invention provides a compound of formula (III) wherein $R^5$ is —$OR_d$ wherein $R_d$ is hydrogen; $R^6$ is hydrogen or alkyl;

$R^1$ is
  propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
    halo,
    —$OR_a$, wherein $R_a$ is hydrogen,
    —$OC(O)R_a$, wherein $R_a$ is methyl, ethyl, or isopropyl,
    —$OC(O)NR_aR_b$, wherein $R_a$ is methyl, ethyl or isopropyl and $R_b$ is hydrogen,
    —$C(O)OR_a$, wherein $R_a$ is methyl, ethyl, or isopropyl,
    —$C=CR_jR_k$, wherein $R_j$ and $R_k$ together with the carbon atom to which they are attached form a ring selected from the group consisting of cyclopropyl, cyclobutyl, cyclopentyl and cyclohexyl,
    —$R_{1q}$; wherein $R_{1q}$ is phenyl, cyclopropyl, cyclobutyl, cyclopentyl or cyclohexyl;
  allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
    —$C(O)OR_a$, wherein $R_a$ is methyl, ethyl or isopropyl, and
    —$R_{1q}$, wherein $R_{1q}$ is aryl,
  —$C(O)OR_a$, wherein $R_a$ is methyl, ethyl or isopropyl, wherein each of the methyl, ethyl or isopropyl is unsubstituted or substituted with one $R_{1q}$, wherein $R_{1q}$ is a pyrrolidine ring, unsubstituted or substituted with one —$C(O)OR_{101}$, wherein $R_{101}$ is methyl, ethyl or isopropyl,
  —$C(O)NR_aR_b$, wherein $R_a$ is methyl or ethyl, wherein each of the methyl or ethyl is unsubstituted or substituted with one substituent selected from the group consisting of —$OC(O)R_c$, and —$OR_c$, wherein Rc is hydrogen or methyl, and $R_b$ is methyl, alternatively, $R_a$ and $R_b$, together with the nitrogen atom to which they are attached, form a pyrrolidine ring substituted with one methyl wherein the methyl is substituted with one substitutent selected from the group consisting of —$OR_c$, and —$OC(O)R_c$, and wherein $R_c$ is hydrogen or methyl,
  or
  $R_{1p}$; wherein $R_{1p}$ is 4,5-dihydro-1,3-oxazol-2-yl;

$R^2$ is propyl, butyl, methyl, ethyl, 2-methylbutyl, 3-methylbutyl, 3,3-dimethylbutyl, 5,5-dimethylhexyl, or 3-methylpentyl;

$R^7$ is
  formyl,
  —$OR_a$, wherein $R_a$ is hydrogen, or methyl substituted with one substituent selected from the group consisting of cyano and —$C(O)NR_cR_d$, wherein $R_c$ is hydrogen, and $R_d$ is hydrogen,
  —$OP(=O)(R_e)(OR_e)$, wherein $R_e$ at each occurrence is independently selected from the group consisting of hydrogen, methyl and ethyl.
  —$NR_aR_b$, wherein $R_a$ is hydrogen, or methyl substituted with one cyano, and $R_b$ is hydrogen, —N($R_e$)C(=NH)$R_e$, wherein $R_e$ at each occurrence is independently selected from the group consisting of hydrogen and methyl, —N($R_e$)C(O)$R_a$, wherein $R_a$ is methyl or ethyl wherein each of the methyl or ethyl is unsubstituted or substituted with 1, 2 or 3 halo, and $R_e$ is hydrogen or methyl, —N($R_e$)C(O)N$R_aR_b$, wherein $R_a$ is hydrogen, $R_b$ is hydrogen, and $R_e$ is hydrogen or methyl, —N($R_e$)C(=S)N$R_aR_b$, wherein $R_a$ is hydrogen, $R_b$ is hydrogen, and $R_e$ is hydrogen or methyl, —N($R_e$)C(=S)N($R_e$)C(O)$R_a$, $R_e$ at each occurrence is independently selected from the group consisting of hydrogen and methyl, and $R_a$ is $R_p$, wherein $R_p$ is phenyl, —N($R_e$)C(O)O$R_a$, wherein $R_a$ is tert-butyl and $R_e$ is hydrogen or methyl, —N($R_e$)SO$R_a$, wherein $R_a$ is methyl, and $R_e$ is hydrogen or methyl, —N($R_e$)SO$_2R_a$, wherein $R_e$ is hydrogen or methyl, $R_a$ is methyl, ethyl, propyl, isopropyl, butyl, ethylenyl or $R_p$, wherein $R_p$ is selected from the group consisting of imidazolyl, thienyl, benzimidazolyl, phenyl, and naphthyl, wherein each of the methyl, ethyl, propyl, isopropyl and butyl is independently unsubstituted or substituted with 1, 2 or 3 substituents independently selected from the group consisting of halo, —C(O)O$R_c$, wherein $R_c$ is hydrogen, methyl or tert-butyl, —O$R_c$, wherein $R_c$ is hydrogen, and —C(O)N$R_cR_d$, wherein $R_c$ is hydrogen, and $R_d$ is hydrogen, —N($R_e$)SO$_2$N$R_aR_b$, wherein $R_e$ is hydrogen or methyl, $R_b$ is hydrogen, and $R_a$ is hydrogen, methyl, or ethyl, wherein each of the methyl or ethyl is independently unsubstituted or substituted with one substituent selected from the group consisting of:

—O$R_c$, wherein $R_c$ is hydrogen,

—N$R_cR_d$, wherein $R_c$ and $R_d$ are hydrogen, and

—OC(O)N$R_cR_d$, wherein $R_c$ and $R_d$ together with the nitrogen atom to which they are attached, form a heterocycle ring wherein the heterocycle is azetidine; alternatively, $R_a$ and $R_b$, together with the nitrogen atom to which they are attached, form a heterocycle ring wherein the heterocycle is pyrrolidine or azetidine;

—N($R_e$)SO$_2$N($R_e$)C(O)$R_a$, wherein $R_e$ at each occurrence is independently selected from the group consisting of hydrogen and methyl, and $R_a$ is methyl, ethyl, propyl or butyl;

—N($R_e$)SO$_2$N($R_e$)C(O)O$R_a$, wherein $R_e$ at each occurrence is independently selected from the group consisting of hydrogen and methyl, and $R_a$ is methyl substituted with one $R_q$ wherein $R_q$ is phenyl;

methyl substituted with one substituent selected from the group consisting of $N_3$, —O$R_a$, wherein $R_a$ is hydrogen, or methyl substituted with one —O$R_c$ wherein $R_c$ is methyl;

—N$R_aR_b$, wherein $R_a$ is hydrogen and $R_b$ is hydrogen;

—N($R_e$)SO$R_a$, wherein $R_a$ is methyl, and $R_e$ is hydrogen or methyl;

—N($R_e$)SO$_2R_a$, wherein $R_e$ is hydrogen or methyl, and $R_a$ is methyl or ethyl; wherein each of the methyl or ethyl is independently unsubstituted or substituted with one substituent selected from the group consisting of halo and $R_q$; wherein $R_q$ is morpholinyl;

—N($R_e$)SO$_2$N$R_aR_b$, wherein $R_a$ and $R_b$ are hydrogen, and $R_e$ is hydrogen or methyl;

—N($R_e$)SO$_2$N($R_e$)C(O)O$R_a$, wherein $R_e$ at each occurrence is independently selected from the group consisting of hydrogen and methyl, $R_a$ is methyl substituted with $R_q$, wherein $R_q$ is phenyl;

—C(O)N$R_aR_b$ wherein $R_a$ is hydrogen and $R_b$ is hydrogen, and $R_{7q}$, wherein $R_{7q}$ is 1,1-dioxidoisothiazolidin-2-yl;

or ethyl substituted with —C(O)N$R_aR_b$, wherein $R_a$ and $R_b$ are hydrogen; and n is 0 or 1.

For example, the third embodiment of the present invention provides a compound of formula (III) wherein $R^5$ is —O$R_d$ wherein $R_d$ is hydrogen, $R^6$ is hydrogen or alkyl, $R^1$ is —C(O)O$R_a$, —C(O)N$R_aR_b$, $R_{1p}$, alkyl or alkenyl, $R^2$ is alkyl, $R^7$ is formyl, —O$R_a$, —OP(=O)($R_e$)(O$R_e$), —N$R_aR_b$, —N($R_e$)C(=NH)$R_e$, —N($R_e$)C(O)$R_a$, —N($R_e$)C(O)N$R_aR_b$, —N($R_e$)C(=S)N$R_aR_b$, —N($R_e$)C(=S)N($R_e$)C(O)$R_a$, —N($R_e$)C(O)O$R_a$, —N($R_e$)SO$R_a$, —N($R_e$)SO$_2R_a$, —N($R_e$)SO$_2$N$R_aR_b$, —N($R_e$)SO$_2$N($R_e$)C(O)$R_a$, —N($R_e$)SO$_2$N($R_e$)C(O)O$R_a$, or alkyl substituted with one substituent selected from the group consisting of $N_3$, —O$R_a$, —N$R_aR_b$, —N($R_e$)SO$R_a$, —N($R_e$)SO$_2R_a$, —N($R_e$)SO$_2$N$R_aR_b$, —N($R_e$)SO$_2$N($R_e$)C(O)O$R_a$, —C(O)N$R_aR_b$ and $R_{7q}$, $R^8$ is halo or —O$R_a$, m is 0 or 1; and n is 0 or 1.

For example, the third embodiment of the present invention provides a compound of formula (III) wherein $R^5$ is —O$R_d$ wherein $R_d$ is hydrogen; $R^6$ is hydrogen or alkyl;

$R^1$ is alkyl, wherein the alkyl is unsubstituted or substituted with 1 or 2 substituents selected from the group consisting of halo, —O$R_a$, wherein $R_a$ is hydrogen, —OC(O)$R_a$, wherein $R_a$ is alkyl, —OC(O)N$R_aR_b$, wherein $R_a$ is alkyl, $R_b$ is hydrogen, —C(O)O$R_a$, wherein $R_a$ is alkyl, —C=C$R_jR_k$, wherein $R_j$ and $R_k$ together with the carbon atom to which they are attached form a cycloalkyl ring; and —$R_{1q}$; wherein $R_{1q}$ is aryl or cycloalkyl;

alkenyl, wherein the alkenyl is unsubstituted or substituted with one substituent selected from the group consisting of —C(O)O$R_a$, wherein $R_a$ is alkyl, and —$R_{1q}$, wherein $R_{1q}$ is aryl, —C(O)O$R_a$, wherein $R_a$ is alkyl, or alkyl substituted with one $R_{1q}$, wherein $R_{1q}$ is a heterocyclic ring, unsubstituted or substituted with one —C(O)O$R_{101}$, wherein $R_{101}$ is alkyl, —C(O)N$R_aR_b$, wherein $R_a$ is alkyl, or alkyl substituted with one substituent selected from the group consisting of —OC(O)$R_c$, and —O$R_c$, wherein $R_c$ is hydrogen or alkyl, and $R_b$ is alkyl, alternatively, $R_a$ and $R_b$, together with the nitrogen atom to which they are attached, form a heterocyclic ring substituted with one alkyl substitutent wherein the alkyl is substituted with one substituent selected from the group consisting of —O$R_c$, and —OC(O)$R_c$, and wherein $R_c$ is hydrogen or alkyl, or $R_{1p}$, wherein $R_{1p}$ is heterocycle;

$R^2$ is alkyl;
$R^7$ is
formyl,
—$OR_a$, wherein $R_a$ is hydrogen or alkyl substituted with one substituent selected from the group consisting of cyano and —$C(O)NR_cR_d$, wherein $R_c$ is hydrogen, and $R_d$ is hydrogen,
—$OP(=O)(R_e)(OR_e)$, wherein $R_e$ at each occurrence is independently selected from the group consisting of hydrogen and alkyl,
—$NR_aR_b$, wherein $R_a$ is hydrogen or alkyl substituted with one cyano, and $R_b$ is hydrogen,
—$N(R_e)C(=NH)R_e$, wherein $R_e$ at each occurrence is independently selected from the group consisting of hydrogen and alkyl,
—$N(R_e)C(O)R_a$, wherein $R_a$ is alkyl, or alkyl substituted with 1, 2 or 3 halo, and $R_e$ is hydrogen or alkyl,
—$N(R_e)C(O)NR_aR_b$, wherein $R_a$ is hydrogen, $R_b$ is hydrogen, and $R_e$ is hydrogen or alkyl,
—$N(R_e)C(=S)NR_aR_b$, wherein $R_a$ is hydrogen, $R_b$ is hydrogen, and $R_e$ is hydrogen or alkyl,
—$N(R_e)C(=S)N(R_e)C(O)R_a$, wherein $R_e$ at each occurrence is independently selected from the group consisting of hydrogen and alkyl, and $R_a$ is $R_p$ wherein $R_p$ is aryl,
—$N(R_e)C(O)OR_a$, wherein $R_a$ is alkyl and $R_e$ is hydrogen or alkyl,
—$N(R_e)SOR_a$, wherein $R_a$ is alkyl, and $R_e$ is hydrogen or alkyl,
—$N(R_e)SO_2R_a$, wherein $R_e$ is hydrogen or alkyl, $R_a$ is alkyl, alkenyl, $R_p$, wherein $R_p$ is selected from the group consisting of heteroaryl and aryl, or alkyl substituted with 1, 2 or 3 substituents independently selected from the group consisting of
halo,
—$C(O)OR_c$, wherein $R_c$ is hydrogen or alkyl,
—$OR_c$, wherein $R_c$ is hydrogen, and
—$C(O)NR_cR_d$, wherein $R_c$ is hydrogen, and $R_d$ is hydrogen,
—$N(R_e)SO_2NR_aR_b$, wherein $R_e$ is hydrogen or alkyl, $R_b$ is hydrogen, and $R_a$ is hydrogen, alkyl, or alkyl substituted with one substituent selected from the group consisting of:
—$OR_c$, wherein $R_c$ is hydrogen,
—$NR_cR_d$, wherein $R_c$ and $R_d$ are hydrogen, and
—$OC(O)NR_cR_d$, wherein $R_c$ and $R_d$ together with the nitrogen atom to which they are attached, form a heterocycle ring; alternatively, $R_a$ and $R_b$, together with the nitrogen atom to which they are attached, form a heterocycle ring;
—$N(R_e)SO_2N(R_e)C(O)R_a$, wherein $R_e$ at each occurrence is independently selected from the group consisting of hydrogen and alkyl, and $R_a$ is alkyl,
—$N(R_e)SO_2N(R_e)C(O)OR_a$, wherein $R_e$ at each occurrence is independently selected from the group consisting of hydrogen and alkyl, and $R_a$ is alkyl substituted with one $R_q$ wherein $R_q$ is aryl,
or
alkyl substituted with one substituent selected from the group consisting of
$N_3$,
—$OR_a$, wherein $R_a$ is hydrogen or alkyl substituted with one —$OR_c$ wherein $R_c$ is alkyl,
—$NR_aR_b$, wherein $R_a$ is hydrogen and $R_b$ is hydrogen,
—$N(R_e)SOR_a$, wherein $R_a$ is alkyl and $R_e$ is hydrogen or alkyl,
—$N(R_e)SO_2R_a$, wherein $R_e$ is hydrogen or alkyl, and $R_a$ is alkyl, or alkyl substituted with one substituent selected from the group consisting of halo and $R_q$, wherein $R_q$ is heterocycle;
—$N(R_e)SO_2NR_aR_b$, wherein $R_a$, $R_b$ are hydrogen, and $R_e$ is hydrogen or alkyl,
—$N(R_e)SO_2N(R_e)C(O)OR_a$, wherein $R_e$ at each occurrence is independently selected from the group consisting of hydrogen and alkyl, $R_a$ is alkyl substituted with $R_q$, wherein $R_q$ is aryl,
—$C(O)NR_aR_b$ wherein $R_a$ is hydrogen and $R_b$ is hydrogen, and
$R_{7q}$, wherein $R_{7q}$ is heterocycle;
$R^8$ is halo or —$OR_a$, wherein $R_a$ is hydrogen or alkyl;
m is 0 or 1; and
n is 0 or 1.

For example, the third embodiment of the present invention provides a compound of formula (III) wherein $R^5$ is —$OR_d$ wherein $R_d$ is hydrogen; $R^6$ is hydrogen or alkyl;
$R^1$ is
propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is unsubstituted or substituted with 1 or 2 substituents selected from the group consisting of
halo,
—$OR_a$, wherein $R_a$ is hydrogen,
—$OC(O)R_a$, wherein $R_a$ is methyl, ethyl, or isopropyl,
—$OC(O)NR_aR_b$, wherein $R_a$ is methyl, ethyl or isopropyl and $R_b$ is hydrogen,
—$C(O)OR_a$, wherein $R_a$ is methyl, ethyl, or isopropyl,
—$C=CR_jR_k$, wherein $R_j$ and $R_k$ together with the carbon atom to which they are attached form a ring selected from the group consisting of cyclopropyl, cyclobutyl, cyclopentyl and cyclohexyl,
—$R_{1q}$; wherein $R_{1q}$ is phenyl, cyclopropyl, cyclobutyl, cyclopentyl or cyclohexyl;
allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—$C(O)OR_a$, wherein $R_a$ is methyl, ethyl or isopropyl, and
—$R_{1q}$, wherein $R_{1q}$ is aryl,
—$C(O)OR_a$, wherein $R_a$ is methyl, ethyl or isopropyl, wherein each of the methyl, ethyl or isopropyl is unsubstituted or substituted with one $R_{1q}$, wherein $R_{1q}$ is a pyrrolidine ring, unsubstituted or substituted with one —$C(O)OR_{101}$, wherein $R_{101}$ is methyl, ethyl or isopropyl,
—$C(O)NR_aR_b$, wherein $R_a$ is methyl or ethyl, wherein each of the methyl or ethyl is unsubstituted or substituted with one substituent selected from the group consisting of —$OC(O)R_c$, and —$OR_c$, wherein $R_c$ is hydrogen or methyl, and $R_b$ is methyl, alternatively, $R_a$ and $R_b$, together with the nitrogen atom to which they are attached, form a pyrrolidine ring substituted with one methyl wherein the methyl is substituted with one substitutent selected from the group consisting of —$OR_c$, and —$OC(O)R_c$, and wherein $R_c$ is hydrogen or methyl,
or
$R_{1p}$; wherein $R_{1p}$ is 4,5-dihydro-1,3-oxazol-2-yl;
$R^2$ is propyl, butyl, methyl, ethyl, 2-methylbutyl, 3-methylbutyl, 3,3-dimethylbutyl, 5,5-dimethylhexyl, or 3-methylpentyl;

$R^7$ is
formyl,
—$OR_a$, wherein $R_a$ is hydrogen, or methyl substituted with one substituent selected from the group consisting of cyano and —$C(O)NR_cR_d$, wherein $R_c$ is hydrogen, and $R_d$ is hydrogen,
—$OP(=O)(R_e)(OR_e)$, wherein $R_e$ at each occurrence is independently selected from the group consisting of hydrogen, methyl and ethyl.
—$NR_aR_b$, wherein $R_a$ is hydrogen, or methyl substituted with one cyano, and $R_b$ is hydrogen,
—$N(R_e)C(=NH)R_e$, wherein $R_e$ at each occurrence is independently selected from the group consisting of hydrogen and methyl,
—$N(R_e)C(O)R_a$, wherein $R_a$ is methyl or ethyl wherein each of the methyl or ethyl is unsubstituted or substituted with 1, 2 or 3 halo, and $R_e$ is hydrogen or methyl,
—$N(R_e)C(O)NR_aR_b$, wherein $R_a$ is hydrogen, $R_b$ is hydrogen, and $R_e$ is hydrogen or methyl,
—$N(R_e)C(=S)NR_aR_b$, wherein $R_a$ is hydrogen, $R_b$ is hydrogen, and $R_e$ is hydrogen or methyl,
—$N(R_e)C(=S)N(R_e)C(O)R_a$, $R_e$ at each occurrence is independently selected from the group consisting of hydrogen and methyl, and $R_a$ is $R_p$, wherein $R_p$ is phenyl,
—$N(R_e)C(O)OR_a$, wherein $R_a$ is tert-butyl and $R_e$ is hydrogen or methyl,
—$N(R_e)SOR_a$, wherein $R_a$ is methyl, and $R_e$ is hydrogen or methyl,
—$N(R_e)SO_2R_a$, wherein $R_e$ is hydrogen or methyl, $R_a$ is methyl, ethyl, propyl, isopropyl, butyl, ethylenyl or $R_p$, wherein $R_p$ is selected from the group consisting of imidazolyl, thienyl, benzimidazolyl, phenyl, and naphthyl, wherein each of the methyl, ethyl, propyl, isopropyl and butyl is independently unsubstituted or substituted with 1, 2 or 3 substituents independently selected from the group consisting of
halo,
—$C(O)OR_c$, wherein $R_c$ is hydrogen, methyl or tert-butyl,
—$OR_c$, wherein $R_c$ is hydrogen, and
—$C(O)NR_cR_d$, wherein $R_c$ is hydrogen, and $R_d$ is hydrogen,
—$N(R_e)SO_2NR_aR_b$, wherein $R_e$ is hydrogen or methyl, $R_b$ is hydrogen, and $R_a$ is hydrogen, methyl, or ethyl, wherein each of the methyl or ethyl is independently unsubstituted or substituted with one substituent selected from the group consisting of:
—$OR_c$, wherein $R_c$ is hydrogen,
—$NR_cR_d$, wherein $R_c$ and $R_d$ are hydrogen, and
—$OC(O)NR_cR_d$, wherein $R_c$ and $R_d$ together with the nitrogen atom to which they are attached, form a heterocycle ring wherein the heterocycle is azetidine; alternatively, $R_a$ and $R_b$, together with the nitrogen atom to which they are attached, form a heterocycle ring wherein the heterocycle is pyrrolidine or azetidine;
—$N(R_e)SO_2N(R_e)C(O)R_a$, wherein $R_e$ at each occurrence is independently selected from the group consisting of hydrogen and methyl, and $R_a$ is methyl, ethyl, propyl or butyl;
—$N(R_e)SO_2N(R_e)C(O)OR_a$, wherein $R_e$ at each occurrence is independently selected from the group consisting of hydrogen and methyl, and $R_a$ is methyl substituted with one $R_q$ wherein $R_q$ is phenyl;
methyl substituted with one substituent selected from the group consisting of
$N_3$,
—$OR_a$, wherein $R_a$ is hydrogen, or methyl substituted with one —$OR_c$ wherein $R_c$ is methyl;
—$NR_aR_b$, wherein $R_a$ is hydrogen and $R_b$ is hydrogen;
—$N(R_e)SOR_a$, wherein $R_a$ is methyl, and $R_e$ is hydrogen or methyl;
—$N(R_e)SO_2R_a$, wherein $R_e$ is hydrogen or methyl, and $R_a$ is methyl or ethyl; wherein each of the methyl or ethyl is independently unsubstituted or substituted with one substituent selected from the group consisting of halo and $R_q$; wherein $R_q$ is morpholinyl;
—$N(R_e)SO_2NR_aR_b$, wherein $R_a$ and $R_b$ are hydrogen, and $R_e$ is hydrogen or methyl;
—$N(R_e)SO_2N(R_e)C(O)OR_a$, wherein $R_e$ at each occurrence is independently selected from the group consisting of hydrogen and methyl, $R_a$ is methyl substituted with $R_q$, wherein $R_q$ is phenyl;
—$C(O)NR_aR_b$ wherein $R_a$ is hydrogen and $R_b$ is hydrogen, and
$R_{7q}$, wherein $R_{7q}$ is 1,1-dioxidoisothiazolidin-2-yl;
or
ethyl substituted with —$C(O)NR_aR_b$, wherein $R_a$ and $R_b$ are hydrogen;
$R^8$ is halo or $OR_a$, wherein $R_a$ is hydrogen or methyl;
m is 0 or 1; and
n is 0 or 1.

Exemplary compounds of the third embodiment include, but are not limited to, the following:

1,1-dibutyl-4-hydroxy-3-{7-[(methoxymethoxy)methyl]-1,1-dioxido-4H-thieno[2,3-e][1,2,4]thiadiazin-3-yl}-2(1H)-naphthalenone;

1,1-dibutyl-4-hydroxy-3-[7-(hydroxymethyl)-1,1-dioxido-4H-thieno[2,3-e][1,2,4]thiadiazin-3-yl]-2(1H)-naphthalenone;

(1R)-4-hydroxy-3-{7-[(methoxymethoxy)methyl]-1,1-dioxido-4H-thieno[2,3-e][1,2,4]thiadiazin-3-yl}-1-methyl-1-(3-methylbutyl)naphthalen-2(1H)-one;

(1R)-4-hydroxy-3-[7-(hydroxymethyl)-1,1-dioxido-4H-thieno[2,3-e][1,2,4]thiadiazin-3-yl]1-methyl-1-(3-methylbutyl)naphthalen-2(1H)-one;

(1R)-3-[7-(azidomethyl)-1,1-dioxido-4H-thieno[2,3-e][1,2,4]thiadiazin-3-yl]-4-hydroxy-1-methyl-1-(3-methylbutyl)naphthalen-2(1H)-one;

(1R)-3-[7-(aminomethyl)-1,1-dioxido-4H-thieno[2,3-e][1,2,4]thiadiazin-3-yl]-4-hydroxy-1-methyl-1-(3-methylbutyl)naphthalen-2(1H)-one;

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)methanesulfonamide;

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)-2-morpholin-4-ylethanesulfonamide;

(1R)-1-(3,3-dimethylbutyl)-4-hydroxy-3-{7-[(methoxymethoxy)methyl]-1,1-dioxido-4H-thieno[2,3-e][1,2,4]thiadiazin-3-yl}-1-methylnaphthalen-2(1H)-one;

(1R)-1-(3,3-dimethylbutyl)-4-hydroxy-3-[7-(hydroxymethyl)-1,1-dioxido-4H-thieno[2,3-e][1,2,4]thiadiazin-3-yl]-1-methylnaphthalen-2(1H)-one;

(1R)-3-[7-(aminomethyl)-1,1-dioxido-4H-thieno[2,3-e][1,2,4]thiadiazin-3-yl]-1-(3,3-dimethylbutyl)-4-hydroxy-1-methylnaphthalen-2(1H)-one;

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)methanesulfonamide;

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)-N-methylmethanesulfonamide;

N-({3-[(4R)-4-(3,3-dimethylbutyl)-1-hydroxy-4-methyl-3-oxo-3,4-dihydronaphthalen-2-yl]-4-methyl-1,1-dioxido-4H-thieno[2,3-e][1,2,4]thiadiazin-7-yl}methyl)-N-methylmethanesulfonamide;

benzyl[({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)amino]sulfonylcarbamate;

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)sulfamide;

3-chloro-N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)propane-1-sulfonamide; and (1R)-1-(3,3-dimethylbutyl)-3-{7-[(1,1-dioxidoisothiazolidin-2-yl)methyl]-1,1-dioxido-4H-thieno[2,3-e][1,2,4]thiadiazin-3-yl}-4-hydroxy-1-methylnaphthalen-2(1H)-one; or a pharmaceutically acceptable form, stereoisomer, or tautomer, or combination thereof.

In a fourth embodiment the present invention is directed to a pharmaceutical composition comprising a compound or combination of compounds of formula (I), (II) or (III), or a pharmaceutically acceptable salt form, stereoisomer, or tautomer, or combination thereof, in combination with a pharmaceutically acceptable carrier.

For example, the fourth embodiment of the present invention provides a pharmaceutical composition comprising a compound or combination of compounds selected from the group consisting of N-{3-[(4R)-4-(3,3-dimethylbutyl)-7-fluoro-1-hydroxy-4-methyl-3-oxo-3,4-dihydronaphthalen-2-yl]-1,1-dioxido-4H-1,2,4-benzothiadiazin-7-yl}methanesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide;

N-{3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide;

N-(2-hydroxyethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

2-hydroxy-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide;

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide;

N-{3-[(4R)-4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide;

methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate;

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)methanesulfonamide; and N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)sulfamide; or a pharmaceutically acceptable salt form, stereoisomer, or tautomer, or combination thereof, in combination with a pharmaceutically acceptable carrier, wherein the pharmaceutically acceptable salt form is potassium, sodium, calcium or magnesium.

Any one of the aforementioned pharmaceutical compositions can be used for the treatment or prevention of an infection caused by an RNA-containing virus, specifically when the RNA-containing virus is hepatitis C virus (HCV).

In a fifth embodiment the present invention is directed to a method of inhibiting the replication of an RNA-containing virus comprising contacting said virus with a therapeutically effective amount of a compound or combination of compounds of formula (I), (II) or (III), or a pharmaceutically acceptable salt, stereoisomer, tautomer or combination thereof.

In a sixth embodiment the present invention is directed to a method of treating or preventing infection caused by an RNA-containing virus comprising administering to a patient in need of such treatment a therapeutically effective amount of a compound or combination of compounds of formula (I), (II) or (III), or a pharmaceutically acceptable salt, stereoisomer, or tautomer, or combination thereof.

For example, the sixth embodiment of the present invention is directed to a method of treating or preventing infection caused by an RNA-containing virus comprising administering to a patient in need of such treatment a therapeutically effective amount of a compound or combination of compounds of formula (I), (II) or (III), or a pharmaceutically acceptable salt, stereoisomer, tautomer, or combination thereof, wherein the RNA-containing virus is hepatitis C virus.

For example, the sixth embodiment of the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of formula (I), (II) or (III), or a pharmaceutically acceptable salt, stereoisomer, tautomer, or combination thereof.

For example, the sixth embodiment of the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of formula (I), (II) or (III), or a pharmaceutically acceptable salt, stereoisomer, tautomer, or combination thereof, wherein the host immune modulator is selected from the group consisting of interferon-alpha, pegylated-interferon-alpha, interferon-beta, interferon-gamma, a cytokine, a vaccine, and a vaccine comprising an antigen and an adjuvant.

For example, the sixth embodiment of the present invention provides a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of formula (I), (II) or (III), or a pharmaceutically acceptable salt, stereoisomer, tautomer, or combination thereof, wherein said second antiviral agent inhibits replication of HCV by inhibiting host cellular functions associated with viral replication.

For example, the sixth embodiment of the present invention provides a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of formula (I), (II) or (III), or a pharmaceutically acceptable salt, stereoisomer, tautomer, or combination thereof, wherein said second antiviral agent inhibits replication of HCV by targeting proteins of the viral genome.

For example, the sixth embodiment of the present invention provides a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of formula (I), (II) or (III), or a pharmaceutically acceptable salt, stereoisomer, tautomer, or combination thereof.

For example, the sixth embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of formula (I), (II) or (III), or a pharmaceutically acceptable salt, stereoisomer, tautomer, or combination thereof. An agent that treats patients for disease caused by hepatitis B (HBV) infection may be for example, but not limited thereto, L-deoxythymidine, adefovir, lamivudine or tenofovir, or any combination thereof.

For example, the sixth embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of formula (I), (II) or (III), or a pharmaceutically acceptable salt, stereoisomer, tautomer or combination thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

In a seventh embodiment, the present invention provides the use of a compound or a combination of compounds having formula (I), (II) or (III), or a therapeutically acceptable salt form, stereoisomer, or tautomer, or combination thereof, to prepare a medicament for the treatment of infection caused by RNA-containing virus in a patient.

For example, the seventh embodiment of the present invention provides the use of a compound or a combination of compounds having formula (I), (II) or (III), or a therapeutically acceptable salt form, stereoisomer, or tautomer, or combination thereof, to prepare a medicament for the treatment of infection caused by hepatitis C virus in a patient.

For example, the seventh embodiment of the present invention provides the use of a compound or a combination of compounds having formula (I), (II) or (III), or a therapeutically acceptable salt form, stereoisomer, or tautomer, or combination thereof, and one or more agents selected from the group consisting of a host immune modulator and a second antiviral agent, or a combination thereof, to prepare a medicament for the treatment of an infection caused by an RNA-containing virus in a patient.

For example, the seventh embodiment of the present invention provides the use of a compound or a combination of compounds having formula (I), (II) or (III), or a therapeutically acceptable salt form, stereoisomer, or tautomer, or a combination thereof, and one or more agents selected from the group consisting of a host immune modulator and a second antiviral agent, or a combination thereof, to prepare a medicament for the treatment of an infection caused by an RNA-containing virus in a patient, wherein the host immune modulator is selected from the group consisting of interferon-alpha, pegylated-interferon-alpha, interferon-beta, interferon-gamma, a cytokine, a vaccine, and a vaccine comprising an antigen and an adjuvant.

For example, the seventh embodiment of the present invention provides the use of a compound or a combination of compounds having formula (I), (II) or (III), or a therapeutically acceptable salt form, stereoisomer, or tautomer, or combination thereof, and one or more agents selected from the group consisting of a host immune modulator and a second antiviral agent, or a combination thereof, to prepare a medicament for the treatment of an infection caused by an RNA-containing virus in a patient, wherein said second antiviral agent inhibits replication of HCV by inhibiting host cellular functions associated with viral replication.

For example, the seventh embodiment of the present invention provides the use of a compound or a combination of compounds having formula (I), (II) or (III), or a therapeutically acceptable salt form, stereoisomer, or tautomer, or combination thereof, and one or more agents selected from the group consisting of a host immune modulator and a second antiviral agent, or a combination thereof, to prepare a medicament for the treatment of an infection caused by an RNA-containing virus in a patient, wherein said second antiviral agent inhibits replication of HCV by targeting proteins of the viral genome.

For example, the seventh embodiment of the present invention provides the use of a compound or a combination of compounds having formula (I), (II) or (III), or a therapeutically acceptable salt form, stereoisomer, or tautomer, or combination thereof, and an agent or combination of agents that treat or alleviate symptoms of HCV infection including cirrhosis and inflammation of the liver, to prepare a medicament for the treatment of an infection caused by an RNA-containing virus in a patient.

For example, the seventh embodiment of the present invention provides the use of a compound or a combination of compounds having formula (I), (II) or (III), or a therapeutically acceptable salt form, stereoisomer, or tautomer, or combination thereof, and one or more agents that treat patients for disease caused by hepatitis B (HBV) infection, to prepare a medicament for the treatment of an infection caused by an RNA-containing virus in a patient. An agent that treats patients for disease caused by hepatitis B (HBV) infection may be for example, but is not limited thereto, L-deoxythymidine, adefovir, lamivudine or tenofovir, or any combination thereof.

For example, the seventh embodiment of the present invention provides the use of a compound or a combination of compounds having formula (I), (II) or (III), or a therapeutically acceptable salt form, stereoisomer, or tautomer, or combination thereof, and one or more agents that treat patients for disease caused by human immunodeficiency virus (HIV) infection, to prepare a medicament for the treatment of an infection caused by an RNA-containing virus in a patient. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof.

A "patient" is any individual treated with a compound of the present invention, or a therapeutically acceptable salt form, stereoisomer, or tautomer, as defined herein. Patients include humans, as well as other animals such as companion animals (e.g. dogs and cats) and livestock. Patients may be experiencing one or more symptoms of a condition responsive to inhibition of HCV, or may be free of such symptom(s) (i.e. treatment may be prophylactic).

In an eighth embodiment the present invention provides an intermediate of formula (IV) used in the preparation of a compound of formula (I), (II) or (III)

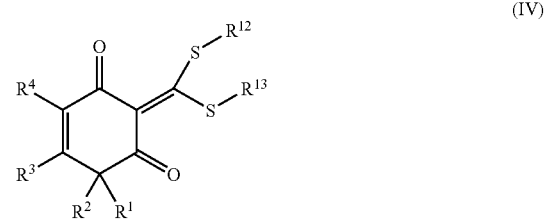

(IV)

or a pharmaceutically acceptable salt form, tautomer or stereoisomer, or a combination thereof, wherein:

$R^1$ is hydrogen, alkyl, alkenyl, alkynyl, —C(O)OR$_a$, —C(O)NR$_a$R$_b$ or R$_{1p}$;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N═CR$_j$R$_k$, —C(R$_e$)═CR$_j$R$_k$, and R$_{1q}$;

$R^2$ is hydrogen, alkyl, alkenyl or alkynyl;

wherein each of the alkyl, alkenyl and alkynyl is independently substituted with 0, 1 or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$Ra, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N═CR$_j$R$_k$, and R$_{2q}$;

alternatively, $R^1$ and $R^2$, together with the carbon atom to which they are attached, form a monocyclic ring selected from the group consisting of cycloalkyl and cycloalkenyl;

wherein each of the cycloalkyl and cycloalkenyl is unsubstituted or substituted with 1, 2 or 3 substituents selected from the group consisting of halo, —OH, —O(alkyl), —NH$_2$, —N(H)(alkyl), —N(alkyl)$_2$, alkyl and haloalkyl;

$R^3$ is hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, or R$_{3p}$;

wherein each of the alkyl, alkenyl and alkynyl is independently substituted with 0, 1, 2 or 3 substituents independently selected from the group consisting of cyano, formyl, oxo, halo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_a$)C(O)NR$_a$R$_b$, —N(R$_a$)C(O)OR$_a$, —N(R$_e$)SO$_2$R$_a$, —N(R$_a$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{3q}$;

$R^4$ is hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O) NR$_a$R$_b$, —N(R$_e$)C(O)OR$_a$, —N(R$_e$)SO$_2$R$_a$, —N(R$_e$) SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, or R$_{4p}$;

wherein each of the alkyl, alkenyl and alkynyl is independently substituted with 0, 1, 2 or 3 substituents independently selected from the group consisting of cyano, formyl, oxo, halo, nitro, —$OR_a$, —$OC(O)R_a$, —$OC(O)OR_a$, —$OC(O)NR_aR_b$, —$OSO_2R_a$, —$OSO_2NR_aR_b$, —$SR_a$, —$S(O)R_a$, —$SO_2R_a$, —$SO_2OR_a$, —$SO_2NR_aR_b$, —$NR_aR_b$, —$N(R_e)C(O)R_a$, —$N(R_e)C(O)NR_aR_b$, —$N(R_e)C(O)OR_a$, —$N(R_e)SO_2Ra$, —$N(R_e)SO_2NR_aR_b$, —$N(R_e)SO_2N(R_e)C(O)OR_a$, —$C(O)R_a$, —$C(O)OR_a$, —$C(O)NR_aR_b$, and $R_{4q}$;

alternatively, $R^3$ and $R^4$, together with the carbon atoms to which they are attached, form a ring selected from the group consisting of aryl, heteroaryl, cycloalkyl, cycloalkenyl and heterocycle, wherein each of the of aryl, heteroaryl, cycloalkyl, cycloalkenyl and heterocycle is independently substituted with $(R^8)_m$;

$R^8$ at each occurrence is independently selected from the group consisting of cyano, formyl, nitro, oxo, halo, alkyl, alkenyl, alkynyl, —$OR_a$, —$OC(O)R_a$, —$OC(O)OR_a$, —$OC(O)NR_aR_b$, —$OSO_2R_a$, —$OSO_2NR_aR_b$, —$SR_a$, —$S(O)R_a$, —$SO_2R_a$, —$SO_2OR_a$, —$SO_2NR_aR_b$, —$NR_aR_b$, —$N(R_e)C(O)R_a$, —$N(R_e)C(O)NR_aR_b$, —$N(R_e)C(O)OR_a$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, and $R_{8p}$;

wherein each of the alkyl, alkenyl and alkynyl is independently substituted with 0, 1, 2 or 3 substituents selected from the group consisting of cyano, formyl, nitro, oxo, halo, —$OR_a$, —$OC(O)R_a$, —$OC(O)OR_a$, —$OC(O)NR_aR_b$, —$OSO_2R_a$, —$OSO_2NR_aR_b$, —$SR_a$, —$S(O)R_a$, —$SO_2R_a$, —$SO_2OR_a$, —$SO_2NR_aR_b$, —$NR_aR_b$, —$N(R_e)C(O)R_a$, —$N(R_e)C(O)NR_aR_b$, —$N(R_e)C(O)OR_a$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, and $R_{8q}$;

$R_a$ at each occurrence is independently selected from the group consisting of hydrogen, alkyl, alkenyl, alkynyl, and $R_p$;

wherein each of the alkyl, alkenyl and alkynyl is independently substituted with 0, 1, 2 or 3 substituents independently selected from the group consisting of cyano, formyl, oxo, halo, nitro, —$OR_c$, —$OC(O)R_c$, —$OC(O)OR_c$, —$OC(O)NR_cR_d$, —$OSO_2R_c$, —$OSO_2NR_cR_d$, —$SR_c$, —$S(O)R_c$, —$SO_2R_c$, —$SO_2OR_c$, —$SO_2NR_cR_d$, —$NR_cR_d$, —$N(R_e)C(O)R_c$, —$N(R_e)C(O)NR_cR_d$, —$N(R_e)C(O)OR_c$, —$N(R_e)SO_2R_c$, —$N(R_e)SO_2NR_cR_d$, —$N(R_e)SO_2N(R_e)C(O)OR_c$, —$C(O)R_c$, —$C(O)OR_c$, —$C(O)NR_cR_d$, —$C(O)N(R_e)NR_cR_d$, and $R_q$;

$R_b$ at each occurrence is independently selected from the group consisting of hydrogen, alkyl, alkenyl, alkynyl, $R_{106}$, haloalkyl, hydroxyalkyl, alkoxyalkyl, and -alkyl$R_{106}$;

alternatively, $R_a$ and $R_b$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —$OR_c$, —$OC(O)R_c$, —$OC(O)OR_c$, —$OC(O)NR_cR_d$, —$OSO_2R_c$, —$OSO_2NR_cR_d$, —$SR_c$, —$S(O)R_c$, —$SO_2R_c$, —$SO_2OR_c$, —$SO_2NR_cR_d$, —$NR_cR_d$, —$N(R_e)C(O)R_c$, —$N(R_e)C(O)NR_cR_d$, —$N(R_e)C(O)OR_c$, —$N(R_e)SO_2R_c$, —$N(R_e)SO_2NR_cR_d$, —$N(R_e)SO_2N(R_e)C(O)OR_c$, —$C(O)R_c$, —$C(O)OR_c$, and —$C(O)NR_cR_d$; and wherein each of the alkyl, alkenyl and alkynyl is independently substituted with 0, 1 or 2 substituents selected from the group consisting of cyano, halo, nitro, oxo, —$OR_c$, —$OC(O)R_c$, —$OC(O)OR_c$, —$OC(O)NR_cR_d$, —$OSO_2R_c$, —$OSO_2NR_cR_d$, —$SR_c$, —$S(O)R_c$, —$SO_2R_c$, —$SO_2OR_c$, —$SO_2NR_cR_d$, —$NR_cR_d$, —$N(R_e)C(O)R_c$, —$N(R_e)C(O)NR_cR_d$, —$N(R_e)C(O)OR_c$, —$N(R_e)SO_2R_c$, —$N(R_e)$ $SO_2NR_cR_d$, —$N(R_e)SO_2N(R_e)C(O)OR_c$, —$C(O)R_c$, —$C(O)OR_c$, —$C(O)NR_cR_d$, and $R_q$;

$R_c$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, formyl, oxo, halo, nitro, —$OR_f$, —$OC(O)R_f$, —$OC(O)OR_f$, —$OC(O)NR_fR_g$, —$OSO_2R_f$, —$OSO_2NR_fR_g$, —$SR_f$, —$S(O)R_f$, —$SO_2R_f$, —$SO_2OR_f$, —$SO_2NR_fR_g$, —$NR_fR_g$, —$N(R_e)C(O)R_f$, —$N(R_e)C(O)NR_fR_g$, —$N(R_e)C(O)OR_f$, —$N(R_e)SO_2R_f$, —$N(R_e)SO_2NR_fR_g$, —$N(R_e)SO_2N(R_e)C(O)OR_f$, —$C(O)R_f$, —$C(O)OR_f$, —$C(O)NR_fR_g$, and $R_{103}$;

$R_d$ at each occurrence is independently selected from the group consisting of hydrogen, alkyl, alkenyl, alkynyl, $R_{106}$, haloalkyl, alkoxyalkyl, hydroxyalkyl, and -alkyl$R_{106}$;

alternatively, $R_c$ and $R_d$, together with the nitrogen atom to which they are attached, form a ring selected from the group consisting of heterocycle and heteroaryl;

wherein each of the heteroaryl and heterocycle is independently substituted with 0, 1, 2 or 3 substituents independently selected from the group consisting of alkyl, alkenyl, alkynyl, cyano, formyl, halo, nitro, oxo, —$OR_f$, —$OC(O)R_f$, —$OC(O)OR_f$, —$OC(O)NR_fR_g$, —$OSO_2R_f$, —$OSO_2NR_fR_g$, —$SR_f$, —$S(O)R_f$, —$SO_2R_f$, —$SO_2OR_f$, —$SO_2NR_fR_g$, —$NR_fR_g$, —$N(R_e)C(O)R_f$, —$N(R_e)C(O)NR_fR_g$, —$N(R_e)C(O)OR_f$, —$N(R_e)SO_2R_f$, —$N(R_e)SO_2NR_fR_g$, —$N(R_e)SO_2N(R_e)C(O)OR_f$, —$C(O)R_f$, —$C(O)OR_f$, and —$C(O)NR_fR_g$; and wherein each of the alkyl, alkenyl and alkynyl is independently substituted with 0, 1, 2 or 3 substituents independently selected from the group consisting of cyano, halo, nitro, oxo, —$OR_f$, —$OC(O)R_f$, —$OC(O)OR_f$, —$OC(O)NR_fR_g$, —$OSO_2R_f$, —$OSO_2NR_fR_g$, —$SR_f$, —$S(O)R_f$, —$SO_2R_f$, —$SO_2OR_f$, —$SO_2NR_fR_g$, —$NR_fR_g$, —$N(R_e)C(O)R_f$, —$N(R_e)C(O)NR_fR_g$, —$N(R_e)C(O)OR_f$, —$N(R_e)SO_2R_f$, —$N(R_e)SO_2NR_fR_g$, —$N(R_e)SO_2N(R_e)C(O)OR_f$, —$C(O)R_f$, —$C(O)OR_f$, —$C(O)NR_fR_g$, and $R_{103}$;

$R_e$ at each occurrence is independently selected from the group consisting of hydrogen, alkyl, alkenyl, alkynyl, $R_{106}$, haloalkyl, and -alkyl$R_{106}$;

$R_f$ at each occurrence is independently selected from the group consisting of hydrogen, alkyl, alkenyl, alkynyl, and $R_{103}$;

wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —O($R_{106}$), —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl), —C(O)N(alkyl)$_2$, and $R_{103}$;

$R_g$ at each occurrence is independently selected from the group consisting of hydrogen, alkyl, alkenyl, alkynyl, $R_{106}$, haloalkyl and -alkyl$R_{106}$;

alternatively, $R_f$ and $R_g$, together with the nitrogen atom to which they are attached, form a ring selected from the group consisting of heterocycle and heteroaryl;

wherein each of the heterocycle and heteroaryl is independently substituted with 0, 1, 2 or 3 substituents independently selected from the group consisting of alkyl, alkenyl, alkynyl, cyano, formyl, halo, nitro, oxo, —OH, —O(alkyl), —O(cyanoalkyl), —O(haloalkyl), —O$R_{106}$, —$NH_2$, —N(H)(alkyl), —N(alkyl)$_2$, —N(H)($R_{106}$), —N(alkyl)($R_{106}$), —C(O)OH, —C(O)Oalkyl, —C(O)$NH_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

R$_j$ at each occurrence is independently selected from the group consisting of hydrogen, alkyl, alkenyl, alkynyl, R$_{103}$, haloalkyl and -alkylR$_{103}$;

R$_k$ at each occurrence is independently selected from the group consisting of hydrogen, alkyl, alkenyl and alkynyl;

alternatively, R$_j$ and R$_k$, together with the carbon atom to which they are attached, form a ring selected from the group consisting of cycloalkyl, cycloalkenyl, heterocycle, aryl and heteroaryl; wherein each ring is independently substituted with 0, 1, 2, 3, 4 or 5 substituents independently selected from the group consisting of alkyl, alkenyl, alkynyl, nitro, cyano, formyl, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl) and —C(O)N(alkyl)$_2$; and wherein each of the alkyl, alkenyl and alkynyl is independently substituted with 0, 1, 2 or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

m is 0, 1, 2, 3 or 4;

R$_p$, R$_q$, R$_{1p}$, R$_{1q}$, R$_{2q}$, R$_{3p}$, R$_{3q}$, R$_{4p}$, R$_{4q}$, R$_{8p}$, and R$_{8q}$, at each occurrence, are independently selected from the group consisting of cycloalkyl, cycloalkenyl, aryl, heteroaryl, and heterocycle; wherein each of the R$_p$, R$_q$, R$_{1p}$, R$_{1q}$, R$_{2q}$, R$_{3p}$, R$_{3q}$, R$_{4p}$, R$_{4q}$, R$_{8p}$, and R$_{8q}$, at each occurrence, is independently substituted with 0, 1, 2, 3, 4 or 5 substituents selected from the group consisting of alkyl, alkenyl, alkynyl, cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, —SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{101}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$; and wherein each of the alkyl, alkenyl and alkynyl is independently substituted with 0, 1, 2 or 3 substituents independently selected from the group consisting of cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, —SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{101}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$, R$_{101}$ at each occurrence is independently selected from the group consisting of hydrogen, alkyl, alkenyl, alkynyl, R$_{103}$, -alkylR$_{103}$, -alkenylR$_{103}$, -alkynylR$_{103}$, haloalkyl, cyanoalkyl, -alkylC(O)R$_{104}$, -alkylC(O)OR$_{104}$, -alkylC(O)NR$_{104}$R$_{105}$, -alkyl-OR$_{104}$, -alkyl-OC(O)R$_{104}$, -alkyl-OC(O)OR$_{104}$, -alkylSR$_{104}$, -alkylS(O)R$_{104}$, -alkylSO$_2$R$_{104}$, -alkylSO$_2$OR$_{104}$, -alkyl SO$_2$NR$_{104}$R$_{105}$, -alkylNR$_{104}$R$_{105}$, -alkylN(R$_{105}$)C(O)R$_{104}$, -alkylN(R$_{105}$)C(O)OR$_{104}$, -alkylN(R$_{105}$)C(O)NR$_{104}$R$_{105}$, -alkylN(R$_{105}$)SO$_2$R$_{104}$, and -alkylN(R$_{105}$)SO$_2$NR$_{104}$R$_{105}$;

R$_{103}$ at each occurrence is independently selected from the group consisting of cycloalkyl, cycloalkenyl, aryl, heteroaryl and heterocycle; wherein each R$_{103}$ is independently substituted with 0, 1, 2, 3, 4 or 5 substituents independently selected from the group consisting of alkyl, alkenyl, alkynyl, halo, nitro, cyano, oxo, formyl, haloalkyl, —OR$_{104}$, —OC(O)R$_{104}$, —OC(O)OR$_{104}$, —OC(O)NR$_{104}$R$_{105}$, —OSO$_2$NR$_{104}$R$_{105}$, —SO$_2$R$_{105}$, —S(O)R$_{104}$, —NR$_{104}$R$_{105}$, —N(R$_{105}$)C(O)NR$_{104}$R$_{105}$, —N(R$_{105}$)COR$_{104}$, —N(R$_{105}$)SO$_2$R$_{104}$, —N(R$_{105}$)SO$_2$NR$_{104}$R$_{105}$, —C(O)R$_{104}$, —C(O)OR$_{104}$, —C(O)NR$_{104}$R$_{105}$, -alkylOR$_{104}$, -alkylOC(O)R$_{104}$, -alkylOC(O)OR$_{104}$, -alkylOC(O)NR$_{104}$R$_{105}$, -alkylOSO$_2$NR$_{104}$R$_{105}$, -alkylSO$_2$R$_{104}$, -alkylS(O)R$_{104}$, -alkylNR$_{104}$R$_{105}$, -alkylN(R$_{105}$)COR$_{104}$, -alkylN(R$_{105}$)SO$_2$R$_{104}$, -alkylN(R$_{104}$)C(O)NR$_{104}$R$_{105}$, -alkylN(R$_{105}$)SO$_2$NR$_{104}$R$_{105}$, -alkylC(O)R$_{104}$, -alkylC(O)OR$_{104}$, and -alkylC(O)NR$_{104}$R$_{105}$;

R$_{102}$, R$_{104}$, and R$_{105}$, at each occurrence, are independently selected from the group consisting of hydrogen, alkyl, alkenyl, alkynyl, hydroxyalkyl, alkoxyalkyl, haloalkyl and benzyl;

alternatively, R$_{101}$ and R$_{102}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

alternatively, R$_{104}$ and R$_{105}$ together with the nitrogen atom to which they are attached, form a ring selected from the group consisting of heterocycle and heteroaryl, wherein the heterocycle or heteroaryl ring is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

R$_{106}$ at each occurrence is independently selected from the group consisting of aryl and heteroaryl, wherein each R$_{106}$ is independently substituted with 0, 1, 2, 3, 4 or 5 substituents selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl; and R$^{12}$ and R$^{13}$ are independently selected from the group consisting of alkyl, alkenyl and alkynyl.

For example, the eighth embodiment of the present invention provides an intermediate of formula (IV) wherein $R^3$ and $R^4$ together with the carbon atoms to which they are attached form an aryl ring.

For example, the eighth embodiment of the present invention provides an intermediate of formula (IV) $R^3$ and $R^4$ together with the carbon atoms to which they are attached form an aryl ring, $R^1$ is —C(O)OR$_a$, —C(O)NR$_a$R$_b$, R$_{1p}$, alkyl or alkenyl; and $R^2$ is alkyl.

For example, the eighth embodiment of the present invention provides an intermediate of formula (IV) $R^3$ and $R^4$ together with the carbon atoms to which they are attached form an aryl ring, $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; and $R^2$ is alkyl.

For example, the eighth embodiment of the present invention provides an intermediate of formula (IV) $R^3$ and $R^4$ together with the carbon atoms to which they are attached form an aryl ring; $R^1$ is
  alkyl, wherein the alkyl is unsubstituted or substituted with 1 or 2 substituents selected from the group consisting of halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;
  alkenyl, wherein the alkenyl is unsubstituted or substituted with one substituent selected from the group consisting of
    —C(O)OR$_a$, wherein R$_a$ is alkyl, and
    —R$_{1q}$ wherein R$_{1q}$ is aryl,
  —C(O)OR$_a$, wherein R$_a$ is alkyl, or alkyl substituted with one R$_{1q}$, wherein R$_{1q}$, is a heterocyclic ring, unsubstituted or substituted with one —C(O)OR$_{101}$, wherein R$_{101}$ is alkyl,
  —C(O)NR$_a$R$_b$, wherein R$_a$ is alkyl, or alkyl substituted with one substituent selected from the group consisting of —OC(O)R$_c$, and —OR$_c$, wherein R$_c$ is hydrogen or alkyl, and R$_b$ is alkyl, alternatively, R$_a$ and R$_b$, together with the nitrogen atom to which they are attached, form a heterocyclic ring substituted with one alkyl substitutent wherein the alkyl is substituted with one substituent selected from the group consisting of —OR$_c$, and —OC(O)R$_c$, and wherein R$_c$ is hydrogen or alkyl, or
  R$_{1p}$; wherein R$_{1p}$ is heterocycle; and
$R^2$ is alkyl.

For example, the eighth embodiment of the present invention provides an intermediate of formula (IV) $R^3$ and $R^4$ together with the carbon atoms to which they are attached form an aryl ring; $R^1$ is
  propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is independently unsubstituted or substituted with 1 or 2 substituents selected from the group consisting of
    halo,
    —OR$_a$, wherein R$_a$ is hydrogen,
    —OC(O)R$_a$, wherein R$_a$ is methyl, ethyl, or isopropyl,
    —OC(O)NR$_a$R$_b$, wherein R$_a$ is methyl, ethyl or isopropyl and R$_b$ is hydrogen,
    —C(O)OR$_a$, wherein R$_a$ is methyl, ethyl, or isopropyl,
    —C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
    —R$_{1q}$; wherein R$_{1q}$ is phenyl, cyclopropyl, cyclobutyl, cyclopentyl or cyclohexyl;
  allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
    —C(O)OR$_a$, wherein R$_a$ is methyl, ethyl or isopropyl, and
    —R$_{1q}$, wherein R$_{1q}$ is aryl,
  —C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
  —C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substituent selected from the group consisting of —OR$_c$, and —OC(O)R$_c$, and wherein R$_c$ is hydrogen or methyl, or
  R$_{1p}$; wherein R$_{1p}$ is 4,5-dihydro-1,3-oxazol-2-yl; and
$R^2$ is propyl, butyl, methyl, ethyl, 2-methylbutyl, 3-methylbutyl, 3,3-dimethylbutyl, 5,5-dimethylhexyl, or 3-methylpentyl.

For example, the eighth embodiment of the present invention provides an intermediate of formula (IV) $R^3$ and $R^4$ together with the carbon atoms to which they are attached form an aryl ring, $R^1$ is —C(O)OR$_a$, —C(O)NR$_a$R$_b$, R$_{1p}$, alkyl or alkenyl; $R^2$ is alkyl; $R^{12}$ is alkyl and $R^{13}$ is alkyl.

For example, the eighth embodiment of the present invention provides an intermediate, of formula (IV) $R^3$ and $R^4$ together with the carbon atoms to which they are attached form an aryl ring, $R^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; $R^2$ is alkyl; $R^{12}$ is alkyl; and $R^{13}$ is alkyl.

For example, the eighth embodiment of the present invention provides an intermediate of formula (IV) $R^3$ and $R^4$ together with the carbon atoms to which they are attached form an aryl ring; $R^1$ is
  alkyl, wherein the alkyl is unsubstituted or substituted with 1 or 2 substituents selected from the group consisting of halo,
    —OR$_a$, wherein R$_a$ is hydrogen,
    —OC(O)R$_a$, wherein R$_a$ is alkyl,
    —OC(O)NR$_a$R$_b$, wherein R$_a$ is alkyl, R$_b$ is hydrogen,
    —C(O)OR$_a$, wherein R$_a$ is alkyl,
    —C=CR$_j$R$_k$, wherein R$_j$ and R$_k$ together with the carbon atom to which they are attached form a cycloalkyl ring; and
    —R$_{1q}$; wherein R$_{1q}$ is aryl or cycloalkyl;

alkenyl, wherein the alkenyl is unsubstituted or substituted with one substituent selected from the group consisting of
—C(O)OR$_a$, wherein R$_a$ is alkyl, and
—R$_{1q}$, wherein R$_{1q}$ is aryl,
—C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$, wherein R$_{101}$ is alkyl,
—C(O)NR$_a$R$_b$, wherein R$_a$ is alkyl, or alkyl substituted with one substituent selected from the group consisting of —OC(O)R$_c$, and —OR$_c$, wherein R$_c$ is hydrogen or alkyl, and R$_b$ is alkyl, alternatively, R$_a$ and R$_b$, together with the nitrogen atom to which they are attached, form a heterocyclic ring substituted with one alkyl substituent wherein the alkyl is substituted with one substituent selected from the group consisting of —OR$_c$, and —OC(O)R$_c$, and wherein R$_c$ is hydrogen or alkyl, or
R$_{1p}$; wherein R$_{1p}$ is heterocycle;
R$^2$ is alkyl; R$^{12}$ is alkyl; and R$^{13}$ is alkyl.

For example, the eighth embodiment of the present invention provides an intermediate of formula (IV) R$^3$ and R$^4$ together with the carbon atoms to which they are attached form an aryl ring; R$^1$ is
propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is independently unsubstituted or substituted with 1 or 2 substituents selected from the group consisting of
halo,
—OR$_a$, wherein R$_a$ is hydrogen,
—OC(O)R$_a$, wherein R$_a$ is methyl, ethyl, or isopropyl,
—OC(O)NR$_a$R$_b$, wherein R$_a$ is methyl, ethyl or isopropyl and R$_b$ is hydrogen,
—C(O)OR$_a$, wherein R$_a$ is methyl, ethyl, or isopropyl,
—C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
—R$_{1q}$; wherein R$_{1q}$ is phenyl, cyclopropyl, cyclobutyl, cyclopentyl or cyclohexyl;
allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—C(O)OR$_a$, wherein R$_a$ is methyl, ethyl or isopropyl, and
—R$_{1q}$, wherein R$_{1q}$ is aryl,
—C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
—C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substituent selected from the group consisting of —OR$_c$, and —OC(O)R$_c$, and wherein R$_c$ is hydrogen or methyl, or
R$_{1p}$; wherein R$_{1p}$ is 4,5-dihydro-1,3-oxazol-2-yl;
R$^2$ is propyl, butyl, methyl, ethyl, 2-methylbutyl, 3-methylbutyl, 3,3-dimethylbutyl, 5,5-dimethylhexyl, or 3-methylpentyl;
R$^{12}$ is methyl; and
R$^{13}$ is methyl.

For example, the eighth embodiment of the present invention provides an intermediate of formula (IV) R$^3$ and R$^4$ together with the carbon atoms to which they are attached form an aryl ring, R$^1$ is —C(O)OR$_a$, —C(O)NR$_a$R$_b$, R$_{1p}$, alkyl or alkenyl; R$^2$ is alkyl; R$^{12}$ is alkyl, R$^{13}$ is alkyl, R$_8$ is halo or —OR$_a$ wherein R$_a$ is hydrogen or alkyl, and m is 0 or 1.

For example, the eighth embodiment of the present invention provides an intermediate of formula (IV) R$^3$ and R$^4$ together with the carbon atoms to which they are attached form an aryl ring, R$^1$ is —C(O)OR$_a$, —C(O)NR$_a$R$_b$, R$_{1p}$, alkyl or alkenyl, wherein the alkyl and alkenyl are independently substituted with 0, 1 or 2 substituents selected from the group consisting of halo, —OR$_a$, —OC(O)R$_a$, —OC(O)NR$_a$R$_b$, —C(O)OR$_a$, —C=CR$_j$R$_k$, and —R$_{1q}$; R$^2$ is alkyl; R$^{12}$ is alkyl; R$^{13}$ is alkyl, R$_8$ is halo or —OR$_a$ wherein R$_a$ is hydrogen or alkyl; and m is 0 or 1.

For example, the eighth embodiment of the present invention provides an intermediate of formula (IV) R$^3$ and R$^4$ together with the carbon atoms to which they are attached form an aryl ring; R$^1$ is
alkyl, wherein the alkyl is unsubstituted or substituted with 1 or 2 substituents selected from the group consisting of
halo,
—OR$_a$, wherein R$_a$ is hydrogen,
—OC(O)R$_a$, wherein R$_a$ is alkyl,
—OC(O)NR$_a$R$_b$, wherein R$_a$ is alkyl, R$_b$ is hydrogen,
—C(O)OR$_a$, wherein R$_a$ is alkyl,
—C=CR$_j$R$_k$, wherein R$_j$ and R$_k$ together with the carbon atom to which they are attached form a cycloalkyl ring; and
—R$_{1q}$; wherein R$_{1q}$ is aryl or cycloalkyl;
alkenyl, wherein the alkenyl is unsubstituted or substituted with one substituent selected from the group consisting of
—C(O)OR$_a$, wherein R$_a$ is alkyl, and
—R$_{1q}$, wherein R$_{1q}$ is aryl,
—C(O)OR$_a$, wherein R$_a$ is alkyl, or alkyl substituted with one R$_{1q}$, wherein R$_{1q}$ is a heterocyclic ring, unsubstituted or substituted with one —C(O)OR$_{101}$, wherein R$_{101}$ is alkyl,
—C(O)NR$_a$R$_b$, wherein R$_a$ is alkyl, or alkyl substituted with one substituent selected from the group consisting of —OC(O)R$_c$, and —OR$_c$, wherein R$_c$ is hydrogen or alkyl, and R$_b$ is alkyl, alternatively, R$_a$ and R$_b$, together with the nitrogen atom to which they are attached, form a heterocyclic ring substituted with one alkyl substituent wherein the alkyl is substituted with one substituent selected from the group consisting of —OR$_c$, and —OC(O)R$_c$, and wherein R$_c$ is hydrogen or alkyl, or
R$_{1p}$; wherein R$_{1p}$ is heterocycle;
R$^2$ is alkyl; R$^{12}$ is alkyl; R$^{13}$ is alkyl, R$_8$ is halo or —OR$_a$ wherein R$_a$ is hydrogen or alkyl; and m is 0 or 1.

For example, the eighth embodiment of the present invention provides an intermediate of formula (IV) R$^3$ and R$^4$ together with the carbon atoms to which they are attached form an aryl ring; R$^1$ is
propyl, butyl, methyl, ethyl, 2-methylbutyl, 3-methylbutyl, 3,3-dimethylbutyl, 5,5-dimethylhexyl, 3-methylpentyl, wherein each of the propyl, butyl, methyl, ethyl, 2-methylbutyl, 3-methylbutyl, 3,3-dimethylbutyl, 5,5-dimethylhexyl, 3-methylpentyl is independently unsubstituted or substituted with 1 or 2 substituents selected from the group consisting of
halo,
—OR$_a$, wherein R$_a$ is hydrogen,
—OC(O)R$_a$, wherein R$_a$ is methyl, ethyl, or isopropyl,
—OC(O)NR$_a$R$_b$, wherein R$_a$ is methyl, ethyl or isopropyl and R$_b$ is hydrogen,
—C(O)OR$_a$, wherein R$_a$ is methyl, ethyl, or isopropyl,
—C=CR$_j$R$_k$, wherein R$_j$ and R$_k$ together with the carbon atom to which they are attached form a ring selected from the group consisting of cyclopropyl, cyclobutyl, cyclopentyl and cyclohexyl,
—R$_{1q}$; wherein R$_{1q}$ is phenyl, cyclopropyl, cyclobutyl, cyclopentyl or cyclohexyl;
allyl, 3-methylbut-2-enyl, or 4-ethylpenta-2,4-dienyl, wherein each of the allyl, 3-methylbut-2-enyl or 4-ethylpenta-2,4-dienyl is unsubstituted or substituted with one substituent selected from the group consisting of
—C(O)OR$_a$, wherein R$_a$ is methyl, ethyl or isopropyl, and
—R$_{1q}$, wherein R$_{1q}$ is aryl,
—C(O)OR$_a$, wherein R$_a$ is methyl, ethyl or isopropyl, wherein each of the methyl, ethyl or isopropyl is unsubstituted or substituted with one R$_{1q}$, wherein R$_{1q}$ is a pyrrolidine ring, unsubstituted or substituted with one —C(O)OR$_{101}$, wherein R$_{101}$ is methyl, ethyl or isopropyl,
—C(O)NR$_a$R$_b$, wherein R$_a$ is methyl or ethyl, wherein each of the methyl or ethyl is unsubstituted or substituted with one substituent selected from the group consisting of —OC(O)R$_c$, and —OR$_c$, wherein R$_c$ is hydrogen or methyl, and R$_b$ is methyl, alternatively, R$_a$ and R$_b$, together with the nitrogen atom to which they are attached, form a pyrrolidine ring substituted with one methyl wherein the methyl is substituted with one substituent selected from the group consisting of —OR$_c$, and —OC(O)R$_c$, and wherein R$_c$ is hydrogen or methyl, or
R$_{1p}$; wherein R$_{1p}$ is 4,5-dihydro-1,3-oxazol-2-yl;
R$^2$ is propyl, butyl, methyl, ethyl, 2-methylbutyl, 3-methylbutyl, 3,3-dimethylbutyl, 5,5-dimethylhexyl, or 3-methylpentyl;
R$^{12}$ is methyl;
R$^{13}$ is methyl;
R$_8$ is halo or —OR$_a$ wherein R$_a$ is hydrogen or methyl; and
m is 0 or 1.

Exemplary compounds of the seventh embodiment having formula (IV), of the present invention, include but not limited to the following:

2-[bis(methylthio)methylene]-4,4-bis(3-methylbutyl)naphthalene-1,3(2H,4H)-dione;
2-[bis(methylthio)methylene]-7-fluoro-4,4-dipropylnaphthalene-1,3(2H,4H)-dione;
2-[bis(methylthio)methylene]-4,4-dibutyl-7-fluoronaphthalene-1,3(2H,4H)-dione;
(4R)-2-[bis(methylthio)methylene]-7-fluoro-4-methyl-4-(3-methylbutyl)naphthalene-1,3(2H,4H)-dione;
(4S)-2-[bis(methylthio)methylene]-7-fluoro-4-methyl-4-(3-methylbutyl)naphthalene-1,3(2H,4H)-dione;
(4R)-2-[bis(methylthio)methylene]-4-(3,3-dimethylbutyl)-7-fluoro-4-methylnaphthalene-1,3(2H,4H)-dione;
(4S)-2-[bis(methylthio)methylene]-4-(3,3-dimethylbutyl)-7-fluoro-4-methylnaphthalene-1,3(2H,4H)-dione;
2-[bis(methylthio)methylene]-4-methyl-4-propylnaphthalene-1,3(2H,4H)-dione;
2-[bis(methylthio)methylene]-4-butyl-4-methylnaphthalene-1,3(2H,4H)-dione;
2-[bis(methylthio)methylene]-4-methyl-4-(3-methylbutyl)naphthalene-1,3(2H,4H)-dione;
2-[bis(methylthio)methylene]-4-(5,5-dimethylhexyl)-4-methylnaphthalene-1,3(2H,4H)-dione;
2-[bis(methylthio)methylene]-4-(3-cyclohexylpropyl)-4-methylnaphthalene-1,3(2H,4H)-dione;
(4R)-2-[bis(methylthio)methylene]-4-methyl-4-(3-methylbutyl)naphthalene-1,3(2H,4H)-dione;
(4S)-2-[bis(methylthio)methylene]-4-methyl-4-(3-methylbutyl)naphthalene-1,3(2H,4H)-dione;
2-[bis(methylthio)methylene]-4-(cyclohexylmethyl)-4-methylnaphthalene-1,3(2H,4H)-dione;
2-[bis(methylthio)methylene]-4-(3,3-dimethylbutyl)-4-methylnaphthalene-1,3(2H,4H)-dione;
2-[bis(methylthio)methylene]-4-methyl-4-[(3S)-3-methylpentyl]naphthalene-1,3(2H,4H)-dione;
(4S)-2-[bis(methylthio)methylene]-4-(3,3-dimethylbutyl)-4-methylnaphthalene-1,3(2H,4H)-dione;
(4R)-2-[bis(methylthio)methylene]-4-(3,3-dimethylbutyl)-4-methylnaphthalene-1,3(2H,4H)-dione;
2-[bis(methylthio)methylene]-4-ethyl-4-(3-methylbutyl)naphthalene-1,3(2H,4H)-dione;
2-[bis(methylthio)methylene]-4-(cyclopentylmethyl)-4-methylnaphthalene-1,3(2H,4H)-dione;
2-[bis(methylthio)methylene]-4-(cyclobutylmethyl)-4-methylnaphthalene-1,3(2H,4H)-dione;
2-[bis(methylthio)methylene]-4,4-dipropyl-1,3(2H,4H)-naphthalenedione;
4-allyl-2-[bis(methylthio)methylene]-4-methylnaphthalene-1,3(2H,4H)-dione;
2-[bis(methylthio)methylene]-7-methoxy-4-methyl-4-(3-methylbutyl)naphthalene-1,3(2H,4H)-dione;
2-[bis(methylthio)methylene]-4-(2-cyclopropylethyl)-4-methylnaphthalene-1,3(2H,4H)-dione;
2-[bis(methylthio)methylene]-4-(cyclopropylmethyl)-4-methylnaphthalene-1,3(2H,4H)-dione;
methyl 3-[bis(methylthio)methylene]-1-butyl-2,4-dioxo-1,2,3,4-tetrahydronaphthalene-1-carboxylate;
isopropyl 3-[bis(methylthio)methylene]-1-methyl-2,4-dioxo-1,2,3,4-tetrahydronaphthalene-1-carboxylate;
3-[bis(methylthio)methylene]-N,N-dimethyl-1-(3-methylbutyl)-2,4-dioxo-1,2,3,4-tetrahydronaphthalene-1-carboxamide;
(4R)-2-[bis(methylthio)methylene]-4-{[(2S)-2-(methoxymethyl)pyrrolidin-1-yl]carbonyl}-4-(3-methylbutyl)naphthalene-1,3(2H,4 H)-dione;
((2R)-1-{[(1S)-3-[bis(methylthio)methylene]-1-(3-methylbutyl)-2,4-dioxo-1,2,3,4-tetrahydronaphthalen-1-yl]carbonyl}pyrrolidin-2-yl)methyl acetate;
2-[bis(methylthio)methylene]-4-(4,5-dihydro-1,3-oxazol-2-yl)-4-(3-methylbutyl)naphthalene-1,3(2H,4 H)-dione;
2-[{[3-[bis(methylthio)methylene]-1-(3-methylbutyl)-2,4-dioxo-1,2,3,4-tetrahydronaphthalen-1-yl]carbonyl}(methyl)amino]ethyl acetate;
methyl 3-[bis(methylthio)methylene]-1-(3-methylbutyl)-2,4-dioxo-1,2,3,4-tetrahydronaphthalene-1-carboxylate;
[3-[bis(methylthio)methylene]-1-(3-methylbutyl)-2,4-dioxo-1,2,3,4-tetrahydronaphthalen-1-yl]methyl acetate;
[3-[bis(methylthio)methylene]-1-(3-methylbutyl)-2,4-dioxo-1,2,3,4-tetrahydronaphthalen-1-yl]methyl isopropylcarbamate; and
2-[bis(methylthio)methylene]-4-(3-methylbutyl)-4-vinylnaphthalene-1,3(2H,4 H)-dione; or a pharmaceutically acceptable salt form, stereoisomer or tautomer, or a combination thereof.

In a ninth embodiment, the present invention provides a process for the preparation of a compound of formula (V)

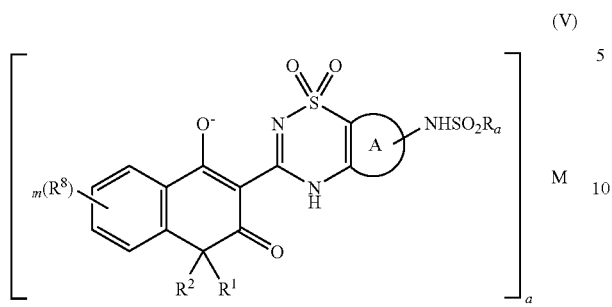
(V)

or a tautomer thereof, wherein:
M is $Na^+$, $K^+$, $Ca^{2+}$ and $Mg^{2+}$;
a is 1 when M is $Na^+$ or $K^+$;
a is 2 when M is $Ca^{2+}$ or $Mg^{2+}$;
A is a monocyclic ring selected from the group consisting of aryl, cycloalkyl, cycloalkenyl, heteroaryl and heterocycle;
$R^1$ is alkyl, alkenyl, or alkynyl;
$R^2$ is alkyl, alkenyl or alkynyl;
$R^8$ at each occurrence is independently selected from the group consisting of cyano, formyl, nitro, oxo, halo, alkyl, alkenyl, alkynyl, cyanoalkyl, hydroxyalkyl or alkoxyalkyl; and
$R_a$ is alkyl, alkenyl or alkynyl;
m is 0 or 1;

wherein said process comprises the step of:
(a) contacting a compound of formula (33)

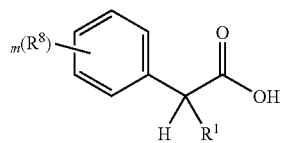
(33)

with a compound having formula $R^2X$ wherein X is Cl, Br or I and a base in a solvent to provide a compound of formula (34)

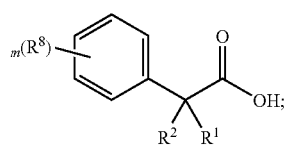
(34)

(b) contacting the compound of formula (34) with a chlorinating agent in a solvent to provide a compound of formula (35);

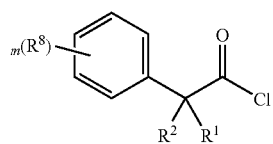
(35)

(c) contacting the compound of formula (35) with a reagent having formula $CH_2(C(O)OR^t)_2$ wherein $R^t$ is alkyl, a base and $MgCl_2$, in a solvent, to provide a compound of formula (36);

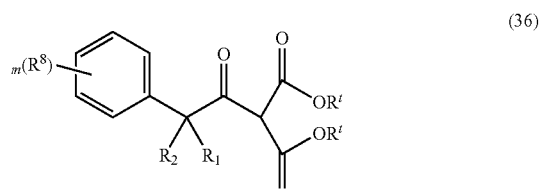
(36)

(d) contacting the compound of formula (36) with an acid to provide a compound of formula (37) wherein $R^t$ is alkyl;

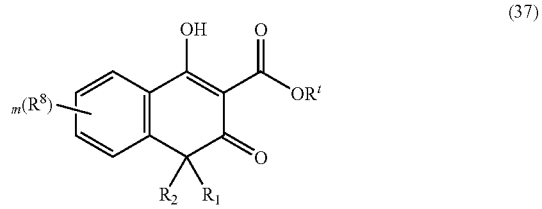
(37)

(e) contacting the compound of formula (37) with a compound of formula (38) wherein $R_A$ is a nitrogen protecting group, and a base, in a solvent, to provide a compound of formula (39);

(38)

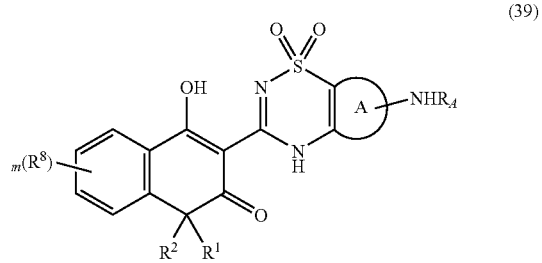
(39)

(f) contacting the compound of formula (39) with a deprotecting agent in a solvent to provide an acid salt of a compound of formula (40);

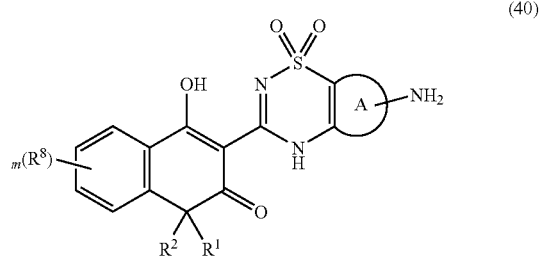
(40)

(g) contacting the acid salt of the compound of formula (40) with a neutralizing agent in a solvent to provide the compound of formula (40);

(h) contacting the compound of formula (40) with a sulfonating agent having formula $R_aSO_2Cl$ in a solvent to provide a compound of formula (41); and

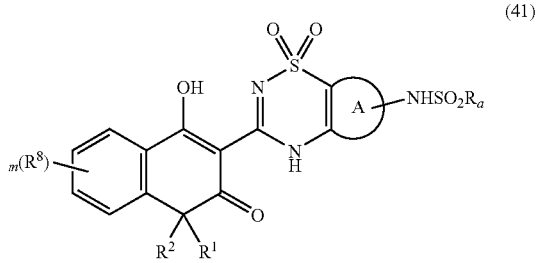

(i) contacting the compound of formula (41) with a base in a solvent to provide a compound of formula (V).

For example, the present invention provides a process for the preparation of a compound of formula (V) wherein $R^1$ is alkyl or alkenyl, $R^2$ is alkyl or alkenyl, m is 0, and $R_a$ is alkyl.

For example, the ninth embodiment of the present invention provides a process for the preparation of a compound of formula (V) wherein $R^1$ is methyl or allyl, $R^2$ is 3-methyl butyl, 3,3-dimethyl butyl, allyl or 3-methylbut-2-enyl, m is 0, and $R_a$ is methyl.

For the eight embodiment of the present invention provides a process for the preparation of sodium (4R)-4-(3,3-dimethylbutyl)-4-methyl-2-{7-[(methylsulfonyl) amino]-1,1-dioxido-4H-1,2,4-benzothiadiazin-3-yl}-3-oxo-3,4-dihydronaphthalen-1-olate.

For example, the ninth embodiment of the present invention provides a process for the preparation of a compound of formula (V) wherein in step (a) $R^1$ is alkyl or alkenyl, Examples of $R^2X$ include, but are not limited to, 1-bromo-3-methyl but-2-ene (prenyl bromide), 3-methylbutyl bromide, and 3,3-dimethyl-1-iodobutane, examples of the bases in step (a) include, but are not limited to, lithium bis(trimethylsilyl) amide, sodium bis(trimethylsilyl)amide, lithium diisopropylamide, sodium hydroxide, and potassium hydroxide, preferably lithium diisopropylamide and lithium bis(trimethylsilyl) amide, and more preferably lithium bis(trimethylsilyl)amide. Examples of the solvent used in step (a) include, but are not limited to, tetrahydrofuran, N,N-dimethylformamide, dioxane, and dimethoxyethane; preferably tetrahydrofuran and dioxane; and more preferably tetrahydrofuran. The reaction in step (a) is generally performed at a temperature from about 25° C. to about 70° C.; preferably at a temperature from about 40° C. to about 65° C., and most preferable at a temperature from about 50° C. to about 60° C.

For example, the ninth embodiment of the present invention provides a process for the preparation of a compound of formula (V) wherein in step (b) the chlorinating agent include, but are not limited to, oxalyl chloride with a catalytic amount of N,N-dimethylformamide, thionyl chloride and phosphorus oxychloride; preferred chlorinating agent is thionyl chloride and oxalyl chloride with a catalytic amount of N,N-dimethylformamide; most preferred chlorinating agent is oxalyl chloride with about 1% in total volume of N,N-dimethyl formamide. Examples of the solvent that can be employed in step (b) include, but are not limited to, dichloromethane, hexanes, heptanes, and tetrahydrofuran; preferred solvent is hexanes or heptanes; more preferred solvent is heptanes. The reaction can be performed at a temperature from about 0° C. to about 30° C.; preferably at a temperature from about 10° C. to about 25° C., and most preferable at a temperature from about 20° C. to about 25° C.

For example, the ninth embodiment of the present invention provides a process for the preparation of a compound of formula (V) wherein in step (c) the examples of the reagent having formula $CH_2(C(O)OR^r)_2$ include, but are not limited to, $CH_2(C(O)OC_2H_5)_2$, $CH_2(C(O)O(t-butyl))_2$; preferably $CH_2(C(O)OC_2H_5)_2$. Examples of the base include, but are not limited to, triethylamine and diisopropylethyl amine, preferably triethylamine. Examples of the solvent include, but are not limited to, acetonitrile, N,N-dimethylformamide and tetrahydrofuran; preferably acetonitrile or tetrahydrofuran; and more preferably acetonitrile. The reaction of step (c) can be performed at a temperature from about 20° C. to about 60° C.; preferably at a temperature from about 40° C. to about 60° C., and more preferable at a temperature from about 50° C. to about 55° C.

For example, the ninth embodiment of the present invention provides a process for the preparation of a compound of formula (V) wherein in step (d) the acid is sulfuric acid or methanesulfonic acid, and preferably methanesulfonic acid. The reaction of step (d) can be performed at a temperature from about 0° C. to about 50° C.; preferably at a temperature from about 10° C. to about 40° C., and most preferable at a temperature from about 20° C. to about 25° C.

For example, the ninth embodiment of the present invention provides a process for the preparation of a compound of formula (V) wherein in step (e) $R_A$ is tert-butyloxycarbonyl or benzyloxycarbonyl, preferably tert-butyloxycarbonyl. Examples of the base include, but are not limited to, triethylamine, N,N-diisopropylethylamine, sodium hydroxide, cesium carbonate and DABCO™ (1,4-diazabicyclo[2.2.2] octane, Aldrich, catalog number 29,073-4), preferably DABCO™ or triethylamine, and more preferably triethylamine. Examples of the solvent that can be employed in step (e) include, but are not limited to toluene, water, xylene, acetonitrile, and s-butanol, preferably acetonitrile or toluene, and more preferably, toluene. The reaction can be performed at a temperature from about 60° C. to about 140° C.; preferably at a temperature from about 80° C. to about 105° C., and more preferably at a temperature from about 90° C. to about 100° C.

For example, the ninth embodiment of the present invention provides a process for the preparation of a compound of formula (V) wherein in step (f) the deprotecting agent include, but are not limited to, anhydrous hydrogen chloride in dioxane or trifluoroacetic acid; and more preferably anhydrous hydrogen chloride in dioxane. Examples of the solvent include, but are not limited to, ethyl acetate, toluene, dichloromethane and dioxane; preferably dichloromethane or dioxane; more preferably dichloromethane. The reaction can be performed at a temperature from about 0° C. to about 40° C.; preferably at a temperature from about 10° C. to about 30° C., and most preferable at a temperature from about 20° C. to about 25° C.

For example, the ninth embodiment of the present invention provides a process for the preparation of a compound of formula (V) wherein in step (g) examples of the neutralizing agent include, but are not limited to, $Na_2CO_3$, $NaHCO_3$, and pH 7 phosphate buffer; preferably $NaHCO_3$ or a pH 7 phosphate buffer; and more preferably a pH 7 phosphate buffer. Examples of the solvent include, but are not limited to, dichloromethane, toluene, ethyl acetate, and isopropyl acetate, preferably toluene or ethyl acetate; and more preferably ethyl acetate. The reaction can be performed at a temperature from about 0° C. to about 40° C.; preferably at a temperature from about 10° C. to about 30° C., and more preferably at a temperature from about 20° C. to about 25° C.

For example, the ninth embodiment of the present invention provides a process for the preparation of a compound of formula (V) wherein examples of the solvent that can be employed in step (h) include, but are not limited to, isopropyl acetate, dichloromethane, tetrahydrofuran, ethyl acetate and acetone, preferably acetone or dichloromethane, and more preferably dichloromethane. The reaction can be performed at a temperature from about 0° C. to about 40° C.; preferably at a temperature from about 10° C. to about 30° C., and more preferably at a temperature from about 20° C. to about 25° C.

For example, the ninth embodiment of the present invention provides a process for the preparation of a compound of formula (V) wherein in step (i) examples of the base include, but are not limited to, alkali metal ethoxide, alkali metal hydroxide, and alkali metal carbonate, preferably alkali metal hydroxide or alkali metal ethoxide; more preferably alkali metal ethoxide and most preferably sodium ethoxide. Examples of the solvent include, but are not limited to, water, acetone, ethanol, acetonitrile, and mixture of water and ethanol; preferably acetone or ethanol; more preferably ethanol. The reaction can be performed at a temperature from about 10° C. to about 80° C.; preferably at a temperature from about 30° C. to about 75° C., and most preferable at a temperature from about 50° C. to about 75° C.

The process of the ninth embodiment of the present invention further comprises the process of resolving the chiral amine salt by contacting the compound of formula (34) with a chiral amine, isolating the chiral acid-amine salt and contacting the chiral acid-amine salt with an acid in a solvent. Examples of the chiral amine include, but are not limited to, (R) 2-amino-1-butanol, (S) phenethylamine, (+) pseudoephedrine, (−) and cinchonidine; preferred chiral amine is (+) pseudoephedrine or (S) phenethylamine; more preferred chiral amine is (S) phenethylamine. Examples of the solvent include, but are not limited to, acetone, methyl tert-butyl ether, ethanol and ethyl acetate, preferably methyl tert-butyl ether or ethyl acetate; and more preferably ethyl acetate. The reaction can be performed at a temperature from about 0° C. to about 60° C., preferably at a temperature from about 10° C. to about 40° C., and more preferably at a temperature from about 20° C. to about 30° C. The steps of isolating the chiral acid-amine salt comprises of filtering precipitate, dissolving the precipitate in a solvent to a solution, cooling the solution to room temperature and filtering the precipitate, wherein the solvent is ethyl acetate. Examples of the acid used to contact the chiral acid-amine salt include aqueous hydrochloric acid, sulfuric acid, and phosphoric acid; preferably sulfuric acid or aqueous hydrochloric acid; more preferably aqueous hydrochloric acid. Examples of the solvent employed include, but are not limited to, ethyl acetate, heptanes or isopropyl acetate; preferably heptanes or ethyl acetate; and more preferably ethyl acetate. The reaction can be performed at a temperature from about 0° C. to about 40° C.; preferably at a temperature from about 10° C. to about 30° C., and more preferably at a temperature from about 20° C. to about 25° C.

For example, the ninth embodiment of the present invention provides a process for the preparation of sodium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate or sodium (4R)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate, wherein in step (a) $R^1$ is methyl, $R^2$ is 3,3-dimethylbutyl, X is iodo, the base is lithium bis(trimethylsilyl)amide, and the solvent is tetrahydrofuran;

in step (b) the chlorinating agent is oxalyl chloride and 1% in volume of N,N-dimethylformamide, the base is triethylamine and the solvent is heptane;

in step (c) the reagent is $CH_2(C(O)OC_2H_5)_2$ and the solvent is acetonitrile;

in step (d) the acid is methanesulfonic acid;

in step (e) A is phenyl, $R_A$ is tert-butyloxycarbonyl, the base is triethylamine and the solvent is toluene;

in step (f) the deprotecting agent is anhydrous hydrogen chloride in dioxane, and the solvent is dichloromethane;

in step (g) the neutralizing agent is pH 7 phosphate buffer and the solvent is ethyl acetate;

in step (h) the sulfonating reagent is $R_aSO_2Cl$ wherein $R_a$ is methyl, and the solvent is dichloromethane; and in step (i) the base is sodium ethoxide and the solvent is ethanol. The process further comprises contacting the compound of formula (34) from step (a) with (S)-α-methyl benzylamine in ethyl acetate, isolating the chiral-amine salt by filtration of the precipitate, dissolution of the precipitate in ethyl acetate to a solution, cooling the solution to room temperature and filtering the precipitate, and contacting the chiral acid-amine salt with hydrochloric acid in ethyl acetate.

It will be appreciated by those skilled in the art that the compounds of this invention, exemplified by formula (I) wherein B is a six membered ring, exist in tautomeric forms. All tautomeric forms of the compounds described herein are intended to be encompassed within the scope of the present invention. Examples of some of the possible tautomer forms of the compounds of this invention include, but are not limited to:

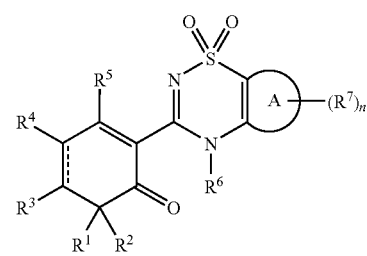

1-A

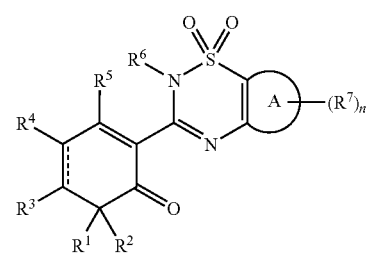

1-B

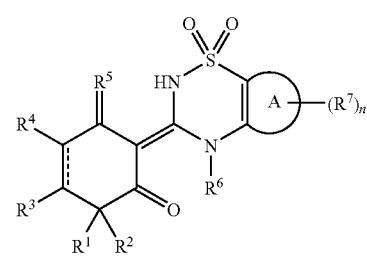

1-C

-continued

1-D

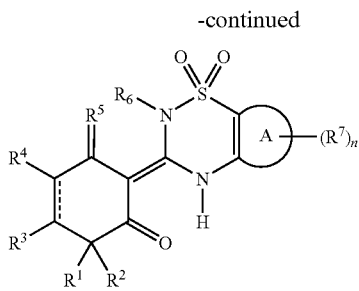

As a convention, the compounds exemplified herein have been assigned names based on the structure of the tautomer of formula I-A. It is to be understood that any reference to such named compounds is intended to encompass all tautomers of the named compounds and any mixture of tautomers of the named compounds.

Compounds of this invention may contain at least one chiral center and may exist as single stereoisomers (e.g. single enantiomer), mixtures of stereoisomers (e.g. any mixture of enantiomers or diastereomers) or racemic mixtures thereof. As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds containing either stereoisomer of each chiral center present in the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis from commercially available optically pure (enantiomerically pure) or substantially optically pure starting materials. Alternatively, these compounds may be obtained by resolution/separation of a mixture of stereoisomers, including racemic mixtures, using conventional procedures. Exemplary procedures that may be useful for the resolution/separation of mixtures of stereoisomers include enzymatic resolution, chromatographic separation, crystallization/re-crystallization, and conversion of enantiomers in an enantiomeric mixture to diastereomers followed by separation/resolution of the diastereomers using techniques known in the art, such as recrystallization and or chromatographic resolution, and regeneration of the individual enantiomers. Other useful methods may be found in "Enantiomers, Racemates, and Resolutions," J. Jacques et al., 1981, John Wiley and Sons, New York, N.Y., the disclosure of which is incorporated herein by reference.

Stereospecific synthesis involves the use of appropriate chiral starting materials and synthetic reactions which do not cause racemization or inversion of stereochemistry at the chiral centers. Starting materials of particular stereochemistry are either commercially available or can be made and resolved by techniques known in the art.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again. Alternatively, the diastereomers can also be separated by crystallization/re-crystallization and the individual enantiomers regenerated therefrom.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

The present compounds may exhibit the phenomena of tautomerism or structural isomerism. As the drawings within this specification can only represent one possible tautomeric or structural isomeric form, it should be understood that the invention encompasses any tautomeric or structural isomeric form, or mixtures thereof, which possess the ability to inhibit hepatitis C, and is not limited to any one tautomeric or structural isomeric form utilized within the drawings.

In addition, solvates and hydrates of the compounds of the invention are meant to be included in this invention.

When any variable (for example $R^7$, $R^8$, $R_a$, $R_b$, $R_c$, $R_d$, $R_e$, $R_f$, $R_g$, $R_j$, $R_k$, $R_p$, $R_q$, $R_{1p}$, $R_{1q}$, $R_{2p}$, $R_{2q}$, $R_{3p}$, $R_{3q}$, $R_{4p}$, $R_{4q}$, $R_{7p}$, $R_{7q}$, $R_{8p}$, $R_{9p}$, $R_{9q}$, $R_{101}$, $R_{102}$, $R_{103}$, $R_{104}$, $R_{105}$, $R_{106}$, m, n, etc.) occurs more than one time in any substituent or in the compound of the invention or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can exist as pharmaceutically acceptable salts. The term "pharmaceutically acceptable salt," as used herein, represents acid or base salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a basic group (for example, a nitrogen containing group) with a suitable acid. Representative acid addition salts include acetates, acrylates, adipates, alginates, aspartates, benzoates, benzenesulfonates, bisulfates, bisulfites, butyrates, camphorates, camphorsulfonates, caproates, caprylates, citrates, chlorobenzoates, digluconates, dinitrobenzoates, formates, fumarates, glutamates, glycerophosphates, hemisulfates, heptanoates, hexanoates, hydrochloride, hydrobromide, hydroiodides, 2-hydroxyethansulfonates, lactates, maleates, mandelates, methoxybenzoates, methylbenzoates, malonates, mesitylenesulfonate, methanesulfonates, naphthylenesulfonates, nicotinates, nitrates, nitrites, 2-naphthalenesulfonates, oxalates, pamoates, pectinates, persulfates, phenylbutyrates, phenylproprionates, phosphates, phthalates, picrates, pivalates, propanesulfonates, propionates, pyrosulfates, salicylates, succinates, sulfonates, tartrate, trichloroacetate, trifluoroacetate, para-toluenesulfonates, and undecanoates. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, nitric acid, sulfuric, and phosphoric, and the like, and organic acids such as acetic, fumaric, trifluoroacetic, mandelic, methanesulfonic, pyruvic, oxalic, glycolic, salicylic, oxalic, maleic, succinic, tartaric, aspartic, glutamic, cinnamic and citric.

Basic addition salts can be prepared during the final isolation and purification of the compounds by reacting an acidic group (for example, a carboxy group or an enol) with a suitable base such as the alkoxide, (for example, ethoxide or methoxide and the like) hydroxide, carbonate, or bicarbonate of a metal cation or with ammonia or an organic primary, secondary, or tertiary amine. The cations of pharmaceutically acceptable salts include lithium, sodium, potassium, calcium, copper, manganese, iron, zinc, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of basic addition salts include amino acids such as glycine and arginine, primary, secondary and tertiary amines such as ethylenediamine, ethanolamine, and diethanolamine, and cyclic amines such as dicyclohexylamine, morpholine, piperidine, and piperazine.

Representative pharmaceutically acceptable salts of the compounds of the present invention include sodium, potassium, calcium, magnesium, triethylamine, trifluoroacetate, methanesulfonate, hydrobromide and hydrochloride.

The present compounds can also exist as pharmaceutically acceptable prodrugs. The term "pharmaceutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. "Prodrugs" are considered to be any covalently bonded carriers which release the active parent drug of formula (I), (II) or (III) in vivo metabolically or by solvolysis when such prodrugs is administered to a mammalian subject. Prodrugs of the compounds of formula (I), (II) or (III) can be prepared by modifying functional groups present in the compounds in such a way that the modifications are cleaved, either in routine manipulation or in vivo, to the parent compounds respectively. Examples of such modification include, but not limited to, treatment of a compound of formula (I), (II) or (III), containing an amino, amido or hydroxyl moiety with a suitable derivatising agent, for example, a carboxylic acid halide or acid anhydride, treatment of a compound of formula (I), (II) or (III), containing a carboxyl moiety, to an ester or amide and treatment of a compound of formula (I), (II) or (III), containing a carboxylic acid ester moiety to an enol-ester. Prodrugs include compounds wherein hydroxy, amine, carboxy, or sulfhydryl groups are bonded to any group that, when administered to a mammalian subject, cleaves under physiological conditions to form a free hydroxyl, amino, carboxy, or sulfhydryl group, respectively. Examples of prodrugs include, but are not limited to, acetate, formate, and benzoate derivatives of the hydroxy, carboxy and amine functional groups in the compounds of formula (I), (II) or (III).

The term "pharmaceutically acceptable carrier, adjuvants, diluents or vehicles" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be formulated in a conventional manner using one or more of the aforementioned pharmaceutically acceptable carriers.

In accordance with methods of treatment and pharmaceutical compositions of the invention, the compounds of formula (I), (II) or (III), or a tautomer, stereoismer, or a pharmaceutically acceptable salt thereof, can be administered alone or in combination with other antiviral agents. When using the compounds of formula (I), (II) or (III), the specific pharmaceutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidentally with the compound used. The compounds of formula (I), (II) or (III), or a tautomer, stereoisomer, or pharmaceutically acceptable salt thereof can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The antiviral effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes thereof. Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The compounds of formula (I), (II) or (III), or their pharmaceutically acceptable salts, stereoisomers or tautomers thereof, inhibit HCV RNA dependent RNA polymerase, an enzyme essential for HCV viral replication. They can be administered as the sole active pharmaceutical agent, or used in combination with one or more agents to treat hepatitis C infections or the symptoms associated with HCV infection. Other agents to be administered in combination with a compound of the present invention include therapies for disease caused by HCV infection that suppresses HCV viral replication by direct or indirect mechanisms. These include agents such as host immune modulators, for example, interferon-alpha, pegylated interferon-alpha, interferon-beta, interferon-gamma, CpG oligonucleotides and the like, or antiviral compounds that inhibit host cellular functions such as inosine monophosphate dehydrogenase, for example, ribavirin and the like. Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO0190121(A2), or U.S. Pat. No. 6,348,587B1 or WO0160315 or WO0132153 or non-nucleoside inhibitors such as, for example, benzimidazole polymerase inhibitors described in EP 162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agent include but are not limited to therapies for disease caused by hepatitis B (HBV) infection such as, for example, adefovir, lamivudine, and tenofovir or therapies for disease caused by human immunodeficiency virus (HIV) infection such as, for example, protease inhibitors: ritonavir, lopinavir, indinavir, nelfinavir, saquinavir, amprenavir, atazanavir, tipranavir, TMC-114, fosamprenavir; reverse transcriptase inhibitors: zidovudine, lamivudine, didanosine, stavudine, tenofovir, zalcitabine, abacavir, efavirenz, nevirapine, delavirdine, TMC-125; integrase inhibitors: L-870812, S-1360, or entry inhibitors: enfuvirtide (T-20), T-1249.

Other agents to be administered in combination with a compound of the present invention include any agent or combination of agents that treat or alleviate symptoms of HCV infection including cirrhosis and inflammation of the liver.

When administered as a combination, the therapeutic agents can be formulated as separate compositions which are given at the same time or within a predetermined period of time, or the therapeutic agents can be given as a single unit dosage form.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated; the treatment desired; the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of formula (I), (II) or (III), or pharmaceutically acceptable salts, stereoisomers of tautomers thereof, administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

HCV Polymerase Inhibition Assay: Biochemical $IC_{50}$

Either two-fold serial dilutions (fractional inhibition assay) or a narrower range of dilutions spanning the $IC_{50}$ of the inhibitor (tight binding assay) of the inhibitors were incubated with 20 mM Tris-Cl pH 7.5, 5 mM $MgCl_2$, 50 mM NaCl, 1 mM dithiothreitol, 1 mM ethylene diamine tetraacetic acid (EDTA), 300 µM GTP and 150 to 300 nM NS5B (HCV Strain 1B (J4, Genbank accession number AF054247, or H77, Genbank accession number AF011751)) for 15 minutes at room temperature. The reaction was initiated by the addition of 20 µM CTP, 20 µM ATP, 1 µM 3H-UTP (10 mCi/umol), 150 nM template RNA and 0.4 U/µl RNase inhibitor (RNasin, Promega), and allowed to proceed for 2 to 4 hours at room temperature. Reaction volume was 50 µl. The reaction was terminated by the addition of 1 volume of 4 mM spermine in 10 mM Tris-Cl pH 8.0, 1 mM EDTA. After incubation for at least 15 minutes at room temperature, the precipitated RNA was captured by filtering through a GF/B filter (Millipore) in a 96 well format. The filter plate was washed three times with 200 µl each of 2 mM spermine, 10 mM Tris-Cl pH 8.0, 1 mM EDTA, and 2 times with ethanol. After air drying, 30 µl of Microscint 20 scintillation cocktail (Packard) was added to each well, and the retained cpm were determined by scintillation counting. IC50 values were calculated by a two-variable nonlinear regression equation using an uninhibited control and a fully inhibited control sample to determine the minimum and maximum for the curve. Tight-binding assays were performed on those compounds exhibiting IC50 values less than 0.15 µM in the fractional inhibition assay in order to more precisely measure the IC50 values. Retained cpm were plotted vs. inhibitor concentration and fit to equation 1 using non-linear regression (ref. 1) to obtain the IC50 values.

$$\text{Retained } cpm = A[sqrt\{(IC_{50}+I_t-E_t)^2+4IC_{50}E_t\}-(IC_{50}+I_t-E_t)] \quad \text{eqn 1.}$$

where $A=V_{max}[S]/2(K_m+[S])$; $I_t$=total inhibitor concentration and $E_t$=total active concentration of enzyme. Ref. 1: Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was:

5'GGGCGAAUUGGGCCCUCUAGAUGCAUGCUCGAGCGGCCGCCAGUGUGA

UGGAUAUCUGCAGAAUUCGCCCUUGGUGGCUCCAUCUUAGCCCUAGUCAC

GGCUAGCUGUGAAAGGUCCGUGAGCCGCUUGACUGCAGAGAGUGCUGAUA

CUGGCCUCUCUGCAGAUCAAGUC-3'

When tested by the above method, the compounds of the present invention inhibit HCV polymerase 1B with $IC_{50}$'s in the range of 0.002 µM to 500 µM.

Evaluation of the HCV Inhibitors in HCV Replicon: Cell Culture $EC_{50}$

The cell lines and assays were conducted according to the methods described by Ikeda M, Yi M, Li K, Lemon S M., J Virol 2002 March; 76(6):2997-3006, and Blight K. J, Kolykhalov A., Rice C. M., Science 2000 December, 290: 1972-1974) with the following modifications: RNA assay Replicon cells were plated at $3 \times 10^3$ cells per well in 96-well plate in DMEM medium containing 5% fetal calf serum. At day 1, culture medium was removed and replaced with fresh medium containing eight serial 2-fold dilutions of compound. The final concentration of DMSO in medium was 0.5%. The untreated control culture was treated in an identical manner except no inhibitor was added to the medium. Plates were incubated in a $CO_2$ incubator at 37° C. On Day 4, 100 µL lysis buffer (RTL) (Qiagen) was added to each well after removal of culture medium. RNA was purified according to manufacturer's recommendations (Qiagen RNAeasy) and eluted in 200 µl of water. The HCV RNA level was quantified from a portion (5 µL out of 200 µL) of the purified RNA by real-time RT-PCR method. The primers and probe are derived from specific sequence in the 5'UTR region. RT-PCR reaction was performed at 48° C. for 30 min, followed by 40 cycles set to 95° C., 15 s; 54° C., 30 s; and 72° C., 40 s. The percentage reduction of HCV RNA in the presence of compound was calculated and the 50% inhibitory concentration ($IC_{50}$) was calculated by non-linear regression analysis using the Prism program.

When tested by the above method, the compounds of the present invention inhibit replicon production with EC50's in the range of 0.005 µM to >100 µM.

Cytotoxity Assays

Cytotoxicity assays were performed in replicon cells. Briefly, HCV replicon cells were plated at $3 \times 10^3$ cells per well in 96-well plate in DMEM medium containing 5% FCS. At day 1, culture medium was removed and replaced with fresh medium containing eight serial 2-fold dilutions of compound. The final concentration of DMSO in medium was 0.5%. All experiments were performed in duplicate. The untreated control culture was treated in an identical manner except no inhibitor was added to the medium. Plates were incubated in a $CO_2$ incubator at 37° C. On day 4, stock solution of the tetrazolium salt, MTT (4 mg/ml in PBS, Sigma cat.# M 2128) was added to each well at 25 µL per well. Plates were further incubated for 4 hours, treated with 20% SDS plus 0.02 N HCl at 50 µL per well to lyse the cells. After an overnight incubation, optical density was measured by reading the plates at 570/650 nm wavelengths. The percent reduction of formazan blue color formed relative to control was calculated and the cytopathic effect was described as a 50% toxicity concentration ($TC_{50}$) was calculated by non-linear regression analysis using the Prism program.

Cell culture assays for agents targeted toward hepatitis C are not yet available because of the inability to produce infectious virus in a sustained cell line. The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in the references above. The mechanism of RNA replication in these cell lines is considered to be identical to the replication of full length HCV RNA in infected hepatocytes. The compounds and methods of this invention are inhibitors of HCV RNA replication in the replicon assay systems described above. This forms the basis of the claim for their potential as therapies in treating disease resulting from hepatitis C viral infection.

Synthetic Methods

Abbreviations which have been used in the descriptions of the schemes and the examples that follow are: THF is tetrahydrofuran and DBU is 1,8-diazabicyclo[5.4.0]undec-7-ene.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^1$, $R^2$, $R^3$, $R^4$, $R^7$, $R^8$, $R_{10}$, $R_{11}$, m and n are as defined above unless otherwise noted below.

This invention is intended to encompass compounds having formula (I), (II) or (III) when prepared by synthetic processes or by metabolic processes. Preparation of the compounds of the invention by metabolic processes include those occurring in the human or animal body (in vivo) or processes occurring in vitro.

Scheme 1

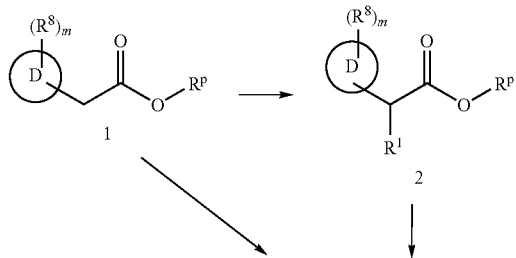

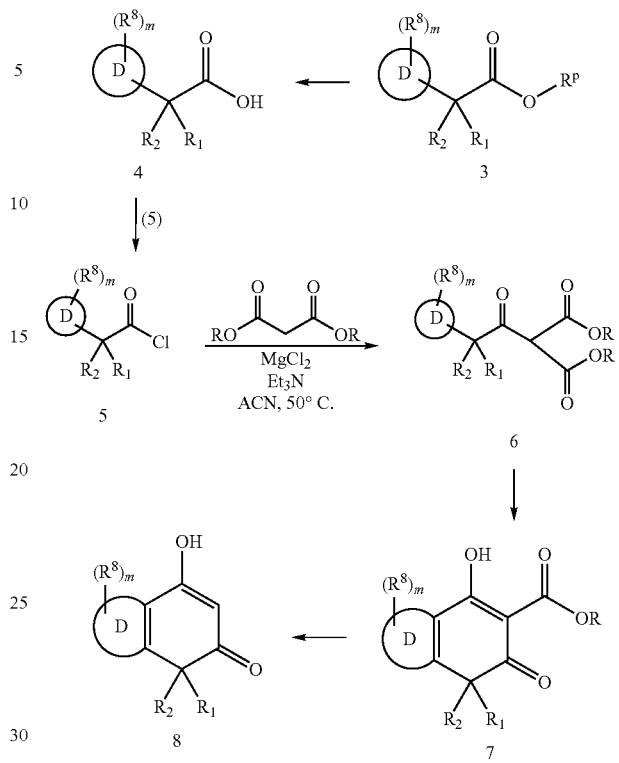

Compounds of formula (8) wherein $R^1$ is alkyl, alkenyl or alkynyl, $R^2$ is alkyl, alkenyl or alkynyl, and $R^8$ is as defined in formula (I), ring D represents the ring formed by $R^3$, $R^4$ (as defined in formula (I)), and the carbon atoms to which they are attached, and is selected from the group consisting of aryl, heteroaryl, cycloalkenyl, cycloalkyl and heterocycle, can be prepared as shown in Scheme 1. Examples of D include, but are not limited to, phenyl, furanyl and thienyl.

Compounds of formula (I) wherein $R_p$ is hydrogen, alkyl, alkenyl, alkynyl or benzyl, wherein the alkyl, alkenyl and benzyl are unsubstituted or substituted, can be monoalkylated with one equivalent of an alkylating agent having formula $R^1X$, wherein X is Cl, Br or I, in the presence of appropriate amount of a base (for example, if $R^p$ is hydrogen, about two equivalents of the base can be used, if $R^p$ is other than hydrogen, than about one equivalent of the base can be used) in a solvent such as, but not limited to, tetrahydrofuran, diethyl ether, N, N-dimethylformamide, or mixtures thereof, at a temperatures from about −78° C. to about 70° C. to afford compounds of formula (2).

Compounds of formula (2), either purchased or prepared as shown above, can be alkylated again by treatment with the same or a second alkylating agent by reaction with a base and an alkylating agent having formula $R^2X$, wherein X is Cl, Br or I. The reaction can be carried out in a solvent such as, but not limited to, tetrahydrofuran, diethyl ether, N,N-dimethylformamide, or mixtures thereof, at a temperatures from about −78° C. to about 70° C. The reaction can be performed with or without an additive such as lithium or sodium iodide or hexamethylphosphoric triamide (HMPA) and the like. Most conveniently, in the case where $R^1$ is the same as $R^2$, compounds of formula (I) can be transformed in a one step operation to compounds of formula (3) by using an excess of an alkylating agent, in the presence of about two equivalents of the base (if $R_p$ is not hydrogen) or about three equivalents of the base (if $R_p$ is hydrogen), in a solvent such as tetrahydrofuran, diethyl ether, N,N-dimethylformamide, or mixtures thereof, at a temperature from about 0° C. to about 100° C., with or without the presence of an additive such as lithium, sodium or potassium iodide, tetrabutylammonium iodide, 18-crown-6, or hexamethylphosphoric triamide (HMPA), and the like.

Examples of $R_p$ include, but not limited to hydrogen, methyl, ethyl, tert-butyl and benzyl.

Examples of the alkylating agents include, but not limited, to methyl iodide, ethyl iodide, 3,3-dimethyl-1-iodobutane, 3,3-dimethyl-1-bromobutane, 1-chloro-3-methyl-2-butene, allyl bromide, 1-bromo-3-methylbut-2-ene, crotyl bromide and crotyl iodide.

Examples of the bases include, but not limited to, sodium hydride, potassium hydride, lithium bis(trimethylsilyl) amide, lithium diisopropyl amide, lithium tetramethyl piperidide, and potassium tert-butoxide, Compounds of formula (3) wherein $R_p$ is methyl can be converted into carboxylic acid of formula (4) by treatment with potassium trimethylsilanoate in a solvent such as tetrahydrofuran, dioxane, dichloromethane, acetonitrile, toluene, and the like, or mixtures thereof, at a temperature from about 60° C. to about 100° C. Compounds of formula (3) wherein $R_p$ is benzyl can be converted to compounds of formula (4) by hydrogenation with hydrogen over a metal catalyst such as 5-10% palladium on carbon or platinum oxide (Adam's catalyst) and the like, in a solvent such as ethyl acetate, ethanol, methanol, or mixtures thereof, at a pressure of about 1-20 atmospheres and at a temperature from about 25° C. to about 80° C.

Compounds of formula (3) wherein $R^1$ and $R^2$ are allyl, crotyl, or 3-methylbut-2-ene, and $R_p$ is benzyl can be converted to compounds of formula (4) wherein $R^1$ and $R^2$ are n-propyl, n-butyl, or 3-methylbutyl by either one step or stepwise hydrogenation using the conditions as specified above.

Compounds of formula (5) can be prepared from compounds of formula (4) by refluxing for several days with excess thionyl chloride. A preferred method of transformation can be accomplished by treatment of a hexane or heptane solution of acid (4) and one equivalent of N,N-dimethylformamide with an excess of oxalyl chloride. The acid chloride (5) is reacted with the magnesium salt of either diethyl or dimethyl malonate (generated in acetonitrile according as described by Ratlike (Rathke, M. W.; Cowan, P. J. *J. Org. Chem.* 1985, 50, 2622) at a temperatures of about 40° C. to about 60° C. The ketodiester (6), wherein R is methyl or ethyl, is then subjected to Friedel-Crafts-type cyclization by treatment with an acid such as, but not limited to, concentrated sulfuric acid, methanesulfonic acid, or polyphosphoric acid, and the like, at a temperature from about 25° C. to about 100° C., to afford the diketo ester (7). Transformation of the diketo ester (7) to the compounds of formula (8) can be achieved by treatment with a dilute aqueous acid such as, but not limited to, hydrochloric acid or sulfuric acid, methanesulfonic acid or p-toluenesulfonic acid, admixed with a solvent such as tetrahydrofuran, dioxane, and the like, at preferably reflux temperature.

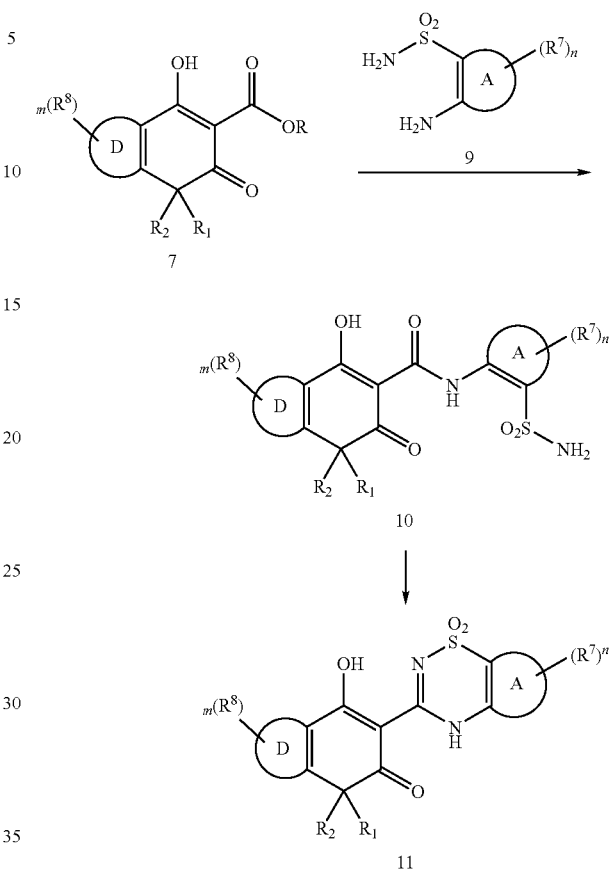

Scheme 2

Compounds of formula (11) wherein $R^1$, $R^2$, $R^7$, $R^8$, m and n are as defined in formula (I), and ring D is formed by $R^3$, $R^4$ (as defined in formula (I)) and the carbon atoms to which they are attached, can be prepared as shown in Scheme 2 from compounds of formula (7) by (a) reacting with an aminobenzenesulfonamide derivatives of formula (9) in a solvent such as toluene, xylene, dioxane and the like, at a temperature from about 80° C. to about 140° C., and (b) reacting the product of step (a) with a base at a temperature from about 80° C. to about 150° C. in a solvent such as, but not limited to, water, pyridine, picoline or collidine, and the like, to facilitate the cyclization of compounds of formula (10) to compounds of formula (11).

Examples of the base are, but not limited to, 5-20% of aqueous solution of sodium or potassium hydroxide, anhydrous cesium carbonate, potassium carbonate and 1,8 diazabicyclo[5.4.0]undec-7-ene.

A preferred method of step (b) is to treat compounds of formula (10) with one equivalent of anhydrous potassium or cesium carbonate in a solvent such as pyridine, picoline or collidine at a temperature from about 80° C. to about 150° C.

A more preferred method for the transformation is to treat compounds of formula (10) with 1,8diazabicyclo[5.4.0]undec-7-ene in a solvent such as pyridine, picoline or collidine, and the like, at a temperature from about 80° C. to about 150° C.

Scheme 3

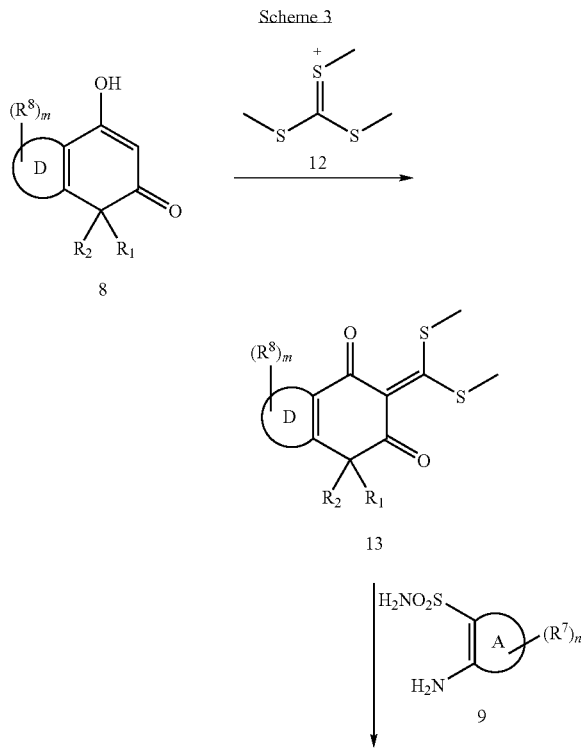

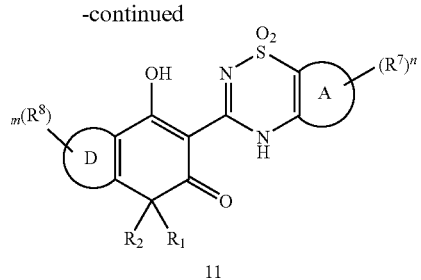

Another route for the preparation of compounds of formula (11) is illustrated above in Scheme 3. Compounds of formula (8) can be treated with 1-10 equivalents of a tris(alkylthio) methyl salt of formula (12) (prepared according to the procedure of Degani, *Synthesis* 1988, 22), in the presence of an excess of a base, in a dipolar aprotic solvent such as, but not limited to, tetrahydrofuran, acetonitrile, toluene, xylene or dioxane, or mixtures therefore, at a temperature of about 25° C. to about 130° C. to afford compounds of formula (13). A preferred tris(alkylthio)methyl salt is tris(methylthio)methyl methyl sulfate or tris(methylthio)methyl tetrafluoroborate.

Examples of the base are, but not limited to, pyridine, picoline and collidine.

Compounds of formula (13) can be converted to compounds of formula (11) by treating with an amino benzenesulfonamide of formula (9) in a solvent such as toluene, xylene or dioxane, and the like, or mixtures thereof, at a temperatures from about 70° C. to about 150° C.

Scheme 4

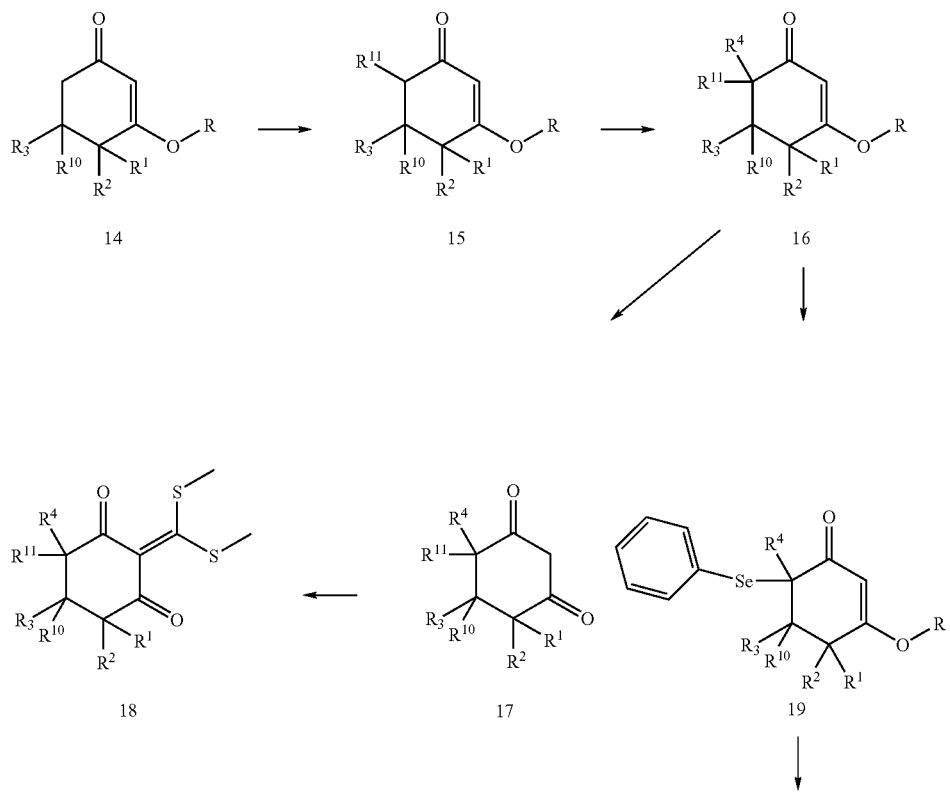

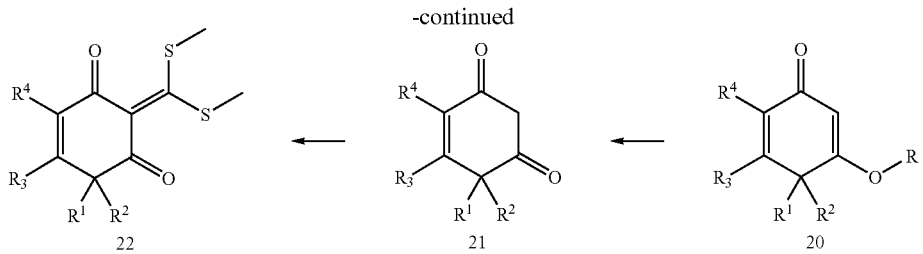

Compounds of this invention having formula (I) wherein B is a five, six or seven membered ring, and wherein $R^3$ and $R^4$ together do not form a ring, or wherein $R^3$ and $R^4$ together form a cycloalkyl or cycloalkenyl ring, can be prepared as shown in schemes 4 and Using methodology developed by Stork (Stork, G.; Danheiser, R. L. *J. Org. Chem.* 1973, 38, 1775), alkoxydihydroresorcinol derivative (14) wherein R is methyl, ethyl, n-propyl, or isobutyl can be converted to compounds of formula (15) by (a) reacting with a base in a solvent such as, but not limited to, tetrahydrofuran or 2-methyltetrahydrofuran, or mixtures thereof, at a temperature from about −78° C. to about 0° C., and with or without the presence of an additive, and (b) treating the product from step (a) with an alkylating agent of formula $R^{11}X$, wherein X is Cl, Br, or I, at a temperature from about −78° C. to about 25° C. Compounds of formula (15) can be further alkylated with the same or a second alkylating agent of formula $R^4X$, wherein X is Cl, Br, or I, by the conditions as described in steps (a) and (b) to afford compounds of formula (16).

Examples of the alkylating agents include, but not limited to, allyl bromide, methyl iodide, 1-chloro-3-methyl-2-butene, ethyl iodide, crotyl bromide and crotyl iodide.

Examples of the base include, but are not limited to, lithium bis(trimethylsilyl)amide (LiHMDS), Lithium tetramethyl piperidide and lithium diisopropyl amide (LDA).

Examples of the additives include, but not limited to, hexamethylphosphoric triamide (HMPA), N,N'-dimethylpropylene urea (DMPU) and 1,3-dimethyl-2-imidazolidinone (DMI).

Compounds of formula (16) can be directly hydrolyzed to the diketone derivatives of formula (17) by treatment with an acid such as dilute aqueous hydrochloric acid, dilute aqueous sulfuric acid, aqueous sodium bisulfate or aqueous trifluoroacetic acid in a solvent, such as tetrahydrofuran, acetone, dioxane, and the like, or mixtures thereof, at a temperatures from about 0° C. to about 25° C. Compounds of formula (18) can be prepared from diketones of formula (17), using the conditions for the transformation of compounds of formula (8) to compounds of formula (13).

Alternatively, using methodology developed independently by Nicolaou and Suzuki (Nicolaou, K. C.; et al. *Chem. Commun.* 2002, 2478; *Angew. Chem. Int. Ed. Eng.* 2002, 41, 3276; Bode, J. W.; Suzuki, K. *Tetrahedron Lett.* 2003, 44, 3559), compounds of formula (16) wherein $R^{10}$ and $R^{11}$ are hydrogen, can be treated with a base such as, but not limited to, lithium diisopropyl amide (LDA) in a solvent such as tetrahydrofuran, 2-methyltetrahydrofuran or diethyl ether, and the like, or mixtures thereof, in the presence of an additive such as hexamethylphosphoric triamide (HMPA) or 1,3-dimethyl-2-imidazolidinone (DMI) at a temperature from about −78° C. to about 0° C., followed by the addition of phenyl selenyl chloride and warming the reaction to ambient temperature. The resulting selenium derivative (19) can be treated with an oxidizing agent such as, but not limited to, aqueous hydrogen peroxide, m-chloroperbenzoic acid, sodium periodate, peracetic acid or monoperphthalic acid, at a temperatures from about 30° C. to about 50° C. The resulting dienone (20) can be hydrolyzed using a base such as, but not limited to, lithium hydroxide hydrate in a solvent mixture such as methanol or ethanol in water, at a temperatures of about 50° C. to about 100° C. to afford the diketone (21). The diketone (21) can be transformed to compounds of formula (22) using the conditions for the transformation of compounds of formula (8) to compounds of formula (13).

Scheme 5

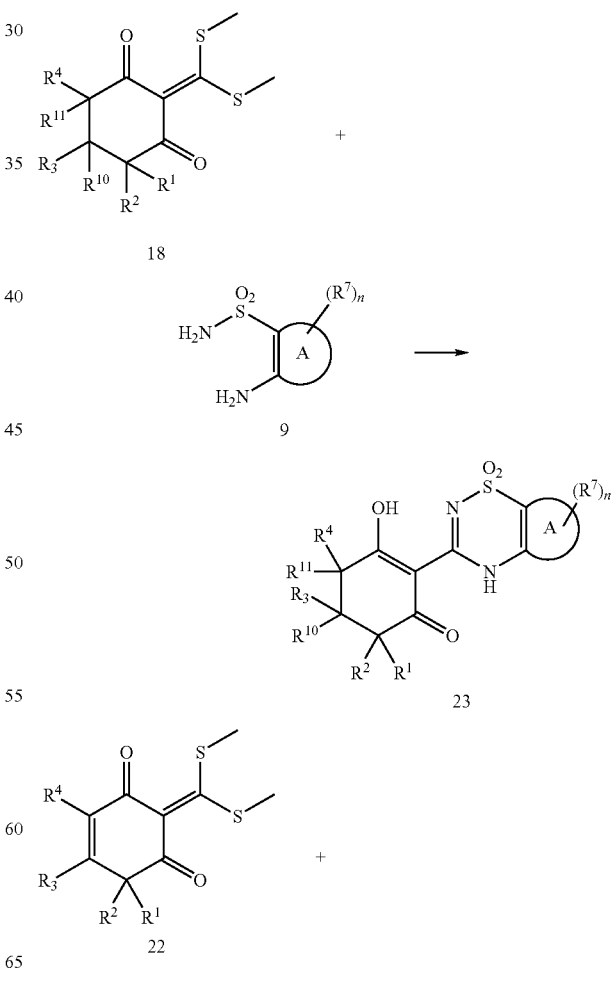

-continued

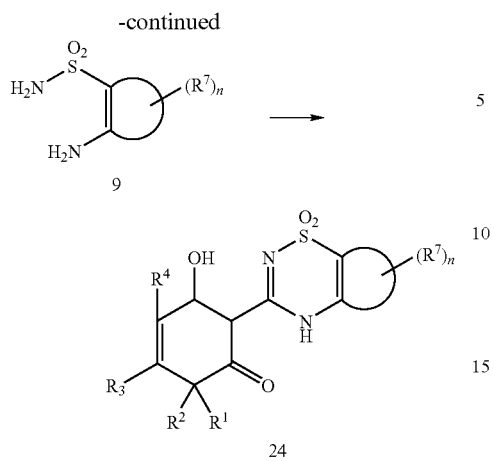

Compounds of formulae (18) and (22) can be converted to compounds of formulae (23) and (24), respectively, using the conditions for the transformation of compounds of formula (13) to compounds of formula (11).

Scheme 6

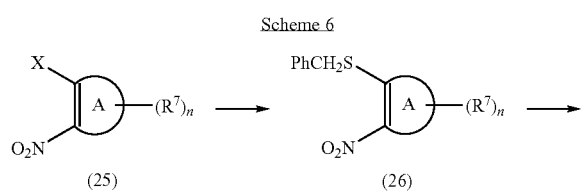

-continued

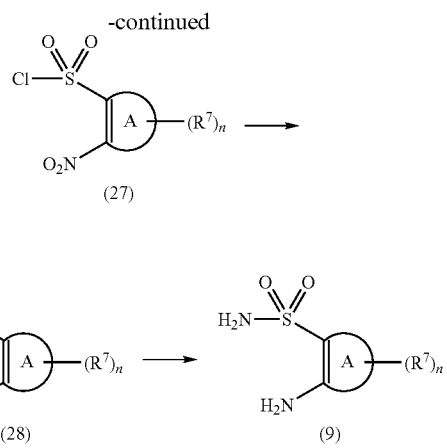

Compounds of the formula (25) wherein X is I, Br, Cl or F can be treated with alkyl thiols such as benzene methylthiol in the presence of a base such as sodium carbonate in solvents such as ethanol and the like under heated conditions to give compounds of the formula (26). Treatment of (26) with chlorine gas in hydrochloric acid or acetic acid provides compounds of the formula (27). Compounds of the formula (27) in solvents such as but not limited to dichloromethane, tetrahydrofuran or dioxane can be treated with ammonia or ammonium hydroxide to give compounds of the formula (28). Reduction of compounds of the formula (32) with iron powder and ammonium chloride in aqueous alcoholic solvents such as methanol or ethanol under heated conditions optionally with iron powder in acetic acid under heated conditions to provide compounds of the formula (9).

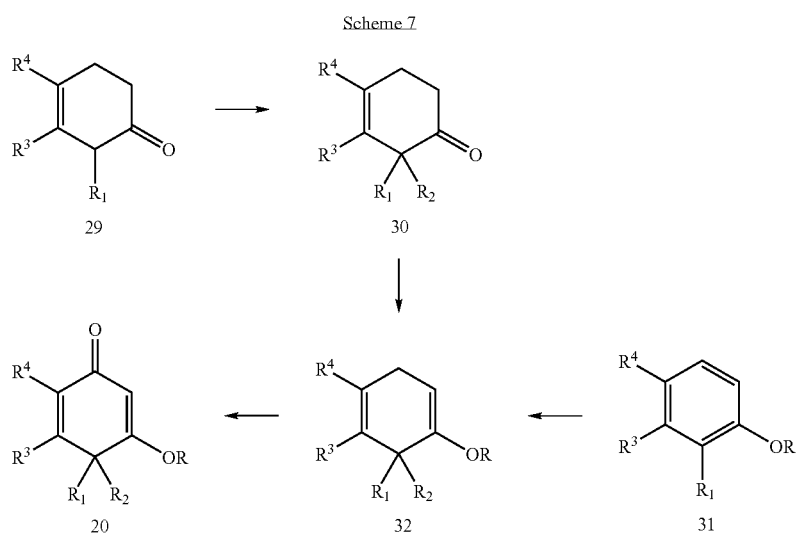

Alternatively, compounds of formula (20) wherein $R^1$, $R^2$, $R^3$ and $R^4$ are as defined in formula (I) and R is methyl, ethyl, isopropyl or butyl, can be prepared as shown in Scheme 7.

Compounds of formula (29), either purchased or prepared by methodologies known to one skilled in the art, can be transformed to compounds of formula (30), wherein $R^2$ is allyl, by reaction with a base, a palladium reagent, a ligand and allyl acetate. The reaction is typically performed in a solvent such as, but not limited to, tetrahydrofuran, dichloromethane, diethyl ether, N,N-dimethylformamide, dimethoxyethane or tert-butyl methyl ether, at a temperature from about room temperature to about 100° C. Examples of the base include, but are not limited to cesium carbonate. Examples of the palladium reagent include, but are not limited to, tris(dibenzylideneacetone)dipalladium(0) and allylpalladium chloride dimmer. Examples of the ligand include, but are not limited to, 1,2-diaminocyclohexane-N, N'-bis(2'-diphenylphosphinobenzoyl) and (+)-11(S), 12(S)-Bis[2'-(diphenylphosphino)benzaamido]-9,10-dihydro-9, 10ethanoanthracene. Compounds of formula (29) wherein $R^2$ is an alkyl or substituted alkyl, as defined in formula (I), can be converted to compounds of formula (30) by reaction with a base and an alkylating agent having formula $R^2X$, wherein X is Cl, Br or I, optionally in the presence of hexamethylphosphoric triamide (HMPA) or 1,3-Dimethyl-2-imidazolidinone (DMI). The reaction can be performed at a temperature from about −78° C. to about room temperature for about 1 to 48 hours. The reaction is generally carried out in an aprotic solvent such as, but are not limited to, tetrahydrofuran, dimethoxyethane or tert-butyl methyl ether. Examples of the base include, but are not limited to, lithium diisopropylamide, and lithium hexamethyldisilazide.

Compounds of formula (30) can be converted to compounds of formula (32) by reaction with a trialkylorthoformated of formula $CH(OR_3)_3$, and p-toluenesulfonic acid in an alcoholic solvent such as, but not limited to, methanol. The reaction is generally carried out at a temperature from about room temperature to about 70° C.

Alternatively, compounds of formula (32) can be obtained from compounds of formula (31) wherein $R^1$ is an electron withdrawing group such as —C(O)$R_a$ or —C(O)O$R_a$, by reaction with an alkylating agent having formula $R^2X$, wherein X is Cl, Br, or I, with a metal, ammonia and a proton source. The reaction can be carried out at about −78° C. and optionally in the presence of a co-solvent such as, but are not limited to, tetrahydrofuran and diethyl ether. Examples of the metal include potassium or sodium. Examples of the proton source include, but are not limited to, tert-butanol and a weak acid such as, but not limited to, water.

Conversion of compounds of formula (32) to compounds of formula (20) can be achieved by reaction with pyridinium dichromate and tert-butyl hydroperoxide. The reaction can be performed in a solvent such as, but not limited to, benzene, chloroform or dichloromethane, at a temperature from about room temperature to about 60° C., for about 1 hour to about 24 hours.

The present invention will now be described in connection with certain preferred embodiments which are not intended to limit its scope. On the contrary, the present invention covers all alternatives, modifications, and equivalents as can be included within the scope of the claims. Routine experimentation, including appropriate manipulation and protection of any chemical functionality, synthesis of the compounds of formula (I), (II) or (III) may be accomplished by methods analogous to those described above and in the following examples. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 5.06 (developed by Advanced Chemistry Development, Inc., Toronto, ON, Canada) or were given names consistent with ACD nomenclature.

EXAMPLE 1

3-(1,1-dioxido-4H-1,2,4-benzothiadiazin-3-yl)-4-hydroxy-1,1-dipropyl-2(1H)-naphthalenone

EXAMPLE 1A

Methyl 2-allyl-2-phenyl-4-pentenoate

A solution of methyl 2-phenylacetate (12.0 g, 80 mmol), allyl bromide (17.3 mL, 200 mmol) and sodium iodide (1 g) in tetrahydrofuran (160 mL) at 0° C. was treated portionwise with sodium hydride (7.36 g, 60% in oil, 184 mmol) over 10 minutes. The solution was allowed to warm to 25° C. and heated at reflux for 18 hours. The mixture was cooled to 0° C., treated with glacial acetic acid (2 mL) and concentrated in vacuo. The residue was partitioned between ethyl acetate and water. The organic phase was washed with saturated sodium bicarbonate solution and saturated sodium chloride solution, dried ($Na_2SO_4$), filtered, and concentrated in vacuo. The residue was filtered through a plug of 70-230 mesh silica gel eluting first with hexane and then with 10% ethyl acetate in hexane to give the title compound (17.89 g, 97%). $^1$H NMR (300 MHz, $CDCl_3$): δ 7.29 (m, 5 H), 5.52 (m, 2 H), 5.06 (m, 4 H), 3.65 (s, 3 H), 2.78 (m, 4 H).

EXAMPLE 1B

Methyl 2-phenyl-2-propylpentanoate

A solution of the product of Example 1A (7.5 g, 32.61 mmol) in ethyl acetate (125 mL) was treated with 10% palladium on carbon (600 mg) and stirred at 25° C. under hydrogen gas for 18 hours. The solution was filtered through Celite® and the filtrate was concentrated in vacuo to give the title compound (7.63 g, 100%). $^1$H NMR (300 MHz, $CDCl_3$): δ 7.27 (m, 5 H), 3.64 (m, 3 H), 1.96 (m, 4 H), 1.08 (m, 4 H), 0.89 (t, J=7.17 Hz, 6 H).

EXAMPLE 1C 2-phenyl-2-propylpentanoic Acid

A solution of the product of Example 1B (7.63 g, 32.61 mmol) and potassium trimethylsilanoate (23.2 g of 90% material, 163 mmol) in tetrahydrofuran (163 mL) was warmed at reflux for 18 hours. The solution was cooled to 25° C. and concentrated in vacuo to remove the tetrahydrofuran. A solution of the residue in water (250 mL) was cooled to 0° C., and adjusted to pH 1 by addition of 4 N HCl solution. The resulting precipitate was collected by filtration, washed with water and dried to give the title compound (6.78 g, 95%). $^1$H NMR (300 MHz, $CDCl_3$): δ 7.25 (m, 5 H), 1.99 (m, 4 H), 1.12 (m, 4 H), 0.90 (t, J=7.17 Hz, 6 H).

EXAMPLE 1D 2-phenyl-2-propylpentanoyl Chloride

A suspension of the product of Example 1C (4.13 g, 18.77 mmol) and N,N-dimethylformamide (1.45 mL, 18.77 mmol) in hexanes (700 mL) was treated with oxalyl chloride (4.91 mL, 56.31 mmol) and stirred at 25° C. for 2 hours. The mixture was treated with Celite®, and then filtered through a pad of Celite®. The filtrate was concentrated in vacuo to afford the title compound which was used directly in the next procedure.

EXAMPLE 1E

Diethyl 2-(2-phenyl-2-propylpentanoyl)malonate

A solution of diethyl malonate (3.03 g, 18.77 mmol) and anhydrous magnesium chloride in acetonitrile (36 mL) at 0° C. was treated with triethylamine (5.2 mL, 37.55 mmol), stirred at 0° C. for 30 min, stirred at 25° C. for 3 hours, cooled to 0° C. and treated dropwise with a solution of the product of Example 1D (18.77 mmol) in acetonitrile (15 mL) over 10 min and stirred at 50° C. for 18 hours. The solution was cooled to 25° C. and concentrated in vacuo. The solids were suspended in ethyl acetate and cooled to 0° C., treated with 4N HCl solution until all solids had dissolved. The organic layer was extracted with water (2×) and with saturated sodium chloride solution, dried ($Na_2SO_4$), filtered and concentrated in vacuo to afford the title compound (4.51 g, 66%). $^1$H NMR (300 MHz, $CDCl_3$): δ 7.32 (m, 5 H), 4.50 (s, 1 H), 4.04 (q, J=7.35 Hz, 4 H), 1.97 (m, 4 H), 1.28 (m, 3 H), 0.98 (m, 10 H).

EXAMPLE 1F

Ethyl 1-hydroxy-3-oxo-4,4-dipropyl-3,4-dihydro-2-naphthalenecarboxylate

The product of Example 1E (4.51 g, 12.4 mmol) was treated with concentrated sulfuric acid (25 mL) and stirred at 25° C. for 3 hours. The mixture was then poured into a mixture of ice and water (500 mL) and stirred until all the ice melted. The mixture was extracted with ethyl acetate (2×). The combined organic layers were washed with water and saturated sodium chloride solution, dried ($Na_2SO_4$), filtered, and concentrated in vacuo. The residue was chromatographed on silica gel, eluting with methyl t-butyl ether in hexane to afford the title compound (1.73 g, 44%). $^1$H NMR (300 MHz, $CDCl_3$): δ 15.15 (d, J=13.24 Hz, 1 H), 8.18 (m, 1 H), 7.59 (m, 1 H), 7.40 (m, 2 H), 4.47 (m, 2 H), 2.25 (m, 2 H), 1.91 (m, 1H), 1.70 (m, 1 H), 1.47 (q, J=7.23 Hz, 3 H), 1.25 (m, 1 H), 0.93 (m, 2 H), 0.67 (m, 7 H).

EXAMPLE 1G

N-[2-(aminosulfonyl)phenyl]-1-hydroxy-3-oxo-4,4-dipropyl-3,4-dihydro-2-naphthalenecarboxamide A suspension of the product of Example 1F (490 mg, 1.55 mmol) and 2-aminobenzenesulfonamide (Aldrich) (267 mg, 1.55 mmol) in toluene (25 mL) was stirred at reflux for 18 hours, cooled to 25° C. and concentrated in vacuo. The residue was recrystallized from ether-hexane solution to afford the title compound (410 mg, 60%). $^1$H NMR (300 MHz, $CDCl_3$): δ 17.76 (d, J=12.13 Hz, 1 H), 12.67 (s, 1 H), 8.34 (m, 1 H), 8.09 (dd, J=8.09, 1.47 Hz, 1 H), 7.63 (m, 1 H), 7.38 (m, 3 H), 6.83 (m, 1 H), 5.57 (s, 2 H), 4.85 (m, 1 H), 2.32 (m, 2 H), 1.93 (m, 2 H), 0.97 (m, 2 H), 0.68 (m, 8 H).

EXAMPLE 1H 3-(1,1-dioxido-4H-1,2,4-benzothiadiazin-3-yl)-4-hydroxy-1,1-dipropyl-2(1 H)-naphthalenone A suspension of the product of Example 1G (150 mg, 0.34 mmol) in 10% potassium hydroxide solution (9 mL) was stirred at 130° C. for 30 hours, cooled to 25° C., acidified to pH 3 by addition of 1 M citric acid, stirred with ethyl acetate, and filtered through Celite®. The organic layer from the filtrate was washed with saturated sodium chloride solution, dried ($Na_2SO_4$), filtered and concentrated in vacuo. The residue was recrystallized from ether-hexane solution to afford the title compound (83 mg, 57%). $^1$H NMR (300 MHz, $CDCl_3$): δ 16.70 (s, 1 H), 14.22 (s, 1 H), 8.26 (d, J=8.09 Hz, 1 H), 7.99 (d, J=8.09 Hz, 1 H), 7.67 (m, 1H), 7.47 (m, 3 H), 7.29 (m, 2 H), 2.25 (m, 2 H), 1.86 (m, 2 H), 0.89 (m, 2 H), 0.70 (m, 8 H).

EXAMPLE 1I

Sodium 2-(1,1-dioxido-4H-1,2,4-benzothiadiazin-3-yl)-3-oxo-4,4-dipropyl-3,4-dihydro-1-naphthalenolate A suspension of the product of Example 1H (55 mg, 0.13 mmol) in 1:1 acetonitrile-water was treated with 1N NaOH solution (130 μL 0.13 mmol) and stirred at 25° C. for 2 hours. The solution was then lyophilized to afford the title compound (59 mg, 100%) a fluffy white solid. $^1$H NMR (300 MHz, DMSO-$d_6$): δ 5.52 (s, 1 H), 8.06 (d, J=7.72 Hz, 1 H), 7.64 (d, J=7.72 Hz, 1 H), 7.49 (m, 3 H), 7.30 (m, 3 H), 2.10 (m, 2 H), 1.67 (m, 2 H), 0.88 (m, 2 H), 0.59 (m, 8 H).

EXAMPLE 2

4-hydroxy-3-(7-hydroxy-1,1-dioxido-4H-1,2,4-benzothiadiazin-3-yl)-1,1-dipropyl-2(1 H)-naphthalenone

EXAMPLE 2A 4-(benzyloxy)-2-fluoro-1-nitrobenzene

A solution of 2-fluoro-4-hydroxynitrobenzene (5.08 g, 32.36 mmol), cesium carbonate (11.71 g, 36.24 mmol), benzyl bromide (4.31 mL, 36.24 mmol), and tetrabutylamunonium iodide (50 mg) in N,N-dimethylformamide (50 mL) was stirred at 25° C. for 24 hours, diluted with water (200 mL) and extracted with ethyl acetate (3×). The combined organic layers were washed with water (3×) and saturated sodium chloride solution, dried ($Na_2SO_4$), filtered and concentrated in vacuo to give the title compound (7.72 g, 97%). $^1$H NMR (300 MHz, $CDCl_3$): δ 8.10 (m, 1 H), 7.40 (m, 5 H), 6.82 (m, 2 H), 5.15 (s, 2 H).

EXAMPLE 2B 4-(benzyloxy)-2-(benzylsulfanyl)-1-nitrobenzene

A solution of the product of Example 2A (7.72 g, 31.26 mmol), sodium carbonate (3.31 g, 31.26 mmol) and benzyl mercaptan (3.90 mL, 30.21 mmol) in absolute ethanol (50 mL) was stirred at reflux for 6 hours, cooled to 25° C. and added to water (200 mL). The precipitate was collected by filtration, washed with water and dried to give the title compound (10.71 g, 98%). $^1$H NMR (300 MHz, $CDCl_3$): δ 8.26

(d, J=9.19 Hz, 1 H), 7.36 (m, 10 H), 6.91 (d, J=2.57 Hz, 1 H), 6.78 (dd, J=9.19, 2.57 Hz, 1 H), 5.06 (s, 2 H), 4.12 (s, 2 H).

EXAMPLE 2C 5-(benzyloxy)-2-nitrobenzenesulfonamide

A suspension of the product of Example 2B (10.71 g, 30.51 mmol) in glacial acetic acid (100 mL) and water (11 mL) at 0° C. was treated with chlorine gas for 10 min, stirred at 0° C. for 45 min, poured into a mixture of ice and water (500 mL), stirred for 30 min at 0° C. and then extracted with dichloromethane (2×). The combined organic layers were cooled to 0° C. and treated portionwise with 28% ammonium hydroxide solution (80 mL), stirred for 30 min, treated with water (120 mL) and the layers were separated. The organic layer was washed with 1 M citric acid solution, water, and saturated sodium chloride solution, dried ($Na_2SO_4$), filtered, and concentrated in vacuo. The residue was triturated with ether, collected by filtration and dried to give the title compound (7.26 g, 77%). $^1$H NMR (300 MHz, DMSO-$d_6$): δ 8.01 (d, J=8.82 Hz, 1 H), 7.79 (s, 1 H), 7.63 (d, J=2.57 Hz, 1 H), 7.43 (m, 5 H), 5.28 (s, 2 H).

EXAMPLE 2D 2-amino-5-(benzyloxy)benzenesulfonamide

A suspension of the product of Example 2C (7.26 g, 23.57 mmol), ammonium chloride (8.27 g, 155 mmol), and iron powder (8.11 g, 145 mmol) in methanol (188 mL) and water (94 mL) was stirred at reflux for 2 hours. The mixture was filtered while hot through Celite®, and the filter cake was washed with hot methanol (200 mL). The filtrate was concentrated to an approximate volume of 100 mL and then extracted with ethyl acetate (400 mL). The organic layer was washed with water and saturated sodium chloride solution, dried ($Na_2SO_4$), filtered through Celite® and concentrated in vacuo to afford the title compound (6.37 g, 97%). $^1$H NMR (300 MHz, DMSO-$d_6$): δ 7.38 (m, 7 H), 7.22 (m, 2 H), 7.01 (dd, J=8.82, 2.94 Hz, 1 H), 6.76 (d, J=8.82 Hz, 1 H), 5.46 (s, 2 H), 4.98 (s, 2 H).

EXAMPLE 2E

N-[2-(aminosulfonyl)-4-(benzyloxy)phenyl]-1-hydroxy-3-oxo-4,4-dipropyl-3,4-dihydro-2-naphthalenecarboxamide A suspension of the product of Example 1F (617 mg, 1.95 mmol) and the product of Example 2D (542 mg, 1.95 mmol) in toluene (20 mL) was stirred at reflux for 18 hours and concentrated in vacuo to afford the title compound (1.1 g, 100%). $^1$H NMR (300 MHz, CDCl$_3$): δ 17.85 (d, J=12.13 Hz, 1 H), 12.49 (s, 1 H), 12.35 (s, 1 H), 8.32 (d, J=6.62 Hz, 1 H), 8.18 (m, 1 H), 7.98 (d, J=9.19 Hz, 1 H), 7.66 (m, 2 H), 7.42 (m, 3 H), 7.27 (m, 4 H), 5.49 (s, 1 H), 5.37 (s, 1 H), 5.07 (d, J=30.89 Hz, 2 H), 2.31 (m, 2 H), 1.86 (m, 2 H), 0.94 (m, 2 H), 0.72 (m, 8 H).

EXAMPLE 2F

3-[7-(benzyloxy)-1,1-dioxido-4H-1,2,4-benzothiadiazin-3-yl]-4-hydroxy-1,1-dipropyl-2(1 H)-naphthalenone A solution of the compound of Example 2E (300 mg, 0.547 mmol) in anhydrous pyridine (5.2 mL) was treated with 1,8-diazabicyclo[5.4.0]undec-7-ene (82 μL, 0.55 mmol) and stirred at 140° C. for 18 hours, cooled to 25° C. and the pyridine removed by short path distillation under high vacuum (50° C./0.3 mm Hg). A solution of the residue in ethyl acetate was washed with water (2×) and saturated sodium chloride solution, dried ($Na_2SO_4$), filtered and concentrated in vacuo. The residue was chromatographed on silica gel, eluting with ethyl acetate in hexane to give the title compound (110 mg, 38%). $^1$H NMR (300 MHz, DMSO-$d_6$): δ 8.11 (d, J=7.72 Hz, 1 H), 7.64 (m, 1 H), 7.41 (m, 8 H), 5.21 (s, 2 H), 2.14 (m, 2 H), 1.83 (m, 2 H), 0.87 (m, 2 H), 0.64 (m, 8 H).

EXAMPLE 2G 4-hydroxy-3-(7-hydroxy-1,1-dioxido-4H-1,2,4-benzothiadiazin-3-yl)-1,1-dipropyl-2(1 H)-naphthalenone A suspension of the compound of Example 2F (110 mg, 0.21 mmol) in 1:1:1 tetrahydrofuran-ethyl acetate-methanol (20 mL) was treated with 10% palladium on carbon (30 mg) and stirred at 25° C. under hydrogen atmosphere for 18 hours. The mixture was filtered through Celite® and the filtrate concentrated in vacuo to afford the title compound (86 mg, 94%). $^1$H NMR (300 MHz, DMSO-$d_6$): δ 13.87 (m, 1 H), 10.33 (s, 2 H), 8.15 (d, J=7.72 Hz, 1 H), 7.72 (m, 2 H), 7.52 (m, 2 H), 7.16 (m, 2 H), 2.15 (m, 2 H), 1.97 (m, J=11.77 Hz, 2H), 0.89 (m, 2 H), 0.60 (m, 8 H).

EXAMPLE 3

2-{[3-(1-hydroxy-3-oxo-4,4-dipropyl-3,4-dihydro-2-naphthalenyl)-1,1-dioxido-4H-1,2,4-benzothiadiazin-7-yl]oxy}acetamide A solution of the product of Example 2G (14 mg, 0.032 mmol), 2-bromoacetamide (9 mg, 0.064 mmol), cesium carbonate (22 mg, 0.067 mmol) and tetrabutylammonium iodide (3 mg) in N,N-dimethylformamide (0.5 mL) was stirred at 25° C. for 18 hours. The solution was acidified with 1M citric acid solution (1 mL) and extracted with ethyl acetate. The organic layer was washed with water (3×) and saturated sodium chloride solution, dried ($Na_2SO_4$), filtered and concentrated in vacuo. A suspension of the residue in acetonitrile (2 mL) was treated with 1N sodium hydroxide solution (26 μL) and stirred at 25° C. for 2 hours. The solution was lyophilized to afford the title compound (12 mg, 52%). $^1$H NMR (300 MHz, DMSO-$d_6$): δ 8.12 (d, J=8.09 Hz, 1 H), 7.61 (m, 4

H), 7.31 (m, 2 H), 4.55 (s, 2 H), 2.15 (m, 2H), 1.87 (m, 2 H), 1.29 (m, 2 H), 0.87 (m, 2 H), 0.60 (m, 7 H).

EXAMPLE 4

1,1-dibutyl-3-(1,1-dioxido-4H-1,2,4-benzothiadiazin-3-yl)-4-hydroxy-2(1 H)-naphthalenone

EXAMPLE 4A

Methyl (4E)-2-[(2E)-2-butenyl]-2-phenyl-4-hexenoate

The title compound was prepared according to the procedure of Example 1A, substituting crotyl bromide for allyl bromide (9.56 g, 93%). $^1$H NMR (300 MHz, CDCl$_3$): δ 7.26 (m, 5 H), 5.47 (m, 2 H), 5.12 (m, 2 H), 3.64 (m, 3 H), 2.72 (m, 4 H), 1.58 (m, 6 H).

EXAMPLE 4B

Methyl 2-butyl-2-phenylhexanoate

A solution of the product of Example 4A (7.78 g, 30.16 mmol) in methanol (70 mL) was treated with Adams' catalyst (PtO$_2$, 790 mg) and hydrogenated under 60 psi hydrogen pressure for 16 hours at 25° C. The catalyst was removed by filtration and the filtrate concentrated in vacuo to give the title compound (7.59 g, 96%). $^1$H NMR (300 MHz, CDCl$_3$): δ 7.27 (m, 5 H), 3.64 (s, 3 H), 1.99 (m, 4 H), 1.29 (m, 4 H), 1.03 (m, 4 H), 0.86 (t, J=7.17 Hz, 6 H).

EXAMPLE 4C 2-butyl-2-phenylhexanoic Acid

The title compound (7.05 g, 98%) was prepared following the procedure of Example 1C, substituting the product of Example 4B for the product of Example 1B. $^1$H NMR (300MHz, CDCl$_3$): δ 7.28 (m, 5 H), 2.01 (m, 4 H), 1.28 (m, 4 H), 1.09 (m, 4 H), 0.87 (t, J=7.35 Hz, 6 H).

EXAMPLE 4D 2-butyl-2-phenylhexanoyl Chloride

The title compound (4.3 g) was prepared following the procedure of Example 1D, substituting the product of Example 4C for the product of Example 1C.

EXAMPLE 4E

Diethyl 2-(2-butyl-2-phenylhexanoyl)malonate

The title compound (6.22 g, 98%) was prepared following the procedure of Example 1E, substituting the product of Example 4D for the product of Example 1D. $^1$H NMR (300 MHz, CDCl$_3$): δ 7.32 (m, 5 H), 4.50 (s, 1 H), 4.03 (q, J=6.99 Hz, 4 H), 2.00 (m, 4 H), 1.29 (m, 4 H), 1.12 (m, 8 H), 0.90 (m, 8 H).

EXAMPLE 4F

Ethyl 4,4-dibutyl-1-hydroxy-3-oxo-3,4-dihydro-2-naphthalenecarboxylate

The title compound (1.2 g, 21%) was prepared following the procedure of Example 1F, substituting the product of Example 4E for the product of Example 1E. $^1$H NMR (300 MHz, CDCl$_3$): δ 15.16 (d, J=13.97 Hz, 1 H), 8.22 (m, 1 H), 7.59 (m, 2 H), 7.36 (m, 2 H), 4.47 (m, 2 H), 2.25 (m, 2 H), 1.92 (m, 2 H), 1.71 (m, 2 H), 1.50 (m, 2 H), 1.24 (m, 2 H), 1.11 (m, 2H), 0.89 (m, 1 H), 0.65 (m, 7 H).

EXAMPLE 4G

N-[2-(aminosulfonyl)phenyl]-4,4-dibutyl-1-hydroxy-3-oxo-3,4-dihydro-2-naphthalenecarboxamide The title compound (305 mg, 94%) was prepared following the procedure of Example 1G, substituting the product of Example 4F for the product of Example 1F. $^1$H NMR (300 MHz, CDCl$_3$): δ 17.77 (d, J=1.84 Hz, 1 H), 12.69 (s, 1 H), 12.55 (s, 1 H), 8.38 (m, 1 H), 8.24 (m, 1 H), 8.09 (m, 1 H), 7.65 (m, 1 H), 7.45 (m, 1 H), 7.30 (m, 3 H), 5.57 (s, 1 H), 5.41 (s, 1H), 2.32 (m, 2 H), 1.90 (m, 2 H), 1.15 (m, 3 H), 0.90 (m, 2 H), 0.66 (m, 8 H).

EXAMPLE 4H 1,1-dibutyl-3-(1,1-dioxido-4H-1,2,4-benzothiadiazin-3-yl)-4-hydroxy-2(H1)-naphthalenone A solution of the product of Example 4G (298 mg, 0.63 mmol) and cesium carbonate (123 mg, 0.38 mmol) in pyridine (6 mL) was stirred at 140° C. for 18 hours, cooled to 25° C. and the pyridine removed by short path distillation under high vacuum (50° C./0.3 mm Hg). A suspension of the residue in ethyl acetate was treated with saturated ammonium chloride solution. The organic layer was washed with water and saturated sodium chloride solution, dried (Na$_2$SO$_4$), filtered and concentrated in vacuo. The residue was purified by flash chromatography on silica gel, eluting with ethyl acetate in hexane to afford the title compound (157 mg, 55%). $^1$H NMR (300 MHz, CDCl$_3$): δ 16.71 (d, J=3.68 Hz, 1 H), 14.39 (s, 1 H), 14.24 (s, 1 H), 8.28 (d, J=8.09 Hz, 1 H), 7.99 (d, J=8.09 Hz, 1 H), 7.66 (m, 1 H), 7.46 (m, 1 H), 7.31 (m, 6 H), 2.30 (m, 2 H), 1.92 (m, 2 H), 1.16 (m, 3 H), 0.88 (m, 2 H), 0.62 (m, 7 H).

EXAMPLE 4I

Sodium 4,4-dibutyl-2-(1,1-dioxido-4H-1,2,4-benzothiadiazin-3-yl)-3-oxo-3,4-dihydro-1-naphthalenolate The title compound (142 mg, 88%) was prepared following the procedure of Example 1I substituting the product of Example 4H for the product of Example 1H. $^1$H NMR (300 MHz, DMSO-d$_6$): δ 15.55 (s, 1 H), 8.06 (d, J=7.72 Hz, 1 H), 7.64 (d, J=6.99 Hz, 1 H), 7.49 (m, 4 H), 7.29 (m, 4 H), 2.12 (m, 2 H), 1.69 (m, 2 H), 1.04 (m, 3 H), 0.89 (m, 2 H), 0.65 (t, J=7.35 Hz, 6 H), 0.51 (m, 1 H).

EXAMPLE 5

2-{[3-(4,4-dibutyl-1-hydroxy-3-oxo-3,4-dihydro-2-naphthalenyl)-1,1-dioxido-4H-1,2,4-benzothiadiazin-7-yl]oxy}acetamide

EXAMPLE 5A

[bis(methylsulfanyl)methylene](methyl)sulfonium methyl sulfate

Dimethyl trithiocarbonate (2.76 g, 20 mmol) was treated with dimethyl sulfate (2.5 g, 20 mmol) and stirred at 90° C. for 1 h, and cooled to 25° C. The solid was broken up under ether, collected by filtration, and washed with ether to give the title compound (5.1 g, 91%).

EXAMPLE 5B 1,1-dibutyl-4-hydroxy-2(1H)-naphthalenone

A solution of the product of Example 4F (200 mg, 0.58 mmol) in dioxane (3 mL) and 10% HCl solution (10 mL) was stirred at 100° C. for 5 hours, cooled to 25° C. and extracted with dichloromethane (3×). The combined organic layers were dried ($Na_2SO_4$), filtered and concentrated in vacuo. The residue was recrystallized from hexanes to give the title compound (140 mg, 88%). $^1$H NMR (300 MHz, DMSO-$d_6$): δ 11.72, 11.46 (s, 1 H), 7.92 (m, 1 H), 7.61 (m, 1 H), 7.37 (m, 2 H), 5.81, 5.64 (two s, 1 H), 1.99 (m, 4 H), 1.05 (m, 4 H), 0.82 (m, 2 H), 0.67 (t, J=6.99 Hz, 6 H), 0.44 (m, 2 H).

EXAMPLE 5C

2-[bis(methylsulfanyl)methylene]-4,4-dibutyl-1,3(2H,4H)-naphthalenedione

A solution of the product of Example 5B (25 mg, 0.092 mmol) in dioxane (4 mL) was treated with the product of Example 5A (71 mg, 0.27 mmol) and stirred at 100° C. for 2 hours, cooled to 25° C., diluted with ice water and extracted with ethyl acetate (3×). The combined organic layers were washed with water (3×) and saturated sodium chloride solution, dried ($Na_2SO_4$), filtered and concentrated in vacuo to give the title compound. $^1$H NMR (300 MHz, DMSO-$d_6$): δ 8.05 (m, 1 H), 7.66 (m, 1 H), 7.56 (d, J=7.72 Hz, 1 H), 7.43 (t, J=6.80 Hz, 1 H), 2.51 (m, 6 H), 2.10 (m, 2 H), 1.82 (m, 2 H), 1.09 (m, 4 H), 0.69 (m, 10 H).

EXAMPLE 5D

3-[7-(benzyloxy)-1,1-dioxido-4H-1,2,4-benzothiadiazin-3-yl]-1,1-dibutyl-4-hydroxy-2(1H)-naphthalenone A solution of the product of Example 5C (52 mg, 0.14 mmol) and the product of Example 2D (38 mg, 0.14 mmol) in toluene (12 mL) was stirred at reflux for 6 hours, cooled to 25° C. and concentrated in vacuo. The residue was triturated with ether-hexane and collected by filtration to give the title compound (65 mg, 84%). $^1$H NMR (300 MHz, CDCl$_3$): δ 16.66 (m, 1 H), 14.33 (s, 1 H), 8.27 (d, J=8.09 Hz, 1 H), 7.66 (m, 1 H), 7.38 (m, 10 H), 5.14 (s, 2 H), 2.35 (m, 2 H), 1.96 (m, 2 H), 1.12 (m, 4 H), 0.89 (m, 2 H), 0.70 (m, 6 H), 0.55 (m, 2H).

EXAMPLE 5E 1,1-dibutyl-4-hydroxy-3-(7-hydroxy-1,1-dioxido-4H-1,2,4-benzothiadiazin-3-yl)-2(1H)-naphthalenone The title compound was prepared following the procedure of Example 2G, substituting the product of Example 5D for the product of Example 2F to afforded the title compound (70 mg, 100%). $^1$H NMR (300 MHz, DMSO-$d_6$): δ 8.16 (d, J=8.09 Hz, 1 H), 7.74 (m, 1 H), 7.54 (m, 2 H), 7.17 (m, 2 H), 7.07 (m, 1 H), 2.16 (m, 2 H), 2.00 (m, 2 H), 1.05 (m, 4H), 0.88 (m, 2 H), 0.67 (t, J=7.17 Hz, 6 H), 0.50 (m, 2 H).

EXAMPLE 5F

2-{[3-(4,4-dibutyl-1-hydroxy-3-oxo-3,4-dihydro-2-naphthalenyl)-1,1-dioxido-4H-1,2,4-benzothiadiazin-7-yl]oxy}acetamide A solution of the product of Example 5E (69 mg, 0.15 mmol), 2-bromoacetamide (80 mg, 0.58 mmol), cesium carbonate (96 mg, 0.58 mmol), and tetrabutylammonium iodide (26 mg, 0.08 mmol) in N,N-dimethylformamide (2.4 mL) was stirred at 25° C. for 48 hours, diluted with ethyl acetate and treated with saturated ammonium chloride solution (2 mL). The organic layer was washed with water (3×) and saturated sodium chloride solution, dried ($Na_2SO_4$), filtered and concentrated in vacuo to afford the title compound (58 mg, 76%). $^1$H NMR (300 MHz, DMSO-$d_6$): δ 13.73 (s, 1 H), 8.17 (d, J=7.72 Hz, 1 H), 7.74 (m, 3 H), 7.55 (m, 1 H), 7.40 (m, 2 H), 4.59 (s, 2 H), 2.19 (m, 2 H), 2.02 (d, 2 H), 1-06 (m, 4 H), 0.90 (m, 2H), 0.69 (q, J=7.60 Hz, 6 H), 0.52 (m, 2 H).

EXAMPLE 5G

Sodium 2-[7-(2-amino-2-oxoethoxy)-1,1-dioxido-4H-1,2,4-benzothiadiazin-3-yl]-4,4-dibutyl-3-oxo-3,4-dihydro-1-naphthalenolate The title compound (58 mg, 96%) was prepared following the procedure of Example 3, substituting the product of Example 5F for the product of Example 2G. $^1$H NMR (300 MHz, DMSO-$d_6$): δ 15.50 (s, 1 H), 8.05 (d, J=7.35 Hz, 1 H), 7.62 (s, 1 H), 7.45 (m, 2 H), 7.30 (m, 2 H), 7.18 (m, 2 H), 4.48 (s, 2 H), 2.12 (m, 2 H), 1.68 (m, 2 H), 1.04 (m, 4H), 0.86 (m, 2 H), 0.65 (t, J=7.35 Hz, 6 H), 0.50 (m, 2 H).

EXAMPLE 6

3-(1,1-dioxido-4H-1,2,4-benzothiadiazin-3-yl)-4-hydroxy-1,1-diisopentyl-2(1H)-naphthalenone

EXAMPLE 6A

Methyl 5-methyl-2-(3-methyl-2-butenyl)-2-phenyl-4-hexenoate

The title compound (11.4 g, 100%) was prepared following the procedure of Example 1A, substituting 1-chloro-3-methyl-2-butene for allyl bromide. $^1$H NMR (300 MHz, CDCl$_3$): δ 7.28 (m, 5 H), 4.88 (m, 2 H), 3.64 (s, 3 H), 2.75 (m, 2 H), 2.63 (dd, J=14.34, 6.62 Hz, 2 H), 1.66 (s, 6 H), 1.49 (s, 6 H).

EXAMPLE 6B

Methyl 2-isopentyl-5-methyl-2-phenylhexanoate

The title compound was prepared following the procedure of Example 4B, substituting the product of Example 6A for the product of Example 1A. $^1$H NMR (300 MHz, CDCl$_3$): δ 7.26 (m, 5 H), 3.64 (s, 3 H), 1.99 (m, 6 H), 1.48 (m, 2 H), 0.92 (m, 14 H).

EXAMPLE 6C 2-isopentyl-5-methyl-2-phenylhexanoic acid

The title compound was prepared following the procedure of Example 1C, substituting the product of Example 6B for the product of Example 1B. $^1$H NMR (300 MHz, CDCl$_3$): δ 7.28 (m, 5 H), 2.01 (m, 4 H), 1.49 (m, 2 H), 0.98 (m, 4 H), 0.87 (m, 12 H).

EXAMPLE 6D 2-isopentyl-5-methyl-2-phenylhexanoyl chloride

The title compound was prepared according to the procedure of Example 1D, substituting the product of Example 6C for the product of Example 1C.

EXAMPLE 6E

Dimethyl 2-(2-isopentyl-5-methyl-2-phenylhexanoyl)malonate

The title compound was prepared following the procedure of Example 1E, substituting dimethyl malonate for diethyl malonate, and substituting the product of Example 6D for the product of Example 1D. $^1$H NMR (300 MHz, CDCl$_3$): δ 7.32 (m, 5 H), 4.54 (s, 1 H), 3.56 (s, 6 H), 2.00 (m, 4 H), 1.49 (m, 2 H), 0.87 (m, 16 H).

EXAMPLE 6F

Methyl 1-hydroxy-4,4-diisopentyl-3-oxo-3,4-dihydro-2-naphthalenecarboxylate

The title compound was prepared according to the procedure of Example 1F, substituting the product of Example 6E for the product of Example 1E. $^1$H NMR (300 MHz, CDCl$_3$): δ 15.02 (d, J=4.04 Hz, 1 H), 8.21 (m, 1 H), 7.61 (m, 1 H), 7.41 (m, 2 H), 3.99 (s, 3H), 2.26 (m, 2 H), 1.92 (m, 2 H), 1.30 (m, 2 H), 0.79 (m, 14 H), 0.47 (m, 2 H).

EXAMPLE 6G

N-[2-(aminosulfonyl)phenyl]-1-hydroxy-4,4-diisopentyl-3-oxo-3,4-dihydro-2-naphthalenecarboxamide The title compound was prepared according to the procedure of Example 1G, substituting the product of Example 6F for the product of Example 1F. $^1$H NMR (300 MHz, CDCl$_3$): δ 17.78 (m, 1 H), 12.70, 12.56 (s, 1 H), 8.39 (m, 1 H), 8.24 (m, 1 H), 8.09 (m, 1 H), 7.64 (m, 2 H), 7.46 (m, 2 H), 7.31 (m, 1 H), 5.72, 5.53 (s, 1 H), 2.31 (m, 2 H), 1.90 (m, 2 H), 1.33 (m, 4 H), 0.82 (m, 14 H), 0.49 (m, 2 H).

EXAMPLE 6H 3-(1,1-dioxido-4H-1,2,4-benzothiadiazin-3-yl)-4-hydroxy-1,1-diisopentyl-2(1 H)-naphthalenone The title compound was prepared according to the procedure of Example 4H, substituting the product of Example 6G for the product of Example 4G. $^1$H NMR (300 MHz, CDCl$_3$): δ 16.69 (d, J=12.13 Hz, 1 H), 14.39, 14.25 (s, 1 H), 8.28 (d, J=8.09 Hz, 1 H), 7.99 (d, J=8.09 Hz, 1 H), 7.67 (m, 2 H), 7.48 (q, J=7.72 Hz, 2 H), 7.31 (m, 2 H), 2.29 (m, 2 H), 1.93 (m, 2 H), 1.32 (m, 2 H), 0.82 (m, 14 H), 0.44 (m, 2 H).

EXAMPLE 6I

Sodium 2-(1,1-dioxido-4H-1,2,4-benzothiadiazin-3-yl)-4,4-diisopentyl-3-oxo-3,4-dihydro-1-naphthalenolate The title compound was prepared according to the procedure of Example 1I, substituting the product of Example 6H for the product of 1H. $^1$H NMR (300 MHz, DMSO-d$_6$): δ 15.59 (s, 1 H), 8.05 (d, J=7.72 Hz, 1 H), 7.64 (d, J=7.72 Hz, 1 H), 7.49 (m, 3 H), 7.29 (m, 3 H), 2.13 (m, 2 H), 1.71 (m, 2 H), 1.24 (m, 2 H), 0.75 (m, 14 H), 0.38 (m, 2 H).

EXAMPLE 7

4-hydroxy-3-(7-hydroxy-1,1-dioxido-4H-1,2,4-benzothiadiazin-3-yl)-1,1-diisopentyl-2(1 H)-naphthalenone

EXAMPLE 7A

N-[2-(aminosulfonyl)-4-(benzyloxy)phenyl]-1-hydroxy-4,4-diisopentyl-3-oxo-3,4-dihydro-2-naphthalenecarboxamide The title compound was prepared according to the procedure of Example 2E, substituting the product of Example 6F for the product of Example 1F. $^1$H NMR (300 MHz, CDCl$_3$): δ 17.86 (m, 1 H), 12.52, 12.38 (s, 1 H), 8.33 (dd, J=8.27, 1.65 Hz, 1 H), 8.23 (m, 1H), 8.01 (d, J=8.82 Hz, 1 H), 7.66 (m, 2 H), 7.35 (m, 7 H), 5.57, 5.40 (s, 1 H), 5.12 (s, 3 H), 2.33 (m, 2 H), 1.90 (m, 2 H), 1.33 (m, 2 H), 0.80 (m, 14 H), 0.50 (m, 2 H).

EXAMPLE 7B

3-[7-(benzyloxy)-1,1-dioxido-4H-1,2,4-benzothiadiazin-3-yl]-4-hydroxy-1,1-diisopentyl-2(1 H)-naphthalenone The title compound was prepared according to the procedure of Example 2F, substituting the product of Example 7A for the product of Example 2E. $^1$H NMR (300 MHz, CDCl$_3$): δ 16.62 (m, 1 H), 14.33, 14.19 (s, 1 H), 8.27 (d, J=8.09 Hz, 1 H), 7.67 (m, 1 H), 7.42 (m, 10 H), 5.14 (s, 2 H), 2.31 (m, 2 H), 1.93 (m, 2 H), 1.34 (m, 2 H), 0.82 (m, 14 H), 0.45 (m, 2 H).

EXAMPLE 7C 4-hydroxy-3-(7-hydroxy-1,1-dioxido-4H-1,2,4-benzothiadiazin-3-yl)-1,1-diisopentyl-2(1H)-naphthalenone The title compound was prepared by the procedure of Example 2G, substituting the product of Example 7B for the product of Example 2F. $^1$H NMR (300 MHz, DMSO-$d_6$): δ 13.69 (s, 1 H), 10.42 (s, 1 H), 8.17 (d, J=7.72 Hz, 1 H), 7.77 (m, 1 H), 7.56 (m, 3 H), 7.19 (m, 2 H), 2.12 (m, 4 H), 1.29 (m, 2 H), 0.75 (m, 14 H), 0.38 (m, 2 H).

EXAMPLE 8

2-{[3-(1-hydroxy-4,4-diisopentyl-3-oxo-3,4-dihydro-2-naphthalenyl)-1,1-dioxido-4H-1,2,4-benzothiadiazin-7-yl]oxy}acetamide

EXAMPLE 8A

2-{[3-(1-hydroxy-4,4-diisopentyl-3-oxo-3,4-dihydro-2-naphthalenyl)-1,1-dioxido-4H-1,2,4-benzothiadiazin-7-yl]oxy}acetamide The title compound was prepared according to the procedure of Example 5F, substituting the product of Example 7C for the product of Example 5E. $^1$H NMR (300 MHz, DMSO-$d_6$): δ 13.71 (s, 1 H), 8.17 (d, J=7.72 Hz, 1 H), 7.75 (m, 3 H), 7.55 (m, 1 H), 7.41 (m, 2 H), 4.60 (s, 2 H), 2.18 (m, 4 H), 1.26 (m, 2 H), 0.76 (m, 14 H), 0.37 (m, 2 H).

EXAMPLE 8B

Sodium 2-[7-(2-amino-2-oxoethoxy)-1,1-dioxido-4H-1,2,4-benzothiadiazin-3-yl]-4,4-diisopentyl-3-oxo-3,4-dihydro-1-naphthalenolate The title compound was prepared according to the procedure of Example 1I, substituting the product of Example 8A for the product of Example 1H. $^1$H NMR (300 MHz, DMSO-$d_6$): δ 15.53 (s, 1 H), 8.04 (d, J=7.72 Hz, 1 H), 7.63 (s, 1 H), 7.45 (m, 2 H), 7.31 (m, 2H), 7.17 (m, 2 H), 4.49 (s, 2 H), 2.12 (m, 2 H), 1.70 (m, 2 H), 1.23 (m, 2 H), 0.72 (m, 14 H), 0.38 (m, 2 H).

EXAMPLE 9

3-(1,1-dioxido-4H-1,2,4-benzothiadiazin-3-yl)-4-hydroxy-1,1-dimethyl-2(1H)-naphthalenone

EXAMPLE 9A

Methyl 2-methyl-2-phenylpropanoate

A solution of methyl 2-phenylacetate (10.0 g, 66.7 mmol) and methyl iodide (10.4 mL, 167 mmol) in tetrahydrofuran (67 mL) at 0° C. was treated portionwise with sodium hydride (5.9 g of 60% in oil, 147 mmol), warmed to 25° C., stirred at 25° C. for 18 hours, cooled to 0° C. and quenched by addition of glatial acetic acid (2 mL). The mixture was concentrated in vacuo. A solution of the residue in ethyl acetate was washed with water, saturated sodium bicarbonate solution (2×) and saturated sodium chloride solution, dried ($Na_2SO_4$), filtered and concentrated in vacuo to afforded an oil which was distilled (70-75° C./0.3 mm Hg) to afford the title compound (10 g, 85%). $^1$H NMR (300 MHz, CDCl$_3$): δ 7.27 (m, 5 H), 3.65 (s, 3 H), 1.60 (m, 6 H).

EXAMPLE 9B 2-methyl-2-phenylpropanoic Acid

The title compound was prepared according to the procedure of Example 1C, substituting the product of Example 9A for the product of Example 1B. $^1$H NMR (300 MHz, CDCl$_3$): δ 7.33 (m, 5 H), 1.60 (s, 6 H).

EXAMPLE 9C 2-methyl-2-phenylpropanoyl Chloride

The title compound was prepared according to the procedure of Example 1D, substituting the product of Example 9B for the product of Example 1C.

EXAMPLE 9D diethyl 2-(2-methyl-2-phenylpropanoyl)malonate

The title compound was prepared according to the procedure of Example 1E, substituting the product of Example 9C for the product of Example 1D. $^1$H NMR (300 MHz, CDCl$_3$): δ 7.32 (m, 5 H), 4.53 (s, 1 H), 4.10 (q, J=6.99 Hz, 4 H), 1.58 (m, 6 H), 1.20 (t, J=7.23 Hz, 6 H).

EXAMPLE 9E

Ethyl 1-hydroxy-4,4-dimethyl-3-oxo-3,4-dihydro-2-naphthalenecarboxylate

The title compound was prepared according to the procedure of Example 1F, substituting the product of Example 9D for the product of Example 1E. $^1$H NMR (300 MHz, CDCl$_3$): δ 15.16, 15.03 (two s, 1 H), 8.18 (m, 1 H), 7.52 (m, 3 H), 4.47 (m, 2 H), 1.66 (s, 3H), 1.51 (s, 3 H), 1.45 (t, J=6.62 Hz, 3 H).

EXAMPLE 9F 4-hydroxy-1,1-dimethyl-2(1H)-naphthalenone

A solution of the product of Example 9E (2.25 g, 8.65 mmol) in dioxane (50 mL) was treated with 1 N HCl solution (60 mL) and the mixture was stirred at reflux for 6 hours, cooled to 25° C., diluted with ethyl acetate and water. The organic layer was washed with water (2×) and saturated sodium chloride solution (1×), dried($Na_2SO_4$), filtered and concentrated in vacuo. The residue was triturated with ether and filtered.

The solid was washed with 1:1 ether-hexane and dried to give the title compound (1.0 g, 61%). $^1$H NMR (300 MHz, DMSO-$d_6$): δ 11.79, 11.59 (two s, 1 H), 7.91 (m, 1 H), 7.58 (m, 2H), 7.38 (m, 1 H), 5.63 (s, 1 H), 1.48 (s, 3 H), 1.38 (s, 3 H).

EXAMPLE 9G

2-[bis(methylsulfanyl)methylene]-4,4-dimethyl-1,3(2H,4H)-naphthalenedione

A solution of the product of Example 9F (200 mg, 1.1 mmol) in N,N-dimethylformamide (8 mL) at 25° C. was treated with sodium hydride (60% mineral dispersion, 94 mg, 2.2 mmol), stirred at 25° C. for 10 min, treated with carbon disulfide (178 mg, 2.2 mmol), stirred at 25° C. for 1.5 hours, followed by addition of methyl iodide (145 μL, 2.2 mmol), stirred for 30 min and concentrated in vacuo. The residue was triturated with pH 7 buffer, and extracted twice with ethyl acetate. The combined organic layers were washed with saturated sodium chloride solution, dried (Na$_2$SO$_4$), filtered and concentrated in vacuo to give the title compound (450 mg). $^1$H NMR (300 MHz, CDCl$_3$): δ 8.20 (dd, J=7.72, 1.47 Hz, 1 H), 7.49 (m, 3 H), 2.57 (s, 6 H), 1.56 (s, 6 H).

EXAMPLE 9H 3-(1,1-dioxido-4H-1,2,4-benzothiadiazin-3-yl)-4-hydroxy-1,1-dimethyl-2(1 H)-naphthalenone A solution of the product of Example 9G (450 mg) and 2-aminobenzenesulfonamide (180 mg, 1.05 mmol) in toluene (10 mL) was stirred at 100° C. for 2.5 hours, cooled to 25° C. and filtered. The filtrate was concentrated in vacuo, and the residue was chromatographed eluting with dichloromethane to give the title compound (57 mg, 15%). $^1$H NMR (300 MHz, CDCl$_3$): δ 16.77, 16.61 (two s, 1 H), 14.36, 13.98 (two s, 1 H), 8.27 (m, 2 H), 7.99 (d, J=8.09 Hz, 2 H), 7.57 (m, 2 H), 7.31 (m, 2 H), 1.71 (s, 3 H), 1.56 (s, 3 H).

EXAMPLE 9I

Sodium 2-(1,1-dioxido-4H-1,2,4-benzothiadiazin-3-yl)-4,4-dimethyl-3-oxo-3,4-dihydro-1-naphthalenolate The title compound was prepared according to the procedure of Example 1I, substituting the product of Example 9H for the product of Example 1H. $^1$H NMR (300 MHz, DMSO-d$_6$): δ 14.42 (s, 1 H), 8.11 (d, J=7.72 Hz, 1 H), 7.80 (d, J=7.35 Hz, 1 H), 7.65 (m, 3H), 7.46 (m, 3 H), 1.46 (m, 6 H).

EXAMPLE 10

1,1-dibutyl-4-hydroxy-3-{7-[(methoxymethoxy)methyl]-1,1-dioxido-4H-thieno[2,3-e][1,2,4]thiadiazin-3-yl}-2(1 H)-naphthalenone

EXAMPLE 10A

Methyl 4-(benzylsulfanyl)-5-nitro-3-thiophenecarboxylate

The title compound was prepared according to the procedure as described in Stanetty, P. et al., *J. Heterocyclic Chem.* 1999, 36, 761-765.

EXAMPLE 10B (4-(benzylsulfanyl)-5-nitro-3-thienyl)methanol

The product of Example 10A (5 g, 16.2 mmol) in dichloromethane (150 mL) at −40° C. was treated dropwise with diisobutylaluminum hydride (1 M in dichloromethane, 36 mL, 36 mmol). The solution was stirred for 15 minutes at −40° C., followed by quenching with 10% aqueous sodium potassium tartrate solution and stirred at 25° C. for 1 h. The organic layer was separated, filtered through Celite® and the filtrate concentrated in vacuo. The resulting oil was chromatographed on silica gel eluting with methanol in dichloromethane to give the title compound (4.32 g, 95%). $^1$H NMR (300 MHz, CDCl$_3$): δ 7.40 (s, 1 H), 7.23 (m, 2 H), 7.11 (m, 3 H), 4.39 (s, 2 H), 4.21 (s, 2 H).

EXAMPLE 10C 3-(benzylsulfanyl)-4-[(methoxymethoxy)methyl]-2-nitrothiophene

A mixture of the product of Example 10B (3.9 g, 13.9 mmol) and diisopropylethylamine (7.42 mL, 43 mmol) in dichloromethane (8 mL) was treated with methoxymethyl chloride (2.38 mL, 32 mmol), stirred at 25° C. for 16 hours. The mixture was concentrated in vacuo and the residue was chromatographed on silica gel, eluting with dichloromethane to give the title compound (4.32 g, 94%). $^1$H NMR (300 MHz, CDCl$_3$): δ 7.40 (s, 1 H), 7.21 (m, 2 H), 7.13 (m, 3 H), 4.62 (s, 2 H), 4.34 (s, 2 H), 4.20 (s, 2 H), 3.36 (s, 3 H).

EXAMPLE 10D

4-[(methoxymethoxy)methyl]-2-nitro-3-thiophenesulfonamide

A solution of the product of Example 10C (4 g, 12.3 mmol) in dichloromethane (70 mL) and 1 N hydrochloric acid (35 mL) at 0° C. was treated with chlorine gas over a period of 0.5 hour, stirred at 0° C. for 1 h. The mixture was purged with nitrogen gas to remove excess chlorine and treated slowly with solid sodium bisulfite (11 g) over 5 minutes and diluted with dichloromethane and water. The organic layer was separated and eluted through 40 g of a 1:1 mixture of MgSO$_4$/Na$_2$SO$_4$. The filtrate was concentrated in vacuo. A solution of the residue in dichloromethane (100 mL) at −40° C. was treated with ammonia gas over a period of 10 min, stirred for an additional 15 min, purged with nitrogen gas to expel the excess ammonia and concentrated in vacuo. The residue was chromatographed on silica gel, eluting with methanol in dichloromethane to give the title compound (2.3 g, 66%). $^1$H NMR (300 MHz, CDCl$_3$): δ 7.88 (s, 1 H), 7.85 (m, 2 H), 4.73 (s, 2 H), 4.70 (s, 2 H), 3.31 (m, 3 H).

EXAMPLE 10E 2-amino-4-[(methoxymethoxy)methyl]-3-thiophenesulfonamide

A solution of the product of Example 10D (1.8 g, 6.4 mmol) in acetic acid (70 mL) was treated with iron powder (1.43 g, 25.5 mmol), stirred at 50° C. for 7.5 h and concentrated. A mixture of the residue in 5% methanol in dichloromethane (60 mL) and water (6 mL) was filtered through silica gel (20 g), and rinsed with 5% methanol in dichloromethane (300 mL). The filtrate was concentrated in vacuo and the residue was chromatographed on silica gel, eluting with methanol in dichloromethane to give the title compound (1 g, 62%). $^1$H NMR (300 MHz, DMSO-d$_6$): δ 6.94 (s, 2 H), 6.61 (s, 2 H), 6.28 (s, 1 H), 4.66 (s, 2 H), 4.53 (s, 2 H), 3.30 (s, 3 H).

EXAMPLE 10F 1,1-dibutyl-4-hydroxy-3-{7-[(methoxymethoxy)methyl]-1,1-dioxido-4H-thieno[2,3-e][1,2,4]thiadiazin-3-yl}-2(1 H)-naphthalenone A mixture of the product of Example 5C (66 mg, 0.18 mmol) and the product of Example 10E (44 mg, 0.18 mmol)

in toluene (10 mL) was stirred at reflux for 2 h, cooled to 25° C. and concentration in vacuo. The residue was chromatographed on silica gel, eluting with ethyl acetate in hexane to give the title compound (54 mg, 58%). $^1$H NMR (300 MHz, CDCl$_3$): δ 16.44 (s, 1 H), 15.03, 14.86 (two s, 1 H), 8.27 (m, 1 H), 7.69 (m, 1 H), 7.49 (t, J=7.17 Hz, 1 H), 7.26 (m, 1 H), 7.08 (s, 1 H), 4.84 (s, 2 H), 4.80 (s, 2 H), 3.45 (s, 3 H), 2.33 (m, 2 H), 1.95 (m, 2 H), 1.13 (m, 4 H), 0.86 (m, 2 H), 0.69 (m, 6 H), 0.56 (m, 2 H).

EXAMPLE 10G

Sodium 4,4-dibutyl-2-{7-[(methoxymethoxy)methyl]-1,1-dioxido-4H-thieno[2,3-e][1,2,4]thiadiazin-3-yl}-3-oxo-3,4-dihydro-1-naphthalenolate The title compound was prepared according to the procedure of Example 1I, substituting the product of Example 10F for the product of Example 1H. $^1$H NMR (300 MHz, DMSO-d$_6$): δ 16.86 (s, 1 H), 8.04 (d, J=7.72 Hz, 1 H), 7.48 (m, 2 H), 7.32 (m, 1 H), 7.05 (s, 1H), 4.72 (s, 2 H), 4.61 (s, 2 H), 3.33 (m, 3 H), 2.10 (m, 2 H), 1.70 (m, 2 H), 1.03 (m, 4 H), 0.83 (m, 2 H), 0.65 (t, J=7.35 Hz, 6 H), 0.49 (m, 2 H).

EXAMPLE 11

1,1-dibutyl-4-hydroxy-3-[7-(hydroxymethyl)-1,1-dioxido-4H-thieno[2,3-e][1,2,4]thiadiazin-3-yl]-2(1 H)-naphthalenone A solution of the product of Example 10F (27 mg, 0.051 mmol) in 4.0 N HCl in dioxane (4 mL) was stirred at 25° C. for 18 hours and concentrated in vacuo. A suspension of the residue in acetonitrile (2 mL) was treated with 1.0 N sodium hydroxide solution (51 μL, 0.051 mmol) and stirred at 25° C. for 1 h. The solution was lyophilized to afford the title compound (28 mg, 100%). $^1$H NMR (300 MHz, DMSO-d$_6$): δ 16.82 (m, 1 H), 8.04 (d, J=7.35 Hz, 1 H), 7.47 (m, 2 H), 7.32 (t, J=7.35 Hz, 1 H), 6.95 (s, 1 H), 5.32 (t, J=5.70 Hz, 1H), 4.61 (m, 2 H), 2.09 (m, 2 H), 1.70 (m, 2 H), 1.02 (m, 4 H), 0.84 (m, 2 H), 0.67 (m, 6 H), 0.49 (s, 2 H).

EXAMPLE 12

N-[3-(4,4-dibutyl-1-hydroxy-3-oxo-3,4-dihydro-2-naphthalenyl)-1,1-dioxido-4H-1,2,4-benzothiadiazin-7-yl]methanesulfonamide

EXAMPLE 12A 2-amino-4-[(methylsulfonyl)amino]-3-thiophenesulfonamide 2,5-Diamino-benzenesulfonamide (288 mg, 1.5 mol, prepared according to the procedure as described in Goldfarb A. R. et. al., *J. Amer. Chem. Soc.* 1943, 65, 738) in dichloromethane (5 mL) and pyridine (5 mL) at 0° C. was treated dropwise with methanesulfonyl chloride (119 μL, 1.5 mmol) over 3 minutes. The reaction mixture was warmed to 25° C. and stirred for 18 hours and concentrated under reduced pressure. The residue was chromatographed on silica gel, eluting with methanol in dichloromethane to yield the title compound (68% yield). $^1$H NMR (300 MHz, DMSO-d$_6$): δ 9.21 (m, 1 H), 7.45 (d, J=2.57 Hz, 1 H), 7.29 (s, 2 H), 7.13 (dd, J=8.64, 2.39 Hz, 1 H), 6.78 (d, J=8.82 Hz, 1 H), 5.80 (s, 1 H), 3.39 (s, 1 H), 2.87 (s, 3 H).

EXAMPLE 12B

N-[3-(4,4-dibutyl-1-hydroxy-3-oxo-3,4-dihydro-2-naphthalenyl)-1,1-dioxido-4H-1,2,4-benzothiadiazin-7-yl]methanesulfonamide The title compound was prepared by the procedure of Example 5D, substituting the product of Example 12A for the product of Example 2D. $^1$H NMR (300 MHz, DMSO-d$_6$): δ 13.72 (s, 1 H), 10.27 (s, 1 H), 8.17 (d, J=7.72 Hz, 1 H), 7.77 (m, 3 H), 7.58 (m, 3 H), 3.09 (s, 3 H), 2.18 (m, 2 H), 2.04 (m, 2 H), 1.08 (m, 4 H), 0.88 (m, 2 H), 0.69 (m, 6 H), 0.49 (m, 2 H).

EXAMPLE 12C

Sodium 4,4-dibutyl-2-{7-[(methylsulfonyl)amino]-1,1-dioxido-4H-1,2,4-benzothiadiazin-3-yl}-3-oxo-3,4-dihydro-1-naphthalenolate A suspension of the compound of Example 12B (45 mg, 0.082 mmol) in acetonitrile (2 mL) was treated with 1.0 N NaOH solution (82 μL, 0.082 mmol) followed by stirring at 25° C. for 30 min. The solution was lyophilized to afford the title compound (46 mg, 98%). $^1$H NMR (300 MHz, DMSO-d$_6$): δ 15.61 (s, 1 H), 9.87 (s, 1 H), 8.05 (d, J=7.72 Hz, 1 H), 7.38 (m, 6 H), 2.98 (s, 3 H), 2.11 (m, 2 H), 1.69 (m, 2 H), 1.02 (m, 4 H), 0.87 (m, 2 H), 0.65 (t, J=7.35 Hz, 6 H), 0.52 (d, J=5.52 Hz, 2 H).

EXAMPLE 13

Sodium 4,4-bis(3-methylbutyl)-2-{7-[(methylsulfonyl)amino]-1,1-dioxido-4H-1,2,4-benzothiadiazin-3-yl}-3-oxo-3,4-dihydronaphthalen-1-olate

EXAMPLE 13A 4-hydroxy-1,1-bis(3-methylbutyl)naphthalen-2(1 H)-one

The title compound was prepared according the procedure of Example 5B, substituting the product of Example 6F for the product of Example 4F. $^1$H NMR (300 MHz, CDCl$_3$): δ 0.44 (m, 2 H) 0.73 (m, 14 H) 1.32 (m, 2 H) 1.94 (m, 2 H) 2.30 (m, 2 H) 7.49 (t, J=7.54 Hz, 2 H) 7.72 (m, 1 H) 8.26 (m, 1 H) 15.77, 15.72 (two s, 1 H).

EXAMPLE 13B

2-[bis(methylthio)methylene]-4,4-bis(3-methylbutyl)naphthalene-1,3(2H,4 H)-dione The title compound was prepared according to the procedure of Example 5C, substituting the compound of Example 13A for the product of Example 5B. $^1$H NMR (300 MHz, CDCl$_3$): δ 0.74 (m, 16 H) 1.32 (m, 2 H) 1.78 (m, 2 H) 2.27 (m, 2 H) 2.56 (s, 6 H) 7.39 (t, J=9.01 Hz, 2 H) 7.58 (t, J=7.54 Hz, 1 H) 8.25 (d, J=8.09 Hz, 1 H).

EXAMPLE 13C

N-{3-[1-hydroxy-4,4-bis(3-methylbutyl)-3-oxo-3,4-dihydronaphthalen-2-yl]-1,1-dioxido-4H-1,2,4-benzothiadiazin-7-yl}methanesulfonamide The title compound was prepared following the procedure of Example 5D, substituting the product of Example 13B for the product of Example 5C, and substituting the compound of Example 12A for the product of Example 2D. $^1$H NMR (300 MHz, DMSO-$d_6$): δ 0.34 (m, 2 H) 0.70 (m, 14 H) 1.25 (m, 2 H) 2.14 (m, 4 H) 3.03 (s, 3 H) 7.52 (m, 3 H) 7.72 (m, 3 H) 8.12 (d, J=7.72 Hz, 1 H) 10.21 (s, 1 H) 13.70 (s, 1 H).

EXAMPLE 13D

Sodium 4,4-bis(3-methylbutyl)-2-{7-[(methylsulfonyl)amino]-1,1-dioxido-4H-1,2,4-benzothiadiazin-3-yl}-3-oxo-3,4-dihydronaphthalen-1-olate The title compound was prepared following the procedure of Example 1 I, substituting the product of Example 13C for the product of Example 1H. $^1$H NMR (300 MHz. (DMSO-$d_6$): δ 0.40 (m, 2 H) 0.73 (m, 14 H) 1.27 (m, 2 H) 1.80 (s, 2 H) 2.12 (m, 2 H) 3.01 (s, 3 H) 7.47 (m, 6 H) 8.07 (d, J=7.72 Hz, 1 H) 9.97 (s, 1 H), 15.26 (br s, 1 H).

EXAMPLE 14

Sodium 2-(1,1-dioxido-4H-1,2,4-benzothiadiazin-3-yl)-7-fluoro-3-oxo-4,4-dipropyl-3,4-dihydronaphthalen-1-olate

EXAMPLE 14A

Methyl (4-fluorophenyl)acetate

A solution of 2-(4-fluorophenyl)acetic acid (15.4 g, 0.1 mol) in methanol (600 mL) was treated with a solution of hydrogen chloride in dioxane (4 N, 100 mL) followed by warming at reflux for 18 h. The solution was cooled and concentrated in vacuo. The residue was distilled under reduced pressure (55-58° C./0.5 mm Hg) to afford the title compound as colorless oil (13.6 g, 81%). $^1$H NMR (300 MHz, CDCl$_3$): δ 3.60 (s, 2 H) 3.70 (s, 3 H) 7.02 (m, 2 H) 7.24 (m, 2 H).

EXAMPLE 14B

Methyl 2-allyl-2-(4-fluorophenyl)pent-4-enoate

The title compound was prepared according to the procedure of Example 1A, substituting the compound of Example 14A for methyl 2-phenylacetate. $^1$H NMR (300 MHz, CDCl$_3$): δ 2.76 (m, 4 H) 3.70 (m, 3 H) 5.06 (dd, J=13.60, 1.84 Hz, 4 H) 5.51 (m, 2 H) 7.02 (m, 2 H) 7.23 (m, 2 H).

EXAMPLE 14C

Methyl 2-(4-fluorophenyl)-2-propylpentanoate

The title compound was prepared according to the procedure of Example 1B, substituting the compound of Example 14B for the compound of Example 1A. $^1$H NMR (300 MHz, CDCl$_3$): δ 0.89 (t, J=6.99 Hz, 6 H) 1.07 (m, 4 H) 1.95 (m, 4 H) 3.63 (s, 3 H) 6.99 (t, J=8.64 Hz, 2 H) 7.22 (m, 2 H).

EXAMPLE 14D 2-(4-fluorophenyl)-2-propylpentanoic Acid

The title compound was prepared according to the procedure of Example 1C, substituting the compound of Example 14C for the compound of Example 1B. $^1$H NMR (300 MHz, CDCl$_3$): δ 0.90 (t, J=7.17 Hz, 6 H) 1.14 (m, 4 H) 1.97 (m, 4 H) 7.01 (m, 2 H) 7.29 (m, 2 H).

EXAMPLE 14E 2-(4-fluorophenyl)-2-propylpentanoyl Chloride

The title compound was prepared according to the procedure of Example 1D, substituting the compound of Example 14D for the compound of Example 1C. The compound was used directly in the next procedure.

EXAMPLE 14F

Diethyl 2-[2-(4-fluorophenyl)-2-propylpentanoyl]malonate

The title compound was prepared according to the procedure of Example 1E, substituting the compound of Example 14E for the compound of Example 1D. $^1$H NMR (300 MHz, CDCL$_3$): δ 0.88 (m, 6 H) 1.03 (m, 4 H) 1.17 (m, 6 H) 1.94 (m, 4 H) 4.06 (q, J=6.99 Hz, 4 H) 4.49 (s, 1 H) 7.03 (t, J=8.82 Hz, 2 H) 7.26 (m, 2 H).

EXAMPLE 14G 6-fluoro-4-hydroxy-1,1-dipropylnaphthalen-2(1H)-one

The compound of Example 14F (6.0 g, 15.75 mmol) was dissolved in methanesulfonic acid (35 mL) and warmed at 50° C. for 5 h. The mixture was cooled and added to a mixture of ice and dichloromethane, followed by stirring until all ice had melted. The layers were separated and the aqueous phase was extracted again with dichloromethane. The combined organic layers were dried (Na$_2$SO$_4$) and concentrated in vacuo to afford an amber oil, which was dissolved in tetrahydrofuran (60 mL) and warmed at reflux with 1 N HCl solution (50 mL) for 18 h. The mixture was cooled and diluted with water and extracted with ethyl acetate. The organic layer was extracted with water and saturated NaCl solution. Drying (Na$_2$SO$_4$) and concentration in vacuo afforded a brown solid, which was triturated with ether-hexane and collected by filtration. These procedures afforded the title compound (2.89 g, 70%) as an off-white solid. $^1$H NMR (300 MHz, DMSO-$d_6$): δ 0.51 (m, 2 H) 0.64 (m, 6 H) 0.84 (m, 2 H) 1.84 (m, 2 H) 1.99 (m, 2 H) 5.80 (s, 1 H) 7.43 (m, 1 H) 7.57 (dd, J=9.56, 2.57 Hz, 1 H) 7.67 (d, J=5.52 Hz, 1 H) 11.75 (s, 1 H).

EXAMPLE 14H

2-[bis(methylthio)methylene]-7-fluoro-4,4-dipropyl-naphthalene-1,3(2H,4H)-dione

The title compound was prepared according to the procedure of Example 5C, substituting the compound of Example 14G for the compound of Example 5B. $^1$H NMR (300 MHz, CDCl$_3$): δ 0.74 (m, 8 H) 0.88 (m, 2 H) 1.70 (m, 2 H) 2.24 (m, 2 H) 2.57 (s, 6 H) 7.27 (m, 1 H) 7.37 (m, 1 H) 7.90 (dd, J=9.56, 2.94 Hz, 1 H).

EXAMPLE 14I 3-(1,1-dioxido-4H-1,2,4-benzothiadiazin-3-yl)-6-fluoro-4-hydroxy-1,1-dipropylnaphthalen-2(1H)-one The title compound was prepared according to the procedure of Example 5D, substituting the compound of Example 14H for the compound of Example 5C, and also substituting 2-aminobenzenesulfonamide for the compound of Example 2D. $^1$H NMR (300 MHz, DMSO-$d_6$): δ 0.58 (m, 2 H) 0.67 (m, 6 H) 0.93 (m, 2 H) 2.01 (m, 2 H) 2.17 (m, 2 H) 7.72 (m, 7 H) 13.48 (s, 1-H).

EXAMPLE 14J

Sodium 2-(1,1-dioxido-4H-1,2,4-benzothiadiazin-3-yl)-7-fluoro-3-oxo-4,4-dipropyl-3,4-dihydronaphthalen-1-olate The title compound was prepared according to the procedure of Example 1I, substituting the compound of Example 14I for the compound of Example 1H. $^1$H NMR (300 MHz, DMSO-$d_6$): δ 0.60 (m, 8 H) 0.87 (m, 2 H) 1.66 (m, 2 H) 2.09 (m, 2 H) 7.30 (m, 3 H) 7.53 (m, 2 H) 7.69 (m, 2 H) 15.27 (s, 1 H).

EXAMPLE 15

6-fluoro-4-hydroxy-3-(7-hydroxy-1,1-dioxido-4H-1,2,4-benzothiadiazin-3-yl)-1,1-dipropylnaphthalen-2(1H)-one

EXAMPLE 15A

3-[7-(benzyloxy)-1,1-dioxido-4H-1,2,4-benzothiadiazin-3-yl]-6-fluoro-4-hydroxy 1,1-dipropylnaphthalen-2(1H)-one The title compound was prepared according to the procedure of Example 5D, substituting the compound of Example 14H for the compound of Example 5C. $^1$H NMR (300 MHz, DMSO-$d_6$): δ 0.64 (m, 8 H) 0.91 (d, J=11.40 Hz, 2 H) 2.03 (m, 2 H) 2.17 (m, 2 H) 5.25 (s, 2 H) 7.40 (m, 7 H) 7.63 (m, 2 H) 7.82 (m, 2 H) 13.49 (s, 1 H).

EXAMPLE 15B 6-fluoro-4-hydroxy-3-(7-hydroxy-1,1-dioxido-4H-1,2,4-benzothiadiazin-3-yl)-1,1-dipropylnaphthalen-2(1H)-one The title compound was prepared according to the procedure of Example 2G, substituting the compound of Example 15A for the compound of Example 2F. $^1$H NMR (300 MHz, DMSO-$d_6$): δ 0.57 (m, 2 H) 0.68 (m, 6 H) 0.89 (m, 2 H) 2.01 (dd, J=12.13, 8.82 Hz, 2H) 2.17 (m, 2 H) 7.18 (m, 2 H) 7.62 (m, 2 H) 7.83 (m, 2 H) 10.41 (s, 1 H) 13.46 (s, 1 H).

EXAMPLE 16

Sodium 2-[7-(2-amino-2-oxoethoxy)-1,1-dioxido-4H-1,2,4-benzothiadiazin-3-yl]-7-fluoro-3-oxo-4,4-dipropyl-3,4-dihydronaphthalen-1-olate The title compound was prepared according to the procedure of Example 3, substituting the compound of Example 15B for the compound of Example 2G. $^1$H NMR (300 MHz, DMSO-$d_6$): δ 0.63 (m, 8 H) 0.89 (m, 2 H) 1.98 (m, 2 H) 2.16 (m, 2 H) 4.58 (s, 2 H) 7.38 (m, 3 H) 7.61 (m, 3 H) 7.81 (m, 1 H) 13.60 (s, 1 H).

EXAMPLE 17

Sodium 2-{7-[(aminosulfonyl)amino]-1,1-dioxido-4H-1,2,4-benzothiadiazin-3-yl}-7-fluoro-3-oxo-4,4-dipropyl-3,4-dihydronaphthalen-1-olate

EXAMPLE 17A tert-butyl 4-amino-3-(aminosulfonyl)phenylcarbamate

Method A:

A mixture of 2,5-diaminobenzenesulfonamide (prepared according to the procedure as described in Goldfarb A. R. et. al., J. Amer. Chem. Soc. 1943, 65, 738) (0.168 g, 0.896 mmol) and di-tert-butyl dicarbonate (0.196 g, 0.896 mmol) in tetrahydrofuran (10 mL) was stirred at rt for 16 h. The solvent was then evaporated under reduced pressure and the residue purified by chromatography on silica gel, eluting with 3:2 hexane/ethyl acetate, to provide the title compound (0.202 g, 78% yield) as a beige powder. $^1$H NMR (300 MHz, DMSO-$d_6$) δ 1.45 (s, 9 H) 5.53 (s, 2 H) 6.70 (d, J=8.46 Hz, 1 H) 7.20 (m, 3 H) 7.77 (s, 1 H) 9.06 (s, 1 H).

Method B:

EXAMPLE 17A-1

2-chloro-5-nitrobenzenesulfonamide

To a solution of thionyl chloride (240 mL) and 2-chloro-5-nitro-benzenesulfonic acid (104 g, 437.6 mmol) was added N,N-dimethylformamide (2 mL) and the reaction mixture was heated up to reflux for 4 hours. The reaction mixture was then carefully quenched into water and the product was isolated by filtration. The sulfonyl chloride 2 was then dissolved in toluene and added to a mixture of NH$_4$OH (520 mL) and tetrahydrofuran (520 mL) at −10° C. After mixing for 1 h, the reaction was quenched by addition of 6 M HCl to a final pH of 4. The layers were separated and the organic layer was concentrated to a slush. Pentane was added and the product was isolated by filtration and dried to give the title compound (82.6 g, 80%).

EXAMPLE 17A-2

2-amino-5-nitrobenzenesulfonamide

A mixture of the product of Example 17A-1 (95 g, 401.5 mmol), ammonium carbonate (95 g, MW=96.07, 988.9 mmol), and CuSO$_4$ (18.91 g, MW=159.60, 118.5 mmol) in conc. aq. NH$_4$OH solution (475 mL) was heated for four hours at 120° C. in a pressure reaction vessel. The mixture was then cooled to room temperature and the resulting solid was collected by filtration, washed with water and dried to give the title compound (66.3 g, 76% yield).

EXAMPLE 17A-3

2,5-diaminobenzenesulfonamide

A mixture of the product of Example 17A-2 (50 g, 230 mmol), Ra—Ni (50 g), in THF (800 mL) and methanol (800 mL) was stirred at rt for 2 hours under H$_2$ pressure (40 psi). The mixture was then filtered and concentrated under reduced pressure to a smaller volume (about 80 mL). The solid was collected and washed with methyl tert-butyl ether (200 mL) and then dried under a vacuum to give the title compound (38.8 g, 90% yield).

EXAMPLE 17A-4 tert-butyl 4-amino-3-(aminosulfonyl)phenylcarbamate

To a suspension of Example 17A-3 158.9 g, 0.85 mol) in methanol (1120 mL) at 16° C. was added a solution of Boc anhydride (196.48 g, 0.90 mol) in methanol (470 mL). The solution was warmed to RT and mixed for 2 h then the reaction was quenched by addition of N,N-dimethylethylenediamine (14 mL). The solution was concentrated, chased with ethyl acetate then the product was isolated from ethyl acetate/heptane (1/1, 4 volumes) to give the title compound (201.7 g, 82.7%).

EXAMPLE 17B tert-butyl 3-(7-fluoro-1-hydroxy-3-oxo-4,4-dipropyl-3,4-dihydronaphthalen-2-yl)-1,1-dioxido-4H-1,2,4-benzothiadiazin-7-ylcarbamate The title compound was prepared according to the procedure of Example 5D, substituting the compound of Example 14H for the compound of Example 5C, and the compound of Example 17A for the compound of Example 2D. $^1$H NMR (300 MHz, DMSO-d$_6$): δ 0.62 (m, 8 H) 0.91 (m, 2 H) 1.47 (d, J=17.28 Hz, 9 H) 1.93 (m, 2 H) 2.10 (m, 2 H) 7.63 (m, 5 H) 8.03 (s, 1 H) 9.77 (s, 1 H) 14.21 (s, 1 H).

EXAMPLE 17C 3-(7-amino-1,1-dioxido-4H-1,2,4-benzothiadiazin-3-yl)-6-fluoro-4-hydroxy-1,1-dipropylnaphthalen-2(1H)-one The compound of Example 17B (76 mg, 0.14 mmol) was added to trifluoroacetic acid (6 mL) and stirred at ambient temperature for 30 min. The solution was concentrated in vacuo and the residue was stirred with ethyl acetate and saturated sodium bicarbonate solution for 30 min. The organic layer was extracted with saturated NaCl solution, dried (Na$_2$SO$_4$) and concentrated in vacuo to afford the title compound (69 mg, 100%) as a foam. $^1$H NMR (300 MHz, DMSO-d$_6$): δ 0.62 (m, 8 H) 0.86 (dd, J=12.32, 6.43 Hz, 2 H) 2.00 (s, 2H) 2.16 (m, 2 H) 6.96 (m, 2 H) 7.43 (d, J=8.82 Hz, 1 H) 7.63 (m, 1 H) 7.82 (m, 2 H) 13.48 (s, 1 H).

EXAMPLE 17D

Benzyl {[3-(7-fluoro-1-hydroxy-3-oxo-4,4-dipropyl-3,4-dihydronaphthalen-2-yl)-1,1-dioxido-4H-1,2,4-benzothiadiazin-7-yl]amino}sulfonylcarbamate A solution of chlorosulfonyl isocyanate (14.2 μL, 0.163 mmol) in dichloromethane (2 mL) was treated with benzyl alcohol (17 μL, 0.163 mmol) followed by stirring at ambient temperature for 30 min. The solution was added to the product of Example 17C (62 mg, 0.136 mmol) in dichloromethane (2 mL) followed by addition of triethylamine (76 μL, 0.54 mmol). The solution was stirred at ambient temperature for 2 h, and diluted with dichloromethane and extracted with water (2×). Drying (Na$_2$SO$_4$) and concentration in vacuo afforded the title compound (28 mg, 31%) as a brown solid. $^1$H NMR (300 MHz, DMSO-d$_6$): δ 0.69 (m, 8 H) 0.92 (m, 2 H) 2.00 (dd, J=12.13, 8.82 Hz, 2 H) 2.16 (m, 2 H) 5.12 (s, 2 H) 7.35 (m, 5 H) 7.47 (dd, J=8.82, 2.57 Hz, 1 H) 7.63 (m, 3 H) 7.82 (m, 2 H) 11.09 (s, 1 H) 12.13 (s, 1 H) 13.54 (s, 1 H).

EXAMPLE 17E

N-[3-(7-fluoro-1-hydroxy-3-oxo-4,4-dipropyl-3,4-dihydronaphthalen-2-yl)-1,1-dioxido-4H-1,2,4-benzothiadiazin-7-yl]sulfamide A solution of the product of Example 17D (28 mg, 0.042 mmol) in 2:1 methanol-ethyl acetate (15 mL) was treated with 10% Pd/C (20 mg) and hydrogenated at one atmosphere for 18 h. The mixture was filtered through Celite® and the filtrate concentrated in vacuo to afford the title compound (13 mg).

EXAMPLE 17F

Sodium 2-{7-[(aminosulfonyl)amino]-1,1-dioxido-4H-1,2,4-benzothiadiazin-3-yl}-7-fluoro-3-oxo-4,4-dipropyl-3,4-dihydronaphthalen-1-olate A solution of Example 17E (13 mg) was dissolved in acetonitrile (1 mL) and treated with sodium hydroxide solution (1.0 N, 24.3 μL, 0.0243 mmol). After stirring for 30 min, the solution was frozen and lyophilized to afford the title compound as a fluffy grey solid (12.8 mg, 55% overall). $^1$H NMR (300 MHz, DMSO-d$_6$): δ 0.65 (m, 8 H) 0.86 (d, J=2.94 Hz, 2 H) 1.65 (d, J=3.68 Hz, 2 H) 2.05 (m, 2 H) 7.43 (m, 6 H) 9.58 (s, 1 H) 15.21 (s, 1 H).

EXAMPLE 18

Sodium 4,4-dibutyl-2-(1,1-dioxido-4H-1,2,4-benzothiadiazin-3-yl)-7-fluoro-3-oxo-3,4-dihydronaphthalen-1-olate

EXAMPLE 18A

Methyl 2-(but-2-enyl)-2-(4-fluorophenyl)hex-4-enoate

The title compound was prepared according to the procedure of Example 1A, substituting the compound of Example 14A for methyl 2-phenylacetate, and crotyl bromide for allyl bromide. $^1$H NMR (300 MHz, CDCl$_3$): δ 1.54 (m, 6 H) 2.67 (m, 4 H) 3.64 (d, J=2.21 Hz, 3 H) 5.12 (m, 2 H) 5.47 (m, 2 H) 7.01 (m, 2 H) 7.20 (m, 2 H).

EXAMPLE 18B

Methyl 2-butyl-2-(4-fluorophenyl)hexanoate

The title compound was prepared according to the procedure of Example 4B, substituting the compound of Example 18B for the compound of Example 4A. $^1$H NMR (300 MHz, CDCl$_3$): δ 0.87 (t, J=7.35 Hz, 6 H) 1.01 (m, 4 H) 1.29 (m, 4 H) 1.94 (m, 4 H) 3.63 (s, 3H) 6.99 (m, 2 H) 7.22 (m, 2 H).

EXAMPLE 18C 2-butyl-2-(4-fluorophenyl)hexanoic Acid

The title compound was prepared according to the procedure of Example 1C, substituting the compound of Example 18B for the compound of Example 1B. $^1$H NMR (300 MHz, CDCl$_3$): δ 0.87 (t, J=7.17 Hz, 6 H) 1.08 (m, 4 H) 1.31 (m, 4 H) 1.98 (m, 4 H) 7.02 (m, 2 H) 7.29 (m, 2 H).

EXAMPLE 18D 2-butyl-2-(4-fluorophenyl)hexanoyl Chloride

The title compound was prepared according to the procedure of Example 1D, substituting the compound of Example 18C for the compound of Example 1C. The title compound was used directly in the next procedure.

EXAMPLE 18E

Diethyl 2-[2-butyl-2-(4-fluorophenyl)hexanoyl]malonate

The title compound was prepared according to the procedure of Example 1E, substituting the compound of Example 18D for the compound of Example 1D. $^1$H NMR (300 MHz, CDCl$_3$): δ 0.86 (m, 6 H) 1.05 (m, 4 H) 1.15 (m, 6 H) 1.30 (m, 4 H) 1.98 (m, 4 H) 4.04 (m, 4 H) 4.48 (d, J=2.21 Hz, 1 H) 7.04 (m, 2 H) 7.25 (m, 2 H).

EXAMPLE 18F 1,1-dibutyl-6-fluoro-4-hydroxynaphthalen-2(1 H)-one

The title compound was prepared according to the procedure of Example 14G, substituting the compound of Example 18E for the compound of Example 14F. $^1$H NMR (300 MHz, CDCl$_3$): δ 0.52 (m, 2 H) 0.68 (t, J=7.35 Hz, 6 H) 0.88 (m, 2 H) 1.09 (m, 4 H) 1.82 (m, 2 H) 2.23 (m, 2 H) 6.17 (s, 1 H) 7.27 (m, 1 H) 7.42 (m, 1 H) 7.80 (dd, J=9.38, 2.76 Hz, 1H).

EXAMPLE 18G

2-[bis(methylthio)methylene]-4,4-dibutyl-7-fluoronaphthalene-1,3(2H,4 H)-dione

The title compound was prepared according to the procedure of Example 14H, substituting the compound of Example 18F for the compound of Example 14G. $^1$H NMR (300 MHz, CDCl$_3$): δ 0.69 (m, 8 H) 0.85 (m, 2 H) 1.13 (m, 4 H) 1.73 (m, 2 H) 2.26 (m, 2 H) 2.57 (m, 6 H) 7.30 (m, 2 H) 7.91 (dd, J=9.56, 2.57 Hz, 1 H).

EXAMPLE 18H 1,1-dibutyl-3-(1,1-dioxido-4H-1,2,4-benzothiadiazin-3-yl)-6-fluoro-4-hydroxynaphthalen-2(1 H)-one A suspension of the compound of Example 18G (39 mg, 0.10 mmol) and 2-aminobenzenesulfonamide (17 mg, 0.10 mmol) in toluene (1 mL) was warmed at reflux for 2 h. The solution was cooled and concentrated in vacuo to afford a yellow foam which was purified by flash chromatography eluting with ethyl acetate in hexane to afford the title compound (33 mg, 0.07 mmol)

EXAMPLE 18I

Sodium 4,4-dibutyl-2-(1,1-dioxido-4H-1,2,4-benzothiadiazin-3-yl)-7-fluoro-3-oxo-3,4-dihydronaphthalen-1-olate A solution of compound of Example 18H (33 mg, 0.07 mmol) in acetonitrile (3 mL) and treated with sodium hydroxide solution (1.0 N, 10 μL, 0.07 mmol) followed by stirring at ambient temperature for 20 min. The solution was frozen and lyophilized to afford the title compound (36 mg, 70% overall yield) as a fluffy white solid. $^1$H NMR (300 MHz, DMSO-d$_6$): δ 0.52 (d, J=6.25 Hz, 2 H) 0.66 (t, J=7.35 Hz, 6 H) 0.85 (m, 2 H) 1.04 (m, 4 H) 1.68 (m, 2 H) 2.11 (m, 2 H) 7.30 (m, 3 H) 7.53 (m, 2 H) 7.69 (m, 2 H) 15.31 (s, 1 H).

EXAMPLE 19

Sodium 4,4-dibutyl-7-fluoro-2-{7-[(methylsulfonyl)amino]-1,1-dioxido-4H-1,2,4-benzothiadiazin-3-yl}-3-oxo-3,4-dihydronaphthalen-1-olate

EXAMPLE 19A

N-[3-(4,4-dibutyl-7-fluoro-1-hydroxy-3-oxo-3,4-dihydronaphthalen-2-yl)-1,1-dioxido-4H-1,2,4-benzothiadiazin-7-yl]methanesulfonamide The title compound was prepared according to the procedure of Example 5D, substituting the compound of Example 18G for the compound of Example 5C, and substituting the compound of Example 12A for the compound of 2D. $^1$H NMR (300 MHz, DMSO-d$_6$): δ0.51 (m, 2 H) 0.69 (t, J=7.35 Hz, 6 H) 0.89 (m, 2 H) 1.08 (m, 4 H) 2.03 (m, 2 H) 2.17 (m, 2 H) 3.08 (s, 3 H) 7.62 (m, 4 H) 7.82 (m, 2 H) 10.22 (s, 1 H) 13.61 (s, 1 H).

EXAMPLE 19B

Sodium 4,4-dibutyl-7-fluoro-2-{7-[(methylsulfonyl)amino]-1,1-dioxido-4H-1,2,4-benzothiadiazin-3-yl}-3-oxo-3,4-dihydronaphthalen-1-olate The title compound was prepared according to the procedure of Example 1I, substituting the compound of Example 19A for the compound of Example 1H. $^1$H NMR (300 MHz, DMSO-d$_6$): δ 0.52 (d, J=5.88 Hz, 2 H) 0.66 (t, J=7.35 Hz, 6 H) 0.84 (m, 2 H) 1.04 (m, 4 H) 1.68 (m, 2 H) 2.11 (m, 2 H) 2.93 (s, 3 H) 7.31 (m, 3 H) 7.44 (m, 2 H) 7.71 (m, 1 H) 9.78 (s, 1 H) 15.29 (s, 1 H).

EXAMPLE 20

Sodium 2-[7-(3-amino-3-oxopropyl)-1,1-dioxido-4H-1,2,4-benzothiadiazin-3-yl]-4,4-dibutyl-7-fluoro-3-oxo-3,4-dihydronaphthalen-1-olate

EXAMPLE 20A 2-amino-5-iodobenzenesulfonamide

A solution of 2-aminobenzenesulfonamide (25.0 g, 145.2 mmol) in chloroform (275 mL) at 0° C. was treated with a solution of iodine monochloride (24.75 g, 152.4 mmol) in chloroform (50 mL) dropwise over 1 h. After addition, the solution was allowed to slowly warm to 25° C. over 18 h. The precipitate was collected by filtration and washed with chloroform (3x), saturated sodium bicarbonate solution (1x), and water (4x). After air drying, these procedures afforded the title compound (23.4 g, 55%) as a red solid. $^1$H NMR (300 MHz, DMSO-d$_6$): δ 6.65 (d, J=8.46 Hz, 1 H) 7.35 (s, 2 H) 7.48 (dd, J=8.82, 2.21 Hz, 1 H) 7.76 (d, J=2.21 Hz, 1 H).

EXAMPLE 20B 1,1-dibutyl-6-fluoro-4-hydroxy-3-(7-iodo-1,1-dioxido-4H-1,2,4-benzothiadiazin-3-yl)naphthalen-2(1H)-one The title compound was prepared according to the procedure of Example 5D, substituting the compound of Example 18G for the compound of Example 5C, and substituting the compound of Example 20A for the compound of 2D. $^1$H NMR (300 MHz, CDCl$_3$): δ 0.56 (m, 2 H) 0.77 (m, 6 H) 0.90 (m, 2 H) 1.18 (m, 4 H) 1.90 (m, 2 H) 2.30 (m, 2H) 7.08 (dd, J=8.46, 4.41 Hz, 2 H) 7.43 (m, 2 H) 7.93 (m, 2 H) 8.28 (d, J=1.84 Hz, 1 H) 16.58 (s, 1 H).

EXAMPLE 20C (2E)-3-[3-(4,4-dibutyl-7-fluoro-1-hydroxy-3-oxo-3,4-dihydronaphthalen-2-yl)-1,1-dioxido-4H-1,2,4-benzothiadiazin-7-yl]acrylamide A solution of the compound of Example 20B (65 mg, 0.11 mmol), acrylamide (9 mg, 0.12 mmol), triethylamine (45 µL, 0.33 mmol), and palladium (II) acetate (1.2 mg, 0.005 mmol) in N,N-dimethylformamide (1.5 mL) in a resealable pressure tube was degassed by evacuation and purging with nitrogen. The pressure tube was sealed and warmed at 100° C. for 1 h. The solution was cooled and diluted with ethyl acetate and water. The mixture was acidified by addition of citric acid solution (1 M, 2 mL). The organic layer was extracted with water (2x) and with saturated NaCl solution. Drying (Na$_2$SO$_4$) and concentration in vacuo afforded a solid, which was purified by flash chromatography eluting with methanol in dichloromethane. These procedures afforded the title compound (33 mg, 56%) as a light amber solid.

EXAMPLE 20D

3-[3-(4,4-dibutyl-7-fluoro-1-hydroxy-3-oxo-3,4-dihydronaphthalen-2-yl)-1,1-dioxido-4H-1,2,4-benzothiadiazin-7-yl]propanamide A solution of the product of Example 20C (33 mg) in ethyl acetate (15 mL) was treated with 10% palladium on carbon (20 mg) and hydrogenated at one atmosphere for 18 h. The mixture was filtered through Celite® and the filtrate was concentrated in vacuo to afford the title compound (25 mg, 76%) as a light beige solid. $^1$H NMR (300 MHz, DMSO-d$_6$): δ 0.53 (m, 2 H) 0.68 (t, J=7.35 Hz, 6 H) 0.90 (m, 2 H) 1.10 (m, 4 H) 2.00 (m, 2 H) 2.19 (m, 2H) 2.42 (t, J=7.35 Hz, 2 H) 2.92 (t, J=7.54 Hz, 2 H) 6.79 (s, 1 H) 7.31 (s, 1 H) 7.60 (m, 3 H) 7.79 (m, 3 H) 13.70 (s, 1 H).

EXAMPLE 20E

Sodium 2-[7-(3-amino-3-oxopropyl)-1,1-dioxido-4H-1,2,4-benzothiadiazin-3-yl]-4,4-dibutyl-7-fluoro-3-oxo-3,4-dihydronaphthalen-1-olate The title compound was prepared according to the procedure of Example 1I, substituting the compound of Example 20D for the compound of Example 1H. $^1$H NMR (300 MHz, DMSO-d$_6$): δ 0.50 (m, 2 H) 0.66 (t, J=7.35 Hz, 6 H) 0.87 (m, 2 H) 1.02 (m, 4 H) 1.67 (m, 2 H) 2.09 (m, 2 H) 2.38 (t, J=7.54 Hz, 2 H) 2.85 (t, J=7.54 Hz, 2 H) 6.77 (s, 1 H) 7.30 (m, 4 H) 7.50 (m, 1 H) 7.71 (dd, J=10.30, 2.57 Hz, 1 H) 15.24 (s, 1 H).

EXAMPLE 21

3-(4,4-dibutyl-7-fluoro-1-hydroxy-3-oxo-3,4-dihydronaphthalen-2-yl)-4H-1,2,4-benzothiadiazine-7-carbaldehyde 1,1-dioxide

EXAMPLE 21A 1,1-dibutyl-3-(1,1-dioxido-7-vinyl-4H-1,2,4-benzothiadiazin-3-yl)-6-fluoro-4-hydroxynaphthalen-2(1H)-one A solution of the compound of Example 20B (120 mg, 0.20 mmol), tri-(2-furyl)phosphine (5 mg, 0.020 mmol), tris-(dibenzylideneacetone)palladium (0) (9 mg, 0.010 mmol) in tetrahydrofuran (2 mL) was stirred at ambient temperature for 10 min, during which time the solution changed from a deep maroon color to pale green. The solution was treated with vinyltributylstannane (118 □L, 0.403 mmol) followed by warming at 50° C. for 1.5 h. The solution was cooled, diluted with ethyl acetate and stirred for 1 h with 1 M KF solution. The mixture was filtered through Celite® and the layers separated. The organic layer was washed with saturated NaCl solution and dried over Na$_2$SO$_4$. Concentration in vacuo afforded an oil which was purified by flash chromatography eluting with ethyl acetate in hexane. These procedures afforded the title compound (52 mg, 52%) as a white solid. $^1$H NMR (300 MHz, CDCl$_3$): δ 0.59 (m, 2 H) 0.73 (m, 6 H) 0.89 (m, 2 H) 1.15 (m, 4 H) 1.88 (m, 2 H) 2.31 (m, 2 H) 5.41 (d, J=11.03 Hz, 1 H) 5.85 (d, J=17.65 Hz, 1 H) 6.74 (dd, J=17.47, 10.85 Hz, 1 H) 7.30 (m, 2 H) 7.43 (m, 2 H) 7.68 (m, 1 H) 7.94 (m, 2 H) 16.80 (s, 1 H).

EXAMPLE 21B 3-(4,4-dibutyl-7-fluoro-1-hydroxy-3-oxo-3,4-dihydronaphthalen-2-yl)-4H-1,2,4-benzothiadiazine-7-carbaldehyde 1,1-dioxide A solution of the compound of Example 21A (52 mg, 0.10 mmol) in dioxane (2 mL) and water (200 µL) was treated with a solution of osmium tetroxide in t-butanol (2.5% (wt/vol), 200 µL) and sodium periodate (45 mg, 0.21 mmol) followed by stirring at ambient temperature for 24 h. The mixture was diluted with water and saturated ammonium chloride solution. The mixture was extracted with ethyl acetate and the organic layer washed with water and saturated NaCl solution. Drying (Na$_2$SO$_4$) and concentration in vacuo afforded the title compound (47 mg, 90%) as a white solid. $^1$H NMR (300 MHz, DMSO-d$_6$): δ 0.51 (m, 2H) 0.69 (t, J=7.35 Hz, 6 H) 0.90 (m, 2 H) 1.10 (m, 4 H) 1.92 (m, 2 H) 2.15 (m, 2 H) 7.52 (m, 1 H) 7.73 (m, 3 H) 8.11 (dd, J=8.64, 1.65 Hz, 1 H) 8.40 (d, J=1.47 Hz, 1 H) 10.03 (s, 1 H) 14.38 (s, 1 H).

EXAMPLE 22

Sodium (4R)-7-fluoro-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate

EXAMPLE 22A

Methyl 2-(4-fluorophenyl)propanoate

A solution of the compound of Example 14A (23.2 g, 0.138 mol) in dry tetrahydrofuran (30 mL) was added dropwise over 30 min to a −78° C. solution of lithium hexamethyldisilazide (prepared from hexamethyldisilazane (35 mL, 0.165 mol) and n-butyllithium in hexane (2.5 M, 58 mL, 0.145 mol)) in dry tetrahydrofuran (100 mL). The solution was stirred at −78° C. for 1 h, and then a large excess of methyl iodide was added. The solution was stirred at −78° C. for 30 min and was then warmed to ambient temperature for 18 h. The solution was quenched by addition of saturated ammonium chloride solution and diluted with water. The mixture was concentrated in vacuo to remove tetrahydrofuran and then extracted with ethyl acetate. The organic layer was extracted with water (2×) and saturated NaCl solution, followed by drying (Na$_2$SO$_4$) and concentration in vacuo. The residue was distilled under reduced pressure (70-75° C./0.5 mm Hg) to afford the title compound (21.9 g, 87%) as a colorless oil. $^1$H NMR (300 MHz, CDCl$_3$): δ 1.49 (d, J=7.35 Hz, 3 H) 3.70 (m, 4 H) 7.01 (m, 2 H) 7.27 (m, 2 H).

EXAMPLE 22B

Methyl 2-(4-fluorophenyl)-2,5-dimethylhexanoate

A solution of the compound of Example 22A (10.0 g, 55 mmol) in tetrahydrofuran (30 mL) was added dropwise over 30 min to a −78° C. solution of lithium hexamethyldisilazide (prepared from hexamethyldisilazane (14.5 mL, 68.7 mmol) and n-butyllithium in hexane (2.5 M, 26.4 mL, 65.9 mmol)). The solution was stirred at −78° C. for 1 h. The solution was then treated with neat isoamyl bromide (9.9 mL, 82.4 mmol) followed by stirring at −78° C. for 30 min, and then warming to ambient temperature for 48 h. The solution was quenched by addition of saturated ammonium chloride solution (6 mL) and diluted with water. The mixture was concentrated in vacuo to remove tetrahydrofuran, and then extracted with ethyl acetate. The organic layer was extracted with water (2×) and saturated NaCl solution. Drying (Na$_2$SO$_4$) and concentration in vacuo afforded a brown oil, which was distilled under reduced pressure (90-93° C./0.3 mm Hg) to afford the title compound (11.8 g, 85%) as a colorless oil. $^1$H NMR (300 MHz, CDCl$_3$): δ 0.87 (m, 6 H) 1.03 (m, 2 H) 1.51 (m, 4 H) 1.95 (m, 2 H) 3.65 (s, 3 H) 7.01 (m, 2 H) 7.28 (m, 2 H).

EXAMPLE 22C 2-(4-fluorophenyl)-2,5-dimethylhexanoic Acid

The title compound was prepared according to the procedure of Example 1C, substituting the compound of Example 22B for the compound of Example 1B. $^1$H NMR (300 MHz, CDCl$_3$): δ 0.86 (t, J=6.43 Hz, 6 H) 1.05 (m, 2 H) 1.51 (m, 4 H) 1.96 (m, 2 H) 7.02 (m, 2 H) 7.34 (m, 2 H).

EXAMPLE 22D (2R)-2-(4-fluorophenyl)-N-[(1R)-2-hydroxy-1-phenylethyl]-2,5-dimethylhexanamide A solution of the compound of Example 22C (11.1 g, 46.6 mmol) and N,N-dimethylformamide (4.0 mL, 51.3 mmol) in hexane (800 mL) was treated with oxalyl chloride (12.1 mL, 140 mmol) followed by stirring at ambient temperature for 1 h. The solution was treated with Celite® and filtered. The filtrate was concentrated in vacuo to afford a light amber oil. This material was dissolved in dichloromethane (1 L) and treated with triethylamine (13 mL, 93 mmol), (R)-(−)-2-phenylglycinol (6.4 g, 46.6 mmol) and 4-(N, N-dimethylamino)-pyridine (200 mg). The solution was stirred at ambient temperature for 24 h. The solution was extracted with 1 N HCl solution and dried (Na$_2$SO$_4$). Concentration in vacuo afforded a light yellow solid, which was purified by flash chromatography, eluting with ethyl acetate in toluene. These procedures afforded two diastereomeric amides. The less polar diastereomer was the title compound (6.15 g, 73%). $^1$H NMR (300 MHz, CDCl$_3$): δ0.85 (m, 6 H) 1.05 (m, 2 H) 1.51 (m, 4 H) 1.99 (m, 2 H) 3.77 (d, J=4.78 Hz, 2 H) 5.02 (m, 1H) 5.83 (d, J=6.99 Hz, 1 H) 7.06 (m, 4 H) 7.30 (m, 5 H).

EXAMPLE 22E (2R)-2-(4-fluorophenyl)-2,5-dimethylhexanoic acid

A solution of the product of Example 22D (6.15 g, 17.2 mmol) in dioxane (100 mL) was treated with 4 M sulfuric acid solution (100 mL), and the mixture was warmed at reflux for 48 h. The solution was cooled and extracted with dichloromethane (3×). The combined organic layers were dried (Na$_2$SO$_4$) and concentrated in vacuo to afford the title compound (4.16 g, 100%) as an amber oil. $^1$H NMR (300 MHz, CDCl$_3$): δ 0.86 (t, J=6.43 Hz, 6 H) 1.05 (m, 2 H) 1.51 (m, 4 H) 1.96 (m, 2 H) 7.02 (m, 2 H) 7.34 (m, 2 H). Specific Rotation: [□]$_D$−10.6°(c 2.15, EtOH).

EXAMPLE 22F (2R)-2-(4-fluorophenyl)-2,5-dimethylhexanoyl chloride

The title compound was prepared according to the procedure of Example 1D, substituting the compound of Example 22E for the compound of Example 1C.

EXAMPLE 22G

Diethyl 2-[(2R)-2-(4-fluorophenyl)-2,5-dimethylhexanoyl]malonate

The title compound was prepared according to the procedure of Example 1E, substituting the compound of Example 22F for the compound of Example 1D. $^1$H NMR (300 MHz, CDCl$_3$): δ 0.82 (m, 8 H) 1.21 (m, 6 H) 1.48 (m, 4 H) 1.94 (m, 2 H) 4.11 (m, 4 H) 4.49 (s, 1 H) 7.05 (m, 2 H) 7.24 (m, 2 H).

EXAMPLE 22H (1R)-6-fluoro-4-hydroxy-1-methyl-1-(3-methylbutyl)naphthalen-2(1H)-one The title compound was prepared according to the procedure of Example 14G, substituting the compound of Example of 22G for the compound of Example 14F. $^1$H NMR (300 MHz, DMSO-d$_6$): δ 0.36 (m, 1 H) 0.71 (m, 7 H) 1.31 (m, 4 H) 1.91 (s, 1 H) 2.05 (m, 1H) 5.72 (s, 1 H) 7.43 (m, 1 H) 7.57 (dd, J=9.56, 2.57 Hz, 1 H) 7.71 (m, 1 H) 11.80 (s, 1 H). Specific Rotation: [□]$_D$+23.5°(c 2.05, EtOH).

EXAMPLE 22I (4R)-2-[bis(methylthio)methylene]-7-fluoro-4-methyl-4-(3-methylbutyl)naphthalene-1,3(2H,4H)-dione The title compound was prepared according to the procedure of Example 5C, substituting the compound of Example 22H for the compound of Example 5B. $^1$H NMR (300 MHz, CDCl$_3$): δ 0.76 (m, 8 H) 1.36 (m, 1 H) 1.53 (s, 3 H) 1.74 (m, 1 H) 2.24 (m, 1 H) 2.58 (s, 6 H) 7.26 (m, 1 H) 7.39 (m, 1 H) 7.89 (dd, J=9.38, 2.76 Hz, 1 H).

EXAMPLE 22J

N-{3-[(4R)-7-fluoro-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide The title compound was prepared according to the procedure of Example 5D, substituting the compound of Example 22I for the compound Example 5C, and the compound of Example 12A for the compound of Example 2D. $^1$H NMR (300 MHz, DMSO-d$_6$): δ 0.42 (m, 1 H) 0.75 (m, 7 H) 1.30 (m, 1 H) 1.57 (s, 3 H) 2.15 (m, 2 H) 3.08 (s, 3 H) 7.61 (m, 4 H) 7.83 (m, 2 H) 10.24 (s, 1 H) 13.60 (s, 1 H). Specific Rotation: [□]$_D$–55.8° (c 1.05, EtOH).

EXAMPLE 22K

Sodium (4R)-7-fluoro-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate The title compound was prepared according to the procedure of Example 1I, substituting the compound of Example 22J for the compound of Example 1H. $^1$H NMR (300 MHz, DMSO-d$_6$): δ 0.43 (m, 1 H) 0.74 (m, 7 H) 1.29 (m, 4 H) 1.72 (m, 1 H) 2.14 (m, 1 H) 2.96 (s, 3 H) 7.41 (m, 5 H) 7.71 (dd, J=10.29, 2.94 Hz, 1 H) 9.89 (s, 1 H) 15.25 (s, 1 H).

EXAMPLE 23

Sodium (4S)-7-fluoro-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate

EXAMPLE 23A (2S)-2-(4-fluorophenyl)-N-[(1R)-2-hydroxy-1-phenylethyl]-2,5-dimethylhexanamide A solution of the compound of Example 22C (11.1 g, 46.6 mmol) and N,N-dimethylformamide (4.0 mL, 51.3 mmol) in hexane (800 mL) was treated with oxalyl chloride (12.1 mL, 140 mmol) followed by stirring at ambient temperature for 1 h. The solution was treated with Celite® and filtered. The filtrate was concentrated in vacuo to afford a light amber oil. This material was dissolved in dichloromethane (1 L) and treated with triethylamine (13 mL, 93 mmol), (R)-(–)-2-phenylglycinol (6.4 g, 46.6 mmol) and 4-(N,N-dimethylamino)-pyridine (200 mg). The solution was stirred at ambient temperature for 24 h. The solution was extracted with 1 N HCl solution and dried (Na$_2$SO$_4$). Concentration in vacuo afforded a light yellow solid, which was purified by flash chromatography, eluting with ethyl acetate in toluene. These procedures afforded two diastereomeric amides. The more polar diastereomer was the title compound (6.25 g, 75%). $^1$H NMR (300 MHz, CDCl$_3$): δ 0.88 (m, 7 H) 1.05 (m, 1 H) 1.49 (m, 1 H) 1.56 (s, 3 H) 1.96 (m, 2 H) 3.77 (m, 2 H) 5.03 (m, 1 H) 5.83 (d, J=6.99 Hz, 1 H) 7.06 (m, 4 H) 7.29 (m, 5 H).

EXAMPLE 23B (2S)-2-(4-fluorophenyl)-2,5-dimethylhexanoic acid

The title compound was prepared according to the procedure of Example 22E, substituting the product of Example 23A, for the product of Example 22D. $^1$H NMR (300 MHz, CDCl$_3$): δ 0.88 (m, 7 H) 1.06 (m, 1 H) 1.48 (m, 1 H) 1.55 (s, 3 H) 1.96 (m, 2 H) 3.76 (m, 2 H) 5.03 (m, 1 H) 5.83 (d, J=6.99 Hz, 1 H) 7.06 (m, 4 H) 7.29 (m, 5 H). Specific rotation: [α]$_D$+12.4° (c 2.16, EtOH).

EXAMPLE 23C (2S)-2-(4-fluorophenyl)-2,5-dimethylhexanoyl chloride

The title compound was prepared according to the procedure of Example 1D, substituting the compound of Example 23B for the compound of Example 1C.

EXAMPLE 23D diethyl 2-[(2S)-2-(4-fluorophenyl)-2,5-dimethylhexanoyl]malonate The title compound was prepared according to the procedure of Example 1E, substituting the compound of Example 23C for the compound of Example 1D. $^1$H NMR (300 MHz, CDCl$_3$): δ 0.84 (m, 7 H) 1.07 (m, 1 H) 1.22 (m, 6 H) 1.48 (m, 4 H) 1.95 (m, 2 H) 4.14 (m, 4 H) 4.49 (s, 1 H) 7.04 (m, 2 H) 7.24 (m, 2 H).

EXAMPLE 23E (1S)-6-fluoro-4-hydroxy-1-methyl-1-(3-methylbutyl)naphthalen-2(1H)-one The title compound was prepared according to the procedure of Example 14G, substituting the compound of Example of 23D for the compound of Example 14F. $^1$H NMR (300 MHz, DMSO-d$_6$): δ 0.33 (m, 1 H) 0.69 (dd, J=10.48, 6.43 Hz, 7 H) 1.32 (m, 4 H) 1.89 (s, 1 H) 2.05 (m, 1 H) 5.72 (s, 1 H) 7.43

(m, 1 H) 7.57 (dd, J=9.56, 2.57 Hz, 1 H) 7.71 (s, 1 H) 11.80 (s, 1 H). Specific rotation: $[\alpha]_D$ –23.1° (c 2.01, EtOH).

EXAMPLE 23F (4S)-2-[bis(methylthio)methylene]-7-fluoro-4-methyl-4-(3-methylbutyl)naphthalene-1,3(2H,4 H)-dione The title compound was prepared according to the procedure of Example 5C, substituting the compound of Example 23E for the compound of Example 5B. $^1$H NMR (300 MHz, CDCl$_3$): δ 0.65 (m, 1 H) 0.72 (m, 6 H) 0.86 (m, 1 H) 1.35 (dd, J=13.24, 6.62 Hz, 1 H) 1.55 (m, 3 H) 1.74 (m, 1 H) 2.24 (m, 1 H) 2.58 (s, 6 H) 7.26 (m, 1 H) 7.39 (m, 1 H) 7.89 (dd, J=9.38, 2.76 Hz, 1 H).

EXAMPLE 23G

N-{3-[(4S)-7-fluoro-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide The title compound was prepared according to the procedure of Example 13C, substituting the compound of Example 23F for the compound of Example 13B. $^1$H NMR (300 MHz, DMSO-d$_6$): δ 0.41 (m, 1 H) 0.76 (m, 7 H) 1.35 (m, 1 H) 1.57 (s, 3 H) 2.06 (m, 1H) 2.22 (m, 1 H) 7.62 (m, 4 H) 7.83 (m, 2 H) 10.25 (s, 1 H) 13.57 (s, 1 H).

EXAMPLE 23H

Sodium (4S)-7-fluoro-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate The title compound was prepared according to the procedure of Example 1I, substituting the compound of Example 23G for the compound of Example 1H. $^1$H NMR (300 MHz, DMSO-d$_6$): δ0.41 (m, 1 H) 0.73 (m, 7 H) 1.27 (m, 1 H) 1.35 (s, 3 H) 1.71 (m, 1 H) 2.15 (m, 1 H) 2.66 (s, 3 H) 7.04 (m, 2 H) 7.27 (m, 2 H) 7.51 (dd, J=8.64, 5.33 Hz, 1 H) 7.70 (dd, J=10.30, 2.94 Hz, 1 H) 14.86 (s, 1 H).

EXAMPLE 24

Sodium (4R)-4-(3,3-dimethylbutyl)-7-fluoro-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 24A

Methyl 2-(4-fluorophenyl)-2,5,5-trimethylhexanoate

A solution of the compound of Example 22A (11.75 g, 64.6 mmol) in tetrahydrofuran (30 mL) was added dropwise over 20 min to a –78° C. solution of lithium hexamethyldisilazide (previously prepared from hexamethyldisilazane (17.0 mL, 80.7 mmol) and n-butyllithium in hexane (2.5 M, 31.0 mL, 77.5 mmol)) in tetrahydrofuran (40 mL) and allowed to stir at that temperature for 1 h. The solution was then treated with 1-bromo-3,3-dimethylbutane (12.0 mL, 83.9 mmol), followed by stirring at –78° C. for 30 min, and then warming to 25° C. for 18 h. The solution was quenched by addition of saturated ammonium chloride solution (4 mL) and then concentrated in vacuo. The residue was diluted with ethyl acetate and water. The organic layer was extracted with water (2×), saturated NaCl solution and dried (Na$_2$SO$_4$). Concentration in vacuo afforded an oil, which was distilled under reduced pressure (90-93° C./0.3 mm Hg) to afford the product (4.85 g, 28%) as a colorless oil. $^1$H NMR (300 MHz, CDCl$_3$): δ 0.86 (s, 9 H) 1.03 (m, 2 H) 1.51 (m, 3 H) 1.86 (m, 1 H) 2.00 (m, 1 H) 3.65 (m, 3H) 7.03 (m, 2 H) 7.27 (m, 2 H).

EXAMPLE 24B 2-(4-fluorophenyl)-2,5,5-trimethylhexanoic Acid

The title compound was prepared according to the procedure of Example 1C, substituting the compound of Example 24A for the compound of Example 1B. $^1$H NMR (300 MHz, CDCl$_3$): δ 0.86 (s, 9 H) 1.05 (m, 2 H) 1.52 (s, 3 H) 1.91 (m, 2 H) 7.03 (m, 2 H) 7.32 (m, 2 H).

EXAMPLE 24C (2R)-2-(4-fluorophenyl)-N-[(1R)-2-hydroxy-1-phenylethyl]-2,5,5-trimethylhexanamide The title compounds were prepared according to the procedure of Example 22D, substituting the compound of Example 24B for the compound of 22C. The less polar diastereoisomer was the title compound. $^1$H NMR (300 MHz, CDCl$_3$): δ 0.84 (s, 9 H) 0.95 (m, 1 H) 1.11 (m, 1 H) 1.53 (m, 3 H) 1.97 (m, 2 H) 3.77 (d, J=4.78 Hz, 2 H) 5.02 (m, 1 H) 5.82 (d, J=6.99 Hz, 1 H) 7.06 (m, 4 H) 7.31 (m, 5 H).

EXAMPLE 24D (2R)-2-(4-fluorophenyl)-2,5,5-trimethylhexanoic Acid

The title compound was prepared according to the Example 22E, substituting the product of Example 24C for the product of Example 22D. $^1$H NMR (300 MHz, CDCl$_3$): δ 0.86 (s, 9 H) 1.05 (m, 2 H) 1.55 (s, 3 H) 1.94 (m, 2 H) 7.03 (m, 2 H) 7.34 (m, 2 H). Specific Rotation: $[\alpha]_D$ –11.8° (c 2.43, EtOH).

EXAMPLE 24E (2R)-2-(4-fluorophenyl)-2,5,5-trimethylhexanoyl chloride

The title compound was prepared according to the procedure of Example 1D, substituting the compound of Example 24D for the compound of Example 1C.

EXAMPLE 24F

Diethyl 2-[(2R)-2-(4-fluorophenyl)-2,5,5-trimethylhexanoyl]malonate

The title compound was prepared according to the procedure of Example 1E, substituting the compound of Example 24E for the compound of Example 1D. $^1$H NMR (300 MHz, CDCl$_3$): δ 0.83 (s, 9 H) 1.17 (m, 8 H) 1.51 (s, 3 H) 1.92 (m, 2 H) 4.13 (m, 4 H) 4.50 (s, 1 H) 7.03 (m, 2 H) 7.24 (m, 2 H).

EXAMPLE 24G (1R)-1-(3,3-dimethylbutyl)-6-fluoro-4-hydroxy-1-methylnaphthalen-2(1H)-one The title compound was prepared according to the procedure of Example 14G, substituting the compound of Example of 24F for the compound of Example 14F. $^1$H NMR (300 MHz, DMSO-d$_6$): δ 0.31 (m, 1 H) 0.76 (m, 10 H) 1.43 (s, 3 H) 1.90 (m, 1 H) 2.05 (m, 1H) 5.72 (s, 1 H) 7.43 (m, 1 H) 7.57 (dd, J=9.56, 2.57 Hz, 1 H) 7.70 (m, 1 H) 11.79 (s, 1 H). Specific rotation: [α]$_D$+29.2°(c 2.09, EtOH).

EXAMPLE 24H (4R)-2-[bis(methylthio)methylene]-4-(3,3-dimethylbutyl)-7-fluoro-4-methylnaphthalene-1,3(2H,4H)-dione The title compound was prepared according to the procedure of Example 5C, substituting the compound of Example 24G for the compound of Example 5B. $^1$H NMR (300 MHz, CDCl$_3$): δ 0.61 (m, 1 H) 0.73 (s, 9 H) 0.85 (m, 1 H) 1.57 (s, 3 H) 1.71 (m, 1 H) 2.25 (m, 1 H) 2.58 (s, 6 H) 7.26 (m, 1 H) 7.38 (m, 1 H) 7.89 (dd, J=9.56, 2.94 Hz, 1 H).

EXAMPLE 24I

N-{3-[(4R)-4-(3,3-dimethylbutyl)-7-fluoro-1-hydroxy-4-methyl-3-oxo-3,4-dihydronaphthalen-2-yl]-1,1-dioxido-4H-1,2,4-benzothiadiazin-7-yl}methanesulfonamide The title compound was prepared according to the procedure of Example 13C, substituting the compound of Example 24H for the compound of Example 13B. $^1$H NMR (300 MHz, DMSO-d$_6$): δ 0.39 (m, 1 H) 0.81 (m, 10 H) 1.59 (s, 3 H) 2.04 (m, 1 H) 2.22 (m, 1H) 3.08 (s, 3 H) 7.62 (m, 4 H) 7.83 (m, 2 H) 10.25 (s, 1 H) 13.57 (s, 1 H). Specific rotation: [α]$_D$−57.5° (c 1.01, EtOH).

EXAMPLE 24J

Sodium (4R)-4-(3,3-dimethylbutyl)-7-fluoro-4-methyl-2-{7-[(methylsulfonyl)amino]-1,1-dioxido-4H-1,2,4-benzothiadiazin-3-yl}-3-oxo-3,4-dihydronaphthalen-1-olate The title compound was prepared according to the procedure of Example 1I, substituting the compound of Example 24I for the compound of Example 1H. $^1$H NMR (300 MHz, DMSO-d$_6$): δ 0.42 (m, 1 H) 0.78 (m, 10 H) 1.39 (s, 3 H) 1.71 (m, 1 H) 2.14 (m, 1 H) 2.97 (s, 3 H) 7.41 (m, 5 H) 7.71 (dd, J=9.93, 2.94 Hz, 1 H) 9.90 (s, 1 H) 15.28 (s, 1 H).

EXAMPLE 25 sodium (4S)-4-(3,3-dimethylbutyl)-7-fluoro-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 25A (2S)-2-(4-fluorophenyl)-N-[(1R)-2-hydroxy-1-phenylethyl]-2,5,5-trimethylhexanamide The title compounds were prepared according to the procedure of Example 22D, substituting the compound of Example 24B for the compound of 22C. The more polar diastereomer was the title compound. $^1$H NMR (300 MHz, CDCl$_3$): δ 0.81 (s, 9 H) 0.87 (m, 1 H) 1.06 (m, 1 H) 1.56 (m, 3 H) 1.93 (m, 2 H) 3.78 (t, J=4.41 Hz, 2 H) 5.03 (m, 1 H) 5.81 (d, J=6.99 Hz, 1 H) 7.05 (m, 4 H) 7.28 (m, 5 H).

EXAMPLE 25B (2S)-2-(4-fluorophenyl)-2,5,5-trimethylhexanoic acid

The title compound was prepared according to the procedure of Example 22E, substituting the product of Example 25A for the product of Example 22D. $^1$H NMR (300 MHz, CDCl$_3$): δ 0.84 (m, 9 H) 1.03 (m, 2 H) 1.55 (s, 3 H) 1.95 (m, 2 H) 7.02 (m, 2 H) 7.34 (m, 2 H). Specific rotation: [α]$_D$+13.4° (c 2.08, EtOH).

EXAMPLE 25C (2S)-2-(4-fluorophenyl)-2,5,5-trimethylhexanoyl Chloride

The title compound was prepared according to the procedure of Example 1D, substituting the compound of Example 25B for the compound of Example 1C.

EXAMPLE 25D diethyl 2-[(2S)-2-(4-fluorophenyl)-2,5,5-trimethylhexanoyl]malonate The title compound was prepared according to the procedure of Example 1E, substituting the compound of Example 25C for the compound of Example 1D. $^1$H NMR (300 MHz, CDCl$_3$): δ 0.81 (m, 10 H) 1.16 (m, 7 H) 1.53 (m, 3 H) 1.92 (m, 2 H) 4.12 (m, 4 H) 4.50 (s, 1 H) 7.04 (m, 2 H) 7.24 (m, 2 H).

EXAMPLE 25E (1S)-1-(3,3-dimethylbutyl)-6-fluoro-4-hydroxy-1-methylnaphthalen-2(1H)-one The compound of Example 25D (1.68 g, 4.25 mmol) was dissolved in Eaton's reagent (15 mL, 1:10 (w/w) phosphorus pentoxide in methanesulfonic acid, cf. P. E. Eaton, et al. J. Am. Chem. Soc. 1973, 38, 4071) and warmed at 70° C. for 18 h. The solution was cooled to 25° C. and added to a mixture of ice and water. The mixture was extracted with dichloromethane (3×) and the combined organic layers dried (Na$_2$SO$_4$) and concentrated in vacuo. The oil obtained was dissolved in tetrahydrofuran (30 mL) and treated with 1 N HCl solution, followed by warming at reflux for 18 h. The mixture was cooled and extracted with ethyl acetate (2×). The combined organic layers were extracted with water (2×) and saturated NaCl solution. Drying (Na$_2$SO$_4$) and concentration in vacuo afforded a brown solid, which was triturated with ether-hexane and the resulting solid collected by filtration. These procedures afforded the title compound (590 mg, 50%) as an off-white solid. $^1$H NMR (300 MHz, DMSO-d$_6$): δ 0.32 (m, 1 H) 0.71 (m, 10 H) 1.43 (s, 3 H) 1.91 (s, 1 H) 2.05 (m, 1 H) 5.73 (s, 1 H) 7.43 (m, 1 H) 7.57 (dd, J=9.56, 2.57 Hz, 1 H) 7.71 (s, 1 H) 11.79 (s, 1 H). Specific rotation: [α]$_D$−27.7°(c 2.11, EtOH).

EXAMPLE 25F (4S)-2-[bis(methylthio)methylene]-4-(3,3-dimethylbutyl)-7-fluoro-4-methylnaphthalene-1,3(2H,4 H)-dione The title compound was prepared according to the procedure of Example 5C, substituting the compound of Example 25E for the compound of Example 5B. $^1$H NMR (300 MHz, CDCl$_3$): δ 0.61 (m, 1 H) 0.74 (s, 9 H) 0.85 (m, 1 H) 1.53 (s, 3 H) 1.70 (m, 1 H) 2.25 (m, 1 H) 2.58 (s, 6 H) 7.26 (m, 1 H) 7.38 (m, 1 H) 7.89 (dd, J=9.38, 2.76 Hz, 1 H).

EXAMPLE 25G

N-{3-[(4S)-4-(3,3-dimethylbutyl)-7-fluoro-1-hydroxy-4-methyl-3-oxo-3,4-dihydronaphthalen-2-yl]-1,1-dioxido-4H-1,2,4-benzothiadiazin-7-yl}methanesulfonamide The title compound was prepared according to the procedure of Example 13C, substituting the compound of Example 25F for the compound of Example 13B.

EXAMPLE 25H sodium (4S)-4-(3,3-dimethylbutyl)-7-fluoro-4-methyl-2-{7-[(methylsulfonyl)amino]-1,1-dioxido-4H-1,2,4-benzothiadiazin-3-yl}-3-oxo-3,4-dihydronaphthalen-1-olate The title compound was prepared according to the procedure of Example 1I, substituting the compound of Example 25G for the compound of Example 1H.

EXAMPLE 26

EXAMPLE 26A benzyl 2-methyl-2-phenylpent-4-enoate

A solution of 2-phenyl-propionic acid benzyl ester (2.0 g, 8.32 mmol), allyl bromide (0.865 mL, 9.99 mmol), and lithium iodide (1 g) in tetrahydrofuran (15 mL) at 0° C. was treated dropwise with the lithium hexamethyldisilazide (9.99 mL, 1M in tetrahydrofuran, 9.99 mmol). The reaction was allowed to warm to 25° C. and stirred for 18 hours. The solvent was removed in vacuo and the residue was partitioned between water and ethyl acetate. The aqueous phase was extracted three times with ethyl acetate and the ethyl acetate layers were combined, dried with sodium sulfate, filtered, and concentrated in vacuo. The residue was chromatographed on silica gel eluting with hexane, then 10% ethyl acetate in hexane, and 20% ethyl acetate in hexane to give the title compound (2.31 g, 99%). $^1$H NMR (300 MHz, CDCl$_3$): δ ppm 1.56 (m, 3 H) 2.68 (m, 1 H) 2.85 (m, 1 H) 5.05 (m, 4 H) 5.59 (m, 1 H) 7.26 (m, 10 H).

EXAMPLE 26B 2-methyl-2-phenylpentanoic Acid

A solution of 2-methyl-2-phenyl-pent-4-enoic acid benzyl ester (2.31 g, 8.24 mmol) in ethyl acetate (20 mL) was treated with 10% palladium on carbon (0.24 g, 10 weight percent) and stirred under a hydrogen balloon for 72 hours. The vessel was purged with nitrogen gas and the mixture was filtered through a pad of celite and the filtrate was concentrated in vacuo to give the title compound (1.58 g, 99%). $^1$H NMR (300 MHz, CDCl$_3$): δ ppm 0.91 (m, 3 H) 1.23 (m, 2 H) 1.57 (m, 3 H) 1.96 (m, 2 H) 7.36 (m, 5 H). MS (DCI/NH$_3$$^+$) m/z 210 (M+NH$_4$)$^+$.

EXAMPLE 26C diethyl 2-(2-methyl-2-phenylpentanoyl)malonate

A solution of diethyl malonate (1.27 mL, 8.36 mmol) in acetonitrile (15 mL) was cooled to 0° C. and treated with magnesium chloride (0.796 g, 8.36 mmol) followed by dropwise addition of triethylamine (2.45 mL, 17.6 mmol). The solution was stirred at 0° C. for 15 minutes and then stirred at 25° C. for 2 hours. A solution of 2-methyl-2-phenyl-pentanoic acid (1.61 g, 8.36 mmol) and dimethylformamide (0.712 mL, 9.20 mmol) in hexane (350 mL) was treated with oxalyl chloride (2.19 mL, 25.1 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo. The residue was chromatographed on silica gel eluting with hexane, then 10% ethyl acetate in hexane, and 20% ethyl acetate in hexane to give the title compound (2.45 g, 87%). $^1$H NMR (300 MHz, CDCl$_3$): δ ppm 0.89 (m, 3 H) 1.02 (m, 2 H) 1.18 (m, 6 H) 1.53 (m, 3 H) 1.94 (m, 2 H) 4.08 (m, 4 H) 4.51 (m, 1 H) 7.34 (m, 5 H). MS (ESI$^+$) m/z 352 (M+NH$_4$)$^+$.

EXAMPLE 26D ethyl 1-hydroxy-4-methyl-3-oxo-4-propyl-3,4-dihydronaphthalene-2-carboxylate 2-(2-methyl-2-phenyl-pentanoyl)-malonic acid diethyl ester (2.45 g, 7.33 mmol) was stirred in methanesulfonic acid (20 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (1.34 g, 63%). $^1$H NMR (300 MHz, CDCl$_3$) δ ppm 0.72 (m, 4 H) 0.96 (m, 1 H) 1.46 (m, 3 H) 1.63 (s, 3 H) 1.74 (m, 0.5 H) 1.92 (m, 0.5 H) 2.26 (m, 1 H) 4.47 (m, 2 H) 7.42 (m, 2 H) 7.59 (m, 1 H) 8.16 (m, 0.5 H) 8.23 (m, 0.5 H) 15.10 (s, 0.5 H) 15.16 (s, 0.5 H). (ESI$^+$) m/z 289 (M+H)$^+$.

EXAMPLE 26E 4-hydroxy-1-methyl-1-propylnaphthalen-2(1 H)-one

A solution of 26D (1.34 g, 4.65 mmol) in 1,4-dioxane (25 mL) was treated with aqueous 1N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (0.778 g, 78%). $^1$H NMR (300 MHz, CDCl$_3$) 3 ppm 0.62 (m, 0.5 H) 0.72 (t, 1.5 H) 0.83 (t, 1.5 H) 0.96 (m, 1 H) 1.19 (m, 0.5 H) 1.55 (s, 1.5 H) 1.57 (s, 1.5 H) 1.78 (m, 0.5 H) 1.89 (m, 0.5 H) 2.02 (m, 0.5 H) 2.26 (m, 0.5 H) 3.74 (s, 0.5 H) 3.75 (s, 0.5 H) 6.31 (s, 0.5 H) 7.46 (m, 2 H) 7.63 (m, 1 H) 8.08 (m, 0.5 H) 8.15 (m, 0.5 H). MS (DCI NH$_3$$^+$) m/z 238 (M+NH$_4$)$^+$.

EXAMPLE 26F

2-[bis(methylthio)methylene]-4-methyl-4-propyl-naphthalene-1,3(2H,4 H)-dione

A solution of 26E (0.775 g, 3.58 mmol) and pyridine (2.31 mL, 28.67 mmol) in 1,4-dioxane (15 mL) was treated with 5A (3.80 g, 14.3 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (1.15 g, 99%). $^1$H NMR (300 MHz, DMSO-d$_6$): δ ppm 0.76 (m, 5 H) 1.46 (m, 3 H) 1.77 (m, 1 H) 2.08 (m, 1 H) 2.56 (m, 6 H) 7.43 (m, 1 H) 7.62 (m, 2 H) 8.04 (m, 1 H). MS (ESI$^+$) m/z 321 (M+H)$^+$.

EXAMPLE 26G

3-[7-(benzyloxy)-1,1-dioxido-4H-1,2,4-benzothiadiazin-3-yl]-4-hydroxy-1-methyl-1-propylnaphthalen-2(1 H)-one A solution of Example 26F (1.16 g, 3.62 mmol) and Example 2D (1.01 g, 3.62 mmol) in toluene (100 mL) was refluxed for 6 hours. The solution was cooled to 25° C. and concentrated in vacuo. The residue was stirred in a solution of diethyl ether and hexane (1:5, 100 mL) and the precipitate was filtered and dried to give the title compound (1.44 g, 79%). $^1$H NMR (300 MHz, DMSO-d$_6$): 3 ppm 0.63 (m, 4 H) 0.90 (m, 1 H) 1.57 (m, 3 H) 2.10 (m, 2 H) 5.25 (m, 2 H) 7.44 (m, 8 H) 7.73 (m, 3 H) 8.16 (m, 1 H) 13.69 (m, 1 H). MS (ESI$^-$) m/z 501 (M–H)$^-$.

EXAMPLE 26H 4-hydroxy-3-(7-hydroxy-1,1-dioxido-4H-1,2,4-benzothiadiazin-3-yl)-1-methyl-1-propylnaphthalen-2(1 H)-one A solution of Example 26G (1.44 g, 2.87 mmol) in tetrahydrofuran (40 mL) was treated with 10% palladium on carbon (0.145 g, 10% weight) and stirred at 25° C. under a hydrogen balloon for 72 hours. The vessel was purged with nitrogen gas and the mixture was filtered through celite. The filtrate was concentrated in vacuo to give the title compound (0.732 g, 62%). $^1$H NMR (300 MHz, DMSO-d$_6$): δ ppm 0.63 (m, 4 H) 0.89 (m, 1 H) 1.57 (m, 3 H) 2.01 (m, 1 H) 2.19 (m, 1 H) 7.17 (m, 2 H) 7.55 (m, 2 H) 7.75 (m, 2 H) 8.15 (m, 1 H) 10.37 (m, 1 H) 13.71 (m, 1 H). MS (ESI$^-$) m/z 411 (M–H)$^-$.

EXAMPLE 26I

2-{[3-(1-hydroxy-4-methyl-3-oxo-4-propyl-3,4-dihydronaphthalen-2-yl)-1,1-dioxido-4H-1,2,4-benzothiadiazin-7-yl]oxy}acetamide A solution of 26H (0.100 g, 0.242 mmol), 2-bromoacetamide (0.100 g, 0.727 mmol), cesium carbonate (0.395 g, 1.21 mmol), and tetrabutylammonium iodide (0.009 g, 0.024 mmol) in dimethylformamide (2.5 mL) was stirred at 25° C. for 72 hours. The mixture was diluted with ethyl acetate, washed with water and brine, dried with sodium sulfate, filtered, and concentrated in vacuo to give the free acid (0.096 g).

EXAMPLE 26J sodium 2-[7-(2-amino-2-oxoethoxy)-1,1-dioxido-4H-1,2,4-benzothiadiazin-3-yl]-4-methyl-3-oxo-4-propyl-3,4-dihydronaphthalen-1-olate A suspension of the product of Example 26I (0.096 g) in water (2 mL) was treated with 0.997N sodium hydroxide solution (0.166 mL, 0.166 mmol) and stirred at 25° C. for 1 hour. The solution was lyophilized to give the title compound (0.078 g, 79% two steps). $^1$H NMR (300 MHz, DMSO-d$_6$): δ ppm 0.66 (m, 3 H) 1.32 (m, 4 H) 1.63 (m, 2 H) 2.08 (m, 1 H) 4.47 (m, 2 H) 7.30 (m, 8 H) 8.00 (m, 1 H) 15.38 (m, 1 H). MS (ESI$^-$) m/z 468 (M–H)$^-$.

EXAMPLE 27 sodium 2-[7-(2-amino-2-oxoethoxy)-1,1-dioxido-4H-1,2,4-benzothiadiazin-3-yl]-4-butyl-4-methyl-3-oxo-3,4-dihydronaphthalen-1-olate

EXAMPLE 27A

Benzyl (4E)-2-methyl-2-phenylhex-4-enoate

A solution of 2-phenyl-propionic acid benzyl ester (2.0 g, 8.32 mmol), crotyl chloride (1.02 mL, 9.99 mmol), and lithium iodide (1 g) in tetrahydrofuran (15 mL) at 0° C. was treated dropwise with the lithium hexamethyldisilazide (9.99 mL, IM in tetrahydrofuran, 9.99 mmol). The reaction was allowed to warm to 25° C. and stirred for 18 hours. The solvent was removed in vacuo and the residue was partitioned between water and ethyl acetate. The aqueous phase was extracted three times with ethyl acetate and the ethyl acetate layers were combined, dried with sodium sulfate, filtered, and concentrated in vacuo. The residue was chromatographed on silica gel eluting with hexane, then 10% ethyl acetate in hexane, and 20% ethyl acetate in hexane to give the title compound (2.43 g, 99%). $^1$H NMR (300 MHz, CDCl$_3$): δ ppm 1.55 (m, 6 H) 2.68 (m, 2 H) 5.10 (m, 2 H) 5.21 (m, 1 H) 5.45 (m, 1 H) 7.26 (m, 10 H). MS (ESI$^+$) m/z 312 (M+NH$_4$)$^+$.

EXAMPLE 27B 2-methyl-2-phenylhexanoic Acid

A solution of Example 27A (2.45 g, 8.32 mmol) in ethyl acetate (20 mL) was treated with 10% palladium on carbon (0.245 g, 10 weight percent) and stirred under a hydrogen balloon for 72 hours. The vessel was purged with nitrogen gas and the mixture was filtered through a pad of celite and the filtrate was concentrated in vacuo to give the title compound (1.71 g, 99%). $^1$H NMR (300 MHz, CDCl$_3$): δ ppm 0.87 (m, 3 H) 1.24 (m, 4 H) 1.57 (m, 3H) 1.98 (m, 2 H) 7.32 (m, 5 H). MS (DCI NH$_3$$^+$) m/z 224 (M+NH$_4$)$^+$.

EXAMPLE 27C diethyl 2-(2-methyl-2-phenylhexanoyl)malonate

A solution of diethyl malonate (1.27 mL, 8.34 mmol) in acetonitrile (15 mL) was cooled to 0° C. and treated with magnesium chloride (0.794 g, 8.34 mmol) followed by dropwise addition of triethylamine (2.44 mL, 17.6 mmol). The solution was stirred at 0° C. for 15 minutes and then stirred at 25° C. for 2 hours. A solution of Example 27B (1.72 g, 8.34 mmol) and dimethylformamide (0.710 mL, 9.17 mmol) in hexane (350 mL) was treated with oxalyl chloride (2.18 mL, 25.0 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo. The residue was chromatographed on silica gel eluting with hexane, then 10% ethyl acetate in hexane, and 20% ethyl acetate in hexane to give the title compound (2.59 g, 89%). $^1$H NMR (300 MHz, CDCl$_3$): δ ppm 0.85 (m, 3 H) 1.23 (m, 10 H) 1.53 (m, 3 H) 1.96 (m, 2 H) 4.08 (m, 4 H) 4.51 (m, 1 H) 7.32 (m, 5 H). MS (ESI$^-$) m/z 347 (M−H)$^-$.

EXAMPLE 27D

Ethyl 4-butyl-1-hydroxy-4-methyl-3-oxo-3,4-dihydronaphthalene-2-carboxylate

Example 27C (2.59 g, 7.43 mmol) was stirred in methanesulfonic acid (10 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (1.92 g, 85%). $^1$H NMR (300 MHz, CDCl$_3$): δ ppm 0.62 (m, 1 H) 0.73 (t, 3 H) 0.92 (m, 1 H) 1.13 (m, 2 H) 1.47 (m, 4.5 H) 1.64 (s, 1.5 H) 1.76 (m, 0.5 H) 1.94 (m, 0.5 H) 2.27 (m, 1 H) 4.47 (m, 2 H) 7.42 (m, 2 H) 7.59 (m, 1 H) 8.16 (m, 0.5 H) 8.24 (m, 0.5 H) 15.09 (s, 0.5 H) 15.17 (s, 0.5 H); MS (ESI$^-$) m/z 301 (M−H)$^-$.

EXAMPLE 27E 1-butyl-4-hydroxy-1-methylnaphthalen-2(1 H)-one

A solution of Example 27D (1.92 g, 6.35 mmol) in 1,4-dioxane (25 mL) was treated with aqueous 1N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (0.527 g, 36%). $^1$H NMR (300 MHz, CDCl$_3$) δ ppm 0.56 (m, 0.5 H) 0.70 (t, 1.5 H) 0.81 (t, 1.5 H) 0.92 (m, 1 H) 1.16 (m, 2.5 H) 1.53 (s, 1.5 H) 1.56 (s, 1.5 H) 1.85 (m, 1 H) 2.03 (m, 0.5 H) 2.26 (m, 0.5 H) 3.74 (s, 0.5 H) 3.75 (s, 0.5 H) 6.22 (s, 0.55 H) 7.44 (m, 2 H) 7.62 (m, 1 H) 8.08 (0.5, 1 H) 8.14 (m, 0.5 H). MS (DCI NH$_3$$^+$) m/z 248 (M+NH$_4$)$^+$.

EXAMPLE 27F

2-[bis(methylthio)methylene]-4-butyl-4-methylnaphthalene-1,3(2H,4 H)-dione

A solution of Example 27E (0.527 g, 2.23 mmol) and pyridine (1.48 mL, 18.31 mmol) in 1,4-dioxane (15 mL) was treated with Example 5A (2.43 g, 9.15 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (0.741 g, 97%). $^1$H NMR (300 MHz, CDCl$_3$): δ ppm 0.73 (m, 3 H) 0.82 (m, 1 H) 0.93 (m, 1 H) 1.13 (m, 2 H) 1.54 (m, 3 H) 1.77 (m, 1 H) 2.23 (m, 1 H) 2.56 (m, 6 H) 7.40 (m, 2 H) 7.57 (m, 1 H) 8.21 (m, 1 H). MS (ESI$^+$) m/z 335 (M+H)$^+$.

EXAMPLE 27G

3-[7-(benzyloxy)-1,1-dioxido-4H-1,2,4-benzothiadiazin-3-yl]-1-butyl-4-hydroxy-1-methylnaphthalen-2(1 H)-one A solution of Example 27F (0.741 g, 2.22 mmol) and Example 2D (0.616 g, 2.22 mmol) in toluene (100 mL) was refluxed for 6 hours. The solution was cooled to 25° C. and concentrated in vacuo. The residue was stirred in a solution of diethyl ether and hexane (1:5, 100 mL) and the precipitate was filtered and dried to give the title compound (1.00 g, 88%). $^1$H NMR (300 MHz, DMSO-d$_6$): δ ppm 0.53 (m, 1 H) 0.70 (m, 3 H) 0.89 (m, 1 H) 1.11 (m, 2H) 1.57 (m, 3 H) 2.13 (m, 2 H) 5.25 (m, 2 H) 7.44 (m, 8 H) 7.73 (m, 3 H) 8.17 (m, 1 H) 13.71 (m, 1 H).

EXAMPLE 27H 1-butyl-4-hydroxy-3-(7-hydroxy-1,1-dioxido-4H-1,2,4-benzothiadiazin-3-yl)-1-methylnaphthalen-2(1 H)-one A solution of Example 27G (1.00 g, 1.94 mmol) in tetrahydrofuran (40 mL) was treated with 10% palladium on carbon (0.100 g, 10% weight) and stirred at 25° C. under a hydrogen balloon for 72 hours. The vessel was purged with nitrogen gas and the mixture was filtered through celite. The filtrate was concentrated in vacuo to give the title compound (0.824 g, 99%). $^1$H NMR (300 MHz, DMSO-d$_6$): δ ppm 0.54 (m, 1 H) 0.69 (m, 3 H) 0.86 (m, 1 H) 1.10 (m, 2 H) 1.56 (m, 3 H) 2.14 (m, 2 H) 7.18 (m, 2 H) 7.56 (m, 2 H) 7.76 (m, 2 H) 8.16 (m, 1 H) 10.40 (m, 1 H) 13.68 (m, 1 H). MS (ESI$^-$) m/z 425 (M−H)$^-$.

EXAMPLE 27I

2-{[3-(4-butyl-1-hydroxy-4-methyl-3-oxo-3,4-dihydronaphthalen-2-yl)-1,1-dioxido-4H-1,2,4-benzothiadiazin-7-yl]oxy}acetamide A solution of Example 27H (0.100 g, 0.235 mmol), 2-bromoacetamide (0.097 g, 0.703 mmol), cesium carbonate (0.382 g, 1.17 mmol), and tetrabutylammonium iodide (0.001 g, 0.024 mmol) in dimethylformamide (2.5 mL) was stirred at 25° C. for 72 hours. The mixture was diluted with ethyl acetate, washed with water and brine, dried with sodium sulfate, filtered, and concentrated in vacuo to give the free acid (0.076 g).

EXAMPLE 27J

Sodium 2-[7-(2-amino-2-oxoethoxy)-1,1-dioxido-4H-1,2,4-benzothiadiazin-3-yl]-4-butyl-4-methyl-3-oxo-3,4-dihydronaphthalen-1-olate A suspension of the product of Example 27I in water (2 mL) was treated with 0.997N sodium hydroxide solution (0.159 mL, 0.158 mmol) and stirred at 25° C. for 1 hour. The solution was lyophilized to give the title compound (0.075 g, 64% two steps). $^1$H NMR (300 MHz, DMSO-d$_6$): δ ppm 0.56 (m, 1 H) 0.69 (m, 3 H) 0.87 (m, 1 H) 1.07 (m, 2 H) 1.28 (m, 1H) 1.38 (m, 3 H) 1.57 (m, 1 H) 1.71 (m, 1 H) 2.13 (m, 1 H) 4.48 (m, 2 H) 7.29 (m, 6 H) 8.05 (m, 1 H) 15.40 (m, 1 H). MS (ESI$^-$) m/z 482 (M–H)$^-$.

EXAMPLE 28

Sodium 2-[7-(2-amino-2-oxoethoxy)-1,1-dioxido-4H-1,2,4-benzothiadiazin-3-yl]-4-methyl-4-(3-methylbutyl)-3-oxo-3,4-dihydronaphthalen-1-olate

EXAMPLE 28A

Benzyl 2,5-dimethyl-2-phenylhex-4-enoate

A solution of 2-phenyl-propionic acid benzyl ester (2.0 g, 8.32 mmol), 4-bromo-2-methyl-2-butene (1.21 mL, 9.99 mmol), and lithium iodide (1 g) in tetrahydrofuran (15 mL) at 0° C. was treated dropwise with the lithium hexamethyldisilazide (9.99 mL, 1M in tetrahydrofuran, 9.99 mmol). The reaction was allowed to warm to 25° C. and stirred for 18 hours. The solvent was removed in vacuo and the residue was partitioned between water and ethyl acetate. The aqueous phase was extracted three times with ethyl acetate and the ethyl acetate layers were combined, dried with sodium sulfate, filtered, and concentrated in vacuo. The residue was chromatographed on silica gel eluting with hexane, then 10% ethyl acetate in hexane, and 20% ethyl acetate in hexane to give the title compound (2.51 g, 98%). $^1$H NMR (300 MHz, CDCl$_3$): δ ppm 1.53 (m, 6 H) 1.63 (m, 3 H) 2.60 (m, 1 H) 2.80 (m, 1 H) 4.94 (m, 1 H) 5.11 (m, 2 H) 7.26 (m, 10 H). MS (ESI$^+$) m/z 326 (M+NH$_4$)$^+$.

EXAMPLE 28B 2,5-dimethyl-2-phenylhexanoic Acid

A solution of Example 28A (2.51 g, 8.14 mmol) in ethyl acetate (20 mL) was treated with 10% palladium on carbon (0.251 g, 10 weight percent) and stirred under a hydrogen balloon for 72 hours. The vessel was purged with nitrogen gas and the mixture was filtered through a pad of celite and the filtrate was concentrated in vacuo to give the title compound (1.72 g, 96%). $^1$H NMR (300 MHz, CDCl$_3$): δ ppm 0.87 (m, 6 H) 1.09 (m, 2 H) 1.51 (m, 4H) 1.98 (m, 2 H) 7.34 (m, 5 H). MS (DCI NH$_3^+$) m/z 238 (M+NH$_4$)$^+$.

EXAMPLE 28C

Diethyl 2-(2,5-dimethyl-2-phenylhexanoyl)malonate

A solution of diethyl malonate (1.16 mL, 7.66 mmol) in acetonitrile (15 mL) was cooled to 0° C. and treated with magnesium chloride (0.730 g, 7.66 mmol) followed by dropwise addition of triethylamine (2.24 mL, 16.1 mmol). The solution was stirred at 0° C. for 15 minutes and then stirred at 25° C. for 2 hours. A solution of Example 28B (1.69 g, 7.66 mmol) and dimethylformamide (0.653 mL, 8.43 mmol) in hexane (350 mL) was treated with oxalyl chloride (2.01 mL, 23.0 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo to give the title compound as a crude product (2.78 g). $^1$H NMR (300 MHz, CDCl$_3$): δ ppm 0.84 (m, 6 H) 1.13 (m, 8 H) 1.50 (m, 4 H) 1.97 (m, 2 H) 4.08 (m, 4 H) 4.51 (m, 1 H) 7.32 (m, 5 H).

EXAMPLE 28D

Ethyl 1-hydroxy-4-methyl-4-(3-methylbutyl)-3-oxo-3,4-dihydronaphthalene-2-carboxylate Example 28C (2.78 g, 7.67 mmol) was stirred in methanesulfonic acid (10 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (2.06 g, 85%). $^1$H NMR (300 MHz, CDCl$_3$) δ ppm 0.52 (m, 1 H) 0.73 (m, 6 H) 0.87 (m, 1 H) 1.36 (m, 1 H) 1.47 (m, 4.5 H) 1.64 (s, 1.5 H) 1.78 (m, 0.5 H) 1.95 (m, 0.5 H) 2.23 (m, 0.5 H) 2.33 (m, 0.5 H) 4.47 (m, 2 H) 7.41 (m, 2 H) 7.59 (m, 1 H) 8.16 (m, 0.5 H) 8.24 (m, 0.5 H) 15.07 (s, 0.5 H) 15.16 (s, 0.5 H). MS (ESI$^-$) m/z 315 (M–H)$^-$.

EXAMPLE 28E 4-hydroxy-1-methyl-1-(3-methylbutyl)naphthalen-2(1H)-one

A solution of Example 28D (2.06 g, 6.52 mmol) in 1,4-dioxane (25 mL) was treated with aqueous 1N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (1.05 g, 66%). $^1$H NMR (300 MHz, CDCl$_3$) δ ppm 0.44 (m, 0.5 H) 0.73 (m, 3.5 H) 0.80 (m, 3 H) 1.06 (m, 1 H) 1.39 (m, 1 H) 1.56 (s, 1.5 H) 1.59 (s, 1.5 H) 2.04 (m, 1 H) 2.30 (m, 1 H) 3.74 (s, 0.5 H) 3.75 (s, 0.5 H) 6.63 (s, 0.5 H) 7.46 (m, 2 H) 7.66 (m, 1H) 8.08 (m, 0.5 H) 8.20 (m, 0.5 H). MS (DCI NH$_3^+$) m/z 262 (M+NH$_4$)$^+$.

EXAMPLE 28F

2-[bis(methylthio)methylene]-4-methyl-4-(3-methylbutyl)naphthalene-1,3(2H,4H)-dione A solution of Example 28E (1.05 g, 4.30 mmol) and pyridine (2.78 mL, 34.4 mmol) in 1,4-dioxane (15 mL) was treated with Example 5A (4.56 g, 17.2 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (1.39 g, 93%). $^1$H NMR (300 MHz, DMSO-d$_6$): δ ppm 0.54 (m, 1 H) 0.73 (m, 7H) 1.30 (m, 1 H) 1.47 (m, 3 H) 1.81 (m, 1 H) 2.11 (m, 1 H) 2.55 (m, 6 H) 7.43 (m, 1 H) 7.62 (m, 2 H) 8.04 (m, 1 H). MS (ESI$^+$) m/z 349 (M+H)$^+$.

EXAMPLE 28G

3-[7-(benzyloxy)-1,1-dioxido-4H-1,2,4-benzothiadiazin-3-yl]-4-hydroxy-1-methyl-1-(3-methylbutyl)naphthalen-2(1 H)-one A solution of Example 28F (1.39 g, 3.99 mmol) and Example 2D (1.11 g, 3.99 mmol) in toluene (100 mL) was refluxed for 6 hours. The solution was cooled to 25° C. and concentrated in vacuo. The residue was stirred in a solution of diethyl ether and hexane (1:5, 100 mL) and the precipitate was filtered and dried to give the title compound (1.68 g, 80%). $^1$H NMR (300 MHz, DMSO-d$_6$): δ ppm 0.41 (m, 1 H) 0.74 (m, 7 H) 1.31 (m, 1 H) 1.57 (m, 3H) 2.14 (m, 2 H) 5.25 (m, 2 H) 7.45 (m, 8 H) 7.74 (m, 3 H) 8.16 (m, 1 H) 13.72 (m, 1 H). MS (ESI$^-$) m/z 529 (M–H)$^-$.

EXAMPLE 28H 4-hydroxy-3-(7-hydroxy-1,1-dioxido-4H-1,2,4-benzothiadiazin-3-yl)-1-methyl-1-(3-methylbutyl)naphthalen-2(1 H)-one A solution of Example 28G (1.68 g, 3.17 mmol) in tetrahydrofuran (40 mL) was treated with 10% palladium on carbon (0.168 g, 10% weight) and stirred at 25° C. under a hydrogen balloon for 72 hours. The vessel was purged with nitrogen gas and the mixture was filtered through celite. The filtrate was concentrated in vacuo to give the title compound (1.38 g, 99%). $^1$H NMR (300 MHz, DMSO-d$_6$): δ ppm 0.43 (m, 1 H) 0.74 (m, 7 H) 1.32 (m, 1 H) 1.58 (m, 3 H) 2.15 (m, 2 H) 7.17 (m, 2 H) 7.57 (m, 2 H) 7.76 (m, 2 H) 8.16 (m, 1 H) 10.40 (m, 1 H) 13.66 (m, 1 H). MS (ESI$^-$) m/z 439 (M–H)$^-$.

EXAMPLE 28I 2-({3-[1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide A solution of Example 28H (0.100 g, 0.227 mmol), 2-bromoacetamide (0.124 g, 0.681 mmol), cesium carbonate (0.390 g, 1.14 mmol), and tetrabutylammonium iodide (0.011 g, 0.024 mmol) in dimethylformamide (2.5 mL) was stirred at 25° C. for 72 hours. The mixture was diluted with ethyl acetate, washed with water and brine, dried with sodium sulfate, filtered, and concentrated in vacuo to give the free acid (0.099 g).

EXAMPLE 28J

Sodium 2-[7-(2-amino-2-oxoethoxy)-1,1-dioxido-4H-1,2,4-benzothiadiazin-3-yl]-4-methyl-4-(3-methylbutyl)-3-oxo-3,4-dihydronaphthalen-1-olate A suspension of the product of Example 28I (0.099 g) in water (2 mL) was treated with 0.997N sodium hydroxide solution (0.200 mL, 0.199 mmol) and stirred at 25° C. for 1 hour. The solution was lyophilized to give the title compound (0.100 g, 85% two steps). $^1$H NMR (300 MHz, DMSO-d$_6$): δ ppm 0.43 (m, 1 H) 0.75 (m, 7 H) 1.31 (m, 5 H) 1.64 (m, 2 H) 2.14 (m, 1 H) 4.45 (m, 2 H) 7.31 (m, 6 H) 8.05 (m, 1 H) 15.42 (m, 1 H). MS (ESI$^-$) m/z 496 (M–H)$^-$.

EXAMPLE 29

Sodium 2-(1,1-dioxido-4H-1,2,4-benzothiadiazin-3-yl)-4-methyl-3-oxo-4-propyl-3,4-dihydronaphthalen-1-olate

EXAMPLE 29A 3-(1,1-dioxido-4H-1,2,4-benzothiadiazin-3-yl)-4-hydroxy-1-methyl-1-propylnaphthalen-2(1 H)-one A solution of Example 26F (0.092 g, 0.287 mmol) and 2-amino-benzenesulfonamide (0.052 g, 0.301 mmol) in toluene (7 mL) was refluxed for 6 hours. The solution was cooled to 25° C. and concentrated in vacuo. The residue was chromatographed on silica gel eluting with hexane followed by 20% and 30% ethyl acetate in hexane to give the desired product (0.113 g, 99%).

EXAMPLE 29B

Sodium 2-(1,1-dioxido-4H-1,2,4-benzothiadiazin-3-yl)-4-methyl-3-oxo-4-propyl-3,4-dihydronaphthalen-1-olate A suspension of the product of Example 29A (0.113 g) in water (2 mL) was treated with 0.997N sodium hydroxide solution (0.286 mL, 0.285 mmol) and stirred at 25° C. for 1 hour. The solution was lyophilized to give the title compound (0.119 g, 99%). $^1$H NMR (300 MHz, DMSO-d$_6$): δ ppm 0.64 (m, 4 H) 0.91 (m, 1 H) 1.40 (m, 3 H) 1.68 (m, 1 H) 2.10 (m, 1H) 7.30 (m, 3 H) 7.49 (m, 3 H) 7.64 (m, 1 H) 8.05 (m, 1 H) 15.44 (m, 1 H). MS (ESI$^-$) m/z 395 (M–H)$^-$.

EXAMPLE 30

Sodium 4-butyl-2-(1,1-dioxido-4H-1,2,4-benzothiadiazin-3-yl)-4-methyl-3-oxo-3,4-dihydronaphthalen-1-olate

EXAMPLE 30A 1-butyl-3-(1,1-dioxido-4H-1,2,4-benzothiadiazin-3-yl)-4-hydroxy-1-methylnaphthalen-2(1 H)-one A solution of Example 27F (0.064 g, 0.191 mmol) and 2-amino-benzenesulfonamide (0.035 g, 0.201 mmol) in toluene (7 mL) was refluxed for 6 hours. The solution was cooled to 25° C. and concentrated in vacuo. The residue was chromatographed on silica gel eluting with hexane followed by 20% and 30% ethyl acetate in hexane to give the desired product (0.067 g, 86%).

EXAMPLE 30B

Sodium 4-butyl-2-(1,1-dioxido-4H-1,2,4-benzothiadiazin-3-yl)-4-methyl-3-oxo-3,4-dihydronaphthalen-1-olate A suspension of the product of Example 30A (0.067 g) in water (2 mL) was treated with 0.997N sodium hydroxide solution (0.163 mL, 0.163 mmol) and stirred at 25° C. for 1 hour. The solution was lyophilized to give the title compound (0.070 g, 99%). $^1$H NMR (300 MHz, DMSO-d$_6$): δ ppm 0.55 (m, 1 H) 0.68 (m, 3 H) 0.87 (m, 1 H) 1.06 (m, 2 H) 1.38 (m, 3H) 1.72 (m, 1 H) 2.13 (m, 1 H) 7.29 (m, 3 H) 7.49 (m, 3 H) 7.64 (m, 1 H) 8.05 (m, 1 H) 15.46 (m, 1 H). MS (ESI$^-$) m/z 409 (M–H)$^-$.

EXAMPLE 31

Sodium 2-(1,1-dioxido-4H-1,2,4-benzothiadiazin-3-yl)-4-methyl-4-(3-methylbutyl)-3-oxo-3,4-dihydronaphthalen-1-olate

EXAMPLE 31A 3-(1,1-dioxido-4H-1,2,4-benzothiadiazin-3-yl)-4-hydroxy-1-methyl-1-(3-methylbutyl)naphthalen-2(1H)-one A solution of Example 28F (0.087 g, 0.250 mmol) and 2-amino-benzenesulfonamide (0.045 g, 0.262 mmol) in toluene (7 mL) was refluxed for 6 hours. The solution was cooled to 25° C. and concentrated in vacuo. The residue was chromatographed on silica gel eluting with hexane followed by 20% and 30% ethyl acetate in hexane to give the desired product (0.105 g, 99%).

EXAMPLE 31B

Sodium 2-(1,1-dioxido-4H-1,2,4-benzothiadiazin-3-yl)-4-methyl-4-(3-methylbutyl)-3-oxo-3,4-dihydronaphthalen-1-olate A suspension of the product of Example 31A (0.105 g) in water (2 mL) was treated with 0.997N sodium hydroxide solution (0.248 mL, 0.2247 mmol) and stirred at 25° C. for 1 hour. The solution was lyophilized to give the title compound (0.110 g, 99%). $^1$H NMR (300 MHz, DMSO-d$_6$): δ ppm 0.47 (m, 1 H) 0.68 (m, 6 H) 0.80 (m, 1 H) 1.28 (m, 1 H) 1.39 (m, 3 H) 1.73 (m, 1 H) 2.15 (m, 1 H) 7.29 (m, 3 H) 7.50 (m, 3 H) 7.65 (m, 1 H) 8.05 (m, 1 H) 15.48 (m, 1 H). MS (ESI$^-$) m/z 423 (M–H)$^-$.

EXAMPLE 32

Sodium 4-methyl-2-{7-[(methylsulfonyl)amino]-1,1-dioxido-4H-1,2,4-benzothiadiazin-3-yl}-3-oxo-4-propyl-3,4-dihydronaphthalen-1-olate

EXAMPLE 32A tert-butyl 3-(1-hydroxy-4-methyl-3-oxo-4-propyl-3,4-dihydronaphthalen-2-yl)-1,1-dioxido-4H-1,2,4-benzothiadiazin-7-ylcarbamate A solution of Example 26F (0.365 g, 1.14 mmol) and Example 17A (0.360 g, 1.25 mmol) in toluene (30 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.570 g, 98%). $^1$H NMR (300 MHz, DMSO-d$_6$): δ ppm 0.63 (m, 4 H) 0.90 (m, 1 H) 1.49 (m, 9 H) 1.55 (m, 3H) 2.00 (m, 1 H) 2.18 (m, 1 H) 7.63 (m, 5 H) 8.13 (m, 2 H) 9.85 (m, 1 H) 13.88 (m, 1 H). MS (ESI$^-$) m/z 510 (M–H)$^-$.

EXAMPLE 32B 3-(7-amino-1,1-dioxido-4H-1,2,4-benzothiadiazin-3-yl)-4-hydroxy-1-methyl-1-propylnaphthalen-2(1H)-one hydrochloride A solution of Example 32A (0.488 g, 0.954 mmol) in 4M hydrochloric acid in 1,4-dioxane (10 mL) was stirred at 25° C. for 1 hour. The solution was concentrated in vacuo and the residue was triturated in diethyl ether to give the title compound (0.363 g, 85%). $^1$H NMR (300 MHz, DMSO-d$_6$): δ ppm 0.63 (m, 4 H) 0.88 (m, 1 H) 1.57 (m, 3 H) 2.10 (m, 2 H) 7.02 (m, 2 H) 7.45 (m, 1 H) 7.55 (m, 1 H) 7.76 (m, 2 H) 8.16 (m, 1 H) 13.56 (m, 1 H). MS (ESI$^-$) m/z 410 (M–H)$^-$.

EXAMPLE 32C

N-[3-(1-hydroxy-4-methyl-3-oxo-4-propyl-3,4-dihydronaphthalen-2-yl)-1,1-dioxido-4H-1,2,4-benzothiadiazin-7-yl]methanesulfonamide A solution of Example 32B (0.050 g, 0.112 mmol), mesyl chloride (0.035 mL, 0.447 mmol), and pyridine (0.073 mL, 0.893 mmol) in acetone (1.5 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.049 g, 89%).

EXAMPLE 32D

Sodium 4-methyl-2-{7-[(methylsulfonyl)amino]-1,1-dioxido-4H-1,2,4-benzothiadiazin-3-yl}-3-oxo-4-propyl-3,4-dihydronaphthalen-1-olate A suspension of the product of Example 32C (0.049 g) in water (2 mL) was treated with 0.997N sodium hydroxide solution (0.099 mL, 0.098 mmol) and stirred at 25° C. for 1 hour. The solution was lyophilized to give the title compound (0.043 g, 86%). $^1$H NMR (300 MHz, DMSO-d$_6$): δ ppm 0.64 (m, 4 H) 0.89 (m, 1 H) 1.38 (m, 3 H) 1.68 (m, 1 H) 2.10 (m, 1H) 2.93 (m, 3 H) 7.28 (m, 3 H) 7.45 (m, 3 H) 8.05 (m, 1 H) 9.85 (m, 1 H) 15.42 (m, 1 H). MS (ESI$^-$) m/z 488 (M–H)$^-$.

EXAMPLE 33

Sodium 4-butyl-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 33A tert-butyl 3-(4-butyl-1-hydroxy-4-methyl-3-oxo-3,4-dihydronaphthalen-2-yl)-1,1-dioxido-4H-1,2,4-benzothiadiazin-7-ylcarbamate A solution of Example 27F (0.296 g, 0.885 mmol) and (4-amino-3-sulfamoyl-phenyl)-carbamic acid tert-butyl ester (0.280 g, 0.973 mmol) in toluene (40 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.430 g, 92%). $^1$H NMR (300 MHz, DMSO-$d_6$): δ ppm 0.53 (m, 1 H) 0.69 (m, 3 H) 0.87 (m, 1 H) 1.08 (m, 2 H) 1.46 (m, 9 H) 1.55 (m, 3 H) 2.01 (m, 1 H) 2.20 (m, 1 H) 7.60 (m, 5 H) 8.13 (m, 2 H) 9.83 (m, 1 H) 13.93 (m, 1 H). MS (ESI$^-$) m/z 524 (M−H)$^-$.

EXAMPLE 33B 3-(7-amino-1,1-dioxido-4H-1,2,4-benzothiadiazin-3-yl)-1-butyl-4-hydroxy-1-methylnaphthalen-2(1 H)-one hydrochloride A solution of Example 33A (0.349 g, 0.664 mmol) in 4M hydrochloric acid in 1,4-dioxane (10 mL) was stirred at 25° C. for 1 hour. The solution was concentrated in vacuo and the residue was triturated in diethyl ether to give the title compound (0.277 g, 90%). $^1$H NMR (300 MHz, DMSO-$d_6$): δ ppm 0.54 (m, 1 H) 0.69 (m, 3 H) 0.86 (m, 1 H) 1.09 (m, 2 H) 1.56 (m, 3 H) 2.13 (m, 2 H) 7.04 (m, 2 H) 7.51 (m, 2 H) 7.76 (m, 2 H) 8.16 (m, 1 H) 13.57 (m, 1 H). MS (ESI$^-$) m/z 424 (M−H)$^-$.

EXAMPLE 33C

N-[3-(4-butyl-1-hydroxy-4-methyl-3-oxo-3,4-dihydronaphthalen-2-yl)-1,1-dioxido-4H-1,2,4-benzothiadiazin-7-yl]methanesulfonamide A solution of Example 33B (0.052 g, 0.112 mmol), mesyl chloride (0.035 mL, 0.447 mmol), and pyridine (0.073 mL, 0.893 mmol) in acetone (1.5 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.054 g, 96%).

EXAMPLE 33D

Sodium 4-butyl-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 33C (0.054 g) in water (2 mL) was treated with 0.997N sodium hydroxide solution (0.108 mL, 0.107 mmol) and stirred at 25° C. for 1 hour. The solution was lyophilized to give the title compound (0.052 g, 93%). $^1$H NMR (300 MHz, DMSO-$d_6$): δ ppm 0.57 (m, 1 H) 0.68 (m, 3 H) 0.87 (m, 1 H) 1.06 (m, 2 H) 1.38 (m, 3H) 1.71 (m, 1 H) 2.13 (m, 1 H) 2.95 (m, 3 H) 7.31 (m, 3 H) 7.46 (m, 3 H) 8.05 (m, 1 H) 9.86 (m, 1 H) 15.48 (m, 1 H). MS (ESI$^-$) m/z 502 (M−H)$^-$.

EXAMPLE 34

Sodium 4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate

EXAMPLE 34A tert-butyl 3-[1-hydroxy-4-methyl-4-(3-methylbutyl)-3-oxo-3,4-dihydronaphthalen-2-yl]-1,1-dioxido-4H-1,2,4-benzothiadiazin-7-ylcarbamate A solution of Example 28F (0.518 g, 1.49 mmol) and Example 17A (0.448 g, 1.56 mmol) in toluene (40 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.615 g, 77%). $^1$HNMR (300 MHz, DMSO-$d_6$): δ ppm 0.42 (m, 1 H) 0.69 (m, 6 H) 0.84 (m, 1 H) 1.30 (m, 1H) 1.48 (m, 9 H) 1.57 (m, 3 H) 2.14 (m, 2 H) 7.53 (m, 1 H) 7.70 (m, 4 H) 8.14 (m, 2 H) 9.88 (m, 1 H) 13.79 (m, 1 H).

EXAMPLE 34B 3-(7-amino-1,1-dioxido-4H-1,2,4-benzothiadiazin-3-yl)-4-hydroxy-1-methyl-1-(3-methylbutyl)naphthalen-2(1 H)-one hydrochloride A solution of Example 34A (0.615 g, 1.14 mmol) in 4M hydrochloric acid in 1,4-dioxane (10 mL) was stirred at 25° C. for 1 hour. The solution was concentrated in vacuo and the residue was triturated in diethyl ether to give the title compound (0.456 g, 84%). $^1$H NMR (300 MHz, DMSO-$d_6$): δ ppm 0.42 (m, 1 H) 0.74 (m, 7 H) 1.32 (m, 1 H) 1.58 (m, 3 H) 2.15 (m, 2 H) 7.07 (m, 2 H) 7.51 (m, 2 H) 7.77 (m, 2 H) 8.16 (m, 1 H) 13.57 (m, 1 H). MS (ESI$^-$) m/z 438 (M−H)$^-$.

EXAMPLE 34C

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide A solution of Example 34B (0.053 g, 0.112 mmol), mesyl chloride (0.035 mL, 0.447 mmol), and pyridine (0.073 mL, 0.893 mmol) in acetone (1.5 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.049 g, 84%). $^1$HNMR (300 MHz, DMSO-$d_6$): δ ppm 0.43 (m, 1 H) 0.74 (m, 7 H) 1.34 (m, 1 H) 1.57 (m, 3 H) 2.15 (m, 2 H) 3.08 (m, 3 H) 7.56 (m, 3 H) 7.75 (m, 3 H) 8.16 (m, 1 H) 10.26 (m, 1 H) 13.76 (m, 1 H).

EXAMPLE 34D

Sodium 4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate A suspension of the product of Example 34C (0.049 g) in water (2 mL) was treated with 0.997N sodium hydroxide solution (0.095 mL, 0.095 mmol) and stirred at 25° C. for 1 hour. The solution was lyophilized to give the title compound (0.051 g, 99%). $^1$H NMR (300 MHz, DMSO-d$_6$): δ ppm 0.46 (m, 1 H) 0.69 (m, 6 H) 0.80 (m, 1 H) 1.29 (m, 1 H) 1.38 (m, 3H) 1.72 (m, 1 H) 2.14 (m, 1 H) 2.90 (m, 3 H) 7.34 (m, 6 H) 8.05 (m, 1 H) 15.42 (m, 1 H). MS (ESI$^-$) m/z 516 (M–H)$^-$.

EXAMPLE 35

Sodium 4-(5,5-dimethylhexyl)-2-(1,1-dioxido-4H-1,2,4-benzothiadiazin-3-yl)-4-methyl-3-oxo-3,4-dihydronaphthalen-1-olate

EXAMPLE 35A 5,5-dimethylhex-1-en-3-ol

A solution of 3,3-dimethylbutyraldehyde (5.0 mL, 39.8 mmol) in tetrahydrofuran (30 mL) was added dropwise to a solution of vinylmagnesium bromide (47.8 mL, 1 M in tetrahydrofuran, 47.8 mmol) stirring at –20° C. The solution was stirred for 30 minutes at –20° C. at which time saturated ammonium chloride solution (75 mL) was added and the reaction was allowed to warm to 25° C. The solution was diluted with water and extracted three times with ethyl acetate. The ethyl acetate layers were combined and washed with brine, dried with sodium sulfate, filtered, and concentrated in vacuo. The residue was chromatographed on silica gel eluting with hexane, followed by 5% and 10% ethyl acetate in hexane to give the title compound (0.780 g, 15%). $^1$H NMR (300 MHz, CDCl$_3$): δ ppm 0.98 (m, 9 H) 1.45 (m, 2H) 4.26 (m, 1 H) 5.06 (m, 1 H) 5.21 (m, 1 H) 5.90 (m, 1 H).

EXAMPLE 35B (2E)-1-bromo-5,5-dimethylhex-2-ene

To a solution of Example 35A (2.38 g, 18.56 mmol) and 1,5-hexadiene (1.65 mL, 13.9 mmol) in 1,2-dichloroethane (30 mL), stirring at 0° C., was added thionyl bromide (2.16 mL, 27.8 mmol). The reaction was stirred for 2 hours at 0° C. and then quenched with water. The mixture was extracted with diethyl ether and the diethyl ether layer was washed with saturated sodium bicarbonate solution, dried with sodium sulfate, filtered, and concentrated in vacuo to give the title compound 3.15 g, 89%). $^1$H NMR (300 MHz, CDCl$_3$): δ ppm 0.87 (m, 9 H) 1.94 (m, 2 H) 3.97 (m, 2 H) 5.74 (m, 2 H).

EXAMPLE 35C

Benzyl (4E)-2,7,7-trimethyl-2-phenyloct-4-enoate

A solution of 2-phenyl-propionic acid benzyl ester (3.15 g, 13.1 mmol) in tetrahydrofuran (25 mL) at –78° C. was treated dropwise with a lithium hexamethyldisilazide solution (14.4 mL, IM in tetrahydrofuran, 14.4 mmol) and stirred for 30 minutes at –78° C. Example 35B (3.26 g, 17.0 mmol) was added to the solution and the reaction was allowed to warm to 25° C. and stirred for an additional 4 hours. The solvent was removed in vacuo and the residue was partitioned between water and ethyl acetate. The aqueous phase was extracted three times with ethyl acetate and the ethyl acetate layers were combined, washed with a saturated sodium bicarbonate solution, dried with sodium sulfate, filtered, and concentrated in vacuo. The residue was chromatographed on silica gel eluting with hexane, then 5% ethyl acetate in hexane, and 10% ethyl acetate in hexane to give the title compound (3.32 g, 72%). $^1$H NMR (300 MHz, CDCl$_3$): δ ppm 0.80 (m, 9 H) 1.53 (m, 3 H) 1.79 (m, 2H) 2.63 (m, 1 H) 2.82 (m, 1 H) 5.10 (m, 2 H) 5.18 (m, 1 H) 5.47 (m, 1 H) 7.27 (m, 10 H). MS (ESI$^+$) m/z 368 (M+NH$_4$)$^+$.

EXAMPLE 35D 2,7,7-trimethyl-2-phenyloctanoic Acid

A solution of Example 35C (3.32 g, 9.47 mmol) in ethyl acetate (50 mL) was treated with 10% palladium on carbon (0.332 g, 10 weight percent) and stirred under a hydrogen balloon for 72 hours. The vessel was purged with nitrogen gas and the mixture was filtered through a pad of celite and the filtrate was concentrated in vacuo to give the title compound (2.48 g, 99%). $^1$H NMR (300 MHz, CDCl$_3$): δ ppm 0.84 (m, 9 H) 1.19 (m, 6 H) 1.57 (m, 3H) 1.98 (m, 2 H) 7.34 (m, 5 H).

EXAMPLE 35E

Diethyl 2-(2,7,7-trimethyl-2-phenyloctanoyl)malonate

A solution of diethyl malonate (1.53 mL, 9.95 mmol) in acetonitrile (20 mL) was cooled to 0° C. and treated with magnesium chloride (0.966 g, 9.95 mmol) followed by dropwise addition of triethylamine (2.91 mL, 20.9 mmol). The solution was stirred at 0° C. for 15 minutes and then stirred at 25° C. for 2 hours.

A solution of Example 35D (2.61 g, 9.95 mmol) and dimethylformamide (0.85 mL, 10.9 mmol) in hexane (475 mL) was treated with oxalyl chloride (2.65 mL, 29.8 mmol) and stirred at 25° C. for 2 hours. The hexane supernatant was decanted from the residue, filtered through celite, and concentrated in vacuo to give the acid chloride.

The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo to give the desired product which was taken onto the next reaction without further purification (4.01 g, 99%).

EXAMPLE 35F

Ethyl 4-(5,5-dimethylhexyl)-1-hydroxy-4-methyl-3-oxo-3,4-dihydronaphthalene-2-carboxylate Example 35E (4.02 g, 9.94 mmol) was stirred in methanesulfonic acid (20 mL) at 25° C. for 3 hours. The solution was partitioned between cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (1.84 g, 51%). $^1$H NMR (300 MHz, CDCl$_3$): δ ppm 0.63 (m, 1 H) 0.76 (s, 9 H) 0.99 (m, 3 H) 1.26 (m, 2 H) 1.46 (m, 4.5 H) 1.64 (s, 1.5 H) 1.77 (m, 0.5 H) 1.95 (m, 0.5 H)

2.28 (m, 1 H) 4.46 (m, 2 H) 7.37 (m, 2 H) 7.59 (m, 1 H) 8.15 (m, 0.5 H) 8.24 (m, 0.5 H) 15.07 (s, 0.5 H) 15.15 (s, 0.5 H). MS (ESI⁻) m/z 357 (M−H)⁻.

EXAMPLE 35G 1-(5,5-dimethylhexyl)-4-hydroxy-1-methylnaphthalen-2(1H)-one

A solution of Example 35F (1.84 g, 5.13 mmol) in 1,4-dioxane (20 mL) was treated with aqueous 1N hydrochloric acid solution (20 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (1.06 g, 72%). ¹H NMR (300 MHz, CDCl₃) δ ppm 0.57 (m, 1 H) 0.75 (s, 4.5 H) 0.80 (s, 4.5 H) 1.02 (m, 5 H) 1.51 (s, 1.5 H) 1.56 (s, 1.5 H) 1.84 (m, 1 H) 2.04 (m, 0.5 H) 2.25 (m, 0.5 H) 3.74 (s, 0.5 H) 3.75 (s, 0.5 H) 6.00 (s, 0.5 H) 7.51 (m, 3 H) 8.09 (m, 1 H). (ESI⁺) m/z 287 (M+H)⁺.

EXAMPLE 35H

2-[bis(methylthio)methylene]-4-(5,5-dimethylhexyl)-4-methylnaphthalene-1,3(2H,4H)-dione A solution of Example 35G (1.06 g, 3.70 mmol) and pyridine (2.40 mL, 29.6 mmol) in 1,4-dioxane (15 mL) was treated with [bis(methylsulfanyl)methylene](methyl)sulfonium methyl sulfate (3.93 g, 14.8 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (1.45 g, 99%). ¹H NMR (300 MHz, CDCl₃): δ ppm 0.78 (m, 10 H) 1.01 (m, 5 H) 1.56 (m, 3 H) 1.77 (m, 1 H) 2.23 (m, 1 H) 2.56 (m, 6 H) 7.39 (m, 2 H) 7.56 (m, 1 H) 8.21 (m, 1 H). MS (ESI⁺) m/z 391 (M+H)⁺.

EXAMPLE 35I 1-(5,5-dimethylhexyl)-3-(1,1-dioxido-4H-1,2,4-benzothiadiazin-3-yl)-4-hydroxy-1-methylnaphthalen-2(1H)-one A solution of Example 35H (0.097 g, 0.249 mmol) and 2-amino-benzenesulfonamide (0.045 g, 0.262 mmol) in toluene (7 mL) was refluxed for 6 hours. The solution was cooled to 25° C. and concentrated in vacuo. The residue was chromatographed on silica gel eluting with hexane followed by 20% and 30% ethyl acetate in hexane to give the desired product (0.99 g, 85%).

EXAMPLE 35J

Sodium 4-(5,5-dimethylhexyl)-2-(1,1-dioxido-4H-1,2,4-benzothiadiazin-3-yl)-4-methyl-3-oxo-3,4-dihydronaphthalen-1-olate A suspension of the product of Example 35I (0-99 g) in water (2 mL) was treated with 0.997N sodium hydroxide solution (0.213 mL, 0.212 mmol) and stirred at 25° C. for 1 hour. The solution was lyophilized to give the title compound (0.104 g, 99%). ¹H NMR (300 MHz, DMSO-d₆): δ ppm 0.59 (m, 1 H) 0.74 (m, 9 H) 0.95 (m, 5 H) 1.39 (m, 3 H) 1.72 (m, 1 H) 2.14 (m, 1 H) 7.30 (m, 3 H) 7.50 (m, 3 H) 7.65 (m, 1 H) 8.05 (m, 1 H) 15.45 (m, 1 H). MS (ESI⁻) m/z 465 (M−H)⁻.

EXAMPLE 36

Sodium 4-(3-cyclohexylpropyl)-2-(1,1-dioxido-4H-1,2,4-benzothiadiazin-3-yl)-4-methyl-3-oxo-3,4-dihydronaphthalen-1-olate

EXAMPLE 36A 1-cyclohexylprop-2-en-1-ol

A solution of cyclohexanecarbaldehyde (4.79 mL, 39.8 mmol) in tetrahydrofuran (30 mL) was added dropwise to a solution of vinylmagnesium bromide (47.8 mL, 1 M in tetrahydrofuran, 47.8 mmol) stirring at −20° C. The solution was stirred for 30 minutes at −20° C. at which time saturated ammonium chloride solution (75 mL) was added and the reaction was allowed to warm to 25° C. The solution was diluted with water and extracted three times with ethyl acetate. The ethyl acetate layers were combined and washed with brine, dried with sodium sulfate, filtered, and concentrated in vacuo. The residue was chromatographed on silica gel eluting with hexane, followed by 5% and 10% ethyl acetate in hexane to give the title compound (2.11 g, 38%). ¹H NMR (300 MHz, CDCl₃): δ ppm 1.40 (m, 11 H) 3.85 (m, 1H) 5.17 (m, 2 H) 5.86 (m, 1 H).

EXAMPLE 36B

[(1E)-3-bromoprop-1-enyl]cyclohexane

To a solution of Example 36A (5.62 g, 40.1 mmol) and 1,5-hexadiene (3.56 mL, 30.1 mmol) in 1,2-dichloroethane (70 mL), stirring at 0° C., was added thionyl bromide (4.66 mL, 60.12 mmol). The reaction was stirred for 2 hours at 0° C. and then quenched with water. The mixture was extracted with diethyl ether and the diethyl ether layer was washed with saturated sodium bicarbonate solution, dried with sodium sulfate, filtered, and concentrated in vacuo to give the title compound (3.46 g, 43%). ¹H NMR (300 MHz, CDCl₃): δ ppm 1.16 (m, 6 H) 1.69 (m, 4 H) 1.98 (m, 1 H) 3.94 (m, 2 H) 5.65 (m, 2 H).

EXAMPLE 36C

Benzyl (4E)-5-cyclohexyl-2-methyl-2-phenylpent-4-enoate

A solution of Example 36B (3.15 g, 13.1 mmol) in tetrahydrofuran (25 mL) at −78° C. was treated dropwise with a lithium hexamethyldisilazide solution (14.4 mL, 1 M in tetrahydrofuran, 14.4 mmol) and stirred for 30 minutes at −78° C. (3-bromo-propenyl)-cyclohexane (3.46 g, 17.0 mmol) was added to the solution and the reaction was allowed to warm to 25° C. and stirred for an additional 4 hours. The solvent was removed in vacuo and the residue was partitioned between water and ethyl acetate. The aqueous phase was extracted three times with ethyl acetate and the ethyl acetate layers were combined, washed with a saturated sodium bicarbonate solution, dried with sodium sulfate, filtered, and concentrated in vacuo. The residue was chromatographed on silica gel eluting with hexane, then 5% ethyl acetate in hexane, and 10% ethyl acetate in hexane to give the title compound (3.52 g, 74%). ¹H NMR (300 MHz, CDCl$_3$): δ ppm 1.09 (m, 6 H) 1.50 (m, 3 H) 1.64 (m, 5H) 2.56 (m, 1 H) 2.78 (m, 1 H) 5.14 (m, 3 H) 5.38 (m, 1 H) 7.27 (m, 10 H). MS (ESI$^+$) m/z 380 (M+NH$_4$)+

EXAMPLE 36D 5-cyclohexyl-2-methyl-2-phenylpentanoic Acid

A solution of Example 36C (3.52 g, 9.71 mmol) in ethyl acetate (50 mL) was treated with 10% palladium on carbon (0.352 g, 10 weight percent) and stirred under a hydrogen balloon for 72 hours. The vessel was purged with nitrogen gas and the mixture was filtered through a pad of celite and the filtrate was concentrated in vacuo to give the title compound (2.79 g, 99%).

EXAMPLE 36E

Diethyl 2-(5-cyclohexyl-2-methyl-2-phenylpentanoyl)malonate

A solution of diethyl malonate (1.54 mL, 10.2 mmol) in acetonitrile (20 mL) was cooled to 0° C. and treated with magnesium chloride (0.968 g, 10.2 mmol) followed by dropwise addition of triethylamine (2.98 mL, 21.4 mmol). The solution was stirred at 0° C. for 15 minutes and then stirred at 25° C. for 2 hours.

A solution of Example 36D (2.79 g, 10.2 mmol) and dimethylformamide (0.87 mL, 11.2 mmol) in hexane (475 mL) was treated with oxalyl chloride (2.66 mL, 30.5 mmol) and stirred at 25° C. for 2 hours. The hexane supernatant was decanted from the residue, filtered through celite, and concentrated in vacuo to give the acid chloride.

The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo to give the desired product which was taken onto the next reaction without further purification (4.01 g, 95%).

EXAMPLE 36F

Ethyl 4-(3-cyclohexylpropyl)-1-hydroxy-4-methyl-3-oxo-3,4-dihydronaphthalene-2-carboxylate Example 36E (4.01 g, 9.63 mmol) was stirred in methanesulfonic acid (20 mL) at 25° C. for 3 hours. The solution was partitioned between cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (2.14 g, 60%). $^1$H NMR (300 MHz, CDCl$_3$): δ ppm 1.16 (m, 23 H) 4.08 (m, 2 H) 7.37 (m, 2 H) 7.58 (m, 1 H) 8.19 (m, 0.5 H) 8.21 (m, 0.5H) 15.07 (s, 0.5 H) 15.11 (s, 0.5 H). MS (ESI$^-$) m/z 369 (M−H)$^-$.

EXAMPLE 36G 1-(3-cyclohexylpropyl)-4-hydroxy-1-methylnaphthalen-2(1 H)-one

A solution of Example 36F (2.14 g, 5.78 mmol) in 1,4-dioxane (20 mL) was treated with aqueous 1N hydrochloric acid solution (20 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (0.513 g, 30%).

EXAMPLE 36H

2-[bis(methylthio)methylene]-4-(3-cyclohexylpropyl)-4-methylnaphthalene-1,3(2H,4 H)-dione A solution of Example 36G (0.513 g, 1.72 mmol) and pyridine (1.11 mL, 13.8 mmol) in 1,4-dioxane (15 mL) was treated with Example 5A (1.83 g, 6.88 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (0.668 g, 97%). $^1$H NMR (300 MHz, CDCl$_3$): δ ppm 0.90 (m, 11 H) 1.53 (m, 7 H) 1.74 (m, 1 H) 2.18 (m, 1 H) 2.57 (m, 6 H) 7.40 (m, 2 H) 7.56 (m, 1 H) 8.22 (m, 1 H). MS (ESI$^+$) m/z 403 (M+H)$^+$.

EXAMPLE 36I 1-(3-cyclohexylpropyl)-3-(1,1-dioxido-4H-1,2,4-benzothiadiazin-3-yl)-4-hydroxy-1-methylnaphthalen-2(1 H)-one A solution of Example 36H (0.075 g, 0.186 mmol) and 2-amino-benzenesulfonamide (0.034 g, 0.195 mmol) in toluene (7 mL) was refluxed for 6 hours. The solution was cooled to 25° C. and concentrated in vacuo. The residue was chromatographed on silica gel eluting with hexane followed by 20% and 30% ethyl acetate in hexane to give the desired product (0.77 g, 87%).

EXAMPLE 36J

Sodium 4-(3-cyclohexylpropyl)-2-(1,1-dioxido-4H-1,2,4-benzothiadiazin-3-yl)-4-methyl-3-oxo-3,4-dihydronaphthalen-1-olate A suspension of the product of Example 36I (0.77 g) in water (2 mL) was treated with 0.997N sodium hydroxide solution (0.161 mL, 0.160 mmol) and stirred at 25° C. for 1 hour. The solution was lyophilized to give the title compound (0.79 g, 99%). $^1$H NMR (300 MHz, DMSO-d$_6$): δ ppm 0.84 (m, 11 H) 1.45 (m, 7 H) 1.68 (m, 1 H) 2.10 (m, 1 H) 7.31 (m, 3 H) 7.49 (m, 3 H) 7.65 (m, 1 H) 8.05 (m, 1 H) 15.45 (m, 1 H). MS (ESI$^-$) m/z 477 (M−H)$^-$.

EXAMPLE 37

Sodium 4-(5,5-dimethylhexyl)-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 37A tert-butyl 3-[4-(5,5-dimethylhexyl)-1-hydroxy-4-methyl-3-oxo-3,4-dihydronaphthalen-2-yl]-1,1-dioxido-4H-1,2,4-benzothiadiazin-7-ylcarbamate A solution of Example 35H (1.07 g, 2.75 mmol) and Example 17A (0.829 g, 2.88 mmol) in toluene (50 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.775 g, 48%). $^1$H NMR (300 MHz, DMSO-d$_6$): δ ppm 0.54 (m, 1 H) 0.73 (m, 9 H) 0.95 (m, 5 H) 1.48 (m, 9H) 1.58 (m, 3 H) 2.15 (m, 2 H) 7.54 (m, 1 H) 7.73 (m, 4 H) 8.15 (m, 2 H) 9.87 (m, 1 H) 13.71 (m, 1 H). MS (ESI$^-$) m/z 580 (M−H)$^-$.

EXAMPLE 37B 3-(7-amino-1,1-dioxido-4H-1,2,4-benzothiadiazin-3-yl)-1-(5,5-dimethylhexyl)-4-hydroxy-1-methylnaphthalen-2(1 H)-one hydrochloride A solution of Example 37A (0.775 g, 1.33 mmol) in 4M hydrochloric acid in 1,4-dioxane (10 mL) was stirred at 25° C. for 1 hour. The solution was concentrated in vacuo and the residue was triturated in diethyl ether to give the title compound (0.374 g, 54%).

EXAMPLE 37C

N-{3-[4-(5,5-dimethylhexyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 37B (0.374 g, 0.722 mmol), mesyl chloride (0.224 mL, 2.89 mmol), and pyridine (0.467 mL, 5.78 mmol) in acetone (15 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.302 g, 75%).

EXAMPLE 37D

Sodium 4-(5,5-dimethylhexyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 37C (0.302 g) in water (10 mL) was treated with 0.997N sodium hydroxide solution (0.545 mL, 0.540 mmol) and stirred at 25° C. for 1 hour. The solution was lyophilized to give the title compound (0.308 g, 98%). $^1$H NMR (300 MHz, DMSO-d$_6$): δ ppm 0.58 (m, 1 H) 0.73 (m, 9 H) 0.95 (m, 5 H) 1.38 (m, 3 H) 1.71 (m, 1H) 2.13 (m, 1 H) 2.94 (m, 3 H) 7.32 (m, 3 H) 7.46 (m, 3 H) 8.04 (m, 1 H) 9.88 (m, 1 H) 15.46 (m, 1 H). MS (ESI$^-$) m/z 558 (M−H)$^-$.

EXAMPLE 38

Sodium 4-(3-cyclohexylpropyl)-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 38A tert-butyl 3-[4-(3-cyclohexylpropyl)-1-hydroxy-4-methyl-3-oxo-3,4-dihydronaphthalen-2-yl]-1,1-dioxido-4H-1,2,4-benzothiadiazin-7-ylcarbamate A solution of Example 36G (0.418 g, 1.04 mmol) and Example 17A (0.313 g, 1.09 mmol) in toluene (30 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.570 g, 92%). $^1$H NMR (300 MHz, DMSO-d$_6$): δ ppm 0.80 (m, 11 H) 1.48 (m, 16 H) 1.98 (m, 1 H) 2.17 (m, 1 H) 7.61 (m, 5 H) 8.12 (m, 2 H) 9.82 (m, 1 H) 13.93 (m, 1 H). MS (ESI$^-$) m/z 592 (M−H)$^-$.

EXAMPLE 38B 3-(7-amino-1,1-dioxido-4H-1,2,4-benzothiadiazin-3-yl)-1-(3-cyclohexylpropyl)-4-hydroxy-1-methyl-naphthalen-2(1 H)-one hydrochloride A solution of Example 38 A (0.570 g, 0.960 mmol) in 4M hydrochloric acid in 1,4-dioxane (10 mL) was stirred at 25° C. for 1 hour. The solution was concentrated in vacuo and the residue was triturated in diethyl ether to give the title compound (0.357 g, 70%).

EXAMPLE 38C

N-{3-[4-(3-cyclohexylpropyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 38B (0.357 g, 0.674 mmol), mesyl chloride (0.209 mL, 2.69 mmol), and pyridine (0.436 mL, 5.39 mmol) in acetone (15 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.339 g, 88%).

EXAMPLE 38D

Sodium 4-(3-cyclohexylpropyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 38C (0.339 g) in water (10 mL) was treated with 0.997N sodium hydroxide solution (0.595 mL, 0.593 mmol) and stirred at 25° C. for 1 hour. The solution was lyophilized to give the title compound (0.334 g, 95%). $^1$H NMR (300 MHz, DMSO-d$_6$): δ ppm 0.63 (m, 3 H) 0.98 (m, 8 H) 1.45 (m, 7 H) 1.68 (m, 1 H) 2.09 (m, 1H) 2.93 (m, 3 H) 7.30 (m, 3 H) 7.45 (m, 3 H) 8.05 (m, 1 H) 9.87 (m, 1 H) 15.45 (m, 1 H). MS (ESI$^-$) m/z 570 (M−H)$^-$.

EXAMPLE 39

Sodium (4R)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate Method A:

EXAMPLE 39A (2R)—N-[(1S)-2-hydroxy-1-phenylethyl]-2,5-dimethyl-2-phenylhexanamide A solution of 2,5-dimethyl-2-phenyl-hexanoic acid (0.964 g, 4.38 mmol) and dimethylformamide (0.373 mL, 4.81 mmol) in hexane (175 mL) was treated with oxalyl chloride (1.15 mL, 13.1 mmol) and stirred at 25° C. for 2 hours. The mixture was filtered through celite and the filtrate was concentrated in vacuo to give the acid chloride residue. To a solution of the residue in methylene chloride (100 mL) was added triethylamine (1.28 mL, 9.19 mmol), 4-(dimethylamino)pyridine (0.027 g, 0.219 mmol), and (S)-2-phenylglycinol (0.613 g, 4.38 mmol). The solution was stirred at 25° C. for 18 hours and then washed with a solution of 1N hydrochloric acid and brine. The methylene chloride layer was dried with sodium sulfate, filtered, and concentrated in vacuo. The residue was chromatographed on silica gel eluting with toluene, 15% ethyl acetate in toluene, and 30% ethyl acetate in toluene to give the two diastereomers. The more polar diastereomer was the title compound (0.426 g, 29%). $^1$H NMR (300 MHz, CDCl$_3$): δ ppm 0.82 (m, 6 H) 1.01 (m, 2H) 1.47 (m, 1 H) 1.58 (m, 3 H) 1.99 (m, 2 H) 3.76 (m, 2 H) 5.03 (m, 1 H) 5.79 (m, 1 H) 7.07 (m, 2 H) 7.29 (m, 4 H) 7.35 (m, 4 H). MS (ESI$^-$) m/z 338 (M−H)$^-$.

EXAMPLE 39B (2R)-2,5-dimethyl-2-phenylhexanoic Acid

To a solution of Example 39A (4.26 g, 12.55 mmol) in 1,4-dioxane (15 mL) was added 4M sulfuric acid (15 mL) and the reaction was stirred at reflux for 48 hours. The solution was concentrated in vacuo and partitioned between water and methylene chloride. The methylene chloride layer was dried with sodium sulfate, filtered, and concentrated in vacuo. The residue was chromatographed on silica gel eluting with hexane, 10% ethyl acetate in hexane, and 20% ethyl acetate in hexane to give the title compound (2.70 g, 97%). $^1$H NMR (300 MHz, CDCl$_3$): δ ppm 0.88 (m, 6 H) 1.09 (m, 2 H) 1.52 (m, 4 H) 1.99 (m, 2 H) 7.35 (m, 5 H).

EXAMPLE 39C

Diethyl 2-[(2R)-2,5-dimethyl-2-phenylhexanoyl]malonate

A solution of diethyl malonate (1.77 mL, 11.7 mmol) in acetonitrile (20 mL) was cooled to 0° C. and treated with magnesium chloride (1.11 g, 11.7 mmol) followed by dropwise addition of triethylamine (3.41 mL, 24.5 mmol). The solution was stirred at 0° C. for 15 minutes and then stirred at 25° C. for 2 hours. A solution of Example 39B (2.57 g, 11.7 mmol) and dimethylformamide (0.993 mL, 12.8 mmol) in hexane (400 mL) was treated with oxalyl chloride (3.06 mL, 35.0 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo to give the title compound as a crude product (4.23 g, 99%). $^1$H NMR (300 MHz, CDCl$_3$): δ ppm 0.84 (m, 6 H) 1.13 (m, 8 H) 1.50 (m, 4 H) 1.97 (m, 2 H) 4.08 (m, 4 H) 4.51 (m, 1 H) 7.32 (m, 5 H).

EXAMPLE 39D

Ethyl (4R)-1-hydroxy-4-methyl-4-(3-methylbutyl)-3-oxo-3,4-dihydronaphthalene-2-carboxylate Example 39C (4.23 g, 11.7 mmol) was stirred in methanesulfonic acid (15 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (3.10 g, 84%). $^1$H NMR (300 MHz, CDCl$_3$): δ ppm 0.52 (m, 1 H) 0.73 (m, 6 H) 0.87 (m, 1 H) 1.36 (m, 1 H) 1.47 (m, 4.5 H) 1.64 (s, 1.5 H) 1.78 (m, 0.5 H) 1.95 (m, 0.5 H) 2.23 (m, 0.5 H) 2.33 (m, 0.5 H) 4.47 (m, 2 H) 7.41 (m, 2 H) 7.59 (m, 1 H) 8.16 (m, 0.5 H) 8.24 (m, 0.5 H) 15.07 (s, 0.5 H) 15.16 (s, 0.5 H).

EXAMPLE 39E (1R)-4-hydroxy-1-methyl-1-(3-methylbutyl)naphthalen-2(1 H)-one

A solution of Example 39D (3.10 g, 9.80 mmol) in 1,4-dioxane (25 mL) was treated with aqueous 1N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (2.10 g, 88%). $^1$H NMR (300 MHz, CDCl$_3$): δ ppm 0.44 (m, 0.5 H) 0.73 (m, 3.5 H) 0.80 (m, 3 H) 1.06 (m, 1 H) 1.39 (m, 1 H) 1.56 (s, 1.5 H) 1.59 (s, 1.5 H) 2.04 (m, 1 H) 2.30 (m, 1 H) 3.74 (s, 0.5 H) 3.75 (s, 0.5 H) 6.63 (s, 0.5 H) 7.46 (m, 2 H) 7.66 (m, 1H) 8.08 (m, 0.5 H) 8.20 (m, 0.5 H).

EXAMPLE 39F (4R)-2-[bis(methylthio)methylene]-4-methyl-4-(3-methylbutyl)naphthalene-1,3(2H,4 H)-dione A solution of Example 39E (2.10 g, 8.61 mmol) and pyridine (5.38 mL, 66.5 mmol) in 1,4-dioxane (40 mL) was treated with Example 5A (8.83 g, 33.3 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (2.96 g, 99%). $^1$H NMR (300 MHz, DMSO-d$_6$): δ ppm 0.54 (m, 1 H) 0.73 (m, 7H) 1.30 (m, 1 H) 1.47 (m, 3 H) 1.81 (m, 1 H) 2.11 (m, 1 H) 2.55 (m, 6 H) 7.43 (m, 1 H) 7.62 (m, 2 H) 8.04 (m, 1 H). (ESI$^+$) m/z 349 (M+H)$^+$.

EXAMPLE 39G tert-butyl 3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-ylcarbamate A solution of Example 39F (0.553 g, 1.59 mmol) and Example 17A (0.479 g, 1.67 mmol) in toluene (25 mL) was refluxed for 6 hours. The solution was cooled to 25° C. and concentrated in vacuo. The residue was chromatographed on silica gel eluting with hexane followed by 20% and 30% ethyl acetate in hexane to give the title compound (0.715 g, 83%). $^1$H NMR (300 MHz, DMSO-d$_6$): δ ppm 0.42 (m, 1 H) 0.69 (m, 6 H) 0.84 (m, 1 H) 1.30 (m, 1H) 1.48 (m, 9 H) 1.57 (m, 3 H) 2.14 (m, 2 H) 7.53 (m, 1 H) 7.70 (m, 4 H) 8.14 (m, 2 H) 9.88 (m, 1 H) 13.79 (m, 1 H).

EXAMPLE 39H (1R)-3-(7-amino-1,1-dioxido-4H-1,2,4-benzothiadi-azin-3-yl)-4-hydroxy-1-methyl-1-(3-methylbutyl) naphthalen-2(1 H)-one hydrochloride A solution of Example 39G (0.713 g, 1.32 mmol) in 4M hydrochloric acid in 1,4-dioxane (10 mL) was stirred at 25° C. for 1 hour. The solution was concentrated in vacuo and the residue was triturated in diethyl ether to give the title compound (0.537 g, 85%). $^1$H NMR (300 MHz, DMSO-d$_6$): δ ppm 0.42 (m, 1 H) 0.74 (m, 7 H) 1.32 (m, 1 H) 1.58 (m, 3 H) 2.15 (m, 2 H) 7.07 (m, 2 H) 7.51 (m, 2 H) 7.77 (m, 2 H) 8.16 (m, 1 H) 13.57 (m, 1 H). MS (ESI$^-$) m/z 438 (M–H)$^-$.

EXAMPLE 39I

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide A solution of Example 39H (2.76 g, 5.80 mmol), mesyl chloride (1.79 mL, 23.2 mmol), and pyridine (3.75 mL, 46.4 mmol) in acetone (80 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (2.71 g, 90%). $^1$H NMR (300 MHz, DMSO-d$_6$): δ ppm 0.43 (m, 1 H) 0.74 (m, 7 H) 1.34 (m, 1 H) 1.57 (m, 3 H) 2.15 (m, 2 H) 3.08 (m, 3 H) 7.56 (m, 3 H) 7.75 (m, 3 H) 8.16 (m, 1 H) 10.26 (m, 1 H) 13.76 (m, 1 H).

EXAMPLE 39J

Sodium (4R)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate A suspension of the product of Example 39I (2.71 g) in water (10 mL) and treated with 0.997N sodium hydroxide solution (5.25 mL, 5.24 mmol) and stirred at 25° C. for 1 hour. The solution was lyophilized to give the title compound (2.46 g, 87%). $^1$H NMR (300 MHz, DMSO-d$_6$): δ ppm 0.46 (m, 1 H) 0.69 (m, 6 H) 0.80 (m, 1 H) 1.29 (m, 1 H) 1.38 (m, 3 H) 1.72 (m, 1 H) 2.14 (m, 1 H) 2.90 (m, 3 H) 7.34 (m, 6 H) 8.05 (m, 1 H) 15.42 (m, 1 H). MS (ESI$^-$) m/z 516 (M–H)$^-$.

Method B:

EXAMPLE 39-1

2,5-dimethyl-2-phenylhexanoic Acid

To a solution of lithium bis(trimethylsilyl)amide (278.57 g, 1.66 mol) in tetrahydrofuran (700 mL) was added 2-phenyl propionic acid (100.0 g, 0.666 mol) over 40 minutes maintaining the temperature below 15° C. The solution was warmed 40-45° C. for 20 minutes, then cooled below 25° C. and 1-bromo-3-methylbutane (156.0 g, 1.03 mol) was added. The reaction mixture was heated to 50° C. for 10 h, then was cooled to RT, and concentrated to a thick sludge. Methyl tert-butyl ether (900 mL) and water (1100 mL) were added, and the layers were separated. The organic phase was extracted with H$_2$O (200 mL). The combined aqueous phases were treated with 3 M HCl (520 mL) to adjust the pH to approximately 2. The product was extracted with ethyl acetate (1000 mL) and the organic layer was concentrated to a thick oil to give the title compound. The crude oil (assayed for 136.99 g of Example 39-1, 95.3% assay yield) was used directly.

EXAMPLE 39-2

(2R)-2,5-dimethyl-2-phenylhexanoic acid (1S)-1-phenylethanamine Salt

The product of Example 39-1 (136.99 g, 0.622 mol) was dissolved in ethyl acetate (2055 mL). To this solution was added (S)-α-methyl benzylamine (44.47 g, 0.375 mol). A white solid precipitated and the slurry was mixed for 19 h at RT. The product was isolated by filtration and the wet cake was dried under vacuum at ambient temperature to give 74.32 g of white solid. This solid was heated with ethyl acetate (1115 mL) to 73° C. to give a clear solution, which was cooled slowly to room temperature and a white solid precipitated. After mixing for 18 h at RT, the product was isolated by filtration and the product was dried to give the title compound (65.11 g, 30.7% 97.3% ee measured using the following conditions: Column: ChiralPak, AD-RH; mobile phase: acetonitrile (60%)/H$_2$O (40%), trifluoroacetic acid (0.06%); column temp: ambient; flow rate: 0.8 mL/min; and λ: 220 nm).

EXAMPLE 39-3

Diethyl 2-[(2R)-2,5-dimethyl-2-phenylhexanoyl]malonate

A suspension of acid-amine salt of Example 39-2 (532.0 g, 1.56 mol) in ethyl acetate (3350 mL) was treated with water (1500 mL) then enough 3 M HCl to bring the pH to <2. The solution was mixed and the layers were separated. The organic phase was concentrated to thick oil. The oil was dissolved in heptane (500 mL) and concentrated then redissolved in heptane (1700 mL). To this solution was added N,N-dimethylformamide (10.3 g, 0.141 mol) and oxalyl chloride (312.2 g, 2.46 mol). The solution was mixed at RT overnight, filtered through celite and concentrated to a residue. The crude acid chloride was dissolved in acetonitrile (300 mL) and concentrated to a residue then dissolved in acetonitrile (240 mL). To a separate vessel containing a 0° C. solution of diethyl malonate (254.0 g, 1.59 mol), and MgCl$_2$ (151.0 g, 1.59 mol) in acetonitrile (2.2 L) was added triethylamine (320.8 g, 3.17 mol). The solution was warmed to RT and mixed for 1 h, then cooled back to 0-10° C. The acid chloride/CH$_3$CN solution was added over 30 minutes and the reaction mixture was heated to 50° C. for 3 h. The reaction mixture was cooled and concentrated to a thick sludge. Ethyl acetate (2400 mL) and water (2400 mL) were added and the pH was adjusted to 6 with concentrated HCl. The layers were separated and the organic solution was washed with 10% NaCl. The organic layer was concentrated to a thick oil then chased with heptane (400 mL). The crude oil was used directly (assayed for 565.7 g, 100%).

EXAMPLE 39-4

Ethyl (4R)-1-hydroxy-4-methyl-4-(3-methylbutyl)-3-oxo-3,4-dihydronaphthalene-2-carboxylate To the crude diester of Example 39-4 (565.7 g, 1.56 mol) at 10-15° C. was added methanesulfonic acid (1715 mL). The solution was warmed to 30° C. and mixed for 24 h. The reaction mixture was slowly quenched into a mixture of $H_2O$ (2240 mL) and ethyl acetate (3.24 mL) at 5° C. The layers were separated and the organic layer was washed with 10% NaCl. The solution was concentrated and the resulting oil was dissolved in toluene (1330 mL). The crude product of Example 39-4/toluene solution (assayed for 454.14 g of Example 39-4, 92%) was used directly.

EXAMPLE 39-5 tert-butyl 3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-ylcarbamate To a solution of the product of Example 39-4 (320 g, 1.01 mol) in toluene (1100 mL) was added product of Example 17A-4 (291 g, 1.01 mol). The solution was heated to 100° C. for 4 h then cooled to RT. The solution was transferred to a pressure bottle and triethylamine (472, 4.66 mol) was added and the solution was heated to 100° C. for 26 h. The solution was concentrated to ⅓ of the original volume and ethyl acetate (2000 mL) was added. The organic layer was washed with 10% $KH_2PO_4$ and 10% NaCl then concentrated to a thick oil then chased with $CH_2Cl_2$. The crude product of Example 39-5 (assay for 406.5 g, 74.5%) was used directly.

EXAMPLE 39-6

(1R)-3-(7-amino-1,1-dioxido-4H-1,2,4-benzothiadiazin-3-yl)-4-hydroxy-1-methyl-1-(3-methylbutyl)naphthalen-2(1 H)-one To a solution of the product of Example 39-5 (407 g, 0.754 mol) in dichloromethane (550 mL) was added 4 M HCl in dioxane (760 mL, 3.04 mol) and the solution was mixed at RT for 3.5 h. The reaction was quenched by addition of ethyl acetate (1.5 L) and pH 7 phosphate buffer (1.7 L) and the layers were separated. The aqueous layer was back-extracted with ethyl acetate (400 mL) and the combined organic layers were concentrated and chased with ethanol to a final volume of approximately 2500 mL. The product precipitated and was isolated by filtration and dried to give the title compound (309.7 g, 93.4%).

EXAMPLE 39-7

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide To a solution of the product of Example 39-6 (310 g, 0.705 mol) and pyridine (167.6 g, 2.12 mol) in dichloromethane (1645 mL) at 18-20° C. was added methanesulfonyl chloride (121.1 g, 1.06 mol) over 45 minutes. The solution was mixed at RT for 16 h then quenched with 1 M HCl (2000 mL). The layers were separated and the organic layer was concentrated under vacuum. The product was crystallized from ethyl acetate/heptane (1/1, 8 volumes) to give the title compound (236.0 g, 65%).

EXAMPLE 39-8

Sodium (4R)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate A solution of 7.54 M NaOH (20.2 mL, 0.152 mol) was added over 5 minutes to a solution of the product of Example 39-7 (71.72 g, 0.139 mol) in ethanol (1450 mL) at 30-35° C. The product precipitated and the slurry was cooled slowly to RT and the product was isolated by filtration and dried to give the title compound (62.24 g, 83%).

EXAMPLE 40

Sodium (4S)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate

EXAMPLE 40A (2R)—N-[(1S)-2-hydroxy-1-phenylethyl]-2,5-dimethyl-2-phenylhexanamide A solution of 2,5-dimethyl-2-phenyl-hexanoic acid (0.964 g, 4.38 mmol) and dimethylformamide (0.373 mL, 4.81 mmol) in hexane (175 mL) was treated with oxalyl chloride (1.15 mL, 13.1 mmol) and stirred at 25° C. for 2 hours. The mixture was filtered through celite and the filtrate was concentrated in vacuo to give the acid chloride residue. To a solution of the residue in methylene chloride (100 mL) was added triethylamine (1.28 mL, 9.19 mmol), 4-(dimethylamino)pyridine (0.027 g, 0.219 mmol), and (S)-2-phenylglycinol (0.613 g, 4.38 mmol). The solution was stirred at 25° C. for 18 hours and then washed with a solution of 1N hydrochloric acid and brine. The methylene chloride layer was dried with sodium sulfate, filtered, and concentrated in vacuo. The residue was chromatographed on silica gel eluting with toluene, 15% ethyl acetate in toluene, and 30% ethyl acetate in toluene to give the two diastereomers. The less polar diastereomer was the title compound (0.470 g, 32%). $^1$H NMR (300 MHz, CDCl$_3$): δ ppm 0.87 (m, 6H) 1.06 (m, 2H) 1.53 (m, 4H) 2.03 (m, 2H) 3.76 (m, 2H) 5.02 (m, 1H) 5.80 (m, 1H) 7.07 (m, 2H) 7.29 (m, 4H) 7.37 (m, 4H). MS (ESI$^-$) m/z 338 (M–H)$^-$.

EXAMPLE 40B (2S)-2,5-dimethyl-2-phenylhexanoic acid

To a solution of Example 40A (4.26 g, 12.55 mmol) in 1,4-dioxane (15 mL) was added 4M sulfuric acid (15 mL) and the reaction was stirred at reflux for 48 hours. The solution was concentrated in vacuo and partitioned between water and methylene chloride. The methylene chloride layer was dried with sodium sulfate, filtered, and concentrated in vacuo. The residue was chromatographed on silica gel eluting with hexane, 10% ethyl acetate in hexane, and 20% ethyl acetate in hexane to give the title compound (2.02 g, 73%). $^1$H NMR (300 MHz, CDCl$_3$): δ ppm 0.88 (m, 6H) 1.09 (m, 2H) 1.52 (m, 4H) 1.99 (m, 2H) 7.35 (m, 5H).

EXAMPLE 40C

Diethyl 2-[(2S)-2,5-dimethyl-2-phenylhexanoyl]malonate

A solution of diethyl malonate (1.41 mL, 9.17 mmol) in acetonitrile (20 mL) was cooled to 0° C. and treated with magnesium chloride (0.891 g, 9.17 mmol) followed by dropwise addition of triethylamine (2.68 mL, 19.3 mmol). The solution was stirred at 0° C. for 15 minutes and then stirred at 25° C. for 2 hours. A solution of Example 40B (2.02 g, 9.17 mmol) and dimethylformamide (0.781 mL, 10.1 mmol) in hexane (400 mL) was treated with oxalyl chloride (2.45 mL, 27.5 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo to give the title compound as a crude product (3.31 g, 99%). $^1$H NMR (300 MHz, CDCl$_3$): δ ppm 0.84 (m, 6H) 1.13 (m, 8H) 1.50 (m, 4H) 1.97 (m, 2H) 4.08 (m, 4H) 4.51 (m, 1H) 7.32 (m, 5H).

EXAMPLE 40D

Ethyl (4S)-1-hydroxy-4-methyl-4-(3-methylbutyl)-3-oxo-3,4-dihydronaphthalene-2-carboxylate Example 40C (3.32 g, 9.16 mmol) was stirred in methanesulfonic acid (20 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (2.60, 90%). $^1$H NMR (300 MHz, CDCl$_3$): δ ppm 0.52 (m, 1H) 0.73 (m, 6H) 0.87 (m, 1H) 1.36 (m, 1H) 1.47 (m, 4.5H) 1.64 (s, 1.5H) 1.78 (m, 0.5H) 1.95 (m, 0.5H) 2.23 (m, 0.5H) 2.33 (m, 0.5H) 4.47 (m, 2H) 7.41 (m, 2H) 7.59 (m, 1H) 8.16 (m, 0.5H) 8.24 (m, 0.5H) 15.07 (s, 0.5H) 15.16 (s, 0.5H).

EXAMPLE 40E (1S)-4-hydroxy-1-methyl-1-(3-methylbutyl)naphthalen-2(1H)-one

A solution of Example 40D (2.60, 8.22 mmol) in 1,4-dioxane (25 mL) was treated with aqueous 1N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (1.60 g, 80%). $^1$H NMR (300 MHz, CDCl$_3$): δ ppm 0.44 (m, 0.5H) 0.73 (m, 3.5H) 0.80 (m, 3H) 1.06 (m, 1H) 1.39 (m, 1H) 1.56 (s, 1.5H) 1.59 (s, 1.5H) 2.04 (m, 1H) 2.30 (m, 1H) 3.74 (s, 0.5H) 3.75 (s, 0.5H) 6.63 (s, 0.5H) 7.46 (m, 2H) 7.66 (m, 1H) 8.08 (m, 0.5H) 8.20 (m, 0.5H).

EXAMPLE 40F (4S)-2-[bis(methylthio)methylene]-4-methyl-4-(3-methylbutyl)naphthalene-1,3(2H,4H)-dione A solution of Example 40E (1.60 g, 6.55 mmol) and pyridine (4.24 mL, 52.4 mmol) in 1,4-dioxane (40 mL) was treated with Example 5A (6.95 g, 26.2 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (2.28 g, 99%). $^1$H NMR (300 MHz, DMSO-d$_6$): δ ppm 0.54 (m, 1H) 0.73 (m, 7H) 1.30 (m, 1H) 1.47 (m, 3H) 1.81 (m, 1H) 2.11 (m, 1H) 2.55 (m, 6H) 7.43 (m, 1H) 7.62 (m, 2H) 8.04 (m, 1H). (ESI$^+$) m/z 349 (M+H)$^+$.

EXAMPLE 40G tert-butyl 3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-ylcarbamate A solution of Example 40F (2.28 g, 6.54 mmol) and Example 17A (2.07 g, 7.20 mmol) in toluene (40 mL) was refluxed for 6 hours. The solution was cooled to 25° C. and concentrated in vacuo. The residue was chromatographed on silica gel eluting with hexane followed by 20% and 30% ethyl acetate in hexane to give the title compound (3.24 g, 92%). $^1$H NMR (300 MHz, DMSO-d$_6$): δ ppm 0.42 (m, 1H) 0.69 (m, 6H) 0.84 (m, 1H) 1.30 (m, 1H) 1.48 (m, 9H) 1.57 (m, 3H) 2.14 (m, 2H) 7.53 (m, 1H) 7.70 (m, 4H) 8.14 (m, 2H) 9.88 (m, 1H) 13.79 (m, 1H).

EXAMPLE 40H (1S)-3-(7-amino-1,1-dioxido-4H-1,2,4-benzothiadiazin-3-yl)-4-hydroxy-1-methyl-1-(3-methylbutyl)naphthalen-2(1H)-one hydrochloride A solution of Example 40G (3.24, 6.00 mmol) in 4M hydrochloric acid in 1,4-dioxane (10 mL) was stirred at 25° C. for 1 hour. The solution was concentrated in vacuo and the residue was triturated in diethyl ether to give the title compound (2.86 g, 99%). $^1$H NMR (300 MHz, DMSO-d$_6$): δ ppm 0.42 (m, 1H) 0.74 (m, 7H) 1.32 (m, 1H) 1.58 (m, 3H) 2.15 (m, 2H) 7.07 (m, 2H) 7.51 (m, 2H) 7.77 (m, 2H) 8.16 (m, 1H) 13.57 (m, 1H). MS (ESI$^-$) m/z 438 (M−H)$^-$.

EXAMPLE 40I

N-{3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide A solution of Example 40H (2.89 g, 6.07 mmol), mesyl chloride (1.88 mL, 24.3 mmol), and pyridine (3.93 mL, 48.6 mmol) in acetone (80 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (2.12 g, 68%). $^1$H NMR (300 MHz, DMSO-d$_6$): δ ppm 0.43 (m, 1H) 0.74 (m, 7H) 1.34 (m, 1H) 1.57 (m, 3H) 2.15 (m, 2H) 3.08 (m, 3H) 7.56 (m, 3H) 7.75 (m, 3H) 8.16 (m, 1H) 10.26 (m, 1H) 13.76 (m, 1H).

EXAMPLE 40J

Sodium (4S)-4-methyl-4-(3-methylbutyl)-2-{7-[(methylsulfonyl)amino]-1,1-dioxido-4H-1,2,4-benzothiadiazin-3-yl}-3-oxo-3,4-dihydronaphthalen-1-olate A suspension of the product of Example 40I (2.12 g) in water (10 mL) and treated with 0.997N sodium hydroxide solution (0.969 mL, 0.966 mmol) and stirred at 25° C. for 1 hour. The solution was lyophilized to give the title compound (0.412 g, 79%). $^1$H NMR (300 MHz, DMSO-d$_6$): δ ppm 0.46 (m, 1H) 0.69 (m, 6H) 0.80 (m, 1H) 1.29 (m, 1H) 1.38 (m, 3H) 1.72 (m, 1H) 2.14 (m, 1H) 2.90 (m, 3H) 7.34 (m, 6H) 8.05 (m, 1H) 15.42 (m, 1H). MS (ESI$^-$) m/z 516 (M−H)$^-$.

EXAMPLE 41

Sodium 4-(cyclohexylmethyl)-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 41A

Methyl 3-cyclohexyl-2-methyl-2-phenylpropanate

A solution of 2-phenyl-propionic acid methyl ester (3.0 g, 18.27 mmol) in tetrahydrofuran (25 mL) at −78° C. was treated dropwise with the lithium hexamethyldisilazide (21.9 mL, 1M in tetrahydrofuran, 21.9 mmol) and stirred for 1 hour. Bromomethyl-cyclohexane (3.09 mL, 21.92 mmol) was added to the reaction and the reaction was allowed to warm to 25° C. and stirred for 18 hours. The solvent was removed in vacuo and the residue was partitioned between water and ethyl acetate. The aqueous phase was extracted three times with ethyl acetate and the ethyl acetate layers were combined, dried with sodium sulfate, filtered, and concentrated in vacuo. The residue was chromatographed on silica gel eluting with hexane, then 2.5% ethyl acetate in hexane, and 5% ethyl acetate in hexane to give the title compound (4.02 g, 84%). $^1$H NMR (300 MHz, CDCl$_3$): δ ppm 1.11 (m, 10H) 1.55 (m, 4H) 1.80 (m, 1H) 2.04 (m, 1H) 3.64 (m, 3H) 7.29 (m, 5H).

EXAMPLE 41B 3-cyclohexyl-2-methyl-2-phenylpropanoic acid

A solution of Example 41A (4.02 g, 15.4 mmol) and potassium trimethyl silanolate (11.0 g, 77.2 mmol) in tetrahydrofuran (80 mL) was heated to reflux for 18 hours. The mixture was cooled to 25° C., treated with water (10 mL), and concentrated in vacuo to remove the tetrahydrofuran. The residue was dissolved in water and washed with hexane. The aqueous layer was acidified to pH 1 with 1N hydrochloric acid and extracted three times with ethyl acetate. The ethyl acetate layers were combined, washed with brine, dried with sodium sulfate, filtered, and concentrated in vacuo to give the title compound (3.80 g, 99%). $^1$H NMR (300 MHz, CDCl$_3$): δ ppm 1.10 (m, 6H) 1.57 (m, 8H) 1.82 (m, 1H) 2.04 (m, 1H) 7.32 (m, 5H).

EXAMPLE 41C

Diethyl 2-(3-cyclohexyl-2-methyl-2-phenylpropanoyl)malonate

A solution of diethyl malonate (2.37 mL, 15.4 mmol) in acetonitrile (25 mL) was cooled to 0° C. and treated with magnesium chloride (1.50 g, 15.4 mmol) followed by dropwise addition of triethylamine (4.51 mL, 32.4 mmol). The solution was stirred at 0° C. for 15 minutes and then stirred at 25° C. for 2 hours. A solution of Example 41B (3.80 g, 15.4 mmol) and dimethylformamide (1.31 mL, 17.0 mmol) in hexane (600 mL) was treated with oxalyl chloride (4.12 mL, 46.3 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1N hydrochloric acid solution. The aqueous phase was extracted three times with ethyl acetate, dried with sodium sulfate, filtered, and concentrated in vacuo. The residue was chromatographed on silica gel eluting with hexane, then 10% ethyl acetate in hexane, and 20% ethyl acetate in hexane to give the title compound (5.94 g, 99%). $^1$H NMR (300 MHz, CDCl$_3$): δ ppm 0.74 (m, 1H) 1.12 (m, 11H) 1.57 (m, 8H) 1.88 (m, 2H) 4.10 (m, 4H) 4.49 (m, 1H) 7.31 (m, 5H).

EXAMPLE 41D

Ethyl 4-(cyclohexylmethyl)-1-hydroxy-4-methyl-3-oxo-3,4-dihydronaphthalene-2-carboxylate Example 41C (5.94 g, 15.3 mmol) was stirred in methanesulfonic acid (30 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give the title compound (4.56 g, 87%). $^1$H NMR (300 MHz, CDCl$_3$): δ ppm 0.82 (m, 6H) 1.23 (m, 2H) 1.54 (m, 9H) 1.82 (m, 0.5H) 2.00 (m, 0.5H) 2.33 (m, 1H) 4.49 (m, 2H) 7.42 (m, 2H) 7.59 (m, 1H) 8.16 (m, 0.5H) 8.25 (m, 0.5H) 15.05 (s, 0.5H) 15.20 (s, 0.5H).

EXAMPLE 41E 1-(cyclohexylmethyl)-4-hydroxy-1-methylnaphthalen-2(1H)-one

A solution of Example 41D (4.56 g, 13.3 mmol) in 1,4-dioxane (30 mL) was treated with aqueous 1N hydrochloric acid solution (30 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and filtered. The precipitate was dried to give the title compound (2.72 g, 76%). $^1$H NMR (300 MHz, CDCl$_3$): δ ppm 0.85 (m, 6H) 1.43 (m, 8H) 2.03 (m, 2H) 3.80 (m, 1H) 6.05 (m, 0.5H) 7.51 (m, 3-H) 8.06 (m, 0.5H) 8.13 (m, 0.5H). MS (ESI$^-$) m/z 269 (M−H)$^-$.

EXAMPLE 41F

2-[bis(methylthio)methylene]-4-(cyclohexylmethyl)-4-methylnaphthalene-1,3(2H,4H)-dione A solution of Example 41E (2.72 g, 10.0 mmol) and pyridine (6.50 mL, 80.3 mmol) in 1,4-dioxane (45 mL) was treated with Example 5A (10.66 g, 40.2 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give the title compound (3.13 g, 83%). $^1$H NMR (300 MHz, CDCl$_3$): δ ppm 0.82 (m, 6H) 1.22 (m, 2H) 1.43 (m, 3H) 1.51 (m, 3H) 1.79 (m, 1H) 2.30 (m, 1H) 2.56 (m, 6H) 7.40 (m, 2H) 7.56 (m, 1H) 8.22 (m, 1H). MS (ESI$^+$) m/z 375 (M+H)$^+$.

EXAMPLE 41G tert-butyl 3-[4-(cyclohexylmethyl)-1-hydroxy-4-methyl-3-oxo-3,4-dihydronaphthalen-2-yl]-1,1-dioxido-4H-1,2,4-benzothiadiazin-7-ylcarbamate A solution of Example 41F (1.00, 2.67 mmol) and Example 17A (0.844 g, 2.94 mmol) in toluene (15 mL) was refluxed for 6 hours. The solution was cooled to 25° C. and concentrated in vacuo. The residue was chromatographed on silica gel eluting with hexane followed by 20% and 30% ethyl acetate in hexane to give the title compound (1.45 g, 96%). $^1$H NMR (300 MHz, DMSO-d$_6$): δ ppm 1.02 (m, 11H) 1.55 (m, 12H) 2.20 (m, 2H) 7.55 (m, 1H) 7.67 (m, 2H) 7.77 (m, 2H) 8.17 (m, 2H) 9.89 (m, 1H) 13.81 (m, 1H). MS (ESI$^-$) m/z 564 (M–H)$^-$.

EXAMPLE 41H 3-(7-amino-1,1-dioxido-4H-1,2,4-benzothiadiazin-3-yl)-1-(cyclohexylmethyl)-4-hydroxy-1-methylnaphthalen-2(1H)-one hydrochloride A solution of Example 41G (1.44, 2.56 mmol) in 4M hydrochloric acid in 1,4-dioxane (10 mL) was stirred at 25° C. for 1 hour. The solution was concentrated in vacuo and the residue was triturated in diethyl ether to give the title compound (1.17 g, 91%). $^1$H NMR (300 MHz, DMSO-d$_6$): δ ppm 0.78 (m, 7H) 1.35 (m, 7H) 2.20 (m, 2H) 7.02 (m, 2H) 7.50 (m, 2H) 7.76 (m, 2H) 8.16 (m, 1H) 13.61 (m, 1H).

EXAMPLE 41I

N-{3-[4-(cyclohexylmethyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 41H (1.17 g, 2.33 mmol), mesyl chloride (0.720 mL, 9.31 mmol), and pyridine (1.51 mL, 18.61 mmol) in acetone (30 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give the desired product (0.968 g, 42%). $^1$H NMR (300 MHz, DMSO-d$_6$): δ ppm 0.84 (m, 7H) 1.34 (m, 4H) 1.53 (m, 3H) 2.20 (m, 2H) 3.07 (m, 3H) 7.57 (m, 3H) 7.76 (m, 3H) 8.17 (m, 1H) 10.28 (m, 1H) 13.83 (m, 1H).

EXAMPLE 41J

Sodium 4-(cyclohexylmethyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 41I (0.968 g) in water (5 mL) and treated with 0.997N sodium hydroxide solution (1.78 mL, 1.77 mmol) and stirred at 25° C. for 1 hour. The solution was lyophilized to give the title compound (0.602 g, 60%). $^1$H NMR (300 MHz, DMSO-d$_6$): δ ppm 0.75 (m, 6H) 1.10 (m, 1H) 1.38 (m, 7H) 1.75 (m, 1H) 2.22 (m, 1H) 2.95 (m, 3H) 7.31 (m, 3H) 7.45 (m, 3H) 8.05 (m, 1H) 9.87 (m, 1H) 15.55 (m, 1H). MS (ESI$^-$) m/z 542 (M–H)$^-$.

EXAMPLE 42

Sodium 4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 42A 2,5,5-trimethyl-2-phenylhexanoic Acid

Lithium bis(trimethylsilyl)amide (32.3 g, 193 mmol) was added to 80 mL of tetrahydrofuran and the resulting solution was cooled in an ice bath. Addition of a solution of 2-phenylpropionic acid (11.6 g, 77.3 mmol) in 10 mL of tetrahydrofuran to the reaction solution was followed by addition of 1-bromo-3,3-dimethyl-butane (20.4 g, 124 mmol). The reaction vessel was removed from the cooling bath, placed in a 50° C. oil bath, and the reaction solution was stirred for 17 hours. After concentration, the resulting residue was dissolved in 250 mL of 1 N NaOH, washed with 250 mL of 2:1 hexane/iso-propyl acetate, acidified to pH 1 with 6 N HCl, and extracted with ethyl acetate (3×300 mL). The combined organic layers were dried over Na$_2$SO$_4$ and concentrated to give 17.3 g (96%) of clear oil. $^1$H NMR (300 MHz, CDCl$_3$): δ ppm 0.86 (s, 9H) 1.09 (m, 2H) 1.56 (s, 3H) 1.99 (m, 2H) 7.33 (m, 5H).

EXAMPLE 42B

Ethyl 4-(3,3-dimethylbutyl)-1-hydroxy-4-methyl-3-oxo-3,4-dihydronaphthalene-2-carboxylate A solution of diethyl malonate (1.53 mL, 10.1 mmol) in acetonitrile (25 mL) was cooled to 0° C. and treated with magnesium chloride (0.961 g, 10.1 mmol) followed by dropwise addition of triethylamine (2.95 mL, 21.2 mmol). The solution was stirred at 0° C. for 15 minutes and then stirred at 25° C. for 2 hours. A solution of Example 42A (2.37 g, 10.1 mmol) and dimethylformamide (0.783 mL, 10.1 mmol) in hexane (350 mL) was treated with oxalyl chloride (2.65 mL, 30.3 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1 N hydrochloric acid solution. The aqueous phase was extracted three times with ethyl acetate, dried with sodium sulfate, filtered, and concentrated in vacuo to give a clear oil.

The crude oil was stirred in methanesulfonic acid (10 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give 2.93 g (88%) a clear oil. $^1$H NMR (300 MHz, CDCl$_3$): δ ppm 0.51 (m, 1H) 0.73 (s, 4.5H) 0.75 (s, 4.5H) 0.88 (m, 1H) 1.46 (m, 3H) 1.55 (s, 1.5H) 1.65 (s, 1.5H) 1.76 (m, 0.5H) 1.94 (m, 0.5H) 2.28 (m, 1H) 4.46 (m, 2H) 7.41 (m, 2H) 7.59 (m, 1H) 8.20 (m, 1H) 15.02 (s, 0.5H) 15.14 (s, 0.5H); MS (ESI$^-$) m/z 329 (M−H)$^-$.

EXAMPLE 42C 1-(3,3-dimethylbutyl)-4-hydroxy-1-methylnaphtha-len-2(1H)-one

A solution of Example 42B (2.65 g, 8.02 mmol) in 1,4-dioxane (25 mL) was treated with aqueous 1 N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and dried to give 1.62 g (61%) of a white solid. $^1$H NMR (300 MHz, CDCl$_3$): δ ppm 0.43 (m, 0.5H) 0.83 (m, 10H) 1.06 (m, 0.5H) 1.51 (s, 1.5H) 1.56 (s, 1.5H) 1.83 (m, 1H) 2.02 (m, 0.5H) 2.26 (m, 0.5H) 3.74 (s, 1H) 6.09 (s, 0.5H) 7.51 (m, 3H) 8.10 (td, J=7.81, 1.29 Hz, 1H); (ESI$^-$) m/z 257 (M−H)$^-$.

EXAMPLE 42D

2-[bis(methylthio)methylene]-4-(3,3-dimethylbutyl)-4-methylnaphthalene-1,3(2H,4H)-dione A solution of Example 42C (1.61 g, 6.23 mmol) and pyridine (4.03 mL, 49.9 mmol) in 1,4-dioxane (20 mL) was treated with Example 5A (6.62 g, 24.9 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give 2.04 g (90%) of a yellow solid. $^1$H NMR (300 MHz, CDCl$_3$): δ ppm 0.64 (td, J=12.96, 3.86 Hz, 1H) 0.74 (s, 9H) 0.87 (td, J=13.05, 4.41 Hz, 1H) 1.55 (s, 3H) 1.76 (td, J=13.05, 4.04 Hz, 1H) 2.25 (td, J=13.05, 4.41 Hz, 1H) 2.57 (s, 6H) 7.38 (m, 2H) 7.57 (td, J=7.54, 1.47 Hz, 1H) 8.22 (d, J=8.09 Hz, 1H); MS (ESI$^+$) m/z 363 (M+H)$^+$.

EXAMPLE 42E tert-butyl 3-[4-(3,3-dimethylbutyl)-1-hydroxy-4-methyl-3-oxo-3,4-dihydronaphthalen-2-yl]-1,1-di-oxido-4H-1,2,4-benzothiadiazin-7-ylcarbamate A solution of Example 42D (1.41 g, 3.89 mmol) and Example 17A (1.17 g, 4.08 mmol) in toluene (50 mL) was refluxed for 6 hours. The solution was cooled to 25° C. and concentrated in vacuo. The residue was chromatographed on silica gel eluting with hexane followed by 20% and 30% ethyl acetate in hexane to give 1.92 g (89%) of a pale yellow foam. $^1$H NMR (300 MHz, DMSO-d$_6$): δ ppm 0.39 (td, J=12.32, 3.31 Hz, 1H) 0.71 (s, 9H) 0.80 (td, J=12.96, 4.96 Hz, 1H) 1.51 (s, 9H) 1.58 (s, 3H) 2.06 (m, 1H) 2.23 (td, J=12.69, 4.78 Hz, 1H) 7.54 (m, 1H) 7.67 (m, 2H) 7.76 (m, 2H) 8.15 (m, 2H) 9.89 (s, 1H) 13.78 (s, 1H); MS (ESI$^-$) m/z 552 (M−H)$^-$.

EXAMPLE 42F

3-[7-(chloroamino)-1,1-dioxido-4H-1,2,4-benzothia-diazin-3-yl]-1-(3,3-dimethylbutyl)-4-hydroxy-1-methylnaphthalen-2(1H)-one A solution of Example 42E (1.91 g, 3.45 mmol) in 4 M hydrochloric acid in 1,4-dioxane (30 mL) was stirred at 25° C. for 1 hour. The solution was concentrated in vacuo and the residue was triturated in diethyl ether to give 1.58 g (93%) of a yellow solid. $^1$H NMR (300 MHz, DMSO-d$_6$): δ ppm 0.38 (td, J=12.87, 3.68 Hz, 1H) 0.78 (m, 10H) 1.59 (s, 3H) 2.08 (m, 1H) 2.23 (td, J=12.78, 4.60 Hz, 1H) 7.07 (m, 2H) 7.53 (m, 2H) 7.77 (m, 2H) 8.16 (d, J=7.72 Hz, 1H) 13.58 (s, 1H); MS (ESI$^+$) m/z 454 (M+H)$^+$.

EXAMPLE 42G

N-{3-[4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 42F (0.250 g, 0.510 mmol), mesyl chloride (0.158 mL, 2.04 mmol), and pyridine (0.330 mL, 4.08 mmol) in acetone (3 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give a yellow solid.

EXAMPLE 42H

Sodium 4-(3,3-dimethylbutyl)-4-methyl-2-{7-[(me-thylsulfonyl)amino]-1,1-dioxido-4H-1,2,4-ben-zothiadiazin-3-yl}-3-oxo-3,4-dihydronaphthalen-1-olate A suspension of the product of Example 42G in water (3 mL) and treated with 0.997N sodium hydroxide solution (0.410 mL) and stirred at 25° C. for 1 hour. The solution was lyophilized to give 209 mg (74%) of a yellow solid. $^1$H NMR (300 MHz, DMSO-d$_6$): δ ppm 0.43 (m, 1H) 0.70 (s, 9H) 0.81 (m, 1H) 1.38 (s, 3H) 1.71 (m, 1H) 2.16 (m, 1H) 2.90 (s, 3H) 7.28 (m, 3H) 7.44 (m, 3H) 8.05 (d, J=7.35 Hz, 1H) 9.87 (s, 1H) 15.44 (s, 1H); MS (ESI$^-$) m/z 530 (M−H)$^-$.

EXAMPLE 43

Sodium 4-methyl-4-[(3S)-3-methylpentyl]-2-{7-[(methylsulfonyl)amino]-1,1-dioxido-4H-1,2,4-ben-zothiadiazin-3-yl}-3-oxo-3,4-dihydronaphthalen-1-olate

EXAMPLE 43A (5S)-2,5-dimethyl-2-phenylheptanoic Acid

Lithium bis(trimethylsilyl)amide (3.23 g, 19.3 mmol) was added to 8 mL of tetrahydrofuran and the resulting solution was cooled in an ice bath. Addition of a solution of 2-phenylpropionic acid (1.16 g, 7.73 mmol) in 1 mL of tetrahydrofuran to the reaction solution was followed by addition of (S)-1-bromo-3-methyl-pentane (2.05 g, 12.4 mmol). The reaction vessel was removed from the cooling bath, placed in a 50° C. oil bath, and the reaction solution was stirred for 17 hours.

After concentration, the resulting residue was dissolved in 25 mL of 1 N NaOH, washed with 25 mL of 2:1 hexane/isopropyl acetate, acidified to pH 1 with 6 N HCl, and extracted with ethyl acetate (3× 30 mL). The combined organic layers were dried over $Na_2SO_4$ and concentrated to give 1.63 g (90%) of a clear oil. $^1$H NMR (300 MHz, $CDCl_3$): δ ppm 0.83 (m, 6H) 1.20 (m, 5H) 1.57 (s, 3H) 1.98 (m, 2H) 7.35 (m, 5H).

EXAMPLE 43B

Ethyl 1-hydroxy-4-methyl-4-[(3S)-3-methylpentyl]-3-oxo-3,4-dihydronaphthalene-2-carboxylate A solution of diethyl malonate (0.525 mL, 3.46 mmol) in acetonitrile (10 mL) was cooled to 0° C. and treated with magnesium chloride (0.329 g, 3.46 mmol) followed by dropwise addition of triethylamine (1.01 mL, 7.26 mmol). The solution was stirred at 0° C. for 15 minutes and then stirred at 25° C. for 2 hours. A solution of Example 43A (0.810 g, 3.46 mmol) and dimethylformamide (0.268 mL, 3.46 mmol) in hexane (30 mL) was treated with oxalyl chloride (0.905 mL, 10.4 mmol) and stirred at 25° C. for 2 hours. The hexane supernatant was decanted from the residue, filtered through celite, and concentrated in vacuo to give the acid chloride. The resulting acid chloride was dissolved in acetonitrile (5 mL) and added dropwise to the magnesium malonate solution stirring at 0° C. The reaction was stirred at 50° C. for 18 hours, cooled, and concentrated in vacuo. The residue was partitioned between ethyl acetate and 1 N hydrochloric acid solution. The aqueous phase was extracted three times with ethyl acetate, dried with sodium sulfate, filtered, and concentrated in vacuo to give a clear oil.

The crude oil was stirred in methanesulfonic acid (5 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give 528 mg (46%) of a clear oil. $^1$H NMR (300 MHz, $CDCl_3$): δ ppm 0.50 (m, 1H) 0.70 (m, 6H) 0.93 (m, 2H) 1.15 (m, 2H) 1.46 (m, 3H) 1.55 (s, 1.5H) 1.64 (s, 1.5H) 1.86 (m, 1H) 2.27 (m, 1H) 4.48 (m, 2H) 7.41 (m, 2H) 7.58 (m, 1H) 8.19 (ddd, J=24.82, 7.91, 1.10 Hz, 1H) 15.03 (s, 0.5H) 15.15 (s, 0.5H); MS (ESI$^-$) m/z 329 (M−H)$^-$.

EXAMPLE 43C 4-hydroxy-1-methyl-1-[(3S)-3-methylpentyl]naphthalen-2(1H)-one

A solution of Example 43B (528 mg, 1.60 mmol) in 1,4-dioxane (5 mL) was treated with aqueous 1 N hydrochloric acid solution (5 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and dried to give 248 mg (60%) of a white solid. $^1$H NMR (300 MHz, $CDCl_3$): δ ppm 0.47 (m, 0.5H) 0.73 (m, 6H) 1.07 (m, 4.5H) 1.55 (m, 3H) 1.97 (m, 2H) 3.74 (m, 1H) 6.04 (s, 0.5H) 7.52 (m, 3H) 8.10 (m, 1H); MS (ESI$^-$) m/z 257 (M−H)$^-$.

EXAMPLE 43D

2-[bis(methylthio)methylene]-4-methyl-4-[(3S)-3-methylpentyl]naphthalene-1,3(2H,4H)-dione A solution of Example 43C (234 mg, 0.910 mmol) and pyridine (0.586 mL, 7.25 mmol) in 1,4-dioxane (3 mL) was treated with Example 5A (0.962 mg, 3.62 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give 285 mg (87%) of a yellow solid. $^1$H NMR (300 MHz, $CDCl_3$): δ ppm 0.61 (m, 1H) 0.76 (m, 7H) 1.08 (m, 3H) 1.55 (s, 3H) 1.77 (m, 1H) 2.26 (m, 1H) 2.57 (s, 6H) 7.39 (m, 2H) 7.56 (m, 1H) 8.22 (dd, J=7.54, 1.29 Hz, 1H); MS (ESI$^+$) m/z 363 (M+H)$^+$.

EXAMPLE 43E tert-butyl 3-{1-hydroxy-4-methyl-4-[(3S)-3-methylpentyl]-3-oxo-3,4-dihydronaphthalen-2-yl}-1,1-dioxido-4H-1,2,4-benzothiadiazin-7-ylcarbamate A solution of Example 43D (150 mg, 0.410 mmol) and Example 17A (125 mg, 0.430 mmol) in toluene (3 mL) was refluxed for 6 hours. The solution was cooled to 25° C. and concentrated in vacuo. The residue was chromatographed on silica gel eluting with hexane followed by 20% and 30% ethyl acetate in hexane to give 154 mg (67%) of a pale yellow foam. $^1$H NMR (300 MHz, CD)Cl$_3$): δ ppm 0.49 (m, 1H) 0.71 (m, 6H) 0.95 (m, 2H) 1.19 (m, 2H) 1.54 (s, 4.5H) 1.60 (s, 4.5H) 1.67 (s, 3H) 1.95 (m, 1H) 2.35 (m, 1H) 6.68 (s, 1H) 7.48 (m, 3H) 7.68 (t, J=7.54 Hz, 1H) 7.85 (m, 2H) 8.26 (m, 1H) 14.07 (s, 0.5H) 14.33 (s, 0.5H) 16.68 (m, 1H); MS (ESI$^-$) m/z 552 (M−H)$^-$.

EXAMPLE 43F 3-(7-amino-1,1-dioxido-4H-1,2,4-benzothiadiazin-3-yl)-4-hydroxy-1-methyl-1-[(3S)-3-methylpentyl]naphthalen-2(1H)-one hydrochloride A solution of Example 43E (152 mg, 0.270 mmol) in 4 M hydrochloric acid in 1,4-dioxane (3 mL) was stirred at 25° C. for 1 hour. The solution was concentrated in vacuo and the residue was triturated in diethyl ether to give 119 mg (88%) of a yellow solid. $^1$H NMR (300 MHz, DMSO-d$_6$): δ ppm 0.45 (m, 1H) 0.66 (m, 6H) 0.92 (m, 2H) 1.12 (m, 2H) 1.57 (s, 3H) 2.15 (m, 2H) 7.01 (m, 2H) 7.46 (d, J=8.82 Hz, 1H) 7.54 (m, 1H) 7.77 (m, 2H) 8.16 (m, 1H) 13.57 (s, 1H); MS (ESI$^+$) m/z 454 (M+H)$^+$.

EXAMPLE 43H

N-(3-{1-hydroxy-4-methyl-4-[(3S)-3-methylpentyl]-3-oxo-3,4-dihydronaphthalen-2-yl}-1,1-dioxido-4H-1,2,4-benzothiadiazin-7-yl)methanesulfonamide A solution of Example 43F (0.119 g, 0.240 mmol), mesyl chloride (0.075 mL, 0.970 mmol), and pyridine (0.157 mL, 1.94 mmol) in acetone (3 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give a yellow solid.

EXAMPLE 43I

Sodium 4-methyl-4-[(3S)-3-methylpentyl]-2-{7-[(methylsulfonyl)amino]-1,1-dioxido-4H-1,2,4-benzothiadiazin-3-yl}-3-oxo-3,4-dihydronaphthalen-1-olate A suspension of the product of Example 43H in water (3 mL) was treated with 0.997N sodium hydroxide solution (0.204 mL) and stirred at 25° C. for 1 hour. The solution was lyophilized to give 112 mg (84%) of a yellow solid. $^1$H NMR (300 MHz, DMSO-$d_6$): δ ppm 0.49 (m, 1H) 0.66 (m, 6H) 0.92 (m, 2H) 1.11 (m, 2H) 1.38 (s, 3H) 1.72 (m, 1H) 2.14 (m, 1H) 2.96 (s, 3H) 7.33 (m, 3H) 7.45 (m, 3H) 8.05 (d, J=7.72 Hz, 1H) 9.88 (s, 1H) 15.50 (s, 1H); MS (ESI$^-$) m/z 530 (M−H)$^-$.

EXAMPLE 44A

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}acetamide A solution of Example 39H (0.050 g, 0.105 mmol), acetic anhydride (0.011 mL, 0.116 mmol), and pyridine (0.068 mL, 0.840 mmol) in methylene chloride (2 mL) was stirred at 25° C. for 4 hours. The solution was concentrated in vacuo and the residue was chromatographed on silica gel eluting with methylene chloride and 2.5% methanol in methylene chloride to give the desired product (0.046 g, 90%). $^1$H NMR (300 MHz, DMSO-$d_6$): 5 ppm 0.43 (m, 1H) 0.77 (m, 7H) 1.33 (m, 1H) 1.56 (m, 3H) 2.06 (m, 4H) 2.23 (m, 1H) 7.53 (m, 1H) 7.66 (m, 1H) 7.77 (m, 3H) 8.16 (m, 1H) 8.29 (m, 1H) 10.38 (m, 1H) 13.84 (m, 1H).

EXAMPLE 44B

Sodium (4R)-2-[7-(acetylamino)-1,1-dioxido-4H-1,2,4-benzothiadiazin-3-yl]-4-methyl-4-(3-methylbutyl)-3-oxo-3,4-dihydronaphthalen-1-olate A suspension of the product of Example 44A (0.046 g) in water (1 mL) was treated with 0.997N sodium hydroxide solution (0.090 mL, 0.090 mmol) and stirred at 25° C. for 1 hour. The solution was lyophilized to give the title compound (0.45 g, 99%). $^1$H NMR (300 MHz, DMSO-$d_6$): δ ppm 0.45 (m, 1H) 0.69 (m, 6H) 0.80 (m, 1H) 1.27 (m, 1H) 1.37 (m, 3H) 1.72 (m, 1H) 2.06 (m, 3H) 2.15 (m, 1H) 7.23 (m, 1H) 7.32 (m, 1H) 7.46 (m, 2H) 7.65 (m, 1H) 8.03 (m, 2H) 10.13 (m, 1H) 15.44 (m, 1H). MS (ESI$^-$) m/z 480 (M−H)$^-$.

EXAMPLE 45

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethanimidamide trifluoroacetate A solution of Example 39H (0.500 g, 1.05 mmol) in 25 mL of acetonitrile was heated at reflux for 24 hours. The reaction solution was concentrated and purified by reverse phase HPLC containing 0.1% trifluoroacetic acid to give 128 mg (20%) of a light brown solid. $^1$H NMR (300 MHz, DMSO-$d_6$): δ ppm 0.44 (m, 1H) 0.70 (dd, J=8.09, 6.62 Hz, 6H) 0.82 (m, 1H) 1.32 (m, 1H) 1.52 (s, 3H) 1.97 (m, 1H) 2.22 (m, 1H) 2.33 (s, 3H) 7.48 (m, 1H) 7.66 (m, 4H) 7.80 (d, J=1.47 Hz, 1H) 8.13 (d, J=7.72 Hz, 1H) 8.72 (s, 1H) 9.52 (s, 1H) 11.22 (s, 1H) 14.43 (s, 1H). MS (ESI$^-$) m/z 479 (M−H)$^-$.

EXAMPLE 46

Sodium (4R)-4-methyl-4-(3-methylbutyl)-2-{7-[methyl(methylsulfonyl)amino]-1,1-dioxido-4H-1,2,4-benzothiadiazin-3-yl}-3-oxo-3,4-dihydronaphthalen-1-olate To a solution of Example 39I (104 mg, 0.193 mmol) in 3 mL of water was added 0.997 N NaOH (0.194 mL, 0.193 mmol). After stirring for 2 hours, the reaction mixture was concentrated to dryness. To a solution of the resulting residue in 3 mL of dimethylformamide was added methyl iodide (0.012 mL, 0.193 mmol). After stirring at room temperature overnight, the reaction solution was concentrated and chromatographed on silica gel eluting with hexane followed by 60% and 80% ethyl acetate in hexane. The resulting yellow solid was suspended in 3 mL of water and 0.997 N NaOH was added (0.160 mL, 0.160 mmol). After stirring for 4 hours, the suspension was lyophilized to 84 mg (79%) of a yellow solid. $^1$H NMR (300 MHz, DMSO-$d_6$): δ ppm 0.46 (m, 1H) 0.69 (t, J=7.17 Hz, 6H) 0.82 (m, 1H) 1.28 (m, 1H) 1.39 (s, 3H) 1.73 (m, 1H) 2.15 (m, 1H) 2.97 (s, 3H) 3.27 (s, 3H) 7.33 (m, 2H) 7.46 (m, 2H) 7.57 (dd, J=8.82, 2.21 Hz, 1H) 7.66 (d, J=2.57 Hz, 1H) 8.05 (d, J=7.72 Hz, 1H) 15.64 (s, 1H). MS (ESI$^-$) m/z 530 (M−H)$^-$.

EXAMPLE 48

Sodium (4S)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate

EXAMPLE 48A (2S)—N-[(1S)-2-hydroxy-1-phenylethyl]-2,5,5-trimethyl-2-phenylhexanamide A solution of Example 42A (8.42 g, 35.9 mmol) and dimethylformamide (2.78 mL, 35.9 mmol) in hexane (500 mL) was treated with oxalyl chloride (9.40 mL, 108 mmol) and stirred at 25° C. for 2 hours. The mixture was filtered through celite and the filtrate was concentrated in vacuo to give the acid chloride residue.

To a solution of the residue in methylene chloride (500 mL) was added triethylamine (10.5 mL, 75.5 mmol), 4-(dimethylamino)pyridine (0.027 g, 0.219 mmol), and (S)-2-phenylglycinol (7.39 g, 53.9 mmol). The solution was stirred at 25° C. for 18 hours and then washed with a solution of 1 N hydrochloric acid and brine. The methylene chloride layer was dried with sodium sulfate, filtered, and concentrated in vacuo. The residue was chromatographed on silica gel eluting with toluene, 15% ethyl acetate in toluene, and 30% ethyl acetate in toluene to give two diastereomers. The less polar diastereomer was the title compound (4.48 g, 35%). $^1$H NMR (300 MHz, CDCl$_3$): δ ppm 0.87 (s, 9H) 0.98 (m, 1H) 1.13 (m, 1H) 1.54 (m, 4H) 2.02 (m, 2H) 3.76 (d, J=4.78 Hz, 2H) 5.02 (dt, J=7.08, 4.92 Hz, 1H) 5.79 (d, J=6.62 Hz, 1H) 7.06 (dd, J=7.54, 2.02 Hz, 2H) 7.29 (m, 4H) 7.36 (m, 4H); MS (ESI$^-$) m/z 352 (M−H)$^-$.

EXAMPLE 48B (2S)-2,5,5-trimethyl-2-phenylhexanoic Acid

To a solution of Example 48A (4.48 g, 12.7 mmol) in 1,4-dioxane (60 mL) was added 4 M sulfuric acid (60 mL) and the reaction was stirred at reflux for 48 hours. The solution was concentrated in vacuo, dissolved in 1 N NaOH (250 mL), and washed with hexane (200 mL). The aqueous layer was acidified to pH 1 with 6 N HCl and extracted with ethyl acetate (3×200 mL). The combined ethyl acetate layers were dried over sodium sulfate, filtered, and concentrated in vacuo to give a clear oil (2.66 g, 90%). $^1$H NMR (300 MHz, CDCl$_3$): δ ppm 0.86 (s, 9H) 1.09 (m, 2H) 1.56 (s, 3H) 1.99 (m, 2H) 7.33 (m, 5H).

EXAMPLE 48C

Ethyl (4S)-4-(3,3-dimethylbutyl)-1-hydroxy-4-methyl-3-oxo-3,4-dihydronaphthalene-2-carboxylate A solution of diethyl malonate (1.53 mL, 10.1 mmol) in acetonitrile (25 mL) was cooled to 0° C. and treated with magnesium chloride (0.961 g, 10.1 mmol) followed by dropwise addition of triethylamine (2.95 mL, 21.2 mmol). The solution was stirred at 0° C. for 15 minutes and then stirred at 25° C. for 2 hours. A solution of Example 48B (2.37 g, 10.1 mmol) and dimethylformamide (0.783 mL, 10.1 mmol) in hexane (350 mL) was treated with oxalyl chloride (2.65 mL, 30.3 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1 N hydrochloric acid solution. The aqueous phase was extracted three times with ethyl acetate, dried with sodium sulfate, filtered, and concentrated in vacuo to give a clear oil.

The crude oil was stirred in methanesulfonic acid (10 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane to give 2.93 g (88%) of a clear oil. $^1$H NMR (300 MHz, CDCl$_3$): δ ppm 0.51 (m, 1H) 0.73 (s, 4.5H) 0.75 (s, 4.5H) 0.88 (m, 1H) 1.46 (m, 3H) 1.55 (s, 1.5H) 1.65 (s, 1.5H) 1.76 (m, 0.5H) 1.94 (m, 0.5H) 2.28 (m, 1H) 4.46 (m, 2H) 7.41 (m, 2H) 7.59 (m, 1H) 8.20 (m, 1H) 15.02 (s, 0.5H) 15.14 (s, 0.5H); MS (ESI$^-$) m/z 329 (M−H)$^-$.

EXAMPLE 48D (1S)-1-(3,3-dimethylbutyl)-4-hydroxy-1-methylnaphthalen-2(1H)-one A solution of Example 48C (2.65 g, 8.02 mmol) in 1,4-dioxane (25 mL) was treated with aqueous 1 N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and dried to give 1.62 g (61%) of a white solid. $^1$H NMR (300 MHz, CDCl$_3$): δ ppm 0.43 (m, 0.5H) 0.83 (m, 10H) 1.06 (m, 0.5H) 1.51 (s, 1.5H) 1.56 (s, 1.5H) 1.83 (m, 1H) 2.02 (m, 0.5H) 2.26 (m, 0.5H) 3.74 (s, 1H) 6.09 (s, 0.5H) 7.51 (m, 3H) 8.10 (td, J=7.81, 1.29 Hz, 1H); MS (ESI$^-$) m/z 257 (M−H)$^-$.

EXAMPLE 48E (4S)-2-[bis(methylthio)methylene]-4-(3,3-dimethylbutyl)-4-methylnaphthalene-1,3(2H,4H)-dione A solution of Example 48D (1.61 g, 6.23 mmol) and pyridine (4.03 mL, 49.9 mmol) in 1,4-dioxane (20 mL) was treated with Example 5A (6.62 g, 24.9 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give 2.04 g (90%) of a yellow solid. $^1$H NMR (300 MHz, CDCl$_3$): δ ppm 0.64 (td, J=12.96, 3.86 Hz, 1H) 0.74 (s,9H) 0.87 (td, J=13.05, 4.41 Hz, 1H) 1.55 (s, 3H) 1.76 (td, J=13.05, 4.04 Hz, 1H) 2.25 (td, J=13.05, 4.41 Hz, 1H) 2.57 (s, 6H) 7.38 (m, 2H) 7.57 (td, J=7.54, 1.47 Hz, 1H) 8.22 (d, J=8.09 Hz, 1H); MS (ESI$^+$) m/z 363 (M+H)$^+$.

EXAMPLE 48F tert-butyl 3-[(4S)-4-(3,3-dimethylbutyl)-1-hydroxy-4-methyl-3-oxo-3,4-dihydronaphthalen-2-yl]-1,1-dioxido-4H-1,2,4-benzothiadiazin-7-ylcarbamate A solution of Example 48E (1.41 g, 3.89 mmol) and Example 17A (1.17 g, 4.08 mmol) in toluene (50 mL) was refluxed for 6 hours. The solution was cooled to 25° C. and concentrated in vacuo. The residue was chromatographed on silica gel eluting with hexane followed by 20% and 30% ethyl acetate in hexane to give 1.92 g (89%) of a pale yellow foam. $^1$H NMR (300 MHz, DMSO-d$_6$): δ ppm 0.39 (td, J=12.32, 3.31 Hz, 1H) 0.71 (s, 9H) 0.80 (td, J=12.96, 4.96 Hz, 1H) 1.51 (s, 9H) 1.58 (s, 3H) 2.06 (m, 1H) 2.23 (td, J=12.69, 4.78 Hz, 1H) 7.54 (m, 1H) 7.67 (m, 2H) 7.76 (m, 2H) 8.15 (m, 2H) 9.89 (s, 1H) 13.78 (s, 1H); MS (ESI$^-$) m/z 552 (M−H)$^-$.

EXAMPLE 48G (1S)-3-(7-amino-1,1-dioxido-4H-1,2,4-benzothiadiazin-3-yl)-1-(3,3-dimethylbutyl)-4-hydroxy-1-methylnaphthalen-2(1H)-one hydrochloride A solution of Example 48F (1.91 g, 3.45 mmol) in 4 M hydrochloric acid in 1,4-dioxane (30 mL) was stirred at 25° C. for 1 hour. The solution was concentrated in vacuo and the residue was triturated in diethyl ether to give 1.58 g (93%) of a yellow solid. $^1$H NMR (300 MHz, DMSO-d$_6$): δ ppm 0.38 (td, J=12.87, 3.68 Hz, 1H) 0.78 (m, 10H) 1.59 (s, 3H) 2.08 (m, 1H) 2.23 (td, J=12.78, 4.60 Hz, 1H) 7.07 (m, 2H) 7.53 (m, 2H) 7.77 (m, 2H) 8.16 (d, J=7.72 Hz, 1H) 13.58 (s, 1H); MS (ESI$^+$) m/z 454 (M+H)$^+$.

EXAMPLE 48H

N-{3-[(4S)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 48G (0.250 g, 0.510 mmol), mesyl chloride (0.158 mL, 2.04 mmol), and pyridine (0.330 mL, 4.08 mmol) in acetone (3 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give a yellow solid.

EXAMPLE 48I

Sodium (4S)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 48H in water (3 mL) was treated with 0.997N sodium hydroxide solution (0.410 mL) and stirred at 25° C. for 1 hour. The solution was lyophilized to give 209 mg (74%) of a yellow solid. $^1$H NMR (300 MHz, DMSO-$d_6$): δ ppm 0.43 (m, 1H) 0.70 (s, 9H) 0.81 (m, 1H) 1.38 (s, 3H) 1.71 (m, 1H) 2.16 (m, 1H) 2.90 (s, 3H) 7.28 (m, 3H) 7.44 (m, 3H) 8.05 (d, J=7.35 Hz, 1H) 9.87 (s, 1H) 15.44 (s, 1H); MS (ESI$^-$) m/z 530 (M−H)$^-$.

EXAMPLE 49

Sodium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate Method A:

EXAMPLE 49A (2R)—N-[(1S)-2-hydroxy-1-phenylethyl]-2,5,5-trimethyl-2-phenylhexanamide A solution of Example 42A (8.42 g, 35.9 mmol) and dimethylformamide (2.78 mL, 35.9 mmol) in hexane (500 mL) was treated with oxalyl chloride (9.40 mL, 108 mmol) and stirred at 25° C. for 2 hours. The mixture was filtered through celite and the filtrate was concentrated in vacuo to give the acid chloride residue. To a solution of the residue in methylene chloride (500 mL) was added triethylamine (10.5 mL, 75.5 mmol), 4-(dimethylamino)pyridine (0.027 g, 0.219 mmol), and (S)-2-phenylglycinol (7.39 g, 53.9 mmol). The solution was stirred at 25° C. for 18 hours and then washed with a solution of 1 N hydrochloric acid and brine. The methylene chloride layer was dried with sodium sulfate, filtered, and concentrated in vacuo. The residue was chromatographed on silica gel eluting with toluene, 15% ethyl acetate in toluene, followed by 30% ethyl acetate in toluene to give two diastereomers. The more polar diastereomer was the title compound (3.78 g, 30%). $^1$H NMR (300 MHz, CDCl$_3$): δ ppm 0.82 (s, 9H) 0.90 (m, 1H) 1.08 (m, 1H) 1.56 (m, 4H) 1.97 (m, 2H) 3.76 (m, 2H) 5.03 (dt, J=7.08, 4.92 Hz, 1H) 5.78 (d, J=7.35 Hz, 1H) 7.06 (dd, J=7.17, 2.02 Hz, 2H) 7.28 (m, 4H) 7.35 (m, 4H); MS (ESI) m/z 352 (M−H)$^-$.

EXAMPLE 49B (2R)-2,5,5-trimethyl-2-phenylhexanoic Acid

To a solution of Example 49A (3.78 g, 10.7 mmol) in 1,4-dioxane (60 mL) was added 4 M sulfuric acid (60 mL) and the reaction was stirred at reflux for 48 hours. The solution was concentrated in vacuo, dissolved in 1 N NaOH (250 mL), and washed with hexane (200 mL). The aqueous layer was acidified to pH 1 with 6 N HCl and extracted with ethyl acetate (3× 200 mL). The combined ethyl acetate layers were dried over sodium sulfate, filtered, and concentrated in vacuo to give a clear oil (2.47 g, 98%). $^1$H NMR (300 MHz, CDCl$_3$): δ ppm 0.86 (s, 9H) 1.09 (m, 2H) 1.56 (s, 3H) 1.99 (m, 2H) 7.33 (m, 5H).

EXAMPLE 49C

Ethyl (4R)-4-(3,3-dimethylbutyl)-1-hydroxy-4-methyl-3-oxo-3,4-dihydronaphthalene-2-carboxylate A solution of diethyl malonate (1.53 mL, 10.1 mmol) in acetonitrile (25 mL) was cooled to 0° C. and treated with magnesium chloride (0.961 g, 10.1 mmol) followed by dropwise addition of triethylamine (2.95 mL, 21.2 mmol). The solution was stirred at 0° C. for 15 minutes and then stirred at 25° C. for 2 hours. A solution of Example 49B (2.37 g, 10.1 mmol) and dimethylformamide (0.783 mL, 10.1 mmol) in hexane (350 mL) was treated with oxalyl chloride (2.65 mL, 30.3 mmol) and stirred at 25° C. for 2 hours. The hexane supernatant was decanted from the residue, filtered through celite, and concentrated in vacuo to give the acid chloride. The resulting acid chloride was dissolved in acetonitrile (10 mL) and added dropwise to the magnesium malonate solution stirring at 0° C. The reaction was stirred at 50° C. for 18 hours, cooled, and concentrated in vacuo. The residue was partitioned between ethyl acetate and 1 N hydrochloric acid solution. The aqueous phase was extracted three times with ethyl acetate, dried with sodium sulfate, filtered, and concentrated in vacuo to give a clear oil. The crude oil was stirred in methanesulfonic acid (10 mL) at 25° C. for 3 hours. The solution was partitioned cold water and ethyl acetate and the aqueous phase was extracted three times with ethyl acetate. The ethyl acetate layers were combined, dried with sodium sulfate, filtered, and concentrated in vacuo. The residue was chromatographed on silica gel eluting with hexane followed by 5%, 10%, and 20% ethyl acetate in hexane respectively to give 2.93 g (88%) of title compound. $^1$H NMR (300 MHz, CDCl$_3$): δ ppm 0.51 (m, 1H) 0.73 (s, 4.5H) 0.75 (s, 4.5H) 0.88 (m, 1H) 1.46 (m, 3H) 1.55 (s, 1.5H) 1.65 (s, 1.5H) 1.76 (m, 0.5H) 1.94 (m, 0.5H) 2.28 (m, 1H) 4.46 (m, 2H) 7.41 (m, 2H) 7.59 (m, 1H) 8.20 (m, 1H) 15.02 (s, 0.5H) 15.14 (s, 0.5H); MS (ESI$^-$) m/z 329 (M−H)$^-$.

EXAMPLE 49D (1R)-1-(3,3-dimethylbutyl)-4-hydroxy-1-methyl-naphthalen-2(1H)-one A solution of Example 49C (2.65 g, 8.02 mmol) in 1,4-dioxane (25 mL) was treated with aqueous 1 N hydrochloric acid solution (25 mL) and refluxed for 3 hours. The mixture was cooled to 25° C. and partitioned between ethyl acetate and water. The ethyl acetate layer was washed with water and brine, dried with sodium sulfate, filtered, and concentrated in vacuo. The residue was triturated in hot hexane and dried to give 1.62 g (61%) of the title compound. $^1$H NMR (300 MHz, CDCl$_3$): δ ppm 0.43 (m, 0.5H) 0.83 (m, 10H) 1.06 (m, 0.5H) 1.51 (s, 1.5H) 1.56 (s, 1.5H) 1.83 (m, 1H) 2.02 (m, 0.5H) 2.26 (m, 0.5H) 3.74 (s, 1H) 6.09 (s, 0.5H) 7.51 (m, 3H) 8.10 (td, J=7.81, 1.29 Hz, 1H); MS (ESI$^-$) m/z 257 (M−H)$^-$.

EXAMPLE 49E (4R)-2-[bis(methylthio)methylene]-4-(3,3-dimethylbutyl)-4-methylnaphthalene-1,3(2H,4H)-dione A solution of Example 49D (1.61 g, 6.23 mmol) and pyridine (4.03 mL, 49.9 mmol) in 1,4-dioxane (20 mL) was treated with Example 5A (6.62 g, 24.9 mmol) and stirred at 100° C. for 1 hour. The mixture was cooled to 25° C. and partitioned between ethyl acetate and water. The ethyl acetate layer was washed with water and brine, dried with sodium sulfate, filtered, and concentrated in vacuo. The residue was chromatographed on silica gel eluting with hexane followed by 5%, 10%, and 20% ethyl acetate in hexane to give 2.04 g (90%) of the title compound. $^1$H NMR (300 MHz, CDCl$_3$): δ ppm 0.64 (td, J=12.96, 3.86 Hz, 1H) 0.74 (s, 9H) 0.87 (td, J=13.05, 4.41 Hz, 1H) 1.55 (s, 3H) 1.76 (td, J=13.05, 4.04 Hz, 1H) 2.25 (td, J=13.05, 4.41 Hz, 1H) 2.57 (s, 6H) 7.38 (m, 2H) 7.57 (td, J=7.54, 1.47 Hz, 1H) 8.22 (d, J=8.09 Hz, 1H); MS (ESI$^+$) m/z 363 (M+H)$^+$.

EXAMPLE 49F tert-butyl 3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-ylcarbamate A solution of Example 49E (1.41 g, 3.89 mmol) and Example 17A (1.17 g, 4.08 mmol) in toluene (50 mL) was refluxed for 6 hours. The solution was cooled to 25° C. and concentrated in vacuo. The residue was chromatographed on silica gel eluting with hexane followed by 20% and 30% ethyl acetate in hexane respectively to give 1.92 g (89%) of the title compound. $^1$H NMR (300 MHz, DMSO-d$_6$): δ ppm 0.39 (td, J=12.32, 3.31 Hz, 1H) 0.71 (s, 9H) 0.80 (td, J=12.96, 4.96 Hz, 1H) 1.51 (s, 9H) 1.58 (s, 3H) 2.06 (m, 1H) 2.23 (td, J=12.69, 4.78 Hz, 1H) 7.54 (m, 1H) 7.67 (m, 2H) 7.76 (m, 2H) 8.15 (m, 2H) 9.89 (s, 1H) 13.78 (s, 1H); MS (ESI$^-$) m/z 552 (M–H)$^-$.

EXAMPLE 49G (1R)-3-(7-amino-1,1-dioxido-4H-1,2,4-benzothiadiazin-3-yl)-1-(3,3-dimethylbutyl)-4-hydroxy-1-methylnaphthalen-2(1H)-one hydrochloride A solution of Example 49F (1.91 g, 3.45 mmol) in 4 M hydrochloric acid in 1,4-dioxane (30 mL) was stirred at 25° C. for 1 hour. The solution was concentrated in vacuo and the residue was triturated in diethyl ether to give 1.58 g (93%) of the title compound. $^1$H NMR (300 MHz, DMSO-d$_6$): δ ppm 0.38 (td, J=12.87, 3.68 Hz, 1H) 0.78 (m, 10H) 1.59 (s, 3H) 2.08 (m, 1H) 2.23 (td, J=12.78, 4.60 Hz, 1H) 7.07 (m, 2H) 7.53 (m, 2H) 7.77 (m, 2H) 8.16 (d, J=7.72 Hz, 1H) 13.58 (s, 1H); MS (ESI$^+$) m/z 454 (M+H)$^+$.

EXAMPLE 49H

N-{3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide A solution of Example 49G (0.250 g, 0.510 mmol), mesyl chloride (0.158 mL, 2.04 mmol), and pyridine (0.330 mL, 4.08 mmol) in acetone (3 mL) was stirred at 25° C. for 18 hours. The solution was partitioned between ethyl acetate and dilute citric acid and the layers were separated. The ethyl acetate layer was dried with sodium sulfate, filtered, and concentrated in vacuo. The residue was chromatographed on silica gel eluting with methylene chloride and 2.5% methanol in methylene chloride to give a yellow solid.

EXAMPLE 49I

Sodium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 49H in water (3 mL) was treated with 0.997N sodium hydroxide solution (0.410 mL) and stirred at 25° C. for 1 hour. The solution was lyophilized to give 209 mg (74%) of a yellow solid. $^1$H NMR (300 MHz, DMSO-d$_6$): δ ppm 0.43 (m, 1H) 0.70 (s, 9H) 0.81 (m, 1H) 1.38 (s, 3H) 1.71 (m, 1H) 2.16 (m, 1H) 2.90 (s, 3H) 7.28 (m, 3H) 7.44 (m, 3H) 8.05 (d, J=7.35 Hz, 1H) 9.87 (s, 1H) 15.44 (s, 1H); MS (ESI$^-$) m/z 530 (M–H)$^-$.

Method B:

EXAMPLE 49-1

2,5,5-trimethyl-2-phenylhexanoic Acid

To a solution of lithium bis(trimethylsilyl)amide in (154.48 g, 0.923 mol) in tetrahydrofuran (350 mL) was added 2-phenyl propionic acid (50.0 g, 0.333 mol) over 27 minutes maintaining the temperature below 25° C. Following a THF rinse (35 mL), the solution was heated to 50° C. for 23 minutes. The solution was then cooled below 25° C. and 3,3-dimethyl-1-iodobutane (110.3 g, 0.416 mol) was added. The reaction mixture was heated to 60° C. for 31 h, then was cooled to RT, and concentrated to a thick oil. Water (500 mL) was added and the solution was cooled to 10-15° C. and the pH was adjusted to <2 by the addition of 6 N HCl (75.59 g). The product was extracted with ethyl acetate (440 mL) and the organic layer was washed with 10% NaCl. The crude ethyl acetate solution (assayed for 66.8 g of 49-1, 85.6%) was concentrated to a thick oil and used in the resolution.

EXAMPLE 49-2

(2R)-2,5,5-trimethyl-2-phenylhexanoic acid (1S)-α-phenylethanamine Salt

The crude racemic acid of Example 49-1 in ethyl acetate (401.5 g of 49-1, 1.71 mol) was dissolved in ethyl acetate (9 L). To this solution was added (S)-α-methyl benzylamine (145.3 g, 1.20 mol). A white solid precipitated and the slurry was mixed for 18 h at room temperature. The product was isolated by filtration and dried to give the first crop salt (231.27 g). The first crop salt was dissolved in ethyl acetate (4 L) at 73° C. The solution was cooled slowly to room temperature and a white solid precipitated. After mixing for 18 h at room temperature, the product was isolated by filtration and the product was dried to give the title compound (194.30 g, 32% 97.6% ee measured using the following conditions: Column: ChiralPak, AD-R$^H$; mobile phase: acetonitrile (60%)/H$_2$O (40%), trifluoroacetic acid (0.06%); column temp: ambient; flow rate: 0.8 mL/min; and λ: 220 nm.).

EXAMPLE 49-3

Diethyl 2-[(2R)-2,5,5-trimethyl-2-phenylhexanoyl]malonate

A suspension of Example 49-2 (63.5 g, 0.179 mol) in ethyl acetate (400 mL) was treated with water (200 mL) then enough 3 M HCl to bring the pH to <2. The solution was mixed and the layers were separated. The organic phase was concentrated to thick oil. The oil was dissolved in heptane (500 mL) and concentrated then redissolved in heptane (210 mL). To this solution was added N,N-dimethylformamide (1.2 g, 17.1 mmol) and oxalyl chloride (34.0 g, 0.268 mol). The solution was mixed at room temperature overnight, filtered through celite and concentrated to a residue. The crude acid chloride was dissolved in $CH_3CN$ (50 mL). To a separate vessel containing a 0° C. solution of diethyl malonate (30.0 g, 0.187 mol), and $MgCl_2$ (17.8 g, 0.187 mol) in acetonitrile (240 mL) was added triethylamine (38.0 g, 0.376 mol). The solution was warmed to room temperature and mixed for 1 h, then cooled back to 0-10° C. The acid chloride/$CH_3CN$ solution was added over 30 minutes and the reaction mixture was heated to 50° C. for 3 h. The reaction mixture was cooled and concentrated to a thick sludge. Ethyl acetate (400 mL) and water (400 mL) were added and the pH was adjusted to 6 with concentrated HCl. The layers were separated and the organic solution was washed with 10% NaCl. The organic layer was concentrated to a thick oil then chased with heptane (300 mL) to give the title compound (assayed for 62.6 g, 93%).

EXAMPLE 49-4

Ethyl (4R)-4-(3,3-dimethylbutyl)-1-hydroxy-4-methyl-3-oxo-3,4-dihydronaphthalene-2-carboxylate To the product of Example 49-4 (260.86 g, 0.693 mol) at 10-15° C. was added methanesulfonic acid (780 mL). The solution was warmed to room temperature and mixed for 24 h. The reaction mixture was slowly quenched into a mixture of $H_2O$ (1150 mL) and ethyl acetate (1800 mL) at 5° C. The layers were separated and the organic layer was washed with 10% NaCl. The solution was concentrated and the resulting oil was dissolved in toluene (1100 mL). The crude title compound/toluene solution (assayed for 224 g of the title compound, 98%) was used directly in the next step.

EXAMPLE 49-5 tert-butyl 3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-ylcarbamate To a solution of the product of Example 49-4 (330.1 g, 0.999 mol) in toluene (1500 mL) was added the product of Example 17A-4 (287.1 g, 0.999 mol). The solution was heated to 100° C. for 4 h then cooled to RT. The solution was transferred to a pressure bottle and triethylamine (505.4, 4.99 mol) was added and the solution was heated to 100° C. for 26 h. The solution was concentrated to ⅓ of the original volume and ethyl acetate (1500 mL) was added. The organic layer was washed with 10% $KH_2PO_4$ and 10% NaCl then concentrated to a thick oil then chased with dichloromethane. The crude title compound (assay for 375.8 g, 68%) was used directly in the next step.

EXAMPLE 49-6

(1R)-3-(7-amino-1,1-dioxido-4H-1,2,4-benzothiadiazin-3-yl)-1-(3,3-dimethylbutyl)-4-hydroxy-1-methylnaphthalen-2(1H)-one To a solution of the product of Example 49-5 (185.0 g, 0.334 mol) in dichloromethane (220 mL) was added 4 M HCl in dioxane (430 mL, 1.72 mol) and the solution was mixed at room temperature for 3.5 h. The reaction was quenched by addition of ethyl acetate (1 L) and pH 7 phosphate buffer (1.5 L) and the layers were separated. The organic layer was concentrated and chased with ethanol to a final volume of approximately 1100 mL. The product precipitated and was isolated by filtration and dried to give the title compound (105.79 g, 70%).

EXAMPLE 49-7

N-{3-[(4R)-4-(3,3-dimethylbutyl)-1-hydroxy-4-methyl-3-oxo-3,4-dihydronaphthalen-2-yl]-1,1-dioxido-4H-1,2,4-benzothiadiazin-7-yl}methanesulfonamide To a solution of the product of Example 49-6 (235.0 g, 0.518 mol) and pyridine (123.0 g, 1.55 mol) in dichloromethane (1645 mL) at 18-20° C. was added methane sulfonyl chloride (89.0 g, 0.777 mol) over 45 minutes. The solution was mixed at RT for 3.5 h then quenched with 1 M HCl (1500 mL). The layers were separated and the organic layer was concentrated under vacuum. The product was crystallized from ethyl acetate/heptane (1/1, 8 volumes) to give the title compound (240.01 g, 87%).

EXAMPLE 49-8

Sodium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate A solution of sodium ethoxide (31.4 g, 0.462 mol) in ethanol (450 mL) was added over 50 minutes to a solution of the product of Example 49-7 (223.16 g, 0.420 mol) in ethanol (1700 mL) at 73° C. The product precipitated and the slurry was cooled slowly to room temperature and the product was isolated by filtration and dried to give the title compound (216.9 g, 93%).

EXAMPLE 50

N-{3-[4-ethyl-1-hydroxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 50A

Methyl 2-phenylbutanoate

2-Phenylbutyric acid (10 g, 61 mmole) was dissolved in methanol (30 ml) treated with concentrated HCl (1 ml) and heated at reflux for 20 hours. The heating was stopped and the reaction mixture cooled to room temperature. The solvent was removed in vacuo and the oily residue was treated with ethyl acetate (100 ml). The organic layer was washed with saturated sodium bicarbonate solution and saturated sodium chloride solution, dried ($Na_2SO_4$), filtered and concentrated in vacuo to give the title compound as a clear oil. Yield 10.61 g (97%). $^1$H NMR (300 MHz, DMSO-d$_6$): δ ppm 0.81 (t, J=7.35 Hz, 3H) 1.69 (m, 1H) 1.98 (m, 1H) 3.53 (d, J=7.35 Hz, 1H) 3.58 (s, 3H) 7.30 (m, 5H).

EXAMPLE 50B

Methyl 2-ethyl-5-methyl-2-phenylhexanoate

Example 50A (3 g, 16.8 mmole) dissolved in tetrahydrofuran (10 ml) was added dropwise to a solution containing lithium hexamethyldisilazide in tetrahydrofuran (1.0 M, 19.4 ml, 19.4 mmole) at −78° C. over 10 minutes. The solution was stirred at −50° C. for 30 minutes, warmed to 0° C. and stirred 30 minutes. The reaction mixture was cooled to −78° C. and 1-Bromo-3-methyl butane (2.5 ml, 20.3 mmole) was added dropwise over 5 minutes. The mixture was warmed to room temperature and stirred 48 hours. The mixture was quenched with 1N HCl (20 ml), stirred 30 minutes, then partitioned between ethyl acetate (50 ml) and water. The layers were separated and the aqueous layer was extracted with additional ethyl acetate (50 ml). The combined organic extracts were washed with saturated sodium chloride solution, dried (Na$_2$SO$_4$), filtered and concentrated in vacuo. The residue was purified on silica gel eluting first with hexane, then 5% ethyl acetate in hexane to give the title compound (2.4 g, 58%). $^1$H NMR (300 MHz, DMSO-d$_6$): δ ppm 0.65 (t, J=7.54 Hz, 3H) 0.83 (m, 6H) 0.89 (m, 2H) 1.46 (m, 1H) 1.94 (m, 4H) 3.57 (s, 3H) 7.27 (m, 5H).

EXAMPLE 50C 2-ethyl-5-methyl-2-phenylhexanoic Acid

Example 50B (2.4 g, 9.67 mmole) was treated with tetrahydrofuran (30 ml) and potassium trimethylsilanoate (6.2 g, 48.35 mmole) and heated at reflux 18 hr. The reaction mixture was cooled and concentrated in vacuo. The resulting solid was dissolved in water (40 ml) and extracted with ethyl ether (2×10 ml). The aqueous layer was made acidic (pH 2) by the addition of 2N HCl solution. The resulting slurry was extracted with ethyl acetate (2×50 ml). The combined organic extracts were washed with saturated sodium chloride solution, dried (Na$_2$SO$_4$), filtered and concentrated in vacuo to give the title compound as a yellow oil (1.8 g, 79%). $^1$H NMR (300 MHz, DMSO-d$_6$): δ ppm 0.67 (t, J=7.54 Hz, 3H) 0.84 (m, 6H) 0.89 (m, 1H) 1.45 (dd, J=13.24, 6.62 Hz, 2H) 1.92 (m, 4H) 7.27 (m, 5 H) 12.26 (s, 1H).

EXAMPLE 50D

Diethyl 2-(2-ethyl-5-methyl-2-phenylhexanoyl)malonate

A solution of diethyl malonate (0.33 ml, 2.18 mmole) in acetonitrile (4 ml) was cooled in an ice bath to 0° C. and treated with magnesium chloride (0.21 g, 2.18 mmole), followed by dropwise addition of triethylamine (0.64 ml, 4.58 mmole). The resulting slurry was stirred at 0° C. 15 minutes, then stirred for another 2 hr at room temperature. Example 50C (0.51 g, 2.18 mmole) was treated with hexane (40 ml), oxalyl chloride (0.6 ml, 6.54 mmole) and dimethylformamide (0.18 ml, 2.4 mmole) and stirred at room temperature for 2 hr. The resulting solution was treated with 1 g Celite, filtered and concentrated in vacuo to give 2-Ethyl-5-methyl-2-phenylhexanoyl chloride as a yellow oil. The oil was dissolved in acetonitrile (5 ml) and added dropwise to the slurry prepared from diethyl malonate and magnesium chloride recooled to 0° C. When addition was complete, the reaction mixture is heated and stirred at 50° C. 18 hr. The mixture was cooled to room temperature and concentrated in vacuo. The residue was suspended in Ethyl acetate/1N HCl (3:1) and stirred approximately 30 minutes until all solid had dissolved. The layers were separated and the aqueous layer was extracted with additional ethyl acetate (2×25 ml). The combined organic extracts were washed with saturated sodium chloride, dried (Na$_2$SO$_4$), filtered and concentrated in vacuo. The residue was purified on silica gel eluting first with hexane, then hexane/ethyl acetate (95:5) to give the title compound as a yellow oil (0.59 g, 72%). $^1$H NMR (300 MHz, DMSO-d$_6$): δ ppm 0.65 (m, 3H) 0.84 (dd, J=8.82, 6.62 Hz, 6H) 1.06 (t, J=7.17 Hz, 3H) 1.20 (m, 3H) 1.48 (m, 2H) 1.98 (m, 4H) 3.47 (s, 1H) 3.92 (m, 2H) 4.11 (q, is J=7.11 Hz, 2H) 7.31 (m, 5H).

EXAMPLE 50E

Ethyl 4-ethyl-1-hydroxy-4-(3-methylbutyl)-3-oxo-3,4-dihydronaphthalene-2-carboxylate Example 50D (0.59 g, 1.57 mmole) was treated with methanesulfonic acid (3 ml) and stirred 15 hr at 25° C. The mixture was treated with water (50 ml) and extracted with ethyl acetate (2×50 ml). The combined organic extracts were washed with saturated sodium chloride, dried (Na$_2$SO$_4$), filtered and concentrated in vacuo to give the title compound (0.48 g, 92%). $^1$H NMR (300 MHz, DMSO-d$_6$): δ ppm 0.37 (q, J=7.35 Hz, 3H) 0.68 (m, 6H) 0.83 (m, 2H) 1.07 (m, 1H) 1.16 (m, 3H) 1.96 (m, 2H) 2.13 (t, J=12.87 Hz, 2H) 4.06 (m, 2H) 7.50 (m, 4H) 12.09 (s, 1H).

EXAMPLE 50F 4-ethyl-4-(3-methylbutyl)naphthalene-1,3(2H,4H)-dione

Example 50E (0.48 g, 1.45 mmole) was treated with dioxane/1N HCl (1:1, 20 ml) and heated at reflux 17 hr. The mixture cooled and concentrated in vacuo. The residue was dissolved in ethyl acetate (50 ml) washed with water and saturated sodium chloride, dried (Na$_2$SO$_4$), filtered and concentrated in vacuo to give the title compound (0.15 g, 39%). $^1$H NMR (300 MHz, DMSO-d$_6$): δ ppm 0.31 (m, 3H) 0.65 (m, 6H) 0.83 (m, 2H) 1.26 (d, J=12.50 Hz, 2H) 1.46 (s, 1H) 1.92 (m, 2H) 5.84 (s, 1H) 7.36 (m, 4H) 11.46 (s, 1H).

EXAMPLE 50G

2-[bis(methylthio)methylene]-4-ethyl-4-(3-methylbutyl)naphthalene-1,3(2H,4H)-dione Example 50F (0.15 g, 0.58 mmole) was treated with Example 5A and pyridine (0.38 ml, 4.64 mmole) in dioxane (10 ml) and the mixture was heated at 100° C. for 2.5 hr. The reaction mixture was cooled, diluted with ethyl acetate (100 ml), washed with water (20 ml), and saturated sodium chloride, dried (Na$_2$SO$_4$), filtered and concentrated in vacuo. The residue was purified by chromatography on silica gel eluting first with hexane, then 95/5 hexane/ethyl acetate to give the title compound as a yellow oil (0.15 g, 71%). $^1$H NMR (300 MHz, DMSO-d$_6$): δ ppm 0.40 (t, J=7.35 Hz, 3H) 0.68 (t, J=6.80 Hz, 6H) 1.06 (s, 1H) 1.29 (s, 2H) 1.87 (m, 2H) 2.11 (m, 2H) 3.32 (s, 6H) 7.65 (m, 4H).

EXAMPLE 50H tert-butyl 3-[4-ethyl-1-hydroxy-4-(3-methylbutyl)-3-oxo-3,4-dihydronaphthalen-2-yl]-1,1-dioxido-4H-1,2,4-benzothiadiazin-7-ylcarbamate Example 50G (0.15 g, 0.414 mmole) and Example 17A (0.12 g, 0.435 mmole) were heated at reflux in toluene (5 ml) 7 hr. The mixture was cooled and the solvent removed in vacuo. The residue was purified by chromatography on silica gel eluting first with 80/20 hexane/ethyl acetate then 70/30 hexane/ethyl acetate to give the title compound, (0.15 g, 61%). $^1$H NMR (300 MHz, DMSO-$d_6$): δ ppm 0.38 (s, 3H) 0.69 (dd, J=10.11, 6.43 Hz, 6H) 1.04 (m, 1H) 1.16 (m, J=6.99 Hz, 1H) 1.30 (m, 2H) 1.50 (s, 9H) 1.99 (s, 2H) 2.19 (s, 2H) 7.75 (m, 7H) 9.81 (s, 1H).

EXAMPLE 50I 3-(7-amino-1,1-dioxido-4H-1,2,4-benzothiadiazin-3-yl)-1-ethyl-4-hydroxy-1-(3-methylbutyl)naphthalen-2(1H)-one hydrochloride Example 50H (0.14 g, 0.253 mmole) was treated with 4N HCl/dioxane (2 ml) and stirred 18 hr at room temperature. The solvent was removed in vacuo. The residue was triturated with ether to give the title compound as a yellow solid (0.11 g, 92%). $^1$H NMR (300 MHz, DMSO-$d_6$): δ ppm 0.39 (t, J=7.35 Hz, 3H) 0.70 (m, 6H) 0.77 (m, 3H) 1.31 (m, 2H) 2.21 (m, 2H) 3.68 (bs, 2H) 7.49 (m, 7H) 13.58 (s, 1H).

EXAMPLE 50J

N-{3-[4-ethyl-1-hydroxy-4-(3-methylbutyl)-3-oxo-3,4-dihydronaphthalen-2-yl]-1,1-dioxido-4H-1,2,4-benzothiadiazin-7-yl}methanesulfonamide Example 50I (0.11 g, 0.225 mmole) in acetone (4 ml) was treated with pyridine (0.072 ml, 0.89 mmole) and methane sulfonyl chloride (0.035 ml, 0.45 mmole) and stirred 18 hr at 25° C. The solvent was removed in vacuo. The residue was partitioned between ethyl acetate (50 ml) and 3% aqueous citric acid solution (10 ml). The organic layer was washed with saturated sodium chloride, dried (Na$_2$SO$_4$), filtered and concentrated in vacuo. The residue was purified on silica gel eluting with methylene chloride/methanol (98/2) to give the title compound (0.11 g, 92%). $^1$H NMR (300 MHz, DMSO-$d_6$): δ ppm 0.40 (t, J=7.17 Hz, 3H) 0.70 (dd, J=9.93, 6.62 Hz, 6H) 0.80 (m, 1H) 1.30 (m, J=6.25 Hz, 2H) 2.06 (m, 2H) 2.22 (m, 1H) 2.71 (m, 1H) 3.07 (d, J=8.09 Hz, 3H) 7.70 (m, 7H) 10.26 (s, 1H) 13.72 (s, 1H). MS (ESI$^-$) 530 (M+H$^-$).

EXAMPLE 51

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide

EXAMPLE 51A

Methyl 3-cyclopentyl-2-methyl-2-phenylpropanoate

A solution of lithium bis(trimethylsilyl)amide (1M in tetrahydrofuran, 3.04 mL, 3.04 mmol, 1 equiv) under a N$_2$ atmosphere was cooled to 0° C. and treated with a solution of methyl 2-phenylpropionate (0.500 g, 3.04 mmol, 1 equiv) in dry tetrahydrofuran (2 mL). The reaction was stirred at 0° C. for 2 hrs, then cooled to −78° C. and treated with hexamethylphosphoric triamide (0.4 mL) and bromomethylcyclopentane (0.745 g, 4.568 mmol, 1.5 equiv). Stirred the reaction at −78° C. and allowed the bath to slowly warm to room temperature overnight. After 15 hrs, the reaction mixture was quenched with 10% aq NH$_4$Cl (50 mL) and extracted with ethyl acetate (100 mL). The organic extract was washed with H$_2$O (50 mL) and brine, then dried over Na$_2$SO$_4$, filtered, and concentrated by rotary evaporation. The residue was purified by SiO$_2$ flash chromatography with 2:3 dichloromethane/hexanes to give the product as colorless oil (1.38 g, 5.60 mmol, 92%). $^1$H NMR (300 MHz, DMSO-$d_6$): δ ppm 0.90-1.12 (m, 2H) 1.32-1.72 (m, 10H) 1.97-2.12 (m, 2H) 3.58 (s, 3H) 7.19-7.35 (m, 5H); MS (APCI$^+$) m/z 247 (M+H)$^+$.

EXAMPLE 51B 3-cyclopentyl-2-methyl-2-phenylpropanoic acid

Example 51A (1.345 g, 5.46 mmol, 1 equiv) was dissolved in dry tetrahydrofuran (50 mL) under a nitrogen atmosphere and treated with potassium trimethylsilanoate (3.89 g, 27.3 mmol, 5 equiv) at room temperature. The mixture was heated at reflux for 18 hrs, then cooled to room temperature and treated with 1N aq NaOH (60 mL). The basic solution was washed with hexanes (100 mL), then acidified with 2N aq HCl to pH 2 and extracted with ethyl acetate (2×50 mL). The combined organic extracts were washed with brine and dried over Na$_2$SO$_4$, filtered, and concentrated by rotary evaporation. The resulting yellow oil slowly crystallized to give the product (1.25 g, 5.39 mmol, 99%). $^1$H NMR (300 MHz, DMSO-$d_6$): δ ppm 0.87-1.17 (m, 2H) 1.30-1.75 (m, 10H) 1.93-2.09 (m, 2H) 7.17-7.37 (m, 5H) 12.23 (s, 1H). MS (ESI$^-$) m/z 231 (M−H)$^-$.

EXAMPLE 50C 3-cyclopentyl-2-methyl-2-phenylpropanoyl chloride

Example 51B (400 mg, 1.722 mmol, 1 equiv) was dissolved in dry dichloromethane (16 mL) under a N$_2$ atmosphere and treated with oxalyl chloride (2M in dichloromethane, 1.29 mL, 2.58 mmol, 1.5 equiv) and dry N,N-dimethyl formamide (2 drops from 250 μL syringe). After stirring at room temperature for 3 hr, the solvent was removed by rotary evaporation and the residue azeotroped with dry toluene (10 mL). The residue was further dried on hi-vacuum for 30 min before using in Example 1D.

EXAMPLE 51D

Diethyl 2-(3-cyclopentyl-2-methyl-2-phenylpropanoyl)malonate

An oven-dried N$_2$-purged flask was charged with diethylmalonate (278.6 mg, 1.722 mmol, 1 equiv) and dry acetonitrile (3 mL). The solution was cooled to 0° C. and treated with MgCl$_2$ beads (167 mg, 1.722 mmol, 1 equiv) followed by dropwise addition of triethylamine (504 μL, 3.616 mmol, 2.1 equiv). The reaction was stirred at 0° C. for 15 min, then at room temperature for 3 hr. The white mixture was cooled to 0° C. and Example 51C (assume 1.722 mmol, 1 equiv) in dry acetonitrile (3 mL) was added dropwise. The reaction was then heated at 50° for 17 hr, cooled to room temperature, and the solvent removed by rotary evaporation. Added 1N aq HCl (10 mL) and ethyl acetate (30 mL), and stirred until all solids had dissolved. The layers were separated and the aqueous phase extracted with ethyl acetate (2× 30 mL). The combined organic extracts were washed with brine, dried over $Na_2SO_4$, filtered, and concentrated by rotary evaporation to give the product as dark yellow oil (645 mg, 1.722 mmol, quantitative). $^1$H NMR (300 MHz, DMSO-$d_6$): δ ppm 0.70-0.81 (m, 1H) 1.03 (t, J=7.17 Hz, 3H) 1.12 (t, J=6.99 Hz, 3H) 1.19-1.50 (m, 7H) 1.53 (s, 3H) 1.64-1.76 (m, 1H) 1.99 (d, J=5.88 Hz, 2H) 3.91 (q, J=6.99 Hz, 2H) 4.03 (q, J=6.99 Hz, 2H) 4.71 (s, 1H) 7.23-7.40 (m, 5H). MS (ESI$^+$) m/z 375 (M+H)$^+$, 392 (M+NH$_4$)$^+$.

EXAMPLE 51E

Ethyl 4-(cyclopentylmethyl)-1-hydroxy-4-methyl-3-oxo-3,4-dihydronaphthalene-2-carboxylate Example 51D (645 mg, 1.722 mmol) was dissolved in methanesulfonic acid (3 mL) and stirred at room temperature for 19 hr. The reaction was poured into ice-$H_2O$ (25 mL) and extracted with ethyl acetate (2× 30 mL). The combined organic extract was washed with brine, dried over $Na_2SO_4$, filtered, and concentrated by rotary evaporation to yellow oil. Purification by $SiO_2$ flash chromatography with 20:80 ethyl acetate/hexanes afforded the title compound as oil (325 mg, 0.989 mmol, 57%). $^1$H NMR (300 MHz, DMSO-$d_6$): δ ppm 0.54-0.71 (m, 1H) 0.85-1.59 (m, 14H) 2.05-2.18 (m, 1H) 2.21-2.34 (m, 1H) 4.32 (q, J=7.11 Hz, 2H) 7.41-7.49 (m, 1H) 7.61-7.73 (m, 2H) 7.98-8.05 (m, 1H) 13.79 (br s, 1H). MS (ESI$^+$) m/z 329 (M+H)$^+$, 351 (M+Na)$^+$.

EXAMPLE 51F 1-(cyclopentylmethyl)-4-hydroxy-1-methylnaphthalen-2(1H)-one

Example 51E (323 mg, 0.984 mmol) in 1,4-dioxane (5 mL) and 1N aq HCl (5 mL) was refluxed for 2.5 hr. The solution was cooled to room temperature, diluted with $H_2O$ (25 mL), and extracted with ethyl acetate (2×30 mL). The combined organic extract was washed with $H_2O$ (30 mL) and brine, then dried over $Na_2SO_4$, filtered, and concentrated by rotary evaporation to give the product as a white solid (243 mg, 0.948 mmol, 96%). $^1$H NMR (500 MHz, DMSO-$d_6$, 100° C.) δ ppm 0.58-0.71 (m, 1H) 0.93-1.10 (m, 2H) 1.12-1.60 (m, 9H) 1.95-2.05 (m, 1H) 2.20-2.29 (m, 1H) 5.70 (s, 1H) 7.33-7.39 (m, 1H) 7.53 (t, J=7.32 Hz, 1H) 7.58 (m, J=7.33 Hz, 1H) 7.92 (d, J=6.10 Hz, 1H) 11.12 (s, 1H). MS (ESI$^+$) m/z 257 (M+H)$^+$, 279 (M+Na)$^+$.

EXAMPLE 51G

2-[bis(methylthio)methylene]-4-(cyclopentylmethyl)-4-methylnaphthalene-1,3(2H,4H)-dione Example 51F (240 mg, 0.936 mmol, 1 equiv) and dry pyridine (606 μL, 7.49 mmol, 8 equiv) in dry 1,4-dioxane (4 mL) under a $N_2$ atmosphere was treated with Example 5A (994 mg, 3.745 mmol, 4 equiv) in one portion. The reaction was heated in a preheated 100° oil bath for 2 hr as an orange-colored solution. After cooling to room temperature, the reaction was diluted with $H_2O$ (25 mL) and extracted with ethyl acetate (2× 30 mL). The combined organic extracts were washed with $H_2O$ (25 mL) and brine, then dried over $Na_2SO_4$, filtered, and concentrated by rotary evaporation to dark yellow oil. Purification by $SiO_2$ flash chromatography with 15:85 ethyl acetate/hexanes afforded the product as a yellow solid (286 mg, 0.7933 mmol, 85%). $^1$H NMR (300 MHz, DMSO-$d_6$): δ ppm 0.60-0.72 (m, 1H) 0.75-0.90 (m, 1H) 1.05-1.41 (m, 7H) 1.48 (s, 3H) 1.93 (dd, J=13.24, 5.52 Hz, 1H) 2.25 (dd, J=13.42, 6.43 Hz, 1H) 2.55 (s, 6H) 7.37-7.46 (m, 1H) 7.57-7.66 (m, 2H) 8.04 (d, J=7.72 Hz, 1H). MS (ESI$^+$) m/z 361 (M+H)$^+$, 383 (M+Na)$^+$.

EXAMPLE 51H tert-butyl 3-[4-(cyclopentylmethyl)-1-hydroxy-4-methyl-3-oxo-3,4-dihydronaphthalen-2-yl]-1,1-dioxido-4H-1,2,4-benzothiadiazin-7-ylcarbamate Example 51G (283 mg, 0.785 mmol, 1 equiv) and Example 17A (226 mg, 0.785 mmol, 1 equiv) in dry toluene (20 mL) under a $N_2$ atmosphere was heated at reflux for 15 hr. The reaction was cooled to room temperature and the solvent was removed by rotary evaporation to give a yellow solid. Trituration of the solid with $Et_2O$ (3× 10 mL) afforded the product as an off-white solid (358 mg, 0.649 mmol, 83%). $^1$H NMR (300 MHz, DMSO-$d_6$): δ ppm 0.53-0.70 (m, 1H) 0.85-1.07 (m, 2H) 1.09-1.46 (m, 6H) 1.51 (s, 9H) 1.57 (s, 3H) 2.23 (dd, J=13.24, 6.25 Hz, 1H) 2.38 (dd, J=13.29, 6.31 Hz, 1H) 7.50-7.58 (m, 1H) 7.62-7.82 (m, 4H) 8.11-8.20 (m, 2H) 9.90 (s, 1H) 13.79 (s, 1H). MS (ESI$^+$) m/z 552 (M+H)$^+$, 569 (M+NH$_4$)$^+$, 574 (M+Na)$^+$.

EXAMPLE 51I 3-(7-amino-1,1-dioxido-4H-1,2,4-benzothiadiazin-3-yl)-1-(cyclopentylmethyl)-4-hydroxy-1-methylnaphthalen-2(1H)-one hydrochloride Example 51H (355 mg, 0.644 mmol) was dissolved in 4M HCl in 1,4-dioxane (10 mL) under a $N_2$ atmosphere and stirred at room temperature for 1 hr. The solvent was removed by rotary evaporation and the residue was azeotroped with dichloromethane/hexanes on a rotary evaporator to give a yellow solid. Trituration with $Et_2O$ (20 mL) provided the desired product as a yellow solid (307 mg, 0.629 mmol, 98%). $^1$H NMR (300 MHz, DMSO-$d_6$): δ ppm 0.54-0.70 (m, 1H) 0.83-1.47 (m, 8H) 1.57 (s, 3H) 2.23 (dd, J=13.24, 6.25 Hz, 1H) 2.37 (dd, J=13.30, 6.31 Hz, 1H) 6.97-7.06 (m, 2H) 7.47 (d, J=8.82 Hz, 1H) 7.50-7.59 (m, 1H) 7.70-7.82 (m, 2H) 8.17 (d, J=7.72 Hz, 1H) 13.63 (s, 1H). MS (ESI$^+$) m/z 452 (M+H)$^+$, 474 (M+Na)$^+$ for free amine.

EXAMPLE 51J

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide Example 51I (100 mg, 0.205 mmol, 1 equiv) in acetone (3 mL) was treated with dry pyridine (133 μL, 1.64 mmol, 8 equiv) and methanesulfonyl chloride (64 μL, 0.820 mmol, 4 equiv) under a $N_2$ atmosphere at room temperature. The reaction was stirred for 21 hr, and diluted with ethyl acetate (50 mL) and 10% aq citric acid (25 mL). The layers were separated and the organic phase washed with brine, dried over $Na_2SO_4$, filtered, and concentrated by rotary evaporation. Purification by $SiO_2$ flash chromatography with a gradient of 1:99 to 2:98 methanol/dichloromethane afforded the product as a yellow solid (41 mg). Impure fractions were concentrated to a solid which was then extracted with $Et_2O$ (6× 3 mL). The ethereal extracts were combined, concentrated, and purified by SiO$_2$ flash chromatography with 1:99 methanol/dichloromethane to give an additional 34 mg of product. The total yield was 75 mg (0.142 mmol, 69%). $^1$H NMR (300 MHz, DMSO-d$_6$): δ ppm 0.55-0.68 (m, 1H) 0.86-1.49 (m, 8H) 1.57 (s, 3H) 2.22 (dd, J=13.42, 6.43 Hz, 1H) 2.37 (dd, J=13.61, 6.62 Hz, 1H) 3.08 (s, 3H) 7.50-7.65 (m, 3H) 7.69-7.81 (m, 3H) 8.17 (d, J=7.35 Hz, 1H) 10.25 (s, 1H) 13.85 (s, 1H). MS (ESI$^+$) m/z 530 (M+H)$^+$, 547 (M+NH$_4$)$^+$.

EXAMPLE 51K

Sodium 4-(cyclopentylmethyl)-4-methyl-2-{7-[(methylsulfonyl)amino]-1,1-dioxido-4H-1,2,4-benzothiadiazin-3-yl}-3-oxo-3,4-dihydronaphthalen-1-olate A suspension of the product of Example 51J (38.2 mg, 0.072 mmol, 1 equiv) in distilled H$_2$O (5 mL) was treated with 0.998N aq NaOH (72.3 mL, 0.072 mmol, 1 equiv), sonicated to achieve solution, and stirred at room temperature for 1 hr. The solution was diluted with H$_2$O (10 mL), frozen in a dry ice-acetone bath for 20 min, and lyophilized to give the sodium salt of the title compound (40 mg, 0.072 mmol, quantitative). $^1$H NMR (300 MHz, DMSO-d$_6$): δ ppm 0.50-0.66 (m, 1H) 0.82-1.06 (m, 2H) 1.08-1.49 (m, 9H) 1.84 (dd, J=13.24, 6.25 Hz, 1H) 2.31 (dd, J=13.05, 6.07 Hz, 1H) 2.94 (s, 3H) 7.22-7.38 (m, 3H) 7.40-7.50 (m, 3H) 8.05 (d, J=7.35 Hz, 1H) 9.87 (s, 1H) 15.53 (s, 1H).

EXAMPLE 52

N-{3-[(4S)-4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide Example 51J (58 mg, 0.1095 mmol) were separated by chiral HPLC with a Chiralcel OD column (4.6×250, column temperature 40° C.) eluted with 70:15:15 hexane (0.1% trifluoroacetic acid)/ethanol/methanol at 0.8 mL/min (UV detector 330 nm). Retention time 9.25 min. Recovered 26.8 mg (0.051 mmol).

EXAMPLE 53

N-{3-[(4R)-4-(cyclopentylmethyl)-1-hydroxy-4-methyl-3-oxo-3,4-dihydronaphthalen-2-yl]-1,1-dioxido-4H-1,2,4-benzothiadiazin-7-yl}methanesulfonamide Example 51J (58 mg, 0.1095 mmol) were separated by chiral HPLC with a Chiralcel OD column (4.6×250, column temperature 40° C.) eluted with 70:15:15 hexane (0.1% trifluoroacetic acid)/ethanol/methanol at 0.8 mL/min (UV detector 330 nm). Retention time 10.63 min. Recovered 30.0 mg (0.057 mmol).

EXAMPLE 54

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}sulfamide

EXAMPLE 54A

Benzyl({3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}amino)sulfonylcarbamate A solution of chlorosulfonylisocyanate (22.6 μL, 0.259 mmol, 1.3 equiv) in dry dichloromethane (2 mL) under a N$_2$ atmosphere was treated with benzyl alcohol (26.8 μL, 0.259 mmol, 1.3 equiv) at 0° C. and stirred for 30 min at 0° C. A solution of Example 511 (97.3 mg, 0.199 mmol, 1 equiv) and triethylamine (111 mL, 0.798 mmol, 4 equiv) in dry dichloromethane (3 mL) was then added via syringe at 0° C., and the resulting solution stirred at room temperature for 2 hr. The reaction was diluted with dichloromethane (50 mL) and washed with 1N aq HCl (20 mL) and brine, dried over Na$_2$SO$_4$, filtered, and concentrated by rotary evaporation. The residue was purified by SiO$_2$ flash chromatography with 5:95 methanol/dichloromethane to give the product as a yellow solid (119 mg, 0.179 mmol, 90%). $^1$H NMR (300 MHz, DMSO-d$_6$): δ ppm 0.54-0.70 (m, 1H) 0.87-1.07 (m, 2H) 1.09-1.49 (m, 6H) 1.56 (s, 3H) 2.13-2.25 (m, 1H) 2.37 (dd, J=13.97, 6.99 Hz, 1H) 5.11 (s, 2H) 7.22-7.36 (m, 5H) 7.42-7.56 (m, 2H) 7.58-7.79 (m, 4H) 8.16 (d, J=8.09 Hz, 1H) 11.08 (s, 1H) 12.13 (s, 1H) 14.01 (s, 1H). MS (ESI$^+$) m/z 665 (M+H)$^+$, 682 (M+NH$_4$)$^+$.

EXAMPLE 54B

N-{3-[4-(cyclopentylmethyl)-1-hydroxy-4-methyl-3-oxo-3,4-dihydronaphthalen-2-yl]-1,1-dioxido-4H-1,2,4-benzothiadiazin-7-yl}sulfamide Example 54A (115 mg, 0.0782 mmol) was dissolved in methanol (10 mL) and hydrogenated at 1 atm H$_2$ (balloon) with 10% Pd—C (30 mg, 26 wt %) for 1 hr. The reaction was vacuum filtered through a 0.45 g PTFE membrane filter and the catalyst thoroughly washed with methanol (50 mL). The filtrate was concentrated by rotary evaporation to a light yellow solid. Purification by SiO$_2$ flash chromatography with 5:95 methanol/dichloromethane gave the product as a light yellow solid (81 mg, 0.153 mmol, 88%). $^1$H NMR (300 MHz, DMSO-d$_6$): δ ppm 0.54-0.70 (m, 1H) 0.82-1.06 (m, 2H) 1.09-1.48 (m, 6H) 1.56 (s, 3H) 2.15-2.26 (m, 1H) 2.37 (dd, J=13.60, 6.62 Hz, 1H) 7.38 (s, 2H) 7.46-7.61 (m, 3H) 7.64-7.81 (m, 3H) 8.17 (d, J=7.35 Hz, 1H) 10.03 (s, 1H) 13.88 (s, 1H). MS (ESI$^+$) m/z 531 (M+H)$^+$, 548 (M+NH$_4$)$^+$, 553 (M+Na)$^+$.

EXAMPLE 55 tert-butyl 3-[4-(cyclobutylmethyl)-1-hydroxy-4-methyl-3-oxo-3,4-dihydronaphthalen-2-yl]-1,1-dioxido-4H-1,2,4-benzothiadiazin-7-ylcarbamate

EXAMPLE 55A

Methyl 3-cyclobutyl-2-phenylpropanoate

To a stirring solution of freshly prepared lithium diisopropylamine (76.5 mmol) in 500 mL of tetrahydrofuran at 0° C. was added methyl phenylacetate (10.44 g, 69.50 mmol) in 125 mL tetrahydrofuran dropwise over 30 minutes. After stirring at 0° C. for 1 hour the reaction mixture was cooled to −78° C. and treated with 50 mL of hexamethylphosphoric triamide followed by the dropwise addition of bromomethyl cyclobutane (9.37 mL, 83.4 mmol) and LiI (200 mg). The reaction mixture was stirred for 18 hours warming to 25° C. The reaction was quenched over 1 L of water containing 250 mL of sat. NH$_4$Cl and extracted 3× with ethyl acetate. The combined organic layers were washed sequentially with saturated sodium bicarbonate, brine, and dried over MgSO$_4$ yielding the crude product as an oil that was used without further purification. ¹H NMR (300 MHz, CDCl₃): δ ppm 1.59 (m, 2H) 1.89 (m, 5H) 2.17 (m, 2H) 3.47 (t, J=7.54 Hz, 1H) 3.64 (s, 3H) 7.31 (m, 5H). MS (ESI⁺) m/z=236 (M+NH₄)⁺.

EXAMPLE 55B

Methyl 3-cyclobutyl-2-methyl-2-phenylpropanoate

To a freshly prepared solution of lithium diisopropylamine (0.0182 mmol) in 20 mL of tetrahydrofuran at 0° C. was added Example 55A (3.60 g, 0.0165 mmol) in 10 mL of tetrahydrofuran dropwise over 10 minutes. The solution was then cooled to −78° C. and treated with hexamethylphosphoric triamide (5 mL) followed by the addition of methyl iodide (1.54 mL, 24.8 mmol). The reaction mixture was allowed to warm to 25° C. while stirring overnight. An additional portion of MeI (5.15 mL, 82.7 mmol) was added and the reaction was continued for 2 days). The reaction was quenched over 250 mL of water containing 25 mL of sat. NH₄Cl and extracted 3× with ethyl acetate. The combined organic layers were washed sequentially with saturated sodium bicarbonate, brine, and dried over MgSO₄ yielding the crude product after solvent was removed in. vacuo. as a reddish oil that was used without further purification. ¹H NMR (300 MHz, CDCl₃): δ ppm 1.50 (s, 3H) 1.64 (m, 3H) 1.82 (m, 2H) 2.01 (m, 2H) 2.21 (m, 2H) 3.63 (s, 3H) 7.29 (m, 5H).). MS (ESI⁺) m/z=250 (M+NH₄)⁺.

EXAMPLE 55C 3-cyclobutyl-2-methyl-2-phenylpropanoic Acid

Example 55B (3.0 g, 12.9 mmol) was taken up in 200 mL of tetrahydrofuran and treated with sodium trimethylsilanoate (7.28 g, 64.9 mmol). The resulting solution was refluxed for 16 hours, cooled, and poured over 1N NaOH. Extract the basic layer with hexane (discarded) and acidify to pH=2 with 2N HCl to produce a cloudy suspension that was extracted 3× with ethyl acetate. The combined ethyl acetate layers were washed sequentially with water, brine, and dried over MgSO₄. Solvent was removed in vacuo to yield an oil that solidifies upon standing. The title compound (2.67 g, 95% yield) was used without further purification. ¹H NMR (300 MHz, DMSO-d₆): δ ppm 1.39 (s, 3H) 1.53 (m, 1H) 1.72 (m, 4H) 1.98 (m, 3H) 2.20 (m, 1H) 7.26 (m, 5H) 12.29 (s, 1H). MS (ESI⁺) m/z=236 (M+NH₄)⁺.

EXAMPLE 55D

Diethyl 2-(3-cyclobutyl-2-methyl-2-phenylpropanoyl)malonate

To a round bottom flask was added Example 55C (0.230 g, 1.05 mmol), oxalyl chloride (0.276 mL, 3.20 mmol), dichloromethane (10 mL), and 1 drop of N,N-dimethyl formamide. After the bubbling ceased, the reaction mixture was filtered through a pad of celite and concentrated in vacuo and used in the next step without further manipulation. To a second round bottom flask was added diethylmalonate (0.167 mL, 1.05 mmol) and CH₃CN and the resulting mixture was cooled in an ice bath. Then, MgCl₂ (0.104 g, 1.05 mmol) was added portionwise over 5 minutes followed by the addition of Et₃N (0.320 mL, 2.30 mmol). This slurry was warmed to 25° C. and stirred for 2 hours. The acid chloride was dissolved in 10 mL of CH₃CN and added dropwise to the stirring slurry containing the diethylmalonate. After the complete addition, the reaction mixture was stirred at 25° C. for 12 hours and then heated at 60° C. for 24 hours. The reaction mixture was cooled and quenched with 1n HCl. The aqueous layer was extracted with 3× ethyl acetate and then the combined organic layers dried over MgSO₄. Ethyl acetate was removed in vacuo producing an oil that was used without further purification.

EXAMPLE 55E

Ethyl 4-(cyclobutylmethyl)-1-hydroxy-4-methyl-3-oxo-3,4-dihydronaphthalene-2-carboxylate To a round bottom flask was added Example 55D (0.150 g, 0.1462 mmol) and 4 mL of methanesulfonic acid. The reaction mixture was stirred at room temperature for 16 hours and then was partitioned between ethyl acetate and water. The aqueous layer was extracted 2× with ethyl acetate and the combined organic layers were dried over MgSO₄. The product was purified by flash chromatography on SiO₂ eluting with a 5% acetone/hexane yielding the title compound (0.055 g, 42% yield) as an off white solid. ¹H NMR (300 MHz, DMSO-d₆): δ ppm 1.30 (t, J=7.17 Hz, 3H) 1.48 (s, 2H) 1.55 (m, 3H) 1.72 (m, 4H) 2.01 (m, 2H) 2.23 (m, 1H) 4.31 (q, J=7.11 Hz, 2H) 7.30 (m, 1H) 7.45 (m, 1H) 7.68 (m, 2H) 8.00 (d, J=6.99 Hz, 1H). MS (ESI⁺) m/z=315 (M+H)⁺.

EXAMPLE 55F 1-(cyclobutylmethyl)-4-hydroxy-1-methylnaphthalen-2(1H)-one

A solution of Example 55E (0.055 g, 0.174 mmol) in 4 mL of dioxane and 4 mL of 1N HCl was refluxed for 3 hours. The solution was cooled to room temperature, diluted with water and extracted with 3× ethyl acetate. The combined organic layers were dried over MgSO₄, and concentrated in vacuo to yield the title compound (0.035 g, 83% yield) as an oil that solidifies on standing. ¹H NMR (300 MHz, DMSO-d₆): δ ppm 1.16 (m, 3H) 1.48 (s, 3H) 1.70 (m, 3H) 2.04 (m, 2H) 2.21 (m, 1H) 5.76 (m, 1H) 7.30 (m, 1H) 7.44 (m, 1H) 7.63 (m, 1H) 8.00 (d, J=8.09 Hz, 1H). MS (ESI⁺) m/z=243 (M+H)⁺.

EXAMPLE 55G

2-[bis(methylthio)methylene]-4-(cyclobutylmethyl)-4-methylnaphthalene-1,3(2H,4H)-dione Combine Example 55F (0.150 g, 0.619 mmol), pyridine (0.396 mL, 4.952 mmol), and Example 5A (0.657 g, 2.476 mmol) in 4 mL of dioxane and place directly in a preheated oil bath at 100° C. for 1.5 hours. After cooling to room temperature, the reaction mixture was partitioned between ethyl acetate and water. The ethyl acetate layer was washed sequentially with bicarb, brine, and dried over MgSO₄. The product was purified by flash chromatography on SiO₂ eluting with a 0-20% ethyl acetate/hexane gradient yielding the title compound (0.175 g, 84% yield) as a yellow solid that solidifies upon standing.

EXAMPLE 55H tert-butyl 3-[4-(cyclobutylmethyl)-1-hydroxy-4-methyl-3-oxo-3,4-dihydronaphthalen-2-yl]-1,1-dioxido-4H-1,2,4-benzothiadiazin-7-ylcarbamate Example 55G (0.087 g, 0.2511 mmol) was combined with Example 17A (0.075 g, 0.263 mmol) and toluene (10 mL). The reaction mixture was stirred at 100° C. overnight. After cooling to room temperature, the reaction mixture was concentrated in. vacuo and purified by flash chromatography on SiO$_2$ eluting with a 0-35% ethyl acetate/hexane gradient yielding the title compound (0.083 g, 62% yield) as a light yellow solid.

EXAMPLE 56

3-(7-amino-1,1-dioxido-4H-1,2,4-benzothiadiazin-3-yl)-1-(cyclobutylmethyl)-4-hydroxy-1-methylnaphthalen-2(1H)-one A solution of Example 55H (0.105 g, 0.195 mmol) in dichloromethane (2 mL) was treated with trifluoroacetic acid (2 mL) at room temperature for 1 hour. After concentrating in. vacuo, the resulting oil was partitioned between ethyl acetate and NaHCO$_3$(aq,), the organic layer was removed and the bicarb layer extracted 3× with ethyl acetate. The combined organic layers were dried over MgSO$_4$, filtered, and concentrated in. vacuo. to yield a solid that was used without further purification. $^1$H NMR (300 MHz, DMSO-d$_6$): δ ppm 1.22 (m, 3H) 1.47 (m, 3H) 1.57 (s, 3H) 1.71 (m, 2H) 2.18 (m, 1H) 2.32 (m, 1H) 7.01 (m, 2H) 7.45 (d, J=8.46 Hz, 1H) 7.54 (t, J=7.17 Hz, 1H) 7.76 (m, 2H) 8.15 (d, J=7.72 Hz, 1H) 13.54 (m, 1H). MS (ESI$^+$) m/z=438 (M+H)$^+$.

EXAMPLE 57

N-{3-[4-(cyclobutylmethyl)-1-hydroxy-4-methyl-3-oxo-3,4-dihydronaphthalen-2-yl]-1,1-dioxido-4H-1,2,4-benzothiadiazin-7-yl}methanesulfonamide To a stirring solution of Example 56 (0.080 g, 0.189 mmol) and pyridine (0.122 mL, 1.512 mmol) in dichloromethane was added methanesulfonyl chloride (0.017 mL, 0.227 mmol) dropwise over 5 minutes and the resulting reaction mixture stirred for 12 hours. The solution was concentrated in. vacuo and purified by flash chromatography on SiO$_2$ eluting with a 0-100% ethyl acetate/hexane gradient yielding the title compound (0.079 g, 84% yield) as a light yellow solid. $^1$H NMR (300 MHz, DMSO-d$_6$) δ ppm 0.85 (m, 2H) 1.15 (m, 1H) 1.26 (m, 4H) 1.47 (m, 3H) 1.57 (s, 3H) 1.72 (m, 2H) 2.14 (m, 1H) 2.31 (m, 1H) 3.08 (s, 3H) 7.53 (m, 1H) 7.61 (dd, J=11.77, 2.21 Hz, 1H) 8.15 (d, J=7.35 Hz, 1H) 10.25 (s, 1H) 13.83 (s, 1H). MS (ESI$^+$) m/z=516 (M+H)$^+$.

EXAMPLE 58

N-{3-[4-(cyclobutylmethyl)-1-hydroxy-4-methyl-3-oxo-3,4-dihydronaphthalen-2-yl]-1,1-dioxido-4H-1,2,4-benzothiadiazin-7-yl}-2,2,2-trifluoroacetamide To a solution of Example 56 (0.064 g, 0.146 mmol) in dichloromethane (2 mL) and pyridine was added methanesulfonyl chloride (0.023 mL, 0.307 mmol) and stirred at room temperature overnight. The reaction mixture was partitioned between ethyl acetate and ½ saturated NH$_4$Cl. The organic layer was washed sequentially with bicarb and brine. The product was purified by flash chromatography on SiO$_2$ eluting with a 5% ethyl acetate/dichloromethane yielding not the desired methansulfonamide but rather the title compound (0.037 g, 49% yield) as a light yellow solid. $^1$H NMR (300 MHz, DMSO-d$_6$) δ ppm 1.21 (m, 3H) 1.21 (m, 2H) 1.48 (m, 3H) 1.57 (s, 2H) 1.75 (m, 1H) 2.18 (dd, J=13.42, 6.80 Hz, 1H) 2.32 (m, 1H) 7.53 (t, J=7.17 Hz, 1H) 7.76 (m, 3H) 7.99 (dd, J=9.19, 2.21 Hz, 1H) 8.15 (d, J=8.09 Hz, 1H) 8.28 (d, J=1.84 Hz, 1H) 11.64 (s, 1H) 13.82 (s, 1H). MS (ESI$^+$) m/z=551 (M+NH$_4$)$^+$.

EXAMPLE 59

(1R)-4-hydroxy-3-{7-[(methoxymethoxy)methyl]-1,1-dioxido-4H-thieno[2,3-e][1,2,4]thiadiazin-3-yl}-1-methyl-1-(3-methylbutyl)naphthalen-2(1H)-one Example 10E (1.03 g, 4.08 mmol) was treated with Example 39F (1.29 g, 3.70 mmol) dissolved in 100 mL of toluene. The mixture was warmed to reflux for 4 h, cooled, and concentrated. The crude material was purified on silica gel with 1% methanol in dichloromethane to afford the title compound (1.65 g, 83%). $^1$H NMR (300 MHz, DMSO-d$_6$) δ ppm 0.43 (m, 1H) 0.69 (d, J=6.62 Hz, 3H) 0.73 (d, J=6.62 Hz, 3H) 0.81 (m, 1H) 1.33 (m, 1H) 1.56 (s, 3H) 2.06 (m, 1H) 2.22 (m, 1H) 3.33 (s, 3H) 4.63 (s, 2H) 4.71 (s, 2H) 7.40 (s, 1H) 7.52 (m, 1H) 7.75 (d, J=3.68 Hz, 2H) 8.13 (d, J=7.72 Hz, 1H) 13.97 (s, 1H); (APCI−) m/z 503 (M−H)$^-$.

EXAMPLE 60

(1R)-4-hydroxy-3-[7-(hydroxymethyl)-1,1-dioxido-4H-thieno[2,3-e][1,2,4]thiadiazin-3-yl]-1-methyl-1-(3-methylbutyl)naphthalen-2(1H)-one Example 59 (1.56 g, 3.09 mmol) was dissolved in 10 mL of dioxane, cooled to 0° C., and treated with 30 mL of 4N HCl in dioxane, and the cooling bath was removed. After 2 h, the mixture was concentrated in vacuo to give the title compound (1.5 g, 100%). A portion of this material was further purified on silica gel with a gradient of methanol in dichloromethane (0-5%) followed by recrystallization from ethyl acetate with hexane to afford the title compound (69 mg). $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.84 (m, 1H) 1.33 (m, 1H) 1.55 (s, 3H) 2.04 (m, 1H) 2.21 (td, J=12.87, 4.78 Hz, 1H), 4.61 (d, J=1.47 Hz, 2H) 7.26 (s, 1H) 7.51 (m, 1H) 7.74 (m, J=3.68 Hz, 2H) 8.13 (d, J=8.09 Hz, 1H) 14.04 (s, 1H); (ESI$^-$) m/z 459 (M−H)$^-$.

EXAMPLE 61

(1R)-3-[7-(azidomethyl)-1,1-dioxido-4H-thieno[2,3-e][1,2,4]thiadiazin-3-yl]-4-hydroxy-1-methyl-1-(3-methylbutyl)naphthalen-2(1H)-one Example 60 (1.3 g, 2.82 mmol) was dissolved in 30 mL of dichloromethane and treated with 1,8diazabicyclo[5.4.0]undec-7-ene (2.3 mL, 16.7 mmol) and diphenylphosphoryl azide (3.2 mL, 14.8 mmol). The solution was stirred at room temp for 14 h and then concentrated in vacuo. The crude material was on silica gel with dichloromethane to give the title compound (1.03 g, 76%). $^1$H NMR (300 MHz, DMSO-d$_6$) δ ppm 0.44 (m, 1H) 0.70 (d, J=6.99 Hz, 3H) 0.73 (d, J=6.62 Hz, 3H) 0.81 (m, 1H) 1.32 (m, 1H) 1.55 (s, 3H) 2.03 (m, 1H) 2.21 (m, 1H) 4.56 (s, 2H) 7.29 (m, 1H) 7.54 (s, 1H) 7.73 (d, J=3.68 Hz, 2H) 8.13 (d, J=7.72 Hz, 1H) 14.13 (s, 1H); (ESI$^+$) m/z 503 (M+NH$_4$)$^+$.

EXAMPLE 62

(1R)-3-[7-(aminomethyl)-1,1-dioxido-4H-thieno[2,3-e][1,2,4]thiadiazin-3-yl]-4-hydroxy-1-methyl-1-(3-methylbutyl)naphthalen-2(1H)-one Example 61 (875 mg, 1.8 mmol) was dissolved in 14 mL of pyridine and 9 mL of ammonium hydroxide and treated with triphenylphosphine (1.14 g, 4.35 mmol). After 3 h, the mixture was concentrated in vacuo, taken up in ~15 mL of 30% hexane in toluene, filtered, and washed with more 30% hexane in toluene to give 184 mg of an off white solid. The crude material was purified on silica gel with a gradient of methanol in dichloromethane (5-10%) to afford the title compound (110 mg, 13%). $^1$H NMR (300 MHz, DMSO-$d_6$) δ ppm 0.44 (m, J=11.03 Hz, 1H) 0.68 (d, J=6.62 Hz, 3H) 0.70 (d, J=6.62 Hz, 3H) 0.80 (m, 1H) 1.29 (m, 1H) 1.39 (s, 3H) 1.77 (m, 1H) 2.13 (m, 1H) 4.13 (s, 2H) 7.22 (s, 1H) 7.34 (m, 1H) 7.49 (m, 2H) 8.04 (d, J=7.72 Hz, 1H) 8.21 (s, 2H) 16.97 (s, 1H); (APCI+) m/z 460 (M+H)

EXAMPLE 63

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)methanesulfonamide Example 62 (179 mg, 0.39 mmol) was slurried in 6 mL of acetone and treated with pyridine (240 μL, 3.0 mmol) and methanesulfonyl chloride (115 μL, 1.48 mmol). After 30 min, the mixture was warmed to 50° C. After 2.5 hours at 50° C., the mixture was cooled and more pyridine (200 μL, 2.5 mmol) and methanesulfonyl chloride (100 μL, 1.29 mmol) were added and the mixture was warmed to 50° C. After 1 h, the mixture was cooled and partitioned between ethyl acetate and H$_2$O. The organic phase was washed with 10% citric acid and water and concentrated in vacuo. The crude material was purified on silica gel with a gradient of methanol in dichloromethane (0-2%) to afford the title compound (112 mg, 54%). $^1$H NMR (300 MHz, DMSO-$d_6$) δ ppm 0.42 (m, 1H) 0.69 (d, J=6.62 Hz, 3H) 0.72 (d, J=6.62 Hz, 3H) 0.83 (m, 1H) 1.33 (m, 1H) 1.55 (s, 3H) 2.02 (m, 1H) 2.19 (m, 1H) 2.98 (s, 3H) 4.28 (d, J=6.25 Hz, 2H) 7.35 (m, 1H) 7.52 (m, 1H) 7.71 (m, 2H) 8.12 (d, J=7.72 Hz, 1H) 14.19 (s, 1H); (ESI$^+$) m/z 538 (M+H)$^+$.

EXAMPLE 64

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)-2-morpholin-4-ylethanesulfonamide Example 62 (21 mg, 0.05 mmol) was dissolved in 1 mL of dichloromethane and treated with triethyl amine (30 μL, 0.23 mmol) and 2-chloroethyl sulfonylchloride (10 μL, 0.1 mmol). After 1 h, the reaction mixture was diluted with dichloromethane and washed with H$_2$O and concentrated in vacuo. The crude material was dissolved in 1 mL of tetrahydrofuran and treated with morpholine (10 μL, 0.1 mmol). After 17 h, the reaction mixture was concentrated in vacuo and purified on silica gel with a gradient of methanol in dichloromethane (2-5%) to afford the title compound (12 mg, 50% yield). $^1$H NMR (300 MHz, DMSO-$d_6$) δ ppm 0.41 (m, 1H) 0.71 (d, J=6.62 Hz, 3H) 0.74 (d, J=6.62 Hz, 3H) 0.84 (m, 1H) 1.36 (m, 1H) 1.59 (s, 3H) 2.09 (m, 1H) 2.23 (m, J=12.13 Hz, 1H) 3.19 (m, 2H) 3.62 (m, 8H) 4.01 (m, 2H) 4.35 (s, 2H) 7.39 (s, 1H) 7.54 (m, 1H) 7.77 (d, J=3.68 Hz, 2H) 8.15 (d, J=8.09 Hz, 1H); (ESI$^-$) m/z 635 (M-H)$^-$.

EXAMPLE 65

3-(1-hydroxy-3-oxo-4,4-dipropyl-3,4-dihydronaphthalen-2-yl)-1,1-dioxido-4H-1,2,4-benzothiadiazin-7-yl methyl methylphosphonate Example 2G (48 mg, 0.11 mmol) in 2 mL of tetrahydrofuran was cooled to 0° C. and treated with methylphosphonic dichloride (18 mg, 0.14 mmol) and triethyl amine (140 μL, 1.0 mmol). After 2 h, methanol (1 mL) was added and the cloudy mixture quickly became a clear solution. After 1 h at 0° C., the cooling bath was removed. After 2 h at room temp, the mixture was partitioned between ethyl acetate and H$_2$O. The organic phase was washed with H$_2$O and concentrated to afford 39 mg which was purified by reverse phase HPLC to afford the title compound (17 mg, 28%). $^1$H NMR (300 MHz, DMSO-$d_6$) δ ppm 0.57 (m, 2H) 0.68 (m, 6H) 0.90 (m, 2H) 1.74 (d, J=17.65 Hz, 3H) 2.02 (m, 2H) 2.18 (m, 2H) 3.78 (d, J=11.40 Hz, 3H) 7.56 (m, 2H) 7.76 (m, 4H) 8.17 (d, J=7.35 Hz, 1H) 13.71 (s, 1H); (ESI$^+$) m/z 533 (M+H)$^+$.

EXAMPLE 66

3-(1-hydroxy-3-oxo-4,4-dipropyl-3,4-dihydronaphthalen-2-yl)-1,1-dioxido-4H-1,2,4-benzothiadiazin-7-yl hydrogen methylphosphonate Example 2G (48 mg, 0.11 mmol) in 2 mL of tetrahydrofuran was cooled to 0° C. and treated with methylphosphonic dichloride (18 mg, 0.14 mmol) and triethyl amine (140 μL, 1.0 mmol). After 2 h, methanol (1 mL) was added and the cloudy mixture quickly became a clear solution. After 1 h at 0° C., the cooling bath was removed. After 2 h at room temp, the mixture was partitioned between ethyl acetate and H$_2$O. The aqueous phase was acidified with 1 N aq. HCl and extracted with ethyl acetate. The organic phase was concentrated in vacuo to give the title compound (24 mg, 40%). $^1$H NMR (300 MHz, DMSO-$d_6$) δ ppm 0.56 (m, 2H) 0.68 (m, 6H) 0.92 (m, 2H) 1.56 (d, J=17.28 Hz, 3H) 2.01 (m, 2H) 2.18 (m, 2H) 7.53 (m, 2H) 7.74 (m, 4H) 8.16 (d, J=7.35 Hz, 1H) 13.78 (s, 1H); $^{13}$C NMR (125 MHz, DMSO-$d_6$) δ 11.63, 12.75, 13.89, 17.2, 20.69, 44.37, 59.67, 113.52, 121.56, 123.14, 125.77, 125.93, 126.62, 127.22, 130.46, 134.21, 148.66, 148.72, 155.17; anal. calc'd for: C, 55.59; H, 5.25; N, 5.40. found: C, 55.51; H, 5.31; N, 5.06.

EXAMPLE 67

Ethyl 3-(1-hydroxy-3-oxo-4,4-dipropyl-3,4-dihydronaphthalen-2-yl)-1,1-dioxido-4H-1,2,4-benzothiadiazin-7-yl methylphosphonate Example 2G (53 mg, 0.12) was dissolved in 1 mL of tetrahydrofuran and treated with methylphosphonic dichloride (78 mg, 0.59 mmol) and triethyl amine (140 μL, 1.0 mmol). After 1 h, ethanol (3 mL) was added. After 4 h, the solution was partitioned between water and ethyl acetate. The organic phase was washed with water and concentrated to afford a brown solid that was purified by reverse phase HPLC to afford the title compound (7 mg, 11%). $^1$H NMR (300 MHz, DMSO-$d_6$) δ ppm 0.59 (m, 2H) 0.67 (m, 6H) 0.89 (m, J=6.25 Hz, 2H) 1.26 (t, J=6.99 Hz, 3H) 1.72 (d, J=17.65 Hz, 3H) 1.95 (m, 2H) 2.15 (m, J=11.40 Hz, 2H) 4.15 (m, 2H) 7.53 (m, 2H) 7.71 (m, J=4.60, 4.60 Hz, 4H) 8.15 (d, J=7.72 Hz, 1H); (APCI) m/z 545 (M-H)$^-$.

EXAMPLE 68 tert-butyl 3-(4,4-dibutyl-1-hydroxy-3-oxo-3,4-dihydronaphthalen-2-yl)-1,1-dioxido-4H-1,2,4-benzothiadiazin-7-ylcarbamate Example 5C (45 mg, 0.11 mmol) was dissolved in 10 mL of toluene and treated with Example 17A (34 mg, 0.12 mmol), warmed to reflux for 4 hours, cooled and concentrated. The crude material was chromatographed on silica gel with a gradient of dichloromethane in hexane (0-100%) to afford the desired compound (14 mg). $^1$H NMR (300 MHz, DMSO-d$_6$) δ ppm 0.50 (m, 2H) 0.67 (t, J=7.35 Hz, 6H) 0.87 (m, 2H) 1.09 (m, 4H) 1.51 (s, 9H) 2.04 (m, J=16.18 Hz, 2H) 2.19 (m, 2H) 7.55 (m, 1H) 7.67 (s, 2H) 7.77 (m, 2H) 8.16 (m, 2H) 9.91 (s, 1H) 13.72 (s, 1H); (ESI$^-$) m/z 566 (M−H)$^-$.

EXAMPLE 69

3-(7-amino-1,1-dioxido-4H-1,2,4-benzothiadiazin-3-yl)-1,1-dibutyl-4-hydroxynaphthalen-2(1H)-one trifluoroacetate Example 68 (16.4 mg, 0.03 mmol) was dissolved in 1 mL of dichloromethane, treated with 0.5 mL of trifluoroacetic acid for 30 min, and concentrated in vacuo to afford the desired product (16.5 mg). $^1$H NMR (300 MHz, CDCl$_3$) δ ppm 0.57 (m, 2H) 0.72 (t, J=7.35 Hz, 6H) 0.88 (m, 2H) 1.11 (m, 4H) 1.90 (m, 2H) 2.29 (m, 2H) 6.95 (m, 1H) 7.15 (dd, J=8.82, 3.31 Hz, 1H) 7.21 (d, J=2.21 Hz, 1H) 7.46 (m, 2H) 7.68 (m, 1H) 8.25 (dd, J=8.09, 1.10 Hz, 1H) 14.12 (d, J=43.39 Hz, 1H) 16.74 (d, J=4.04 Hz, 1H); (ESI$^+$) m/z 468 (M+H)$^+$, (ESI$^-$) m/z 438 (M+CF$_3$COO$^-$)$^-$.

EXAMPLE 70 tert-butyl 3-(1-hydroxy-3-oxo-4,4-dipropyl-3,4-dihydronaphthalen-2-yl)-1,1-dioxido-4H-1,2,4-benzothiadiazin-7-ylcarbamate

EXAMPLE 70A 1,1-dipropyl-4-hydroxy-2(1H)-naphthalenone

The title compound was prepared according the procedure of Example 5B, substituting the product of Example 1F for the product of Example 4F. $^1$H NMR (300 MHz, CDCl$_3$) δ ppm 0.55 (m, 2H) 0.67 (m, 4.8H) 0.79 (m, 1.2H) 0.98 (m, 2H) 1.78 (m, 2H) 2.19 (m, 2H) 3.69 (s, 0.4H) 6.13 (s, 0.8H) 7.41 (m, 2H) 7.56 (m, 0.8H) 7.67 (m, 0.2H) 8.07 (m, 0.2H) 8.13 (m, 0.8H).

EXAMPLE 70B

2-[bis(methylthio)methylene]-4,4-dipropyl-1,3(2H,4H)-naphthalenedione

The title compound was prepared according to the procedure of Example 5C, substituting the compound of Example 70A for the product of Example 5B. $^1$H NMR (300 MHz, DMSO-d$_6$): δ ppm 0.64 (m, 8H) 0.79 (m, 2H) 1.79 (m, 2H) 2.07 (m, 2H) 2.53 (s, 6H) 7.43 (m, 1H) 7.57 (m, 1H) 7.65 (m, 1H) 8.05 (m, 1H).

EXAMPLE 70C tert-butyl 3-(1-hydroxy-3-oxo-4,4-dipropyl-3,4-dihydronaphthalen-2-yl)-1,1-dioxido-4H-1,2,4-benzothiadiazin-7-ylcarbamate Example 70B (35 mg, 0.10 mmol) was dissolved in 8 mL of toluene, treated with Example 17A (27 mg, 0.09 mmol), heated to reflux for 4 h, and concentrated in vacuo. The crude material was chromatographed on silical gel with a gradient of dichloromethane in hexane (0-100%) to afford the desired material (32 mg, 60%). $^1$H NMR (300 MHz, CDCl$_3$) δ ppm 0.67 (m, 8H) 0.94 (m, 2H) 1.54 (s, 9H) 1.90 (m, 2H) 2.30 (m, 2H) 6.67 (s, 1H) 7.47 (m, 2H) 7.68 (m, 1H) 7.85 (m, 2H) 8.25 (m, 1H) 8.25 (m, 1H) 14.24 (d, J=44.49 Hz, 1H) 16.69 (d, J=6.99 Hz, 1H); MS (ESI$^+$) m/z 540 (M+H)$^+$.

EXAMPLE 71

3-(7-amino-1,1-dioxido-4H-1,2,4-benzothiadiazin-3-yl)-4-hydroxy-1,1-dipropylnaphthalen-2(1H)-one trifluoroacetate Example 70C (28 mg, 0.05 mmol) was dissolved in 1 mL of dichloromethane, treated with 0.5 mL of trifluoroacetic acid for 30 min, and then concentrated in vacuo. The residue was taken up in diethyl ether, treated with hexane, and the supernate removed to afford the desired compound (21 mg, 73%). $^1$H NMR (300 MHz, CDCl$_3$) δ ppm 0.66 (m, 8H) 0.92 (m, 2H) 1.88 (m, 2H) 2.26 (m, 2H) 6.93 (m, 1H) 7.13 (dd, J=8.64, 4.96 Hz, 1H) 7.19 (d, J=2.57 Hz, 1H) 7.46 (m, 2H) 7.67 (m, 1H) 8.25 (dd, J=8.27, 1.29 Hz, 1H) 14.10 (d, J=41.92 Hz, 1H) 16.79 (d, J=3.68 Hz, 1H); MS (ESI$^+$) m/z 440 (M+H)$^+$, (ESI$^-$) m/z 438 (M−H)$^-$.

EXAMPLE 72

2,2,2-trifluoro-N-[3-(1-hydroxy-3-oxo-4,4-dipropyl-3,4-dihydronaphthalen-2-yl)-1,1-dioxido-4H-1,2,4-benzothiadiazin-7-yl]acetamide Example 71 (25 mg, 0.05 mmol) was dissolved in 1 mL of acetone, treated with pyridine (8 μL, 0.1 mmol) and trifluoromethyl sulfonyl chloride (21 mg, 0.011 mmol), shaken for 16 h, adsorbed on to silica gel and purified by column chromatography on silica gel with a gradient of methanol in dichloromethane (0-2%) to afford the desired product (21 mg, 70%). $^1$H NMR (300 MHz, DMSO-d$_6$) δ ppm 0.62 (m, 9H) 0.91 (m, 2H) 2.00 (m, 2H) 2.18 (m, 2H) 7.54 (m, 1H) 7.76 (m, 3H) 7.99 (dd, J=9.01, 2.39 Hz, 1H) 8.17 (d, J=7.72 Hz, 1H) 8.27 (d, J=2.57 Hz, 1H) 11.62 (s, 1H) 13.80 (s, 1H); (ESI$^+$) m/z 536 (M+H)$^+$, MS (ESI$^-$) m/z 534 (M−H)$^-$.

EXAMPLE 73

N-[3-(1-hydroxy-3-oxo-4,4-dipropyl-3,4-dihydronaphthalen-2-yl)-1,1-dioxido-4H-1,2,4-benzothiadiazin-7-yl]butane-1-sulfonamide Example 71 (12 mg, 0.03 mmol) was dissolved in 1 mL of acetone, treated with pyridine (8 μL, 0.1 mmol) and n-butyl sulfonyl chloride (13 μL), stirred for 16 h, treated with pyridine (8 μL, 0.1 mmol) and n-butyl sulfonyl chloride (13 μL), stirred for 16 h, treated with pyridine (30 μL, 0.37 mmol), heated to 50° C. for 16 h, and adsorbed on to silica gel. The crude product was purified by silica gel chromatography with a gradient of methanol in dichloromethane (0-5%) for afford the desired product, which could be further purified by recrystallization from diethyl ether with hexane to afford the desired product (3 mg, 20% yield). $^1$H NMR (300 MHz, CDCl$_3$) δ ppm 0.64 (m, 2H) 0.73 (m, 6H) 0.92 (m, 2H) 0.94 (t, J=7.35 Hz, 3H) 1.45 (dd, J=15.07, 7.35 Hz, 2H) 1.89 (m, 4H) 2.30 (m, 2H) 3.13 (m, 2H) 6.56 (s, 1H) 7.32 (m, 1H) 7.48 (m, 2H)

7.69 (m, 3H) 8.26 (dd, J=8.27, 1.65 Hz, 1H) 14.41 (d, J=46.33 Hz, 1H) 16.49 (d, J=8.82 Hz, 1H); MS (ESI⁻) m/z 558 (M−H)⁻.

EXAMPLE 74

N-[3-(1-hydroxy-3-oxo-4,4-dipropyl-3,4-dihydronaphthalen-2-yl)-1,1-dioxido-4H-1,2,4-benzothiadiazin-7-yl]methane sulfonamide Example 71 (25 mg, 0.06 mmol) was dissolved in 1.2 mL of acetone, treated with pyridine (10 μL, 0.12 mmol) and methane sulfonyl chloride (9 μL, 0.12 mmol), agitated for 16 h, treated with pyridine (30 μL, 0.37 mmol), warmed to 50° C. for 16 h, cooled and adsorbed on to silica gel. The crude material was purified by silica gel chromatography with a gradient of methanol in dichloromethane (0-2%) to afford the desired product (22 mg, 71%). ¹H NMR (300 MHz, CDCl₃) δ ppm 0.65 (m, 2H) 0.73 (m, 6H) 0.92 (m, 2H) 1.92 (m, 2H) 2.29 (m, 2H) 3.08 (d, J=1.47 Hz, 3H) 6.68 (s, 1H) 7.34 (dd, J=8.64, 5.33 Hz, 1H) 7.48 (m, 2H) 7.69 (m, 3H) 8.26 (dd, J=8.27, 1.29 Hz, 1H) 14.44 (d, J=47.43 Hz, 1H) 16.46 (d, J=9.19 Hz, 1H); MS (ESI⁺) m/z 518 (M+H)⁺ MS (ESI⁻) m/z 516 (M−H)⁻.

EXAMPLE 75

N-[3-(1-hydroxy-3-oxo-4,4-dipropyl-3,4-dihydronaphthalen-2-yl)-1,1-dioxido-4H-1,2,4-benzothiadiazin-7-yl]-1-methyl-1H-imidazole-4-sulfonamide Example 71 (25 mg, 0.06 mmol) was dissolved in 1.2 mL of acetone, treated with pyridine (10 μL, 0.12 mmol) and 1-methyl-1H-imidazole-4-sulfonyl chloride (22 mg, 0.12 mmol), agitated for 16 h, treated with pyridine (30 μL, 0.37 mmol), warmed to 50° C. for 16 h, cooled and adsorbed on to silica gel. The crude material was purified by silica gel chromatography with a gradient of methanol in dichloromethane (0-2%) to afford the desired product, which could be further purified by recrystallization from diethyl ether with hexane to afford the desired product (13 mg, 38% yield). ¹H NMR (300 MHz, DMSO-d₆) δ ppm 0.57 (m, 2H) 0.67 (m, 6H) 0.89 (m, 2H) 2.00 (m, 2H) 2.16 (m, 2H) 3.66 (s, 3H) 5.75 (s, 1H) 7.56 (m, 4H) 7.75 (m, 3H) 7.89 (d, J=1.10 Hz, 1H) 8.15 (d, J=7.72 Hz, 1H) 10.72 (s, 1H) 13.68 (s, 1H); MS (ESI⁺) m/z 584 (M+H)⁺.

EXAMPLE 76

N-[3-(1-hydroxy-3-oxo-4,4-dipropyl-3,4-dihydronaphthalen-2-yl)-1,1-dioxido-4H-1,2,4-benzothiadiazin-7-yl]-2-methoxybenzenesulfonamide Example 71 (25 mg, 0.06 mmol) was dissolved in 1.2 mL of acetone, treated with pyridine (10 μL, 0.12 mmol) and 2-methoxy-phenyl-sulfonyl chloride (25 mg, 0.12 mmol), agitated for 16 h, treated with pyridine (30 μL, 0.37 mmol), warmed to 50° C. for 16 h, cooled and adsorbed on to silica gel. The crude material was purified by silica gel chromatography with a gradient of methanol in dichloromethane (0-2%) to afford the desired product, which could be further purified by recrystallization from diethyl ether with hexane to afford the desired product (8 mg, 23% yield). ¹H NMR (300 MHz, CDCl₃) δ ppm 0.62 (m, 2H) 0.71 (m, 6H) 0.88 (m, 2H) 1.88 (m, 2H) 2.26 (m, 2H) 4.07 (s, 3H) 7.01 (m, 2H) 7.13 (s, 1H) 7.20 (dd, J=8.82, 5.52 Hz, 1H) 7.46 (m, 4H) 7.68 (m, 2H) 7.81 (m, 1H) 8.23 (m, 1H) 14.29 (d, J=44.86 Hz, 1H) 16.47 (d, J=8.46 Hz, 1H); MS (ESI⁺) m/z 610 (M+H)⁺, MS (ESI⁻) m/z 608 (M−H)⁻.

EXAMPLE 77

N-[3-(1-hydroxy-3-oxo-4,4-dipropyl-3,4-dihydronaphthalen-2-yl)-1,1-dioxido-4H-1,2,4-benzothiadiazin-7-yl]thiophene-2-sulfonamide Example 71 (25 mg, 0.06 mmol) was dissolved in 1.2 mL of acetone, treated with pyridine (10 μL, 0.12 mmol) and thiophene-2-sulfonyl chloride (22 mg, 0.12 mmol), agitated for 16 h, treated with pyridine (30 μL, 0.37 mmol), warmed to 50° C. for 16 h, cooled and adsorbed on to silica gel. The crude material was purified by silica gel chromatography with a gradient of methanol in dichloromethane (0-2%) to afford the desired product, which could be further purified by recrystallization from diethyl ether with hexane to afford the desired product (3 mg, 10% yield). ¹H NMR (300 MHz, CDCl₃) δ ppm 0.66 (m, 2H) 0.73 (m, 6H) 0.90 (m, 2H) 1.90 (m, 2H) 2.28 (m, 2H) 6.95 (s, 1H) 7.05 (m, 1H) 7.30 (m, 1H) 7.60 (m, 7H) 8.25 (m, 1H) 14.39 (d, J=44.86 Hz, 1H) 16.46 (d, J=9.93 Hz, 1H); MS (ESI⁺) m/z 586 (M+H)⁺, MS (ESI⁻) m/z 584 (M−H)⁻.

EXAMPLE 78

{[3-(4,4-dibutyl-1-hydroxy-3-oxo-3,4-dihydronaphthalen-2-yl)-1,1-dioxido-4H-1,2,4-benzothiadiazin-7-yl]oxy}acetonitrile Example 5E (21 mg, 0.04 mmol) was dissolved in 1 mL of N,N-dimethyl formamide, treated with bromoacetonitrile (6 μL, 0.09 mmol), cesium carbonate (29 mg, 0.09 mmol), and tetrabutylammonium iodide (4 mg, 0.01 mmol), stirred for 16 h, treated with bromoacetonitrile (6 μL, 0.09 mmol) and cesium carbonate (29 mg, 0.09 mmol), stirred for 16 h, treated with bromoacetonitrile (50 μL, 0.71 mmol), stirred for 3 d, adsorbed on to silica gel, and purified by silica gel chromatography with a gradient of methanol in dichloromethane (0-5%) to afford the desired compound, which could be further purified by recrystallization from dichloromethane and hexanes and diethyl ether to afford the title compound (12.8 mg, 56% yield). ¹H NMR (300 MHz, CDCl₃) δ ppm 0.58 (m, 2H) 0.72 (t, J=7.35 Hz, 6H) 0.86 (m, 2H) 1.12 (m, 4H) 1.93 (m, 2H) 2.31 (m, 2H) 4.85 (s, 2H) 7.33 (m, 2H) 7.49 (m, 3H) 7.70 (m, 1H) 8.27 (dd, J=8.27, 1.29 Hz, 1H) 14.40 (m, 1H) 16.50 (d, J=1.47 Hz, 1H); MS (ESI⁺) m/z 508 (M+H)⁺, MS (ESI⁻) m/z 506 (M−H)⁻.

EXAMPLE 79

{[3-(1-hydroxy-3-oxo-4,4-dipropyl-3,4-dihydronaphthalen-2-yl)-1,1-dioxido-4H-1,2,4-benzothiadiazin-7-yl]amino}acetonitrile Example 71 (30 mg, 0.05 mmol) was dissolved in 1 mL of N,N-dimethyl formamide, treated with bromoacetonitrile (8 μL, 0.11 mmol), cesium carbonate (49 mg, 0.15 mmol), and tetrabutylammonium iodide (5 mg, 0.01 mmol), stirred for 16 h, treated with bromoacetonitrile (8 μL, 0.11 mmol) and cesium carbonate (49 mg, 0.11 mmol), stirred for 16 h, treated with bromoacetonitrile (50 μL, 0.71 mmol), stirred for 3 d, adsorbed on to silica gel, and purified by silica gel chromatography with a gradient of methanol in dichloromethane (0-5%) to afford the desired compound, which could be further purified by recrystallization from dichloromethane and hexanes and diethyl ether to afford the title compound (7 mg, 28% yield). $^1$H NMR (300 MHz, DMSO-$d_6$) δ ppm 0.59 (m, 2H) 0.68 (m, 6H) 0.89 (m, 2H) 2.01 (m, 2H) 2.18 (m, 2H) 4.44 (d, J=5.15 Hz, 2H) 6.91 (t, J=6.99 Hz, 1 H) 7.15 (m, 2H) 7.55 (m, 1H) 7.61 (d, J=8.46 Hz, 1H) 7.76 (m, 2H) 8.17 (d, J=7.35 Hz, 1H) 13.67 (s, 1H); MS (ESI$^+$) m/z 479 (M+H)$^+$, MS (ESI$^-$) m/z 477 (M–H)$^-$.

EXAMPLE 80

1-chloro-N-[3-(1-hydroxy-3-oxo-4,4-dipropyl-3,4-dihydronaphthalen-2-yl)-1,1-dioxido-4H-1,2,4-benzothiadiazin-7-yl]methanesulfonamide Example 71 (50 mg, 0.11 mmol) was dissolved in 2.2 mL of acetone, treated with pyridine (71 μL, 0.88 mmol) and chloromethanesulfonyl chloride (44 μL, 0.44 mmol), stirred for 16 h, partitioned between ethyl acetate and 1% aqueous citric acid. The organic phase was washed with brine, dried over Na$_2$SO$_4$, filtered and concentrated in vacuo. The crude material was purified by silica gel chromatography with a gradient of methanol in dichloromethane (0-2%) to afford the desired product (24 mg, 40% yield). $^1$H NMR (300 MHz, DMSO-$d_6$) δ ppm 0.58 (m, 2H) 0.67 (m, 6H) 0.91 (m, 2H) 1.99 (m, 2H) 2.17 (m, 2H) 5.14 (s, 2H) 7.64 (m, 6H) 8.16 (d, J=7.35 Hz, 1H) 10.83 (s, 1H) 13.82 (s, 1H); MS (ESI$^+$) m/z 552 (M+H)$^+$, (ESI$^+$) m/z 569 (M+NH$_4$)$^+$, MS (ESI$^-$) m/z 550 (M–H)$^-$.

EXAMPLE 81

2-chloro-N-[3-(1-hydroxy-3-oxo-4,4-dipropyl-3,4-dihydronaphthalen-2-yl)-1,1-dioxido-4H-1,2,4-benzothiadiazin-7-yl]benzenesulfonamide Example 71 (50 mg, 0.11 mmol) was dissolved in 2.2 mL of acetone, treated with pyridine (71 μL, 0.88 mmol) and 2-chlorophenylsulfonyl chloride (60 μL, 0.44 mmol), stirred for 16 h, partitioned between ethyl acetate and 1% aqueous citric acid. The organic phase was washed with brine, dried over Na$_2$SO$_4$, filtered and concentrated in vacuo. The crude material was triturated with diethyl ether to afford the desired product (52 mg, 77% yield). $^1$H NMR (300 MHz, DMSO-$d_6$) δ ppm 0.56 (m, 2H) 0.65 (m, 6H) 0.87 (m, 2H) 1.99 (m, 2H) 2.16 (m, 2H) 7.56 (m, 7H) 7.75 (m, 2H) 8.11 (dd, J=13.42, 7.91 Hz, 2H) 11.17 (s, 1H) 13.62 (s, 1H); MS (ESI$^+$) m/z 614 (M+H)$^+$ (ESI$^-$) m/z 612 (M–H)$^-$.

EXAMPLE 82

2,2,2-trifluoro-N-[3-(1-hydroxy-3-oxo-4,4-dipropyl-3,4-dihydronaphthalen-2-yl)-1,1-dioxido-4H-1,2,4-benzothiadiazin-7-yl]ethanesulfonamide Example 71 (50 mg, 0.11 mmol) was dissolved in 2.2 mL of acetone, treated with pyridine (71 μL, 0.88 mmol) and 2,2,2-trifluorethylsulfonyl chloride (49 μL, 0.44 mmol), stirred for 16 h, partitioned between ethyl acetate and 1% aqueous citric acid. The organic phase was washed with brine, dried over Na$_2$SO$_4$, filtered and concentrated in vacuo. The crude material was purified by silica gel chromatography with a gradient of methanol in dichloromethane (0-2%) to afford the desired product (16 mg, 25% yield). $^1$H NMR (300 MHz, DMSO-$d_6$) δ ppm 0.57 (m, 2H) 0.68 (m, 6H) 0.90 (m, 2H) 2.00 (m, 2H) 2.17 (m, 2H) 4.70 (q, J=9.68 Hz, 2H) 7.58 (m, 3H) 7.76 (m, 3H) 8.17 (d, J=7.72 Hz, 1H) 10.91 (s, 1H) 13.75 (s, 1H); MS (ESI$^+$) m/z 586 (M+H)$^+$ (ESI$^+$) m/z 603 (M+NH$_4$)$^+$ (ESI$^+$) m/z 1193 (2M+Na)$^+$ (ESI$^-$) m/z 584 (M–H)$^-$.

EXAMPLE 83

Methyl({[3-(1-hydroxy-3-oxo-4,4-dipropyl-3,4-dihydronaphthalen-2-yl)-1,1-dioxido-4H-1,2,4-benzothiadiazin-7-yl]amino}sulfonyl)acetate Example 71 (50 mg, 0.11 mmol) was dissolved in 2.2 mL of acetone, treated with pyridine (71 μL, 0.88 mmol) and chlorosulfonyl acetic acid methyl ester(63 μL, 0.55 mmol), stirred for 16 h, partitioned between ethyl acetate and 1% aqueous citric acid. The organic phase was washed with brine, dried over Na$_2$SO$_4$, filtered and concentrated in vacuo. The crude material was purified by silica gel chromatography with a gradient of methanol in dichloromethane (0-2%) to afford the desired product (22 mg, 34% yield). $^1$H NMR (300 MHz, DMSO-$d_6$) δ ppm 0.57 (m, 2H) 0.68 (m, 6H) 0.90 (m, 2H) 2.00 (m, 2H) 2.18 (m, 2H) 3.64 (s, 3H) 4.37 (s, 2H) 7.57 (m, 3H) 7.75 (m, 3H) 8.16 (d, J=7.72 Hz, 1H) 10.68 (s, 1H) 13.76 (s, 1H); MS (ESI$^+$) m/z 576 (M+H)$^+$, (ESI$^+$) m/z 593 (M+NH$_4$)$^+$ (ESI$^+$) m/z 1173 (2M+Na)$^+$ (ESI$^-$) m/z 574 (M–H)$^-$.

EXAMPLE 84

4-{[3-chloro-5-(trifluoromethyl)pyridin-2-yl]oxy}-N-[3-(1-hydroxy-3-oxo-4,4-dipropyl-3,4-dihydronaphthalen-2-yl)-1,1-dioxido-4H-1,2,4-benzothiadiazin-7-yl]benzenesulfonamide Example 71 (40 mg, 0.09 mmol) was dissolved in 1 mL of acetone, treated with pyridine (58 μL, 0.72 mmol) and 4-(3-chloro-5-trifluoromethyl-pyridine-2-yloxy)-benzenesulfonyl chloride (134 mg, 0.36 mmol), stirred for 16 h, partitioned between ethyl acetate and 1% aqueous citric acid. The organic phase was washed with brine, dried over Na$_2$SO$_4$, filtered and concentrated in vacuo. The crude material was purified by silica gel chromatography with a gradient of methanol in dichloromethane (0-2%) to afford the desired product (55 mg, 79% yield). $^1$H NMR (500 MHz, DMSO-$d_6$) δ ppm 0.55 (m, 2H) 0.65 (t, J=7.32 Hz, 6H) 0.88 (m, 2H) 1.96 (m, 2H) 2.14 (m, 2H) 7.49 (m, 5H) 7.62 (d, J=9.16 Hz, 1H) 7.72 (m, 2H) 7.86 (m, 2H) 7.98 (s, 1H) 8.05 (d, J=2.44 Hz, 1H) 8.13 (d, J=7.93 Hz, 1H) 8.50 (m, 1H) 8.59 (m, 1H) 10.83 (s, 1H) 12.75 (s, 1H) 13.79 (s, 1H); (ESI$^+$) m/z 775 (M+H)$^+$ (ESI$^+$) m/z 797 (M+Na)$^+$ (ESI$^-$) m/z 773 (M–H)$^-$.

EXAMPLE 85

Benzyl {[3-(1-hydroxy-3-oxo-4,4-dipropyl-3,4-dihydronaphthalen-2-yl)-1,1-dioxido-4H-1,2,4-benzothiadiazin-7-yl]amino}sulfonylcarbamate A solution of chlorosulfonyl isocyante (25 mL, 0.281 mmol) in dichloromethane, was treated with benzyl alcohol (29 μL, 0.281 mmol) dropwise at room temp, stirred for 30 min, treated with a solution of example 71 (103 mg, 0.234 mmol) and triethylamine (130 μL, 0.936 mmol) in 3 mL of dichloromethane, stirred for 2 h, diluted with 10 mL of dichloromethane and 10 mL of 1N HCl. The organic phase was dried over Na$_2$SO$_4$, concentrated, and purified by silica gel chromatography with a gradient of methanol in dichloromethane (0-3%) to afford the desired product (26 mg, 17% yield). $^1$H NMR (300 MHz, DMSO-$d_6$) δ ppm 0.59 (m, 2H)

0.68 (m, 6H) 0.91 (m, 2H) 2.01 (m, 2H) 2.18 (m, 2H) 5.11 (s, 2H) 7.50 (m, 11H) 8.17 (d, J=7.72 Hz, 1H) 10.04 (s, 1H) 11.10 (s, 1H) 12.13 (s, 1H) 13.74 (d, J=21.69 Hz, 1H); (ESI$^+$) m/z 653 (M+H)$^+$ (ESI$^+$) m/z 670 (M+NH$_4$)$^+$ (ESI$^+$) m/z 675 (M+Na)$^+$ (ESI$^+$) m/z 1327 (2M+Na)$^+$ (ESI$^-$) m/z 1303 (2M−H)$^-$ (ESI$^-$) m/z 651 (M−H)$^-$

EXAMPLE 86

N-[3-(1-hydroxy-3-oxo-4,4-dipropyl-3,4-dihydronaphthalen-2-yl)-1,1-dioxido-4H-1,2,4-benzothiadiazin-7-yl]sulfamide A solution of Example 85 (56 mg, 0.086 mmol) in 7 mL of methanol was treated with 10% palladium on carbon (28 mg, 50 wt %) and placed under an atmosphere of hydrogen. The mixture was stirred at room temp for 5 h, filtered through a 0.45 □M syringe filter, and concentrated in vacuo to afford the desired product (35 mg, 79% yield). $^1$H NMR (300 MHz, DMSO-d$_6$) δ ppm 0.56 (m, 2H) 0.67 (m, 6H) 0.87 (m, 2H) 1.96 (m, J=11.40, 11.40 Hz, 2H) 2.16 (m, 2H) 7.37 (s, 2H) 7.59 (m, 6H) 8.15 (d, J=7.72 Hz, 1H) 9.99 (s, 1H) 13.94 (s, 1H); (ESI$^+$) m/z 519 (M+H)$^+$ (ESI$^+$) m/z 536 (M+NH$_4$)$^+$ (ESI$^+$) m/z 541 (M+Na)$^+$ (ESI$^+$) m/z 1054 (2M+NH4)$^+$ (ESI$^-$) m/z 517 (M−H)$^-$ (ESI$^-$) m/z 1035 (2M−H)$^-$

EXAMPLE 87

Benzyl({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonylcarbamate A solution of chlorosulfonyl isocyanate (60 μL, 0.6 mmol) in 4 mL anhydrous dichloromethane at room temperature was treated drop wise with benzyl alcohol (60 uL, 0.6 mmol). After one hour, a solution of Example 34B (238 mg, 0.5 mmol), triethyl amine (300 μL, 2 mmol) in 2 mL dichloromethane, was added drop wise. The reaction was diluted with dichloromethane and extracted with 1 N HCl. The aqueous layer was extracted with dichloromethane and the combined organic layers dried with anhydrous MgSO$_4$, concentrated and purified by chromatography to give the desired product (225 mg, 69%). $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.81 (m, 1H) 1.32 (m, 1H) 1.58 (s, 3H) 2.08 (m, 1H) 2.23 (m, 1H) 5.11 (s, 2H) 7.30 (m, 6H) 7.47 (dd, J=9.01, 2.39 Hz, 1H) 7.54 (m, 1H) 7.62 (d, J=2.57 Hz, 1H) 7.70 (d, J=9.19 Hz, 1H) 7.77 (d, J=3.68 Hz, 2H) 8.17 (d, J=8.09 Hz, 1H) 11.12 (s, 1H) 12.15 (s, 1H) 13.78 (s, 1H). MS (ESI$^-$) m/z=651 (M−H)$^-$.

EXAMPLE 88

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide Example 87 (20 mg, 0.03 mmol) in 4 mL methanol was added 10% Pd/C (5 mg) and the slurry stirred for 18 hours under a H$_2$ atmosphere. The reaction was filtered and concentrated to yield the desired (12 mg, 77%). $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.83 (m, 1H) 1.32 (m, 1H) 1.56 (s, 3H) 2.05 (m, 1H) 2.22 (m, 1H) 7.38 (s, 1H) 7.51 (m, 2H) 7.58 (d, J=2.21 Hz, 1H) 7.66 (d, J=8.82 Hz, 1H) 7.74 (d, J=3.68 Hz, 2H) 8.16 (d, J=8.09 Hz, 1H) 10.01 (s, 1H) 13.88 (s, 1H). MS (ESI$^-$) m/z=517(M−H)$^-$.

EXAMPLE 89

Benzyl[{3-[1-hydroxy-4-methyl-4-(3-methylbutyl)-3-oxo-3,4-dihydronaphthalen-2-yl]-1,1-dioxido-4H-1,2,4-benzothiadiazin-7-yl}(methyl)amino]sulfonyl(methyl)carbamate Example 87 (25 mg, 0.04 mmol) in 10 mL anhydrous tetrahydrofuran was treated with 60% sodium hydride (4 mg, 0.1 mmol) for 1 hour at room temperature. Iodomethane (10 μL, 0.16 mmol) was added and the reaction stirred overnight. The reaction was diluted with water and extracted three times with 10 mL ethyl acetate. The combined ethyl acetate layers were concentrated and the residue purified by chromatography to yield the desired product (12 mg, 44%). $^1$H NMR (300 MHz, DMSO-d$_6$) δ ppm 0.45 (m, 1H) 0.71 (m, 6H) 0.83 (m, 1H) 1.31 (m, 1H) 1.59 (s, 3H) 2.17 (m, 2H) 3.16 (s, 3H) 3.34 (s, 3H) 5.18 (s, 2H) 7.26 (m, 5H) 7.58 (m, 3H) 7.80 (m, 3H) 8.17 (d, J=8.09 Hz, 1H) 13.74 (s, 1H).

EXAMPLE 90

N-(2-hydroxyethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide

EXAMPLE 90A

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-2-oxo-1,3-oxazolidine-3-sulfonamide A solution of chlorosulfonyl isocyanate (191 μL, 2.2 mmol) in dichloromethane (30 mL) was cooled to 0° C. and 2-chloroethanol (147 μL, 2.2 mmol) was added dropwise. The mixture was stirred at 0° C. for 2 hours followed by the addition of a solution containing Example 34B (952 mg, 2.0 mmol) and triethylamine (20 mL) in dichloromethane (20 mL). The mixture was stirred for 2 days at rt followed by the addition of 2N aqueous Hydrochloric acid (100 mL). The organic layer was separated and the aqueous layer was extracted by dichloromethane (2× 50 mL). The organic layers were combined, washed with brine, dried with MgSO$_4$, filtered and evaporated. The residue was purified with silica gel eluting with dichloromethane/methanol (99:1) to give title compound (1.02 g, 87%). $^1$H NMR (300 MHz, DMSO-d$_6$) δ ppm 0.41 (m, 1H) 0.69 (d, J=6.62 Hz, 3H) 0.72 (d, J=6.99 Hz, 3H) 0.80 (m, 1H) 1.32 (m, 1H) 1.56 (s, 3H) 2.13 (m, 2H) 3.97 (t, J=7.72 Hz, 2H) 4.35 (t, J=7.72 Hz, 2H) 7.60 (m, 6H) 8.15 (d, J=8.09 Hz, 1H) 11.52 (s, 1H) 13.87 (s, 1H); (ESI$^-$) m/z 587 (M−H)—.

EXAMPLE 90B

N-(2-hydroxyethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide Example 90A (30 mg, 0.05 mmol) in tetrahydrofuran (2 ml) was added water (0.1 ml) and sodium ethoxide in ethanol (20%, 1 ml). The mixture was stirred at r.t. for 1 day. The solution was evaporated and the residue was stirred in 1M HCl (2 ml) for 10 minutes. The solid was filtered and dried to give the title product (26 mg, 93%). $^1$H NMR (300 MHz, DMSO-$d_6$) δ ppm 0.40 (m, 1H) 0.69 (d, J=6.62 Hz, 3H) 0.72 (d, J=6.62 Hz, 3H) 0.82 (m, 1H) 1.33 (m, 1H) 1.58 (s, 3H) 2.07 (m, 1H) 2.23 (m, 1H) 2.91 (m, 2H) 3.38 (t, J=6.62 Hz, 2H) 7.55 (m, 3H) 7.74 (m, 3H) 7.82 (t, J=5.70 Hz, 1H) 8.17 (d, J=8.09 Hz, 1H) 10.22 (s, 1H) 13.69 (s, 1H); (ESI$^-$) m/z 561 (M–H)$^-$.

EXAMPLE 91

2-{[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]amino}ethyl 3-hydroxyazetidine-1-carboxylate Example 90A (30 mg, 0.05 mmol) in acetonitrile (2 ml) was added azetidin-3-ol hydrochloride (11 mg, 0.1 mmol). The mixture was microwaved at 80° C. for 2 hours. The solvent was evaporated and the residue was purified by reverse phase eluting with 0.1% trifluoroacetic acid aqueous/methanol (80:20) to (5:95) to give product (2 mg, 6%). $^1$H NMR (300 MHz, DMSO-$d_6$) δ ppm 0.41 (m, 1H) 0.69 (d, J=6.62 Hz, 3H) 0.72 (d, J=6.99 Hz, 3H) 0.80 (m, 1H) 1.30 (m, 1H) 1.58 (s, 3H) 2.07 (m, 1H) 2.22 (m, 1H) 3.07 (m, 2H) 3.59 (m, 2H) 3.94 (m, 4H) 4.35 (m, 1H) 7.54 (m, 3H) 7.73 (m, 3H) 8.03 (t, J=5.88 Hz, 1H) 8.17 (d, J=8.09 Hz, 1H) 10.29 (s, 1H) 13.73 (s, 1H); (ESI$^-$) m/z 660 (M–H)$^-$.

EXAMPLE 92

3-hydroxy-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}azetidine-1-sulfonamide Example 90A (30 mg, 0.05 mmol) in acetonitrile (2 ml) was added triethylamine (0.1 ml) and azetidin-3-ol hydrochloride (11 mg, 0.1 mmol). The mixture was heated at 70° C. for overnight. The solvent was evaporated and the residue was purified by reverse phase eluting with 0.1% trifluoroacetic acid aqueous/methanol (80:20) to (5:95) to give product (4 mg, 14%). $^1$H NMR (300 MHz, DMSO-$d_6$) δ ppm 0.43 (m, 1H) 0.69 (d, J=6.62 Hz, 3H) 0.72 (d, J=6.62 Hz, 3H) 0.79 (m, 1H) 1.32 (m, 1H) 1.58 (s, 3H) 2.08 (m, 1H) 2.25 (m, 1H) 3.65 (m, 2H) 3.91 (m, 2H) 4.37 (m, 1H) 7.57 (m, 3H) 7.74 (m, 3H) 8.16 (d, J=8.09 Hz, 1H) 10.55 (s, 1H) 13.69 (s, 1H); (ESI$^-$) m/z 573 (M–H)$^-$.

EXAMPLE 93

3-amino-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}pyrrolidine-1-sulfonamide hydrochloride

EXAMPLE 93A tert-butyl 1-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]pyrrolidin-3-ylcarbamate Example 90A (30 mg, 0.05 mmol) in acetonitrile (2 ml) was added pyrrolidin-3-yl-carbamic acid tert-butyl ester (18 mg, 0.1 mmol). The mixture was microwaved at 80° C. for 2 hours. The solvent was evaporated and the residue was purified by reverse phase eluting with 0.1% trifluoroacetic acid aqueous/methanol (50:50) to (5:95) to give product (7 mg, 20%).

EXAMPLE 93B 3-amino-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}pyrrolidine-1-sulfonamide hydrochloride Example 93A (7 mg, 0.01 mmol) in 4M HCl/dioxane (1 ml) was stirred at r.t. for overnight. The solvent was evaporated and the residue was purified with silica gel eluting with dichloromethane/methanol (95:5) to give the title compound (5 mg, 79%). $^1$H NMR (300 MHz, DMSO-$d_6$) δ ppm 0.45 (m, 1H) 0.69 (m, 6H) 0.83 (m, 1H) 1.27 (m, 1H) 1.43 (s, 3H) 1.84 (m, 2H) 2.15 (m, 2H) 3.21 (m, 2H) 3.46 (m, 2H) 3.74 (m, 1H) 7.44 (m, 6H) 8.07 (m, is 4H) 10.29 (s, 1H) 15.09 (s, 1H); (ESI$^-$) m/z 586 (M–H)$^-$.

EXAMPLE 94

N-(2-aminoethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide hydrochloride

EXAMPLE 94A tert-butyl 2-{[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]amino}ethylcarbamate Example 90A (59 mg, 0.1 mmol) in acetonitrile (2 ml) was added Example 17A (32 mg, 0.2 mmol). The mixture was microwaved at 80° C. for 2 hours. The solvent was evaporated and the residue was purified by reverse phase eluting with 0.1% trifluoroacetic acid aqueous/methanol (90:10) to (5:95) to give product (37 mg, 56%).

EXAMPLE 94B

N-(2-aminoethyl)-N'-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide hydrochloride Example 94A (36 mg, 0.054 mmol) in 4M HCl/dioxane (4 ml) was stirred at rt for overnight. The solvent was evaporated and the residue was purified with silica gel eluting with dichloromethane/methanol (98:2) to (90:10) to give the title compound (31 mg, 95%). $^1$H NMR (300 MHz, DMSO-$d_6$) δ ppm 0.45 (m, 1H) 0.68 (d, J=6.62 Hz, 3H) 0.71 (d, J=6.62 Hz, 3H) 0.80 (m, 1H) 1.31 (m, 1H) 1.48 (s, 3H) 1.91 (m, 1H) 2.19 (m, 1H) 2.87 (m, 2H) 3.14 (m, 2H) 7.49 (m, 6H) 7.95 (m, 4H) 8.10 (d, J=7.72 Hz, 1H) 10.21 (s, 1H) 14.62 (s, 1H); (ESI$^-$) m/z 560 (M–H)$^-$.

EXAMPLE 95

Benzyl({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl(methyl)carbamate Example 87 (130 mg, 0.2 mmol) in tetrahydrofuran/H$_2$O (4 ml, 3:1) was added NaOH (1N, 200 µl) and stirred for 30 min.

The tetrahydrofuran was evaporated and acetonitrile was added till the mixture became solution. The solution was cooled with dry ice/aceton with swirring and lyophilized overnight to give salt. The salt was dissolved in acetonitrile (5 ml) and the methyl iodide (125 μL, d=2.28, 2 mmol) was added. The mixture was stirred at rt for overnight. The solvent was evaporated and the residue was purified with silica gel eluting with dichloromethane/methanol (99:1) to give the title compound (113 mg, 85%). $^1$H NMR (300 MHz, DMSO-$d_6$) δ ppm 0.42 (m, 1H) 0.69 (d, J=6.62 Hz, 3H) 0.72 (d, J=6.62 Hz, 3H) 0.79 (m, 1H) 1.32 (m, 1H) 1.59 (s, 3H) 2.09 (m, 1H) 2.24 (m, 1H) 3.20 (s, 3H) 5.19 (s, 2H) 7.32 (m, 5H) 7.51 (m, 3H) 7.72 (m, 3H) 8.17 (d, J=8.09 Hz, 1H) 11.26 (s, 1H) 13.66 (s, 1H); (ESI$^-$) m/z 665 (M–H)$^-$.

EXAMPLE 96

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-N'-methylsulfamide Example 95 (108 mg, 0.16 mmol) in dichloromethane/methanol (20 ml, 4:1) was added palladium on charcoal (50 mg, 10%) and hydrogenated for 1 hour. The catalyst was filtered and washed with methanol. The filtrate was evaporated and purified with silica gel eluting with dichloromethane/methanol (99:1) to give the title compound (66 mg, 77%). $^1$H NMR (300 MHz, DMSO-$d_6$) δ ppm 0.43 (m, 1H) 0.69 (d, J=6.62 Hz, 3H) 0.72 (d, J=6.62 Hz, 3H) 0.81 (m, 1H) 1.30 (m, 1H) 1.54 (s, 3H) 1.98 (m, 1H) 2.22 (m, 1H) 2.49 (d, J=5.15 Hz, 3H) 7.57 (m, 7H) 8.14 (d, J=7.72 Hz, 1H) 10.17 (s, 1H) 14.01 (s, 1H); (ESI$^-$) m/z 531 (M–H)$^-$.

EXAMPLE 97

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetamide

EXAMPLE 97A

Acetylsulfamoyl Chloride

Acetic acid (0.60 g, 10 mmol) was added slowly dropwise to chlorosulfonyl isocyanate (1.42 g, 10 mmol), with ice/water bath cooling as required to maintain gentle gas evolution. After the addition was complete, the residue was recrystallized from refluxing benzene (10 mL), to provide the title compound (1.5 g, 95%) as a crystalline, hygroscopic solid.

EXAMPLE 97B

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetamide A mixture of the product of Example 34B (50.9 mg, 0.107 mmol) and Example 97A (84.2 mg, 0.535 mmol) in dichloromethane (5 mL) was treated with triethylamine (64.9 mg, 0.641 mmol). The mixture was stirred at rt for 18 hours. The reaction mixture was then treated with water (20 mL) and then extracted with dichloromethane. The organic phase was dried (MgSO$_4$), filtered, and concentrated in vacuo. The residue was purified by HPLC to give the title compound (21 mg, 35%). $^1$H NMR (300 MHz, DMSO-$d_6$) δ 0.42 (m, 1H) 0.69 (d, J=6.62 Hz, 3H) 0.72 (d, J=6.62 Hz, 3H) 0.80 (m, 1H) 1.33 (m, 1H) 1.57 (s, 3H) 1.90 (s, 3H) 2.05 (m, 1H) 2.23 (m, 1H) 5.76 (s, 1H) 7.48 (dd, J=9.01, 2.39 Hz, 1H) 7.54 (m, 1H) 7.60 (d, J=2.21 Hz, 1H) 7.71 (d, J=8.82 Hz, 1H) 7.76 (d, J=3.68 Hz, 2H) 8.16 (d, J=8.09 Hz, 1H) 10.97 (s, 1H) 12.04 (s, 1H) 13.79 (s, 1H). MS (ESI$^+$) m/z 561.1 (M+H)$^+$, 578.2 (M+NH$_4$)$^+$, (ESI$^-$) m/z 559.1 (M–H)$^-$.

EXAMPLE 98

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]pentanamide

EXAMPLE 98A

Pentanoylsulfamoyl Chloride n-Pentanoic acid (1.02 g, 10 mmol) was added slowly dropwise to chlorosulfonyl isocyanate (1.42 g, 10 mmol), with ice/water bath cooling as required to maintain gentle gas evolution. After the addition was complete, the residue was taken up in benzene (10 mL) and the mixture concentrated in vacuo to provide the title compound (2.0 g, quantitative) as a crystalline, hygroscopic solid.

EXAMPLE 98B

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]pentanamide A mixture of the product of Example 34B (50.9 mg, 0.107 mmol) and Example 98A (109 mg, 0.535 mmol) in dichloromethane (5 mL) was treated with triethylamine (64.9 mg, 0.641 mmol). The mixture was stirred at rt for 15 minutes. The reaction mixture was partitioned between diehloromethane and 1N hydrochloric acid, and the aqueous phase extracted with additional dichloromethane. The organic phase was dried (MgSO$_4$), filtered, and concentrated in vacuo. The residue was purified by HPLC to give the title compound (32 mg, 49%). $^1$H NMR (300 MHz, DMSO-$d_6$) δ ppm 0.44 (m, 1H) 0.68 (d, J=6.62 Hz, 3H) 0.71 (d, J=6.62 Hz, 3H) 0.79 (m, 1H) 1.01 (m, 2H) 1.32 (m, 2H) 1.57 (s, 3H) 2.12 (t, J=7.17 Hz, 2H) 2.22 (m, 1H) 2.50 (s, 3H) 7.48 (dd, J=8.82, 2.21 Hz, 1H) 7.54 (m, 1H) 7.60 (d, J=2.21 Hz, 1H) 7.73 (d, J=9.19 Hz, 1H) 7.76 (d, J=4.04 Hz, 1H) 8.16 (d, J=8.09 Hz, 1H) 10.96 (s, 1H) 12.00 (s, 1H) 13.77 (s, 1H). MS (ESI$^+$) m/z 603.1 (M+H)$^+$, 625.1 (M+Na)$^+$, (ESI$^-$) 601.2 (M–H).

EXAMPLE 99

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]butanamide

EXAMPLE 99A

Butyrylsulfamoyl Chloride n-Butanoic acid (0.881 g, 10 mmol) was added slowly dropwise to chlorosulfonyl isocyanate (1.42 g, 10 mmol), with ice/water bath cooling as required to maintain gentle gas evolution. After the addition was complete, the residue was taken up in benzene (10 mL) and the mixture concentrated in vacuo to provide the title compound (1.85 g, quantitative) as a crystalline, hygroscopic solid.

EXAMPLE 99B

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]butanamide A mixture of the product of Example 34B (52.2 mg, 0.110 mmol) and the product of Example 99A (102 mg, 0.55 mmol) in dichloromethane (5 mL) was treated with triethylamine (66.5 mg, 0.658 mmol). The mixture was stirred at r.t. for 15 minutes. The reaction mixture was partitioned between dichloromethane and 1N hydrochloric acid, and the aqueous phase extracted with additional dichloromethane. The organic phase was dried (MgSO$_4$), filtered, and concentrated in vacuo. The residue was purified by HPLC to give the title compound (38 mg, 59%). $^1$H NMR (300 MHz, DMSO-d$_6$) δ 0.41 (m, 1H) 0.69 (m, 9H) 0.79 (m, 1H) 1.37 (m, 4H) 1.56 (s, 3H) 2.04 (m, 1H) 2.11 (t, J=7.35 Hz, 2H) 2.22 (m, 1H) 7.48 (dd, J=8.82, 2.21 Hz, 1H) 7.53 (m, 1H) 7.59 (d, J=2.21 Hz, 1H) 7.71 (d, J=8.82 Hz, 1H) 7.76 (d, J=4.04 Hz, 2H) 8.15 (d, J=7.72 Hz, 1H) 10.95 (s, 1H) 11.99 (s, 1H) 13.81 (s, 1H). MS (ESI$^+$) m/z 589.1 (M+H)$^+$, 606.1 (M+NH$_4$)$^+$, (ESI$^-$) 587.2 (M−H).

EXAMPLE 100

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]propanamide

EXAMPLE 100A

Propionylsulfamoyl Chloride n-Propionic acid (0.741 g, 10 mmol) was added slowly dropwise to chlorosulfonyl isocyanate (1.42 g, 10 mmol), with ice/water bath cooling as required to maintain gentle gas evolution. After the addition was complete, the residue was taken up in benzene (10 mL) and the mixture concentrated in vacuo to provide the title compound (1.71 g, quantitative) as a crystalline, hygroscopic solid.

EXAMPLE 100B

N-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]propanamide A mixture of Example 34B (52.2 mg, 0.110 mmol) and the product of Example 100A (94.6 mg, 0.55 mmol) in dichloromethane (5 mL) was treated with triethylamine (66.5 mg, 0.658 mmol). The mixture was stirred at rt for 15 minutes. The reaction mixture was partitioned between dichloromethane and 1N hydrochloric acid, and the aqueous phase extracted with additional dichloromethane. The organic phase was dried (MgSO$_4$), filtered, and concentrated in vacuo. The residue was purified by HPLC to give the title compound (36.3 mg, 57%). $^1$H NMR (300 MHz, DMSO-d$_6$) δ 0.41 (s, 2H) 0.69 (d, J=6.62 Hz, 3H) 0.72 (d, J=6.62 Hz, 3H) 0.88 (t, J=7.54 Hz, 3H) 1.33 (m, 2H) 1.57 (s, 3H) 2.04 (m, 1H) 2.14 (q, J=7.35 Hz, 2H) 2.25 (m, J=13.97, 3.31 Hz, 1H) 7.48 (dd, J=9.01, 2.39 Hz, 1H) 7.54 (m, J=8.27, 3.86 Hz, 1H) 7.59 (d, J=2.21 Hz, 1H) 7.71 (d, J=8.82 Hz, 1H) 7.76 (d, J=3.68 Hz, 2H) 8.16 (d, J=8.09 Hz, 1H) 10.94 (s, 1H) 11.98 (s, 1H) 13.80 (s, 1H).). MS (ESI$^+$) m/z 575.2 (M+H)$^+$, 592.2 (M+NH$_4$)$^+$, (ESI$^-$).

EXAMPLE 101

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethylenesulfonamide 2-Chloro-1-ethanesulfonyl chloride (0.535 g, 3.28 mmol) was added slowly dropwise to a solution of Example 39H (1.042 g, 2.19 mmol) and triethylamine (1.11 g, 10.9 mmol) in 30 mL of dichloromethane at room temperature. The reaction mixture was stirred for 20 min and then partitioned between dichloromethane and water. The organic phase was dried (MgSO$_4$), filtered, and concentrated in vacuo. The residue was purified by chromatography on silica gel, eluting with a 0-1% methanol/dichloromethane gradient to give the title compound (0.60 g, 52%). $^1$H NMR (300 MHz, DMSO-d$_6$) δ ppm 0.41 (m, 1H) 0.69 (d, J=6.62 Hz, 3H) 0.72 (d, J=6.62 Hz, 3H) 0.79 (m, 1H) 1.32 (m, 1H) 1.56 (s, 3H) 2.05 (m, 1H) 2.21 (m, 1H) 6.12 (d, J=10.30 Hz, 1H) 6.16 (d, J=16.55 Hz, 1H) 6.88 (dd, J=16.55, 9.93 Hz, 1H) 7.52 (m, 3H) 7.69 (d, J=9.19 Hz, 1H) 7.75 (d, J=3.68 Hz, 2H) 8.15 (d, J=7.72 Hz, 1H) 10.52 (s, 1H) 13.77 (s, 1H). MS (ESI$^+$) m/z 530.0 (M+H)$^+$, (ESI$^-$) m/z 528.0 (M−H)$^-$.

EXAMPLE 102

Sodium (4R)-2-{7-[(ethylsulfonyl)amino]-1,1-dioxido-4H-1,2,4-benzothiadiazin-3-yl}-4-methyl-4-(3-methylbutyl)-3-oxo-3,4-dihydronaphthalen-1-olate

EXAMPLE 102A

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide Ethane sulfonylchloride (75.6 mg, 0.588 mmol) was added carefully dropwise to a solution of Example 39H (70.0 mg, 0.147 mmol) and pyridine (93.1 mg, 1.18 mmol) in acetone (7 mL). The reaction mixture was stirred for 4 h and then concentrated in vacuo. The residue was partitioned between ethyl acetate and water. The organic phase was dried (MgSO$_4$), filtered, and concentrated in vacuo. The residue was purified by chromatography on silica gel, eluting with a 0-25% ethyl acetate/hexane gradient to give the title compound (74 mg, 95%). $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.80 (m, 1H) 1.22 (t, J=7.35 Hz, 3H) 1.33 (m, 1H) 1.57 (s, 3H) 2.07 (m, 1H) 2.22 (m, 1H) 3.19 (m, 2H) 5.76 (s, 1H) 7.53 (dd, J=7.91, 4.23 Hz, 1H) 7.57 (dd, J=8.82, 2.21 Hz, 1H) 7.63 (d, J=2.21 Hz, 1H) 7.71 (d, J=8.82 Hz, 1H) 7.76 (d, J=3.68 Hz, 2H) 8.16 (d, J=7.72 Hz, 1H) 10.31 (s, 1H) 13.77 (s, 1H).). MS (ESI$^+$) m/z 532.0 (M+H)$^+$, 549.1 (M+NH$_4$)$^+$ (ESI$^-$) m/z 530.1 (M−H)$^-$.

EXAMPLE 102B

Sodium (4R)-2-{7-[(ethylsulfonyl)amino]-1,1-dioxido-4H-1,2,4-benzothiadiazin-3-yl}-4-methyl-4-(3-methylbutyl)-3-oxo-3,4-dihydronaphthalen-1-olate A mixture of Example 102A (70.4 mg, 0.132 mmol) and 0.998 M sodium hydroxide (0.133 mL, 0.132 mmol) in 3 mL water was stirred at rt for 16 h. The reaction mixture was concentrated in vacuo to give the title compound (64 mg, 87% yield). $^1$H NMR (300 MHz, DMSO-$d_6$) δ 0.46 (m, 1H) 0.68 (d, J=6.62 Hz, 3H) 0.70 (d, J=6.62 Hz, 3H) 0.79 (m, 1H) 1.19 (t, J=7.35 Hz, 3H) 1.29 (m, 1H) 1.38 (s, 3H) 1.72 (m, 1H) 2.15 (m, 1H) 3.02 (m, 2H) 7.23 (d, J=7.72 Hz, 1H) 7.31 (m, 2H) 7.44 (m, 3H) 8.04 (d, J=7.35 Hz, 1H) 9.96 (s, 1H) 15.43 (s, 1H). MS (ESI$^+$) m/z 532.0 (M+H–Na)$^+$, 549.0 (M–Na+NH4)$^+$, (ESI$^−$) m/z 530.0 (M–H–Na)$^−$.

EXAMPLE 103

Sodium (4R)-4-methyl-4-(3-methylbutyl)-2-{7-[(2-naphthylsulfonyl)amino]-1,1-dioxido-4H-1,2,4-benzothiadiazin-3-yl}-3-oxo-3,4-dihydronaphthalen-1-olate

EXAMPLE 103A

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}naphthalene-2-sulfonamide A mixture of Example 39H (23.8 mg, 0.050 mmol), pyridine (31.6 mg, 0.40 mmol), and 2-naphthalenesulfonyl chloride (45.3 mg, 0.20 mmol) in acetone (1.5 mL) was stirred at rt for 18 h. The reaction mixture was evaporated in vacuo and partitioned between ethyl acetate and 1 N HCl. The organic phase was separated, dried (MgSO$_4$), filtered, and evaporated in vacuo. The residue was purified by chromatography on silica gel eluting with 4:1 hexane/ethyl acetate to provide the title compound (12.3 mg, 39% yield). $^1$H NMR (300 MHz, DMSO-$d_6$) δ ppm 0.37 (m, 1H) 0.66 (d, J=6.62 Hz, 3H) 0.68 (d, J=6.62 Hz, 3H) 0.77 (m, 1H) 1.29 (m, 1H) 1.52 (s, 3H) 2.02 (m, 1H) 2.18 (m, 1H) 7.52 (m, 4H) 7.68 (m, 2H) 7.73 (d, J=4.04 Hz, 2H) 7.79 (dd, J=8.46, 1.84 Hz, 1H) 8.01 (d, J=7.72 Hz, 1H) 8.13 (m, 3H) 8.50 (s, 1H) 10.93 (s, 1H) 13.71 (s, 1H). MS (ESI$^+$) m/z 630.0 (M+H)$^+$, 647.1 (M+NH$_4$)$^+$, (ESI$^−$) m/z 628.1 (M–H)$^−$.

EXAMPLE 103B

Sodium (4R)-4-methyl-4-(3-methylbutyl)-2-{7-[(2-naphthylsulfonyl)amino]-1,1-dioxido-4H-1,2,4-benzothiadiazin-3-yl}-3-oxo-3,4-dihydronaphthalen-1-olate A mixture of Example 103A (10.0 mg, 0.016 mmol) and 0.998 M sodium hydroxide (0.016 mL, 0.016 mmol) in water (1 mL) was stirred at rt for 16 h. The reaction mixture was concentrated in vacuo to give the title compound (10.0 mg, quant. yield). $^1$H NMR (300 MHz, DMSO-$d_6$) δ 0.40 (m, 1H) 0.65 (d, J=6.62 Hz, 3H) 0.67 (m, 3H) 0.76 (m, 1H) 1.27 (m, 1H) 1.34 (s, 3H) 1.69 (m, 1H) 2.11 (m, 1H) 7.26 (m, 4H) 7.43 (m, 2H) 7.64 (m, 2H) 7.75 (dd, J=8.46, 1.84 Hz, 1H) 8.03 (m, 4H) 8.38 (s, 1H) 10.54 (s, 1H) 15.37 (s, 1H). MS (ESI$^+$) m/z 630.0 (M+H–Na)$^+$, 647.1.0 (M–Na+NH$_4$)$^+$.

EXAMPLE 104

Sodium (4R)-2-[7-({[6-(acetylamino)-2-naphthyl]sulfonyl}amino)-1,1-dioxido-4H-1,2,4-benzothiadiazin-3-yl]-4-methyl-4-(3-methylbutyl)-3-oxo-3,4-dihydronaphthalen-1-olate

EXAMPLE 104A

N-{6-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]-2-naphthyl}acetamide A mixture of Example 39H (23.8 mg, 0.050 mmol), pyridine (31.6 mg, 0.40 mmol) and 6-acetylamino-2-naphthalenesulfonyl chloride (56.7 mg, 0.20 mmol, prepared by the procedure as described in J. Med. Chem., 1995, 38, 8, p. 1344-1354) in acetone (1.5 mL) was stirred at rt for 18 h. The reaction mixture was evaporated in vacuo and partitioned between ethyl acetate and 1 N HCl. The organic phase was separated, dried (MgSO$_4$), filtered, and evaporated in vacuo. The residue was purified by chromatography on silica gel eluting with 99:1 dichloromethane/methanol to provide the title compound (20.8 mg, 61% yield). $^1$H NMR (300 MHz, DMSO-$d_6$) δ 0.38 (m, 1H) 0.66 (d, J=7.35 Hz, 3H) 0.68 (d, J=6.99 Hz, 3H) 0.80 (m, 1H) 1.30 (m, 1H) 1.53 (s, 3H) 2.02 (m, 1H) 2.10 (s, 3H) 2.18 (m, 1H) 7.52 (m, 4H) 7.69 (m, 4H) 7.99 (d, J=8.82 Hz, 1H) 8.07 (d, J=8.82 Hz, 1H) 8.11 (d, J=8.09 Hz, 1H) 8.38 (s, 2H) 10.32 (s, 1H) 10.87 (s, 1H) 13.72 (s, 1H).

EXAMPLE 104B

Sodium (4R)-2-[7-({[6-(acetylamino)-2-naphthyl]sulfonyl}amino)-1,1-dioxido-4H-1,2,4-benzothiadiazin-3-yl]-4-methyl-4-(3-methylbutyl)-3-oxo-3,4-dihydronaphthalen-1-olate A mixture of Example 104A (5.0 mg, 0.0072 mmol) and 0.998 M sodium hydroxide (0.0072 mL, 0.0072 mmol) in water (1 mL) was stirred at rt for 16 h. The reaction mixture was concentrated in vacuo to give the title compound (5.1 mg, quant. yield). $^1$H NMR (300 MHz, DMSO-$d_6$) δ 0.42 (m, 1H) 0.66 (t, J=6.80 Hz, 6H) 0.75 (m, 1H) 1.26 (m, 1H) 1.36 (s, 3H) 1.73 (m, 1H) 2.10 (m, 4H) 7.21 (d, J=9.93 Hz, 1H) 7.31 (m, J=8.46, 2.21 Hz, 2H) 7.38 (d, J=2.21 Hz, 1H) 7.46 (m, 2H) 7.67 (m, 2H) 8.01 (m, 3H) 8.30 (s, 1H) 8.37 (s, 1H) 10.31 (s, 1H) 10.51 (s, 1H) 15.31 (s, 1H). MS (ESI$^+$) m/z 709.1 (M+H)$^+$, 687.6 (M+H–Na)$^+$, 704.1 (M–Na+NH$_4$)$^+$, (ESI–) m/z 707.1 (M–H)$^−$, 685.0 (M–H–Na)$^−$.

EXAMPLE 105

Sodium (4R)-4-methyl-4-(3-methylbutyl)-2-{7-[(1-naphthylsulfonyl)amino]-1,1-dioxido-4H-1,2,4-benzothiadiazin-3-yl}-3-oxo-3,4-dihydronaphthalen-1-olate

EXAMPLE 105A

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}naphthalene-1-sulfonamide A mixture of Example 39H (23.8 mg, 0.050 mmol), pyridine (31.6 mg, 0.80 mmol), and 1-naphthalenesulfonyl chloride (45.3 mg, 0.20 mmol) in acetone (1.5 mL) was stirred at rt for 72 h. The reaction mixture was evaporated in vacuo and partitioned between ethyl acetate and 1 N HCl. The organic phase was separated, dried (MgSO$_4$), filtered, and evaporated in vacuo. The residue was purified by chromatography on silica gel eluting with 99:1 dichloromethane/methanol to provide the title compound (32.0 mg, quant. yield).

EXAMPLE 105B

Sodium (4R)-4-methyl-4-(3-methylbutyl)-2-{7-[(1-naphthylsulfonyl)amino]-1,1-dioxido-4H-1,2,4-benzothiadiazin-3-yl}-3-oxo-3,4-dihydronaphthalen-1-olate A mixture of Example 105A (30.0 mg, 0.048 mmol) and 0.998 M sodium hydroxide (0.048 mL, 0.048 mmol) in water (3 mL) was stirred at rt for 16 h. The reaction mixture was concentrated in vacuo to give the title compound (21 mg, 68% yield). $^1$H NMR (300 MHz, DMSO-d$_6$) δ 0.40 (m, 1H) 0.65 (d, J=6.62 Hz, 3H) 0.67 (m, 3H) 0.75 (m, 1H) 1.26 (m, 1H) 1.34 (s, 3H) 1.69 (m, 1H) 2.10 (m, 1H) 7.12 (m, 2H) 7.23 (s, 1H) 7.29 (m, 1H) 7.44 (m, 2H) 7.64 (m, 2H) 7.74 (m, 1H) 8.00 (d, J=7.72 Hz, 1H) 8.07 (d, J=7.72 Hz, 1H) 8.16 (d, J=7.35 Hz, 1H) 8.20 (m, 1H) 8.76 (s, 1H) 10.82 (s, 1H) 15.39 (s, 1H). MS (ESI$^+$) m/z 652.0 (M+H)$^+$, 630.0 (M+H–Na)$^+$, 647 (M–Na+NH$_4$)$^+$, (ESI$^-$) m/z 628.0 (M–H–Na)$^-$.

EXAMPLE 106

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-1H-benzimidazole-2-sulfonamide A mixture of Example 39H (47.6 mg, 0.10 mmol), pyridine (64 mg, 0.80 mmol), and 2-benzimidazole sulfonyl chloride (87 mg, 0.40 mmol, prepared according to the procedure reported by S. M. Deshpande et al, J. Med. Chem. 1970,13, 143-144) in acetone (2 mL) was stirred at rt for 16 h. The reaction mixture was evaporated in vacuo and partitioned between ethyl acetate and water. The organic phase was separated, dried (MgSO$_4$), filtered, and evaporated in vacuo. The residue was purified by chromatography on silica gel eluting with 99:1 dichloromethane/methanol to provide the title compound (28.0 mg, 45% yield). $^1$H NMR (300 MHz, DMSO-d$_6$) δ 0.39 (m, 1H) 0.67 (d, J=6.62 Hz, 3H) 0.70 (d, J=6.62 Hz, 3H) 0.77 (m, 1H) 1.29 (m, 1H) 1.54 (s, 3H) 2.04 (m, 1H) 2.19 (m, 1H) 7.35 (dd, J=6.25, 2.94 Hz, 2H) 7.51 (m, 1H) 7.64 (m, 8H) 8.13 (d, J=7.72 Hz, 1H) 11.51 (s, 1H) 13.77 (s, 1H). MS (ESI$^+$) m/z 620.0 (M+H)$^+$, 641.9 (M+H–Na)$^+$, (ESI$^-$) m/z 618.0 (M–H)$^-$.

EXAMPLE 107

2-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]-1H-benzimidazole-6-carboxylic acid

EXAMPLE 107A 2-mercapto-1H-benzimidazole-5-carboxylic Acid

A mixture of 3,4-diaminobenzoic acid (1.52 g, 10 mmol), carbon disulfide (0.837 g, 11 mmol), and potassium hydroxide (0.617 g, 11 mmol) in water (30 mL) and ethanol (8 mL) was heated under reflux for 16 h and then cooled to rt. The reaction mixture was evaporated in vacuo and then taken up in water (25 mL). The resulting mixture was neutralized by the addition of 1 N HCl and the resulting brown solid isolated by vacuum filtration, washed with water and air dried to provide the title compound (1.15 g, 59% yield). $^1$H NMR (300 MHz, DMSO-d$_6$) δ ppm 7.20 (d, J=8.09 Hz, 1H) 7.66 (s, 1H) 7.76 (dd, J=8.46, 1.47 Hz, 1H) 12.76 (s, 1H) 12.82 (s, 1H). MS (ESI$^-$) m/z 193.0 (M–H)$^-$.

EXAMPLE 107B 2-(chlorosulfonyl)-1H-benzimidazole-5-carboxylic Acid

Chlorine gas was bubbled through a solution of Example 107A (0.253 g, 1.30 mmol) in water (24 mL) and acetic acid (6 mL) with stirring at 0° C. for 30 min. The solid that resulted was isolated by vacuum filtration and rinsed quickly with water and air-dried to provide the title compound (0.170 g, 50%).

EXAMPLE 107C

2-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]-1H-benzimidazole-6-carboxylic Acid A mixture of Example 39H (77.7 mg, 0.163 mmol), pyridine (103 mg, 1.31 mmol), and Example 107B (0.170 g, 0.653 mmol) in acetone (3 mL) was stirred at rt for 16 h. The reaction mixture was evaporated in vacuo and the residue partitioned between ethyl acetate and 1 N HCl. The organic phase was dried over anhydrous magnesium sulfate, filtered, and evaporated. The residue was purified by chromatography on silica gel eluting with 99:1 to 95:5 dichloromethane/methanol to provide the title compound (10.0 mg, 9% yield). $^1$H NMR (300 MHz, DMSO-d$_6$) δ 0.42 (m, 1H) 0.66 (d, J=6.99 Hz, 3H) 0.69 (d, J=6.99 Hz, 3H) 0.82 (dd, J=13.79, 7.17 Hz, 1H) 1.28 (m, 1H) 1.41 (s, 3H) 1.81 (m, 1H) 2.15 (m, 1H) 7.39 (m, 3H) 7.59 (m, 4H) 7.88 (m, 2H) 8.06 (d, J=7.72 Hz, 1H) 8.33 (s, 1H) 11.36 (s, 1H) 12.95 (s, 1H) 13.59 (s, 1H) 14.18 (s, 1H). MS (ESI$^+$) m/z 663.8 (M+H)$^+$, 685.5 (M+Na)$^+$, (ESI$^-$) m/z 661.8 (M–H)$^-$.

EXAMPLE 108

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-6-nitro-1H-benzimidazole-2-sulfonamide

EXAMPLE 108A 5-nitro-1H-benzimidazole-2-sulfonyl Chloride

Chlorine gas was bubbled through a solution of 5-nitro-1H-benzoimidazole-2-thiol (0.150 g, 0.768 mmol) in water (8 mL) and acetic acid (2 mL) with stirring at 0° C. for 30 min. The solid that resulted was isolated by vacuum filtration and rinsed quickly with water and air-dried to provide the title compound (0.150 g, 75%).

EXAMPLE 108B

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}-6-nitro-1H-benzimidazole-2-sulfonamide A mixture of Example 39H (51 mg, 0.11 mmol), pyridine (68 mg, 0.857 mmol), and Example 108A (0.150 g, 0.537 mmol) in acetone (3 mL) was stirred at rt for 16 h. The reaction mixture was evaporated in vacuo and the residue partitioned between ethyl acetate and 1 N HCl. The organic phase was dried over anhydrous magnesium sulfate, filtered, and evaporated. The residue was purified by chromatography on silica gel eluting with 99:1 dichloromethane/methanol to provide the title compound (54 mg, 76% yield). $^1$H NMR (300 MHz, DMSO-$d_6$) δ 0.41 (m, 1H) 0.67 (d, J=6.62 Hz, 3H) 0.70 (d, J=6.62 Hz, 3H) 0.78 (m, 1H) 1.31 (m, 1H) 1.54 (s, 3H) 2.03 (m, 1H) 2.20 (m, 1H) 7.51 (m, 1H) 7.59 (dd, J=8.82, 2.21 Hz, 1H) 7.65 (s, 1H) 7.67 (d, J=2.57 Hz, 1H) 7.75 (m, 3H) 7.84 (m, 1H) 8.13 (d, J=7.72 Hz, 1H) 8.24 (dd, J=9.19, 2.21 Hz, 1H) 8.58 (s, 1H) 8.74 (d, J=4.41 Hz, 1H) 13.76 (s, 1H). MS (ESI$^+$) m/z 664.8 (M+H)$^+$, 682.0 (M+NH$_4$)$^+$, (ESI$^-$) m/z 663.0 (M–H)$^-$.

EXAMPLE 109

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide Example 34B (172 mg, 0.36 mmol) was dissolved in 5 mL of acetone and treated with ethyl sulfonyl chloride (150 uL, 1.59 mmol)) and pyridine (250 uL, 3.1 mmol). The mixture was stirred at room temp over night. The mixture was diluted with ethyl acetate and washed with 10% citric acid. The organic phase was washed with water and concentrated in vacuo to afford a yellow oil, which was purified by reverse phase HPLC to afford the title compound (100 mg, 50%). $^1$H NMR (300 MHz, DMSO-$d_6$) δ ppm 0.41 (m, 1H) 0.70 (m, 6H) 0.82 (m, 1H) 1.22 (t, J=7.35 Hz, 3H) 1.33 (m, J=13.97 Hz, 1H) 1.57 (s, 3H) 2.07 (m, 1H) 2.22 (m, 1H) 3.19 (q, J=6.99 Hz, 2H) 7.57 (m, 3H) 7.74 (m, 3H) 8.16 (d, J=8.09 Hz, 1H) 10.31 (s, 1H) 13.76 (s, 1H); (ESI) m/z 530 (M–H)$^-$. Anal. calc'd for: C, 56.48; H, 5.50; N, 7.90. found: C, 56.21; H, 5.37; N, 7.94.

EXAMPLE 110

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}propane-2-sulfonamide Example 34B (180 mg, 0.38 mmol) was dissolved in 5 mL of acetone and treated with isopropyl sulfonyl chloride (180 uL, 1.60 mmol) and pyridine (250 uL, 3.1 mmol). The mixture was stirred at room temp over night and then treated with additional isopropyl sulfonyl chloride (200 uL, 1.78 mmol) and pyridine (250 uL, 3.1 mmol) and stirred at room temp for 3 days. The mixture was partitioned between ethyl acetate and 10% citric acid. The phases were separated and the organic phase was washed with water, concentrated in vacuo, and purified by reverse phase HPLC (52 mg, 25%). $^1$H NMR (300 MHz, DMSO-$d_6$) δ ppm. 0.41 (s, 1H) 0.69 (d, J=6.62 Hz, 3H) 0.72 (d, J=6.62 Hz, 3H) 0.81 (m, 1H) 1.27 (d, J=6.99 Hz, 6H) 1.32 (m, 1H) 1.57 (s, 3H) 2.05 (m, 1H) 2.22 (m, 1H) 3.30 (m, 1H) 7.61 (m, 6H) 8.15 (d, J=7.72 Hz, 1H) 10.29 (s, 1H) 13.78 (s, 1H). (APCI) m/z 546 (M+H)$^+$.

EXAMPLE 111

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-4-nitrobenzenesulfonamide Example 34B (145 mg, 0.30 mmol) was dissolved in 5 mL of acetone and treated with 4-nitrophenyl sulfonyl chloride (340 mg, 1.53 mmol) and pyridine (250 uL, 3.1 mmol). The mixture was stirred at room temp over night, diluted with ethyl acetate, and washed with H$_2$O and 10% citric acid and H$_2$O. The organic phase was concentrated in vacuo and purified on silica gel with a gradient of methanol in dichloromethane (0-5%). $^1$H NMR (300 MHz, DMSO-$d_6$) δ ppm 0.39 (m, 1H) 0.68 (d, J=6.62 Hz, 3H) 0.70 (d, J=6.62 Hz, 3H) 0.79 (m, 1H) 1.30 (m, J=13.24, 6.62 Hz, 1H) 1.54 (s, 3H) 2.03 (m, 1H) 2.20 (m, 1H) 7.50 (m, 3H) 7.64 (m, 1H) 7.74 (d, J=3.68 Hz, 2H) 8.04 (m, 2H) 8.13 (d, J=7.72 Hz, 1H) 8.41 (m, 2H) 11.12 (s, 1H) 13.73 (s, 1H); MS (APCI) m/z 440 (parent amine+H)$^+$.

EXAMPLE 112

N-{4-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]phenyl}acetamide Example 34B (145 mg, 0.30 mmol) was dissolved in 5 mL of acetone and treated with 4-(acetylamino)benzenesulfonyl chloride (355 mg, 0.52 mmol) and pyridine (250 uL, 3.10 mmol). The mixture was stirred at room temp over night, diluted with ethyl acetate, washed water and with 10% citric acid and water, and then concentrated in vacuo. The crude material was chromatographed on silica gel with a gradient of methanol in dichloromethane (0-5%) to give the title compound (168 mg, 87%). $^1$H NMR (300 MHz, DMSO-$d_6$) δ ppm 0.40 (m, 1H) 0.67 (d, J=6.62 Hz, 3H) 0.70 (d, J=6.62 Hz, 3H) 0.79 (m, 1H) 1.30 (m, 1H) 1.52 (s, 3H) 1.99 (m, 1H) 2.05 (s, 3H) 2.20 (m, 1H) 7.48 (m, 4H) 7.72 (m, 6H) 8.12 (d, J=7.72 Hz, 1H) 10.32 (s, 1H) 10.65 (s, 1H) 13.96 (s, 1H); MS (APCI) m/z 637 (M+H)$^+$.

EXAMPLE 113

N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}-1,2-dimethyl-1H-imidazole-4-sulfonamide Example 87 (155 mg, 0.33 mmol) was dissolved in 5 mL of acetone and treated with 1,2-dimethyl-1H-imidazole-4-sulfonyl chloride (320 mg, 1.64 mmol) and pyridine (250 uL, 3.1 mmol). The mixture was stirred at room temp over night, diluted with ethyl acetate, washed with water and with 10% citric acid and water, and concentrated in vacuo. The crude material was recrystallized from ethyl acetate with a small amount of methanol (103 mg, 53%). $^1$H NMR (300 MHz, DMSO-$d_6$) δ ppm 0.40 (m, 1H) 0.68 (d, J=6.62 Hz, 3H) 0.71 (d, J=6.62 Hz, 3H) 0.78 (m, J=11.40 Hz, 1H) 1.32 (m, 1H) 1.56 (s, 3H) 2.08 (m, J=8.46 Hz, 1H) 2.20 (m, 1H) 2.26 (s, 3H) 3.56 (s, 3H) 7.56 (m, 4H) 7.76 (m, 3H) 7.83 (s, 1H) 8.15 (d, J=7.72 Hz, 1H) 10.70 (s, 1H) 13.67 (s, 1H); (APCI) m/z 598 (M+H)$^+$. Anal. calc'd for: C, 56.27; H, 5.23; N, 11.72. found: C, 55.95; H, 5.16; N, 11.52.

EXAMPLE 114

Methyl[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetate Example 87 (100 mg, 0.21 mmol) was dissolved in 5 mL of acetone and treated with chlorosulfonyl-acetic acid methyl ester (150 uL, 0.87 mmol) and pyridine (150 uL, 1.90 mmol). The mixture was stirred at room temp over night, diluted with ethyl acetate, washed with water and 10% citric acid and water, and concentrated in vacuo. The crude material was chromatographed on silica gel with a gradient methanol in dichloromethane (0-5%) to afford the title compound (83 mg, 68%). $^1$H NMR (300 MHz, DMSO-$d_6$) δ ppm 0.41 (m, J=7.72 Hz, 1H) 0.69 (d, J=6.62 Hz, 3H) 0.72 (d, J=6.62 Hz, 3H) 0.82 (m, 1H) 1.31 (m, J=13.05, 6.80 Hz, 1H) 1.57 (s, 3H) 2.05 (m, 1H) 2.22 (m, 1H) 3.64 (s, 3H) 4.38 (s, 2H) 7.57 (m, 3H) 7.74 (m, 3H) 8.16 (d, J=8.09 Hz, 1H) 10.68 (s, 1H) 13.82 (s, 1H); MS (APCI) m/z 574 (M−H)$^-$.

EXAMPLE 115

2-hydroxy-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}ethanesulfonamide Example 114 was dissolved in 1.5 mL of tetrahydrofuran and 0.1 mL of methanol and treated with lithium borohydride (50 µL, 2.0 M in tetrahydrofuran, 0.1 mmol) dropwise. The yellow solution was stirred at room temp for several hours and an additional aliquot of lithium borohydride solution (0.5 ml, 1.0 mmol) was added. After 2 h, the reaction was quenched by the addition of water. The mixture was diluted with Rochelle's salt and exhaustively extracted with ethyl acetate and the combined organic phases were concentrated in vacuo to give 66 mg of yellow solid. The crude material was chromatographed on silica gel with a gradient of methanol in dichloromethane (0-10%) to afford the desired material (34 mg, 51%). $^1$H NMR (300 MHz, DMSO-$d_6$) δ ppm 0.43 (m, 1H) 0.68 (d, J=6.62 Hz, 3H) 0.71 (d, J=6.62 Hz, 3H) 0.83 (m, 1H) 1.32 (m, 1H) 1.50 (s, 3H) 1.97 (d, J=12.50 Hz, 1H) 2.21 (m, 1H) 3.30 (m, J=13.05, 6.43 Hz, 2H) 3.76 (t, J=6.25 Hz, 2H) 7.53 (m, 6H) 8.12 (d, J=7.72 Hz, 1H) 10.10 (s, 1H); MS (APCI) m/z 548 (M+H)$^+$.

EXAMPLE 116

4-amino-N-{3-[1-hydroxy-4-methyl-4-(3-methylbutyl)-3-oxo-3,4-dihydronaphthalen-2-yl]-1,1-dioxido-4H-1,2,4-benzothiadiazin-7-yl}benzenesulfonamide Example 111 (87 mg, 0.14 mmol) was slurried in 6 mL of methanol, 6 mL of tetrahydrofuran, and 2 mL of H$_2$O and treated with iron powder (45 mg, 0.80 mmol) and ammonium chloride (27 mg, 0.51 mmol). The mixture was warmed to 65° C. for 1 h, cooled, and filtered through celite with excess methanol. The filtrate was concentrated in vacuo and chromatographed on silica gel with a gradient of methanol in dichloromethane (0-5%) to afford the title compound (72 mg, 87%). $^1$H NMR (300 MHz, DMSO-$d_6$) δ ppm 0.42 (m, 1H) 0.68 (d, J=6.62 Hz, 3H) 0.70 (d, J=6.62 Hz, 3H) 0.76 (m, 1H) 1.29 (m, 1H) 1.52 (s, 3H) 2.00 (m, 1H) 2.19 (m, J=4.41 Hz, 1H) 6.06 (br. s, 1H) 6.55 (m, 2H) 7.40 (m, 3H) 7.49 (m, 3H) 7.70 (d, J=3.68 Hz, 2H) 8.12 (d, J=7.72 Hz, 1H) 10.34 (s, 1H) 13.97 (s, 1H); MS (APCI) m/z 595 (M+H)$^+$.

EXAMPLE 117

2-[({3-[1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetamide Example 114 (80 mg, 0.14 mmol) was dissolved in 5 mL of conc. ammonium hydroxide, left at room temperature for 3 h, diluted with water acidified with conc. HCl, and then extracted with ethyl acetate. The organic phases were washed with water and concentrated in vacuo. The crude material was chromatographed on silica gel with a gradient of methanol in dichloromethane (0-10%) to afford the title compound (41 mg, 53%). $^1$H NMR (500 MHz, C$_6$D$_6$) δ ppm 0.58 (m, 1H) 0.70 (d, J=6.71 Hz, 3H) 0.72 (d, J=6.71 Hz, 3H) 0.87 (m, 1H) 1.32 (m, 1H) 1.46 (s, 3H) 1.78 (m, 1H) 2.19 (td, J=12.51, 4.88 Hz, 1H) 3.94 (s, 2H) 7.13 (bs, 2H) 7.31 (m, 2H) 7.47 (m, 3H) 7.61 (s, 1H) 8.11 (d, J=7.93 Hz, 1H) 9.64 (s, 1H) 15.05 (s, 1H); MS (APCI) m/z 559 (M−H)$^-$.

EXAMPLE 118

N-[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)carbonothioyl]benzamide Example 39H (35 mg, 0.07 mmol) was dissolved in 1 mL of acetone and treated with triethylamine (15 µL, 0.11 mmol) and benzoylthioisocyanate (30 µL, 0.08 mmol), and warmed to 60° C. After several hours, the mixture was cooled, treated with H$_2$O, and extracted with ethyl acetate. The organic phase was washed with water, concentrated in vacuo, and chromatographed on silica gel with a gradient of methanol in dichloromethane (0-1%). The material was triturated with hot ethanol to afford the title compound (27 mg, 61%). $^1$H NMR (300 MHz, DMSO-$d_6$) δ ppm 0.45 (m, 1H) 0.70 (d, J=6.62 Hz, 3H) 0.73 (d, J=6.99 Hz, 3H) 0.84 (m, 1H) 1.34 (m, 1H) 1.58 (s, 3H) 2.06 (m, 1H) 2.23 (m, 1H) 7.54 (m, 3H) 7.71 (m, 4H) 7.93 (dd, J=8.82, 2.21 Hz, 1H) 8.01 (d, J=7.35 Hz, 2H) 8.17 (d, J=7.72 Hz, 1H) 8.42 (s, 1H) 11.72 (s, 1H) 12.66 (s, 1H) 13.88 (s, 1H); MS (ESI$^-$) m/z 601 (M−H)$^-$.

EXAMPLE 119

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}thiourea Example 118 (23 mg, 0.04 mmol) was slurried in 1:1 methanol/acetone (2 mL) and potassium carbonate (10 mg, 0.08 mmol) was added. The mixture was warmed to 60° C. for 2 h, the mixture was allowed to cool, and was treated with acetic acid (~0.5 mL) and water. A yellow/white precipitate formed and was collected by filtration to afford the title compound (14 mg, 80%). $^1$H NMR (300 MHz, DMSO-$d_6$) δ ppm 0.44 (m, 1H) 0.69 (d, J=6.62 Hz, 3H) 0.72 (d, J=6.62 Hz, 3H) 0.83 (m, 1H) 1.33 (m, 1H) 1.58 (s, 3H) 2.08 (m, J=4.04 Hz, 1H) 2.23 (m, J=4.78 Hz, 1H) 7.54 (m, 2H) 7.65 (d, J=8.82 Hz, 1H) 7.78 (m, 4H) 8.18 (m, 2H) 10.01 (s, 1H) 13.78 (s, 1H); MS (ESI$^+$) m/z 499 (M+H)$^+$.

EXAMPLE 120

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}urea Example 39H (43 mg, 0.09 mmol) was dissolved in 1 mL of tetrahydrofuran and treated with potassium isocyanate (18 mg, 0.22 mmol). After 2 h, water (~1 mL) was added. After 2 h, triethylamine (15 µL) was added and the mixture was stirred for 10 min before acetic acid (1 mL) was added and the mixture was stirred at room temperature over night. The mixture was partitioned between ethyl acetate and water and the phases were separated. The organic phase was washed with water, concentrated in vacuo, and purified on silica gel with a gradient of methanol in dichloromethane (0-10%) to afford the title compound (12 mg, 28% yield). $^1$H NMR (300 MHz, DMSO-d$_6$) δ ppm 0.43 (m, 1H) 0.68 (d, J=6.62 Hz, 3H) 0.71 (d, J=6.62 Hz, 3H) 0.83 (m, 1H) 1.32 (m, 1H) 1.52 (s, 3H) 1.97 (m, 1H) 2.20 (m, 1H) 6.04 (s, 2H) 7.52 (m, 3H) 7.67 (m, 2H) 8.12 (m, 2H) 8.95 (s, 1H); MS (ESI$^-$) m/z 481 (M–H)$^-$.

EXAMPLE 121

[({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}amino)sulfonyl]acetic Acid Example 39H (189 mg, 0.40 mmol) was dissolved in 5 mL of acetone and treated with chlorosulfonyl-acetyl chloride (140 µL, 1.32 mmol) and pyridine (250 uL, 3.1 mmol). The mixture was stirred at room temp for 2 h and the mixture was concentrated in vacuo and taken up in conc. NH$_4$OH. The amber solution was stirred at room temp for 24 hours, concentrated, and then partitioned between H$_2$O and ethyl acetate. The organic phase was concentrated in vacuo, and a portion was purified by reverse phase HPLC to afford the title compound (15 mg, 7%). $^1$H NMR (300 MHz, DMSO-d$_6$) δ ppm 0.40 (m, 1H) 0.71 (dd, J=9.56, 6.62 Hz, 6H) 0.83 (m, 1H) 1.33 (m, 1H) 1.59 (s, 3H) 2.08 (m, 1H) 2.24 (m, J=4.41 Hz, 1H) 3.54 (s, 2H) 7.55 (m, 1H) 7.73 (m, 4H) 8.17 (d, J=8.09 Hz, 1H) 8.38 (s, 1H) 10.39 (s, 1H) 13.65 (s, 1H); MS (ESI$^-$) m/z 559.9 (M–H)$^-$.

EXAMPLE 122

1-chloro-N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide Example 39H (181 mg) was dissolved in 5 mL of acetone and treated with chloromethylsulfonylchloride (140 uL) and pyridine (250 uL). The mixture was stirred at room temp for 24 hours and then partitioned between H$_2$O and ethyl acetate. The organic phase was washed with 10% citric acid and H$_2$O and concentrated in vacuo. The crude material was chromatographed on silica gel with a gradient of methanol in dichloromethane (0-1%) to give a yellow solid (215 mg, 100%). $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.82 (m, 1H) 1.33 (m, 1H) 1.56 (s, 3H) 2.05 (m, 1H) 2.20 (m, J=7.72 Hz, 1H) 5.15 (s, 2H) 7.52 (m, 1H) 7.66 (m, 5H) 8.15 (d, J=8.09 Hz, 1H) 10.85 (s, 1H) 13.86 (s, 1H); MS (ESI$^-$) m/z 550 (M–H)$^-$.

EXAMPLE 123

N-[3-(4-allyl-1-hydroxy-4-methyl-3-oxo-3,4-dihydronaphthalen-2-yl)-1,1-dioxido-4H-1,2,4-benzothiadiazin-7-yl]methanesulfonamide

EXAMPLE 123A 1-allyl-1-methyl-3,4-dihydronaphthalen-2(1H)-one

To a solution of 1-methyl-2-tetralone (10.0 g, 62.4 mmol), allyl acetate (7.42 mL, 68.7 mmol), cesium carbonate (20.3 g, 62.4 mmol), tris(dibenzylideneacetone)dipalladium(0) (0.143 g, 0.156 mmol), 1,2-diaminocyclohexane-N,N'-bis(2'-diphenylphosphinobenzoyl) (0.215 g, 0.312 mmol) in tetrahydrofuran (300 mL) was bubbled a stream of nitrogen through the mixture for ten minutes. The solution was then stirred at room temperature for 4 days followed by the addition of ethyl acetate (200 mL) and a saturated aqueous solution of ammonium chloride. The organic layer was separated, dried (MgSO$_4$), filtered, and concentrated in vacuo. The residue was purified by column chromatography employing 70-230 mesh silica gel eluting with a mixture of 10% ethyl acetate in hexane to provide the title compound as a light yellow oil (10.07 g, 90%). $^1$H NMR (300 MHz, CDCl$_3$): δ 1.43 (s, 3H), 2.46 (m, 1H), 2.63 (m, 2H), 2.78 (m, 1H), 3.03 (m, 2H), 4.90 (m, 2H), 5.40 (m, 1H), 7.18 (m, 2H), 7.30 (m, 2H).

EXAMPLE 123B 1-allyl-1-methyl-1,4-dihydronaphthalen-2-yl methyl ether

To a solution of Example 123A (10.1 g, 50.5 mmol), trimethylorthoformate (20 mL), p-toluenesulfonic acid monohydrate (60 mg, 0.315 mmol) in methanol (100 mL) was heated at 60 C for 2 hours. After cooling to room temperature, the solution was concentrated in vacuo, and the resultant residue was purified by column chromatography employing 70-230 mesh silica gel eluting with hexane to provide the title compound as a colorless oil (7.8 g, 73%). $^1$H NMR (300 MHz, DMSO-d$_6$): δ 1.38 (s, 3H), 2.44 (dd, J=13.8, 7.4 Hz, 1H), 2.65 (dd, J=13.6, 7.0 Hz, 1H), 3.41 (d, J=3.7 Hz, 2H), 3.54 (s, 3H), 4.75 (m, 2H), 4.90 (t, J=3.7 Hz, 1H), 5.24 (m, 1H), 7.10 (m, 2H), 7.19 (m, 1H), 7.40 (d, J=7.8 Hz, 1H).

EXAMPLE 123C 4-allyl-3-methoxy-4-methylnaphthalen-1(4H)-one

To a solution of Example 123B (7.72 g, 36.1 mmol) in benzene (400 mL) was added celite (15 g), pyridinium dichromate (54.3 g, 144.3 mmol) and tert-butylhydroperoxide (70% in water) (19.9 mL, 144.3 mmol). The resultant solution was stirred at room temperature for 1.25 hours, followed by filtering the solution through a plug of celite (20 g) which was rinsed with benzene (100 mL). The combined filtrate was concentrated in vacuo, and the resultant residue was purified by column chromatography employing 70-230 mesh silica gel eluting with a mixture of 20% ethyl acetate in hexane followed by 50% ethyl acetate in hexane to provide the title compound as a light yellow oil (2.05 g, 25%). $^1$H NMR (300 MHz, DMSO-d$_6$): δ 1.53 (s, 3H), 2.77 (m, 2H), 3.82 (s, 3H), 4.75 (m, 2H), 5.02 (m, 1H), 5.84 (s, 1H), 7.42 (m, 1H), 7.65 (dt, J=8.1, 1.5 Hz, 1H), 7.76 (d, J=8.1 Hz, 1H), 7.96 (dd, J=7.7, 1.5 Hz, 1H).

EXAMPLE 123D 1-allyl-4-hydroxy-1-methylnaphthalen-2(1H)-one

To a solution of Example 123C (2.69 g, 11.8 mmol) in methanol (75 ml) was added a solution of 1N aqueous sodium hydroxide (75 mL) and the resultant mixture heated to reflux for 16 hours. After cooling to room temperature a solution of 1N aqueous hydrochloride (80 mL) was added to make the mixture acidic which caused a precipitate to form. This solid was collected by filtration, washed with water (5×20 mL) and dried in a vacuum oven to provide the title compound as a light brown solid (1.97 g, 78%). $^1$H NMR (300 MHz, DMSO-$d_6$): δ 1.44 (s, 3H), 2.65 (dd, J=13.2, 7.0 Hz, 1H), 2.80 (dd, J=13.6, 7.0 Hz, 1H), 4.72 (m, 2H), 5.08 (m, 1H), 5.66 (s, 1H), 7.36 (dt, J=7.2, 1.3 Hz, 1H), 7.56 (m, 1H), 7.65 (d, J=7.7 Hz, 1H), 7.89 (d, J=7.7 Hz, 1H).

EXAMPLE 123E 4-allyl-2-[bis(methylthio)methylene]-4-methylnaphthalene-1,3(2H,4H)-dione A suspension of Example 123D (1.0 g, 4.1 mmol), Example 5A (4.3 g, 16.4 mmol), and pyridine (2.6 mL, 33 mmol) in 15 mL p-dioxane was stirred in a preheated 100° C. oil bath for 90 minutes. The cooled reaction was diluted with 50 mL EA and extracted with 25 mL water. The organic layer was concentrated and the residue chromatographed on silica with dichloromethane to give the desired product (1.43 g, 96%). $^1$H NMR (300 MHz, CDCl$_3$) δ ppm 0.65 (m, 1H) 0.74 (t, J=6.80 Hz, 6H) 0.87 (m, 1H) 1.36 (m, 1H) 1.55 (s, 3H) 1.78 (td, J=12.87, 4.41 Hz, 1H) 2.24 (td, J=12.87, 4.41 Hz, 1H) 2.57 (s, 6H) 7.39 (m, 2H) 7.57 (m, 1H) 8.22 (dd, J=7.72, 1.10 Hz, 1H).

EXAMPLE 123F

N-[3-(4-allyl-1-hydroxy-4-methyl-3-oxo-3,4-dihydronaphthalen-2-yl)-1,1-dioxido-4H-1,2,4-benzothiadiazin-7-yl]methanesulfonamide Example 123E (1.28 g, 4.0 mmol) in 100 mL p-dioxane was treated with Example 12A (1.3 g, 5.0 mmol) and the slurry heated to 85° C. for 18 hours. The solvent was removed under vacuum and the residue chromatographed on silica with 2% methanol in dichloromethane to yield the desired (0.9 g, 46%). $^1$H NMR (300 MHz, DMSO-$d_6$) δ ppm 1.61 (s, 3H) 2.88 (m, 2H) 3.08 (s, 3H) 4.79 (m, 2H) 5.21 (m, 1H) 7.58 (m, 3H) 7.77 (m, 3H) 8.15 (d, J=7.72 Hz, 1H) 10.27 (s, 1H) 13.73 (s, 1H). MS (ESI$^-$) m/z=486(M−H)$^-$.

EXAMPLE 124

N-(3-{1-hydroxy-4-methyl-3-oxo-4-[3-phenylprop-2-enyl]-3,4-dihydronaphthalen-2-yl}-1,1-dioxido-4H-1,2,4-benzothiadiazin-7-yl)methanesulfonamide Example 123F (50 mg, 0.1 mmol) and styrene (225 uL, 2.0 mmol) in 5 mL dichloromethane was thoroughly purged with N$_2$. [1,3-bis-(2,4,6-trimethylphenyl)-2-imidazolidinylidene) dichloro(phenylmethylene)-(tricyclohexylphosphine)ruthenium] Grubb's II catalyst (1 mg, 0.002 mmol) was added and the reaction refluxed for 18 hours. The slurry was filtered and the filtrate concentrated under vacuum. The crude product was purified by chromatography to the desired (33 mg, 59%). $^1$H NMR (300 MHz, DMSO-$d_6$) δ ppm 1.65 (s, 3H) 2.96 (dd, J=13.42, 7.91 Hz, 1H) 3.08 (s, 3H) 3.08 (m, 1H) 5.69 (m, 1H) 6.19 (d, J=15.81 Hz, 1H) 7.14 (m, 5H) 7.52 (t, J=6.99 Hz, 1H) 7.57 (dd, J=9.01, 2.39 Hz, 1H) 7.63 (d, J=2.21 Hz, 1H) 7.72 (d, J=8.82 Hz, 1H) 7.78 (d, J=6.99 Hz, 1H) 7.84 (m, 1H) 8.12 (dd, J=8.09, 1.10 Hz, 1H) 10.25 (s, 1H) 13.76 (s, 1H).

EXAMPLE 125

Ethyl 4-(4-hydroxy-1-methyl-3-{7-[(methylsulfonyl)amino]-1,1-dioxido-4H-1,2,4-benzothiadiazin-3-yl}-2-oxo-1,2-dihydronaphthalen-1-yl)but-2-enoate Example 123F (50 mg, 0.1 mmol) and ethyl acrylate (225 uL, 2.0 mmol) in 5 mL dichloromethane was thoroughly purged with N$_2$. [1,3-bis-(2,4,6-trimethylphenyl)-2-imidazolidinylidene)dichloro(phenylmethylene)-(tricyclohexylphosphine)ruthenium] (Grubb's II catalyst, 1 mg, 0.002 mmol) was added and the reaction refluxed for 18 hours. The slurry was filtered and the filtrate concentrated under vacuum. The crude product was purified by chromatography to the desired (33 mg, 59%). $^1$H NMR (300 MHz, DMSO-$d_6$) δ ppm 1.08 (t, J=7.17 Hz, 3H) 1.59 (s, 3H) 3.08 (s, 3H) 3.09 (m, 2H) 3.96 (q, J=7.11 Hz, 2H) 5.70 (d, J=15.44 Hz, 1H) 6.28 (ddd, J=15.53, 7.63, 7.35 Hz, 1H) 7.64 (m, 6H) 8.15 (d, J=7.35 Hz, 1H) 10.23 (s, 1H) 13.70 (s, 1H).

EXAMPLE 126

N-{3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide Example 88 (110 mg) was chromatographed on a Chiralcel AS (4.6×250 cm) column using a mobile phase of Hexane/EtOH/methanol/trifluoroacetic acid (70/15/15/1) to yield the desired enantiomer (51 mg, 97% pure). $[α]_D^{21.6}$=−50.3°.

EXAMPLE 127

N-{3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}sulfamide Example 88 (110 mg) was chromatographed on a Chiralcel AS (4.6×250 cm) column using a mobile phase of Hex/EtOH/methanol/trifluoroacetic acid (70/15/15/1) to yield the desired enantiomer (59 mg, 95% pure). $[α]_D^{21.9}$=+41.5°.

EXAMPLE 128

Ethyl 4-(4-hydroxy-1-methyl-3-{7-[(methylsulfonyl)amino]-1,1-dioxido-4H-1,2,4-benzothiadiazin-3-yl}-2-oxo-1,2-dihydronaphthalen-1-yl)butanoate Example 125 (22 mg, 0.04 mmol), 1 mg 5% Pd/C in 10 mL methanol was stirred under an atmosphere of H2 for 18 hours. The reaction was filtered and the filtrate concentrated under vacuum. The residue was chromatographed on silica with 2% methanol in dichloromethane to give the desired (18 mg, 80%). $^1$H NMR (300 MHz, DMSO-$d_6$) δ ppm 0.85 (m, 1H) 1.10 (t, J=7.17 Hz, 3H) 1.23 (m, 1H) 1.55 (s, 3H) 2.14 (m, 4H) 3.08 (s, 3H). 3.96 (q, J=6.99 Hz, 2H) 7.57 (m, 3H) 7.72 (m, 3H) 8.16 (d, J=7.72 Hz, 1H) 10.24 (s, 1H) 13.81 (s, 1H). MS (ESI$^-$) m/z=560(M−H)$^-$.

EXAMPLE 129

N-{3-[1-hydroxy-4-methyl-3-oxo-4-(3-phenylpropyl)-3,4-dihydronaphthalen-2-yl]-1,1-dioxido-4H-1,2,4-benzothiadiazin-7-yl}methanesulfonamide Example 124 (23 mg, 0.04 mmol), 1 mg 5% Pd/C in 10 mL methanol was stirred under an atmosphere of $H_2$ for 18 hours. The reaction was filtered and the filtrate concentrated under vacuum. The residue was chromatographed on silica with 2% methanol in dichloromethane to give the desired (15 mg, 65%). $^1$H NMR (300 MHz, DMSO-$d_6$) δ ppm 0.88 (m, 1H) 1.22 (m, 3H) 1.53 (s, 3H) 2.23 (m, 2H) 3.07 (s, 3H) 7.11 (m, 5H) 7.60 (m, 6H) 8.13 (d, J=8.09 Hz, 1H) 10.21 (s, 1H) 13.90 (s, 1H). MS (ESI$^-$) m/z=564(M−H)$^-$.

EXAMPLE 130 tert-butyl 3-(4-allyl-1-hydroxy-4-methyl-3-oxo-3,4-dihydronaphthalen-2-yl)-1,1-dioxido-4H-1,2,4-benzothiadiazin-7-ylcarbamate Example 123E (2.9 g, 9.1 mmol) in 150 mL of toluene was treated with Example 17A (2.6 g, 9.1 mmol) and the solution heated to 108° C. for 3 hours. The solvent was removed under vacuum and the residue chromatographed on silica with ethyl acetate/dichloromethane (5/95) to yield the desired (4.1 g, 88%). $^1$H NMR (300 MHz, DMSO-$d_6$) δ ppm 1.51 (s, 9H) 1.61 (s, 3H) 2.88 (ddd, J=31.16, 13.70, 6.99 Hz, 2H) 4.79 (m, 2H) 5.21 (m, 1H) 7.54 (m, J=7.35, 7.35, 1.47 Hz, 1H) 7.67 (m, 2H) 7.77 (m, 2H) 8.15 (m, 2H) 9.90 (s, 1H) 13.67 (s, 1H).

EXAMPLE 131 tert-butyl 3-{1-hydroxy-4-methyl-3-oxo-4-[3-phenylprop-2-enyl]-3,4-dihydronaphthalen-2-yl}-1,1-dioxido-4H-1,2,4-benzothiadiazin-7-ylcarbamate Example 130 (1.02 g, 2.0 mmol) and styrene (4.6 mL, 40 mmol) in 50 mL anhydrous dichloromethane was thorough degassed with $N_2$. [1,3-bis-(2,4,6-trimethylphenyl)-2-imidazolidinylidene)dichloro(phenylmethylene)-(tricyclohexylphosphine)ruthenium] (Grubb's II catalyst, 63 mg, 0.1 mmol) was added and the reaction refluxed for 18 hours. The cooled reaction was filtered and the filtrate concentrated under vacuum. The residue was chromatographed on silica using ethyl acetate/hexane (25/75) to yield the desired (935 mg, 80%). $^1$H NMR (300 MHz, DMSO-$d_6$) δ ppm 1.51 (s, 9H) 1.65 (s, 3H) 3.03 (m, 2H) 5.69 (m, 1H) 6.19 (d, J=15.44 Hz, 1H) 7.13 (m, 5H) 7.52 (m, 1H) 7.66 (s, 2H) 7.79 (m, 2H) 8.12 (m, 2H) 9.90 (s, 1H) 13.68 (s, 1H). MS (ESI$^-$) m/z=584 (M−H)$^-$.

EXAMPLE 132 tert-butyl 3-[1-hydroxy-4-methyl-3-oxo-4-(3-phenylpropyl)-3,4-dihydronaphthalen-2-yl]-1,1-dioxido-4H-1,2,4-benzothiadiazin-7-ylcarbamate Example 131 (1.6 mmol) in 50 mL anhydrous methanol was protected with $N_2$. 5% Pd/C (50 mg, 5%) was added and the slurry stirred for at room temperature under a $H_2$ atmosphere. After 24 hours, the reaction was filtered and the filtrate concentrated under reduced pressure. The residue was chromatographed on silica with ethyl acetate/dichloromethane (25/75) to give the desired (825 mg, 88%). $^1$H NMR (300 MHz, DMSO-$d_6$) δ ppm 1.03 (m, 2H) 1.51 (s, 9H) 1.55 (s, 3H) 2.22 (m, 4H) 7.00 (s, 1H) 7.16 (m, 3H) 7.54 (t, J=8.09 Hz, 1H) 7.70 (m, 4H) 8.16 (m, 1H) 8.15 (m, 1H) 8.14 (s, 1H) 9.89 (s, 1H) 13.67 (s, 1H). MS (ESI$^-$) m/z=586(M−H)$^-$.

EXAMPLE 133

Ethyl 4-(3-{7-[(tert-butoxycarbonyl)amino]-1,1-dioxido-4H-1,2,4-benzothiadiazin-3-yl}-4-hydroxy-1-methyl-2-oxo-1,2-dihydronaphthalen-1-yl)but-2-enoate Example 130 (255 mg, 0.5 mmol) and ethyl acrylate (1.1 mL, 10 mmol) in 10 mL anhydrous dichloromethane was thorough degassed with $N_2$. [1,3-bis-(2,4,6-trimethylphenyl)-2-imidazolidinylidene)dichloro(phenylmethylene)-(tricyclohexylphosphine)ruthenium] (Grubb's II catalyst, 5 mg, 0.008 mmol) was added and the reaction refluxed for 4 hours. The cooled reaction was filtered and the filtrate concentrated under vacuum. The residue was chromatographed on silica using ethyl acetate/dichloromethane (25/75) to yield the desired (205 mg, 70%). $^1$H NMR (300 MHz, DMSO-$d_6$) δ ppm 1.08 (t, J=7.17 Hz, 3H) 1.51 (s, 9H) 1.60 (s, 3H) 3.10 (m, 2H) 3.96 (q, J=7.11 Hz, 2H) 5.71 (d, J=15.44 Hz, 1H) 6.27 (m, 1H) 7.56 (td, J=7.35, 1.47 Hz, 1H) 7.66 (m, 2H) 7.78 (m, 2H) 8.16 (m, 2H) 9.89 (s, 1H) 13.56 (s, 1H). MS (ESI$^-$) m/z=580 (M−H)$^-$.

EXAMPLE 134

3-(7-amino-1,1-dioxido-4H-1,2,4-benzothiadiazin-3-yl)-4-hydroxy-1-methyl-1-(3-phenylpropyl)naphthalen-2(1H)-one Example 132 (250 mg, 0.425 mmol) was dissolved in 5 mL p-dioxane and 5 mL of 4 N HCl in dioxane added. The reaction was stirred at room temperature for 3 hours at which time the solvent was removed under vacuum and the desired product (162 mg, 78%) isolated by filtration after the addition of 50 mL diethyl ether. $^1$H NMR (300 MHz, DMSO-$d_6$) δ ppm 0.85 (m, 1H) 1.21 (m, 1H) 1.55 (s, 3H) 2.07 (m, 1H) 2.21 (m, 1H) 2.40 (m, 2H) 3.90 (s, 3H) 7.00 (m, 4H) 7.15 (m, 3H) 7.45 (d, J=8.82 Hz, 1H) 7.54 (t, J=7.35 Hz, 1H) 7.73 (m, 2H) 8.15 (dd, J=7.91, 1.29 Hz, 1H) 13.53 (s, 1H). MS (ESI$^-$) m/z=486(M−H)$^-$.

EXAMPLE 135

2-({3-[1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide Example 28H (440 mg, 1.0 mmol) in 15 mL dry dimethylforamide was treated with cesium carbonate (488 mg, 1.5 mmol), tetrabutylammonium iodide (5 mg, 0.01 mmol), and 2-bromoacetamide (274 mg, 2.0 mmol) for 4 hours at room temperature. The reaction was diluted with 50 mL ethyl acetate and 50 mL water. The aqueous layer was extracted with ethyl acetate and the organic layers combined and concentrated. The residue was chromatographed on silica 1% methanol in dichloromethane to give the title compound (295 mg, 60%). $^1$H NMR (300 MHz, DMSO-$d_6$) δ ppm 0.41 (m, 1H) 0.69 (d, J=9.19 Hz, 3H) 0.72 (d, J=9.19 Hz, 3H) 0.81 (m, 1H) 1.33 (m, 1H) 1.58 (s, 3H) 2.07 (m, 1H) 2.24 (m, 1H) 4.60 (s, 2H) 7.40 (m, 3H) 7.55 (m, 1H) 7.65 (s, 1H) 7.75 (m, 3H) 8.17 (d, J=7.72 Hz, 1 H) 13.69 (s, 1H). MS (ESI$^-$) m/z=496 (M−H)$^-$.

EXAMPLE 136

Benzyl({3-[1-hydroxy-4-methyl-3-oxo-4-(3-phenyl-propyl)-3,4-dihydronaphthalen-2-yl]-1,1-dioxido-4H-1,2,4-benzothiadiazin-7-yl}amino)sulfonylcarbamate A solution of chlorosulfonyl isocyanate (36 uL, 0.4 mmol) in 5 mL anhydrous dichloromethane at room temperature was treated drop wise with benzyl alcohol (42 uL, 0.4 mmol). After one hour, a solution of Example 134 (150 mg, 0.31 mmol), triethyl amine (200 μL, 2.4 mmol) in 3 mL dichloromethane, was added drop wise. After 3 hours, the reaction was diluted with dichloromethane and extracted with 1 N HCl. The aqueous layer was extracted with dichloromethane and the combined organic layers dried with anhydrous $MgSO_4$, concentrated and purified by chromatography on silica using a ethyl acetate/dichloromethane gradient to give the desired product (102 mg, 47%). $^1H$ NMR (300 MHz, DMSO-$d_6$) δ ppm 0.87 (m, 1H) 1.23 (m, 1H) 1.55 (s, 3H) 2.05 (td, J=12.69, 4.41 Hz, 1H) 2.25 (m, 1H) 2.40 (m, 2H) 5.11 (s, 2H) 6.99 (d, J=8.09 Hz, 2H) 7.16 (m, 3H) 7.29 (m, 4H) 7.50 (m, 2H) 7.68 (m, 4H) 8.15 (dd, J=8.09, 1.10 Hz, 1H) 11.10 (s, 1H) 12.13 (s, 1H) 13.80 (s, 1H). MS (ESI$^-$) m/z=699(M−H)$^-$.

EXAMPLE 137

N-{3-[1-hydroxy-4-methyl-3-oxo-4-(3-phenylpropyl)-3,4-dihydronaphthalen-2-yl]-1,1-dioxido-4H-1,2,4-benzothiadiazin-7-yl}sulfamide Example 136 (100 mg, 0.14 mmol) in 10 mL methanol was added 10% Pd/C (10 mg) and the slurry stirred for 2 hours under a $H_2$ atmosphere. The reaction was filtered and concentrated to yield the desired (73 mg, 92%). $^1H$ NMR (300 MHz, DMSO-$d_6$) δ ppm 0.86 (m, 1H) 1.23 (m, 1H) 1.53 (s, 3H) 2.03 (td, J=12.32, 3.68 Hz, 1H) 2.24 (td, J=12.32, 4.04 Hz, 1H) 2.40 (m, 2H) 6.99 (m, 2H) 7.15 (m, 3H) 7.37 (s, 1H) 7.50 (m, 2H) 7.65 (m, 4H) 8.14 (dd, J=7.72, 1.10 Hz, 1H) 9.99 (s, 1H) 13.88 (s, 1H). MS (ESI$^-$) m/z=565(M−H)$^-$.

EXAMPLE 138

Ethyl 4-(3-{7-[(tert-butoxycarbonyl)amino]-1,1-dioxido-4H-1,2,4-benzothiadiazin-3-yl}-4-hydroxy-1-methyl-2-oxo-1,2-dihydronaphthalen-1-yl)butanoate Example 133 (900 mg, 1.55 mmol) in 100 mL methyl alcohol was treated with 100 mg of 10% Pd/C and the reaction stirred at room temperature under a $H_2$ atmosphere for 3 hours. The catalyst was removed by filtration through Celite and the filtrate concentrated to give the desired (800 mg, 88%). $^1H$ NMR (300 MHz, DMSO-$d_6$) δ ppm 0.87 (m, 1H) 1.10 (t, J=7.17 Hz, 3H) 1.22 (m, 1H) 1.51 (s, 9H) 1.57 (s, 3H) 2.16 (m, 4H) 3.96 (q, J=7.23 Hz, 2 H) 7.56 (m, 1H) 7.71 (m, 4H) 8.17 (m, 2H) 9.90 (s, 1H) 13.68 (s, 1H). MS (ESI$^-$) m/z=582(M−H)$^-$.

EXAMPLE 139

N-{3-[1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide Example 123F (200 mg, 0.41 mmol), 2-methyl-2-butene (5 mL), 1,3-(bis(mesityl)-2-imidazolidinylidene)dichloro-(o-isopropoxyphenylmethylene)ruthenium (Hoveyde-Grubbs catalyst) (10 mg, 0.016 mmol), in dichloromethane (10 mL) was placed in a pressure tube and a stream of nitrogen was bubbled through the mixture for 2 minutes. The tube was then sealed and heated at 70 C for 26 hours. After cooling to room temperature, the tube was opened, the solution concentrated in vacuo, and the resultant residue purified by column chromatography employing 70-230 mesh silica gel eluting with a mixture of 5% methanol in dichloromethane to provide the title compound as a light yellow oil (152 mg, 72%). MS (ESI$^+$) m/z=516 (M+H)$^+$. $^1H$ NMR (300 MHz, DMSO-$d_6$): δ 1.36 (s, 3H), 1.39 (s, 3H), 1.62 (s, 3H), 2.77 (m, 1H), 2.83 (m, 1H), 3.09 (s, 3H), 4.52 (m, 1H), 7.56 (m, 3H), 7.73 (m, 3H), 8.14 (d, J=7.7 Hz, 1H), 10.27 (s, 1H), 13.76 (s, 1H).

EXAMPLE 140

N-{3-[(4R)-1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide Example 139 (90 mg) was chromatographed on a Chiralcel OD (4.6×250 cm) column using a mobile phase of Hexanes/ethanol/methanol/trifluoroacetic acid (70/15/15/0.1) to yield the desired enantiomer (39 mg, 92% ee).

EXAMPLE 141

N-{3-[(4S)-1-hydroxy-4-methyl-4-(3-methylbut-2-enyl)-3-oxo-3,4-dihydronaphthalen-2-yl]-1,1-dioxido-4H-1,2,4-benzothiadiazin-7-yl}methanesulfonamide Example 139 (90 mg) was chromatographed on a Chiralcel OD (4.6×250 cm) column using a mobile phase of Hex/EtOH/methanol/trifluoroacetic acid (70/15/15/0.1) to yield the desired enantiomer (38 mg, >99% ee).

EXAMPLE 142

N-(3-{4-[4-ethylpenta-2,4-dienyl]-1-hydroxy-4-methyl-3-oxo-3,4-dihydronaphthalen-2-yl}-1,1-dioxido-4H-1,2,4-benzothiadiazin-7-yl)methanesulfonamide Example 123F (75 mg, 0.154 mmol), 2-ethyl-1-butene (Aldrich, 2 mL), 1,3-(bis(mesityl)-2-imidazolidinylidene)dichloro-(o-isopropoxyphenylmethylene)ruthenium (Hoveyde-Grubbs catalyst) (5 mg, 0.0077 mmol), in dichloromethane (10 mL) was placed in a pressure tube and a stream of nitrogen was bubbled through the mixture for 2 minutes. The tube was then sealed and heated at 70° C. for 5 days. After cooling to room temperature, the tube was opened, the solution concentrated in vacuo, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 μL/min to provide the title compound as a colorless solid (16 mg, 19%). MS (ESI$^+$) m/z=516 (M+H)$^+$. $^1H$ NMR (300 MHz, DMSO-$d_6$): δ 0.73 (t, J=7.3 Hz, 3H), 1.63 (s, 3H), 1.83 (q, J=7.4 Hz, 2H), 2.83 (m, 1H), 2.92 (m, 1H), 3.09 (s, 3H), 4.72 (d, J=9.2 Hz, 2H), 5.07 (m, 1H), 5.82 (d, J=15.8 Hz, 1H), 7.56 (m, 3H), 7.73 (m, 3H), 8.14 (d, J=8.4 Hz, 1H), 10.26 (s, 1H), 13.74 (s, 1H).

EXAMPLE 143

N-{3-[4-(2-cyclobutylideneethyl)-1-hydroxy-4-methyl-3-oxo-3,4-dihydronaphthalen-2-yl]-1,1-dioxido-4H-1,2,4-benzothiadiazin-7-yl}methanesulfonamide Example 123F (75 mg, 0.154 mmol), methylenecyclobutane (0.57 mL, 6.16 mmol), 1,3-(bis(mesityl)-2-imidazolidinylidene)dichloro-(o-isopropoxyphenylmethylene)ruthenium (Hoveyde-Grubbs catalyst) (5 mg, 0.0077 mmol), in dichloromethane (10 mL) was placed in a pressure tube and a stream of nitrogen was bubbled through the mixture for 2 minutes. The tube was then sealed and heated at 70 C for 5 days. After cooling to room temperature, the tube was opened, the solution concentrated in vacuo, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a colorless solid (23 mg, 28%). MS (ESI$^+$) m/z=528 (M+H)$^+$. $^1$H NMR (300 MHz, DMSO-d$_6$): δ 1.61 (s, 3H), 1.63 (m, 2H), 2.21 (m, 2H), 2.32 (m, 2H), 2.59 (m, 1H), 2.68 (m, 1H), 3.08 (s, 3H), 4.48 (m, 1H), 7.56 (m, 3H), 7.73 (m, 3H), 8.14 (d, J=8.5 Hz, 1H), 10.25 (s, 1H), 13.81 (s, 1H).

EXAMPLE 144

N-{3-[4-(2-cyclobutylethyl)-1-hydroxy-4-methyl-3-oxo-3,4-dihydronaphthalen-2-yl]-1,1-dioxido-4H-1,2,4-benzothiadiazin-7-yl}methanesulfonamide Example 143 (16 mg, 0.030 mmol), 10% palladium on carbon (10 mg) in methanol (5 mL) was added a hydrogen balloon. After evacuating the solution two times the mixture was stirred under the Hydrogen atmosphere at room temperature for 24 hours. The solution was then filtered through celite and the filtrate concentrated to provide the title compound (8 mg, 50%). MS (ESI$^+$) m/z=530 (M+H)$^+$. $^1$H NMR (300 MHz, DMSO-d$_6$): δ 0.62 (m, 1H), 0.99 (m, 1H), 1.36 (m, 2H), 1.55 (s, 3H), 1.63 (m, 2H), 1.84 (m, 3H), 2.03 (m, 2H), 3.08 (s, 3H), 7.56 (m, 3H), 7.73 (m, 3H), 8.16 (d, J=7.7 Hz, 1H), 10.23 (s, 1H).

EXAMPLE 145

N-{3-[4-(2-cyclopentylideneethyl)-1-hydroxy-4-methyl-3-oxo-3,4-dihydronaphthalen-2-yl]-1,1-dioxido-4H-1,2,4-benzothiadiazin-7-yl}methanesulfonamide Example 123F (50 mg, 0.103 mmol), methylenecyclopentane (0.22 mL, 2.05 mmol), 1,3-(bis(mesityl)-2-imidazolidinylidene)dichloro-(o-isopropoxyphenylmethylene)ruthenium (Hoveyde-Grubbs catalyst) (3.1 mg, 0.005 mmol), in 1,2-dichloroethane (5 mL) was placed in a pressure tube and a stream of nitrogen was bubbled through the mixture for 2 minutes. The tube was then sealed and heated at 70 C for 22 hours. After cooling to room temperature, the tube was opened, the solution concentrated in vacuo, and the resultant residue purified by reverse phase preparative HPLC on a Waters Symmetry C8 column (25 mm×10 mm, 7 μm particle size) using a gradient of 10% to 100% acetonitrile/0.1% trifluoroacetic acid in water over 8 minutes (10 minutes run time) at a flow rate of 40 mL/min to provide the title compound as a colorless solid (15 mg, 27%). MS (ESI$^+$) m/z=542 (M+H)$^+$. $^1$H NMR (300 MHz, DMSO-d$_6$): δ 1.38 (m, 4H), 1.61 (s, 3H), 1.89 (m, 4H), 2.69 (m, 1H), 2.80 (m, 1H), 3.08 (s, 3H), 4.63 (m, 1H), 7.56 (m, 3H), 7.73 (m, 3H), 8.13 (d, J=8.1 Hz, 1H), 10.24 (s, 1H), 13.82 (s, 1H).

EXAMPLE 146

N-{3-[4-(2-cyclopentylethyl)-1-hydroxy-4-methyl-3-oxo-3,4-dihydronaphthalen-2-yl]-1,1-dioxido-4H-1,2,4-benzothiadiazin-7-yl}methanesulfonamide Example 145 (10.5 mg, 0.019 mmol), 10% palladium on carbon (5 mg) in methanol (2 mL) and tetrahydrofuran (2 mL) was added a hydrogen balloon. After evacuating the solution two times the mixture was stirred under the Hydrogen atmosphere at room temperature for 24 hours. The solution was then filtered through celite and the filtrate concentrated to provide the title compound (8.3 mg, 79%). MS (ESI$^+$) m/z=544 (M+H)$^+$. $^1$H NMR (300 MHz, DMSO-d$_6$): δ 0.55 (m, 1H), 0.83 (m, 4H), 1.22 (m, 1H), 1.39 (m, 4H), 1.55 (s, 3H), 1.59 (m, 1H), 2.02 (m, 1H), 2.21 (m, 1H), 3.08 (s, 3H), 7.56 (m, 3H), 7.73 (m, 3H), 8.15 (d, J=7.7 Hz, 1H), 10.22 (s, 1H), 13.90 (s, 1H).

EXAMPLE 147

N-{3-[4-(2-cyclohexylideneethyl)-1-hydroxy-4-methyl-3-oxo-3,4-dihydronaphthalen-2-yl]-1,1-dioxido-4H-1,2,4-benzothiadiazin-7-yl}methanesulfonamide Example 123F (75 mg, 0.154 mmol), methylenecyclobutane (0.37 mL, 3.08 mmol), 1,3-(bis(mesityl)-2-imidazolidinylidene)dichloro-(o-isopropoxyphenylmethylene)ruthenium (Hoveyde-Grubbs catalyst) (5 mg, 0.0077 mmol), in 1,2-dichloroethane (7 mL) was placed in a pressure tube and a stream of nitrogen was bubbled through the mixture for 2 minutes. The tube was then sealed and heated at 70 C for 18 hours. After cooling to room temperature, the solution concentrated in vacuo, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a colorless solid (24 mg, 28%). MS (ESI$^+$) m/z=556 (M+H)$^+$. $^1$H NMR (300 MHz, DMSO-d$_6$): δ 0.99 (m, 2H), 1.18 (m, 2H), 1.27 (m, 2H), 1.64 (s, 3H), 1.71 (m, 2H), 1.83 (m, 2H), 2.79 (m, 2H), 3.09 (s, 3H), 4.46 (t, J=7.3 Hz, 1H), 7.56 (m, 3H), 7.73 (m, 3H), 8.14 (d, J=7.7 Hz, 1H), 10.26 (s, 1H), 13.84 (s, 1H).

EXAMPLE 148

N-{3-[4-(2-cyclohexylethyl)-1-hydroxy-4-methyl-3-oxo-3,4-dihydronaphthalen-2-yl]-1,1-dioxido-4H-1,2,4-benzothiadiazin-7-yl}methanesulfonamide To a solution of Example 147 (18 mg, 0.032 mmol), 10% palladium on carbon (5 mg) in methanol (5 mL) and tetrahydrofuran (5 mL) was added a hydrogen balloon. After evacuating the solution two times the mixture was stirred under the hydrogen atmosphere at room temperature for 24 hours. The solution was then filtered through celite and the filtrate concentrated to provide the title compound (18 mg, 100%). MS (ESI$^+$) m/z=558 (M+H)$^+$. $^1$H NMR (300 MHz, DMSO-d$_6$): δ 0.42 (m, 1H), 0.62 (m, 2H), 0.78 (m, 2H), 1.03 (m, 4H), 1.50

(m, 4H), 1.54 (s, 3H), 2.12 (m, 2H), 3.08 (s, 3H), 7.56 (m, 3H), 7.73 (m, 3H), 8.16 (d, J=8.1 Hz, 1H), 10.26 (s, 1H), 13.74 (s, 1H).

EXAMPLE 149

N-{3-[1-hydroxy-4-(3-hydroxypropyl)-4-methyl-3-oxo-3,4-dihydronaphthalen-2-yl]-1,1-dioxido-4H-1,2,4-benzothiadiazin-7-yl}methanesulfonamide To a solution of Example 123F (50 mg, 0.103 mmol) in tetrahydrofuran (2 mL) was added borane (1.0 M in tetrahydrofuran) (1 mL, 1 mmol) dropwise. The solution was stirred at room temperature for 16 hours. Then a solution of hydrogen peroxide (30% in water) (3 mL) followed by 1N aqueous sodium hydroxide (3 mL) was added and stirred for 24 hrs. Afterwards dichloromethane (20 mL) and water (10 mL) was added to the mixture and the organic layer separated. The remaining aqueous solution was made acidic with 1N aqueous hydrochloric acid and then extracted with dichloromethane (10 mL). The combined organic extracts were, dried (MgSO$_4$), filtered, and concentrated in vacuo to provide the title compound (30 mg, 58%). MS (ESI$^+$) m/z=506 (M+H)$^+$. $^1$H NMR (300 MHz, DMSO-d$_6$): δ 1.43 (m, 2H), 1.65 (s, 3H), 1.80 (m, 2H), 3.05 (m, 2H), 3.07 (s, 3H), 7.50 (m, 2H), 7.59 (m, 3H), 7.78 (m, 1H), 7.92 (m, 1H), 10.22 (s, 1H), 13.32 (s, 1H).

EXAMPLE 150

N-{3-[4-(2,3-dihydroxypropyl)-1-hydroxy-4-methyl-3-oxo-3,4-dihydronaphthalen-2-yl]-1,1-dioxido-4H-1,2,4-benzothiadiazin-7-yl}methanesulfonamide To a solution of Example 123F (50 mg, 0.103 mmol) and 4-methylmorpholine N-oxide (24 mg, 0.206 mmol) in acetone (2 mL) and water (0.3 mL) was added osmium tetroxide (4% in water)(65 uL, 0.01 mmol). The solution was stirred at room temperature for 18 hours. Then a solution of 1N aqueous sodium thiosulfate (3 mL) was added and stirred for 2 hrs. The resulting solution was then extracted with dichloromethane (10 mL), the organic extract dried (MgSO$_4$), filtered, and concentrated in vacuo. The resultant residue was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title (10 mg, 19%). MS (ESI) m/z=520 M–H$^+$. $^1$H NMR (300 MHz, DMSO-d$_6$): δ 1.65 (s, 3H), 2.39 (m, 2H), 2.80 (m, 1H), 3.05 (s, 3H), 3.70 (m, 1H), 7.58 (m, 3H), 7.75 (m, 3H), 8.19 (m, 1H), 10.29 (s, 1H), 14.03 (s, 1H).

EXAMPLE 151

N-{3-[1-hydroxy-4-(3-hydroxy-3-methylbutyl)-4-methyl-3-oxo-3,4-dihydronaphthalen-2-yl]-1,1-dioxido-4H-1,2,4-benzothiadiazin-7-yl}methanesulfonamide To a solution of Example 139 (40 mg, 0.078 mmol) in dioxane (3 mL) was added a solution of 6N aqueous hydrochloric acid (3 mL). The mixture was heated at 65 C for 3 hours, and the solvent removed in vacuo. The resultant residue was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title (6 mg, 14%). MS (ESI) m/z=532 (M–H)$^+$. $^1$H NMR (500 MHz, DMSO-d$_6$): δ 0.60 (dq, J=12.8, 3.7 Hz, 1H), 0.91 (s, 6H), 0.98 (dq, J=12.8, 4.3 Hz, 1H), 1.59 (s, 3H), 2.09 (m, 1H), 2.26 (dq, J=12.8, 4.3 Hz, 1H), 3.07 (s, 3H), 7.56 (m, 3H), 7.74 (m, 3H), 8.16 (d, J=7.9 Hz, 1H), 10.22 (s, 1H), 13.77 (s, 1H).

EXAMPLE 152

N-{3-[4-(3-chloro-3-methylbutyl)-1-hydroxy-4-methyl-3-oxo-3,4-dihydronaphthalen-2-yl]-1,1-dioxido-4H-1,2,4-benzothiadiazin-7-yl}methanesulfonamide To a solution of Example 139 (40 mg, 0.078 mmol) in dioxane (3 mL) was added a solution of 6N aqueous hydrochloric acid (3 mL). The mixture was heated at 65 C for 3 hours, and the solvent removed in vacuo. The resultant residue was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title (4 mg, 9%). MS (ESI) m/z=550 (M–H)$^+$. $^1$H NMR (300 MHz, DMSO-d$_6$): δ 0.96 (m, 1H), 1.24 (m, 1H), 1.40 (s, 3H), 1.42 (s, 3H), 1.60 (s, 3H), 2.29 (m, 1H), 2.42 (m, 1H), 3.08 (s, 3H), 7.56 (m, 3H), 7.73 (m, 3H), 8.16 (d, J=7.4 Hz, 1H), 10.24 (s, 1H), 13.81 (s, 1H).

EXAMPLE 153

2-({3-[(4S)-1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide Example 135 (250 mg) was chromatographed on a Chiralcel OD (4.6×250 cm) column using a mobile phase of Hexanes/ethanol/methanol/trifluoroacetic acid (70/15/15/1) to yield the product enantiomer (120 mg, 97% pure). [α]$_D^{21.6}$=+37.80. $^1$H NMR (300 MHz, DMSO-d$_6$) δ ppm 0.42 (m, 1H) 0.69 (d, J=6.62 Hz, 3H) 0.72 (d, J=6.62 Hz, 3H) 0.81 (m, 1H) 1.33 (m, 1H) 1.59 (s, 3H) 2.09 (td, J=12.59, 3.13 Hz, 1H) 2.24 (td, J=12.69, 4.04 Hz, 1H) 4.60 (s, 2H) 7.39 (m, 1H) 7.43 (d, J=2.57 Hz, 1H) 7.44 (s, 1H) 7.55 (m, 1H) 7.66 (s, 1H) 7.76 (m, 3H) 8.17 (d, J=7.72 Hz, 1H) 13.65 (s, 1H). MS (ESI$^-$) m/z=496 (M–H)$^-$.

EXAMPLE 154

2-({3-[(4R)-1-hydroxy-4-methyl-4-(3-methylbutyl)-3-oxo-3,4-dihydronaphthalen-2-yl]-1,1-dioxido-4H-1,2,4-benzothiadiazin-7-yl}oxy)acetamide Example 135 (250 mg) was chromatographed on a Chiralcel OD (4.6×250 cm) column using a mobile phase of Hexane/ethanol/methanol/trifluoroacetic acid (70/15/15/1) to yield the product enantiomer (130 mg, 97% pure). [α]$_D^{21.6}$=−43.9°. $^1$H NMR (300 MHz, DMSO-d$_6$): δ ppm 0.42 (m, 1H) 0.69 (d, J=6.62 Hz, 3H) 0.72 (d, J=6.62 Hz, 3H) 0.82 (m, 1H) 1.33 (m, 1H) 1.59 (s, 3H) 2.15 (m, 2H) 4.60 (s, 2H) 7.39 (q, J=2.57 Hz, 1H) 7.43 (d, J=2.94 Hz, 1H) 7.44 (s, 1H) 7.55 (m, 1H) 7.66 (s, 1H) 7.76 (m, 3H) 8.17 (d, J=7.72 Hz, 1H) 13.66 (s, 1H). MS (ESI$^-$) m/z=496 (M–H)$^-$.

EXAMPLE -155

N-{3-[1-hydroxy-7-methoxy-4-methyl-4-(3-methyl-butyl)-3-oxo-3,4-dihydronaphthalen-2-yl]-1,1-dioxido-4H-1,2,4-benzothiadiazin-7-yl}methanesulfonamide

EXAMPLE 155A

Methyl 2-(4-methoxyphenyl)propanoate

To a solution of methyl 4-methoxyphenyl acetate (18.0 g, 0.1 mol) and hexamethylphosphoric triamide (18 mL, 0.1 mol) in 200 mL anhydrous tetrahydrofuran was added drop wise a solution of 2 M lithium diisopropylamide (55 mL, 0.11 moles) while maintaining the temperature below −70° C. After 30 minutes at −78° C., iodomethane (6.9 mL, 0.11 moles) was added drop wise and the reaction stirred for 18 hours at room temperature. The solvent was removed under vacuum and residue chromatographed on silica using 10% ethyl acetate in hexanes to give the desired as an oil (17.2 g, 89%). $^1$H NMR (300 MHz, CDCl$_3$): δ ppm 1.47 (d, J=6.99 Hz, 3H) 3.65 (s, 3H) 3.68 (q, J=7.35 Hz, 1H) 3.79 (s, 3H) 6.86 (m, 2H) 7.22 (m, 2H).

EXAMPLE 155B

Methyl 2-(4-methoxyphenyl)-2,5-dimethylhexanoate

To a solution of Example 155A (15 g. 77.2 mmol) and hexamethylphosphoric triamide (14.8 mL, 77.2 mmol) in 200 mL anhydrous tetrahydrofuran was added 2 M lithium diisopropyl amide (45 mL, 90 mmol) while maintaining the temperature below −70° C. After minutes at −78° C., 1-bromo-3-methylbutane (10.6 mL, 85 mmol) was added and the reaction stirred for 16 hours at room temperature. Most of the solvent was removed under vacuum and the residue partitioned between ethyl acetate and 1 N HCl. The crude product was purified on silica using 5% ethyl acetate in hexanes to give the product as a colorless oil (18.6 g, 92%). $^1$H NMR (300 MHz, CDCl$_3$) δ ppm 0.86 (d, J=5.15 Hz, 3H) 0.88 (d, J=5.15 Hz, 3H) 1.04 (m, 2H) 1.51 (m, 1H) 1.51 (s, 3H) 1.88 (ddd, J=13.33, 10.57, 6.25 Hz, 1H) 2.02 (m, 1H) 3.64 (s, 3H) 3.79 (s, 3H) 6.85 (m, 2H) 7.23 (m, 2H).

EXAMPLE 155C 2-(4-methoxyphenyl)-2,5-dimethylhexanoic Acid

A slurry of Example 155B (5.2 g, 0.02 mol) and potassium trimethyl silonolate (12.9 g, 0.1 mole) in 100 mL tetrahydrofuran was refluxed for 4 hours. To the cooled slurry was added 300 mL water and the solution acidified with 6 N HCl. The product was extracted out with ethyl acetate and the solvent removed under vacuum to yield the product (94%). $^1$H NMR (300 MHz, CDCl$_3$): δ ppm 0.66 (t, J=6.25 Hz, 6H) 0.86 (m, 2H) 1.28 (m, 1H) 1.33 (s, 3H) 1.75 (m, 2H) 3.58 (s, 3H) 6.66 (m, 2H) 7.10 (m, 2H).

EXAMPLE 155D 2-(4-methoxyphenyl)-2,5-dimethylhexanoyl Chloride

To a cooled solution of Example 155C (8.52 g, 0.034 mol) in 200 mL anhydrous dichloromethane was added 2 N oxalyl chloride in dichloromethane (26 mL, 0.052 mol) and drops of dimethylforamide. The solution was stirred for 30 minutes at 0° C. and then room temperature for 2 hours. The solvent was removed under vacuum and the crude product used directly.

EXAMPLE 155E diethyl 2-[2-(4-methoxyphenyl)-2,5-dimethylhexanoyl]malonate

To a solution of diethylmalonate (5.45 g, 0.034 mol) in 80 mL acetonitrile at 0° C. was added magnesium chloride (3.24 g, 0.034 mol) and triethylamine (10 mL, 0.066 mole). The slurry was stirred at 0° C. for fifteen minutes and then room temperature for two hours. The slurry was then cooled to 0° C. where a solution of Example 155D (0.034 mol) in 100 mL acetonitrile was added. The slurry was heated at 50° C. for 18 hours. The solvent was removed under vacuum and residue portioned between ethyl acetate and 1 N HCl. The organic layer was dried with anhydrous magnesium sulfate and concentrated to yield 14.0 grams of product. A sample was purified on silica using 25% ethyl acetate in hexane. $^1$H NMR (300 MHz, CDCl$_3$): δ ppm 0.83 (d, J=6.25 Hz, 3H) 0.86 (d, J=6.62 Hz, 3H) 1.06 (m, 2H) 1.19 (ddd, J=12.69, 7.17, 6.99 Hz, 6H) 1.49 (s, 3H) 1.93 (dd, J=9.01, 7.91 Hz, 2H) 3.80 (s, 3H) 4.06 (m, 2H) 4.11 (q, J=7.11 Hz, 2H) 4.53 (s, 1H) 6.87 (m, 2H) 7.18 (m, 2H).

EXAMPLE 155F

Ethyl 7-methoxy-4-methyl-4-(3-methylbutyl)-1,3-dioxo-1,2,3,4-tetrahydronaphthalene-2-carboxylate Example 155E (7.85 g, 20.0 mmol) was dissolved in 33 ml methanesulfonic acid and the solution stirred at room temperature for 18 hours. The reaction was diluted with 300 mL of cold water and extracted three times with 100 mL ethyl acetate. The combined ethyl acetate solutions were extracted with brine, dried with anhydrous magnesium sulfate and concentrated to yield 8.1 g of product. $^1$H NMR (300 MHz, CDCl$_3$) δ ppm 0.40-0.63 (m, 1H) 0.65-0.73 (m, 3H) 0.71 (d, J=6.62 Hz, 3H) 0.75 (d, J=6.62 Hz, 3H) 0.80-0.93 (m, 1H) 1.27-1.43 (m, 1H) 1.61 (s, 3H) 1.90 (ddd, J=12.96, 4.23 Hz, 1H) 2.29 (ddd, J=12.78, 4.60 Hz, 1H) 3.87 (s, 3H) 4.43-4.52 (m, 2H) 7.07-7.77 (m, 3H) 15.12 (s, 1H).

EXAMPLE 155G 7-methoxy-4-methyl-4-(3-methylbutyl)naphthalene-1,3(2H,4H)-dione A solution of Example 155F (8.1 g, 23.4 mmol) in 100 mL dioxane and 100 mL 1 N HCl was refluxed for 2 hours. The cooled solution was diluted with 200 mL water and extracted three times with 100 mL ethyl acetate. The combined ethyl acetate solutions were extracted with brine, dried with anhydrous magnesium sulfate and concentrated. The residue was titurated with diethyl ether and the desired isolated by filtration (3 g., 47%). $^1$H NMR (300 MHz, CDCl$_3$) δ ppm 0.43 (m, 1H) 0.68 (d, J=6.62 Hz, 3H) 0.71 (d, J=6.62 Hz, 3H) 0.81 (m, 1H) 1.31 (tt, J=13.28, 6.76 Hz, 1H) 1.46 (s, 3H) 1.82 (td, J=12.87, 4.04 Hz, 1H) 2.21 (td, J=12.87, 4.41 Hz, 1H) 6.03 (s, 3H) 7.10 (dd, J=8.82, 2.94 Hz, 1H) 7.33 (d, J=8.46 Hz, 1H) 7.54 (d, J=2.94 Hz, 1H).

EXAMPLE 155H

2-[bis(methylthio)methylene]-7-methoxy-4-methyl-4-(3-methylbutyl)naphthalene-1,3(2H,4H)-dione A solution of Example 155G (2.0 g, 7.3 mmol) and Example 5A (8 g, 30 mmol) in 50 mL anhydrous dioxane was treated with 5 mL pyridine (62 mmol) and immediately heated to 90° C. for two hours. The cooled solution was partitioned between ethyl acetate and water. The organic layer was extracted with water and brine and then concentrated. The residue was chromatographed on silica using 25% ethyl acetate and hexanes as eluent to give 2.7 grams of the product as a yellow solid (98%).

EXAMPLE 155I

N-{3-[1-hydroxy-7-methoxy-4-methyl-4-(3-methylbutyl)-3-oxo-3,4-dihydronaphthalen-2-yl]-1,1-dioxido-4H-1,2,4-benzothiadiazin-7-yl}methanesulfonamide A solution of Example 155H (1.3 g, 3.43 mmol) and Example 12A (920 mg, 3.43 mmol) in 60 mL dioxane was refluxed for 48 hours. The solvent was removed and the residue chromatographed on silica using 2% methanol in dichloromethane to yield the product (1.4 g, 74%). $^1$H NMR (300 MHz, DMSO-$d_6$): δ ppm 0.43 (m, 1H) 0.72 (d, J=8.82 Hz, 3H) 0.70 (d, J=8.82 Hz, 3H) 0.80 (m, 1H) 1.33 (ddd, J=19.95, 13.33, 6.80 Hz, 1H) 1.56 (s, 3H) 2.05 (td, J=12.78, 3.86 Hz, 1H) 2.20 (td, J=12.69, 4.41 Hz, 1H) 3.09 (s, 3H) 3.87 (s, 3H) 7.36 (dd, J=8.46, 2.94 Hz, 1H) 7.60 (m, 3H) 7.69 (d, J=8.82 Hz, 1H) 7.73 (d, J=8.82 Hz, 1H) 10.27 (s, 1H) 13.72 (s, 1H). MS (ESI$^+$) m/z=548(M–H)$^+$.

EXAMPLE 156

N-{3-[1,7-dihydroxy-4-methyl-4-(3-methylbutyl)-3-oxo-3,4-dihydronaphthalen-2-yl]-1,1-dioxido-4H-1,2,4-benzothiadiazin-7-yl}methanesulfonamide Example 155I (547 mg, 1.0 mmol) in 50 mL dichloromethane was treated 3 mL of 1 N boron tribromide in dichloromethane solution (3 mmol) and the reaction stirred for 18 hours at room temperature. The reaction was diluted with dichloromethane and extracted with water. The product was purified on silica using 2.5% methanol in dichloromethane to give the desired (408 mg, 76%). $^1$H NMR (300 MHz, DMSO-$d_6$) δ ppm 0.44 (m, 1H) 0.69 (d, J=6.62 Hz, 3H) 0.72 (d, J=6.62 Hz, 3H) 0.79 (m, 1H) 1.31 (dq, J=13.05, 6.56 Hz, 1H) 1.53 (s, 3H) 2.00 (td, J=12.87, 3.31 Hz, 1H) 2.18 (td, J=12.59, 4.23 Hz, 1H) 3.09 (s, 3H) 7.17 (dd, J=8.46, 2.57 Hz, 1H) 7.51 (d, J=2.57 Hz, 1H) 7.57 (m, 2H) 7.63 (d, J=2.21 Hz, 1H) 7.74 (d, J=8.82 Hz, 1H) 9.94 (s, 1H) 10.27 (s, 1H) 13.76 (s, 1H). MS (ESI$^-$) m/z=532(M–H)$^-$.

EXAMPLE 157 tert-butyl 3-[4-(2-cyclopropylethyl)-1-hydroxy-4-methyl-3-oxo-3,4-dihydronaphthalen-2-yl]-1,1-dioxido-4H-1,2,4-benzothiadiazin-7-ylcarbamate

EXAMPLE 157A 1-(2-cyclopropylethyl)-1-methyl-3,4-dihydronaphthalen-2(1H)-one To a stirring solution of diisopropylamine (4.81 mL, 34.3 mmol) in 50 mL of tetrahydrofuran cooled to 0° C. in an ice bath was added dropwise 1.6M n-butyl lithium in tetrahydrofuran (21.45 mL, 34.3 mmol) over 30 minutes. The solution was cooled to –30° C. and 1-methyl-2-tetralone (5.0 g, 31.2 mmol) in 10 mL of tetrahydrofuran added. The resulting reaction mixture was placed in an ice bath for 2 hour. Cool the solution to –78° C., and added hexamethylphosphoric triamide 20 mL followed by the dropwise addition of (2-Bromoethyl)-cyclopropane (6.97 g, 46.8 mmol). The reaction was stirred at rt for 48 hours. Partition the reaction mixture between ethyl acetate and saturated aqueous NH$_4$Cl, extract the aqueous layer 3 times with ethyl acetate. The combined organic layers were washed sequentially with saturated sodium bicarbonate, brine, and then dried over MgSO$_4$. The product was purified by flash chromatography on SiO$_2$, eluting with a 0-10% diethyl ether/hexane gradient yielding the product (4.488 g, 63% yield). $^1$H NMR (300 MHz, CDCl$_3$): δ ppm 0.01 (m, 2H) 0.47 (m, 2H) 0.67 (m, 1H) 0.98 (m, 2H) 1.55 (s, 3H) 1.95 (td, J=12.78, 4.60 Hz, 1H) 2.37 (ddd, J=13.60, 12.13, 4.78 Hz, 1H) 2.80 (m, 2H) 3.19 (m, 2H) 7.31 (m, 2H) 7.44 (m, 2H). MS (ESI$^+$) m/z=229 (M+H)$^+$.

EXAMPLE 157B 1-(2-cyclopropylethyl)-1-methyl-1,4-dihydronaphthalen-2-yl methyl Ether A mixture of p-toluenesulfonic acid (cat., 5 mg), methanol (50 mL), trimethyl orthoformate (6.47 mL, 59.1 mmol), and Example 157A (1.35 g, 5.9 mmol) was heated at reflux for 2 hours. After cooling the reaction mixture to room temperature, the solution was concentrated in vacuo to oil and used without further purification.

EXAMPLE 157C 4-(2-cyclopropylethyl)-3-methoxy-4-methylnaphthalen-1(4H)-one

Example 157B was taken up in benzene (25 mL) and treated with pyridinium dichromate (PDC) (8.87 g, 23.60 mmol). After stirring for 20 minutes at room temperature, tert-butyl hydroperoxide ($^t$BuOOH) (2.36 mL, 23.60 mmol) was added. Then, the reaction mixture was stirred overnight at room temperature. The reaction mixture was filtered though a pad of celite and concentrated in. vacuo. The product was purified by flash chromatography on SiO$_2$ eluting with a 0-10% ethyl acetate/hexane gradient yielding the title compound (0.544 g, 37% yield) as a crystalline solid. $^1$H NMR (300 MHz, DMSO-$d_6$): δ ppm -0.52 (m, 2H) –0.01 (m, 2H) 0.15 (m, 2H) 0.44 (m, 1H) 1.24 (s, 3H) 1.88 (m, 2H) 3.57 (s, 3H) 5.59 (s, 1H) 7.16 (t, J=6.80 Hz, 1H) 7.39 (td, J=7.54, 1.47 Hz, 1H) 7.46 (m, 1H) 7.71 (d, J=6.62 Hz, 1H). MS (ESI$^+$) m/z=257 (M+H)$^+$.

EXAMPLE 157D 1-(2-cyclopropylethyl)-4-hydroxy-1-methylnaphthalen-2(1H)-one

To a solution of Example 157C (1.06 g, 4.10 mmol) in dioxane (10 mL) was added 1 N NaOH (10 mL, 10 mmol) and the reaction mixture heated at 95° C. for 16 hours. After cooling the solution to room temperature, the reaction mixture was diluted with 50 mL of water, the pH adjusted to 2.0 with 1N HCl, and the aqueous layer extracted 3 times with ethyl acetate. The combined organic layers were washed with brine and dried over MgSO$_4$. The product was purified by flash chromatography on SiO$_2$ eluting with a 10-25% ethyl acetate/hexane gradient yielding the title compound (0.635 g, 64% yield) as a crystalline solid. $^1$H NMR (300 MHz, DMSO-d$_6$): δ ppm−0.51 (m, 2H) −0.02 (m, 2H) 0.14 (m, 2H) 0.46 (m, 1H) 1.16 (s, 3H) 5.42 (s, 1H) 7.12 (t, J=7.35 Hz, 1H) 7.34 (m, 2H) 7.64 (d, J=7.35 Hz, 1H). MS (ESI$^+$) m/z=243 (M+H)$^+$.

EXAMPLE 157E

2-[bis(methylthio)methylene]-4-(2-cyclopropyl-ethyl)-4-methylnaphthalene-1,3(2H,4H)-dione A mixture of Example 157D (0.635 g, 2.60 mmol), pyridine (1.67 mL, 20.80 mmol), and Example 5A (2.781 g, 10.48 mmol) in 10 mL of dioxane was heated in a preheated oil bath at 100° C. for 1.5 hours. After cooling to room temperature, the reaction mixture was partitioned between ethyl acetate and water. The ethyl acetate layer was washed sequentially with bicarb, brine, and dried over MgSO$_4$. The product was purified by flash chromatography on SiO$_2$ eluting with a 0-20% ethyl acetate/hexane gradient yielding the title compound (0.836 g, 92% yield) as a yellow solid that solidifies upon standing. $^1$H NMR (300 MHz, DMSO-d$_6$): δ ppm -0.24 (m, 2H) 0.53 (m, 2H) 0.78 (m, 2H) 1.47 (s, 3H) 1.91 (m, 1H) 2.21 (m, 1H) 2.54 (s, 6H) 7.42 (t, J=8.09 Hz, 1H) 7.62 (m, 2H) 8.03 (d, J=7.72 Hz, 1H). MS (ESI$^+$) m/z=347 (M+H)$^+$.

EXAMPLE 157F tert-butyl 3-[4-(2-cyclopropylethyl)-1-hydroxy-4-methyl-3-oxo-3,4-dihydronaphthalen-2-yl]-1,1-di-oxido-4H-1,2,4-benzothiadiazin-7-ylcarbamate Example 157E (0.746 G, 2.156 mmol) was combined with Example 17A (0.650 G, 2.264 mmol) and toluene (15 mL). The reaction mixture was stirred at 100° C. overnight. After cooling to room temperature, the reaction mixture was concentrated in. vacuo and purified by flash chromatography on SiO$_2$ eluting with a 0-35% ethyl acetate/hexane gradient yielding the title compound (1.06 g, 92% yield) as a light yellow foam. $^1$H NMR (300 MHz, DMSO-d$_6$): δ ppm -0.23 (m, 2H) 0.25 (m, 2H) 0.46 (m, 2H) 0.84 (m, 1H) 1.48 (m, 9H) 1.57 (m, 3H) 2.14 (m, 1H) 2.32 (m, 1H) 7.52 (m, 1H) 7.64 (m, 2H) 7.75 (m, J=4.04 Hz, 2H) 8.14 (m, J=8.82 Hz, 2H) 9.87 (s, 1H) 13.80 (s, 1H). MS (ESI$^+$) m/z=555 (M+NH$_4$)$^+$.

EXAMPLE 158

3-(7-amino-1,1-dioxido-4H-1,2,4-benzothiadiazin-3-yl)-1-(2-cyclopropylethyl)-4-hydroxy-1-methylnaph-thalen-2(1H)-one A solution of Example 157F (1.06 g, 2.00 mmol) in dichloromethane (10 mL) was treated with trifluoroacetic acid (10 mL) at room temperature for 1 hour. After concentrating in. vacuo, the resulting oil was partitioned between ethyl acetate and aqueous NaHCO$_3$, the organic layer was removed and the aqueous layer extracted 3 times with ethyl acetate. The combined organic layers were dried over MgSO$_4$, filtered, and concentrated in. vacuo to yield a solid that was used without further purification. $^1$H NMR (300 MHz, DMSO-d$_6$): δ ppm− 0.25 (m, 2H) 0.25 (m, 2H) 0.46 (m, 2H) 0.80 (m, 1H) 1.57 (s, 3H) 2.15 (m, 1H) 2.32 (m, 1H) 6.99 (m, 2H) 7.44 (d, J=8.82 Hz, 1H) 7.54 (m, 1H) 7.77 (d, J=4.04 Hz, 2H) 8.15 (d, J=7.72 Hz, 1H) 13.55 (s, 1H). MS (ESI$^+$) m/z=438 (M+H)$^+$, 455 (M+NH$_4$)$^+$.

EXAMPLE 159

N-{3-[4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide To a stirring solution of Example 158 (0.400 g, 0.914 mmol) and pyridine (0.591 mL, 7.312 mmol) in dichloromethane was added methanesulfonyl chloride (0.141 mL, 1.829 mmol) dropwise over 5 minutes and the resulting reaction mixture stirred for 12 hours. The solution was concentrated in. vacuo and purified by flash chromatography on SiO$_2$ eluting with a 0-100% ethyl acetate/hexane gradient yielding the title compound (0.365 g, 77% yield) as a light yellow solid. $^1$H NMR (300 MHz, DMSO-d$_6$): δ ppm -0.22 (m, 2H) 0.24 (m, 2H) 0.85 (m, 2H) 1.57 (s, 3H) 2.14 (m, 1H) 2.32 (m, 1H) 3.08 (s, 3H) 7.56 (m, 4H) 7.73 (m, 4H) 8.14 (d, J=8.09 Hz, 1H) 10.23 (m, 1H) 13.79 (m, 1H). MS (ESI$^+$) m/z=416 (M+H)$^+$.

EXAMPLE 160

N-{3-[4-(2-cyclopropylethyl)-1-hydroxy-4-methyl-3-oxo-3,4-dihydronaphthalen-2-yl]-1,1-dioxido-4H-1,2,4-benzothiadiazin-7-yl}-2,2,2-trifluoroacetamide To a solution of Example 158 (0.064 g, 0.146 mmol) in dichloromethane (2 mL) and pyridine was added methanesulfonyl chloride (0.023 mL, 0.307 mmol) and stirred at room temperature overnight. The reaction mixture was partitioned between ethyl acetate and V$_2$ saturated NH$_4$Cl. The organic layer was washed sequentially with bicarb and brine. The product was purified by flash chromatography on SiO$_2$ eluting with a 5% ethyl acetate/dichloromethane yielding not the desired methansulfonamide but rather the title compound (0.037 g, 49% yield) as a light yellow solid. $^1$H NMR (300 MHz, DMSO-d$_6$): δ ppm−0.21 (m, 2H) 0.26 (m, 2H) 0.47 (m, 2H) 0.86 (m, 1H) 1.24 (m, 1H) 1.57 (s, 3H) 2.15 (m, 1H) 2.34 (m, 1H) 7.53 (m, 1H) 7.75 (m, 3H) 7.99 (dd, J=9.01, 2.39 Hz, 1H) 8.15 (d, J=7.72 Hz, 1H) 8.27 (d, J=2.21 Hz, 1H) 11.63 (s, 1H) 13.81 (s, 1H). MS (ESI$^+$) m/z=551 (M+NH$_4$)$^+$.

EXAMPLE 161 tert-butyl[({3-[4-(2-cyclopropylethyl)-1-hydroxy-4-methyl-3-oxo-3,4-dihydronaphthalen-2-yl]-1,1-di-oxido-4H-1,2,4-benzothiadiazin-7-yl}amino)sulfo-nyl]acetate To a stirring solution of Example 158 (0.070 g, 0.160 mmol) in dichloromethane containing N,N-diisopropylethylamine (0.036 mL, 0.208 mmol) was added chlorosulfonyl-acetic acid tert-butyl ester (0.041 g, 0.192 mmol). The reaction mixture was stirred overnight and then partitioned between ethyl acetate and water. The organic layer was washed sequentially with 10% 1N HCl in water, bicarb, and brine. The product was purified by flash chromatography on SiO$_2$ eluting with 0-50% ethyl acetate/hexanes yielding the title compound (0.030 g, 30.5% yield) as a light yellow solid. $^1$H NMR (300 MHz, DMSO-d$_6$): δ ppm−0.23 (dd, J=9.01, 4.23 Hz, 2H) 0.25 (d, J=6.62 Hz, 2H) 0.45 (m, 2H) 0.85 (m, 1H) 1.25 (m, 1H) 1.39 (s, 9H) 1.57 (m, 3H) 2.34 (m, 1H) 4.22 (m, 2H) 7.55 (m, 2H) 7.62 (dd, J=10.29, 2.21 Hz) 7.75 (m, 3H) 8.15 (d, J=7.72 Hz, 1H) 10.61 (s, 1H) 13.73 (m, 1H). MS (ESI$^+$) m/z=516 (M+H)$^+$.

EXAMPLE 162

N-{3-[(4R)-4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide Example 159 was separated into pure enantiomers by chiral HPLC using a Chiralcel OJ; 4.6×250 mm column and a mobile phase of hexane/ethanol/methanol/trifluoroacetic acid 70/15/15/0.1% at 0.8 mL/min giving the title compound at R=19.968 min. $^1$H NMR (300 MHz, DMSO-$d_6$): δ ppm -0.22 (m, 2H) 0.24 (m, 2H) 0.85 (m, 2H) 1.57 (s, 3H) 2.14 (m, 1H) 2.32 (m, 1H) 3.08 (s, 3H) 7.56 (m, 4H) 7.73 (m, 4H) 8.14 (d, J=8.09 Hz, 1H) 10.23 (m, 1H) 13.79 (m, 1H). MS (ESI$^+$) m/z=416 (M+H)$^+$.

EXAMPLE 163

N-{3-[(4S)-4-(2-cyclopropylethyl)-1-hydroxy-4-methyl-3-oxo-3,4-dihydronaphthalen-2-yl]-1,1-dioxido-4H-1,2,4-benzothiadiazin-7-yl}methanesulfonamide Example 159 was separated into pure enantiomers by chiral HPLC using a Chiralcel OJ; 4.6×250 mm column and a mobile phase of hexane/ethanol/methanol/trifluoroacetic acid 70/15/15/0.1% at 0.8 mL/min, giving the title compound at R=26.874. $^1$H NMR (300 MHz, DMSO-$d_6$): δ ppm -0.22 (m, 2H) 0.24 (m, 2H) 0.85 (m, 2H) 1.57 (s, 3H) 2.14 (m, 1H) 2.32 (m, 1H) 3.08 (s, 3H) 7.56 (m, 4H) 7.73 (m, 4H) 8.14 (d, J=8.09 Hz, 1H) 10.23 (m, 1H) 13.79 (m, 1H). MS (ESI$^+$) m/z=416 (M+H)$^+$.

EXAMPLE 164 tert-butyl 3-[4-(cyclopropylmethyl)-1-hydroxy-4-methyl-3-oxo-3,4-dihydronaphthalen-2-yl]-1,1-dioxido-4H-1,2,4-benzothiadiazin-7-ylcarbamate

EXAMPLE 164A 4-(cyclopropylmethyl)-3-methoxy-4-methylnaphthalen-1(4H)-one

A solution of diazomethane (43.83 mmol) in ether was prepared and added dropwise to a stirring solution of Example 123C (0.500 g, 2.19 mmol), Pd(OAc)$_2$, in 15 mL of tetrahydrofuran. The reaction is complete in less than 20 minutes. Concentrate in. vacuo, suspended in diethyl ether and filter through a pad of celite. Ether is removed in. vacuo to afford an oil that was used without further purification. $^1$H NMR (300 MHz, DMSO-$d_6$): δ ppm–0.41 (m, 2H) 0.00 (none, 1H) 0.12 (m, 2H) 1.47 (m, 3H) 1.76 (m, 1H) 1.86 (m, 1H) 2.09 (dd, J=14.16, 4.60 Hz, 1H) 3.83 (s, 3H) 5.87 (s, 1H) 7.42 (td, J=7.35, 1.10 Hz, 1H) 7.63 (td, J=7.54, 1.47 Hz, 1H) 7.72 (m, 1H) 7.99 (dd, J=8.09, 1.47 Hz, 1H). MS (ESI$^+$) m/z=243 (M+H)$^+$.

EXAMPLE 164B 1-(cyclopropylmethyl)-4-hydroxy-1-methylnaphthalen-2(1H)-one

To a solution Example 164A (0.531 g, 2.19 mmol) in dioxane (20 mL) was added 1 N NaOH (20 mL, 20 mmol) and the reaction mixture heated at 95° C. for 4 days. After cooling the solution to room temperature, the reaction mixture was diluted with 50 mL of water, the pH adjusted to 2.0 with 1N HCl, and the aqueous layer extracted 3× with ethyl acetate. The combined organic layers were washed with brine and dried over MgSO$_4$. The product was purified by flash chromatography on SiO$_2$ eluting with a 0-5% methanol/dichloromethane gradient yielding the title compound (0.257 g, 52% yield) as a crystalline solid. $^1$H NMR (300 MHz, DMSO-$d_6$): δ ppm -0.36 (m, 1H) 0.08 (m, 5H) 1.46 (s, 3H) 5.79 (s, 1H) 7.44 (t, J=7.54 Hz, 1H) 7.62 (m, 1H) 7.70 (m, 1H) 7.98 (d, J=8.09 Hz, 1H). MS (ESI$^+$) m/z=229 (M+H)$^+$.

EXAMPLE 164C

2-[bis(methylthio)methylene]-4-(cyclopropylmethyl)-4-methylnaphthalene-1,3(2H,4H)-dione A mixture of Example 164B (0.257 g, 1.126 mmol), pyridine (0.72 mL, 9.01 mmol), and Example 5A (1.19 g, 4.50 mmol) in 10 mL of dioxane was heated in a preheated oil bath at 100° C. for 1.5 hours. After cooling to room temperature, the reaction mixture was partitioned between ethyl acetate and water. The ethyl acetate layer was washed sequentially with bicarb, brine, and dried over MgSO$_4$. The product was purified by flash chromatography on SiO$_2$ eluting with a 0-20% ethyl acetate/hexane gradient yielding the title compound (0.161 g, 43% yield) as a yellow solid that solidifies upon standing. $^1$H NMR (300 MHz, DMSO-$d_6$): δ ppm–0.34 (m, 1H) –0.20 (m, 1H) 0.11 (m, 3H) 1.51 (s, 3H) 1.85 (d, J=6.25 Hz, 2H) 2.55 (s, 6H) 7.44 (ddd, J=8.00, 5.79, 2.39 Hz, 1H) 7.62 (m, 2H) 8.04 (d, J=8.09 Hz, 1H). MS (ESI$^+$) m/z—333 (M+H)$^+$.

EXAMPLE 164D tert-butyl 3-[4-(cyclopropylmethyl)-1-hydroxy-4-methyl-3-oxo-3,4-dihydronaphthalen-2-yl]-1,1-dioxido-4H-1,2,4-benzothiadiazin-7-ylcarbamate Example 164C (0.161 g, 0.484 mmol) was combined with Example 17A (0.139 g, 0.484 mmol) and toluene (10 mL). The reaction mixture was stirred at 100° C. overnight. After cooling to room temperature, the reaction mixture was concentrated in. vacuo and purified by flash chromatography on SiO$_2$ eluting with a 0-35% ethyl acetate/hexane gradient yielding the title compound (0.153, 60.4% yield) as a light yellow solid. $^1$H NMR (300 MHz, DMSO-$d_6$): δ ppm–0.37 (m, 1H) –0.13 (m, 1H) 0.04 (m, 1H) 0.18 (m, 2H) 1.26 (m, 1H) 1.51 (s, 9H) 1.59 (s, 3H) 2.07 (m, 2H) 7.55 (t, J=8.09 Hz, 1H) 7.68 (m, 2H) 7.78 (m, 2H) 8.17 (m, 2H) 9.91 (s, 1H) 13.76 (s, 1H). MS (ESI$^+$) m/z=524 (M+H)$^+$.

EXAMPLE 165

3-(7-amino-1,1-dioxido-4H-1,2,4-benzothiadiazin-3-yl)-1-(cyclopropylmethyl)-4-hydroxy-1-methylnaphthalen-2(1H)-one A solution of Example 164D (0.100 g, 0.1912 mmol) in dichloromethane (4 mL) was treated with trifluoroacetic acid (4 mL) at room temperature for 1 hour. After concentrating in. vacuo, the resulting oil was partitioned between ethyl acetate and aqueous NaHCO$_3$, the organic layer was removed and the bicarb layer extracted 3× with ethyl acetate. The combined organic layers were dried over MgSO$_4$, filtered, and concentrated in. vacuo to yield a solid that was used without further purification.

EXAMPLE 166

N-{3-[4-(cyclopropylmethyl)-1-hydroxy-4-methyl-3-oxo-3,4-dihydronaphthalen-2-yl]-1,1-dioxido-4H-1,2,4-benzothiadiazin-7-yl}methanesulfonamide To a stirring solution of Example 165 (0.080 g, 0.189 mmol) and pyridine (0.122 mL, 1.512 mmol) in dichloromethane was added methanesulfonyl chloride (0.017 mL, 0.227 mmol) dropwise over 5 minutes and the resulting reaction mixture stirred for 12 hours. The solution was concentrated in. vacuo and purified by flash chromatography on $SiO_2$ eluting with a 0-100% ethyl acetate/hexane gradient yielding the title compound (0.079 g, 84% yield) as a light yellow solid. $^1$H NMR (300 MHz, DMSO-$d_6$): δ ppm -0.39 (m, 1H) -0.13 (m, 1H) 0.03 (m, 2H) 0.21 (m, 1H) 1.24 (m, 1H) 1.43 (s, 3H) 1.78 (m, 1H) 1.99 (m, 1H) 3.01 (s, 3H) 7.38 (m, 3H) 7.50 (m, 3H) 8.07 (d, J=7.35 Hz, 1H) 9.92 (s, 1H) 15.36 (s, 1H).). MS (ESI$^+$) m/z=502 (M+H)$^+$.

EXAMPLE 167

Methyl 1-butyl-4-hydroxy-3-{7-[(methylsulfonyl)amino]-1,1-dioxido-4H-1,2,4-benzothiadiazin-3-yl}-2-oxo-1,2-dihydronaphthalene-1-carboxylate

EXAMPLE 167A

Methyl 1-butyl-2-methoxy-1,4-dihydronaphthalene-1-carboxylate

To a stirred solution of methyl 2-methoxynaphthoate (3.25 g, 15 mmol) and tert-butyl alcohol (1.48 ml, 15 mmol) in tetrahydrofuran (10 mL) at –78° C. was added liquid ammonia (60 mL). Potassium metal (2.9 g, 75 mmol) was added in small pieces until the solution stayed dark blue for 30 min. Butyl iodide (5.47 mL, 48 mmol) was added dropwise (the blue coloration disappeared about half-way through addition) and stirring was continued for 1 hour at –78° C. The solution was allowed to warm to room temperature and purged with nitrogen to remove excess ammonia. To the resulting slurry a solution of saturated sodium bicarbonate (100 mL) was added, and the solution was extracted with ether (3× 50 mL). The combined organic phases were washed with 10% $Na_2S_2O_3$ (aq), dried ($Na_2SO_4$), and concentrated in vacuo. Column chromatography on silica (20% ethyl acetate/hexane) gave the title compound. This oil was triturated with hexane to afford a white solid (3.2 g, 77.6%). $^1$H NMR (300 MHz, CDCl$_3$): δ ppm 0.63 (m, 1H), 0.76 (t, J=7.35 Hz, 3H), 0.99 (m, 1H), 1.18 (m, 2H), 2.04 (m, 1H), 2.26 (m, 1H), 3.55 (d, J=3.68 Hz, 2H), 3.61 (s, 3H), 3.63 (s, 3H), 5.05 (t, J=3.68 Hz, 1H), 7.16 (m, 4H); MS (ESI) m/z 275.1 (M+H)$^+$.

EXAMPLE 167B

Methyl 1-butyl-2-methoxy-4-oxo-1,4-dihydronaphthalene-1-carboxylate

A mixture of Example 167A (1.7 g, 6.2 mmol) and pyridinium dichromate (6.8 g, 15.5 mmol) in chloroform (60 mL) was heated at reflux with a Dean-Stark trap for 18 h. The reaction mixture was cooled to room temperature and filtered through celite. The filtrate was concentrated in vacuo. Column chromatography on silica (20% ethyl acetate/hexane) afforded the title compound as a white solid (1.1 g, 61.6%). $^1$H NMR (300 MHz, CDCl$_3$): δ ppm 0.52 (m, 1H), 0.73 (t, J=7.35 Hz, 3H), 0.83 (dd, J=12.13, 6.62 Hz, 1H), 1.15 (m, 2H), 2.36 (m, 2H), 3.61 (s, 3H), 3.83 (s, 3H), 5.96 (s, 1H), 7.39 (d, J=7.72 Hz, 1H), 7.44 (t, J=7.35 Hz, 1H), 7.55 (m, 1H), 8.19 (d, J=8.09 Hz, 1H); MS (ESI) m/z 289.0 (M+H)$^+$.

EXAMPLE 167C

Methyl 1-butyl-2,4-dioxo-1,2,3,4-tetrahydronaphthalene-1-carboxylate

To a solution of Example 167B (1 g, 3.5 mmol) in acetonitrile (5 mL) was added iodotrimethylsilane (TMSI) (0.7 mL, 5.2 mmol). The reaction solution was stirred at room temperature for 1 h. The reaction mixture was concentrated in vacuo. Column chromatography on silica (ethyl acetate) afforded the title compound as a white solid (0.88 g, 92%). $^1$H NMR (300 MHz, DMSO-$d_6$) δ ppm 0.47 (m, 1H), 0.68 (t, J=7.35 Hz, 3H), 0.85 (dd, J=12.32, 7.17 Hz, 1H), 1.11 (m, 2H), 2.14 (m, 1H), 2.29 (m, 1H), 3.51 (s, 3H), 5.74 (m, 1H), 7.31 (m, 1H), 7.49 (m, 1H), 7.58 (t, J=7.17 Hz, 1H), 7.93 (d, J=7.35 Hz, 1H), 12.11 (s, 1H); MS (ESI) m/z 275.0 (M+H)$^+$.

EXAMPLE 167D

Methyl 3-[bis(methylthio)methylene]-1-butyl-2,4-dioxo-1,2,3,4-tetrahydronaphthalene-1-carboxylate To a solution of Example 167C (0.88 g, 3.2 mmol) in dioxane (10 mL) was added Example 5A (2.76 g, 11.2 mmol) followed by pyridine (1.29 mL, 16 mmol). The heterogeneous solution was heated at 55° C. for 3 h. The solution was cooled to room temperature and concentrated in vacuo. Column chromatography on silica (30% ethyl acetate/hexane) afforded the title compound as an orange oil (1.08 g, 90%). $^1$H NMR (300 MHz, DMSO-$d_6$): δ ppm 0.59 (m, 1H), 0.68 (t, J=7.17 Hz, 3H), 0.80 (m, 1H), 1.12 (m, 2H), 2.13 (m, 1H), 2.35 (m, 1H), 2.61 (m, 3H), 3.55 (m, 3H), 7.25 (d, J=6.99 Hz, 1H), 7.51 (t, J=6.99 Hz, 1H), 7.65 (m, 1H)); MS (ESI) m/z 379.1 (M+H)$^+$.

EXAMPLE 167E

Methyl 1-butyl-4-hydroxy-3-{7-[(methylsulfonyl)amino]-1,1-dioxido-4H-1,2,4-benzothiadiazin-3-yl}-2-oxo-1,2-dihydronaphthalene-1-carboxylate A mixture of Example 167D (1 g, 2.64 mmol) and Example 12A (0.596 g, 2.24 mmol) in dioxane (12 mL) was heated at 85° C. for 18 h. The solution was cooled to room temperature and concentrated in vacuo. The resulting oil was triturated with hexane, filtered, washed with diethyl ether to afford the title compound as a white solid (0.99 g, 81%). $^1$H NMR (300 MHz, DMSO-$d_6$): δ ppm 0.54 (m, 1H), 0.68 (t, J=7.17 Hz, 3H), 0.98 (m, 1H), 1.09 (m, 2H), 2.14 (m, 1H), 2.41 (m, 1H), 3.04 (s, 3H), 3.55 (m, 3H), 7.26 (d, J=7.72 Hz, 1H), 7.51 (m, 4H), 7.60 (m, 1H), 8.13 (m, 1H), 10.09 (s, 1H), 14.07 (s, 1H); MS (ESI) m/z 548.1 (M+H)$^+$.

EXAMPLE 168

Isopropyl 4-hydroxy-1-methyl-3-{7-[(methylsulfonyl)amino]-1,1-dioxido-4H-1,2,4-benzothiadiazin-3-yl}-2-oxo-1,2-dihydronaphthalene-1-carboxylate

EXAMPLE 168A

Isopropyl 2-methoxy-1-naphthoate

To a solution of 2-methoxynaphthoic acid (458 mg, 2.3 mmol) in dry dichloromethane (9 mL) at 0° C. under a $N_2$ atmosphere was added oxalyl chloride (1.4 mL of a 2M solution in dichloromethane, 2.8 mmol) and 4 drops of N,N-dimethyl formamide. The mixture was stirred at 0° C. for 20 minutes then allowed to warm to room temperature and stirred for one hour. The mixture was concentrated in vacuo. To this dry powder was added isopropanol (9 mL) and pyridine (367 µL, 4.5 mmol), with stirring. After stirring for 2 hours at room temperature, the mixture was concentrated and partitioned between $H_2O$ (10 mL) and ethyl acetate (3× 10 mL) and the combined organic layers was washed with saturated NaCl (10 mL). The organic layer was dried over $Na_2SO_4$, and the crude product was purified by column chromatography on silica gel using 10% ethyl acetate in hexane. The title compound was obtained as a colorless solid (260 mg, 47%).

EXAMPLE 168B

Isopropyl 2-methoxy-1-methyl-1,4-dihydronaphthalene-1-carboxylate

Example 168A (254 mg, 1.0 mmol) and tert-butanol (99 µL, 1.0 mmol) were dissolved in anhydrous tetrahydrofuran (2 mL) and cooled to −78° C. under a $N_2$ atmosphere. Ammonia (about 12 mL) was condensed into the mixture and potassium metal was added in small portions until the resulting blue solution persisted for 20 min. To this mixture was added methyl iodide (220 µL, 3.4 mmol) and the resulting solution was allowed to slowly warm to room temperature ($NH_3$ was evaporated using a dry $N_2$ stream). The resulting mixture was partitioned between saturated $NaHCO_3$ (10 mL) and ethyl acetate (3× 10 mL) and the combined organic layers were dried over $Na_2SO_4$. The crude product was purified by column chromatography on silica gel using 5% ethyl acetate in hexane. The title compound was obtained as a colorless solid (175 mg, 65%).

EXAMPLE 168C isopropyl 2-methoxy-1-methyl-4-oxo-1,4-dihydronaphthalene-1-carboxylate To a solution of Example 168B (100 mg, 0.4 mmol) in benzene (8 mL) at room temperature under a $N_2$ atmosphere was added 100 mg Celite® and pyridinium dichromate (578 mg, 1.5 mmol), followed by 70% tert-butyl hydroperoxide (213 µL, 1.5 mmol). The mixture was allowed to stir at room temperature for 1 hour, filtered through a pad of Celite®, and the filtrate was diluted with ethyl acetate (10 mL). The organic solution was washed with 5% $Na_2S_2O$, (3× 10 mL) and with saturated NaCl (1× 10 mL) and dried over $Na_2SO_4$. The crude product was purified by column chromatography using 10% ethyl acetate in hexane. The title compound was obtained as a colorless solid (38 mg, 36%): $^1H$ NMR (300 MHz, $CDCl_3$) δ ppm 8.20 (d, 1H), 7.54 (m, 1H), 7.41 (m, 2H), 5.87 (s, 1H), 4.98 (m, 1H), 3.83 (s, 3H), 1.76 (s, 3H), 1.13 (d, 3H), 0.97 (d, 3H); MS (ESI) m/z=275 [M+H].

EXAMPLE 168D

Isopropyl 2-hydroxy-1-methyl-4-oxo-1,4-dihydronaphthalene-1-carboxylate

A solution of Example 168C (36 mg, 0.13 mmol) and trimethylsilyl iodide (28 uL, 0.2 mmol) in acetonitrile (1 mL) was stirred for one hour at room temperature under a $N_2$ atmosphere. Another 28 µL of trimethylsilyl iodide was added, and the mixture was stirred for one hour, concentrated in vacuo, and the crude product was purified by column chromatography on silica gel using 40% ethyl acetate in hexane. The title compound was obtained as a colorless solid (14 mg, 54%). $^1H$ NMR (300 MHz, $CDCl_3$): δ ppm 8.11 (m, 1H), 7.67 (m, 1H), 7.49 (m, 1H), 7.38 (m, 1H), 6.05 (s, 1H), 4.99 (m, 1H), 1.82 (s, 3H), 1.17 (d, 3H), 1.09 (d, 3H); MS (ESI) m/z=261 [M+H].

EXAMPLE 168E

Isopropyl 4-hydroxy-1-methyl-3-{7-[(methylsulfonyl)amino]-1,1-dioxido-4H-1,2,4-benzothiadiazin-3-yl}-2-oxo-1,2-dihydronaphthalene-1-carboxylate To a solution of Example 168D (11.4 mg, 44 umol) in anhydrous 1,4-dioxane (1 mL) was added pyridine (28 µL, 350 umol), followed by Example 5A (58 mg, 219 umol). The resulting mixture was heated at 60° C. for 2 hours, cooled to room temperature and partitioned between $H_2O$ (5 mL) and ethyl acetate (3× 5 mL). The combined organic extracts were washed with saturated NaCl (1× 5 mL), dried over $Na_2SO_4$, and the resulting crude product was purified by column chromatography on silica gel using 20% ethyl acetate in hexane. The pure compound obtained was dissolved in anhydrous 1,4-dioxane (1 mL) and Example 12A (11.6 mg, 441 mol) was added. The resulting mixture was stirred at reflux for 16 hours, cooled to room temperature, concentrated in vacuo, and the crude product was purified by column chromatography on silica gel using 3% methanol in chloroform. The title compound was obtained as a colorless solid (10 mg, 43%). $^1H$ NMR (300 MHz, $CDCl_3$): δ 13.72 (s, 1H), 8.27 (d, 1H), 7.61 (m, 3H), 7.30 (m, 2H), 6.77 (s, 1H), 5.04 (m, 1H), 3.08 (s, 3H), 1.79 (s, 3H), 1.18 (m, 3H), 1.03 (m, 3H); MS (ESI) m/z=533 [M+H].

EXAMPLE 169

4-hydroxy-N,N-dimethyl-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxamide

EXAMPLE 169A 2-methoxy-N,N-dimethyl-1-naphthamide

To a solution of 2-methoxynaphthoic acid (268 mg, 1.3 mmol) in dry dichloromethane (5 mL) at 0° C. under a $N_2$ atmosphere was added oxalyl chloride (0.8 mL of a 2M solution in dichloromethane, 1.6 mmol) and 4 drops of N,N-dimethyl formamide. The mixture was stirred at 0° C. for 20 minutes, allowed to warm to room temperature, and stirred for one hour. This solution was added dropwise to a solution of dimethylamine (3.3 mL, 6.5 mmol) and triethylamine (0.92 mL, 6.5 mmol) in tetrahydrofuran (20 mL) and $H_2O$ (2 mL), and stirring was continued at room temperature under a $N_2$ atmosphere for 16 hours. The mixture was concentrated in vacuo and the product was purified by column chromatography using 20% ethyl acetate in hexane. The title compound was obtained as a colorless oil (385 mg, 92%). $^1H$ NMR (300 MHz, $CDCl_3$): δ 7.85 (d, 1H), 7.78 (d, 1H), 7.61 (d, 1H), 7.47 (t, 1H), 7.36 (t, 1H), 7.30 (d, 1H), 3.96 (s, 3H), 3.27 (s, 3H), 2.81 (s, 3H). MS (ESI) m/z=230 [M+H].

EXAMPLE 169B 2-methoxy-N,N-dimethyl-1-(3-methylbutyl)-1,4-dihydronaphthalene-1-carboxamide Example 169A (296 mg, 1.3 mmol) and tert-butanol (148 uL, 1.6 mmol) were dissolved in anhydrous tetrahydrofuran (3 mL) and cooled to −78° C. under a $N_2$ atmosphere. Ammonia (about 18 mL) was condensed into the mixture and potassium metal was added in small portions until the resulting blue solution persisted for 20 min. To this mixture was added isoamyl iodide (581 μL, 4.4 mmol) and the resulting solution was allowed to slowly warm to room temperature ($NH_3$ was evaporated using a dry $N_2$ stream). The resulting mixture was partitioned between saturated $NaHCO_3$ (10 mL) and ethyl acetate (3×10 mL), and the combined organic layers were dried over $Na_2SO_4$. The crude product was purified by column chromatography on silica gel using 5% ethyl acetate in hexane. The title compound was used immediately in the next step.

EXAMPLE 169C 2-methoxy-N,N-dimethyl-1-(3-methylbutyl)-4-oxo-1,4-dihydronaphthalene-1-carboxamide To a solution of the product of Example 169B (190 mg, 0.63 mmol) in benzene (4 mL) at room temperature under a $N_2$ atmosphere was added 200 mg Celite® and pyridinium dichromate (474 mg, 1.26 mmol) followed by 70% tert-butyl hydroperoxide (175 μL, 1.26 mmol). The mixture was allowed to stir at room temperature for 1 hour, filtered through a pad of Celite® and the filtrate added to ethyl acetate (10 mL). The organic solution was washed with 5% $Na_2S_2O_5$ (3× 10 mL) and with saturated NaCl (1× 10 mL) and dried over $Na_2SO_4$. The crude product was purified by column chromatography using 50% ethyl acetate in hexane. The title compound was obtained as a colorless oil (59 mg, 30%). $^1$H NMR (300 MHz, $CDCl_3$): δ 8.18 (d, 1H), 7.56 (t, 1H), 7.44 (t, 1H), 7.26 (d, 1H), 5.98 (s, 1H), 3.85 (s, 3H), 2.95, 2.39 (dm, 3H), 2.42, 2.21 (dm, 2H), 1.56 (s, 3H), 1.32 (m, 1H), 0.73 (d, 3H), 0.65 (d, 3H), 0.28 (m, 2H). MS (ESI) m/z=316 [M+H].

EXAMPLE 169D 2-hydroxy-N,N-dimethyl-1-(3-methylbutyl)-4-oxo-1,4-dihydronaphthalene-1-carboxamide Example 169C (56 mg, 0.18 mmol) and trimethylsilyl iodide (38 uL, 0.27 mmol) were dissolved in acetonitrile (1 mL) and stirred for one hour at room temperature under a $N_2$ atmosphere. Another 38 μL of trimethylsilyl iodide was added and the mixture was stirred for one hour, concentrated in vacuo and the crude product was partitioned between $H_2O$ (5 mL) and ethyl acetate (3× 5 mL). The combined organic extracts were washed one time with saturated NaCl (1× 5 mL), dried over $Na_2SO_4$ and purified by column chromatography on silica gel using 5% methanol in chloroform. The title compound was obtained as colorless oil (32 mg, 60%).

EXAMPLE 169E 4-hydroxy-N,N-dimethyl-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxamide To a solution of Example 169D (31.2 mg, 0.1 mmol) in anhydrous 1,4-dioxane (1 mL) was added pyridine (67 μL, 0.83 mmol) followed by Example 5A (137 mg, 0.52 mmol). The resulting mixture was heated at 60° C. for 2 hours, cooled to room temperature and partitioned between $H_2O$ (5 mL) and ethyl acetate (3× 5 mL). The combined organic extracts were washed with saturated NaCl (1× 5 mL), dried over $Na_2SO_4$, and the resulting crude product purified by column chromatography on silica gel using 20% ethyl acetate in hexane. The pure compound obtained was dissolved in anhydrous 1,4-dioxane (1 mL) and Example 12A (27.5 mg, 0.1 mmol) was added. The resulting mixture was stirred at reflux for 16 hours, cooled to room temperature, concentrated in vacuo, and the crude product was purified by column chromatography on silica gel using 3% methanol in chloroform. The title compound was obtained as a colorless solid: $^1$H NMR (300 MHz, $d_6$-DMSO): δ 14.03 (s, 1H), 10.10 (s, 1H), 8.14 (d, 1H), 7.55 (m, 4H), 7.09 (d, 1H), 3.04 (s, 3H), 2.83, 2.29 (dm, 3H), 2.22 (m, 2H), 1.17 (t, 3H), 0.94 (m, 1H), 0.68 (d, 3H), 0.65 (d, 3H), 0.46 (m, 2H). MS (ESI) m/z=575 [M+H].

EXAMPLE 170

N-{3-[(4R)-1-hydroxy-4-{[(2S)-2-(methoxymethyl)pyrrolidin-1-yl]carbonyl}-4-(3-methylbutyl)-3-oxo-3,4-dihydronaphthalen-2-yl]-1,1-dioxido-4H-1,2,4-benzothiadiazin-7-yl}methanesulfonamide

EXAMPLE 170A (2S)-2-(methoxymethyl)-1-(2-methoxy-1-naphthoyl)pyrrolidine

To a solution of 2-methoxy-naphthalene-1-carbonyl chloride (0.50 g, 2.27 mmol) in dry dichloromethane (5 mL) at 0° C. under a $N_2$ atmosphere was added 2-(S)-methoxymethylpyrrolidine (0.32 g, 2.75 mmol) and triethylamine (0.47 mL, 3.39 mmol). The mixture was allowed to warm to rt and stirred overnight, after which time it was poured into N HCl (50 mL) and extracted with dichloromethane (3× 50 mL). The combined organic layers were dried over $Na_2SO_4$, and the crude product was purified by column chromatography on silica gel using a solvent gradient of 10-30% ethyl acetate in hexane. The title compound was obtained as a colorless solid (0.374 g, 55%). $^1$H NMR (300 MHz, $CDCl_3$) δ 1.90 (m, 6H), 2.99 (m, 1H), 3.21 (m, 1H), 3.48 (m, 3H), 3.95 (m, 3H), 4.59 (m, 1H), 7.29 (m, 1H), 7.37 (m, 1H), 7.48 (m, 1H), 7.76 (m, 3H); MS (ESI) m/z=300 [M+H].

EXAMPLE 170B (2S)-2-(methoxymethyl)-1-{[(1R)-2-methoxy-1-(3-methylbutyl)-1,4-dihydronaphthalen-1-yl]carbonyl}pyrrolidine Example 170A (0.37 g, 1.24 mmol) and tert-butanol (0.12 mL, 1.28 mmol) were dissolved in anhydrous tetrahydrofuran (5 mL) and cooled to −78° C. under $N_2$. Ammonia (ca. 20 mL) was condensed into the mixture, and potassium metal was added in small portions until the resulting blue solution persisted for 20 min. To this mixture was added isoamyl iodide (0.29 mL, 2.2 mmol), and the resulting solution was allowed to slowly warm to rt ($NH_3$ was evaporated using a dry $N_2$ stream). The resulting mixture was partitioned between saturated $NaHCO_3$ (10 mL) and ethyl acetate (3× 10 mL), and the combined organic layers were dried over $Na_2SO_4$. The crude product was purified by column chromatography on silica gel using a solvent gradient of 10-30% ethyl acetate in hexane. The title compound was obtained as a colorless solid (0.365 g, 79%). $^1$H NMR (300 MHz, CDCl$_3$) δ 0.50 (m, 1H), 0.70 (d, J=6.62 Hz, 3H), 0.78 (d, J=6.62 Hz, 3H), 0.94 (m, 1H), 1.37 (m, 2H), 1.70 (m, 4H), 2.03 (m, 1H), 2.26 (m, 1H), 2.45 (m, 1H), 3.13 (m, 1H), 3.31 (m, 1H), 3.37 (s, 3H), 3.47 (m, 1H), 3.58 (s, 3H), 3.67 (m, 1H), 4.30 (m, 1H), 4.97 (m, 1H), 7.12 (m, 4H); MS (ESI) m/z=372 [M+H].

EXAMPLE 170C (4R)-3-methoxy-4-{[(2S)-2-(methoxymethyl)pyrrolidin-1-yl]carbonyl}-4-(3-methylbutyl)naphthalen-1(4H)-one To a solution of Example 170B (0.10 g, 0.27 mmol) in benzene (2 mL) was added pyridinium dichromate (PDC) (0.40 g, 1.06 mmol), tert-butylhydroperoxide (70% aq. solution, 0.10 mL, 0.72 mmol), and celite (0.10 g). The mixture was stirred at rt 90 min, filtered and washed with benzene (5 mL), and partitioned between ethyl acetate (10 mL) and 10% aq. Na$_2$S$_2$O$_5$ (2× 5 mL). The organic layer was washed with brine and dried over Na$_2$SO$_4$. The crude product was purified by column chromatography on silica gel using 50% ethyl acetate in hexane. The title compound was obtained a colorless, crystalline solid (67 mg, 65%). $^1$H NMR (300 MHz, CDCl$_3$) δ 0.28 (m, 1H), 0.66 (d, J=6.62 Hz, 3H), 0.73 (d, J=6.62 Hz, 3H), 0.86 (m, 1H), 1.31 (m, 2H), 1.73 (m, 3H), 2.33 (m, 3H), 2.93 (m, 1H), 3.36 (s, 3H), 3.45 (m, 1H), 3.58 (m, 1H), 3.83 (s, 3H), 4.30 (m, 1H), 5.99 (s, 1H), 7.34 (m, 1H), 7.43 (m, 1H), 7.55 (m, 1H), 8.18 (m, 1H); MS (ESI) m/z=386 [M+H].

EXAMPLE 170D (4R)-3-hydroxy-4-{[(2S)-2-(methoxymethyl)pyrrolidin-1-yl]carbonyl}-4-(3-methylbutyl)naphthalen-1(4H)-one A solution of Example 170C (67 mg, 0.17 mmol) in anhydrous acetonitrile (1.5 mL) under a N$_2$ atmosphere was treated dropwise with iodotrimethylsilane (TMSI) (37 µL, 0.26 mmol). The mixture was stirred at rt 90 min, more iodotrimethylsilane (TMSI) was added (20 µL, 0.14 mmol), and the mixture was stirred at rt for 1 h. The mixture was concentrated in vacuo, and the crude product was purified by column chromatography on silica gel using 80% ethyl acetate in hexane. The title compound was obtained as a colorless solid (27 mg, 42%). $^1$H NMR (300 MHz, CDCl$_3$) δ 0.38 (m, 1H), 0.67 (d, J=6.62 Hz, 3H), 0.72 (d, J=6.62 Hz, 3H), 0.88 (m, 1H), 1.33 (m, 3H), 1.74 (m, 3H), 2.27 (m, 1H), 2.43 (m, 2H), 3.02 (m, 1H), 3.39 (s, 3H), 3.61 (m, 2H), 4.30 (m, 1H), 6.17 (s, 1H), 7.35 (m, 1H), 7.46 (m, 1H), 7.55 (m, 1H), 8.13 (m, 1H); MS (ESI) m/z=372 [M+H].

EXAMPLE 170E (4R)-2-[bis(methylthio)methylene]-4-{[(2S)-2-(methoxymethyl)pyrrolidin-1-yl]carbonyl}-4-(3-methylbutyl)naphthalene-1,3(2H,4H)-dione To a solution of Example 170D (24 mg, 0.065 mmol) in anhydrous 1,4-dioxane (1 mL) was added Example 5A (86 mg, 0.325 mmol) and pyridine (26 µL, 0.32 mmol). The resulting mixture was stirred at 60° C. for 16 h, concentrated in vacuo, and the crude product was purified by column chromatography on silica gel using 2:1 ethyl acetate:hexane.

The title compound was obtained as a yellow solid (24 mg, 78%): $^1$H NMR (300 MHz, CDCl$_3$): δ 0.61 (m, 1H), 0.68 (d, J=6.62 Hz, 3H), 0.72 (d, J=6.62 Hz, 3H), 0.92 (m, 1H), 1.35 (m, 1H), 1.65 (m, 2H), 1.81 (m, 1H), 2.28 (m, 4H), 2.60 (s, 6H), 2.79 (m, 1H), 3.32 (m, 1,H), 3.40 (s, 3H), 3.81 (m, 1H), 4.30 (m, 1H), 7.22 (m, 1H), 7.44 (m, 1H), 7.54 (m, 1H), 8.26 (m, 1H); MS (ESI) m/z=476 [M+H].

EXAMPLE 170F

N-{3-[(4R)-1-hydroxy-4-{[(2S)-2-(methoxymethyl)pyrrolidin-1-yl]carbonyl}-4-(3-methylbutyl)-3-oxo-3,4-dihydronaphthalen-2-yl]-1,1-dioxido-4H-1,2,4-benzothiadiazin-7-yl}methanesulfonamide A solution of Example 170E (20 mg, 42 µmol) and Example 12A (11 mg, 42 µmol) in anhydrous 1,4-dioxane (0.5 mL) was stirred at 80° C. for 16 h. The mixture was concentrated in vacuo and the crude product was purified by column chromatography on silica gel using 5% methanol in chloroform. The title compound was obtained as a colorless solid (14 mg, 52%). $^1$H NMR (300 MHz, DMSO-d$_6$) δ 0.48 (m, 1H), 0.62 (d, J=6.25 Hz, 3H), 0.68 (d, J=6.62 Hz, 3H), 0.91 (m, 1H), 1.25 (m, 1H), 1.58 (m, 3H), 1.89 (m, 1H), 2.21 (m, 2H), 2.89 (m, 1H), 2.99 (s, 3H), 3.13 (m, 2H), 3.28 (s, 3H), 3.60 (m, 1H), 4.07 (m, 1H), 7.02 (m, 1H), 7.40 (m, 5H), 8.07 (m, 1H), 9.88 (br s, 1H), 15.09 (br s, 1H); MS (ESI) m/z=645 [M+H].

EXAMPLE 171

{(2R)-1-[((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)carbonyl]pyrrolidin-2-yl}methyl acetate

EXAMPLE 171A

[(2R)-1-(2-methoxy-1-naphthoyl)pyrrolidin-2-yl]methanol

The title compound was prepared using the procedure described for Example 170A, substituting 2-(R)-hydroxymethylpyrrolidine for 2-(S)-methoxymethylpyrrolidine. The title compound was purified by column chromatography on silica gel using a solvent gradient of 65-100% ethyl acetate in hexane, and was obtained as a colorless solid. $^1$H NMR (300 MHz, CDCl$_3$) δ 1.68 (m, 1H), 1.81 (m, 2H), 2.21 (m, 1H), 3.08 (m, 1H), 3.29 (m, 1H), 3.88 (m, 1H), 3.98 (m, 4H), 4.53 (m, 1H), 7.29 (dd, J=8.82, 2.21 Hz, 1H), 7.39 (m, J=8.09 Hz, 1H), 7.50 (m, 1H) 7.71 (m, 1H) 7.81 (d, J=8.09 Hz, 1H) 7.88 (d, J=8.82 Hz, 1H); MS (ESI) m/z=286 [M+H].

EXAMPLE 171B ((2R)-1-{[(1S)-2-methoxy-1-(3-methylbutyl)-1,4-dihydronaphthalen-1-yl]carbonyl}pyrrolidin-2-yl)methanol The title compound was prepared using the procedure described for Example 170B, substituting the product of Example 171A for the product of example 170A. The title compound was purified by column chromatography on silica gel using a solvent gradient of 35-65% ethyl acetate in hexane, and was obtained as a colorless solid. $^1$H NMR (300 MHz, CDCl$_3$) δ 0.53 (m, 1H), 0.71 (d, J=6.62 Hz, 3H), 0.78 (d, J=6.62 Hz, 3H), 0.99 (m, 1H), 1.39 (m, 4H), 1.93 (m, 3H), 2.25 (m, 1H), 2.85 (m, 1H), 2.99 (m, 1H), 3.49 (m, 2H), 3.63 (m, 4H), 3.87 (m, 1H), 4.19 (m, 1H), 5.01 (m, 1H), 7.14 (m, 4H).

EXAMPLE 171C ((2R)-1-{[(1S)-2-methoxy-1-(3-methylbutyl)-1,4-dihydronaphthalen-1-yl]carbonyl}pyrrolidin-2-yl) methyl acetate To a solution of Example 171B (54 mg, 0.15 mmol) in anhydrous pyridine (0.5 mL) was added acetic anhydride (50 µL, 0.53 mmol). The resulting mixture was stirred under a $N_2$ atmosphere at r.t. for 16 h, diluted with dichloromethane (10 mL), and extracted with 0.2 N HCl (2× 10 mL). The organic layer was dried over $Na_2SO_4$, and the crude product was purified by column chromatography on silica gel using a solvent gradient of 25-50% ethyl acetate in hexane. The title compound was obtained as a colorless solid (50 mg, 83%). $^1$H NMR (300 MHz, CDCl$_3$) δ 0.51 (m, 1H), 0.71 (d, J=6.62 Hz, 3H), 0.77 (d, J=6.62 Hz, 3H), 0.94 (m, 2H), 1.39 (m, 2H), 1-64 (m, 3H), 2.04 (m, 1H), 2.04 (s, 3H), 2.26 (m, 1H), 2.49 (m, 1H), 3.16 (m, 1H), 3.47 (m, 1H), 3.59 (s, 3H), 4.11 (m, 1H), 4.25 (m, 1H), 4.41 (m, 1H), 4.97 (m, 1H), 7.14 (m, 4H).

EXAMPLE 171D ((2R)-1-{[(1S)-2-methoxy-1-(3-methylbutyl)-4-oxo-1,4-dihydronaphthalen-1-yl]carbonyl}pyrrolidin-2-yl)methyl acetate The title compound was prepared using the procedure described for Example 170C, substituting the product of Example 171C for the product of Example 170B. The title compound was purified by crystallization from ethyl acetate/hexane and was obtained as a colorless, crystalline solid. $^1$H NMR (300 MHz, CDCl$_3$): δ 0.28 (m, 1H), 0.66 (d, J=6.62 Hz, 3H), 0.73 (m, 4H), 1.33 (m, 2H), 1.68 (m, 3H), 2.05 (s, 3H), 2.25 (m, 1H), 2.40 (m, 2H), 2.96 (m, 1H), 3.84 (s, 3H), 4.20 (m, 2H), 4.41 (m, 1H), 6.00 (s, 1H), 7.34 (m, 1H), 7.45 (m, 1H), 7.56 (m, 1H), 8.18 (m, 1H); MS (ESI) m/z=414 [M+H].

EXAMPLE 171E ((2R)-1-{[(1S)-2-hydroxy-1-(3-methylbutyl)-4-oxo-1,4-dihydronaphthalen-1-yl]carbonyl}pyrrolidin-2-yl)methyl acetate The title compound was prepared using the procedure described for Example 170D, substituting the product of Example 171D for the product of Example 170C. The title compound was purified by column chromatography on silica gel using a solvent gradient of 65-100% ethyl acetate in hexane, and it was obtained as a colorless solid.

EXAMPLE 171F ((2R)-1-{[(1S)-3-[bis(methylthio)methylene]-1-(3-methylbutyl)-2,4-dioxo-1,2,3,4-tetrahydronaphthalen-1-yl]carbonyl}pyrrolidin-2-yl)methyl acetate The title compound was prepared using the procedure described for Example 170E, substituting the product of Example 171E for the product of Example 170D. The title compound was purified by column chromatography on silica gel using a solvent gradient of 50-65% ethyl acetate in hexane, and was obtained as a yellow solid.

EXAMPLE 171G

{(2R)-1-[((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)carbonyl]pyrrolidin-2-yl}methyl Acetate The title compound was prepared using the procedure described for Example 170F, substituting the product of Example 171F for the product of Example 170E. The title compound was purified by column chromatography on silica gel using 5% methanol in chloroform, and was obtained as a lt. yellow solid. $^1$H NMR (300 MHz, DMSO-d$_6$): δ 0.48 (m, 1H), 0.62 (d, J=6.62 Hz, 3H), 0.68 (d, J=6.62 Hz, 3H), 0.91 (m, 2H), 1.24 (m, 2H), 1.61 (m, 3H), 1.89 (m, 1H), 2.04 (s, 3H), 2.17 (m, 1H), 2.30 (m, 1H), 2.93 (m, 1H), 2.99 (s, 3H), 3.91 (m, 1H), 4.18 (m, 2H), 7.02 (d, J=7.35 Hz, 1H), 7.40 (m, 5H), 8.06 (m, J=6.25 Hz, 1H), 9.89 (br s, 1H), 15.03 (br s, 1H); MS (ESI) m/z=673 [M+H].

EXAMPLE 172

N-{3-[(4S)-1-hydroxy-4-{[(2R)-2-(hydroxymethyl)pyrrolidin-1-yl]carbonyl}-4-(3-methylbutyl)-3-oxo-3,4-dihydronaphthalen-2-yl]-1,1-dioxido-4H-1,2,4-benzothiadiazin-7-yl}methanesulfonamide To a solution of Example 171G (0.15 g, 0.22 mmol) in methanol (2 mL) was added $K_2CO_3$ (68 mg, 0.5 mmol). The resulting mixture was stirred at r.t. for 3 hrs, and then poured into N HCl (10 mL), extracted with ethyl acetate (3× 10 mL), and the combined organic layers were dried over $Na_2SO_4$. The crude product was purified by column chromatography on silica gel using 5% methanol in chloroform, and the title compound was obtained as a lt. yellow solid (0.134 g, 97%). $^1$H NMR (300 MHz, DMSO-d$_6$): δ 0.45 (m, 1H), 0.63 (d, J=6.62 Hz, 3H), 0.69 (d, J=6.62 Hz, 3H), 0.94 (m, 1H), 1.27 (m, 1H), 1.61 (m, 3H), 1.99 (m, 1H), 2.23 (m, 2H), 2.89 (m, 1H), 3.03 (s, 3H), 3.20 (m, 1H), 3.65 (dd, J=9.93, 3.68 Hz, 1H), 3.98 (m, 1H), 7.13 (m, 1H), 7.52 (m, 5H), 8.11 (m, 1H), 10.07 (br s, 1H), 14.18 (br s, 1H); MS (ESI) m/z=631 [M+H].

EXAMPLE 173

(2R)-pyrrolidin-2-ylmethyl (1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate hydrochloride Example 172 (50 mg, 0.079 mmol) was added to a solution of acetyl chloride (25 µL, 0.35 mmol) in anhydrous methanol (1 mL). The resulting solution was stirred under a $N_2$ atmosphere at rt 16 h, then concentrated in vacuo to give the title compound as a lt. yellow solid: $^1$H NMR (300 MHz, DMSO-d$_6$) δ 0.44 (m, 1H), 0.68 (d, J=6.62 Hz, 3H), 0.72 (d, J=6.62 Hz, 3H), 0.89 (m, 1H), 1.31 (m, 1H), 1.56 (m, 1H), 1.70 (m, 1H), 1.88 (m, 2H), 2.12 (m, 1H), 2.41 (m, 1H), 2.95 (m, 1H), 3.02 (s, 3H), 3.17 (m, 1H), 3.63 (m, 1H), 4.07 (m, 1H), 4.36 (m, 1H), 7.25 (m, 1H), 7.48 (m, 5H), 8.11 (m, 1H), 8.53 (m, 1H), 8.75 (m, 1H), 10.01 (s, 1H), 14.40 (br s, 1H).

EXAMPLE 174

Methyl (2R)-2-({[((1S)-4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)carbonyl]oxy}methyl)pyrrolidine-1-carboxylate To a solution of Example 173 (0.079 mmol) in dry dichloromethane (1 mL) at 0° C. was added methylchloroformate (0.12 mL, 1.55 mmol) and triethylamine (33 μL, 0.24 mmol). The resulting mixture was stirred at rt 3 h and partitioned between H$_2$O (5 mL) and dichloromethane (3× 5 mL). The combined organic layers were dried over Na$_2$SO$_4$, the drying agent was filtered off, and the solvent was removed in vacuo. To a solution of the resulting residue in methanol (1 mL) was added K$_2$CO$_3$, and the resulting mixture was stirred at rt 90 min. The mixture was partitioned between N HCl (5 mL) and ethyl acetate (3× 5 mL), and the combined organic layers were dried over Na$_2$SO$_4$. The crude product was purified by column chromatography on silica gel using 5% methanol in chloroform, and the title compound was obtained as a lt. yellow solid (48 mg, 88%): $^1$H NMR (300 MHz, DMSO-d$_6$) δ 0.43 (m, 1H), 0.67 (m, J=6.62 Hz, 3H), 0.71 (d, J=6.62 Hz, 3H), 0.89 (m, 2H), 1.33 (m, 1H), 1.45 (m, 3H), 1.67 (m, 1H), 2.10 (m, 1H), 2.40 (m, 1H), 2.70 (m, 1H), 3.02 (s, 3H), 3.74 (m, 1H), 3.93 (m, 1H), 4.13 (m, 1H), 7.16 (m, 1H), 7.49 (m, 5H), 8.12 (m, 1H), 10.01 (s, 1H), 14.54 (br s, 1H); MS (ESI) m/z=689 [M+H].

EXAMPLE 175

N-{3-[4-(4,5-dihydro-1,3-oxazol-2-yl)-1-hydroxy-4-(3-methylbutyl)-3-oxo-3,4-dihydronaphthalen-2-yl]-1,1-dioxido-4H-1,2,4-benzothiadiazin-7-yl}methanesulfonamide

EXAMPLE 175A

N-(2-hydroxyethyl)-2-methoxy-1-naphthamide

A solution of 2-methoxy-naphthalene-1-carboxylic acid (0.50 g, 2.5 mmol) in anhydrous dichloromethane at 0° C. was treated dropwise with a 2.0 M solution of oxalyl chloride in dichloromethane (1.9 mL, 3.8 mmol). The resulting solution was stirred under a N$_2$ atmosphere at 0° C. for 20 min, then allowed to warm to r.t. and stirred 1 hr. The solution was cooled to 0° C., and ethanolamine (0.3 mL, 5.0 mmol) and triethylamine (1.0 mL, 7.2 mmol) were added. The resulting mixture was stirred at 0° C. for 15 min, then allowed to warm to r.t. and stirred 90 min. The mixture was poured into 1N HCl (20 mL) and extracted with dichloromethane (2× 20 mL), and the combined organic layers were washed with saturated NaHCO$_3$ (20 mL) and dried over Na$_2$SO$_4$. The drying agent was filtered off, and the solvent was removed in vacuo to give the title compound as colorless syrup.

EXAMPLE 175B 3-(2-methoxy-1-naphthoyl)-2,2-dimethyl-1,3-oxazolidine

To a solution of Example 175A in anhydrous N,N-dimethyl formamide (10 mL) was added 2,2-dimethoxypropane (0.62 mL, 5.0 mmol) and p-toluenesulfonic acid monohydrate (50 mg, 0.26 mmol). The resulting mixture was stirred under a N$_2$ atmosphere at 60° C. for 16 h. Additional 2,2-dimethoxypropane (0.3 mL, 2.4 mmol) and p-toluenesulfonic acid monohydrate (50 mg, 0.26 mmol) were added, and the mixture was stirred at 60° C. for 6 h. The mixture was partitioned between saturated NaHCO$_3$ (50 mL) and ethyl acetate (3× 50 mL), and the combined organic layers were dried over Na$_2$SO$_4$. The crude product was purified by column chromatography on silica gel using a solvent gradient of 50-65% ethyl acetate in hexane. The title compound was obtained as a colorless, crystalline solid (0.44 g, 62% for two steps). $^1$H NMR (300 MHz, CDCl$_3$) δ 1.83 (s, 3H), 1.88 (s, 3H), 3.13 (m, 1H), 3.40 (m, 1H), 3.92 (m, 2H), 3.98 (s, 3H), 7.28 (m, 1H), 7.37 (m, 1H), 7.49 (m, 1H), 7.71 (m, 1H), 7.80 (m, 1H), 7.86 (m, 1H).

EXAMPLE 175C

3-{[2-methoxy-1-(3-methylbutyl)-1,4-dihydronaphthalen-1-yl]carbonyl}-2,2-dimethyl-1,3-oxazolidine The title compound was prepared using the procedure described for Example 170B, substituting the product of Example 175B for the product of Example 170A. The title compound was purified by column chromatography on silica gel using 1:9 ethyl acetate:hexane, and was obtained as a colorless solid. $^1$H NMR (300 MHz, CDCl$_3$) δ 0.52 (m, 1H), 0.71 (d, J=6.62 Hz, 3H), 0.77 (d, J=6.62 Hz, 3H), 0.96 (m, 1H), 1.37 (m, 1H), 1.54 (s, 3H), 1.61 (s, 3H), 1.97 (m, 1H), 2.27 (m, 1H), 2.57 (m, 1H), 3.35 (m, 1H), 3.52 (m, 2H), 3.60 (m, 1H), 3.62 (s, 3H), 3.70 (m, 1H), 4.99 (m, 1H), 7.15 (m, 4H).

EXAMPLE 175D

4-[(2,2-dimethyl-1,3-oxazolidin-3-yl)carbonyl]-3-methoxy-4-(3-methylbutyl)naphthalen-1(4H)-one The title compound was prepared using the procedure described for Example 170C, substituting the product from Example 175C for the product from Example 170B. The title compound was purified by column chromatography on silica gel using 1:3 ethyl acetate:hexane, and was obtained as a colorless, crystalline solid. $^1$H NMR (300 MHz, CDCl$_3$) δ 0.27 (m, 2H), 0.66 (d, J=6.62 Hz, 3H), 0.72 (m, 1H), 0.73 (d, J=6.62 Hz, 2H), 1.31 (m, 1H), 1.55 (s, 3H), 1.62 (s, 3H), 2.23 (m, 1H), 2.43 (m, 2H), 3-11 (m, 1H), 3.53 (m, 1H), 3.70 (m, 1H), 3.86 (s, 3H), 6.01 (s, 1H), 7.33 (m, 1H), 7.46 (m, 1H), 7.59 (m, 1H), 8.19 (m, 1H); MS (ESI) m/z=394 [M+Na].

EXAMPLE 175E 4-(4,5-dihydro-1,3-oxazol-2-yl)-3-hydroxy-4-(3-methylbutyl)naphthalen-1(4H)-one The title compound was prepared using the procedure described for Example 170D, substituting the product from Example 175D for the product from Example 170C. The title compound was obtained as a colorless solid. $^1$H NMR (300 MHz, CDCl$_3$) δ 0.41 (m, 1H), 0.72 (d, J=6.62 Hz, 3H), 0.77 (d, J=6.62 Hz, 3H), 0.93 (m, 1H), 1.40 (m, 1H), 1.59 (m, 1H), 2.27 (m, 1H), 2.64 (m, 1H), 3.20 (m, 2H), 3.43 (m, 1H), 3.63 (m, 1H), 6.06 (s, 1H), 7.54 (m, 2H), 7.64 (m, 1H), 8.23 (m, 1H); MS (ESI) m/z=300 [M+H].

EXAMPLE 175F

2-[bis(methylthio)methylene]-4-(4,5-dihydro-1,3-oxazol-2-yl)-4-(3-methylbutyl)naphthalene-1,3(2H,4H)-dione The title compound was prepared using the procedure described for Example 170E, substituting the product from Example 175E for the product from Example 170D. The title compound was purified by column chromatography on silica gel using a solvent gradient of 50-65% ethyl acetate in hexane, and was obtained as a yellow solid.

EXAMPLE 175G

N-{3-[4-(4,5-dihydro-1,3-oxazol-2-yl)-1-hydroxy-4-(3-methylbutyl)-3-oxo-3,4-dihydronaphthalen-2-yl]-1,1-dioxido-4H-1,2,4-benzothiadiazin-7-yl}methanesulfonamide The title compound was prepared using the procedure described for Example 170F, substituting the product from Example 175F for the product from Example 170E. The title compound was purified by column chromatography on silica gel using 5% methanol in chloroform, and was obtained as a colorless solid. $^1$H NMR (500 MHz, DMSO-$d_6$) δ 0.43 (m, 1H), 0.65 (d, J=6.10 Hz, 3H), 0.69 (d, J=6.71 Hz, 3H), 0.85 (m, 1H), 1.28 (m, 1H), 2.11 (m, 1H), 2.43 (m, 1H), 3.00 (s, 3H), 3.78 (m, 2H), 4.06 (m, 1H), 4.16 (m, 1H), 7.24 (d, J=7.32 Hz, 1H), 7.45 (m, 5H), 8.07 (d, J=7.32 Hz, 1H), 9.92 (s, 1H), 14.76 (br s, 1H); MS (ESI) m/z=573 [M+H].

EXAMPLE 176

2-{methyl[(1-(3-methylbutyl)-3-{7-[(methylsulfonyl)amino]-1,1-dioxido-4H-1,2,4-benzothiadiazin-3-yl}-2,4-dioxo-1,2,3,4-tetrahydronaphthalen-1-yl)carbonyl]amino}ethyl Acetate

EXAMPLE 176A

N-(2-hydroxyethyl)-2-methoxy-N-methyl-1-naphthamide

The title compound was prepared using the procedure described for Example 175A, substituting 2-(methylamino)ethanol for ethanolamine. The title compound was purified by column chromatography on silica gel using ethyl acetate, and was obtained as a colorless solid: $^1$H NMR (300 MHz, CDCl$_3$) δ 2.87 (s, 3H), 3.30 (m, 1H), 3.77 (m, 1H), 3.99 (m, 5H), 7.29 (d, J=8.82 Hz, 1H), 7.38 (m, 1H), 7.49 (m, 1H), 7.65 (m, 1H), 7.80 (m, 1H), 7.88 (d, J=8.82 Hz, 1H).

EXAMPLE 176B

N-(2-hydroxyethyl)-2-methoxy-N-methyl-1-(3-methylbutyl)-1,4-dihydronaphthalene-1-carboxamide The title compound was prepared using the procedure described for Example 170B, substituting the product from Example 176A for the product from Example 170A. The title compound was purified by column chromatography on silica gel using a solvent gradient of 35-65% ethyl acetate in hexane, and was obtained as a colorless solid.

EXAMPLE 176C

2-[{[2-methoxy-1-(3-methylbutyl)-1,4-dihydronaphthalen-1-yl]carbonyl}(methyl)amino]ethyl Acetate The title compound was prepared using the procedure described for Example 171C, substituting the product from Example 176B for the product from Example 171B. The title compound was purified by column chromatography on silica gel using a solvent gradient of 35-65% ethyl acetate in hexane, and was obtained as a colorless solid.

EXAMPLE 176D

2-[{[2-methoxy-1-(3-methylbutyl)-4-oxo-1,4-dihydronaphthalen-1-yl]carbonyl}(methyl)amino]ethyl Acetate The title compound was prepared using the procedure described for Example 170C, substituting the product from Example 176C for the product from Example 170B. The title compound was purified by column chromatography on silica gel using 1:3 ethyl acetate:hexane, and was obtained as a colorless solid.

EXAMPLE 176E

2-[{[2-hydroxy-1-(3-methylbutyl)-4-oxo-1,4-dihydronaphthalen-1-yl]carbonyl}(methyl)amino]ethyl Acetate The title compound was prepared using the procedure described for Example 170D, substituting the product from Example 176D for the product from Example 170C. The title compound was purified by column chromatography on silica gel using a solvent gradient of 65-100% ethyl acetate in hexane, and was obtained as a colorless solid.

EXAMPLE 176F

2-[{[3-[bis(methylthio)methylene]-1-(3-methylbutyl)-2,4-dioxo-1,2,3,4-tetrahydronaphthalen-1-yl]carbonyl}(methyl)amino]ethyl Acetate The title compound was prepared using the procedure described for Example 170E, substituting the product from Example 176E for the product from Example 170D. The title compound was purified by column chromatography on silica gel using a solvent gradient of 50-65% ethyl acetate in hexane, and was obtained as a yellow solid.

EXAMPLE 176G

2-{methyl[(1-(3-methylbutyl)-3-{7-[(methylsulfonyl)amino]-1,1-dioxido-4H-1,2,4-benzothiadiazin-3-yl}-2,4-dioxo-1,2,3,4-tetrahydronaphthalen-1-yl)carbonyl]amino}ethyl Acetate The title compound was prepared using the procedure described for Example 170F, substituting the product from Example 176F for the product from Example 170E. The title compound was purified by column chromatography on silica gel using a solvent gradient of 2-4% methanol in chloroform, and was obtained as a lt. yellow solid: $^1$H NMR (300 MHz, DMSO-$d_6$) δ 0.48 (m, 1H), 0.63 (d, J=6.62 Hz, 3H), 0.68 (d, J=6.62 Hz, 3H), 0.90 (m, 2H), 1.23 (m, 1H), 1.96 (s, 3H), 2.19 (m, 2H), 2.33 (s, 3H), 3.02 (s, 3H), 3.24 (m, 1H), 3.79 (m, 1H), 4.00 (m, 1H), 4.17 (m, 1H), 7.03 (m, 1H), 7.50 (m, 5H), 8.12 (m, 1H), 10.02 (s, 1H), 14.41 (br s, 1H); MS (ESI) m/z=647 [M+H].

EXAMPLE 177

N-(2-hydroxyethyl)-N-methyl-1-(3-methylbutyl)-3-{7-[(methylsulfonyl)amino]-1,1-dioxido-4H-1,2,4-benzothiadiazin-3-yl}-2,4-dioxo-1,2,3,4-tetrahydronaphthalene-1-carboxamide The title compound was prepared using the procedure described for Example 172 substituting the product of Example 176G for the product of Example 171G. The title compound was purified by column chromatography on silica gel using a solvent gradient of 2-6% methanol in chloroform, and was obtained as a colorless solid. $^1$H NMR (300 MHz, DMSO-$d_6$) δ 0.49 (m, 1H), 0.62 (d, J=6.62 Hz, 3H), 0.67 (d, J=6.62 Hz, 3H), 0.92 (m, 2H), 1.27 (m, 1H), 1.86 (m, 1H), 2.15 (m, 1H), 2.33 (s, 3H), 3.00 (s, 3H), 3.14 (m, 1H), 3.47 (m, 2H), 6.96 (m, 1H), 7.42 (m, 5H), 8.08 (m, 1H), 9.90 (s, 1H), 14.99 (br s, 1H); MS (ESI) m/z=605 [M+H].

EXAMPLE 178

Methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate

EXAMPLE 178A

Methyl 2-methoxy-1-(3-methylbutyl)-1,4-dihydronaphthalene-1-carboxylate

To a stirred solution of methyl 2-methoxynaphthoate (1.0 g, 4.6 mmol) and tert-butyl alcohol (0.44 ml, 4.6 mmol) at −78° C. was added liquid ammonia (20 mL). Potassium metal was added in small pieces until the solution stayed dark blue for 30 min. Isoamyl iodide (1.9 mL, 14.8 mmol) was added dropwise (the blue coloration disappeared about half-way through addition) and stirring was continued for 1 hour at −78° C. The solution was allowed to warm to room temperature and purged with nitrogen to remove excess ammonia. To the resulting slurry a solution of saturated sodium bicarbonate (100 mL) was added, and the solution was extracted with ether (3×50 mL). The combined organic phases were washed with 10% $Na_2S_2O_3$ (aq), dried ($Na_2SO_4$), and concentrated in vacuo. Column chromatography on silica (5%-15% ethyl acetate/hexane) afforded product as a light yellow oil (1.1 g, 85%). $^1$H NMR (300 MHz, $CDCl_3$) δ ppm 0.55 (m, 1H), 0.75 (dd, J=14.71, 6.62 Hz, 6H), 0.88 (m, 1H), 1.39 (m, 1H), 2.06 (m, 1H), 2.27 (m, 1H), 3.55 (d, J=3.31 Hz, 2H), 3.60 (s, 3H), 3.61 (s, 3H), 5.05 (t, J=3.68 Hz, 1H), 7.16 (m, 4H); MS m/z 289.0 $(M+H)^+$.

EXAMPLE 178B

Methyl 2-methoxy-1-(3-methylbutyl)-4-oxo-1,4-dihydronaphthalene-1-carboxylate

A mixture of Example 178A (0.3 g, 1.0 mmol) and pyridinium dichromate (0.98 g, 2.6 mmol) in chloroform (20 mL) was heated at reflux with a Dean-Stark trap for 18 h. The reaction mixture was cooled to room temperature and filtered through celite. The filtrate was concentrated in vacuo. Column chromatography on silica (5%-15% ethyl acetate/hexane) afforded product as a white solid (0.18 g, 58%). $^1$H NMR (300 MHz, $CDCl_3$) δ ppm 0.40 (m, 1H), 0.72 (m, 7H), 1.37 (m, 1H), 2.36 (m, 2H), 3.61 (s, 3H), 3.83 (s, 3H), 5.96 (s, 1H), 7.42 (m, 2H), 7.56 (m, 1H), 8.19 (d, J=7.72 Hz, 1H); MS m/z 303.1 $(M+H)^+$.

EXAMPLE 178C

Methyl 1-(3-methylbutyl)-2,4-dioxo-1,2,3,4-tetrahydronaphthalene-1-carboxylate

To a solution of Example 178B (0.18 g, 0.6 mmol) in acetonitrile (2 mL) was added iodotrimethylsilane (TMSI) (0.13 mL, 0.9 mmol). The reaction solution was stirred at room temperature for 3 h. After which, additional 1.5 equivalents of TMSI (0.13 mL) were added and stirring was continued for 2 h. The solution was quenched with water (5 mL) and extracted with ethyl acetate (2×5 mL). The combined organic extracts were dried ($Na_2SO_4$) and concentrated in vacuo. Column chromatography on silica (40%-80% ethyl acetate/hexane) afforded product as a white solid (0.11 g, 65%). $^1$H NMR (300 MHz, $CDCl_3$) δ ppm 0.46 (m, 1H), 0.79 (m, 7H), 1.41 (m, 1H), 2.29 (m, 1H), 2.53 (m, 1H), 3.60 (s, 3H), 3.83 (m, 1H), 6.11 (s, 1H), 7.52 (m, 3H), 8.12 (d, J=7.72 Hz, 1H); MS m/z 289.0 $(M+H)^+$.

EXAMPLE 178D

Methyl 3-[bis(methylthio)methylene]-1-(3-methylbutyl)-2,4-dioxo-1,2,3,4-tetrahydronaphthalene-1-carboxylate To a solution of Example 178C (0.11 g, 0.38 mmol) in dioxane (3 mL) was added Example 5A (0.33 g, 1.3 mmol) followed by pyridine (0.15 mL, 1.9 mmol). The heterogeneous solution was heated at 55° C. for 3 h. The solution was cooled to room temperature and concentrated in vacuo. Column chromatography on silica (20% ethyl acetate/hexane) afforded product as an orange oil (0.15 g, 100%). $^1$H NMR (300 MHz, $CDCl_3$) δ ppm 0.59 (m, 1H), 0.73 (dd, J=8.82, 6.62 Hz, 6H), 0.82 (m, 1H), 1.38 (m, 1H), 2.22 (m, 1H), 2.55 (m, 7H), 3.62 (s, 3H), 7.25 (d, J=8.46 Hz, 1H), 7.45 (m, 1H), 7.55 (m, 1H), 8.26 (d, J=6.62 Hz, 1H).

EXAMPLE 178E

Methyl 4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalene-1-carboxylate A mixture of Example 178D (0.15 g, 0.38 mmol) and Example 12A (81 mg, 0.3 mmol) in dioxane (2 mL) was heated at 85° C. for 18 h. The solution was cooled to room temperature and concentrated in vacuo. Column chromatography on silica (0-3% methanol/dichloromethane) afforded product as a light yellow solid (1.3 g, 76%). $^1$H NMR (300 MHz, $CDCl_3$) δ ppm 0.47 (m, 1H), 0.78 (m, 7H), 1.37 (m, 1H), 2.51 (m, 2H), 3.09 (m, 3H), 3.63 (s, 3H), 6.75 (s, 1H), 7.39 (m, 2H), 7.56 (t, J=7.72 Hz, 1H), 7.68 (m, 3H), 8.29 (d, J=8.09 Hz, 1H), 13.83 (s, 1H), 16.72 (s, 1H); MS m/z 562.1 $(M+H)^+$.

EXAMPLE 179

(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl Acetate

EXAMPLE 179A

[2-methoxy-1-(3-methylbutyl)-1,4-dihydronaphthalen-1-yl]methanol

To a solution of Example 178A (0.3 g, 1 mmol) in tetrahydrofuran (5 mL) was added a 1.0 M solution of lithium aluminum hydride in tetrahydrofuran (1.2 mL, 1.2 mmol) dropwise. The solution was stirred at room temperature for 1 h and then quenched carefully with a saturated solution of $NH_4Cl$ (5 mL). The mixture was diluted with water (25 mL) and extracted with ethyl acetate (3× 15 mL). The combined organic extracts were dried ($Na_2SO_4$) and concentrated in vacuo. Column chromatography on silica (20% ethyl acetate/hexane) afforded product as a colorless oil (0.20 g, 74%). $^1$H NMR (300 MHz, CDCl$_3$) δ ppm 0.79 (m, 8H), 1.37 (m, 1H), 1.55 (m, 1H), 1.98 (m, 1H), 3.53 (d, J=3.68 Hz, 2H), 3.63 (s, 3H), 3.71 (d, J=10.66 Hz, 1H), 3.95 (m, 1H), 5.09 (t, J=3.68 Hz, 1H), 7.22 (m, 4H); MS m/z 261.0 (M+H)$^+$.

EXAMPLE 179B

[2-methoxy-1-(3-methylbutyl)-1,4-dihydronaphthalen-1-yl]methyl Acetate

A mixture of Example 179A (0.18 g, 0.7 mmol), acetic anhydride (0.2 mL), and pyridin (1 mL) was stirred at room temperature for 18 h. The solution was diluted with water (3 mL) and extracted with ethyl acetate (2× 1 mL). The combined organic extracts were dried (Na$_2$SO$_4$) and concentrated in vacuo. Column chromatography on silica (hexane to 5% ethyl acetate/hexane) afforded product as a colorless oil (0.17 g, 81%). $^1$H NMR (300 MHz, CDCl$_3$) δ ppm 0.66 (m, 1H), 0.76 (dd, J=9.56, 6.62 Hz, 6H), 0.89 (m, 1H), 1.38 (m, 1H), 1.61 (m, 1H), 1.81 (s, 3H), 1.95 (m, 1H), 3.50 (s, 2H), 3.58 (s, 3H), 4.24 (d, J=10.66 Hz, 1H), 4.42 (d, J=10.66 Hz, 1H), 5.01 (t, J=3.49 Hz, 1H), 7.20 (m, 4H).

EXAMPLE 179C

[2-methoxy-1-(3-methylbutyl)-4-oxo-1,4-dihydronaphthalen-1-yl]methyl Acetate

To a solution of Example 179B (0.15 g, 0.5 mmol) in benzene (5 mL) was added celite (0.15 g), pyridinium dichromate (0.75 g, 2.0 mmol), and a solution of 70% t-butyl peroxide in water (0.25 mL, 2.0 mmol). The heterogenous solution was filtered through celite. The filtrate was diluted with ethyl acetate (10 mL), washed with 5% Na$_2$S$_2$O$_5$ (10 mL), dried (Na$_2$SO$_4$), and concentrated in vacuo. Column chromatography on silica (5% to 15% ethyl acetate/hexane gradient) afforded the product as colorless oil (0.12 g, 75%). $^1$H NMR (300 MHz, CDCl$_3$) δ ppm 0.53 (m, 1H), 0.76 (m, 7H), 1.35 (m, 1H), 1.73 (s, 3H), 1.80 (m, 1H), 2.09 (m, 1H), 3.84 (s, 3H), 4.51 (m, 2H), 5.97 (s, 1H), 7.43 (m, 2H), 7.59 (m, 1H), 8.20 (d, J=7.72 Hz, 1H); MS m/z 317.1 (M+H)$^+$.

EXAMPLE 179D

[1-(3-methylbutyl)-2,4-dioxo-1,2,3,4-tetrahydronaphthalen-1-yl]methyl Acetate

To a solution of Example 179C (0.12 g, 0.38 mmol) in acetonitrile (3.5 mL) was added iodotrimethylsilane (TMSI) (81 μL, 0.57 mmol). The reaction solution was stirred at room temperature for 3 h. After which, additional 1.5 equivalents of TMSI (81 μL) were added and stirring was continued for 2 h. The solution was quenched with water (3 mL) and extracted with ethyl acetate (2× 5 mL). The combined organic extracts were dried (Na$_2$SO$_4$) and concentrated in vacuo. Column chromatography on silica (70% ethyl acetate/hexane) afforded product as a white solid (91%). $^1$H NMR (300 MHz, CDCl$_3$) δ ppm 0.55 (s, 1H), 0.77 (m, 12H), 0.93 (m, 2H), 1.36 (m, 3H), 1.79 (m, 8H), 2.19 (m, 3H), 3.77 (m, 2H), 4.42 (d, J=11.03 Hz, 1H), 4.57 (m, 3H), 6.15 (s, 1H), 7.46 (m, 4H), 7.59 (m, 1H), 7.69 (m, 1H), 8.12 (m, 2H); MS m/z 303.0.

EXAMPLE 179E

[3-[bis(methylthio)methylene]-1-(3-methylbutyl)-2,4-dioxo-1,2,3,4-tetrahydronaphthalen-1-yl]methyl Acetate To a solution of Example 179D (50 mg, 0.17 mmol) in dioxane (1.5 mL) was added Example 5A (0.20 g, 0.83 mmol) followed by pyridine (67 μL, 0.83 mmol). The heterogeneous solution was heated at 55° C. for 3 h. The solution was cooled to room temperature and concentrated in vacuo. Column chromatography on silica (20% ethyl acetate/hexane) afforded product as an orange oil (60 mg, 90%). $^1$H NMR (300 MHz, CDCl$_3$) δ ppm 0.68 (m, 7H), 0.82 (m, 1H), 1.35 (m, 1H), 1.73 (m, 4H), 2.21 (m, 1H), 2.58 (s, 6H), 4.57 (m, 2H), 7.41 (m, 2H), 7.58 (m, 1H), 8.26 (d, J=7.72 Hz, 1H); MS m/z 407.0 (M+H)$^+$.

EXAMPLE 179F (4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl acetate A mixture of Example 179E (56 mg, 0.14 mmol) and Example 12A (33 mg, 0.12 mmol) in dioxane (1.5 mL) was heated at 85° C. for 18 h. The solution was cooled to room temperature and concentrated in vacuo. Column chromatography on silica (0-3% methanol/dichloromethane) afforded product as an off-white solid (41 mg, 58%). $^1$H NMR (300 MHz, CDCl$_3$) δ ppm 0.56 (m, 1H), 0.80 (m, 7H), 1.33 (m, 2H), 1.74 (s, 1H), 1.76 (s, 2H), 2.20 (m, 1H), 3.08 (s, 3H), 4.58 (m, 2H), 6.74 (s, 1H), 7.36 (t, J=7.91 Hz, 1H), 7.51 (m, 2H), 7.70 (m, 3H), 8.30 (d, J=6.99 Hz, 1H), 14.09 (s, 1H), 16.60 (s, 1H); MS m/z 576.1 (M+H)$^+$.

EXAMPLE 180

(4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl isopropylcarbamate

EXAMPLE 180A

[2-methoxy-1-(3-methylbutyl)-1,4-dihydronaphthalen-1-yl]methyl isopropylcarbamate To a solution of Example 179A (50 mg, 0.2 mmol) in dichloromethane (1 mL) was added triethylamine (0.13 mL, 1 mmol), 4-dimethylaminopyridine (9 mg, 0.08 mmol), and isopropyl isocyanate (0.1 mL, 1 mmol). The solution was stirred at room temperature for 18 h. After which, additional 5.0 equivalents (0.1 mL) of isopropyl isocyanate were added, and the solution was stirred for another 18 h. The solution was diluted with dichloromethane (2 mL), washed with water (2× 1 mL), dried (Na$_2$SO$_4$), and concentrated in vacuo. Column chromatography on silica (0-5% ethyl acetate/hexane) afforded product (39 mg, 59%). $^1$H NMR (300 MHz, CDCl$_3$) δ ppm 0.70 (m, 7H), 0.91 (m, 8H), 1.37 (m, 1H), 1.60 (m, 1H), 1.93 (m, 1H), 3.49 (d, J=3.68 Hz, 2H), 3.58 (s, 3H), 4.21 (d, J=10.30 Hz, 1H), 4.45 (d, J=10.30 Hz, 1H), 5.00 (t, J=3.68 Hz, 1H), 7.17 (m, 3H), 7.30 (m, 1H).

EXAMPLE 180B

[2-methoxy-1-(3-methylbutyl)-4-oxo-1,4-dihydronaphthalen-1-yl]methyl isopropylcarbamate To a solution of Example 180A (39 mg, 0.11 mmol) in benzene (1 mL) was added celite (39 mg), pyridinium dichromate (0.17 g, 0.45 mmol), and a solution of 70% t-butyl peroxide in water (58 μL, 0.45 mmol). The heterogenous solution was filtered through celite. The filtrate was diluted with ethyl acetate (3 mL), washed with 5% Na$_2$S$_2$O$_5$ (3 mL), dried (Na$_2$SO$_4$), and concentrated in vacuo. Column chromatography on silica (10%-20% ethyl acetate/hexane) afforded product as a white solid (33 mg, 83%). $^1$H NMR (300 MHz, CDCl$_3$) δ ppm 0.53 (m, 1H), 0.75 (m, 7H), 0.93 (d, J=5.88 Hz, 3H), 1.03 (d, J=5.88 Hz, 3H), 1.34 (m, 1H), 1.79 (m, 1H), 2.08 (m, 1H), 3.84 (s, 3H), 4.13 (m, 1H), 4.41 (d, J=10.30 Hz, 2H), 4.57 (m, 1H), 5.96 (s, 1H), 7.43 (m, 2H), 7.59 (m, 1H), 8.19 (d, J=7.72 Hz, 1H).

EXAMPLE 180C

[1-(3-methylbutyl)-2,4-dioxo-1,2,3,4-tetrahydronaphthalen-1-yl]methyl isopropylcarbamate To a solution of Example 180B (32 mg, 0.09 mmol) in acetonitrile (1 mL) was added iodotrimethylsilane (TMSI) (19 μL, 0.13 mmol). The reaction solution was stirred at room temperature for 3 h. After which, additional 1.5 equivalents of TMSI (19 μL) were added and stirring was continued for 2 h. The solution was quenched with water (2 mL) and extracted with ethyl acetate (2× 1 mL). The combined organic extracts were dried (Na$_2$SO$_4$) and concentrated in vacuo. Column chromatography on silica (70% ethyl acetate/hexane) afforded product as a white foam (24 mg, 77%). MS m/z 346.0 (M+H)$^+$

EXAMPLE 180D

[3-[bis(methylthio)methylene]-1-(3-methylbutyl)-2,4-dioxo-1,2,3,4-tetrahydronaphthalen-1-yl]methyl isopropylcarbamate To a solution of Example 180C (23 mg, 0.07 mmol) in dioxane (0.7 mL) was added Example 5A (82 mg, 0.3 mmol) followed by pyridine (27 μL, 0.3 mmol). The heterogeneous solution was heated at 55° C. for 3 h. The solution was cooled to room temperature and concentrated in vacuo. Column chromatography on silica afforded product as a yellow oil (14 mg, 47%).

EXAMPLE 180E (4-hydroxy-1-(3-methylbutyl)-3-{7-[(methylsulfonyl)amino]-1,1-dioxido-4H-1,2,4-benzothiadiazin-3-yl}-2-oxo-1,2-dihydronaphthalen-1-yl)methyl isopropylcarbamate A mixture of Example 180D (14 mg, 0.03 mmol) and Example 12A (7 mg, 0.03 mmol) in dioxane (0.3 mL) was heated at 85° C. for 18 h. The solution was cooled to room temperature and concentrated in vacuo. Column chromatography on silica (0-3% methanol/dichloromethane) afforded product as a light yellow solid (11 mg, 58%). $^1$H NMR (300 MHz, DMSO-d$_6$): δ ppm 0.43 (m, 1H), 0.68 (dd, J=9.38, 6.80 Hz, 6H), 0.85 (dd, J=16.36, 6.07 Hz, 6H), 1.29 (m, 1H), 1.98 (m, 3H), 3.06 (s, 3H), 4.48 (m, 2H), 6.72 (m, 1H), 7.55 (m, 6H), 8.14 (d, J=7.72 Hz, 1H), 10.17 (s, 1H); MS m/z 619.1 (M+H)$^+$.

EXAMPLE 181

N-{3-[1-hydroxy-4-(3-methylbutyl)-3-oxo-4-vinyl-3,4-dihydronaphthalen-2-yl]-1,1-dioxido-4H-1,2,4-benzothiadiazin-7-yl}methanesulfonamide

EXAMPLE 181A 2-methoxy-1-(3-methylbutyl)-1,4-dihydronaphthalene-1-carbaldehyde To a solution of Example 179A (0.6 g, 2.3 mmol) in dichloromethane (15 mL) was added Dess-Martin periodanate (1.5 g, 3.5 mmol). The solution was stirred at room temperature for 18 h and then concentrated in vacuo. Column chromatography on silica (10% -20%-30% dichloromethane/hexane) afforded product as a light yellow oil (0.32 g, 53%). $^1$H NMR (300 MHz, CDCl$_3$) δ ppm 0.63 (m, 1H), 0.76 (dd, J=12.13, 6.62 Hz, 6H), 0.92 (m, 1H), 1.41 (m, 1H), 1.93 (m, 1H), 2.18 (m, 1H), 3.59 (m, 5H), 5.19 (t, J=3.68 Hz, 1H), 7.01 (m, 1H), 7.21 (m, 3H), 9.40 (s, 1H).

EXAMPLE 181B 2-methoxy-1-(3-methylbutyl)-1-vinyl-1,4-dihydronaphthalene

To a suspension of methyltriphenylphosphonium bromide (0.62 g, 1.7 mmol) in tetrahydrofuran (3 mL) at 0° C. was added a solution of 1.0 M potassium t-butoxide in tetrahydrofuran (1.5 mL, 1.5 mmol). The mixture was allowed to warm to room temperature and stirred for 1 h. After which, the solution was cooled to 40° C. and a solution of Example 181A (0.15 g, 0.6 mmol) in tetrahydrofuran (3 mL) was added dropwise. The reaction mixture was stirred at −40° C. for 1 h, and then allowed to warm to room temperature and stirred for 2 h. The solution was quenched with saturated NH$_4$Cl solution (15 mL) and extracted with ethyl acetate (3× 10 mL). The combined organic extracts were dried (Na$_2$SO$_4$), filtered and concentrated in vacuo. Column chromatography on silica (hexane) afforded product as a colorless oil (0.13 g, 87%). $^1$H NMR (300 MHz, CDCl$_3$) δ ppm 0.63 (m, 1H), 0.77 (dd, J=12.87, 6.62 Hz, 6H), 0.90 (m, 1H), 1.40 (m, 1H), 1.79 (m, 1H), 2.17 (m, 1H), 3.50 (d, J=3.68 Hz, 2H), 3.59 (s, 3H), 4.99 (m, 3H), 6.00 (dd, J=17.65, 10.66 Hz, 1H), 7.16 (m, 4H).

EXAMPLE 181C 3-methoxy-4-(3-methylbutyl)-4-vinylnaphthalen-1(4H)-one

To a solution of Example 181B (0.13 g, 0.5 mmol) in benzene (5 mL) was added celite (0.13 g), pyridinium dichromate (0.38 g, 1.0 mmol), and a solution of 70% t-butyl peroxide in water (0.13 mL, 1.0 mmol). The heterogenous solution was filtered through celite. The filtrate was diluted with ethyl acetate (10 mL), washed with 5% Na$_2$S$_2$O$_5$ (10 mL), dried (Na$_2$SO$_4$), and concentrated in vacuo. Column Chromatography on silica (20% dichloromethane/hexane -15% ethyl acetate/hexane) afforded product as a light yellow oil (46 mg, 35%). $^1$H NMR (300 MHz, CDCl$_3$) δ ppm 0.51 (m, 1H), 0.76 (m, 7H), 1.37 (m, 1 H), 2.01 (m, 1H), 2.33 (m, 1H), 3.81 (s, 3H), 5.12 (m, 2H), 5.94 (m, 2H), 7.37 (m, 2H), 7.54 (m, 1H), 8.18 (d, J=8.09 Hz, 1H); MS m/z 270.9 (M+H)$^+$.

EXAMPLE 181D 4-(3-methylbutyl)-4-vinylnaphthalene-1,3(2H,4H)-dione

To a solution of Example 181C (42 mg, 0.16 mmol) in methanol (1 mL) was added a solution of 1 N NaOH (0.5 mL, 0.5 mmol). The reaction solution was stirred at 60° C. for 96 h. The solution was cooled to room temperature, acidified with 0.1 N HCl, and extracted with ethyl acetate (3× 1 mL). The combined organic extracts were dried (Na$_2$SO$_4$) and concentrated in vacuo. Column chromatography on silica (20%-40% ethyl acetate/hexane) afforded product as an off-white solid (24 mg, 60%).

EXAMPLE 181E

2-[bis(methylthio)methylene]-4-(3-methylbutyl)-4-vinylnaphthalene-1,3(2H,4H)-dione To a solution of Example 181D (18 mg, 0.07 mmol) in dioxane (1 mL) was added Example 5A (86 mg, 0.35 mmol) followed by pyridine (28 μL, 0.35 mmol). The heterogeneous solution was heated at 55° C. for 3 h. The solution was cooled to room temperature and concentrated in vacuo. Column chromatography on silica (0-5% ethyl acetate/hexane) afforded product as a yellow solid (20 mg, 80%).

EXAMPLE 181F

N-{3-[1-hydroxy-4-(3-methylbutyl)-3-oxo-4-vinyl-3,4-dihydronaphthalen-2-yl]-1,1-dioxido-4H-1,2,4-benzothiadiazin-7-yl}methanesulfonamide A mixture of Example 181E (20 mg, 0.06 mmol) and Example 12A (13 mg, 0.05 mmol) in dioxane (1 mL) was heated at 85° C. for 18 h. The solution was cooled to room temperature and concentrated in vacuo. Column chromatography on silica (1%-10% methanol/dichloromethane) afforded product as a light yellow solid (11 mg, 38%). $^1$H NMR (300 MHz, DMSO-$d_6$) δ ppm 0.51 (m, 1H), 0.77 (m, 7H), 1.37 (m, 1H), 1.88 (m, 1H), 2.47 (m, 1H), 3.00 (s, 3H), 4.71 (d, J=17.28 Hz, 1H), 4.98 (d, J=10.66 Hz, 1H), 5.94 (dd, J=17.46, 10.48 Hz, 1H), 7.42 (m, 6H), 8.09 (d, J=8.09 Hz, 1H), 9.92 (s, 1H), 15.16 (s, 1H); MS m/z 529.9 (M+H)$^+$.

EXAMPLE 182

N-[3-(1-hydroxy-4,4-dimethyl-3-oxo-3,4-dihydronaphthalen-2-yl)-1,1-dioxido-4H-1,2,4-benzothiadiazin-7-yl]methanesulfonamide A solution of Example 9G (50 mg, 0.17 mmol) and Example 12A (45 mg, 0.17 mmol) in dioxane (8 mL) at 85° C. for 10 h. The solvents were evaporated, and the crude residue was purified using preparative thin layer chromatography (0.5 mm, 20 cm×20 cm, 2 plates using 2% methanol in dichloromethane) to give the title compound (8 mg, 10%). $^1$H NMR (300 MHz, CDCl$_3$): δ ppm 1.6 (s, 6H), 3.06 (s, 3H), 7.59 (m, 3H), 7.77 (m, 3H), 8.18 (d, 1H), 10.24 (br s, 1H), 13.8 (br s, 1H); MS (DCI) m/z=479 (M+NH$_4$)$^+$.

EXAMPLE 183

[3-(1-hydroxy-3-oxo-4,4-dipropyl-3,4-dihydronaphthalen-2-yl)-1,1-dioxido-4H-1,2,4-benzothiadiazin-7-yl][methyl(oxido)-λ$^4$-sulfanylidyne]ammonium A solution of Example 71 (24 mg, 0.055 mmol) and triethylamine (33 mg, 0.33 mmol) in dichloromethane (2 mL) at 0° C. was added methanesulfinyl chloride (11 mg, 0.11 mmol). After 15 min, the reaction mixture was treated with triethylamine (14.5 mg, 0.165 mmol) and methanesulfinyl chloride (11 mg, 0.11 mmol). After 15 min, the reaction mixture was quenched with saturated ammonium chloride and extracted with dichloromethane (3×), the organic layers were combined, dried over sodium sulfate, filtered, and concentrated. The crude residue was purified using preparative thin layer chromatography (0.5 mm, 20 cm×20 cm, 2 plates using 5% methanol in dichloromethane) to give the title compound (16 mg, 58%). $^1$H NMR (300 MHz, CDCl$_3$): δ ppm 0.65 (m, 2H), 0.72 (m, 6H), 0.92 (m, 2H), 1.9 (m, 2H), 2.3 (m, 2H), 2.86 (s, 3H), 6.42 (s, 1H), 7.3 (m, 1H), 7.41 (m, 3H), 7.6 (m, 1H), 7.68 (m, 1H), 8.22 (d, 1H), 14.3 (2s, 1H), 16.6 (2s, 1H); MS (DCI) m/z=501 (M+NH$_4$)$^+$.

EXAMPLE 184

(1R)-1-(3,3-dimethylbutyl)-4-hydroxy-3-{7-[(methoxymethoxy)methyl]-1,1-dioxido-4H-thieno[2,3-e][1,2,4]thiadiazin-3-yl}-1-methylnaphthalen-2(1H)-one A solution of the product of Example 10E (2.02 g, 7.9 mmol) and the product of Example 49E (2.49 g, 6.9 mmol) in 200 mL of toluene was warmed to reflux for 5 h, cooled, and concentrated in vacuo. The crude material was chromatographed on silica gel with methanol/dichloromethane (1:99) to afford the title compound (3.03 g, 85% yield). $^1$H NMR (300 MHz, DMSO-$d_6$) δ ppm 0.39 (td, J=12.59, 3.13 Hz, 1H) 0.72 (s, 9H) 0.82 (m, 1H) 1.57 (s, 3H) 2.04 (m, 1H) 2.22 (td, J=12.69, 4.41 Hz, 1H) 3.33 (s, 3H) 4.63 (s, 2H) 4.71 (s, 2H) 7.40 (s, 1H) 7.53 (m, 1H) 7.74 (d, J=4.04 Hz, 2H) 8.13 (d, J=7.72 Hz, 1H) 14.00 (s, 1H); MS (APCI$^-$) m/z 517 (M−H)$^-$; Analysis calc'd for (C$_{25}$H$_{30}$N$_2$O$_6$S$_2$): C, 57.89; H, 5.83; N, 5.40. Found: C, 57.82; H, 6.12; N, 5.05.

EXAMPLE 185

(1R)-1-(3,3-dimethylbutyl)-4-hydroxy-3-[7-(hydroxymethyl)-1,1-dioxido-4H-thieno[2,3-e][1,2,4]thiadiazin-3-yl]-1-methylnaphthalen-2(1H)-one A solution of Example 184 (2.84 g, 5.5 mmol) in 20 mL of dioxane was cooled to 0° C., treated with 60 mL of 4N HCl in dioxane, allowed to warm to room temp, stirred for 2 hrs, and concentrated in vacuo to afford the title compound (2.96 g, 100% yield). $^1$H NMR (300 MHz, DMSO-$d_6$) δ ppm 0.39 (m, 1H), 0.72 (s, 9H), 0.82 (m, 1H), 1.56 (s, 3H), 2.03 (m, 1H), 2.22 (m, 1H), 4.61 (s, 2H), 7.26 (s, 1H), 7.52 (m, 1H), 7.74 (d, J=4.0 Hz, 2H), 8.13 (d, J=7.7 Hz, 1H), 14.07 (s, 1H); MS (APCI$^+$) m/z 475 (M+H)$^+$.

EXAMPLE 186

(1R)-3-[7-(aminomethyl)-1,1-dioxido-4H-thieno[2,3-e][1,2,4]thiadiazin-3-yl]-1-(3,3-dimethylbutyl)-4-hydroxy-1-methylnaphthalen-2(1H)-one

EXAMPLE 186A (1R)-3-[7-(azidomethyl)-1,1-dioxido-4H-thieno[2,3-e][1,2,4]thiadiazin-3-yl]-1-(3,3-dimethylbutyl)-4-hydroxy-1-methylnaphthalen-2(1H)-one A solution of Example 185 (1 g, 2.11 mmol) in 25 mL of dichloromethane was cooled to 0° C., treated with 1,8-diazabicyclo[5.4.0]undec-7-ene (1.7 mL, 11.2 mmol) and diphenylphosphoryl azide (2.3 mL, 10.9 mmol), allowed to warm to room temp, stirred for 16 h, and concentrated onto silica gel. The crude material was chromatographed on silica gel with hexane, hexane/dichloromethane (1:1), followed by dichloromethane, and methanol/dichloromethane (1:99) to afford the title compound (610 mg, 59% yield). $^1$H NMR (300 MHz, DMSO-$d_6$) δ ppm 0.39 (td, J=12.7, 3.3 Hz, 1H), 0.72 (s, 9H), 0.81 (td, J=13.1, 4.6 Hz, 1H), 1.57 (s, 3H), 2.05 (m, 1H), 2.22 (td, J=12.6, 4.6 Hz, 1H), 4.56 (s, 2H), 7.29 (m, J=8.6, 8.6 Hz, 1H), 7.54 (s, 1H), 7.74 (m, J=4.0 Hz, 2H), 8.13 (d, J=7.7 Hz, 1H), 14.09 (s, 1H); MS (APCI$^+$) m/z 498 (M+H)$^+$.

EXAMPLE 186B (1R)-3-[7-(aminomethyl)-1,1-dioxido-4H-thieno[2,3-e][1,2,4]thiadiazin-3-yl]-1-(3,3-dimethylbutyl)-4-hydroxy-1-methylnaphthalen-2(1H)-one A solution of Example 186A (17 mg, 0.03 mmol) in 2 mL of ethanol was degassed, treated with palladium on carbon (~1 mg, 10%), put under an atmosphere of hydrogen, stirred for 4 h at room temp, filtered through a plug of celite, and concentrated to afford a yellow solid. The crude material was chromatographed on silica gel with a gradient of methanol in dichloromethane (0-10%) to afford the title compound (8.2 mg, 51% yield). $^1$H NMR (300 MHz, DMSO-$d_6$) δ ppm 0.44 (m, 1H) 0.70 (s, 9H) 0.79 (m, 1H) 1.39 (s, 3H) 1.74 (m, J=3.31 Hz, 1H) 2.15 (td, J=12.41, 4.23 Hz, 1H) 4.12 (s, 2H) 7.22 (s, 1H) 7.33 (m, 1H) 7.48 (m, 2H) 8.04 (d, J=7.35 Hz, 1H) 8.17 (br. s, 2H) 16.99 (s, 1H); MS (APCI$^+$) m/z 474 (M+H)$^+$.

EXAMPLE 187

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)methanesulfonamide A solution of Example 186B (168 mg, 0.36 mmol) in 3 mL of N,N-dimethyl formamide was cooled to 0° C., treated with triethylamine (90 µL, 0.82 mmol) and methanesulfonyl chloride (32 µL, 0.41 mmol), allowed to warm to room temp, stirred for 2 h, diluted with water, and extracted with ethyl acetate. The organic phase was washed with water and concentrated in vacuo to afford a yellow foam. The concentrate was purified on silica gel with a gradient of methanol in dichloromethane (0-2%) to afford the title compound (150 mg, 76% yield). $^1$H NMR (500 MHz, C$_6$D$_6$) δ ppm 0.40 (m, 1H) 0.72 (s, 9H) 0.82 (m, 1H) 1.55 (s, 3H) 2.01 (m, 1H) 2.21 (td, J=12.66, 3.97 Hz, 1H) 2.97 (s, 3H) 4.28 (d, J=5.49 Hz, 2H) 7.30 (s, 1H) 7.49 (m, 1H) 7.66 (t, J=6.10 Hz, 1H) 7.70 (s, 2H) 8.12 (d, J=7.32 Hz, 1H) 14.42 (m, 1H); MS (APCI$^-$) m/z 550 (M–H)$^-$.

EXAMPLE 188

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)-N-methylmethanesulfonamide A solution of Example 187 (124 mg, 0.22 mmol) in 2 mL of N,N-dimethyl formamide was cooled to 0° C., treated with sodium hydride (24 mg, 60% in oil, 0.5 mmol), stirred at 0° C. for 1 h, stirred at room temp for 30 min, treated with methyl iodide (9 µL, 0.14 mmol), stirred for 2 h, treated with methyl iodide (7 µL, 0.11 mmol), and stirred at room temp over night. The mixture was diluted with water and ethyl acetate, treated with 1N HCl, and extracted with ethyl acetate. The organic phase was washed with 2× 10 mL of H$_2$O and concentrated in vacuo. The crude material was chromatographed on silica gel with a gradient of methanol in dichloromethane (0-5%) to afford the title compound (48 mg, 39% yield). $^1$H NMR (500 MHz, DMSO-$d_6$) δ ppm 0.40 (td, J=12.8, 3.7 Hz, 1H), 0.72 (s, 9H), 0.81 (td, J=12.9, 4.4 Hz, 1H), 1.56 (s, 3H), 2.01 (m, 1H), 2.21 (td, J=12.8, 4.6 Hz, 1H), 2.85 (s, 3H), 3.02 (s, 3H), 4.39 (s, 2H), 7.32 (s, 1H), 7.50 (m, 1H), 7.71 (m, 2H), 8.12 (d, J=7.8 Hz, 1H), 14.21 (s, 1H); MS (APCI$^-$) m/z 564 (M–H)$^-$.

EXAMPLE 189

N-({3-[(4R)-4-(3,3-dimethylbutyl)-1-hydroxy-4-methyl-3-oxo-3,4-dihydronaphthalen-2-yl]-4-methyl-1,1-dioxido-4H-thieno[2,3-e][1,2,4]thiadiazin-7-yl}methyl)-N-methylmethanesulfonamide A solution of Example 187 (124 mg, 0.22 mmol) in 2 mL of N,N-dimethylamide was cooled to 0° C., treated with sodium hydride (24 mg, 60% in oil, 0.5 mmol), stirred at 0° C. for 1 h, stirred at room temp for 30 min, treated with methyl iodide (9 µL, 0.14 mmol), stirred for 2 h, treated with methyl iodide (7 µL, 0.11 mmol), and stirred at room temp over night. The mixture was diluted with water and ethyl acetate, treated with 1N HCl, and extracted with ethyl acetate. The organic phase was washed with 2× 10 mL of H$_2$O and concentrated in vacuo. The crude material was chromatographed on silica gel with a gradient of methanol in dichloromethane (0-5%) to afford the title compound (67 mg, 53% yield). $^1$H NMR showed a mixture of two atropisomers: Major: $^1$H NMR (300 MHz, DMSO-$d_6$) δ ppm 0.41 (m, 1H), 0.69 (s, 9H), 0.85 (m, 1H), 1.34 (m, 3H), 1.66 (m, 1H), 2.13 (m, 1H), 2.86 (s, 3H), 3.02 (s, 3H), 3.49 (s, 3H), 4.40 (s, 2H), 7.28 (m, 2H), 7.42 (m, 2H), 7.95 (d, J=7.2 Hz, 1H), Minor: $^1$H NMR (300 MHz, DMSO-$d_6$) δ ppm 0.41 (m, 1H), 0.72 (s, 9H), 0.85 (m, 1H), 1.34 (m, 3H), 1.66 (m, 1H), 2.13 (m, 1H), 2.86 (s, 3H), 3.02 (s, 3H), 3.44 (s, 3H), 4.40 (s, 2H), 7.28 (m, 2H), 7.42 (m, 2H), 7.95 (d, J=7.2 Hz, 1H); MS (APCI$^+$) m/z 580 (M+H)$^+$.

EXAMPLE 190

Benzyl [({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)amino]sulfonylcarbamate A solution of chlorosulfonylisocyanate (9 µL, 0.1 mmol) in 1 mL of dichloromethane was treated with benzyl alcohol (10 µL, 0.9 mmol), stirred for 30 minutes, treated with a solution of Example 186B (36 mg, 0.07 mmol) and triethylamine (40 µL, 0.3 mmol) in 1 mL of dichloromethane, stirred for 1.5 h, diluted with dichloromethane, washed with 1 N aqueous HCl and water, and concentrated in vacuo. The crude material was purified by chromatography on silica gel with a gradient of methanol in dichloromethane (0-3%) to afford the title compound (34 mg, 67%). $^1$H NMR (300 MHz, DMSO-$d_6$) δ ppm 0.40 (td, J=12.9, 3.7 Hz, 1H), 0.72 (s, 9H), 0.81 (td, J=12.8, 4.6 Hz, 1H), 1.54 (s, 3H), 2.04 (m, 1H), 2.20 (m, 1H), 4.27 (d, J=5.5 Hz, 2H), 5.17 (s, 2H), 7.19 (s, 1H), 7.37 (m, 5H), 7.49 (m, 1H), 7.62 (s, 1H), 7.70 (d, J=3.7 Hz, 2H), 8.11 (d, J=7.7 Hz, 1H), 8.55 (t, J=6.3 Hz, 1H), 11.52 (s, 1H), 14.44 (s, 1H); MS (APCI$^-$) m/z 685 (M–H)$^-$, m/z 472 (M–[SO$_2$NHCbz]–H)—.

EXAMPLE 191

N-({3-[(4R)-4-(3,3-dimethylbutyl)-1-hydroxy-4-methyl-3-oxo-3,4-dihydronaphthalen-2-yl]-1,1-dioxido-4H-thieno[2,3-c][1,2,4]thiadiazin-7-yl}methyl)sulfamide A solution of Example 190 (28 mg, 0.04 mmol) in 2 mL of methanol was degassed, treated with 10% palladium on carbon (12 mg, 43 wt %), put under an atmosphere of hydrogen, stirred for 20 h, filtered through filter paper, and concentrated in vacuo to afford the title compound (21 mg, 95%). $^1$H NMR (300 MHz, DMSO-d$_6$) δ ppm 0.39 (m, 1H), 0.72 (s, 9H), 0.82 (m, 1H), 1.55 (s, 3H), 2.00 (m, 1H), 2.21 (td, J=13.0, 4.6 Hz, 1H), 4.21 (d, J=5.5 Hz, 2H), 6.77 (s, 2H), 7.21 (t, J=6.6 Hz, 1H), 7.26 (s, 1H), 7.50 (m, 1H), 7.71 (d, J=4.0 Hz, 2H), 8.12 (d, J=8.1 Hz, 1H), 14.34 (s, 1H); MS (APCI$^-$) m/z 551 (M–H)$^-$.

EXAMPLE 192

3-chloro-N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)propane-1-sulfonamide A solution of Example 186B (64 mg, 0.14 mmol) in 1.5 mL of N,N-dimethyl formamide was cooled to 0° C., treated with triethylamine (30 µL, 0.28 mmol) and 3-chloropropylsulfonyl chloride (19 µL, 0.15 mmol), stirred for 30 minutes, allowed to warm to room temp, stirred for 2 h, diluted with water and extracted with ethyl acetate. The organic phase was washed with water and concentrated in vacuo to afford a solid. This crude material was purified by chromatography on silica gel with a gradient of methanol in dichloromethane (0-2%) to afford the title compound as a pale compound (42 mg, 64%). $^1$H NMR (300 MHz, DMSO-d$_6$) δ ppm 0.39 (td, J=12.8, 3.5 Hz, 1H), 0.72 (s, 9H), 0.82 (m, 1H), 1.56 (s, 3H), 2.13 (m, 4H), 3.21 (m, 2H), 3.75 (t, J=6.4 Hz, 2H), 4.28 (d, J=5.9 Hz, 2H), 7.33 (s, 1H), 7.51 (m, 1H), 7.72 (m, 2H), 7.90 (t, J=6.3 Hz, 1H), 8.13 (d, J=7.7 Hz, 1H), 14.09 (s, 1H); MS (APCI$^-$) m/z 612 (M–H)$^-$; Anal calc'd for C$_{26}$H$_{32}$ClN$_3$O$_6$S$_3$: C, 50.84; H, 5.25; N, 6.84. found: C, 51.07; H, 5.28; N, 6.51.

EXAMPLE 193

(1R)-1-(3,3-dimethylbutyl)-3-{7-[(1,1-dioxido-isothiazolidin-2-yl)methyl]-1,1-dioxido-4H-thieno[2,3-e][1,2,4]thiadiazin-3-yl}-4-hydroxy-1-methyl-naphthalen-2(1H)-one A solution of Example 192 (41 mg, 0.07 mmol) in 10 mL of ethanol was treated with sodium ethoxide (50 mg, 0.73 mmol), stirred for 24 h, quenched with 1 N aqueous HCl, and diluted with water. A white precipitate formed and was collected by filtration and purified by chromatography on silica gel with a gradient of methanol in dichloromethane (0-2%) to afford the title compound (23 mg, 60%). $^1$H NMR (300 MHz, DMSO-d$_6$) δ ppm 0.39 (td, 1H), 0.72 (s, 9H), 0.82 (m, 1H), 1.57 (s, 3H), 2.06 (m, J=17.6 Hz, 1H), 2.22 (m, 1H), 2.30 (m, 2H), 3.29 (t, J=7.35 Hz, 2H), 3.32 (t, J=6.6 Hz, 2H), 4.24 (s, 2H), 7.34 (s, 1H), 7.51 (m, 1H), 7.74 (m, J=3.7 Hz, 2H), 8.13 (d, J=7.7 Hz, 1H), 14.07 (s, 1H); MS (APCI$^+$) m/z 578 (M+H)$^+$.

EXAMPLE 194

Potassium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate Placed 245.12 mg of the product of Example 49-7 into a 10 mL receiver flask. Added 6 mL of 50/50 ethanol/water. Warmed to in an oil bath on a hot-plate set to 90° C. and added 29.02 mg of potassium hydroxide. Solution clarified. Cooled in 10° C. increments to 55° C. Solid precipitated. Cooled to 40° C. and held for -1 hour. Cooled to ambient temperature and stirred overnight. Collected solid via vacuum filtration the next morning and dried the solid at 50° C./vacuum for 3 days.

EXAMPLE 195

Calcium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate Placed 52.71 mg of the product of Example 49-7 into a 3 mL reactivial. Added 300 µL of isopropyl alcohol and warmed on a hot-plate. Added 7.34 mg of calcium hydroxide. Solution clarified. Allowed to cool to ambient temperature. Apparent precipitate formed upon cool down. Warmed vial at 40° C. for approximately 20 minutes. No apparent change in precipitate. Allowed to stir at ambient for 6 days. Collected solid by vacuum filtration.

EXAMPLE 196

Magnesium (4R)-4-(3,3-dimethylbutyl)-4-methyl-2-{7-[(methylsulfonyl)amino]-1,1-dioxido-4H-1,2,4-benzothiadiazin-3-yl}-3-oxo-3,4-dihydronaphthalen-1-olate Placed 42.59 mg of the product of Example 49-7 into a 3 mL reactivial. Added 600 µL of 50/50 ethanol/water. Added 2.51 mg of calcium hydroxide. Warmed to boiling, solution clarified. Allowed to cool to ambient. Stirred overnight at ambient. No apparent change the next morning. Loosened the caps on the vials and continued stirring at ambient. 3 days later, there was an apparent gel/faint white precipitate in the vial. Warmed to 50° C., whereby suspension clarified. Capped vials and allowed to cool to ambient. Precipitate formed. Added 100 µL of water and broke up the precipitate. Added an additional 100 µL of water. Stirred at 40° C. overnight. Cooled to ambient and collected solid by vacuum filtration.

The following additional compounds of the present invention, can be prepared by one skilled in the art using known synthetic methodology or by using analogous synthetic methodology described in the Schemes and Examples contained herein, with appropriate manipulation and protection of chemical functionality. If a substituent described herein is not compatible with the synthetic methods of this invention, the substituent may be protected with a suitable protecting group that is stable to the reaction conditions used in these methods. The protecting group may be removed at a suitable point in the reaction sequence of the method to provide a desired target molecule. Suitable protecting groups and the methods for protection and deprotection are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. The additional compounds encompassed by the following tables can be described by taking one core from Table 1 (wherein — represents a single bond or is absent), R$^1$ and R$^2$ substituents from Table 2 (wherein X, represents the core ring structures), R$^3$ and R$^4$ substituents from Table 3 when necessary, and Y from Table 4

TABLE 1
Examples of Core Ring Structures
1
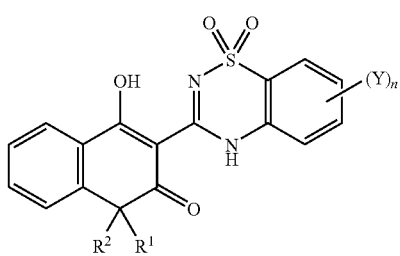
2
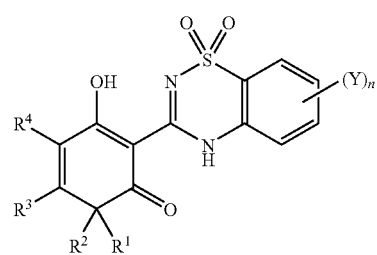
3
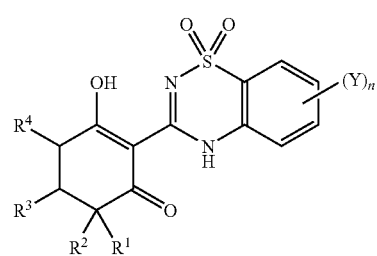
4
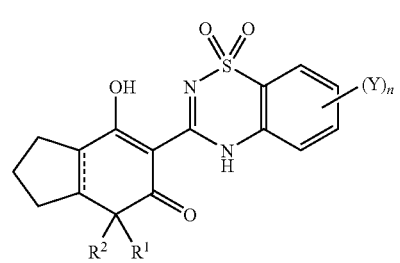
5
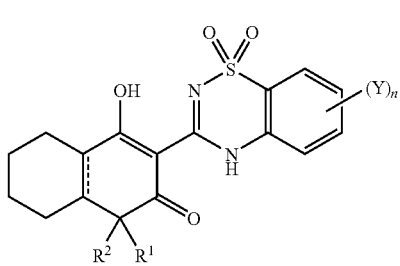
TABLE 1-continued
Examples of Core Ring Structures
6
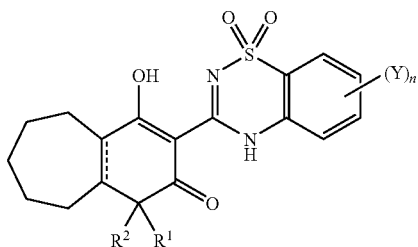
7
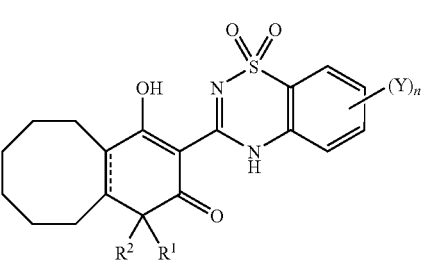
8
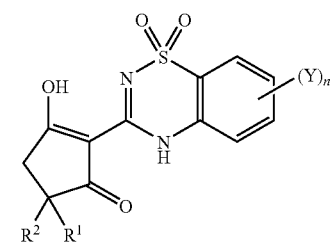
9
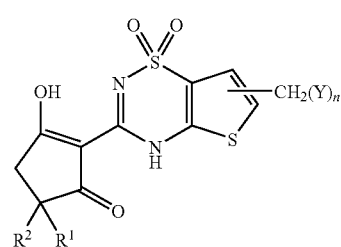
10
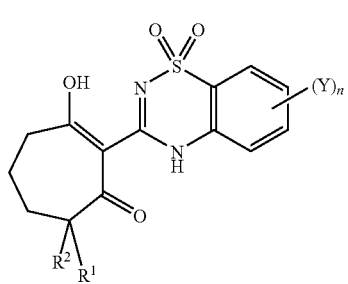

TABLE 1-continued
Examples of Core Ring Structures
12
13
TABLE 2
Examples of $R^1$ and $R^2$ Substituents
1  $X_1$—H
2  $X_1$—CH$_3$
3
4
5
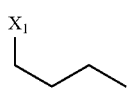
6
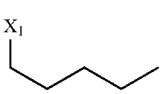
TABLE 2-continued
Examples of $R^1$ and $R^2$ Substituents
7
8
9
10
11
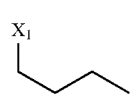
12
TABLE 3
Examples of $R^3$ and $R^4$ Substituents
1  $X_1$—H
2  $X_1$—CH$_3$
3
4
5

TABLE 4
Examples of Y substituent
1 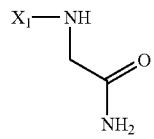
2 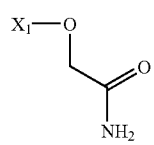
3 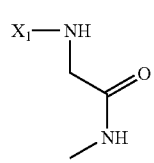
4 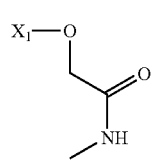
5 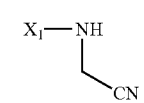
6 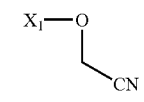
7 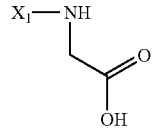
8 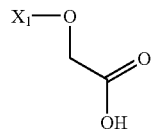
9  X₁—Cl
10  X₁—F
11  X₁—NHCH₃
12  X₁—OCH₃
13 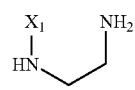
TABLE 4-continued
Examples of Y substituent
14 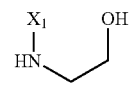
15 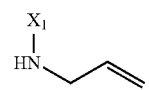
16 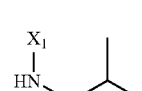
17 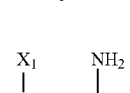
18 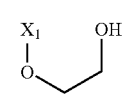
19 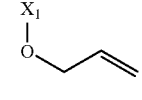
20 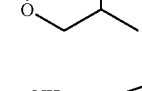
21 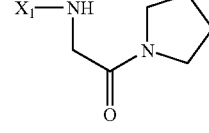
22 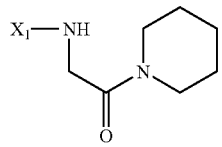
23 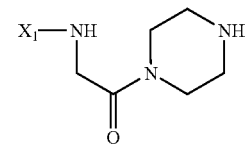
24

TABLE 4-continued
Examples of Y substituent
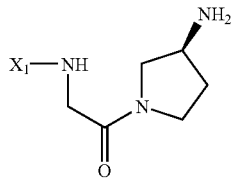
26
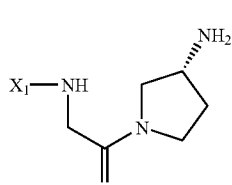
27
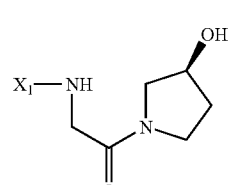
28
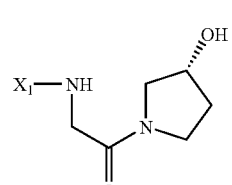
29
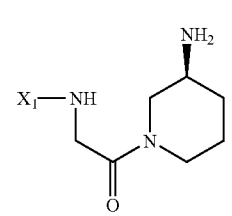
30
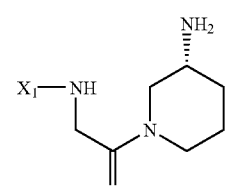
31
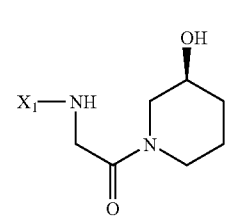
32
TABLE 4-continued
Examples of Y substituent
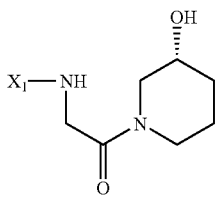
33
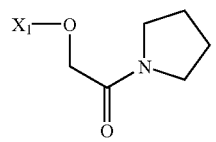
34
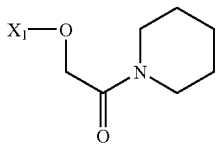
35
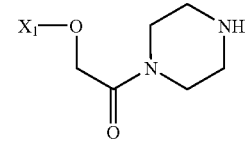
36
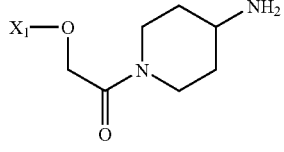
37
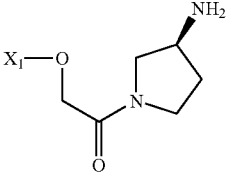
38
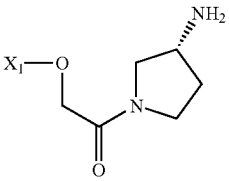
39
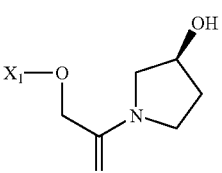
40

TABLE 4-continued
Examples of Y substituent
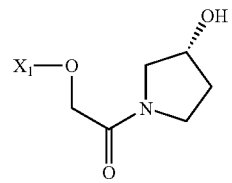
40
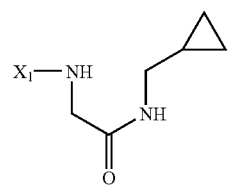
41
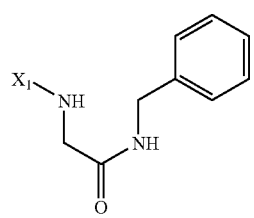
42
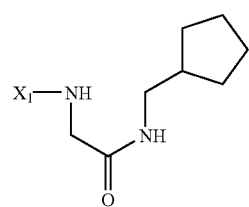
43
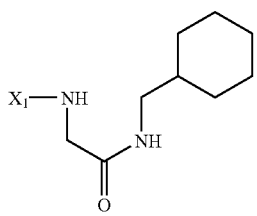
44
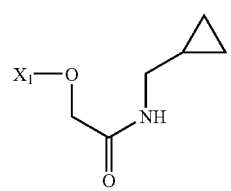
45
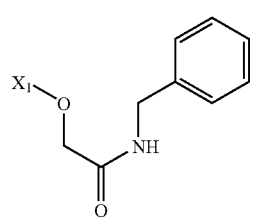
46
TABLE 4-continued
Examples of Y substituent
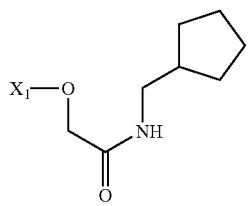
47
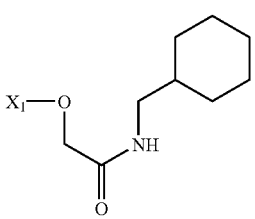
48
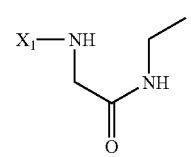
49
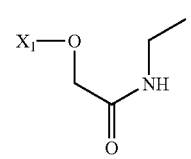
50
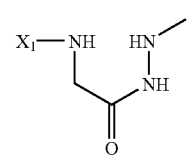
51
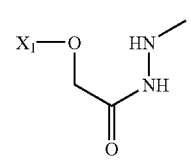
52
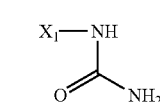
53
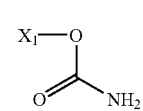
54

TABLE 4-continued

| Examples of Y substituent | |
|---|---|
| (structure) | 56 |
| (structure) | 57 |
| (structure) | 58 |
| (structure) | 59 |
| (structure) | 60 |
| (structure) | 61 |
| (structure) | 62 |
| (structure) | 63 |
| (structure) | 64 |
| (structure) | 65 |

TABLE 4-continued

| Examples of Y substituent | |
|---|---|
| (structure) | 66 |
| (structure) | 67 |
| (structure) | 68 |
| (structure) | 69 |
| (structure) | 70 |
| (structure) | 71 |
| (structure) | 72 |
| (structure) | 73 |
| (structure) | 74 |

TABLE 4-continued
Examples of Y substituent
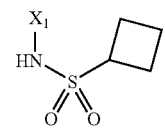
75
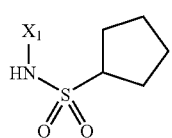
76
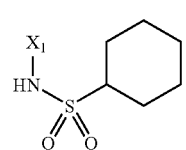
77
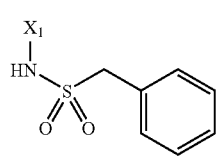
78
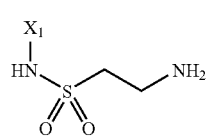
79
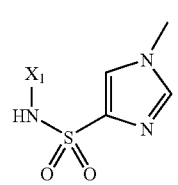
80
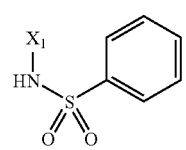
81
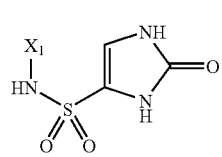
82
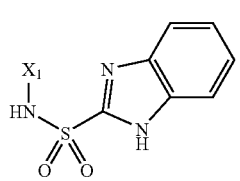
83
TABLE 4-continued
Examples of Y substituent
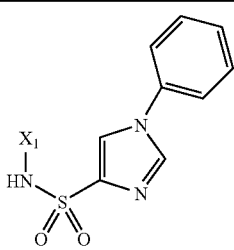
84
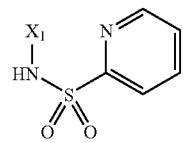
85
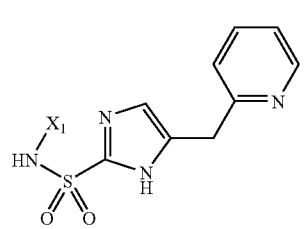
86
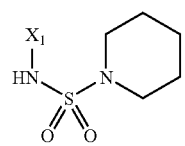
87
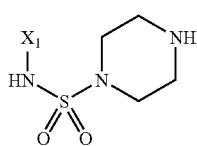
88
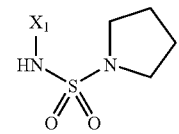
89
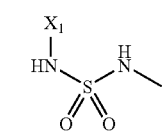
90
91

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound, a stereoisomer of the compound, a tautomer of the compound, a pharmaceutically acceptable salt of the compound, stereoisomer, or tautomer, or a combination thereof, wherein:

the compound corresponds to formula (I):

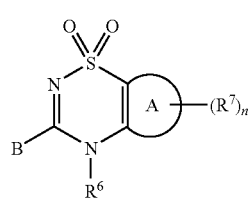

(I)

B is selected from the group consisting of

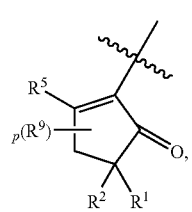

(a)

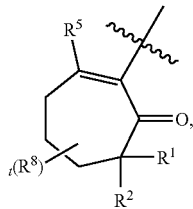

(b)

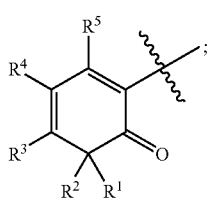

(c) , and (d) ;

A is thienyl;

as to $R^1$ and $R^2$:
  $R^1$ is selected from the group consisting of hydrogen, alkyl, alkenyl, alkynyl, —C(O)OR$_a$, —C(O)NR$_a$R$_b$, and R$_{1p}$, wherein:
    each of the alkyl, alkenyl, and alkynyl is substituted with 0, 1, or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, —C(R$_e$)=CR$_j$R$_k$, and R$_{1q}$; and $R^2$ is selected from the group consisting of hydrogen, alkyl, alkenyl, and alkynyl, wherein:
    each of the alkyl, alkenyl, and alkynyl is substituted with 0, 1, or 2 substituents independently selected from the group consisting of cyano, formyl, halo, nitro, oxo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)OR$_a$, —N(R$_e$)C(O)NR$_a$R$_b$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, —N=CR$_j$R$_k$, and R$_{2q}$; or, alternatively, $R^1$ and $R^2$, together with the carbon atom to which they are attached, form a monocyclic ring selected from the group consisting of cycloalkyl and cycloalkenyl, wherein:
    each of the cycloalkyl and cycloalkenyl is substituted with 0, 1, 2, or 3 substituents independently selected from the group consisting of halo, —OH, —O(alkyl), —NH$_2$, —N(H)(alkyl), —N(alkyl)$_2$, alkyl, and haloalkyl;

as to $R^3$ and $R^4$:
  $R^3$ is selected from the group consisting of hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, and R$_{3p}$, wherein:
    each of the alkyl, alkenyl, and alkynyl is substituted with 0, 1, 2, or 3 substituents independently selected from the group consisting of cyano, formyl, oxo, halo, nitro, —OR$^a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{3q}$; and $R^4$ is selected from the group consisting of hydrogen, cyano, formyl, halo, oxo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, alkyl, alkenyl, alkynyl, and R$_{4p}$, wherein:
    each of the alkyl, alkenyl, and alkynyl is substituted with 0, 1, 2, or 3 substituents independently selected from the group consisting of cyano, formyl, oxo, halo, nitro, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{4q}$; or, alternatively, $R^3$ and $R^4$, together with the carbon atoms to which they are attached, form a ring selected from the group consisting of aryl, heteroaryl, cycloalkyl, cycloalkenyl, and heterocycle, wherein:
    each of the of aryl, heteroaryl, cycloalkyl, cycloalkenyl, and heterocycle is substituted with $(R^8)_m$;

$R^5$ is selected from the group consisting of —OR$_d$, —SR$_d$, —NR$_d$R$_e$, —N(H)C(O)R$_d$, —N(H)C(O)OR$_d$, —N(H)SO$_2$R$_d$, and —N(H)SO$_2$NR$_d$R$_e$;

$R^6$ is selected from the group consisting of hydrogen, alkyl, alkenyl, alkynyl, and -alkylR$_{106}$;

$R^7$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OP(=O)(R$_e$)(OR$_e$), —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(=NH)R$_e$, —N(R$_e$)C(=Nalkyl)R$_e$, —N(R$_e$)C(O)R$_a$, —N(R$_e$)C(O)NR$_a$R$_b$, —N(R$_e$)C(=S)NR$_a$R$_b$, —N(R$_e$)C(=S)N(R$_e$)C(O)R$_a$, —N(R$_e$)C(O)OR$_a$, —N(R$_e$)SOR$_a$, —N(R$_e$)SO$_2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7p}$, wherein:
  each of the alkyl, alkenyl, and alkynyl is substituted with 0, 1, 2, or 3 substituents independently selected from the group consisting of cyano, formyl, oxo, nitro, halo, —N$_3$, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SOR$_a$, —N(R$_e$)SO$_a2$R$_a$, —N(R$_e$)SO$_2$NR$_a$R$_b$, —N(R$_e$)SO$_2$N(R$_e$)C(O)R$_a$, —N(R$_e$)SO$_2$N(R$_e$)C(O)OR$_a$, —C(O)R$_a$, —C(O)OR$_a$, —C(O)NR$_a$R$_b$, and R$_{7q}$;

R$^8$ at each occurrence is independently selected from the group consisting of cyano, formyl, nitro, oxo, halo, alkyl, alkenyl, alkynyl, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8p}$, wherein:
each of the alkyl, alkenyl, and alkynyl is substituted with 0, 1, 2, or 3 substituents independently selected from the group consisting of cyano, formyl, nitro, oxo, halo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{8q}$;

R$^9$ at each occurrence is independently selected from the group consisting of alkyl, alkenyl, alkynyl, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{9p}$, wherein:
each of the alkyl, alkenyl, and alkynyl is substituted with 0, 1, 2, or 3 substituents independently selected from the group consisting of cyano, formyl, nitro, oxo, halo, —OR$_a$, —OC(O)R$_a$, —OC(O)OR$_a$, —OC(O)NR$_a$R$_b$, —OSO$_2$R$_a$, —OSO$_2$NR$_a$R$_b$, —SR$_a$, —S(O)R$_a$, —SO$_2$R$_a$, —SO$_2$OR$_a$, —SO$_2$NR$_a$R$_b$, —NR$_a$R$_b$, —N(R$_e$)C(O)R$_a$, —N(R$_e$)C(O)NR$_a$R$_b$, —N(R$_e$)C(O)OR$_a$, —N(R$_e$)SO$_2$R$_a$, —N(R$_e$)SO$_2$NR$_a$R$_b$, —N(R$_e$)SO$_2$N(R$_e$)C(O)OR$_a$, —C(O)R$_a$, —C(O)OR$_a$, —C(O)NR$_a$R$_b$, and R$_{9q}$;

R$^{10}$ is selected from the group consisting of hydrogen and alkyl;

R$^{11}$ is selected from the group consisting of hydrogen and alkyl;

as to R$_a$ and R$_b$:
R$_a$ at each occurrence is independently selected from the group consisting of hydrogen, alkyl, alkenyl, alkynyl, and R$_p$, wherein:
each of the alkyl, alkenyl, and alkynyl is substituted with 0, 1, 2, or 3 substituents independently selected from the group consisting of cyano, formyl, oxo, halo, nitro, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, —C(O)N(R$_e$)NR$_c$R$_d$, and R$_q$; and R$_b$ at each occurrence is independently selected from the group consisting of hydrogen, alkyl, alkenyl, alkynyl, R$_{106}$, haloalkyl, hydroxyalkyl, alkoxyalkyl, and -alkylR$_{106}$; or, alternatively, R$_a$ and R$_b$, together with the nitrogen atom to which they are attached, form a ring selected from the group consisting of heterocycle and heteroaryl, wherein:
each of the heterocycle and heteroaryl is substituted with 0, 1, 2, or 3 substituents independently selected from the group consisting of alkyl, alkenyl, alkynyl, cyano, formyl, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, and —C(O)NR$_c$R$_d$, wherein:
each of the alkyl, alkenyl, and alkynyl is substituted with 0, 1, or 2 substituents independently selected from the group consisting of cyano, halo, nitro, oxo, —OR$_c$, —OC(O)R$_c$, —OC(O)OR$_c$, —OC(O)NR$_c$R$_d$, —OSO$_2$R$_c$, —OSO$_2$NR$_c$R$_d$, —SR$_c$, —S(O)R$_c$, —SO$_2$R$_c$, —SO$_2$OR$_c$, —SO$_2$NR$_c$R$_d$, —NR$_c$R$_d$, —N(R$_e$)C(O)R$_c$, —N(R$_e$)C(O)NR$_c$R$_d$, —N(R$_e$)C(O)OR$_c$, —N(R$_e$)SO$_2$R$_c$, —N(R$_e$)SO$_2$NR$_c$R$_d$, —N(R$_e$)SO$_2$N(R$_e$)C(O)OR$_c$, —C(O)R$_c$, —C(O)OR$_c$, —C(O)NR$_c$R$_d$, and R$_q$;

as to R$_c$ and R$_d$:
R$_c$ at each occurrence is independently selected from the group consisting of hydrogen, alkyl, alkenyl, alkynyl, and R$_{103}$, wherein:
each of the alkyl, alkenyl, and alkynyl is substituted with 0, 1, 2, or 3 substituents independently selected from the group consisting of cyano, formyl, oxo, halo, nitro, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$; and R$_d$ at each occurrence is independently selected from the group consisting of hydrogen, alkyl, alkenyl, alkynyl, R$_{106}$, haloalkyl, alkoxyalkyl, hydroxyalkyl, and -alkylR$_{106}$; or, alternatively, R$_c$ and R$_d$, together with the nitrogen atom to which they are attached, form a ring selected from the group consisting of heterocycle and heteroaryl, wherein:
each of the heteroaryl and heterocycle is substituted with 0, 1, 2, or 3 substituents independently selected from the group consisting of alkyl, alkenyl, alkynyl, cyano, formyl, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$OR$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(E$_e$)SO$_2$N(R$_e$)C(O)OR$_f$, —C(O)R$_f$, —C(O)OR$_f$ and —C(O)NR$_f$R$_g$, wherein:
each of the alkyl, alkenyl, and alkynyl is substituted with 0, 1, 2, or 3 substituents independently selected from the group consisting of cyano, halo, nitro, oxo, —OR$_f$, —OC(O)R$_f$, —OC(O)OR$_f$, —OC(O)NR$_f$R$_g$, —OSO$_2$R$_f$, —OSO$_2$NR$_f$R$_g$, —SR$_f$, —S(O)R$_f$, —SO$_2$R$_f$, —SO$_2$NR$_f$R$_g$, —NR$_f$R$_g$, —N(R$_e$)C(O)R$_f$, —N(R$_e$)C(O)NR$_f$R$_g$, —N(R$_e$)C(O)OR$_f$, —N(R$_e$)SO$_2$R$_f$, —N(R$_e$)SO$_2$NR$_f$R$_g$, —N(R$_e$)SO$_2$N(R$_e$)C(O)OR$_f$, —C(O)R$_f$, —C(O)OR$_f$, —C(O)NR$_f$R$_g$, and R$_{103}$;

R$_e$ at each occurrence is independently selected from the group consisting of hydrogen, alkyl, alkenyl, alkynyl, R$_{106}$, haloalkyl, and alkylR$_{106}$;

as to R$_f$ and R$_g$:

R$_f$ at each occurrence is independently selected from the group consisting of hydrogen, alkyl, alkenyl, alkynyl, and R$_{103}$, wherein:

each of the alkyl, alkenyl, and alkynyl is substituted with 0, 1, 2, or 3 substituents independently selected from the group consisting of cyano, nitro, halo, oxo, —OH, —O(alkyl), —O(cyanoalkyl), —O(haloalkyl), —O(R$_{106}$), —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$; and R$_g$ at each occurrence is independently selected from the group consisting of hydrogen, alkyl, alkenyl, alkynyl, R$_{106}$, haloalkyl, and -alkylR$_{106}$; or, alternatively, R$_f$ and R$_g$, together with the nitrogen atom to which they are attached, form a ring selected from the group consisting of heterocycle and heteroaryl, wherein:

each of the heterocycle and heteroaryl is substituted with 0, 1, 2, or 3 substituents independently selected from the group consisting of alkyl, alkenyl, alkynyl, cyano, formyl, halo, nitro, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), N(alkyl)(R$_{106}$), C(O)OH, —C(O)Oalkyl, —C(O)NH$_2$, —C(O)N(H)(alkyl), and —C(O)N(alkyl)$_2$, wherein:

each of the alkyl, alkenyl, and alkynyl is substituted with 0, 1, 2, or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

as to R$_j$ and R$_k$:

R$_j$ at each occurrence is independently selected from the group consisting of hydrogen, alkyl, alkenyl, alkynyl, R$_{103}$, haloalkyl, and -alkylR$_{103}$; and R$_k$ at each occurrence is independently selected from the group consisting of hydrogen, alkyl, alkenyl, and alkynyl; or, alternatively, R$_j$ and R$_k$, together with the carbon atom to which they are attached, form a ring selected from the group consisting of cycloalkyl, cycloalkenyl, heterocycle, aryl and heteroaryl, wherein:

each ring is substituted with 0, 1, 2, 3, 4, or 5 substituents independently selected from the group consisting of alkyl, alkenyl, alkynyl, nitro, cyano, formyl, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl) and —C(O)N(alkyl)$_2$, wherein:

each of the alkyl, alkenyl, and alkynyl is substituted with 0, 1, 2, or 3 substituents independently selected from the group consisting of cyano, nitro, halo, oxo, —OH, —O(alkyl), —O(cyanoalkyl), —O(haloalkyl), —OR$_{106}$, —NH$_2$, —N(H)(alkyl), —N(alkyl)$_2$, —N(H)(R$_{106}$), —N(alkyl)(R$_{106}$), —C(O)OH, —C(O)Oalkyl, —C(O)NH$_2$, —C(O)N(H)(alkyl), —C(O)N(alkyl)$_2$, and R$_{103}$;

m is selected from the group consisting of 0, 1, 2, 3, and 4;
n is selected from the group consisting of 0, 1, 2, 3, and 4;
p is selected from the group consisting of 0, 1, and 2;
t is selected from the group consisting of 0, 1, 2, 3, and 4;
R$_p$, R$_q$, R$_{1p}$, R$_{1q}$, R$_{2q}$, R$_{3p}$, R$_{3q}$, R$_{4p}$, R$_{4q}$, R$_{7p}$, R$_{7q}$, R$_{8p}$, R$_{8q}$, R$_{9p}$, and R$_{9q}$, at each occurrence, are independently selected from the group consisting of cycloalkyl, cycloalkenyl, aryl, heteroaryl, and heterocycle; wherein:

each of the cycloalkyl, cycloalkenyl, aryl, heteroaryl, and heterocycle is substituted with 0, 1, 2, 3, 4, or 5 substituents independently selected from the group consisting of alkyl, alkenyl, alkynyl, cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, —SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{101}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$, wherein:

each of the alkyl, alkenyl, and alkynyl is substituted with 0, 1, 2, or 3 substituents independently selected from the group consisting of cyano, formyl, halo, nitro, oxo, —OR$_{101}$, —OC(O)R$_{101}$, —OC(O)OR$_{101}$, —OC(O)NR$_{101}$R$_{102}$, —OSO$_2$R$_{101}$, —OSO$_2$NR$_{101}$R$_{102}$, —SR$_{101}$, —S(O)R$_{101}$, —SO$_2$R$_{101}$, SO$_2$OR$_{101}$, —SO$_2$NR$_{101}$R$_{102}$, —NR$_{101}$R$_{102}$, —N(R$_{102}$)C(O)R$_{101}$, —N(R$_{102}$)C(O)OR$_{101}$, —N(R$_{102}$)C(O)NR$_{101}$R$_{102}$, —N(R$_{102}$)SO$_2$R$_{101}$, —N(R$_{102}$)SO$_2$NR$_{101}$R$_{102}$, —N(R$_{102}$)SO$_2$N(R$_{102}$)C(O)OR$_{101}$, —C(O)R$_{101}$, —C(O)OR$_{101}$, and —C(O)NR$_{101}$R$_{102}$;

as to R$_{101}$ and R$_{102}$:

R$_{101}$ at each occurrence is independently selected from the group consisting of hydrogen, alkyl, alkenyl, alkynyl, R$_{103}$, -alkylR$_{103}$, -alkenylR$_{103}$, -alkynylR$_{103}$, haloalkyl, cyanoalkyl, -alkylC(O)R$_{104}$, -alkylC(O)OR$_{104}$, -alkylC(O)NR$_{104}$R$_{105}$, -alkyl-OR$_{104}$, -alkyl-OC(O)R$_{104}$, -alkyl-OC(O)OR$_{104}$, -alkylSR$_{104}$, -alkylS(O)R$_{104}$, -alkylSO$_2$R$_{104}$, -alkylSO$_2$OR$_{104}$, -alkylSO$_2$NR$_{104}$R$_{105}$, -alkylNR$_{104}$R$_{105}$, -alkylN(R$_{105}$)C(O)R$_{104}$, -alkylN(R$_{105}$)C(O)OR$_{104}$, -alkylN(R$_{105}$)C(O)NR$_{104}$R$_{105}$, -alkylN(R$_{105}$)SO$_2$R$_{104}$, and -alkylN(R$_{105}$)SO$_2$NR$_{104}$R$_{105}$; and R$_{102}$ at each occurrence is independently selected from the group consisting of hydrogen, alkyl, alkenyl, alkynyl, hydroxyalkyl, alkoxyalkyl, haloalkyl, and benzyl; or, alternatively, R$_{101}$ and R$_{102}$, together with the nitrogen atom to which they are attached, form a ring selected from the group consisting of heterocycle and heteroaryl, wherein:

each of the heterocycle or heteroaryl is substituted with 0, 1, 2, 3, 4 or 5 substituents independently selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, -alkylSH, -alkylSalkyl, -alkylS(O)alkyl, -alkylSO$_2$alkyl and -alkylC(O)alkyl;

R$_{103}$ at each occurrence is independently selected from the group consisting of cycloalkyl, cycloalkenyl, aryl, heteroaryl, and heterocycle, wherein:

each of the cycloalkyl, cycloalkenyl, aryl, heteroaryl and heterocycle is independently substituted with 0, 1, 2, 3, 4, or 5 substituents independently selected from the group consisting of alkyl, alkenyl, alkynyl, halo, nitro, cyano, oxo, formyl, haloalkyl, —OR$_{104}$, —OC(O)R$_{104}$, —OC(O)OR$_{104}$, —OC(O)NR$_{104}$R$_{105}$, —OSO$_2$NR$_{104}$R$_{105}$, —SO$_2$R$_{105}$, —S(O)R$_{104}$, —NR$_{104}$R$_{105}$, —N(R$_{105}$)C(O)NR$_{104}$R$_{105}$, —N(R$_{105}$)COR$_{104}$, —N(R$_{105}$)SO$_2$R$_{104}$, —N(R$_{105}$)SO$_2$NR$_{104}$R$_{105}$, —C(O)R$_{104}$, —C(O)OR$_{104}$, —C(O)NR$_{104}$R$_{103}$, -alkylOR$_{104}$, -alkylOC(O)R$_{104}$, -alkylOC(O)OR$_{104}$, -alkylOC(O)NR$_{104}$R$_{105}$, -alkylOSO$_2$NR$_{104}$R$_{105}$, -alkylSO$_2$R$_{104}$, -alkylS(O)R$_{104}$, -alkylNR$_{104}$R$_{105}$, -alkylN(R$_{105}$)COR$_{104}$, -alkylN(R$_{105}$)SO$_2$R$_{104}$, -alkylN(R$_{104}$)C(O)NR$_{104}$R$_{105}$, -alkylN(R$_{105}$)SO$_2$NR$_{104}$R$_{105}$, -alkylC(O)R$_{104}$, -alkylC(O)OR$_{104}$, and -alkylC(O)NR$_{104}$R$_{105}$;

as to R$_{104}$ and R$_{105}$:

R$_{104}$ and R$_{105}$, at each occurrence, are independently selected from the group consisting of hydrogen, alkyl, alkenyl, alkynyl, hydroxyalkyl, alkoxyalkyl, haloalkyl, and benzyl; or, alternatively, R$_{104}$ and R$_{105}$, together with the nitrogen atom to which they are attached, form a ring selected from the group consisting of heterocycle and heteroaryl, wherein:

each of the heterocycle or heteroaryl is substituted with 0, 1, 2, 3, 4, or 5 substituents independently selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), —alkylC(O)N(alkyl)$_2$, —alkylSH, -alkylSalkyl, -alkylS(O)alkyl, -alkylSO$_2$alkyl, and -alkylC(O)alkyl; and R$_{106}$ at each occurrence is independently selected from the group consisting of aryl and heteroaryl, wherein:

each of the aryl and heteroaryl is substituted with 0, 1, 2, 3, 4, or 5 substituents independently selected from the group consisting of alkyl, alkenyl, alkynyl, nitro, formyl, halo, cyano, —OH, —Oalkyl, —NH$_2$, —N(H)(alkyl), —N(alkyl)$_2$, —C(O)OH, —C(O)Oalkyl, —C(O)NH$_2$, —C(O)N(H)(alkyl), —C(O)N(alkyl)$_2$, —SH, —Salkyl, —S(O)alkyl, —SO$_2$alkyl, —C(O)alkyl, haloalkyl, cyanoalkyl, hydroxyalkyl, alkoxyalkyl, -alkylNH$_2$, -alkylN(H)(alkyl), -alkylN(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, —alkylSH, -alkylSalkyl, -alkylS(O)alkyl, -alkylSO$_2$alkyl, and alkylC(O)alkyl.

2. The compound, stereoisomer, tautomer, salt, or combination thereof of claim 1, wherein:

R$^5$ is —OR$_d$, and
R$_d$ is hydrogen.

3. The compound, stereoisomer, tautomer, salt, or combination thereof of claim 1, wherein R$^3$ and R$^4$, together with the carbon atoms they are attached, form a ring selected from the group consisting of cycloalkyl, cycloalkenyl, heterocycle, aryl, and heteroaryl.

4. The compound, stereoisomer, tautomer, salt, or combination thereof of claim 1, wherein:

R$^5$ is —OR$_d$,
R$_d$ is hydrogen, and
R$^6$ is selected from the group consisting of hydrogen and alkyl.

5. The compound, stereoisomer, tautomer, salt, or combination thereof of claim 1, wherein:

R$^5$ is —OR$_d$,
R$_d$ is hydrogen,
R$^6$ is selected from the group consisting of hydrogen and alkyl, and
R$^3$ and R$^4$, together with the carbon atoms to which they are attached, form a ring selected from the group consisting of cycloalkyl, cycloalkenyl, heterocycle, aryl, and heteroaryl.

6. The compound, stereoisomer, tautomer, salt, or combination thereof of claim 1, wherein:

the compound corresponds to formula (III):

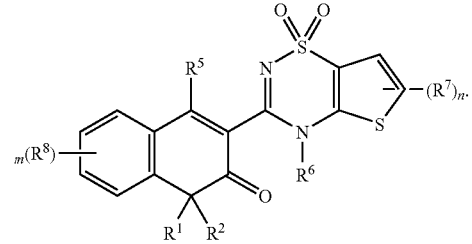

7. The compound, stereoisomer, tautomer, salt, or combination thereof of claim 6, wherein R$^5$ is —OR$_d$, wherein R$_d$ is hydrogen.

8. The compound, stereoisomer, tautomer, salt, or combination thereof of claim 6, wherein:

R$^5$ is —OR$_d$, wherein R$_d$ is hydrogen, and
R$^6$ is selected from the group consisting of hydrogen and alkyl.

9. The compound, stereoisomer, tautomer, salt, or combination thereof of claim 6, wherein:

R$^5$ is —OR$_d$, wherein R$_d$ is hydrogen,
R$^6$ is selected from the group consisting of hydrogen and alkyl,
R$^1$ is selected from the group consisting of:
 (1) alkyl, wherein the alkyl is unsubstituted or substituted with 1 or 2 substituents independently selected from the group consisting of:
  (a) halo,
  (b) —OR$_a$, wherein R$_a$ is hydrogen,
  (c) —OC(O)R$_a$, wherein R$_a$ is alkyl,
  (d) —OC(O)NR$_a$R$_b$, wherein R$_a$ is alkyl and R$_b$ is hydrogen,
  (e) —C(O)OR$_a$, wherein R$_a$ is alkyl,
  (f) —C(R$_e$)=CR$_j$R$_k$, wherein R$_e$ is hydrogen and R$_j$ and R$_k$, together with the carbon atom to which they are attached, form a cycloalkyl ring; and (g) —$R_{1q}$, wherein $R_{1q}$ is selected from the group consisting of aryl and cycloalkyl;
(2) alkenyl, wherein the alkenyl is unsubstituted or substituted with one substituent selected from the group consisting of:
  (a) —C(O)O$R_a$, wherein $R_a$ is alkyl, and
  (b) —$R_{1q}$, wherein $R_{1q}$ is aryl,
(3) —C(O)O$R_a$, wherein $R_a$ is alkyl, wherein the alkyl is unsubstituted or substituted with one $R_q$, wherein $R_q$ is a heterocyclic ring, wherein the heterocyclic ring is unsubstituted or substituted with one —C(O)O$R_{101}$, wherein $R_{101}$ is alkyl,
(4) —C(O)N$R_a R_b$, wherein:
  $R_a$ is alkyl, wherein the alkyl is unsubstituted or substituted with one substituent selected from the group consisting of —OC(O)$R_c$ and —O$R_c$, wherein $R_c$ is selected from the group consisting of hydrogen and alkyl, and
  $R_b$ is alkyl, or, alternatively,
  $R_a$ and $R_b$, together with the nitrogen atom to which they are attached, form a heterocyclic ring substituted with alkyl substituted with one substituent selected from the group consisting of —O$R_c$ and —OC(O)$R_c$, wherein $R_c$ is selected from the group consisting of hydrogen and alkyl, or
(5) $R_{1p}$, wherein $R_{1p}$ is heterocycle; and
$R^2$ is alkyl.

10. The compound, stereoisomer, tautomer, salt, or combination thereof of claim 6, wherein:
$R^5$ is —O$R_d$, wherein $R_d$ is hydrogen,
$R^6$ is selected from the group consisting of hydrogen and alkyl,
$R^1$ is selected from the group consisting of:
(1) alkyl, wherein the alkyl is unsubstituted or substituted with 1 or 2 substituents independently selected from the group consisting of:
  (a) halo,
  (b) —O$R_a$, wherein $R_a$ is hydrogen,
  (c) —OC(O)$R_a$, wherein $R_a$ is alkyl,
  (d) —OC(O)N$R_a R_b$, wherein $R_a$ is alkyl and $R_b$ is hydrogen,
  (e) —C(O)O$R_a$, wherein $R_a$ is alkyl,
  (f) —C($R_e$)=C$R_j R_k$, wherein $R_e$ is hydrogen and $R_j$ and $R_k$, together with the carbon atom to which they are attached, form a cycloalkyl ring; and
  (g) —$R_{1q}$, wherein $R_{1q}$ is selected from the group consisting of aryl and cycloalkyl;
(2) alkenyl, wherein the alkenyl is unsubstituted or substituted with one substituent selected from the group consisting of:
  (a) —C(O)O$R_a$, wherein $R_a$ is alkyl, and
  (b) —$R_{1q}$, wherein $R_{1q}$ is aryl,
(3) —C(O)O$R_a$, wherein $R_a$ is alkyl, wherein the alkyl is unsubstituted or substituted with one $R_q$, wherein $R_q$ is a heterocyclic ring, wherein the heterocyclic ring is unsubstituted or substituted with one —C(O)O$R_{101}$, wherein $R_{101}$ is alkyl,
(4) —C(O)N$R_a R_b$, wherein:
  $R_a$ is alkyl, wherein the alkyl is unsubstituted or substituted with one substituent selected from the group consisting of —OC(O)$R_c$ and —O$R_c$, wherein $R_c$ is selected from the group consisting of hydrogen and alkyl, and
  $R_b$ is alkyl, or, alternatively,
  $R_a$ and $R_b$, together with the nitrogen atom to which they are attached, form a heterocyclic ring substituted with alkyl substituted with one substituent selected from the group consisting of —O$R_c$ and —OC(O)$R_c$, wherein $R_c$ is selected from the group consisting of hydrogen and alkyl, or
(5) $R_{1p}$, wherein $R_{1p}$ is heterocycle;
$R^2$ is alkyl;
$R^7$ is selected from the group consisting of:
(1) formyl,
(2) —O$R_a$, wherein $R_a$, is selected from the group consisting of hydrogen and alkyl, wherein: the alkyl is substituted with one substituent selected from the group consisting of cyano and —C(O)N$R_c R_d$, wherein $R_c$ is hydrogen and $R_d$ is hydrogen,
(3) —OP(=O)($R_e$)(O$R_e$), wherein $R_e$ at each occurrence is independently selected from the group consisting of hydrogen and alkyl,
(4) —N$R_a R_b$, wherein $R_a$ is selected from the group consisting of hydrogen and alkyl substituted with one cyano and $R_b$ is hydrogen,
(5) —N($R_e$)C(=NH)$R_e$, wherein $R_e$ at each occurrence is independently selected from the group consisting of hydrogen and alkyl,
(6) —N($R_e$)C(O)$R_a$, wherein:
  $R_a$ is alkyl, wherein the alkyl is unsubstituted or substituted with 1, 2, or 3 independently selected halo, and
  $R_e$ is selected from the group consisting of hydrogen and alkyl,
(7) —N($R_e$)C(O)N$R_a R_b$, wherein $R_a$ is hydrogen, $R_b$ is hydrogen, and $R_e$ is selected from the group consisting of hydrogen and alkyl,
(8) —N($R_e$)C(=S)N$R_a R_b$, wherein $R_a$ is hydrogen, $R_b$ is hydrogen, and $R_e$ is selected from the group consisting of hydrogen and alkyl,
(9) —N($R_e$)C(=S)N($R_e$)C(O)$R_a$, wherein $R_e$ at each occurrence is independently selected from the group consisting of hydrogen and alkyl, and $R_a$ is $R_p$, wherein $R_p$ is aryl,
(10) —N($R_e$)C(O)O$R_a$, wherein $R_a$ is alkyl and $R_e$ is selected from the group consisting of hydrogen and alkyl,
(11) —N($R_e$)SO$R_a$, wherein $R_a$ is alkyl, and $R_e$ is selected from the group consisting of hydrogen and alkyl,
(12) —N($R_e$)SO$_2 R_a$, wherein:
  $R_e$ is selected from the group consisting of hydrogen and alkyl,
  $R_a$ is selected from the group consisting of alkyl, alkenyl, and $R_q$, wherein:
    $R_q$ is selected from the group consisting of heteroaryl and aryl, and
    the alkyl is unsubstituted or substituted with 1, 2, or 3 substituents independently selected from the group consisting of:
      (a) halo,
      (b) —C(O)O$R_c$, wherein $R_c$ is selected from the group consisting of hydrogen and alkyl,
      (c) —O$R_c$, wherein $R_c$ is hydrogen, and
      (d) —C(O)N$R_c R_d$, wherein $R_c$ is hydrogen and $R_d$ is hydrogen,
(13) —N($R_e$)SO$_2$N$R_a R_b$, wherein:
  $R_e$ is selected from the group consisting of hydrogen and alkyl, and
  as to $R_a$ and $R_b$:
    $R_b$ is hydrogen, and
    $R_a$ is selected from the group consisting of hydrogen and alkyl, wherein the alkyl is unsubstituted or substituted with one substituent selected from the group consisting of:
      (a) —O$R_c$, wherein $R_c$ is hydrogen, (b) —NR$_c$R$_d$, wherein R$_c$ and R$_d$ are hydrogen, and
(c) —OC(O)NR$_c$R$_d$, wherein R$_c$ and R$_d$, together with the nitrogen atom to which they are attached, form a heterocycle ring; or, alternatively, R$_a$ and R$_b$, together with the nitrogen atom to which they are attached, form a heterocycle ring;

(14) —N(R$_e$)SO$_2$N(R$_e$)C(O)R$_a$, wherein R$_e$ at each occurrence is independently selected from the group consisting of hydrogen and alkyl, and R$_a$ is alkyl,

(15) —N(R$_e$)SO$_2$N(R$_e$)C(O)OR$_a$, wherein R$_e$ at each occurrence is independently selected from the group consisting of hydrogen and alkyl, and R$_a$ is alkyl substituted with one R$_q$, wherein R$_q$ is aryl, and

(16) alkyl substituted with one substituent selected from the group consisting of
  (a) N$_3$,
  (b) —OR$_a$, wherein R$_a$ is selected from the group consisting of hydrogen and alkyl substituted with one —OR$_c$, wherein R$_c$ is alkyl,
  (c) —NR$_a$R$_b$, wherein R$_a$ is hydrogen and R$_b$ is hydrogen,
  (d) —N(R$_e$)SOR$_a$, wherein R$_a$ is alkyl and R$_e$ is selected from the group consisting of hydrogen and alkyl,
  (e) —N(R$_e$)SO$_2$R$_a$, wherein R$_b$ is selected from the group consisting of hydrogen and alkyl, and R$_a$ is alkyl, wherein the alkyl is unsubstituted or substituted with one substituent selected from the group consisting of halo and 1R, wherein; is heterocycle;
  (f) —N(R$_e$)SO$_2$NR$_a$R$_b$, wherein R$_a$ and R$_b$ are hydrogen, and R$_e$ is selected from the group consisting of hydrogen and alkyl,
  (g) —N(R$_e$)SO$_2$N(R$_e$)C(O)OR$_a$, wherein R$_e$ at each occurrence is independently selected from the group consisting of hydrogen and alkyl, and R$_a$ is alkyl substituted with R$_q$, wherein R$_q$ is aryl,
  (h) C(O)NR$_a$R$_b$, wherein R$_a$ is hydrogen and R$_b$ is hydrogen, and
  (i) R$_{7q}$, wherein R$_{7q}$ is heterocycle;

R$^8$ is selected from the group consisting of halo and —OR$_a$, wherein R$_a$ is selected from the group consisting of hydrogen and alkyl;

m is selected from the group consisting of 0 and 1; and
n is selected from the group consisting of 0 and 1.

11. The compound, stereoisomer, tautomer, salt, or combination thereof of claim 6 wherein the compound is selected from the group consisting of:

1,1-dibutyl-4-hydroxy-3-{7-[(methoxymethoxy)methyl]-1,1-dioxido-4H-thieno[2,3-e][1,2,4]thiadiazin-3-yl}-2(1H)-naphthalenone;

1,1-dibutyl-4-hydroxy-3-[7-(hydroxymethyl)-1,1-dioxido-4H-thieno[2,3-e][1,2,4]thiadiazin-3-yl]-2(1H)-naphthalenone;

(1R)-4-hydroxy-3-{7-[(methoxymethoxy)methyl]-1,1-dioxido-4H-thieno[2,3-e][1,2,4]thiadiazin-3-yl}-1-methyl-1-(3-methylbutyl)naphthalen-2(1H)-one;

(1R)-4-hydroxy-3-[7-(hydroxymethyl)-1,1-dioxido-4H-thieno[2,3-e][1,2,4]thiadiazin-3-yl]-1-methyl-1-(3-methylbutyl)naphthalen-2(1H)-one;

(1R)-3-[7-(azidomethyl)-1,1-dioxido-4H-thieno[2,3-e][1,2,4]thiadiazin-3-yl]-4-hydroxy-1-methyl-1-(3-methylbutyl)naphthalen-2(1H)-one;

(1R)-3-[7-(aminomethyl)-1,1-dioxido-4H-thieno[2,3-e][1,2,4]thiadiazin-3-yl]-4-hydroxy-1-methyl-1-(3-methylbutyl)naphthalen-2(1H)-one;

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)methanesulfonamide;

N-({3-[(4R)-1-hydroxy-4-methyl-4-(3-methylbutyl)-3-oxo-3,4-dihydronaphthalen-2-yl]-1,1-dioxido-4H-thieno[2,3-e][1,2,4]thiadiazin-7-yl}methyl)-2-morpholin-4-ylethanesulfonamide;

(1R)-1-(3,3-dimethylbutyl)-4-hydroxy-3-{7-[(methoxymethoxy)methyl]-1,1-dioxido-4H-thieno[2,3-e][1,2,4]thiadiazin-3-yl}-1-methylnaphthalen-2(1H)-one;

(1R)-1-(3,3-dimethylbutyl)-4-hydroxy-3-[7-(hydroxymethyl)-1,1-dioxido-4H-thieno[2,3-e][1,2,4]thiadiazin-3-yl]-1-methylnaphthalen-2(1H)-one;

(1R)-3-[7-(aminomethyl)-1,1-dioxido-4H-thieno[2,3-e][1,2,4]thiadiazin-3-yl]-1-(3,3-dimethyl-butyl)-4-hydroxy-1-methylnaphthalen-2(1H)-one;

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)-N-methylmethanesulfonamide;

N-({3-[(4R)-4-(3,3-dimethylbutyl)-1-hydroxy-4-methyl-3-oxo-3,4-dihydronaphthalen-2-yl]-4-methyl-1,1-dioxido-4H-thieno[2,3-e][1,2,4]thiadiazin-7-yl}methyl)-N-methylmethanesulfonamide;

benzyl[({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)amino]sulfonylcarbamate;

3-chloro-N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)propane-1-sulfonamide; and (1R)-1-(3,3-dimethylbutyl)-3-{7-[(1,1-dioxidoisothiazolidin-2-yl)methyl]-1,1-dioxido-4H-thieno[2,3-e][1,2,4]thiadiazin-3-yl}-4-hydroxy-1-methylnaphthalen-2(1H)-one.

12. A compound, a stereoisomer of the compound, a tautomer of the compound, a pharmaceutically acceptable salt of the compound, stereoisomer, or tautomer, or a combination thereof, wherein the compound is selected from the group consisting of:

N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)methanesulfonamide; and N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)sulfamide.

13. The compound, stereoisomer, tautomer, salt, or combination thereof of claim 12, wherein the pharmaceutically acceptable salt is selected from the group consisting of sodium, potassium, calcium, and magnesium salt.

14. A pharmaceutical composition comprising:
a therapeutically effective amount of one or more compounds, stereoisomers, tautomers, or salts of claim 1 or a combination thereof, and
a pharmaceutically acceptable carrier.

15. A method of treating infection caused by a a hepatitis C virus, wherein the method comprises administering to a patient in need of such treatment a therapeutically effective amount of one or more compounds, stereoisomers, tautomers, or salts of claim 1, or a combination thereof.

16. A pharmaceutical composition comprising:
a therapeutically effective amount of one or more compounds, stereoisomers, tautomers, or salts of claim 12 or a combination thereof, and
a pharmaceutically acceptable carrier.

17. A method of treating infection caused by a a hepatitis C virus, wherein the method comprises administering to a patient in need of such treatment a therapeutically effective amount of one or more compounds, stereoisomers, tautomers, or salts of claim 12, or a combination thereof.

18. The compound, stereoisomer, tautomer, salt, or combination thereof of claim 12, wherein the compound is N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)methane-sulfonamide.

19. The compound, stereoisomer, tautomer, salt, or combination thereof of claim 12, wherein the compound is N-({3-[(4R)-4-(3,3-dimethylbutyl)-1-hydroxy-4-methyl-3-oxo-3,4-dihydronaphthalen-2-yl]-1,1-dioxido-4H-thieno[2,3-e][1,2,4]thiadiazin-7-yl}methyl)sulfamide.

* * * * *